US006498022B2

(12) United States Patent
Wei et al.

(10) Patent No.: US 6,498,022 B2
(45) Date of Patent: Dec. 24, 2002

(54) ISOLATED NUCLEIC ACID MOLECULES ENCODING HUMAN CARBONATE TRANSPORTER PROTEINS, AND USES THEREOF

(75) Inventors: Ming-Hui Wei, Germantown, MD (US); Jiayin Li, Potomac, MD (US); Fangcheng Gong, Germantown, MD (US); Andrei Gabrielian, Rockville, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

(*) Notice: Subject to any disclaimer, the term of this patent is extended or adjusted under 35 U.S.C. 154(b) by 29 days.

(21) Appl. No.: 09/734,674

(22) Filed: Dec. 13, 2000

(65) Prior Publication Data

US 2002/0081648 A1 Jun. 27, 2002

(51) Int. Cl.[7] .................................................. C12N 15/12

(52) U.S. Cl. ................ 435/69.1; 435/252.3; 435/320.1; 536/23.5

(58) Field of Search ............................. 435/69.1, 252.3, 435/320.1; 536/23.5

(56) References Cited

U.S. PATENT DOCUMENTS 6,200,776 B1 * 3/2001 Boron et al. ............... 435/69.1

OTHER PUBLICATIONS

Wang et al. "The Na–driven Cl/HCO3 Exchanger". Nov. 10, 2000. J. Biol. Chem. 275(45):35486–35490.*

* cited by examiner

*Primary Examiner*—John Ulm
(74) *Attorney, Agent, or Firm*—Celera Genomics; Justin Karjala

(57) ABSTRACT

The present invention provides amino acid sequences of peptides that are encoded by genes within the human genome, the transporter peptides of the present invention. The present invention specifically provides isolated peptide and nucleic acid molecules, methods of identifying orthologs and paralogs of the transporter peptides, and methods of identifying modulators of the transporter peptides.

9 Claims, 122 Drawing Sheets

```
   1  CGGCCGCGTC GACGTGATTT GATATCTTGA TGATGGCTTA AACAGATACT
  51  GATGGACAGA TCTGTTGTTT GATATTTTTT TCACTAGCCC TGAAGATGCT
 101  GAGACATAGA GATGGCTGTG ATTATCTTTT GTAAGACAGG AAATGCAGTC
 151  TTTAGGGGTT TCTGGAAATA GAAAGGTCAT GCAGTCTGGA ACCTGTGAGC
 201  CTTTTCAATC TCTAAGTCAT CAGAGAAATG ATGAAGAAGC AGTTGTGGAT
 251  AGAGGTGGAA CTCGTTCTAT TCTCAAAACA CACTTTGAGA AAGAAGATTT
 301  AGAAGGTCAT CGAACACTAT TTATTGGAGT ACATGTGCCC TTGGGAGGAA
 351  GAAAAAGCCA TCGACGTCAC AGGCATCGTG GTCATAAACA CAGAAAGAGA
 401  GACAGAGAAA GAGATTCAGG ATTAGAGGAT GGAAGGGAGT CACCTTCTTT
 451  TGACACCCCA TCACAGAGGG TACAGTTTAT TCTTGGAACC GAGGATGATG
 501  ACGAGGAACA CATTCCTCAT GACCTTTTCA CAGAACTGGA TGAGATTTGT
 551  TGGCGTGAAG GTGAGGACGC TGAGTGGCGA GAAACAGCCA GGTGGTTGAA
 601  GTTTGAAGAA GATGTGGAAG ATGGAGGAGA AAGGTGGAGC AAGCCTTATG
 651  TGGCTACTCT TTCATTGCAC AGCTTGTTTG AATTGAGAAG TTGTATTCTG
 701  AATGGAACTG TGTTGCTGGA CATGCATGCC AACACTTTAG AAGAAATTGC
 751  AGATATGGTT CTTGACCAAC AAGTGAGCTC AGGTCAGCTG AATGAAGATG
 801  TACGCCATAG GGTCCATGAG GCATTGATGA AACAGCATCA TCATCAGAAT
 851  CAGAAAAAAC TCACCAACAG GATTCCCATT GTTCGTTCCT TTGCTGATAT
 901  TGGCAAGAAA CAGTCAGAAC CAAATTCCAT GGACAAAAAT GCAGGTCAGG
 951  TTGTTTCTCC TCAGTCTGCT CCAGCCTGTG TTGAAAATAA AAATGATGTT
1001  AGCAGAGAAA ACAGCACTGT TGACTTTAGC AAGGGACTGG GAGGCCAACA
1051  AAAGGGGCAT ACTAGTCCAT GTGGGATGAA ACAAAGGCAT GAAAAAGGAC
1101  CTCCACACCA GCAAGAGAGA GAGGTTGATC TGCATTTTAT GAAAAAGATT
1151  CCTCCAGGTG CTGAAGCATC GAACATCTTA GTGGGAGAAC TGGAGTTCTT
1201  GGATCGAACA GTAGTTGCGT TTGTCAGGTT GTCTCCAGCT GTATTGCTTC
1251  AAGGACTGGC TGAAGTCCCA ATCCCAACCA GATTTTTGTT CATTCTTCTG
1301  GGACCCCTGG GAAAGGGTCA ACAGTACCAT GAGATTGGCA GATCAATTGC
1351  AACCCTAATG ACAGATGAGG TATTTCATGA TGTTGCCTAT AAAGCTAAAG
1401  ATCGTAATGA CTTGGTATCA GGAATTGATG AGTTTCTGGA TCAGGTTACT
1451  GTTCTCCCTC CTGGAGAATG GGATCCAAGC ATTCGAATAG AGCCTCCCAA
1501  AAATGTTCCT TCCCAGGAGA AGAGGAAGAT TCCTGCTGTA CCAAATGGAA
1551  CAGCAGCTCA TGGGGAAGCA GAGCCCCACG GAGGACATAG TGGACCTGAA
1601  CTCCAGCGAA CTGGAAGGAT TTTTGGGGGA CTTATTTTAG ATATCAAAAG
1651  AAAAGCTCCA TACTTCTGGA GTGACTTCAG AGATGCTTTC AGCCTGCAGT
1701  GCTTAGCATC TTTTCTATTT CTCTACTGCG CGTGTATGTC TCCTGTCATC
1751  ACGTTTGGAG GACTGCTGGG AGAAGCAACT GAAGGGCGTA TAAGTGCAAT
1801  TGAATCTCTC TTTGGAGCAT CCATGACCGG GATAGCCTAT TCTCTCTTTG
1851  GTGGACAGCC TCTTACCATA TTAGGCAGTA CAGGACCAGT TTTGGTGTTT
1901  GAAAAGATTT TGTTTAAATT TTGCAAAGAA TATGGGCTGT CATACCTATC
1951  TTTAAGAGCT AGCATTGGAC TTTGGACTGC AACTCTATGT ATCATACTTG
2001  TGGCCACAGA TGCTAGTTCC CTTGTCTGCT ACATCACTCG GTTTACTGAA
2051  GAAGCTTTTG CTTCCCTGAT TTGCATCATT TTCATTTATG AGGCCCTGGA
2101  GAAGTTGTTT GAACTCAGTG AAGCATATCC AATCAACATG CATAATGATC
2151  TGGAACTGCT GACACAATAC TCGTGTAACT GTGTGGAACC GCATAATCCC
2201  AGCAATGGCA CATTGAAGGA ATGGAGGGAA TCCAATATTT CTGCCTCTGA
2251  CATAATTTGG GAGAACCTAA CTGTGTCAGA ATGCAAATCA TTGCATGGAG
```

FIGURE 1A

```
2301 AGTATGTTGG ACGGGCCTGT GGCCATGATC ACCCATATGT TCCAGATGTT
2351 CTATTTTGGT CTGTGATCCT GTTCTTTTCC ACAGTTACTC TGTCAGCCAC
2401 CCTGAAGCAG TTCAAGACTA GCAGATATTT TCCAACCAAG GTTCGATCCA
2451 TAGTGAGTGA CTTTGCTGTC TTTCTTACAA TTCTGTGTAT GGTTTTAATT
2501 GACTATGCCA TTGGGATCCC ATCTCCAAAA CTACAAGTAC CAAGTGTTTT
2551 CAAGCCCACT AGAGATGATC GTGGCTGGTT TGTTACGCCT TTAGGTCCAA
2601 ACCCATGGTG GACAGTAATA GCTGCTATAA TTCCAGCTCT GCTTTGTACT
2651 ATTCTAATTT TTATGGACCA ACAGATTACA GCTGTCATCA TCAACAGGAA
2701 AGAGCATAAG CTAAAGAAAG GTTGTGGGTA CCATCTGGAC CTATTAATGG
2751 TGGCTGTCAT GCTCGGTGTA TGCTCCATCA TGGGCCTGCC ATGGTTTGTG
2801 GCTGCCACAG TCCTCTCCAT CACTCATGTC AATAGCCTAA AACTGGAATC
2851 AGAATGCTCA GCTCCAGGAG AACAACCCAA ATTTCTCGGC ATTCGGGAGC
2901 AAAGGGTTAC TGGGCTTATG ATTTTTATTC TTATGGGTTC ATCAGTCTTT
2951 ATGACCAGTA TTCTGAAGTT TATTCCCATG CCAGTGCTAT ATGGAGTGTT
3001 TCTTTATATG GGTGCTTCAT CTCTAAAGGG AATTCAGTTC TTTGATAGGA
3051 TAAAGCTCTT CTGGATGCCG GCAAAACATC AACCAGATTT TATATACCTA
3101 AGGCACGTAC CGCTTCGAAA AGTGCATCTC TTCACAATTA TTCAGATGAG
3151 TTGCCTTGGC CTTTTGTGGA TAATAAAAGT TTCAAGAGCT GCTATTGTCT
3201 TTCCCATGAT GGTGTTAGCC CTGGTATTTG TAAGAAAGTT GATGGACTTG
3251 TTGTTCACGA AGCGGGAACT CAGCTGGTTG GATGATTTGA TGCCCGAGAG
3301 TAAGAAAAAG AAACTGGAAG ATGCTGAAAA AGAAGAAGAA CAAAGTATGC
3351 TAGCTATGGA AGATGAGGGC ACAGTACAAC TCCCATTGGA AGGGCACTAT
3401 AGAGATGATC CATCTGTGAT CAATATATCT GATGAAATGT CAAAGACTGC
3451 CTTGTGGAGG AACCTTCTGA TTACTGCCGA TAACTCAAAA GATAAGGAGT
3501 CAAGCTTTCC TTCCAAAAGC TCCCCTTCCT AATCACTCTA GAAGCTGATT
3551 CCCCAAAGCA TTGAAAGCCG AAAAGAGAAG AAAGCTGACT CAGGGAAAGG
3601 TGTTGACAGG GAGACTTGTC TATGACTCGA TCTTCAATTT ATTTTTTACA
3651 TATATATGAG AAGAGTGTCA CAATTATTAA TAAAACTGCT TTGATCATGT
3701 ATTGTAAATT CTGTCCCTCA ACCCAAATCC ACCTTCATAC TGTAAGTAGT
3751 GCAATACTTG TTTCATTTCT GTGTTTAAAC TTCTGAGCAG TGAGACATCC
3801 CTGTGAGCAG ATACAATAGC CAATGCAAGA ATCTGTGTGT TCCTTGCTGT
3851 ACGTTAGACA TTTGTAAACT GGATTCTGAT TGTCAGTTTT ATGAGAGCAA
3901 TAGCTTCCTT AAAGAGATAA GTCATATTTA CCTAGTTTGT ATTTTCCTAC
3951 TTTAGTGACC TGAAGATGCC TGATAATTTC ATTCAGAAGA ATTTTTGAAA
4001 GGTAGTCTTA CTTCTTTTTA GTTTTTATAG CTTAGCATTA GTGACTTATT
4051 TCAAAAGACC CAAATCAAAA AGTTAGTTTG AAAGCATTTT TTAATAATTG
4101 TATTTATGCA TTTCCTTGAT TTAATATGAT AAATTTAATA CTTAACAATT
4151 TATATGTAAC TAAAACTTAA AGTCATTTGA AAAATATATA GAAACCTATT
4201 TACAACTTGT TAAGGACAAT CAGACATAAT GCAGAGTTAA GTAGTATTTG
4251 CTTAAAATTC AAGTTGTGAC TAATGATCAA ATACTAGGCT TGTACGAAAT
4301 GCTTTAGAAA AACTTTGTAA CAGTTTTGTG GGATTTTTCA ATATAAACCT
4351 TTATCAGAAA TATACTAAGT TTGTCTCCCA CTGACAACAG ATGTTTTCCA
4401 AATAAACATA TTCTATACAT ACTTGTGGAA TGCCACATGG TGAATCATTG
4451 TATATGAAAT TCCACTCCTG TACAGTTACT CTGCAGCTAA TGGTCATGCA
4501 CTGCTTAATG CTGGTCCTGA ATCATGTTCT CATGTTAGAC CAACAGCTCT
4551 CCAATTGTCA TTTTTTTTCT GCAGAGTTTT TTTTTTTCCA CTTTTAAATT
```

FIGURE 1B

4601 AAATGCATGT TGTGGAAAAA CAGTCTTTTA AAATGAAATT TCAGATTCCA
4651 TTTGAGAAGG TTCTGTAGAT ATTTCAGTCC ATATAAAATA ATACATCTTT
4701 ACTAAACTTA TATAAGGGGA GAGAAAGTTA TGAAGTTTTG GACATTACTA
4751 AAAGTACAGT ATTTGATTTC ACTTTCAATG AATGTGAAGT TAATAAAACT
4801 AAATCTCATA ATGCTCTTGG TTCCTAAGAA TGAGTAGTAA TCATCAACTT
4851 TATAATACTC CAATATTCCG TTTTATAATA ATTCAGAGCC CTGTGGCTTT
4901 TACACACCGT TAATTATGTA CTCTGTTGGA AGTGCACATG AAAAGTGAAG
4951 AAAAGTTCCT CTTGTGATTA AACTAATGGG AGGAAATAAA TCAACAAAGT
5001 CTCCATTAAG TTCTACATTT TGAGACCTTT TAAAAATTCC CCTCACAATT
5051 CTTTAAGGAG CCCCCCTTTT TATGGAACAT GAGCCTAAAA ATTATAGAAA
5101 GAAGAATTTT AAGTTAATAA AGTTTGTATT TATAAATGCT GAAAAAATAC
5151 AGAAACTTTC TGTTCCAAAT GTGTTGCCTT TGTGTATTTT ATAATACAGA
5201 TACTACATTG TAAACATTTC CATTGTTTTA TGATTTAGCC AGTGATTCCC
5251 CAAAGCAGCC TCTTAGTGTT TTAATATATT AATAACTGTT TTGTTAAAAA
5301 TGATCATAGT GAATTTAAAT CTTCACATGA TCACCTATTT GAATAAGCAA
5351 TCATATCCAA TGAAATTCTG TATTTCTGAG TATTTTTATA GTCATTTTGT
5401 TCTTGTGTGA ATTTTAAAGC TATCCCTATG TTAATCCTAA TATTTTGAAA
5451 TCATATAAAA TATAATAAAA ATGTAGTATT ATATATTTAC TTCTAATTTC
5501 AGATTCCTGG TCAAAATTAC TAAATATCTT GAATGTAATT TAGTGCCAAG
5551 TTTAAATAAT GTGTAAATGT GACTAGGATA TTGTGTTTTT CACAATTAAG
5601 AAATGTTATG TGGAAATAAA TATTTATCCT AACTTCCTTG CACATTTTAA
5651 ATTGTGATAC AAAGTGTCTT GTCTTTTTTC TTTGTTTTAA TTAGTAAATC
5701 AGTGTAAAAC AAAAAAAAAA AAAAAAAAAA AAAAA (SEQ ID NO:1)

FIGURE 1C

FEATURES:

5' UTR: 1
Start: 179
Stop: 3530
3' UTR: 3533

HOMOLOGOUS PROTEINS:

Top 10 BLAST Hits:

| | Score | E |
|---|---|---|
| gi\|10946960\|ref\|NP_067505.1\| sodium bicarbonate cotransporter i... | 1702 | 0.0 |
| gi\|4759134\|ref\|NP_004849.1\| solute carrier family 4, sodium bic... | 1677 | 0.0 |
| gi\|3882199\|dbj\|BAA34459.1\| (AB018282) KIAA0739 protein [Homo sa... | 1671 | 0.0 |
| gi\|10436051\|gb\|AAG16773.1\|AF089726_1 (AF089726) sodium bicarbon... | 1626 | 0.0 |
| gi\|4507029\|ref\|NP_003606.1\| solute carrier family 4, sodium bic... | 1503 | 0.0 |
| gi\|6650104\|gb\|AAF21720.1\|AF053755_1 (AF053755) bicarbonate tran... | 1473 | 0.0 |
| gi\|6502527\|gb\|AAF14345.1\|AF069511_1 (AF069511) putative sodium ... | 1288 | 0.0 |
| gi\|5702100\|gb\|AAD47142.1\|AF080106_1 (AF080106) NBC-like protein... | 1288 | 0.0 |
| gi\|5051628\|gb\|AAD38322.1\|AF047033_1 (AF047033) sodium bicarbona... | 1266 | 0.0 |
| gi\|5669564\|gb\|AAD46389.1\|AF070475_1 (AF070475) NBC-like protein... | 1260 | 0.0 |

EXPRESSION INFORMATION FOR MODULATORY USE:

library source:

Expression information from PCR-based tissue screening panels:

Human testis
Human fetal brain
Brain
Placenta
Bone marrow

FIGURE 1D

```
   1 MQSLGVSGNR KVMQSGTCEP FQSLSHQRND EEAVVDRGGT RSILKTHFEK
  51 EDLEGHRTLF IGVHVPLGGR KSHRRHRHRG HKHRKRDRER DSGLEDGRES
 101 PSFDTPSQRV QFILGTEDDD EEHIPHDLFT ELDEICWREG EDAEWRETAR
 151 WLKFEEDVED GGERWSKPYV ATLSLHSLFE LRSCILNGTV LLDMHANTLE
 201 EIADMVLDQQ VSSGQLNEDV RHRVHEALMK QHHHQNQKKL TNRIPIVRSF
 251 ADIGKKQSEP NSMDKNAGQV VSPQSAPACV ENKNDVSREN STVDFSKGLG
 301 GQQKGHTSPC GMKQRHEKGP PHQQEREVDL HFMKKIPPGA EASNILVGEL
 351 EFLDRTVVAF VRLSPAVLLQ GLAEVPIPTR FLFILLGPLG KGQQYHEIGR
 401 SIATLMTDEV FHDVAYKAKD RNDLVSGIDE FLDQVTVLPP GEWDPSIRIE
 451 PPKNVPSQEK RKIPAVPNGT AAHGEAEPHG GHSGPELQRT GRIFGGLILD
 501 IKRKAPYFWS DFRDAFSLQC LASFLFLYCA CMSPVITFGG LLGEATEGRI
 551 SAIESLFGAS MTGIAYSLFG GQPLTILGST GPVLVFEKIL FKFCKEYGLS
 601 YLSLRASIGL WTATLCIILV ATDASSLVCY ITRFTEEAFA SLICIIFIYE
 651 ALEKLFELSE AYPINMHNDL ELLTQYSCNC VEPHNPSNGT LKEWRESNIS
 701 ASDIIWENLT VSECKSLHGE YVGRACGHDH PYVPDVLFWS VILFFSTVTL
 751 SATLKQFKTS RYFPTKVRSI VSDFAVFLTI LCMVLIDYAI GIPSPKLQVP
 801 SVFKPTRDDR GWFVTPLGPN PWWTVIAAII PALLCTILIF MDQQITAVII
 851 NRKEHKLKKG CGYHLDLLMV AVMLGVCSIM GLPWFVAATV LSITHVNSLK
 901 LESECSAPGE QPKFLGIREQ RVTGLMIFIL MGSSVFMTSI LKFIPMPVLY
 951 GVFLYMGASS LKGIQFFDRI KLFWMPAKHQ PDFIYLRHVP LRKVHLFTII
1001 QMSCLGLLWI IKVSRAAIVF PMMVLALVFV RKLMDLLFTK RELSWLDDLM
1051 PESKKKKLED AEKEEEQSML AMEDEGTVQL PLEGHYRDDP SVINISDEMS
1101 KTALWRNLLI TADNSKDKES SFPSKSSPS  (SEQ ID NO:2)
```

FEATURES:
Functional domains and key regions:
[1] PDOC00001 PS00001 ASN_GLYCOSYLATION
N-glycosylation site Number of matches: 7

```
1    187-190 NGTV
2    290-293 NSTV
3    468-471 NGTA
4    688-691 NGTL
5    698-701 NISA
6    708-711 NLTV
7  1094-1097 NISD
```

[2] PDOC00004 PS00004 CAMP_PHOSPHO_SITE
cAMP- and cGMP-dependent protein kinase phosphorylation site Number of matches: 2

```
1    238-241 KKLT
2    255-258 KKQS
```

FIGURE 2A

[3] PDOC00005 PS00005 PKC_PHOSPHO_SITE
Protein kinase C phosphorylation site

Number of matches: 15

| | | |
|---|---|---|
| 1 | 72-74 | SHR |
| 2 | 107-109 | SQR |
| 3 | 148-150 | TAR |
| 4 | 241-243 | TNR |
| 5 | 446-448 | SIR |
| 6 | 490-492 | TGR |
| 7 | 603-605 | SLR |
| 8 | 690-692 | TLK |
| 9 | 753-755 | TLK |
| 10 | 690-692 | TLK |
| 11 | 753-755 | TLK |
| 12 | 759-761 | TSR |
| 13 | 794-796 | SPK |
| 14 | 898-900 | SLK |
| 15 | 960-962 | SLK |

[4] PDOC00006 PS00006 CK2_PHOSPHO_SITE
Casein kinase II phosphorylation site

Number of matches: 17

| | | |
|---|---|---|
| 1 | 46-49 | THFE |
| 2 | 92-95 | SGLE |
| 3 | 116-119 | TEDD |
| 4 | 130-133 | TELD |
| 5 | 177-180 | SLFE |
| 6 | 198-201 | TLEE |
| 7 | 249-252 | SFAD |
| 8 | 291-294 | STVD |
| 9 | 426-429 | SGID |
| 10 | 483-486 | SGPE |
| 11 | 551-554 | SAIE |
| 12 | 690-693 | TLKE |
| 13 | 700-703 | SASD |
| 14 | 710-713 | TVSE |
| 15 | 806-809 | TRDD |
| 16 | 1039-1042 | TKRE |
| 17 | 1044-1047 | SWLD |

[5] PDOC00007 PS00007 TYR_PHOSPHO_SITE
Tyrosine kinase phosphorylation site 978-985 KHQPDFIY

FIGURE 2B

[6] PDOC00008 PS00008 MYRISTYL
N-myristoylation site

Number of matches: 11

| | | |
|---|---|---|
| 1 | 5-10 | GVSGNR |
| 2 | 38-43 | GGTRSI |
| 3 | 68-73 | GGRKSH |
| 4 | 93-98 | GLEDGR |
| 5 | 301-306 | GQQKGH |
| 6 | 339-344 | GAEASN |
| 7 | 539-544 | GGLLGE |
| 8 | 558-563 | GASMTG |
| 9 | 563-568 | GIAYSL |
| 10 | 571-576 | GQPLTI |
| 11 | 609-614 | GLWTAT |

[7] PDOC00009 PS00009 AMIDATION
Amidation site

Number of matches: 2

| | | |
|---|---|---|
| 1 | 68-71 | GGRK |
| 2 | 253-256 | IGKK |

[8] PDOC00040 PS00041 HTH_ARAC_FAMILY_1
Bacterial regulatory proteins, araC family signature 921-961 RVTGLMIFILMGSSVFMTSILKFIPMPVLYGVFLYMGASSL

FIGURE 2C

Membrane spanning structure and domains:

| Helix | Begin | End | Score | Certainty |
|---|---|---|---|---|
| 1 | 371 | 391 | 0.629 | Putative |
| 2 | 520 | 540 | 2.036 | Certain |
| 3 | 555 | 575 | 1.439 | Certain |
| 4 | 605 | 625 | 1.559 | Certain |
| 5 | 634 | 654 | 0.689 | Putative |
| 6 | 734 | 754 | 1.972 | Certain |
| 7 | 774 | 794 | 1.593 | Certain |
| 8 | 821 | 841 | 2.189 | Certain |
| 9 | 867 | 887 | 2.222 | Certain |
| 10 | 922 | 942 | 2.278 | Certain |
| 11 | 945 | 965 | 1.230 | Certain |
| 12 | 994 | 1014 | 1.557 | Certain |
| 13 | 1017 | 1037 | 0.669 | Putative |

FIGURE 2D

```
BLAST Alignment to Top Hit:
>gi|10946960|ref|NP_067505.1| sodium bicarbonate cotransporter isoform
          3 [Mus musculus] >gi|7385123|gb|AAF61705.1|AF224508_1
          (AF224508) sodium bicarbonate cotransporter isoform 3
          kNBC-3 [Mus musculus]
          Length = 1089

 Score = 1702 bits (4360), Expect = 0.0
 Identities = 835/1120 (74%), Positives = 956/1120 (84%), Gaps = 49/1120 (4%)

Query: 13  MQSGTCEPFQSLSHQRNDEEAVVDRGGTRSILKTHFEKEDLEGHRTLFIGVHVPLGGRKS 72
            M +G+ EP    LS+QR DEEAVVD+GGT +IL  H+EKE+LEGHRTL++GV +PLG R+S
Sbjct: 1   MPAGSNEPDGVLSYQRPDEEAVVDQGGTSTILNIHYEKEELEGHRTLYVGVRMPLG-RQS 59

Query: 73  HRRHRHRGHKHRKRDRERDSGL---EDGRESPSFDTPSQRVQFILGTEDDDEEHIPHDLF 129
            HR HR  G KHR+R   R  G    E+G E+ + DTPSQRVQFILGTE+D EEH+PH+LF
Sbjct: 60  HRHHRTHGQKHRRRGG-RGKGASQGEEGLEALAHDTPSQRVQFILGTEED-EEHVPHELF 117

Query: 130 TELDEICWREGEDAEWRETARWLKFEEDVEDGGERWSKPYVATLSLHSLFELRSCILNGT 189
            TELDEIC +EGEDAEW+ETARWLKFEEDVEDGGERWSKPYVATLSLHSLFELRSC++NG+
Sbjct: 118 TELDEICMKEGEDAEWKETARWLKFEEDVEDGGERWSKPYVATLSLHSLFELRSCLINGS 177

Query: 190 VLLDMHANTLEEIADMVLDQQVSSGQLNEDVRHRVHEALMKQHHHQNQKKLTNRIPIVRS 249
            VLLDM A+++EEI+D++LDQQ      L++ VR +V EAL+K+HHHQN+++  N IPIVRS
Sbjct: 178 VLLDMRASSIEEISDLILDQQELLRDLSDSVRVKVREALLKKHHHQNERRRNNLIPIVRS 237

Query: 250 FADIGKKQSEPNSMDKNAGQVVSPQSAPACVENKNDVSRENSTVDFSKGLGGQQKGHTSP 309
            FA++GKKQS+P+SMD++ GQ +SPQSA   +E KN V+ E+S VD SK
Sbjct: 238 FAEVGKKQSDPHSMDRD-GQTMSPQSATN-LEVKNGVNCEHSPVDLSK------------ 283

Query: 310 CGMKQRHEKGPPHQQEREVDLHFMKKIPPGAEASNILVGELEFLDRTVVAFVRLSPAVLL 369
                              VDLHFMKKIP GAEASN+LVGE++ LDR +VAFVRLSPAVLL
Sbjct: 284 ------------------VDLHFMKKIPTGAEASNVLVGEVDTLDRPIVAFVRLSPAVLL 325

Query: 370 QGLAEVPIPTRFLFILLGPLGKGQQYHEIGRSIATLMTDEVFHDVAYKAKDRNDLVSGID 429
             GL EVPIPTRFLFILLGP+GKGQQYHEIGRS+AT+MTDE+FHDVAYKAK+R+DL++GID
Sbjct: 326 SGLTEVPIPTRFLFILLGPVGKGQQYHEIGRSMATIMTDEIFHDVAYKAKERDDLLAGID 385

Query: 430 EFLDQVTVLPPGEWDPSIRIEPPKNVPSQEKRKIPAVPNGTAAHGEAEPHGGHSGPELQR 489
            EFLDQVTVLPPGEWDPSIRIEPPKNVPSQEKRK+P VPNG   H E EPHGGHSGPEL+R
Sbjct: 386 EFLDQVTVLPPGEWDPSIRIEPPKNVPSQEKRKMPGVPNGNVCHIEPEPHGGHSGPELER 445

Query: 490 TGRIFGGLILDIKRKAPYFWSDFRDAFSLQCLASFLFLYCACMSPVITFGGLLGEATEGR 549
            TGR+FGGL+LD+KRKAP++WSD+RDA SLQCLASFLFLYCACMSPVITFGGLLGEATEGR
Sbjct: 446 TGRLFGGLVLDVKRKAPWYWSDYRDALSLQCLASFLFLYCACMSPVITFGGLLGEATEGR 505
```

FIGURE 2E

```
Query: 550  ISAIESLFGASMTGIAYSLFGGQPLTILGSTGPVLVFEKILFKFCKEYGLSYLSLRASIG 609
            ISAIESLFGASMTGIAYSLF GQPLTILGSTGPVLVFEKILFKFCK+Y LSYLSLRA IG
Sbjct: 506  ISAIESLFGASMTGIAYSLFAGQPLTILGSTGPVLVFEKILFKFCKDYALSYLSLRALIG 565

Query: 610  LWTATLCIILVATDASSLVCYITRFTEEAFASLICIIFIYEALEKLFELSEAYPINMHND 669
            LWTA LCI+LVATDASSLVCYITRFTEEAFASLICIIFIYEA+EKL  L+E YPI+MH+
Sbjct: 566  LWTAFLCIVLVATDASSLVCYITRFTEEAFASLICIIFIYEAIEKLIHLAETYPIHMHSQ 625

Query: 670  LELLTQYSCNCVEPHNPSNGTLKEWRESNISASDIIWENLTVSECKSLHGEYVGRACGHD 729
            L+ L+ Y C CV P NP+N TL+ W++ NI A+++ W NLTVSEC+ +HGE++G ACGH
Sbjct: 626  LDHLSLYYCRCVLPENPNNHTLQYWKDHNILAAEVNWANLTVSECQEMHGEFMGSACGHH 685

Query: 730  HPYVPDVLFWSVILFFSTVTLSATLKQFKTSRYFPTKVRSIVSDFAVFLTILCMVLIDYA 789
             PY PDVLFWS ILFF+T  + +TLK FKTSRYFPT+VRS+VSDFAVFLTI  MV++D+
Sbjct: 686  GPYTPDVLFWSCILFFATFIVPSTLKTFKTSRYFPTRVRSMVSDFAVFLTIFTMVVLDFL 745
```

FIGURE 2F

```
Query: 790  IGIPSPKLQVPSVFKPTRDDRGWFVTPLGPNPWWTVIAAIIPALLCTILIFMDQQITAVI 849
            IG+PSPKLQVP+VFKPTRDDRGWF+ P+GPNPWWTVIAAIIPALLCTILIFMDQQITAVI
Sbjct: 746  IGVPSPKLQVPNVFKPTRDDRGWFINPIGPNPWWTVIAAIIPALLCTILIFMDQQITAVI 805

Query: 850  INRKEHKLKKGCGYHLDLLMVAVMLGVCSIMGLPWFVAATVLSITHVNSLKLESECSAPG 909
            INRKEHKLKKGCGYHLDLLMVAVMLGVCSIMGLPWFVAATVLSITHVNSLKLESECSAPG
Sbjct: 806  INRKEHKLKKGCGYHLDLLMVAVMLGVCSIMGLPWFVAATVLSITHVNSLKLESECSAPG 865

Query: 910  EQPKFLGIREQRVTGLMIFILMGSSVFMTSILKFIPMPVLYGVFLYMGASSLKGIQFFDR 969
            EQPKFLGIREQRVTGLMIF+LMG SVFMT++LKFIPMPVLYGVFLYMG SSL+GIQFFDR
Sbjct: 866  EQPKFLGIREQRVTGLMIFVLMGCSVFMTAVLKFIPMPVLYGVFLYMGVSSLQGIQFFDR 925

Query: 970  IKLFWMPAKHQPDFIYLRHVPLRKVHLFTIIQMSCLGLLWIIKVSRAAIVFPMMVLALVF 1029
            +KLF MPAKHQPDFIYLRHVPLRKVHLFT++Q++CL LLW+IK S AAIVFPMMVLALVF
Sbjct: 926  LKLFGMPAKHQPDFIYLRHVPLRKVHLFTLVQLTCLVLLWVIKASPAAIVFPMMVLALVF 985

Query: 1030 VRKLMDLLFTKRELSWLDDLMPESKKKKLEDAEKEEEQSMLAMEDEGTVQLPLEGH---- 1085
            VRK+MDL F+KRELSWLDDLMPESKKKKL+DA+K+EE+     M D G  + PLE
Sbjct: 986  VRKVMDLCFSKRELSWLDDLMPESKKKKLDDAKKKEEEEAEKMLDIGGDKFPLESRKLLS 1045

Query: 1086 -------YRDDPSVINISDEMSKTALWRNLLITADNSKDK 1118
                   +R DPS INISDEM KT +W+ L I + N+K+K
Sbjct: 1046 SPGKSSSFRCDPSEINISDEMPKTTVWKALSINSGNTKEK 1085 (SEQ ID NO:4)
```

Hmmer search results (Pfam):

| Model | Description | Score | E-value | N |
|---|---|---|---|---|
| PF00955 | HCO3- transporter family | 1273.1 | 0 | 1 |

Parsed for domains:

| Model | Domain | seq-f | seq-t | | hmm-f | hmm-t | | score | E-value |
|---|---|---|---|---|---|---|---|---|---|
| PF00955 | 1/1 | 145 | 988 | .. | 1 | 875 | [] | 1273.1 | 0 |

FIGURE 2G

```
1    GCCTTGGGAG CTGTGAGAAA TAAATATTTG TTGTTGTGGC ATTTTGTTAT
51   AGCAGCCCAA ATGGACTAAG ATACACTCTT TTGGCTCTCT CTTCATTCAG
101  TCCAAGGGTG TTCTGCTAGG TTTTGGCTAC TCTTCATTTC TTTTATCAAA
151  TATTTGTTAA GGCTTATTAG GGCCTAAAGT CTAGAGGCAT TCTGCTTTAC
201  TATTATGACC ATATCTTAAT AACACTGGTA TGAGTAACAT ACTGTATGAG
251  TAAATAATTT GTTTTAGAGC AATGGTTTTC TAAAAATGGG AGATCATAGT
301  TTTTAGTAAT TAATTGTGTT AAATTACTAT TAAGAGGGTC AAGTAATAGA
351  TGTTAAGTAA TTTTTTGGAT TAAATAGATC TTATCAACTA GATAATAGAG
401  AGATTAAGAG CTGCTTTGCA CTCAGGTTTC ATGTTTTTAT TGCAAAGATC
451  AATTGTGCTT ACAAGAAAAC ACTGAAGGAA ATTGGGGATT ATATATACTA
501  ATTAATAACA TCCAGAGAAT GATAAAAATA TCAGTGTTTG TATTCTTGCT
551  GTGACAAAAT ACCTGAAGGA AAAGTTCAAT TTTCTTATTT TTCATTATTG
601  ATTCATTTAA TAACTTTGAT ATGTAATAGT ATAGGAGATT AGGAATGAAC
651  CTTGCTTGAT GTTTCGCTTT TCCTCATTTC TCACATTCAA TCCCTGAATT
701  CTATCTTTTT TCAATAAGAT GTGTATCTGG ATCTATTCAT TTCTCTTCAT
751  TCCTATTGCC ACTTCTTTGG TTCAGGCCAT CATCATCCCC TGATTGAAAT
801  TATTTAACAT TCTCCTGATT TGTCTCCCGT CCTCCAGTTT TGTTTTACTC
851  AATTGATTGT CTATAGAGTA GCCGGGATAT TTTAAACCTG ATTATGCTGA
901  CAGTTTGTCA TTTCCCTAAG GGTAAAGCTC ACACTCTTTA AATGGCTCCT
951  GACGCTTACC GTGACTGGGC CTCACTTCTC ATCTCTTCCC TCTGTTCTTA
1001 CACTTTATGG TCTAACCTAT GTTGTATTTG CCATTCCTTG AATGTGACTA
1051 GATCAGAATC TTCTGTTTTA ACAGTACTTC CCTAAGGAAA TCTTTTCTGA
1101 TCCCTAGATT AGGGTAGGAT GCCTTGCTAC GGCTTTCATG TCAACTTTTA
1151 ATTCTTCAGT TATAACAAAA CATGCTTGTT TGATTTATCT GCTTTCTGTG
1201 ATGGCAGGTT TTGTGTTGTT TGTTATGGAG TCCCTAGCAC CTATATAGTA
1251 CCTGACACAT AGTAAGAATT CAATATTTTC TACAGGAAAG AATGAATATA
1301 GAAAGAGAGA CGATGTAGCT TAGGAAGGCT TTATTGAGAA GATAGGTCTT
1351 AAAGGATGAG TACCTATTTT GATTATAATA AGAGGGTAAA TACTACATAG
1401 ATGGAAATAT TTGTTTACAT GTGATTTTTC ATTCAGATGT GTTATAGTAT
1451 ACATACAGCA GAATACCAAG CTCTGTGTCT CCAACCTGTG CAGTTAGAGT
1501 CAGTAGTTTT TCTAAAAGTA TAATTTGGAT CAGCCCAGTT TCTTAAGACT
1551 CATTGTGACT AGTCTCCATC AAATGTTGTG AGTGAAAGAA GGGAAACTAT
1601 TCACAGGTAA ATAAAGTGTT CATAGAGTCG TGAATTCAGG CTATTCATAA
1651 TGTGAGGGCT GTTTCAGGAT AATATGTTGC ACTTGGTGTC TTAATTTTGA
1701 ATGTAGTTGA ATTGACTATA ATCTTAGTCT TTTTTTTTTT TGGTTTGTGT
1751 TTTCTTTAGT TATAAAACAC AACCTTTTGT CACACGGTAA AGAGAAAGCA
1801 TTTCCAATTA TAATTTTTGA GATATTGATT CTATATTAGA ACACTTTATC
1851 AATCTTAAAG TTCCCTGATT CTGCTATGTT GTGGTAAAAG AAAACAGTAC
1901 TCAAACTTTA ATAAATAAGA CACAGTGAAA ATCCATAGTA AAAATGCCAA
1951 CAACTTACAT AGGTTTCATT ACTAGACTTA ACCGTGCAGT TTTAGCATTT
2001 GATAATACCA CATTATCTTT TGCATGTAAA TTCTTTAGAA GAAGATATTA
2051 AATAAAAAGA TAAAATGTAT GTTGGTATGA AGAATCTGAA ACATAAATGA
2101 AATCCCTGAA AATTAAAAGG TGAATATGTA TTTACCTATT TACTATTTAC
2151 ACAACTATCA AAGATTGCCA AAATAAAAAT CCTGTATAGG CGCTCATCAT
2201 TTTGATGGGT GGATAAGTCG TGATACCCAT AGTTTGGAAG GAAGATTCCT
2251 TCAAGAGAGT ACAATTTTGC TTGGTAAATC TTTTGCATGT TAAACTTTTT
```

FIGURE 3A

2301 AGAAGAAGAA ATTAAATAAA AATATAAAAT GTATGTTGGT ATGAAGAATC
2351 TGAAACATAA ATGAAATTCC TGAAAATTAA AGGGTGAATA TGTATTTACC
2401 TATTTACTAT TTATACAACT ATCAAAGATT GCCAAAATAA AAATCCTTTT
2451 TAGGCACTCA TCATTTTGAT GGGTGGATAA GTGATGATAT TCAGAGTTTG
2501 GAGGGAAAAT TCCTTTAAGA GAGTATAATT TTGCTTGGTA AGTCATAAAG
2551 CCTAAAGCTT AGTCACATAT AGAGAAAGCT GCCTAATAAT TAAGAGTTGA
2601 CATTTTAACA TGGTATTTGC AACAGACACA TTGGATACTT AATTAAATGG
2651 AAAACTGCTT ATTTTTAAAG GACTGAAAAA ATTCAACTCT CCTTGGCAAA
2701 TGAAGTCTTC ATAGTATCAG AAATGGGGAA ATCTGAAGGA TGTGGCTCAT
2751 TCTCTGTTTC GATGATGCAG AATTGCTCTA AGCAGTAAGC TTACAGTTTT
2801 CAGACAGCAT CAGCAAATAC AACTGTGTCA GTCTCTCTTA GTATGGGGTG
2851 TTTGTAACTG CACAGGGGAG ATGATAAATA GTATATGTGA TTTGATATCT
2901 TGATGATGGC TTAAACAGAT ACTGATGGAC AGATCTGTTG TTTGATATTT
2951 TTTTCACTAG CCCTGAAGAT GCTGAGACAT AGAGATGGCT GTGATTATCT
3001 TTTGTAAGAC AGGAAATGCA GTCTTTAGGG GTTTCTGGAA ATAGAAAGGT
3051 CATGCAGTCT GGAACCTGTG AGCCTTTTCA ATCTCTAAGT CATCAGGTAT
3101 GACCTCATGA ATTATGATGA TAATATTAGA ATGTAGGGTG CTTGCTTTTT
3151 CTAGTTCTTA CTCATTGAAA ATATATTCAT TAATGTAATT GTTTATTGTC
3201 AGACTTTCCT TAGGATATTT GAACAAGTAA GATTTATGGC AGCTAAACAA
3251 TATGATTATT AGAAATGTGT GTGTATGTGT GTGCCTGTGT GTGTGTATGT
3301 GTTTAAATTT GTGTTTACTT TAGCTTTTTG GGGGAGAGGG CGGTAAAGGA
3351 AGAGATTCTT TGAATGTGAT TAAAAGCAAG GTTTGGGGCA CTTCAGATTT
3401 TTCCAGATTA AGCCTGAATA GAGTCAATCT TTATATTTTA CTTCAAGTGA
3451 TAAAAATAGT ATAAATCGAT CAAACTGATA AGGATACATC GTAGCTAGCT
3501 GCTTACAGAT ACTGATATAT TGCAAATATT TTTATTATTT GGAATTTCTT
3551 AACCATAGAA ACTGATGCTG CTACCATTGT AGTGTGCTAC ATAGCAAAGG
3601 AAGTTTGGTG AATAGAATCA TCTTTGTCAG CATCTGACCT ATAAACTAAT
3651 TTCCTGAAAT TTATGTTGCA TTATCTGAAC TGTTGTAAAG ACACTGGTTT
3701 TAATCATTTC TCAGATCTAT TGAAATATTG ATGCTCTTGG TGCTTTTAAG
3751 GTAGATATAT ACTAACGTAT TGTTCATAGA AGAAAGGAGA CTATAAATCT
3801 GTTTTTCACA AAGAAAGCTT GTGACATTTA AGCTTGTTGA AGATTTTTTG
3851 ACCCAGAGAG CTTCGTCCTT TGCTTACTTT CATTTTCAAA CTGAAAATAC
3901 TTGACTATGT TAAACATGCA AATGATTTGG ATTTCGATGT CCATTTTGTA
3951 CTGAAACTCT GCCATTTATT TTAAACTATT TTCACCCATC AAGTTATATA
4001 TAATGCATTT AACTTTGATT TGTTACAGCA TGTCCTCAGA ATTATATACT
4051 TGGATAAGAA ACTACCTATA TTTGACATTC AGATTTTGAA GGAAATATAT
4101 TTCATTTTTC AAAATATTGT ACATGCTTCT GCCTCAATGT TAGAGAACTT
4151 TTCAGGTACT CCATATTAAA TGATCAAAAA GAGAGAAATA TATTGCAGCA
4201 GTTCTCAACA GCAAGATGGT TTTGTCTTTA TGATTCTGTA GCCTGATTGT
4251 AATTTAATGC CTTATCAGGG TGAAATGACA TAGATTAAAA AAATGAATAT
4301 ATTTAAGGAA GTCTGAAACA ATGAATTGAT TCAGTTAAGG GGTTTCTCCT
4351 TTTTAATTAA AAACACATTC TGCCTACTGA TATTGACTAT AATTTATATG
4401 TTATTCAGGC TACTTAGCCA GCTTATATTC TTATTAGTAG GGAAGATTGG
4451 CATATTCTTA AGCTTGATTA ATTTTGAAAT GATTTGAATA TACCTTTTAA
4501 TTGCAACAAA ATATGTCTAA TCTGTTAGAA TTTATTTCCA GTATTTGCAT
4551 GTATTAGTCA TTATGAGTAC ATTCTGTTTC TTGGCATTGC TTTGGGATTC

FIGURE 3B

4601 CTCTTGGTAT TGGTTTCACA GCATTCTGCT ATTTTTCACT GTATTCCTGA
4651 CCTTTCAAGA GAACCAAACT GTAAAGATTT TTAGTTACTT TCTGTTAGTG
4701 GCATTTAAAT GAGGATATCG ATAATTTTGT AAGGTGGAAA AAAATTACTA
4751 TTTTAGAATT GTCATTTCTG TCACAAATCA GAGAAATTTT TCTCTATTAC
4801 TATTTCAAAA TATACTACAA TAAAAAGCAA AGACTGGTTA GAATGTAGTT
4851 AAATGCAATG TCAATCTTTC TTCTTGCATG GCAGGATAAT CTTGATCTTT
4901 GGAATGATAA AACTGATTGT AAACTTGCCC AGTAATGATT GGTCATCTTC
4951 CTTACAAAGG CTGCCTTCGT TTATACTATT TTACATGCAT TTCATTATAC
5001 ATCATAAAGG TTTTAAAGGT AAGCTGCCTA TAAAAACTAT TTGAGTAATT
5051 CTTCAATTCA GTAAACATAG TAAAGGCTGA GCATTGGATG ATACTGTATG
5101 TATTTGGTGT TATGAGGAAT GCAGAAAAGA AAAAGTCATT TCCGGCTTTC
5151 AAGGAGATTA GTGAATATAT GCAATGAATT GTGTTCACAT TTTGAATTGA
5201 TTTTTGATAG GCAGTATGCT ACAATCAGTT TTAACTTAAT CTATAAGCTG
5251 ATGAATCCTA GAAGGAGTTA CATGTAACCT TTTTTCCTCA TGTAAATTTC
5301 TTGATATTAG ATAAATGAAG GCTTAGGTCA AACTGTATCA TTATGCATCC
5351 CATAACTTTA TTGAAAATTG CATTAAAGAC TTTTAGAGTG CATAGTTTCT
5401 CGTATAGGGC TTTATAAACT GTGAATCAGT AAAATAGCAA AATAGCTTTG
5451 CATGTTGTAT AAGCCATCAT TGTCAGTATG AGACTGAAGG TGCACCCAGT
5501 CCACTGGCAG GAGGCAGAAG TGTCAGCTCA ACATAGAGAC TTGATCAATC
5551 CTGTCTAATT CCAGGCTCAG TGTGGGTAAT TAAGTATTAT GGAAGGGGTT
5601 TTGACTTTAT AGGGATAAAA CTTGGAAATA AAGAGTAGCA AGTATGGAAG
5651 TGTCTGTTAC TAACTAGGTC ATTTGGAGAG TCCTTTGAAT AAAATGGGGG
5701 AATAGGATTT ACCTCAGGTT CTGAGAAAGC GGATCAGGAC CAACTAATTA
5751 TGGAAGTGGA CCTTAGCTGC TGCTTGGTGA ACAGTCAGGC ATTACTCTCT
5801 TCTCTTTCAT TCCAATATGT TTGCTGAAAG TTGCAGGAAG GTGGGTGGAG
5851 AAGATGCAAA GCCCTTGTTT CCCCAGAATC CCAAACTGGA ACACGCTGCC
5901 TGATAGTGCC TCCAAAGTGC CTGTTTCCTT GTATTAGAGC AATAGAAAAT
5951 TGATTTGCAA ATTCTTCTGG TTTGTAATGG CTGGCTGCAG TAAGAGGCTT
6001 GTGCAATGGT TCAGTGTCTG GACTGCCATG TTCTCTGGGT TCAAATCTTA
6051 GCTATGCTAC TTACTGGCTG CATGATCTTG GCTTGTTTCC TGATGTGTAA
6101 TATAGGGATA ATAATGGCAC CTACCTCAAA GAGTTGTGGT AAACATTAAG
6151 TGAGTTAATG TATGTGAAAC ACTTATAAGA GTACCTGACA TATATCAAAC
6201 ATATTATTGT CAACATCCTT TGTCGACAGA CTTTGTTATA GACATTCTAA
6251 GAGGTTGGAT GGGCTATTGG CAAGACTTTG TAACAGTCAT CATGCAGTTT
6301 AGTTTTGTTC CCTCTCCCTT AATCTCTTTA TCAAATAAGA AATTCAGCCA
6351 AAAATATATG CTACACTGAA ATATAGTTAT AAAAATGCAA ACAAAGAACA
6401 ACATGCTATA TCTGATTCAA TTCTAACATT TACTGACAAT AAGAATTGTG
6451 ACTTGATGAA AGATTTTGTG TTTAAACTTT ACATCTACCT GCTAGGCTGA
6501 TCCAAACTCT CTTAGAATTC TATGTGTGCA GATTCTTTGC TTCTCTGTAT
6551 TACACCAACT ACTTTATTCA TGACTGAAAG ATTACTAGGA CTTTGGGAAA
6601 ATTTAACAGC AACTTAAGGT CTTTCTTGTT TATTGTTTAA GACTAAAATT
6651 AAGGGGTAAA AAAAAGCCTT TCTTTAAAGG CTTAAAAAAA ATAATAGGGG
6701 CAAATTTACC TAGCATAGAT TTAGTGATAC TTAGTCATCA AAAATGTCCA
6751 AGACAAAAAA TTTTACCGAA AGTCAAACAC AACTTGTTTT TAATAATTTT
6801 ATTTCTTGGC ATTTTTATTC TAGATGAAAC ACTAAATGAA ATATATTATA
6851 AATAGAATGC TACATATATA AGTAGAACAA TTCAAGTTCC CATTTGATAG

FIGURE 3C

6901 AGTATAATAT TTTGAATTGC TGGTGATTAT TTAATGTAAA AACATTTATC
6951 TGCTTAAAAT TCTCAATAAA CTTCAAAGAG AAGTGAGTAA TATGATATTT
7001 GGATTAAATT TACATGCTTA AATATGGCAT TTTATTACAT CTCTGAATTT
7051 CACTTCTCTT CTCTGAAGAA ATTTCCTCAG TGTGCTGCTG TTTCCCCCAA
7101 ATTGGCAGAG TCAGTTGAAT CTCAGAATAA TGCAATTTTT AAAAACAAAT
7151 ATACAAAATC CTACAATGTT CTAGAAAGAA TTGTACTGGG CAAGGATATA
7201 AAAGTCTGTA GGTCTCTGCC TTCAGGAGGT CACAGGTAAT GGGTTGTAAC
7251 TACAAAATAC AAGTAACTAT GGCAGAATAT GAAAGTAGTG AATGCCATGA
7301 GGTAGTCTTG AAGACTGGCC AACATAGAGA GAAAAGGTCA TTTCAGGCAG
7351 AGGAAACAAC ATCATTAAAG GTAGGGAGGC AGAAAGCAAA TAATAGAATA
7401 GTTCATTTTG GCTATAGCCT AGTGGGATAA CTTAGACTTA CCACAGGAAA
7451 GGTTTGTTGG GACCAGATAA GTGTAGAATC TTGAATGCTA GACTATGATT
7501 TCTAAACTGA GAACATTTCT TTGCTGATGT ACGTATTCCT GGAAAAAATA
7551 AAATAAAAAA AACAAAAGAG CAGTACCTAT ATTTTGAAGT CATTTTCAGA
7601 GCTCTAACCC TCTTGAGACT TTGAGAATGA AAATTAAATT CCTGAGTAGA
7651 TTTAGTAGTT AGTAGACAAG GTAGGGGGTA GAAACAAACT GAAGGATTTT
7701 AATAAAATTT TCTATCAAAA TTGCACATGA GAGCATTTCT CAGTCTATCC
7751 ACAAGCACTC AAAAGTCCTA GATTTCAGAT CCTAAGAGAC CTCCTGCTTG
7801 TCCGTGATGT AAACTCCATT TTATTGGTAC GTAATCTGAT TTAGCTTTGG
7851 CTTTGTTTTT GACATTTCCT AAAGCAAGGA CAATCTAGTG GGATCATTTT
7901 AATACAATGA ATACTCATGT TACTATGGTG AATAGTTGGA TAAAAAGGAC
7951 TTTGTCTTAG GGAAAATTGG AAATTAAAAT TGCCATTTTG AATCACGGAA
8001 GTCGCTGAAT ATTTTACCTT TGTTCTCTGT TCATTTAAAA ATCATAAAGT
8051 AAACCATGTT TGCAAATACT TTTAATATCG CCTTCTTCTA CTCCATACAC
8101 CAGAGGCATT TTAGTATTGC ATGAGGTTAG TAAAAAAGCT GGATACCTTC
8151 CAAGAGCAGA TTTCCTTTAG ATGTGACAGC TGGGATGTGA CTTTTGGTAT
8201 CAGATGCAGG AAGACGTCAT TTGTACATGG TAATTGTGAA AAAATTGGAA
8251 CTTATTACTC TCAGTATAAA TGATCCATAA AAAGTATGTC AGAAGTAAAA
8301 CTCCTGGAAT TCTACAGGGA GAGTTAAAAT AAAACCAGAC ACAGGTGCTC
8351 ATCTGACTCT ATTTTTAGAA CAATAGGAGA CTCATATAAC TGAGAATGCT
8401 CTGTACTTCC TGTATAAATC TACATTATTT GAAAGTCGTA TTTTCTAGAA
8451 GTTCCTGTGA AGTTGTACTT ATTAATCTTT GCAACTTCAC ATTGCCTAGG
8501 AAAGAGCCAT TCACCTGGTA GGAACCCAAC AAATTTTCAG TGCTTGTCTT
8551 AGAATCATAG TCCCATTTCT GAAAGAAACC TTGAATATCA TTGGGCTTCA
8601 AGTTGTTCTA AAAATGTTTA AGCATTTAAA CATGGTTTTC TTTCTCAAAA
8651 AGCAAATAGA AGGCATTTAG AGGAAAAGGA CCCTTTCTTC ACCTTAAGAC
8701 TTTTAAAAAT GGCAATATGG GAAGATTAAT AAGAAGAATA AGTTAAGGGA
8751 GAATTCAATA TTCCTCCATG AAACTACTCT TTCTAAAAGG CAACAGAGAC
8801 TGGTTCCAGT GAAGCATATT ATGATGTGTG GCGTGTAAAT GTATATCATT
8851 ATCCCTACTC ATCTTTTTCC CCAAATTCAA TTTAATACTC ATAAGAATTT
8901 ATTGAGGCTA CTGTATAACA TGGAGGAAAG CTGTATACCA CAGTAGCAAG
8951 GAGCTAGGGC TCCAGAGCGG GACTCCTGTG TTATGATCCC ATATCTTCCA
9001 CTTTACTGGC AATTTTTATC TTAGGAAGTT ACTTAATCTC TCTTTTCTTC
9051 AGTGTTTTCA TCTGTGAAAT GAGGACACTA ATACGTTAAT CTCTAGAGTT
9101 GTAATGAAAA TCAAATAAAA TAATAAATTA ATACTTCAAA CAGTGCCTAG
9151 AGTGTTTGAT ACAGTGCCTA GCTTTTGGTT ATTATAATTA TCCCCACTGA

FIGURE 3D

9201 ACTAGGTAAA TGCTACAAAT ATGTATGTGT ATATTTGTGT GTATACACAC
9251 AAATATGCAT ATATGTACAC ACACATACTG TACATCCTAT GTAAACACAA
9301 TTTTAGTATG TATGTATGTC TATACATACG TATACATTCT ACCTTAAGTA
9351 TATATAGTAT ACTGAAAAAG AAATTTAGTA GTTTGCCCAA GATCAAAATT
9401 GCCTGCAAAG GATAGGACAA TTTGAGTTTC AAACCCAGAA AGTCTAGCTC
9451 TACAGCTGTT GGCCTTAACT ACTGTTTCAT ACTGTTTAGA GTATAAACAC
9501 CTGAATTAGA TAGCCATGTA TAAATTAGCA TATTCTAAAT GCCAAATTGA
9551 GACTAAAGAC ATGAAGGTAA ACTGAAACTA CTGTGAAAGA CTTAATGGAA
9601 GAATTGTGAC TTTTATTTGA TTTTAAGTTC TGGGATACAT GTGCAGGATA
9651 CGCAGGTCTG TTACATAGGT AAATGTGTGC CAAGGTGGTT TGCTGCACCT
9701 ATCAACCCAT CACCTAGGTA TTAAGCCCAG CATGCATTAG CTATTTTTCC
9751 TTATGCTCTC CCTCTTCTCA CACACCCCTC AGCAGACCCC AGTGTGTGTT
9801 TTTCCCCTGC CTGTGTCCAT GTGTTCTCAT CTTTCAGCTC CCAGTGAGAA
9851 CATGTGGTAT TTGGTTTTCT GTTCCTGCGT TAGTTTGCAG ATGATAATGG
9901 CTTCCAGCTC CATCCATATC CCTGTAAAAG ACATGATCTA ATTCCTTTCT
9951 ATGGCCACAT AGTATTCCAG GGTGTCTATG TACCACATTT TCTTTATCCA
10001 GCCTATCATT GATGGGCATT TGGGTTGATT CCATGCCTTT GATATTGTTA
10051 ATAGTGCTGC AATGAATATA CGCACGCATG TATCTTTATA ATAGAATGAT
10101 TTATATTCCT TTGAGTGTAT ACCCAGTAAT AGGGTCAAAT GGTATTTCTG
10151 GTGCAGGTCT TTGAGGAATT GCCACACTGT TTTCTACAAT GTGTGAACTA
10201 ATTTACATTC CCACCAAAAA TGTAAAAGTG TTTCTGTTTC TCCACAGCCC
10251 TCGCTAGCAT CTGTTGTTTC TTGACTTCTT TATAATCACC ATTCTGACTG
10301 GCATGAGATG GTATCTTATT GTGGTTTTAA TTTGAATTTC TCTAATAATC
10351 AGCAATATTA AGCTTTCTCT AAATATGTTT TTTGGCTGCT TATATATCTT
10401 CTTTTGAGAA GTGTCTGTTC ATGTCCTTTG CCCACTTTTT GATGGGTTTT
10451 TTTTTTTTCT TGTAAATTTG TTTATGTTCC TTGTAGAGTC TGGATACTAG
10501 GCCTGTGCCA GATGGATGGA TTGCAAAAAT CTCCCATTCT GTAGGTTGTC
10551 TGTTTTCTCT GATGATAGTT TCTTTTGCTG TGCAGAAGTT CTTTAGTTTA
10601 ATTAGATCCC ATTTGTAAAT TTTTGCTTTT GTTGCAATTG CTTTTGATAT
10651 TTTTGTCATG AAATCTTTGC CCGTGCCTAT GTCCTGAATG GTATTGCCTA
10701 GATTTTCTTC TAGGGTTTTT ATAATTTTGG GTTTTACATT TAAGTCTTTA
10751 CTCCATCTTG AGTTAATTTT TGTAAAAGAT GTAAGGAAAA GGTCCATTTT
10801 CAATTTTCTG CACTATTTAT TAAATAGGGA ATCCTTTCTC CATTGCTTGT
10851 TTTTGTCAGG TTTGTTGAAG ATCAGACAAT TGTAAATGTA TGGTCTTATT
10901 TCTGAGTTCT CTATTCTGTT CCATTGGTCT ATGTGTCTGT TTTTGTACCA
10951 ATACCATGCT GCTTTGGTTA CTGTAGCCTT GTAGTACAGT TTGAAGTTGG
11001 GTAGGGTGAT GTTGCCAGCT TTATTCTTTT TTCTTTAGGA TTGTCTTGAC
11051 TATACCAGCT CTTTTCTGGT TCCATATGAA TTTTAAAATT TTTTTTCTAA
11101 TTCTGTGAAG AATGTCATTG GTAGTTTAAT CATTGAATCT ATAAATTACT
11151 TTGGGCAGTA TGGCCATTTT CATGATGTTG ATTCTTCTTA TCCATGAGTG
11201 TGGATTGTTT TTCGATTTGT TTGAGTCATC TCTGATTTCC TTGAGCAGTG
11251 GTTTGTAGTT CTCCTTGAAG AGGTCCTTCA CATTCCTTGT TAGCTGTATT
11301 CTAGGTATTT TATTCTCTTT GTAGCAATTG TGAATGGGAG TTCATTCATG
11351 ATTTGGCTTT ATGCTTGTCT GTTGTTGGTG TATAGGAATA CCTGTGATTT
11401 TTGCATGTTG ATTTTTTATC CTGAGATTTT GCTGAAGTTG CTTATCTGCT
11451 TAAGAAGCTT TTGGGCTGAG ATGATGGGGT TTTCTAGGTA TGGGATCATG

FIGURE 3E

11501 TCATGGGCAA AGACAATTTG ATTTCTTCTC TTTCTATTTG AATACGCTTT
11551 ATTTATTTCT CTTTGCCTGA TTGCCCTGGC CCAGAACTTC CAATACTATT
11601 TGAATAGGAG TGGTGAGAGA GCATCCTTGT CTTGTGCCAG TTTTCAAGGG
11651 GAATGCTTCC AGCTTTTGCC CATGCAGTAT GATATTGGCT GTGAGTTTGT
11701 CATAAATGGC TTTTATTATT TTGAGGTATG TTCCTTCAAA CCTAGTTTAT
11751 TTAGAGTTTT TAAGACGAAG GGATGTTGAA CTTTATCAAA GTCCTTCTTC
11801 TGCATCTAAT GAGATAATCA CGTGGCTTTT TTCTTTAGTT CTGTTCATGT
11851 GGTGAATTAT GTATATTGAT TTGCATACGC TGAACCACCC TTGCATCCCA
11901 GGGATGAAGT AGACTTGATT GCGATGGATA AGCTTTTTGA TGTGCTGCTG
11951 GATTCATTTT GCCAGCATTT TCTTGAAGAT TTTTGCATTG ATATTCATCA
12001 GGGATATTGG CCTGAAGTTT TCTTTATTTG TTATATCTCT CCCAGGTTTT
12051 GGTGTGAGGA TGACGCTGGC CTCATAAAAT GGTTTACAGA GGAGTCCCTC
12101 CTTTCCAATT GTTTGGAATA GTTTCAGAAG AAATGGTACC AACTCCTCTT
12151 TGTACCTCTG GTAGAATTCA GCTGTAAATT CATCTGGTCC TGGGCTGTTT
12201 TGTTTGGGAG GCTATTTTTA CTGCCTCAAT TTCAGAACTT GTTATTGGTT
12251 ATTGGTTATT GATTATTCTT CAGGGAATCA ACTTCTTTGT GGGTCAGTGT
12301 GAGGAGGGTG TATGTGTCCA GGAATTTATC CATTTCTCCT AGATTTTCTA
12351 GTTTGTTTGC ATAGAGGTGT TTATAGTATT CTCTGATGGT TGTTTGTATT
12401 TCTGTGATAT CCCCTTTATC ATTTTTACTG TGTCTATTTG ATTTTTCTCT
12451 TTTTTCTTCT TTATTAGTCT AGCTAGTGGT CTAGCTATTT TATTAATTTT
12501 TTAAAAAAAT CACCTCCTGG ATTCGTTGAT TTTTTGAAGG GTTTTTTTGT
12551 GTGTCTCTCT CCTTCAGTTC TGCTCTGATC TTGCTTATTT CTTGTCTTCT
12601 GCTAGCTTTG GGGTTTGTTT GCTCTTGGTT CTCTGTAAAT AGTTCTTTCA
12651 GTTGTGATGT TAGGATGTGG GTTTGAGATA TTGCTAGCAT TTTGATGGCA
12701 GCATTTAGTG CTATAAATTT CCCTCTTAAC ACTGCTTTAG CTGTGTCCCA
12751 GAGATTCTGG TATGCTCTCT TTGTTCTCAT TAGTTTCAAA GAACTTCCTG
12801 ATTTTTGCCT TAATTATTTT ATTCACCCAG AAGTCATTCA GGAGTGGGTT
12851 GTTCAATTTC CATGTAGTTG TGTAGTTTTG AGTGAGTTTC TTAATTTTGA
12901 ATTCTAATTT GATTGTGCCA TGGTCTGAGA GACTGTTGTG ATTTCAGTTC
12951 TTTTGCATTT GCTGAAGAGT GTTTTACTTC CACTTATGTG ATCAGTTTTA
13001 GAGTAGGCAC CATGTAGTGC TGAGAAGAAT GTATATTCTG TTGTTTTTGG
13051 GTGGAAAGAT CTGTAGATAA CTATCAAGTT CACTTGATGC AGAGCTGACT
13101 TCAAGTCCTT TGTTGATTTT CTGTCGTGAT GATGAGTCTA ATATTGACAG
13151 CAGGGTGTTA TTATCTCCCA CTGTTTTTTT TATTATTATA CTTTAAGTTT
13201 TAGGGTACAT GTGCACAATG TGCAGGATAG TTACATATGT ATACATGTGC
13251 CATGCTGGTG TGCTGCACCC ATTAACTCCT GCTTGAGCAA TAGTGGTATC
13301 TCCTAAGGTA AACTTTCCCC CTCCCCTAAC CCACAACAGG GCCCAAAGTG
13351 GGTTGGTCCC CCTTCTTNNN NNNNNNNNNN NNNNNNNNNN NNNNNNNNNN
13401 NNNNNNNNNN NNNNNNNNNN NNNNNNNNNN NNNNNNNNNN NNNNNNNNNN
13451 NNNNNNNNAA TATATGTGGC TCCATCTTGG TTCACACTGC TACTCAGTGT
13501 ACTACAAATC ACAGTGAGTT TGAATGCCAT TCATATTACT GCAAACGACA
13551 TTTTATTTAT TTTTATTGCC AGTGCATATC CATCATGCCA GAACAAGAAA
13601 ATAAGAGAAA AATGAACTTT GATTGTCATG CTTTTATAGC ACAGTGGAGT
13651 GTGAATTATT TTATTTAATT AGATGACAAA ATATGTATTT ATTATGTAAA
13701 GACTCTATAG CTATGCTAAA AGAATAGAAT ATATCTCCAC ATAACCAGAT
13751 TAATCACTCA TCACAATATT CCTGACTCAC AAGAAGACAA CAGTCATAAA

FIGURE 3F

13801 TATTAGAAGG CTTAAAATGG AATCTCTCAT TATAGCAGAG TTTTCCTACA
13851 AAACAAAAAG GACAGTGAGA CTTCAACCAA TGTACATTTC TGAATGGCTC
13901 ACTTGTTAGC CAAGTATGCC CTTATAAGAC TGTGGCACTC TAAACAGGGC
13951 TTTCACAATG TCCACCCACA CAATACCTGC CTTAATGAAA AGCTCAGTAC
14001 CAGTTTCAGG CAATTTAAAA ATCTTAGCCT TTATTATATT GAAATTAAGT
14051 CGAATTATTT TTCTATTATG ATCCCTTTTG AAATAAGCTT TTACACATTT
14101 CTAATGCTTT CTTCAGAGCG GCTCATATAA ATCAATGATT TTTTAAAAAA
14151 TTCTTTCATT TCGATTTAAT CTATTAATAC TTTAGATCTC ACTCTCAGGG
14201 AAAAATTACT TTATTGCATG TAAAGTAATT CAAATAGAAT ATAGTTTACA
14251 ATTTTCTTCC AAATTAAGCT TGAGCCTGGA TAAAAATATT TTTAAGTGCC
14301 CAACAATATT TAGATATTAT TTGCCATGTT TCTATTTTCA TAGGAAGAGA
14351 TAATATGTTT AATAAAAAAT ACATATCTAA AAGGATAATC TGATGTTGTA
14401 AAATTATAAA TTCTAATTTT CTGTCAAAAC AACCCTGAAT GTGAACTTAT
14451 CAGAATCTTG TCTGTGTGAC TGCAACCCCT CCCCCAACCT TAAAAAACAT
14501 ACCACCAGCC CCACTCTCCA CCAGTGTGGC CAAACCAAGG GAAGTGAGAA
14551 GCAGGAACAT AGCTACACAG GTCAGAGCTA AATATTAAGA GTAAAAATAG
14601 TATCTTGAGC TTTCAGAACC ACAAATTTTC AAAGTGAGCC AGAGGACAGA
14651 GCAGCAGCTG CATTTTCAAA CAGAAGCAAC TACATTTTTC TAATCAACTG
14701 CTGTGTTATG GAACATGAAC TGCAGGAAAT GATGGACTAA TGTCCTTTTA
14751 TGTATCAGAT AAGCAGGAGG AAGTATCAGT GGTGTGCTTT ACTTGGTGAG
14801 TGAATCTTGA TAAACATATT CAATAAATAT CTTCCACTTA TGTCCTTTAA
14851 TTCAGTACAA TGCTTTTTAA AAAATATTCA ACTTGTGTGT ACATCGACCA
14901 GAAAATGTTC TATATAAAAA CTGTATTTTG CTTGGGTTTC GAGATGAATG
14951 TTTCATAAGA TATCTATATA TGTATTAAAA TTATTTAAAT ATGAGGAAAA
15001 AGAACTTGTT TGCTGTTGGC GATGAAATCA TGTTTAATTA TAGTACTGAA
15051 AAAAATGTGC CAAGAGTAAA CAAACTTGTT TAGTGCTGCT AGTGTTTAGG
15101 TGAGAACCAT TGCTTGAAGA GTTGGGGACA CTGGGAGCAA CATAGATGGT
15151 CAATGAAAAA ATGACAGAAG ACTGATGTCA CCAAAGTGTG GAGTAGGAAA
15201 CCTTCGTCCC CACCACAAAC ACACCAATTC AGGAACAATT CACAGAAAAA
15251 TTCCCTTTGT GGGAAATCCA GCAACTAATT GAAGGGCTCC TGCACCCTGG
15301 GTGAATGCAA AATCAGATCC ATCGAAGCTG GTGAGGATAT TCACGACAGC
15351 TGTCTGCCAA AATTTCTACC CCCAACGCAA CACCATACAA TTGGGAAAAG
15401 AGTCTCAGCT CTCAGCTTCT CCCAGAGGAG GTTTGTACAT CCAATACCCC
15451 AACTTCGATG GGGGCTACCC AAAGGACTGG CTTCTGTCTT CTCTGTCTTA
15501 AAGTGCTAAT GGTGTGGAAT TATCTAGCCA CCTGGGGGAG AATAGAGATG
15551 GTGGCTTAGA TTGGTAGCCA CCATAGCTTT TCCTCCCTAG CTCAGAGCAT
15601 AGAGCAAGCA AACAAAATCC CCACCTTTCA GCTTCTCCCT GGGGATGGAA
15651 AGAGTTGGTA CATACATTAA ACTTTCTGGG GGTTTTCCAA AGGATTGGCT
15701 GAAATCCCAA AGAATTCAGT CTCACTCATC CTGGTGCACT CACAAGACCT
15751 GGCAAACCCT AGACACCTGG GGCTACAAGA AATACACAAG CAAATAAGTT
15801 GAACAAGCAT GAGGTTTAAG AAGCTTTAGA ATCTCTTCCT GGACTTATTG
15851 GTGGGGATCT TCCATATAAG GCCAGCTCTT TGTGAAGACT CAGAGAGAAG
15901 TCTGCTTTAT CTGATGCAAA GACACCAATG CATAGAGTCA AGTAAGATGA
15951 AAAAACAGGA AAATGTGTTC CAAACTAGGT AACAGAAAAA TCTCCAGAAA
16001 TTGACTCTAA TGAAACAAAG ATACACAATT TACCTGGAAA AGAATTTAGA
16051 ATAACTGTCA TAAAGATGCT CACTGAGGAT AAGAGAACGT TGCATGAACA

FIGURE 3G

16101 AAGTGAGAAT TTCAGCAAAG AGATAGAAAA TATCTTAAAA GTACCAAACA
16151 GGAATCATGA AGTTGAAGAA TAAAATAATT AAATTGAAAA ATTCACTAGA
16201 GGGATTCAAC AACATACTAG TATCAAGCTA AAGAAAGAAT CAGTGAACTT
16251 AAGGACAGGC CATTGGAACT TGCTGAGTCA GAGAAACAAA AAGGACAAAA
16301 TAATGAAAAA GAATAAAAAA AGCTTAAAGG ACTTACGAGA CACCATCAAG
16351 TGGATCAATA TATGCATTAT GAGAATTCCA GAAGGAGAAG AGAGAAGGAA
16401 AGAACCAGAA GATTTATTCA AAGAAATAAT AGCTAAAAAC TCCCAAGTAT
16451 GGAAAAGGAA ATGTGTAATC CAAGGACCCC CAAAAAGGAA AACTTAGAGA
16501 TATCAACACT AAGACACCTT ATAATCAAAT TGTCAAAAGT CAATCACAAA
16551 GAGAAAAAGC AACAAGGGAA AAGTTACTTG TTCGGGTACA AGGGAAATTT
16601 CATAAGAGTA TAAGTAGATT TTTCTTCAGC AACTTTTTTG CAGATGAGAA
16651 GGAAATGAGA TGATAGATTC ACAATGCTGG GGGAAAAAGC CAACCAGGAA
16701 ACCTAGACCA AATGAAACTG TCCTTCAACC AGGAAAACTA GACCAAATGA
16751 AACTGTCATT CAATCATGAA AGAGAGATAA AGTCTTTTCC AGACAAACAA
16801 AAACTAAGGA AGTTCATCAC CACCAGACCT CCCTACAAAA AATGCTAAGG
16851 GAACCTCCTT AACTTGAAAT GAAAGGACAC TAAACAGCAA CAAGATAGCA
16901 TAAGAAAGTA TAAAAGTATT GGTAAAGGTA AATATATAGA CAAATGCAGG
16951 ACCGTAATAC TGCAATAGTG GTAGGTAGAC CACTTGTAAT TCAAGTAAAA
17001 AAGTTAAAAG ACAAAGTAGC AAAATACTTT CAATAACTAA AATACTTTTA
17051 ATAAGTAAAA CTATGTTAAT AGATACACAA TATAAAGAAA TGTTAACTGT
17101 GACAACAATA ACAAAATGTG TATGGGAAGG AGAGTAAAAA GAGGCATATT
17151 TTTGTATGTC ATTGAACTTA AGTTGTTATC AGGAAAAAAT AGACTGTCAT
17201 TACTATAAGG TATTATATAA ACCCCATGGT ATCTAATGAG AAAATACCTA
17251 TAGAAAGGTA TCAAAGATTC CCAACAAAAA AAAATCAACA AAACATGAAA
17301 AATGAGAGCA AGAGAGGAAA AAATGCACAA AATAATTACA AGGCTAACAG
17351 AAAACAGTAC ATGACAATAA TAAATCCTTC TCTATCAATA ATTACTTTAA
17401 AACTAAATAA ATTATACTTC CCAATCAAAG ACATAGGGTG GTTGAATGGA
17451 TTAAATGTAT AATGGAATCA CATGCTGTTA TCAAGAGACT CCCTTTAGAA
17501 TTTAGGCTCA ATGTGAAAGA ATGGAAAAAA AAATTCCACG AAAATGTTAA
17551 TGAAAAACGA GCAAGAGTGA CTATACTTAT ATCAGATAAA ATAGACTATA
17601 AGTCAAAACT CTCTCAAAAG ACTGAGAAAG ACATCTTATA ATGATAAAAG
17651 GATCAATTCA CCAGGAATAT ATAACAATTG TAAGTAGTTA TGCACCCAAC
17701 GATTAAGCAC CTAAACATAT AAAGCAAACA TTGACAAAAC TGAAGAGAGA
17751 AACAGGCAGC AACACAATAA TAGTAGGATA TTTCAATACC TCATTTTGAA
17801 TGATGGGTAA AACATATTAT CCATTACCCA CGGGCAAAAC AGAGCAAAAG
17851 GAAATAAAGG ACTTCAACAA CCTTATAGAA AAAAATGGAC CCAATAGACA
17901 TGAACATTTC ACTCAATAGC AGCATAATAC ACATTCTTCT CAAGTGCAGC
17951 CAGAATATTC TCCAGAATAG ATCACATATT AAGCTGAAAA GTATGTTTTA
18001 AAAATTTAAA GTGATCAAAA TTGTACCAAC TATTATTTCT GACTACAATG
18051 GAATGTGAAA GTAGAAATCA ATAGCCATGG GAAAACTGAA AATATTATAA
18101 ATATGTGGAC ATTAAACAAA ACACTCTTGA ACAACTAATG GGTCAGAAAG
18151 AATTCAAAAG AGACATTAGA AAATATCTTG AGAGACATGA AGATGAAAAC
18201 ATAATATACC AAAACTTATG GTATACAGCC AAAGCACTAT TAAAAGATAA
18251 GTTTATAATG ATAAAAGTCT ATATGAAAAA AGAAGACAGA TCTCAAATTT
18301 GCAACCTAAT TATACATTTG AAGGGACTAG AAAAAAAAAA CACACTAGAC
18351 CCAAAGTTAG CTGATAGGAA GAACTAGCAA AGATCAGAGC AGAAATAAAC

FIGURE 3H

18401 AAAATAGATA ATAGAAAACA ATAGGAAAAA ATCAATGAAA TTGGGTTTTT
18451 TTTTAAAAGA TAAAATTGAC AAACCTTTGG CTAGACTTAG AAAAAAGAGA
18501 GGATTCAAAT AAATATAAAT CATATATTAA AGAGGAGGTA TTACCACTGA
18551 TATCACATAA GTTAAAAAGT TCATAAGTAT CTATGATAAA CAATTATATG
18601 CTAAGAAACT CTATGACCTT AAAAATGGAT AAATTCCTAG GAACATAAAA
18651 TCTACCAAAC ACGAAACAAG AAGATATAGA AAATCTGGAC AGACAAATAA
18701 CAAGCAAGAA AATTAAATCA GTAATAAAAG ACCTCCAAAC AAAGAAAATC
18751 CCAGGAACAG ATGGCTTCAC TGGTGAATTT TACCAAACAT TTGAAGAAGA
18801 TTTATGTCAA ACTTTTTTTT ATCTTGAAGA AGAGGAAATA CCTCCAAACT
18851 CATTGTATGA TGCCAGCATT ACCCTGATAC CAAAGCCAGA CAAAGACACT
18901 GCAAGATAAG AAAATTACAT AATAATATCT CTGATGAACA TAGATGCAAA
18951 AATTCTTAAC AACAAAAACT ACCTAGCAAG CTGAATTCAA CAGTACATTA
19001 AAAAGTCATA TGATATTTAT TATAGGAAGC AATGGATACC CTGGGCTGGG
19051 GTTCATTATA TACAAATCAA TAAATGTGAT GTGCCACATT CACAGAGTAA
19101 AGAACAAAAA ATATATTATT ATTTAACATC GTTTCATGAT AAAAACTCTC
19151 AACAAATTAG CTGTAGAAGG GATGTAGCTC AACACAATAA AGGCCATATA
19201 TGACAATCCT ACAGTTTACA TCATACTCAA TGATGAAAAG TTGAAAGCTT
19251 TTCCTCTAAG TTCAGGAACA AGGCAAGGAT GTCTACTCTT GCTACTTCCA
19301 TTCAACATAG TACTAGAAGT CCTAGGAAGA GCGATTAGGC AAGAAAATTT
19351 TTTCATGTGC AGATGAGAAA AAATGTATAT TCTGTGGTCG TTGAATGGAA
19401 TGTTCAGTAG ATGTTTATTA GGTCCATTTG GTCAAGAGTG CAGTTTAAGT
19451 TCAGAGTTTC TTTGTTAGTT TTCTGCTTTA ATGATCTGTC TAGTGCCATC
19501 ATTGGGATGT TGAAGTCCTC CACTGTTATT GTATATCTGT CTGTCTCTTT
19551 TCTGAGGTCT AATGGCATTT GCTTTATAAA TCTGGGTGGT CAGGTATTGG
19601 GTATAAATAT ATTTAGGATA GTTAAATCTT CTTGTAGAAT TGAACTCTTT
19651 GTCATTATAT AATGTTATTC TTTGTCTTTT TTTTAACTAT TATTGGTATA
19701 AATTCTGTTT TTTTCTGATG TAAGAATAGC AACCTATGCT CTTTTTTGTT
19751 TTCCATTGTG TGATATACCT TTCTCCACTC CTTTACTTTG AGCCTGTGGG
19801 TGTCCTTTCA CATTAGATGG ATCTCTTGTA GTCAGCAGAT GTTGAGTCTT
19851 GTTTCTTAAA TGCAATTTGA CAATCTATAT CTTCATTTAG GTCATTTCTG
19901 TTCAAAGTTA ATATTGACAT GTGAAGTTTT GTTCCAATCA TAGTACTGTT
19951 AGCTAATTGC TTTGTAGTCT CAGTGGTGTG ATTGCTTTAT AGGATCTTTG
20001 GATTTTGTAC TTATATGAGC TTTTATGACA GGAGAGTATT GTCCTATATT
20051 CTTTTATGAC ATAAAAGAGT ATACTCTTTT CTGTTCGAAG TTTATGCTTT
20101 ATGACATAAA AGAGTATACT CATTTCTGTT CAAAGTTAAT ATTGACGTGA
20151 AATTTTGTTC CAATCATAGT ATTGTTAGCT AGTTGCTTTG CAGTCTCAGT
20201 AGTGTAATTG CTTTTTAGGA TCTTTGAGTT TTGTACTTAT ATGAGCTTTT
20251 ATGACAGGAG AGTATTGTCC TATATTCTTT TATGACATAA AAGAGTATAC
20301 TCTTTTCTGT TCAAAGTTTA TGCTTTATGA CATAAAAGAG TATACTCATT
20351 TCTGTTCAAA GTTAATATTG ACATGTGAAG TTTTGTCCCA ATCATAGTAT
20401 TGTTAGCTAG TTGCTTTGCA GTCTCAGTGG TGTAATTGCT TTATAGGATC
20451 TTTGAATTTT GTACTTATAT GAGCTTTTAT GACAGGAGAG TATTGTCCTA
20501 TGTTCTTTTA TGACATAAAA GAGTATACTT TTTTATGACA AAGAGTATTG
20551 TCCTTTTTCC CCACGTTTAC AACACCTTTG AGCATTTCTT ATAGCACCAG
20601 TCTCATGGTG ATGAATTTTC TTAATATTTG CTTGTTTGAG AAAGACTTTA
20651 TTTCTCCTTT GCTTATGAAG CTTAGTTAGG CAGGATATAC AATTTGGGGC

FIGURE 3I

20701 TATAATTTTT TGTCCTCAAG AAGGCTAAAA ATAGGCCCCC TATCTTTTTG
20751 GCTTATATGG TTTCTGTTGA GAAAGCCACT GCTAGTCTGA TGGAATTTCC
20801 TTTACAGGTG ACTTGACTGT TCTCTCTAAC TCTCTTTAAG ATTTTTTCTT
20851 TAGCATTGAC CTTGGTTAGT CTGATGACTA TATGCCTTGA TGATGTTCAT
20901 CTTATATAGT ATCTTGCAAG TGTTTTCTGA ATTTCTTTTA TCTGGATGTC
20951 TACCTCCCAA CAAGATCAGG GAAATTTTTC TGAATGATTC CTTTAAATAT
21001 GTTTCCAAAT TGCTTACTTT TCCTTCTTTC TCAGCAATAC CTATAAGCTA
21051 TAGGTTTGGT CAATTTACCC CCTATACCAT CTTTCTCAAA TATTTTGTTT
21101 ATTTTTAAAA TGCTTTTCTA TTTATTTTTG TCTGACTGGA TTAATTTGAA
21151 AGACCAATGT TTAAGCTCTG AAATTCTTTC TTCTACTTGG TCTAGTCTTT
21201 TGTTAATGTT TTCAATTGTA CATTGAAATT ACTTTTGTGA ATTTTTTTAT
21251 TTTCAGAAGT TCTATTTTTA TAAATATAGC TATCTTGTCT TTCATTTTCT
21301 GAGTTGTTCT TCTGGTTTCT TTGTATTGGT TTTCAACATT CTCTTGGATA
21351 TCATTGCACT TCTTTAGAAT CCGTATCTTG AATTCCTTAT CAGTCATTTT
21401 TTATTTTGTT TAGGATCCAT TGCTAGAAAT CTAGCCTGAT CCTTTCAAGG
21451 TGTTAAAACA CTCTGTCTTT TTGTACCACT GGAGTTCTTG CACTGATTCC
21501 TTCCCATGCG AAGGAGTTGT TGCTTCTAAG TTTTGAATTT GCTATTGTTT
21551 GAATGGGACT TTATCATGTT TATTCTTTTT TCCCTTGAGG GTATGACTGT
21601 GGTGTATGTT GTATGTGATT GTTTGGCTTC TTTTCTGGGG TTTCTCGGTG
21651 CCAAGACTCT GCATGGGCTC CTTGGTTATG GATAGCCTTT GTGTGGTGGC
21701 TTTCTCAAAT GCTGCTTGTT GTAGACATGT ATTGGGCATA TGAGCCAACA
21751 CACTATTTTC TGTGTGACTA GGAGAGCAGA GGTCTCAGTA AACTTATCTT
21801 GTACACTAGT ACTATACCCT TCTGACAGTA GGTTTTTTAT TTGGTGGTGC
21851 AATTCAGTCT TCAGTCAAGT AGGAGGTGCT TAAGAGTAAG AATCCACTCA
21901 CCCTCAGGCA GTCTAATGAT GAAGGAAGAC AACTGTCCTA ATTGAGGTTA
21951 GTGTGGGGAG CTTGTGTTGG AGTGAACTGG TCTTGGTGGT AGGGGCAGGG
22001 GGCCTGCATT AGCCCCTCAT CCTGGGCAGG CAGGAATGTG ATCCGTTTTC
22051 CTATCACACC TTTCTGTCAC AGGGCTCATG ATCTTCAGCA TATAGACATT
22101 GTTCTTTGGC TCCCAAGCTG AAGTGTGACT GAGGTCTGGA GAAATGCCCC
22151 TTTGGTGGCT ACCACCAAAA TGAGCTCAGG GCAGAGCCTC TTCCCAGAGC
22201 CCAGAGCAAA CAGTTTTTCA ACTTGTCTGC CCTTCGTTGC TGGGACACTG
22251 CCATTCTGTG TTGGGATGGG GAGACAGGTC CCACCTTTCA TGCATGCCTA
22301 GGTGGCATTG GCTCACTTTC AATGAGGTGT AGCTGCCACG AAGAGTGCTG
22351 GAAAGGCTGT CTCCAAGTGC AATCAGGTCA GCCCTCATCA GGAAAAAGCC
22401 TCTGCTGCAT CCACAACAGT GCCTGCACTG AGGGCTAGAT TTCCATGGAA
22451 CCTGCAGCTC CCCAGAGACC CGCCAGTCTC CTGTGGTTGC CAAAGTCAGA
22501 AGGGGTTCTG AGGTATGTTT GCAGGGGATC TTGTAGTGTG GCAACACAAG
22551 GACTAAGGTT CCTTGGACAG GGCACTGGCC CACAATGAGT GCACAACCAG
22601 TGTGGCACCT GCCATCTCAG TTAGGGCCTG AGGGGAGTGT GGGCACACCA
22651 GCACGAGCTG GCCACCTGAG GCTCCCACCC CAGAGAGTTC CCAAATTGCC
22701 ACCAACTGCA TTGCCTGGGA TTTCAAGGGC AGAGGGGTTC TCTGACAATT
22751 TGTCAGTCAG CAGTTAGTCA CAGGAGTGAG GGGAGCAGAG AAGCACCCCA
22801 ACCTATCCTT TACATGGGAC TCTGAGTTCC TCAGGAGTCA GTGTCTGCCA
22851 GACTTTTGCT GCTTTCCTTG TCTGCACCCC AGTTTCTTCC CATGGGCTCT
22901 CTGAAAGCTC GTGGCTCTCT TCCCTCAGCT TTCCATTTGG ATCATGACCA
22951 TTCAACTGTA ACTTTGATCT TTCTACAAAC TGGTGTCTGA CATCTCTAGT

FIGURE 3J

23001 CAGCCATCTT GAAAAAAAAA AGCTACATTA AAGTTATAAA AATAAAAGTA
23051 ATTGCACTGT GATGTTACAA AGGCTACTAT ATCACTAGGT GACAAGAATT
23101 TTTCAGCCCT ATTATAGTTT TATGGTACCA CTATTTTATA TGCGATCCAT
23151 CATTTGACTG AAACATCATT ATGTATGACT GTACATAACA AATTGCGAAT
23201 AGAATTAGAA AGTGCTTTCT ACTTCTGGAA ATCAATGTTG TCTTCACAGA
23251 GACAGAGGTG GGCTTTGAAG GATAAATAGG AGTTCAGGAG GCAAAGAAGG
23301 AAGGATCTGT TATATTCTGG GAATGGCAAA TATGATGTGG ATAAAGCATT
23351 GGGATTGTGT CTGGGGGCAT AAAATGTGAC TGGATATAAA GTTTAAATCT
23401 TTACATAAGG TAGGTCAAAT TGTGGAGAAT GAATTAATCC TTGAAGTCAC
23451 TCTATCTGAT AAGCACATTA TTATCTCCAT TTCACAGATA AAGAAACTAA
23501 GGTACAGAAG ATTAAATGAC TTAAATAGGT CACCTGACTA GTAAGTCGTA
23551 TGGCAGTGAT TCAAACCCAC AAGGAAGACT TGTACATATT TATTGACTTT
23601 TTCATGATGA TTTTTAAAAA GTTGAGAATA TTCTATTATA AAGCAATAAA
23651 GAATTTGATA TTTAGTAACC ATATCACAAT AGTTTTACAA ATGTTTTAGC
23701 AAAAGTTTGA AAGTTTTATA GTTAGAAAAT TCCCATTGAA CTAAGATTTA
23751 TTCCCATAAT TAGGAAAGCC ACTCTCCCAT TGGAGACTAC TTTTATTATA
23801 GCCTCATGTT CTCTTACTTT AAATTATCTT CTCTGCTGTA CCACAAAATA
23851 AAAAGTCTTA TAATTTCCTT ATTTCAAATG TTTTTTCTTT GAAAAAGAAC
23901 CATTTATTTC TGGTATTATT AGTTGATTAA TTTTTGTGCA ACTTAGTAGT
23951 GTTGATATAG GATCAATGTC AACTGGTGGA GCAATTCTAA GGGTGTTTGC
24001 TCCATTAGTA ATAACCAGTG GAGTTAATTA ATTACACAGG CATTTGAAAT
24051 TGTAGGTTTT GCCTGTTAAA CACTGGATAT TTCAGGATGA GAAATGTGGA
24101 GGTGGACTAA TACTGAACAT TTTATTTCAG AAAATACAGC CAATAGTAAA
24151 TTTCAGTCTT TTATTGAGCT ATCTTTGACA CCTGTGCACA TCTTATAATA
24201 AACTGTTCTG TTTTTCAATG GGTATCCTAG GAACAAGAAC TAAATAAGAG
24251 ACAATTATTT TAAAGTCTTC AATAATAGAA TTTACTTTTG TGTGGGCAAA
24301 AGACACGAAC AGACACTTCT CAAAAGAAGA CATACATGCG GCTGACATAG
24351 GAAAAAAAAG CTCAACATCA CTAATCATTA GAGAAATGCA AATCAAAACC
24401 TCAATAAGAT ATCATCTCAC ATCAGTCAGA ATGGCTATTA TTAAAACGTC
24451 AAGAAACAAC AGATGCTGGT GAGGTTGTGG AGAAAAAGGA TTCCTTTACA
24501 CTATTGGTGG AAACGTAAAT TAGTTCAACC ATTGTGGAAG ACAGTGTGGC
24551 AATTCCTTAA AGACCTAGAG GCAGAAATAC CATTTGACCC AACAATGCCA
24601 TTAATGTGTA TATACCCAAA GGAATATAAA TCATTCTATT ATAAAGATAC
24651 ATGCACGCAC GTGTTCATTG TAGTGCTATT CACAATAGCA AAGACATGGA
24701 ACCAACTAAA ATGCCCATCA GTGATAGACT GGATAAAGAA AATGTTGCAC
24751 ATGTATACCC TGAAATGCTA TGCAGCCATA AAAAGGAACA AGATCATGTC
24801 CTTTGCAGGG ACCTGGATGG AACTGGAAGC CATTACCCTC AGCAAACTAA
24851 AGCAGTAACA GAAAACTAAA TACCACATAT TCTCACTTAT AAGTGGGAGT
24901 AGAATGATGA GAACACATGG ACACATGAGA GGAAACAACA CACACTGAGG
24951 CCTGTTGGAG GGTAGGAGGT GGGAGGAGGG AGCACATCAG GAAGAATAGC
25001 TGATGGACTC TGGGCTTAAT ACCTAGATGA TGGGTTGATC TGTGCAGCAA
25051 ACCACCGTGG TACACATTTA CCTATGCAAC AAAACTGCAC ATATTGCCCT
25101 TGTACATCTG AACTTCAAAA TAAAAGTTGG AGATTAAAAA ACGAAATTAC
25151 TTTTGTTCCA GAATTAACTC TCAGATGTTC CATGTTTCAT CACTTTATTT
25201 TTTCACATAA TTTGTGTATG TGACTCACAT CAATTCATTT TGATATATAA
25251 TTGATTTCTG ATATTTTGTT TGTTTGAAGT GAGAGGTAAC TGGGTAATTA

FIGURE 3K

25301 TCTATACTCT GCTTTTACCA TGCATTTTAT TTCCAGGTAA ATTTGAAAAA
25351 TCTAAATTAT TTTTCTAAAT TTGATCATGG TTTATTTGAC AGTTTACAAG
25401 TACTTGCAGG CATGTGTTTG CATGTGGATA ATAACAAATA ACTAAGAAAT
25451 CTTACAAAAG TATAGCTTCA TAATTTGGGG GTCCTGGTTA TACATTTTAC
25501 ATCTCTAAGT TAGGAACTCA TATTGTTAAT CTCCCTTCAT AGTTCCTTAT
25551 AACTAAACTC TGTTTAGTAT GAGTTTCTAC TTATCAAAGG CATAATAACT
25601 CACTCACTAT TTGGTATATT TGCTCTTTAA TGTGACATGA CATGTTTTCT
25651 GTGGATAAGG AGAACTGTGT ATTTGTGCGT ATATGTATAT ATAATGTTTT
25701 CAACCAATCA CTATTTCAGA GAAAAAATGG ATGAAAATAA ACTTGTATTC
25751 ATTACATTAA ATATAATCCT ATACATATTA AGAGGAAATT TTACAGCAGG
25801 AAATTGTTCC TTTAATCATT ATTTTTCTTG AAAATTATTT AATACTTTTA
25851 AGACAAACCA CGGATGACCA AAGTCTCTTA ATATTTACCA CATAGATTTA
25901 TATTAACACT ATATTTTTGT TTTAAGTTTT CTAGACATCT GAGACTTAAA
25951 TATGTTCTTA TTTAAAGACT TTAATAGTAT GGCAGTTGTA CCATGAAGGT
26001 GGCATAGTGA AGGAGATCAA CTTAGTCTAC TTTTTGACTA AATTCTTAAA
26051 TCTCTATTTC AGCTGTCTTC CCCCTAGAAC TATAGCTTAA AAGCTCCTCA
26101 GCTGCATACA GCACATAGCC TTCACAGGTT ATCGCCTTTC TATAGAGTCC
26151 TCTCACAATA TAAACAGGTG TAGCTACCAA TTAGGACATG TCTCAAGAAA
26201 TTGTTAACAC TCACCAATAT TAATTAAGTG CTAATAGGGT ACTGAGCCAA
26251 ACACTGAGGG TGCTGAGCCA AATTTCCATT TCACATTCTT CATTCTCCAA
26301 GGAGGTTTAG ATACTGGTGC TGTCAATAGG GTGCTTGAGT TCTAGAACCC
26351 ATGGGGAAAA ATAAATTACT GTGGCCACTT TGCACATAAA TGTTTAAATT
26401 TAAAATATCA ATTGATATAA ATACTGATAA TAATGAATAA ATATTAAATA
26451 ATAATTGAAA GGGATGATGT TCTTGGTTTG GGGGATAATA CCCATAATCT
26501 TAGCAGTACC AGAATCATTG CAACCCTAAT AGGATTAATT CCATTTTGGA
26551 ATATCAGTAT TCTGAGATTA CTATTTTGAA TGTTCTCGTT TATATTTTCT
26601 TCAAGTAAAC TTTTTTGCTT CTTCATTCTT TTTCAGAAAT TTTATTATTT
26651 TTAAAATTGA CAGATAAAAT TGTATGTATT TATTATGTAC AACATGATGC
26701 TTTGAAATAT ATATATCTAT GCACTGTAGA ATAACTAAAT ATAGCTAATT
26751 AACATATGCC TTACCTCACA TAGTTATTAT TTTTGTAGTG AAAATACTTA
26801 TCCACTCTCA CTATTTTTCA GGAATACAAT ATGTTATTAA CTATTGTCAC
26851 TATGCTGTAC AATAGATCTC TTGAACTTAT TTCTGCTGTC AAACTAGAAT
26901 TTTATATCCT TTGACTAGCC CCTTCCTCAG CCCCCCAAGT GCCCCAGCCC
26951 CTAGTAGCCA TCATTCTACT CTCTAGTTCT ATGTGTTTGC CTCCTCGTTC
27001 TATCTTTCCT CTTCCTCACT ACCTAGTCAT TCCTAGTGCC CACAGTGTGT
27051 CACAACTGCT GAAAGCATGG TGAAAAAATA TCTGTTTTCT TTTCTTCCCT
27101 TCTCTCTCTC TTCTTAATGC GTTTCAGGTG GGAAGATAAT AAAAGAAACC
27151 AAAATGATTG AAATCATTAT TAGCAGAAAG TAAAATTTTA ATTTCCTGCT
27201 GGTACAATAA GCTTTTGTCT GGGCTCTGGG GACAAAAAGA TTATGAATAT
27251 TCTTTTGTGC CACTTTCAAA CTGCTTCTAA ATATCTTAGG TACATTTGTA
27301 ATATGAAAAT ATGGCAGCCT TATTAGCAAA ATAATTTCTA ATTTTGAGCT
27351 AAATTGTATA AGATTATGCA TGTTTTTCTT TTGCATAACT CAATTTGTTT
27401 CCTGTAATGA TAATTGCCAT GATTGAATTA GAAGATAATA TAGCATAAAA
27451 AAATTTTATG ACATCACAGT GATTAATCCA AAACTATCAG CATCAATGAA
27501 GTTAATAACA ATATTGTTCA TGAAAACAAA GGTCATGTTT ATGAAATTGA
27551 AACATTGTTT ATATGTGAGT GGCCTATTTT TCTCATGCTA CTGCACTAAT

FIGURE 3L

27601 TTTATCTTAG GGTTTATAAA TATGAATCCT AAATATTAAA GTAGTGCTAT
27651 TTATCGCCAA CTCTAGTGGC CTTCTGTCCT CAGCCTTTTT GAATTCACAA
27701 AATTCCTGTA AACTGTGGAC TATTTTCCCC AACTTACAAA TAAAGAAATT
27751 GAGGTTCAAA AAAGTAACTC GCCAATAAAT AGGTTCTAGA TATCTACTAT
27801 ACAGCATAGT GCCTATAGCT AAAAATACTG TATCGTATAC TTAAAATCTT
27851 CCAAGAGGGT GGATCTTATG TTGTATTCTT ACCACGCACA TACAAATAAT
27901 AATAATGATA GTAAAGGCAT TAGGGAGCTT TGGGATGTGA TAGATATATT
27951 TCCATGTGTA AGTGCTGTAA GAGTTCACAA GGGCATAACC CAAGTGCCCC
28001 AGATATGGCC CTTCTGTATT GAATATACCT AAGGTAGACA CACTGAAGAA
28051 GATGGATATA TGAAAAAGTC TAATATACTA GCCTTATTGA GGTAAATTGA
28101 TCAGTTCACA TTGGGTATAG AACATTGTCA GCAACTAGAA AAAGAAAATG
28151 AGGTTGTTCC GTCTCTATGT TCACACGAGG CATGAGGCAG CGACGTTCTA
28201 ATAATCCTCC TGCTCTTCTC CCTTACCCTC CTGCCTCCTC AATAGCCTTA
28251 ATTTGTAGCA TTTTCCAATA TCTGTGGTTA AATTCTTTCC CTATGGCCAA
28301 TTTTATACCA CTGAGGTGTT TTCCCCTGAA CATAAAGTTA GGAAGAGATG
28351 CGTGTAACTG GCACTGGTGA GCTGGGGTAA GCCAGCTCTA GCATACCACT
28401 GCTGCCAGGT TATCTACCGT AGAGTGTAAG CCATAGTTTT CATCAAAAGT
28451 GTCCTGCAAA AAAAAAACAT TGAAAAATGA GAAACAGTTT CTGTATGTCA
28501 ATATAAGTCA ATTTTTATTG CAATGAATAT TGAAGGAGGT AAAATTTTTT
28551 TTTACTTCCT GATGAAAACA GATGAAGTAT GTTAATATAT GTCCCTGGGC
28601 CCTCTGTGTT TCTGTGCCTC CCCTCACAAG GCATGCTATT TTTCTGTACC
28651 TGCCAATACA TATCTTATCT TCCTTACAGG CCTCTCTCCT CTGTTTTTGA
28701 CTATTTCAGC CTACTCCAGC TTGTAGTGCT GTAGAAAAGG CTTTAGATTC
28751 ATTTATTTAT TCAAGAAACA CTTACTGAGC TTTTAATATG CCAGGTACTG
28801 AGAATATAAA CATGATTAGA CAGACCATGC TATAGCTTTG ATTGTATGGC
28851 TTTGGGGCAA TTGCTTTTTT TGTTTTTTAA CTTACTGAGG GATGACTGAC
28901 ATGTAAAAAG CTGTACATAT TTAATGTATA CAACTCAATG AGTTTGGAAT
28951 ATACACCCAT GAAATCATTA CTAGCATCAA AGCCACAGAT ATATCTATCA
29001 CCTCCCAAAG CTTCCTAATG CCTTTATTAT TATTACTATT ATTTTTATTA
29051 TTATTAGTAT GTGTGTGTGT GGTAAGAACA CAACATAAGA TTCAACCTCT
29101 TGGAAGATTT TAAGTATACA ATGCAGTATT GTTAGCTATA GGCACTATGC
29151 TGTGTAGTAG ATCTCTAGAA CCTATTTATC GGAAAGTTAC TTTTTTGAAC
29201 CTCAATTTCA TTATTTGTAA GTTGGGGAAA ATAGTCCATA GATTGCAGCG
29251 ATTTTGTGAA GATTAAATGA GAAAATATAA ATAAAACACT TAGCATAGTA
29301 GATGGTACAT TGTAGATTTT CTATAAAGGC TAGTTTCTTT TTTTTAACTC
29351 TAAACTCTTA TAGCTATCTT AAGTGCCAAA TGAATCGGCA TTTATTTATA
29401 TTCTGCCTTG GATGTTGCTT GCCTTCTCTA GTATCCTCAG CTTGTACCTT
29451 TATGCAGGTT CTTATACATA ATTTGTTGTT CCTATCAACA TTGATCACAA
29501 TGTAGTATCA ATACTTTCTG ATTCTTGGTT CTTAATTTGC CTGCCCATTG
29551 AGATATTGGT CATAAGTTAA CATTTTCCCA TTATTTTCCA TTTTGAATCA
29601 CTTTCCTGGT ACTTTCAATT TTGTATTTTA TATCCTGTCC ATCTGTATTT
29651 TATAATTTTA AATTTTTTCT TCCAAATAAA TTTTAGCATT CAGCTATTGC
29701 TGTGTCACAA TCCATTTCCA AACGCAGTGG CTTCAAACAG CAACATTTTA
29751 TTTAGGTCAT AATTCTGTAG GTTGTGAATT TGGGTTGGAC TCAGCTAGTT
29801 AGTTCTTCTA ATGTGAATCA GCTGGCGCCC GCTTCTACAA TCAGCTGATG
29851 ATTTCACAAC TGAGGCCGGC TGGTTTGTGA AGTCCTCAGC TGGATGACTG

FIGURE 3M

29901 CCAGCTAGGG CTTCTCTCTT CATGGTCTCT GATCTGATCC AGCCAGCTAG
29951 GCTGGGCATG TTTACATGGT GGCATGACTT CCAGAAGCAA CAGCAGGTAA
30001 GAACCTATGC ATAAGAACCC TTCAAACCTC TGTGTCACAT TTGCTAATGC
30051 CCCATTGATC CAGATTCAAG GGTTGGAGGA ATATATTCCA ACTCTTGTTG
30101 GAACAAGCTG CTAAAATATT GTGGCCATTT TAAGAGAATC TACCACATTA
30151 TCTATGTATT TTTCATTTGT AAACATCTAT ACAGAAATGC CAAGTGTTTT
30201 TATCTTTGAT TTCAGATATT TTAATTGTTT CACAGTTGAA TTTCATAAAC
30251 TTTCCTCATG GAAATCTGTT TTTCTCCTCA GCAACTTCTC GGTTTTTCCA
30301 GGCAAGCCTT TCTGTTCTTA ATTACTGTAA TTTTCAGAAT GAGCTACTTT
30351 CTACATGTGC ACATGTCTTT TAAATTAATA TAATACAAAA CTAAATCTGG
30401 AAAATTTTAG TTTTACATTT TTTTGTTCAT CTCCTAACCT ATTTCCCTGA
30451 AGCAAAGTGA CAGGTCTGTT CAGAATTTAT AATTTAATTA AGATGAGATT
30501 GGGGAGGTAA GGAAGTACCA CTTTCTCTTT TGCATTCATT TTTTAAGGAT
30551 CTCAGGACAT ATGTTGATCT ATTTTCTTTC TCTTCCTTGC AAATTAAAAC
30601 AAAATGTTTT AAAATAAATG TTTTAAAATA ATAGTGAAAT TGCGAGCTTT
30651 GCTGATTATA AAAATATATG CTCTATGTCA TCTTGCCTTT TCTTCCCTGC
30701 TCTAATATGA ACTTCACATT ATCCCTTCAA TTGCTCTTCT GTTTTTGCTC
30751 ACGTTATCTC CTTTTTCTAA ATTTTTCACT CCTCTGCTGA TGTAAAACCT
30801 GCTTATTGTT TAAGAGCAAC TCAAGTCCTA CATCCTCCAT GAAATTTTCA
30851 CTGATTGCCC AGGTTATCCT TGATTTTACT CTATTGTGAA CTCCTACAGC
30901 ATTTGATGGC TGGTACCACA CAGTAACATT TGCCTCATTA CAGGTTGGTA
30951 TTGTTTAATG CTTTTAATGT GTATTTTTAA TTTGTATTGT TTGCTGCTGT
31001 TTTCATTGCT GGGCTTGATT CGTTAGCCAG TTTTTTTTTT TACTGATTTG
31051 CACTCCTGGC TCTCTAAGTG CTGTAAATGT CCAGGATTAA GCTGTTTTAT
31101 AATATACCAA AATTGGGAGT TCTCAAGTCA TTTTTTTTAT AAGAAAACAC
31151 ATATTTTTAG GTTTCATTCA CTTATTCAAG ATATATTAAA TGCTTATTAT
31201 GTTTCAAGAT TAAAAATAAA CACTATCTCA AGACACAAAG TTAATTTAGT
31251 TGCTATGTTT TGCTCAAGAC GGTGTTATAA ACTTGTAAGA AACAGTATTT
31301 TTGAAAATGT GCCACAGTAC CTTCTAAACT AGTAAATCTC AGTTAGTGGC
31351 CCTTTTGATG AGCAACTTTA GGACTTTCAA GATTTCTACT TTCTATCTAG
31401 AATAGTCATA GTCATGAAGC CTTTTGTTTT ATAATGATTA TAAATACCCT
31451 TCCCAGGGTC AGGTAACTAT GACCAGCACT AGTTTAACAC TGTCTTTTTC
31501 TTTTAGCAAA ACAACACAAG GAACAATGGC ACAGTAGCCT AGTAATACCT
31551 CTTTGCTATA AACATACACT CACTCCCATC CTCTCAGTCT CTTTGTTTCT
31601 CTGTTACTCT CCCTTAGCAG AAATTTTCCA TTGGACTTCT AGTGCTTTGA
31651 TGTATTATGA TCAATGATGA CTTGTGTTTT CTGACTCTGT TAGAGTCTCC
31701 ATGGAATTAA AGATTATATG CTTATTCAGC TTAATGTACT TGACCTTTTT
31751 GTATGATTGA CACATCTAAA TTTCTGTAGC AACTCAGTCA TTATGCAACA
31801 GCTGTGTTAT ATTCATTTCA TGTAAAAAGC AAAAACAAAA GACATAGAGT
31851 TCTCTTCAAG AGTAGATACC TTGACCCCTT CCCTCCCAGC TAAATAAAGA
31901 ATAGTTTATT AATAACATTA TTAATCAGTT TCCAAATGCG TCTCCTTTCC
31951 TCACCGCATT TTATAAACAT TCAGTATACT GTGACCATAG TCACATCAAG
32001 AATCATTTCA ATACTGATCC TTATTATATA ATTAAAATAT TCAATAATTC
32051 TGAGTCTGTT GAACATAATA ATAGCCACAC AACTTAAGTG TCAAACATCT
32101 AGGATTTGTT AGCAAGATTT GTGCTCAGAA AATAATATGT ACAAACCTTT
32151 GATTTTCTTA ATGATGAAAC TGTATTTTGT CTGAATTGAC ATATGTGTCT

FIGURE 3N

```
32201 TTAAGTTAGA GAGAAAAAAC CTTGACATTT TTCTGTGACT TTTCCTTATC
32251 AACAGCTGTG TTCTACCTGC GTTTATTTTT CTCAGAATTC ATTATGAATT
32301 CTGTATAGGC CTTCAGAAGG CCTATACAGG CTTTCTAACA GAGATTCTAT
32351 AGGAAAAAGT TTTGGTTAAC TGTTTGAAGT ATTAGTTGAA GAAGGCATTC
32401 TAGATAAGGT TTTACAAGAC AGAAGAAAAG AATCAATTCA TTTTTAGTTC
32451 TGAGCCTGAA TTGTGGAAAC TGTACTAACT GCAGATAAAC TCTGAATAAA
32501 TTCTAGTGTT CTCTGCTTAT CTCAAAAAAT CTTTTCTTTT AATGATACTG
32551 TTCCATGCTC ACTAATGTTT TCAAAACATA TTCATATCTA AATGGTTTTG
32601 TATTTTTATT AAATTTTGGA TTTTTTGCAT TACATAAAGT TAATTTTGTT
32651 GACCATTTTA TGAATTTAAG AAATGTCCAC TTGAAAGGAC TCGCTCCTTT
32701 AATTAAATTT TTGGCCTTTA TTTATAAAAT AAAAATTATT CTTTATATGT
32751 TCTTGAAAAG TAAATCAGAT TAGGATTAAT AATTGTCAAG TCATTTTAGA
32801 ACAATGACAT CTATCATTAA ATTTCTTGAA TTTTTTGCCT TCTCAACTGA
32851 TAGCTATCCG GGTGAAAAAT TCAATTATGG ATATTGGAAA AATTGATGGT
32901 AATATTAATC TGGAAATGTT ATTTCTGTAC TATTCTTTAC AGGACCTGAG
32951 GGGATTCTCT AGTTCTTTAG GCCAGTGTTA TAATGTTAGG ATTTACAAAA
33001 GTTGGTAATA TAGAGAGAAA CAGGAAGAAA ATGAAATGGG ACAGGAAAAT
33051 ATCATTCCTT CTTCTTATTC CTTCCTCTAA GTCACTGGCA TTGTGAAGGG
33101 AAAAGGGAAC TAACATGTAT TAGTGTCTAC CATGTAACAG GCATTGTCTT
33151 TCATATTTTA TATTTATCGT ATTAGCTCAT GTAATCTTTG TGGAAAATCT
33201 CCTAAATCTA TTAGTAGGTC TTTAATATCT ATGTTTATTT ATTTTGTCCT
33251 GAAAACAAAT GAAGTTTTTG GATCAAGACA GAGAATTATT ATTACTTATA
33301 GCAATAACCA CCTTGGAAAG AAGGCACACA GTTATGCGCA CAGGAGGGGA
33351 GCCATGAAAT TATGAATCTG GGAATTTATA TAGGAATTAC TATATAAACT
33401 CTTTATATAG TAAATGGTCT TCTCCTGTCT TCTCCTTTTC TGAAAGAGGA
33451 AGAGAAAGTT TATCTCCGTT ATATACAATA AGCAAATCTT TAGGGGAGAG
33501 AATGAGAAGG TCCTGGTTTA AACCCTTTGA AATGTAAACC AGTAGCTCTG
33551 GGATTTTGTT CTCTTTTGAA ATGTAAACAC AGAGCTGTAG AAAATAAGTG
33601 TCTGCATATC TCTGAGGGTC TCTGTCTATT CAGTCCACCT TTAATCCAGA
33651 TTTCAGTTTG TCTTGCTTTA TAACTCCTTA ACCATGCAGA AGCATGAAAA
33701 CATTTTCTCT GTAGTTCCAC ATCATGAATT TTAGCAGTTT TAGTACTGTT
33751 GCTAAAAAAT TGTGGCTATT AGCTTGTTTC CATTCCTTTC ATAAAGTGTT
33801 TAGTAGCATA ATGCATTATT AGGTCTACTT TCTATCTATT ATACTTGAAA
33851 ACCATCCTCT CTATGTAAAA TATCTATTTA TTCAATGGAT ATTTATTGAG
33901 CACCAAAAAC TGTCAAGCAT TGTTCTAGGT ATTTGGGATA CATCAGTCGA
33951 CAAATCAAAG ATACCTGCCT TGCTTGTATT TACAAACTTT GGGGTTAGAA
34001 TGCATAAAAT TGAGATTATG GAGGGGTTGT AATTATTGCC AATGAAAAGC
34051 CTAGGATGAA AGATCACTGG AAGACTAAAG TTTAAGGAAT TGAAAGGCCA
34101 GAATATCAAA AGAATCATCT ATATGTGTTT TGAAATCTTA TGAATTAAGG
34151 CAGTATCGAA GAGAATGACA GTATGCAAAG AGCTCAAATG GTTGAGTGGG
34201 AATTACCTGG ACCTTAGTGG ATAACAGCAA CCATGAGGCA AAGTATGTAG
34251 TGAGTAATGT CGACCATGAG ATTTAAATCT GAAGGATGTC AGGAAGGATA
34301 TGGGGAAATG GTCTGAAAAT GTCAGAATGG AGCAAAGAAA TACCACTTTG
34351 CTTATTCCAC TCACCCAACC AGAGGTCGCA GGAACAAGAA TGACACCTTT
34401 CCATCTTGCA TAAGAACTGT GGGAGAGAAG CAGCCATCAC TGAGAGATTG
34451 TAGGGGAGGC ATTGTCCTCC AGAGAAAGAC AGGTTTATGT TTCAGCTAGG
```

FIGURE 3O

34501 AAAGTAAAGG GAACACTTAG AAAATTGATT TTTGGCTCAC TGGAAGGGTT
34551 TCAGCAGTTG GGAGAGAACA AAGGTAATTT TTACCAGCTT GTAACTTCAC
34601 ATGTATTAAC TGTGTTGCAA AACTAATGAA ACTTACTGTC TATTCTCTTG
34651 CTTTATCTGA TAATATAGAT AAGGGTGTCA CCTGTAATCA TTGTTACCAT
34701 ATTTCTTGAG GCCATTTTCT TATTCTCATT TAACTTTTCT ACTTGTTTCT
34751 TCTTTATTTG TATTTTTCTC TGTTTTTAAT CTTGCTCTTT TTATCATTTC
34801 TGTCTCTTTA TATCCTACTT ACCTCTTAAT CTTTTTGCCC AACTTCTCTC
34851 TTAATATATA TATATTTTTG CTCTTTACTA TTTCTCTTAT CTTTCTATTT
34901 CAAAATTACA CTGTCTGCTG TTTTCTCCAA CTCCCCACAA CTCACCTTAG
34951 GTGTAGTTGG GACTATGCAA TATGCCATCA CACAGGTAGT ACTAATTTTG
35001 ACAGGTAGCA TCTCTACTTC AAACAAAGAA AGCTTTAACC AAAAAGGAAT
35051 TACAGGAGAG AAGACAGTAT TCTCCCCAAC TGATGCTAAC ATTGCCACCT
35101 ACACTTTTGA CGCTTTCTTC AACAGTTAAG ACGTAGCAAC TTATTACTTC
35151 CCCAAATTCC CTGTGCTCTG TTGATCTGTC TTAAACTCTA AAGGGAGAGA
35201 AAGTAGGTTT GTTCATTAGC TGTGGGACTT AAAATGTGAC TTAACTTTTT
35251 TGAACCTTTT GTTTCGTGAA TGATAAAAAA ACACTTTCTG AATGATATAG
35301 CTACTAATAT TTTCATTTTA TAGATAAAGT GAAAGATAAA GTACTTTTTT
35351 TAAAGGTTGC ATAAATATAA GTGACACACA CTGATATGAA TGTAAGCATT
35401 TGACTCAATC CCAGAGATCA TGTTTTAATG AATACTCTAT TGTTTCTCAC
35451 ATAATATAAC TTAATATTGT GGTCAATAAA ATAATAAATA GGACCAGACA
35501 CATATATGTA TTAATTCACT TCCCTTTATT TCCTTTTTCC AAAATTGAGC
35551 CTTATTGGTA AAGGGCTTTT TGTGCATTTT AATTGTCTAT AATCAGGTAC
35601 TTGAACCAAT TATAATTTTT CACTTGCCTG CATGAATCCA TACAGGACAA
35651 AAACCTGAAT ATAGAAACTA TCTTTCAGCT TTCGGTTTGC CAGAGGATTA
35701 ATCTATAATT ATTTTTAGGA TTATAAAAGA TTTACATCCG TTCTTAAAAT
35751 ATACATAATA TCGGATTTTT TTCCAGCAAT AGAGGAATAA CTAATTCTAT
35801 AGTTTCATGC CAATCTCACC TCCAGTCCTT CTAGAATTTG GAGGTAATTT
35851 AACCCCGTGT ATAAAAAATA AATATTTTCT TTTTTGCGTT TTATTGAAAA
35901 AATCACGTAA TTTAAGTACA AATATATCCA CTAAAGTAGG CAAATTTATT
35951 TTAGTAGAAT TCAGTTATCC CTTTCAAAGA AACACTATCA GCCTAAGTGT
36001 TATACATTGG ATATTTTAGA AATCTTACAA TTTCAATTAC ATGTCTTCTG
36051 AAACTCATTA TTGTAAGGCT TTGTTTTAGG CTTTCCTTGC TGTATTAGTT
36101 GACTGGGGCT GCCAGAAAAA AATACCACAG GCTGGGCAGC TTAAACTACA
36151 GAAATGTATT TTCTCACAGT TCTGGAGGCT GGGACACCTA AGATCAAGAT
36201 GGCTAGCCAG GTGGGTCTCA TTCTGAAGAC TTTTCTCTTG GCTTTAGGTG
36251 GTTACCATCT CCTTGCATCA TTGTGTTACC TCTTTGTGTG CTTGGACAGA
36301 GAGCAAGAGA GGTAGCTCTT TGGTGTTTCT TCTTTTAAGA ACACTAATTG
36351 GATGGATCCA GCCCCACTCC TATGGCCTCA TTTAACCTTA ATTACCTCTA
36401 TAAAGGCCCT ATCTCTAAAT ACAGTCACAT TTGGGGTTGG GACTTTAAAA
36451 TATAAACCTC GGGGGACATA AGCCTTCATC CACAGTATTG CCATTATAAT
36501 ATTTTGTGTA CTTTGGCACT TGAGAAAGTA AGATTTTTTT TAACCTAGTA
36551 TTTTAATGTT TTCTTTAGAG GTTTTTTCCC TGATACAACA CTCTCCTATA
36601 CATGATCTAC TTGGTAACAC AAATATCCCT TTGTTTGCTT GTACTTTTGC
36651 TTCCTCATAA ATTTTTCTGT AGCTACAAAT GTTAACTTTG TTGGATAGGC
36701 TTTATTTTTT AGATCAATTT TAAGTTTATA AAAATACTGC ACAGAAAGTT
36751 GAGACAGTTC CCATGTATTT CCTCTCCCTG CTGCACACAA TTTCTTCTCT

FIGURE 3P

36801 TATTAACATT TTACATTAGT GCAGTACATT TGTTACAATT GATAAACCAA
36851 CATTAATAGG TTATTATCAA CCAAAGTCCA TAGTTTACAT TAGGGTTCAC
36901 TCTGTGTTAT ACAGTTCTAT TGGTCTGGAC AAATGTTTAA TGACATGTAT
36951 CTACCATTAC ATTATCAAGG ATGGTTTGAC TTCCCTAAAA ATGCCCTGTG
37001 CTCCACCTGT TCATCCCTAT ACCTTCTCCC TGAAGCCCTG ACAACTGCTG
37051 ATATTTTTAC TGTCTCTATA GTTTTAGCTT TTCCAGAATG TCATACAGTT
37101 GGAATAATAC AGTATGTAGC TTTTAAAACC ATCTTCTTTC ACCTAGCAAT
37151 ATGCATTAAC AGTTCTCTCA TGTCTTTTTT GTGGTTGACA GCTCATTTCC
37201 TTTTCCAGTA GTCCCACTTT ATCTGTAGAG GATACGTTCT AAGACCCCCA
37251 AAAGATGCCT GAAACCTCAG ATAGTACTGA ACCCTATATA TACTGTGTTT
37301 TTCCTTTACA TACATACCTA TGATAAAATT TAATTTATAA ATTAGGCACA
37351 GTAAGAGATT AACAGTAGCT AATAATAAAA TTGAACAATT ATAACAATAT
37401 GCCAGAGTCG AAACTCTTGT GCCTTGGGAC TTTTATTAAG TATAATAGGT
37451 GGCCAATATC AAGTGTAACA TATAGAAATA GGAAAACAGA AAAACCTCTG
37501 TGGAATTTGG CATTAACATA GACCTTAGCG AAACCTGTTT TATTAGAGAC
37551 AGTGATTTTT TAAAAACACT TAACTGTGAA GGGAAGGGAT TTGATGAGAT
37601 AACACAATTG TCTGAAGGTA GAGAGAATAA AAAACAATTT TTTTTCTAAT
37651 GAGAAGAGTA TAATTAAGCA TGGGGAACAG ACACATAGAG ATTATAAAGG
37701 AAGTGATGAT TGCAAAATAT TTAACCAAAT AATTAGTATT ATACATGTTT
37751 GTGATAGAGC TATGGTACAC TTAATTAGGT AAAATGCCAA AAGACAGTGC
37801 CACGCTCCAA GCTTTATGTA TCATAAACAT CAAAAATGAC TTGCTGAATT
37851 AAATTAAATT GAGTCTCCAT TAACATGTAA ATCATCATAT CTGTGCCCTG
37901 GAATAATTCA GAGTTTAATT TGTGGGTTTG CTTCCTTATG AAGGTCATCG
37951 AACACTATTT ATTGGAGTAC ATGTGCCCTT GGGAGGAAGA AAAAGCCATC
38001 GACGTCACAG GCATCGTGGT CATAAACACA GAAAGAGAGA CAGAGAAAGA
38051 GATTCAGGAT TAGAGGATGG AAGGGAGTCA CCTTCTTTTG GTAAGAATCC
38101 TTCTCCTTGT TTTTATTAAG TTAATTATTG TAATATACTT GCTTATACAA
38151 TTATGATTAG GAGTAATACC TTATACTCAT AAAATTGTTT ATACTTTTAT
38201 AAAAGACTTT GGGCCGGTTG GAGAGAAGTG GGAGAGATAA AGCTTGATCT
38251 TTGTTTTTCT CTTATATATT TGCATTGAGA AGCTGAGAAT TGATGAAGAT
38301 TTATGATATA GGAAATACAA TTGAGTAAAG CTCAAAAACT CTTGATAATT
38351 TATACAAATA ATCATCATTA CTCAAAGTGG TTTGAAAATC CAGGGCAAAA
38401 TGCCTTAATT TAGTTCCCAT TTGCACTTTT ACTGATAGTG CCCAAGTTTC
38451 AGTCTTAGGA TGTTGTATTA GTCCGTTTTC ACACTGCTGA TAAAGACATA
38501 CCCGGACTAG ACAATTTACC AAAATAAAAA AGAGGTTTAA TTGGACTTAC
38551 AGTACCACAT GGCTGGGGAA GCCTCACAAT TATGGTGGAA GGCAAGGAGA
38601 AGCAAGTCAT GTCTTACATG GGTGGCAGCA GGCAAAGAGA GCTTGTGCAG
38651 GAAAACTCCC CCTTATAATA ACTATCAGAT CTCATGAGAC TTACTCACTA
38701 TCACGAGAAA AGCACAGGAA AGACCTGTCC TCATTATTCA ATTAACTCCC
38751 ACTGGGTCCC TCCCACAACA CATGGAAAAT TCAAGATGAG ATTTGGGTGA
38801 GGACACAGCC AAACCATATC GTTCCACCCT TGGGCCCTCC CAAATCTCAT
38851 GTCCTCACAT TTCAAAACCA ATCGTGCCTT CCCAACAGTC CTCCAAGGTC
38901 TTAACTTATT TCAGCTTTAA TTCAAAAGTC TATAGTCCAA AATCTCATCT
38951 GAGATAAGGC AAGTCCCTTC CACCTGTGAG CCTGTAAAAT CAAAAGCAAG
39001 CTAGTTACTT CCTAGATACA ACTGGGGTAA AGGCATTAGG TAAATACAGC
39051 CATTCCAAAT GGGAGATATT GGCCAAAACA AAGGGGCTAC AGGCCCAATG

FIGURE 3Q

39101 CAAGTCCAAA ATCCAGCAAG GCAATCAAAT CTTAAAGCTC CGAAATGATC
39151 TCCTTTTACT CCATGTCTCA CATGCAGGTC ATGCTGATGG TTCTCATGGT
39201 CTTGGGCAGC TCTGCCCTCG TGGCTTTGCA GGATATAGCC CACCTCCTGG
39251 CTGCTTTCAT GGGCTGGCGT TGAGTGTCTT GTTGCTTTTC CGGACACACT
39301 ATTCAAGCTG TCAGTGGATC TTCCATTCTG CAGTCAGGAG GACAGTGGCC
39351 CTTTTCTCAC AGCTCCACTA GGTGGTGTCC CAGTAGGGAC TCTGTGGGGG
39401 CTGTAACCCC ACATTTCCCT TCTGCACTGC CCTAGCAGAG GTTCTCCATG
39451 AGGGCCCTGC CCCTGAAGCA AATTTCTGCC TGGGCATCCA GGCATTTCCA
39501 TACATCCTCT GAAATCTAGG CAGAGGTTCC TAAACCCCAA TTCTTGACTT
39551 CCGTACACCT GCAGGCTCAA CACCACATGG AAGCTGCCAA GGCTTGAGGC
39601 TTGCACCCTC TGAAGCCACA GCCTGAGCTC TACATTTGTC CCTTTCAGCT
39651 ATGGCTGGAG CAGCTGAAAC ACAGGGCACC AAGTCCCTAG GCTGTACACA
39701 GGATGGGTAC CCTGTGCCTG ACTGAGAAAA CCACTTTTTC TTCCTGGGCC
39751 TCTGGGTCTG TGATGGGAGG GGCTGCCATA AAGACCTTTG ACATGCCCTG
39801 GAGACATTTT CCCCATTGTC TTGGGGATTA ACATTTGGCT CCTCATTACT
39851 TTTGTGAATT TCTGCATTTG GCTTGAATTT CTCCTCAGAA AATGGAATTT
39901 TCTTTTCTAT TGCACTGTCA GGCTGCAAAT TTTCTGAACT TTTATCCTTT
39951 GCTTCCTTTA TAAAACCGAA TGTCTTTAAC AGCATCCAAG TCACTTCTTG
40001 AATGCTTTGC TGCTTAGAAA TTTCTTCTGC CAGATACCCT AAATCATCTC
40051 TCTCAAGTTC AAAGTTTCAC AGATCTCTAG GGCAGGGGTA AAACACTGCC
40101 AGTCTCTTTG CTAAAACATA ACAAGAGTCA CCTTTGCTCC AGTTCCCAAC
40151 ACGTTCTTCA TCTCCACCTG AGACCACCTG AGATTGCCTG GACCTTATTG
40201 TCCATATCAT TATCAAGCTT TTGGTCAAAG CCATTCAACA CGTCACTAGG
40251 AAGTTCCAAA CTTTCCCACA TTTTCCTATC TTCTTCTGAC CCCTCCAAAC
40301 TGTTCCAACT TCTGCCTGTT ACCCAGTTCC AAAGTCACTT CCACATTTTC
40351 AGGTATCTTT TCAGCAGCAC CCCACTCTAC TGGTATCAAT TTACTATATT
40401 AATATGTTTT CACACTGCTG ATAAAAACAT ACCTGAGACT AGGCAATTTA
40451 CAGAAGAAGG AGGTTTAATT GGACTTACAG TTCCACATGA CTGGGGAAGC
40501 CTCACAATCA TAGCGGAAAG CAAGGAGGAG CAAGTCACAT CTTATGTGAA
40551 TGGCAGCAGG TAAAGAGACC TTGTGCAGGA AAACTCTGCC TTATAATAAC
40601 CATCAGATCT CATGGACTTA CTCACTATCA TGAGAACAGC ACAGGAAAGA
40651 CCTGCCCCCC ATGATTCAAT TACCTCCCAC CAGGTCCCTC CCACAACATG
40701 TGAGAATTCA AGATGAGATT TGGGTGGGGA CACAACCAAA CCATATCAAA
40751 TGTGAACCTT TTACTATTGT GAATGCTCTC TCATTGAAAG CATATTCAGA
40801 ATACCACAAT AAGTGTTTTC GTAGTTGTTA AAAGGTTCTG AATGCCATGA
40851 GAGCCCATGT ACATGACATA ACTGAGAACC TGGCTCTCAG TTCCTTGACC
40901 ATCCCATCTC TTATGACCTT CTCTGTCATT GCACTTTGTT CACCTTCTCA
40951 ACCATATTCA CTCCATCCCT GAAGTCACTA ATTCATTTAT CTTTCTGTCT
41001 GACCACAGCT TCACTCCTTT CTTGCTGTGC AGCTACTTAA CCCCTCTACT
41051 TTTCTTCTAT CCATAAGTTT GTCTTTATTT GTTTATCCTA GTCTGATTGC
41101 ATAGCATGCA GTCTTAGGAA TACTTTAGCA TTACTAGTAT TCCATTTGTA
41151 TTACTAGTAG TCTATTTAGT AATACTAGTA TTCTAAATAT CTTAGGTTCT
41201 AAGTTTTAGT TTTCTTCATA CCTTTACTGC CTCTTTTATT TTCATTTTTA
41251 ATAGGAAGCA GCATTTTATT TAAAATGTTT TTAATAGATT TCTTAAAGAT
41301 GTAAATAATC GAATTAAACT TAGTCTATAT TACTTGTATG AATTAATTTA
41351 CATTTTGTTC ACATTCGTGA AAAATAATTT AGCTAGGTAT GCAATTCCAA

FIGURE 3R

41401 ATTGACAAGT ATTTTAACTC AGCACTTTGA ACATAATATC TATTTATTTA
41451 TCAATTTCAT GAAGATGTTA AGAAAGGAGA TAAAAATCTA TTGTTGCTCT
41501 ACAGTTAATT TGGATTTTAT ATTTTTATGA ATTTAAATCA TTTCCTTTAT
41551 TTTGGTATTT AGTTTTACAT TTATTATGAT ATTTTCAGAC ACACATATAT
41601 GCCTTTTATG CTTTTCTTGG TTGATATTTA ATGAGAATGT ATATTATTAG
41651 TTCTTTAAAA TGCTTAAACA TGTCCTATTT TCTATTATTT TCTCTCCCAC
41701 TTATTTAAAT TCTTTCTTCA AATATTCATT AAGCATATTC CTTTCAATTT
41751 CATTTTCGAT TTATTTTGAT CCCTCTTTTA TATTTTTTCA TCATTTTCTC
41801 CTTGTCCTGA CATTGAAGTG TTTATTTTAG CTAATTCATT TATTCATATT
41851 TTAGCTCATA GTTTTTGCCT TGCTCATATC CCTTTACTTT CTTTAAACAT
41901 TTTGACTACA TGTGTCTTTC ACTTCTTTTA CTTTGGATTC GGGGGCATGT
41951 GTGCAGGTTT GTTACATAAG TATGTTGTGT GATGCTGGGG TTTGGGATAT
42001 GGATGGTCCT ATCACCTAGG TAGTGAGCAC AGAGTATAGT TTTACAACCC
42051 TTGTTCCCCA CCCTCCTTCC CTGCTCTGGT GATTCCCAGT GCCTATTGTT
42101 CCCATCTTAA TGTACATAAG TACCCAATGT TTAGCCCCAC TTATGAGTGA
42151 GAACATGCAG TATTTGGTTT TCTGTTCCTG AGTTAATTTT TTTAGGATAA
42201 TGATCTCCAG CTGCATTCAT GTTGCTGCAA AAGGATATGA TGTCATTCTT
42251 TTTATGGCCA CATAGTATTC CATGATATAT ATGTACCACA TTTTCTTCAT
42301 CCACTTTACC ATAAGGAAAC CTAGTTGATT CCATGTCTTT GCTATGGTGA
42351 ATAACACTGC AGTGAACATA CCAGTGCATG CATCTTTTTG GTGGAATGAT
42401 TCATTTTTCT TTGAGTATAT ACCCAGTAAT GGGATTGCTG GGTTGAATGG
42451 TAGTTCTGTT TTAATTTCTT TGATAAATCT CCAAACTGCT TTCCACAGTG
42501 GCTGAACCAA TTTATATTCC CACCAACAGT GTATAAGCAT TCCGTTTTCT
42551 CTGCAGCCTT GTCAGCATCT ATTATTTTTT GACTTTTTAA TGTTCACCAT
42601 TCTGACTGGT GTGACATGGT ATCTCATTGT GGTTTTGACT TGCATTTCAT
42651 TTGTTGACTG CTTGTATGTT TTCTTTTGAG AAGTGTCTGT TCGTGTCCTT
42701 TGCCCATTTT TAGTAGAATT ATTTGTTTTT TGCTTGTTGA TTTGTTTAAA
42751 TTTTGCTTGT GGATTCGGGG TATCAGACAT TTTTTGAATG CATAGTTTGC
42801 AAATATTTTC TCCCATTCTG TAAGCTATCT GTTTAGACTA TTGAGATTTG
42851 CTGTGCAGAG GCTCTTTAGT TTAATTAGGT CCCACTTGTC AATTTTTGTT
42901 TTTGTTTCAA TTGCTTTTGG AGACTTAGCC ATTAATTCTT TGTCAAAGTT
42951 AATGTTGGGA AGGGTATTTC CTAAGCTTTC TTCTAGAATT ATTATAACTT
43001 AAAGTCTTAC ATTTAACTCT TTAATCCAAC TTGAGTTAAT TTTTGTATAT
43051 GGTGAAAAGT AGGTATCCAG TTTCATTATT TTGCATATGG CTTGACAGTT
43101 ATCCCAGCAC CATTTATTTA ATAGGGAGTC CTTTCTGTAT TAGTTATTCT
43151 TGGTGACTTT GTTGAAGAGC AGACTGTTGT AGGTGTTTGA CTTTATTTCT
43201 GGATTCTCTA TTCTATTCCA TTAGTGTGTG TGTCTGTTTT TTGTACCAGT
43251 ACAATGCTGT TTGGGTTAAT GTAGCCATAG AGTACAGTTT GAAGTCAGGT
43301 AATATGATGC CTCTGACTTT GTTCTTTTTG CTTAGAATTG CTTTGGCTAT
43351 TTGGGCTCTT TTTTGATTCC ATATTAATTT TAGAATAGTT TTTCTAATTC
43401 TGTGAAAAAC AACATTGGTG TTTTGATAGA GATCGGTATT GAATTCTGTA
43451 AATTGCTTTG GGCAGTATGG CCATTTTAAT GATATTGATT CTTCCTATTC
43501 ATGAGTGTGG AACATTTTTA CATTTGTTTG TGTTGTCTCT GATTTCTTTC
43551 AGCAGTGTTT TGTAGTTCTC CTTGTAGAAA TCTTTCACCT CTTTGGTTAG
43601 ATGTATTACA TTTTTTTGTG TGCCTATTGT AAATGGGATT GAGTTTTTGA
43651 CTTGGCTCTC TGATACAATG TTATTGCTGT ACAGAAATAC TATTGACTTT

FIGURE 3S

43701 TGTACATTGA TTTTGTCTCC TGAAACTCTA CTGAAATTGT CAATTCTAGT
43751 TGCCTTTTGG TGGAGTCTTT AGGGTTTTCT ATTTCTAAAA TTATAATCAT
43801 CAGCAAAGGA GAGATAGTTT GACTTCCTCT CTTCCTATTT GAATGCCTTT
43851 TATTTCTTTC TCTTGCCTGA TTGCTCTGGC TAGGTCTTCC TTATACTATG
43901 TTAAATAGGA GTGGTAAGAG TAGGCATCAC TTTCTTGTTC TGGTTCTCCA
43951 GGGGAATAGT TATAGCTTTT GCCCATTCAG TATGATTTTA GCTGTGTGTT
44001 TTTCATAGAT GGCTCTTATT GTTTTGAGGT ATGTTTCTTC AATGACTAGC
44051 CTGTTGAGGG TATTTTATCA TGAAGGGATT TGGGATTCTC TTGAAGGCCT
44101 TTTCTGTATC TATCGAGATA ACCATATGGT TTTGATTTTG ATTCTGTTTA
44151 TGCGATGAAT CATATCTAGT GAATTGTGTA TGTCGAACCA ACCTTGCATT
44201 CCAGGAATGA AGCCCACTTT TCTCATAGTG AATTAGATTT TGATGTGCTG
44251 CTGAATTCAG TTTGCTAGTA TTTTGTTGAG GATTTTGTGT CTATGTTCAT
44301 CAGGGAGTTT AGCCTGAAGT TTTCTGTTTT TGTGTCTCTG CCAGATTTTG
44351 GTATAAGGAT GATGATGACT TTGTATAATA TGTTAGTGAG AAGCCTCCCC
44401 TCATCCTCAA TTTTTTGGAA GAGTTTTAGT AGGATTGGTA CCAGTTCTTC
44451 TTTGTAACTC TAGTAGAATT CAGCTGTGAA TCCGCCTGGT TCAGGGCTTT
44501 TTTTGGTTGG TAGGTTTTTT TAAAATTACC GATTCAATTT CAGAACTTGT
44551 TATTGGCTTA TTCATGTTTT CACATTATCC CTTGTTCAAC CTTGGATGGT
44601 TTTGTGTTTC TGAGAACTTA TCCATTTCCT CTAGATTTTC TAATTTGTTT
44651 GCACAGAGGT GTTCATAATA GTCTCTGAAT ATCTTTTGTA TTTCTGTGGG
44701 ATTGGGTGTA ATGTCATTTG TCATTTTTGA TTGTGCTTAT TTGGGTCTTC
44751 TCTTTTTTTG TTAATCTAAC TAGTAGTCTA TCAATCTTAT TTATTCTTTC
44801 AAAAAACAAA CTCTGTTTCA TTTATCTTTG TATGGACTTT TGCATCTCAA
44851 TTTCTTTCAG TTGTTCTCTG ATTTTAGTAA TCTCTTTTCT TCTGCTAGCT
44901 TTTAAAGCCA TACTTATGTT GGGGTTCCTC CATTTTTCCA TTTTCTCCTT
44951 GCCTCCACAA GCAGATATAC TCTGCTGGAA ATCATCATTC AACAAGGCAG
45001 ATTGTAACCA TTATGAAGTT ATGACTCAAG GAGACCTTCA ACATCTCCTC
45051 CTAATTTCAT TGTGTATCTT TTTTGACATT TGAAATAATT ATTTTTCAAC
45101 TTTCTTCGCC TTCTTCATCA TTCTCCAACA TCCTCTCTTT TCACCATTAC
45151 TTGATAGTAA TCTTGCTTTG TACTTCAGAG GGAAAATATA TCATCAGAAA
45201 GAACTCACTT TACTTTCTTC CTGTTAAAAA GTTATAGCTG AAACCTTTCT
45251 TCCTATTAAA CGGTTAAAAC TGCAAGAAAA TAAGGAAGTT TTCTTTTCCT
45301 TTATGTTTAT TTTCTATTCC CTCTCACCAC TCTGGAAACT TATGCCATTT
45351 CTAATTTAAT TGACCTCTTC CTCTTGAAAT GAATTTTTCT TATCATCTTT
45401 GAAACATGAT AGAGTCTCCA CCATTTTAAG CAGTTCTCCA ACCTCCTGCA
45451 AACCCACCTT TAGTCATTCA GATATGTAAG TTAACTGCAT ATAAATGTTC
45501 TGGGTAGCAA TTTTACTTTT AAATATCTCT CCATATTGCT TTATTTGGTT
45551 TATTCAATAT CTGGCTTCAG TAACTATTGC AGATAAGTCT ATAGTCTCTC
45601 TATTTTTATT TTTTAGGTTT ATGTATTTTA ATCCTGAATG TTTATAGACA
45651 TTTTTCTGTG TCCCTTAATG AAGAAAATTG CTAAGATTGA CCTAATGGTA
45701 GGTGTATTAA AAAACTTTTC CATCCCGCAT ACACGAATAG TTTTCCACCT
45751 AGGGAACATT TTCCTATTAT GTTTCATTCT GTTCCATTTA CTTTGATCTC
45801 TTTGTGAAGA CTTTCTTTGC TCATATCCCT CTACTTTCTT CAAACATTTT
45851 AACTACATAT ATCTTTCATT TTTTTTTAAC TTTGAATTTG GGGGTACATG
45901 TGCAGGTTTG TTACATGAGT ATGTTGTATG ATGCTGAGGT TTGGGGTACA
45951 GATGGTCCTA TCACGCAGGT AGTGAGCACA GAGTATAGTC AATTTTACAA

FIGURE 3T

46001 CCCTTGTTCC CTACCCTCCT TCCCAGCTCC GGTGATTCCA AGTGCCTATT
46051 GTTCCCATCT TTATGTCCAT GAGTACCCAA TGTTTATCTC CCATTTATGA
46101 GTAACAACAT GCAGTATTTG GTTTTCTGTT CCTGAGTTAA TTTGCTTAGA
46151 GTAATGGCCT CCAGCTGCAT TCATGTTACT GCAAAAGGAT ATGATGTCAT
46201 TCTTTTTATG GCTGCACAGT ATTCCATGGT GTATATGTAC CACATTTTCT
46251 TTATCCACCT CACCCTAATG GTACCTAGTT GATTCCATGT CTTTGCTATG
46301 GTGAATAGCA CTAAGATGAA CATGCACGTA TATGTCAGAT TTCTGATTTC
46351 TGCTCTGTAT CCTTTTCCTC TGTAGTTTAA TGTTAGTCTT TTATATTACC
46401 ATTTGATTAT CTGCAGAATA AATTCTGCAT TTTCCTACTT TTATTATGAG
46451 TTTTGGTTTT GCTGTTGCAT TTTTAGTTTT CATTAATTTC TTTCTTATTT
46501 CATCCTATTT TCTTTACATT TTAGCCTGTC CTTTCCTGAA TACTTTTTAT
46551 TTTTTTCTGG TTGGTAGAGT GTATCCCCAG TGATTTCTGG ACGTTTTCAT
46601 TTTATCCTAA AGTAGACAAT TTTCAGAGCT ATGCTTTTCC TTTGGACTGT
46651 CAGATTATTT TTACTCTCCA TTGATTTTTA GTATTTTTTA TGGACTCCTA
46701 GGTTTTTTCC TTTTTTTCTC ATTTTTAAAC AAGGAAAGGT AGATTCCTAC
46751 TATATCTACC TAGCTATATC TTAAGATTGC TTAATGAGGC TGCTGTCAGT
46801 ATGCTCCATG TTTCCAACAG TATGTATAAT AAGCATCACA CTTATCCAAA
46851 TGCCCTGTAC TTCTGCCAGG GGCAGCATAG TTGTTGGTGG CAGAGTATGT
46901 AAAGAAAAGT ACTCTAGGTA TCCTGCACCA CCATGATAAA GAAGGATGGT
46951 TGTCCATAAG AATGGGCAGA TGGGCTGAGA GTGTAGGATA TACTAAGTAT
47001 CTTCTGCATT TTCAGATGTT GTCTCTTTCA TGAAGGAACG TCTTAGAGTG
47051 TAAAAAAATG ACAATTTGGC ATATTTTTCT CATTCAAGTT CCATCTGCTT
47101 ATAGTTAGCA GAGATGCCCT CTTAGACTGC AGGAATGGAT TATCTGTAGG
47151 GCTATGCGCT AATGATGAGT TTTCATCATT TTCTAGTATT TGAGAAAATA
47201 TATTTATATC ATCTTACAAG TATTTCATGA GCAAATAAAA ATAAGCTGTA
47251 TTTATCATTT GTTTGTTCCC TGTGCCTCTT CTTTATTTTT CCCTAACTGG
47301 AGGCATTATG CCAGTTTTTC TAGAACAGTG GTTCTCAATA ATGACTGCAT
47351 TTGAGAATTC TAAAACCGTG CTAATGCTCA ACCCGTACAC CAACCAGAAT
47401 CTCTGTGCCT GGGGCCTAAG CATGAGTATT TTTTGAAAAG TACCCCCAGG
47451 TGATTCTTCT GTGGAGCTGT TGATAGCTCC ACAGAAGGTT GATATCCACT
47501 GTTCTGGAAA CTTTGCTATT TAAATTTAGT TCATCAGGGG TCTAATATCC
47551 AGAATCTATA AGGAACTTAA ACAACTCAAC AAGCAAAAAT CAACGTGATT
47601 AAAAAGTGGG TAAAGACATG AACAGACACT TCTTAAAAGA AGACATATAA
47651 GCAGCCAATA AACATATGAA GAAATGCTCA ATATCACGAA TCATCAGAGA
47701 AATGCAAACC AAAACCACAA TGAGATACTA TCTCACACCA GTCAAAATGG
47751 TGATTATCAA AAAGTTAAAA AATAACAGAT TCTGACAAAG CTGCAGAGAA
47801 AAGGGTATGC TTACACACTG TTGGTGGGAA TATAAATTGG TTCAGCCACT
47851 GTGGAAAGCA GTTTGGAGAT TTCTCGAAGA ACTTAAAACA GAACAACTAT
47901 TGACCCAGCA ATGTCATTAC TGGGCATATA CCCAAAGGCA AATGAATCAT
47951 TCTATCAAAA GGCACATGGA CACGACTGTT AATCACAGTG CTATTCACCA
48001 TGGCAAAGAC ATGGAATCAA CCTAGGTGCT CATCAACAGT GGATTGAATA
48051 AAGAAAATAT ACTCCATGGC ATACATTGCA GCCCTAAAAA AGAGCAAAAT
48101 CATGTTCTTT GCAGCAACAT GTATACAACT GGAGGTCATT ATCCTAAGTG
48151 AATTAATGCA GGAACAGAAA ACCAAATACC ACATGTTCTC ACTTATAAGT
48201 GGGAGCTAAA CATTGGGTAG TTGTGAACAT AACGATGGCA ACAATAGACA
48251 CTGGAAACCA CCAGAGAGGA GAGGGAGGGT GGGGAACTAG GGTTAAAAAA

FIGURE 3U

48301 GTAACTATTG GGTACTATAC TGCCCACTAC TTGGGGGACA GGATCAGTCA
48351 TACCCCAAAC CTCAGCATCA TTCAATATGC CCATATAACA AGCCTGCACA
48401 TGTACTCCCT GAATCTAAAA TAAAAGTAGA AATTATTTTT AAAACTTACC
48451 AAACGTAAAG AAAGAAACCT GTACTGCTAG CTTTTAAAAG TTATTTAATA
48501 AATAAACCTA TTTTATAACA AAAATAGTAA AAATAAATTT CTACTTCAAA
48551 GTATAAAGCC AACAATATTA GCATTAAATT TAAACTTGCC AGAAATGCAG
48601 AATCTCAGGC CCCATCCAGA CCTCTTGAGT CAGGACCTGT ACATTAAAAA
48651 TATATTTAGG TAACTGGTAT GGTTTGGCTC TGTGTCCCCA CCAAAATCTC
48701 ATCTCCATTT ATAATCCCCA TGTGTTGAGG GAGGGACCTG TAATCCCCAT
48751 GTGTCCAAGG AGGGAGGTGA TTGGATTTTG GGGGCGGTTT CCCTCATGCT
48801 GTTCTCGTGA TGGTGAGTGA TTTCTCATGA GATCTGAAGG ATTTATAAGG
48851 CAGTGTTCCC AGCTCTTTGC TCGCTCGCTC TTCTGCCGCC TTGTGAAGAA
48901 AGTGCCTACT TCTCCTTCCG CCATGATTGT AAGTTTCCTG AGGCCTCTCC
48951 AGGCATATGG AGCTGTGAGA CAATTAAACT TCTTTCCTTT ATAAATTACC
49001 CAGCCTCAGG GAAGCTCTTT ATCACAGTGG TGAAACAGAC TAATAACAGT
49051 AACGTATATG AATCTTAAAA TTTGACGCCA AGCGATGCTC TAGAACATTG
49101 CTTATCAAAC CCTTCTGGCA CATTGGGAAT CACTTGAGAA GCTTTAAAAA
49151 AATTATTGAT GCTAGGCTTC AACCTCGAAG GATTTTTATT TAATTAATCT
49201 TGGGTGTTTC CCTAGGCACT GGTATTTTTA AAAAGTACCC CAAATTATTT
49251 AATAACCACT TAAATAATTG ACCAAGAATC AGATTCTGAG AAGCTTCTGC
49301 CTCTCAATTT GGTGAAACTT GGAAATAAGT CGGGTGGCCC AGATTCTCCC
49351 TCTTATTTTT TGCCACTATT TTTGGATGCC ACCTACCTTT TTCCTTCTTC
49401 AATCATCTGA GTATCTTCAG TGACATTTAG ACCTAAATGT GGTTTATCAG
49451 TGACAAATGT TTGGCACTTG GTGGTTTCTA AGCAATGGAA TTTTCTAGAT
49501 TTCACTTTTT TCAGTTTCTC TAGTACTAAT CTTCTGCCTT CATCCTTATT
49551 CCACACTCAG TTTATTTGCT ATAATAAGTA CTCAGTCACA CACAGAGACT
49601 TCAACCAAAC CCTAAACACC ATCCTATCTG ATTTGGGTTT TGATATTCTG
49651 CATAGTGAGA ATATATGACA TTTCCATGCT GAAGGCATTA AAGAAAATTT
49701 CTGCCTACTT AAGAAATAGT TATTTTACGT GGAAGCATTC CAAAGAAAAT
49751 ATTTTGAAGA TATTTCTGCA GGTGCCTCAA AATTCTTTGG AATTCAACTT
49801 CCGAAGAAGT ATAGGATAGA GGAGAATTTA AGAGAGTATC AGGTCTCTCT
49851 GCTATGAAGC TAGATATATG TTGTTAATTG CAGTATGAAT CTGTGAAATC
49901 ATGGAATCAT TAGGGCCCAA ATTATGAAGC AAGCATCAAT TTAACAAAAC
49951 GATTTTTGGA AAAACGTTTG AATTTGGGCA CTCTTTTTTT TATTATTATA
50001 CTTTAAGTTT TAGGGTACAT GTGGACAACG TGCAGGTTTC TTACATACGT
50051 ATACATGTGC CATGTGTGGT GTGCTGCACC CATTAACTCG TCATTTAGCA
50101 TTAGGTATAT CTCCCAATGC TATCCTTCCC CCCCTCCCCC CACCCCACAA
50151 CAGTCCCCAG TGTGTGATGT TCCCCTTCCC TGTGTCCATG TGTTCTCATT
50201 GTTCAATTCC CACCTGTGAG TGACAACATG CGGTGTTTGG TTTTTTGTCC
50251 TTGCAATAGT TTGCTGAGAA TGATGGTTTC CAGCTTCATC CATGTCCCTA
50301 CAAAGGACAT GAACTCATCA TTTTTTATGG CTGCATAGTA TTCCATGGTG
50351 TATATGTGCC ACATTTTCTT AATCCAGTCT ATCATTGTTG GACATTTGGG
50401 TTGGTTCCAA GTCTTTGCTA TTCTGAATAG TGCCGCAATA AACATACATG
50451 TGCATGTGTC TTTATGGCAG CATGATTTAT AGTCCTTTGG GTATATACCC
50501 AGTAATGGGA TTGTTGGGTC AAATGGTATT TCTAGTTCTA GATCCCTGAG
50551 GAATCGCCAC ACTGACTTTC ACAATGATTG AACTAGTTTA CAGTCCCACC

FIGURE 3V

50601 AACAGTGTAA AAGTGTTCCT ATTTCTCCAC ATCCTCTCCA GCACCTGTTG
50651 TTTCCTGACT TTTTAATGAT TGCCATTCTA AGTGGTATGA GATGGTATCT
50701 CATTGTGGTT TTGATTTGCA TTTCTCTGAT GGCCAGTGAT GATGAGCATT
50751 TTTTCATGTG CCTGTTGGCT GCATAAATGT CTTCTTTTGA GAAGTGTCTG
50801 TTCATATCCT TTGCCCACTT TTTGATGGGA CTGTTTGTTT TTTTCTTGTA
50851 AATTTGTTTA AGTTCATTGT AGATTCTGGA TATTAGCCCT TTGTCAGATG
50901 AGTAGGTTGC GAAAATTTTC TCCCATTTTG TAGGTTGCCT GTTCACTCTG
50951 ATGGTAGTTT CTTTTGCTGT GCAGAAGCTC TTTAGTTTAA TTAGATCCCA
51001 TTTGTCAATT TTGGCTTTTT GTTGCCATTG CTTTTGGTGT TTTAGACATG
51051 AAGTCCTTGC CCATGCCTAT GTCCTGAATG GTATTGCCTA GGTTTTCTTC
51101 TAGGGTTTTT ATGGTTTTAG GTCTAACATT TAAGTCTTTA ATCCATCTTG
51151 AATTAATTTT TGTATAAGGT GTAAGGAAGG GATCCAGTTT CAGCTTTCTA
51201 CATATGGCTA GCCAGTTTTC CCAGCACCAT TTATTAAATA GGGAATCCTT
51251 TCCCCATTGC TTGTTTTTCT CAGGTTTGTC AAAGATCAGA TAGTTGTAGA
51301 TATGCAGTGT TATTTCTGAG GGCTCTGTTC TGTTCCATTG ATCTATATCT
51351 CTGTTTTGGT ACCAGTACCA TGCTGTTTTG GTTACTGTAG CCTTGTAGTA
51401 TAGTTTGAAG TCAGGTAGCG TGATGCCTCC AGCTTTGTTC TTTTGGCTTA
51451 GGATTGACTT GGTGATGTGG GTTCTTTTTT GGTTCCATAT GAACTTTAAA
51501 GTAGTTTTTT TCCAATTCTG TGAAGAAAGT CATTGGTAGC TTGATGGGGA
51551 TGGCATTGAA TCTATAAATT ACCTTGTATC TCCCACTGTT ATTGTGTGGG
51601 AGTCTAAGTC TCTTCATAGG TCTCCAAGAA TGTGTTTTAT GAATCTGGGT
51651 GCTCCTGTAT TGGGAGCATA TATAATTAGG ACAGTTAGCT CCTCTTGTTG
51701 AATTGAACCC TTTACCATTA TATAATGCCC TTCTTTGTCT TTTTCGATCT
51751 TTGTTGGGTT AAAGTCTCTT TTGTCAGAAA CTAGGATTTC AACTCCTGCT
51801 TTTTTCTGCT TTCCATTTGC TTGGAAAATT TTCTCCCTCC CTTTATTTGA
51851 GCCTATCTGT ATCTTGGCAT GTGAGATGGA TTTCTTGAAT ACAGCACGCC
51901 AATGAGTCTT GACTCTTTTT TTTTTTCTTT TTTTTCTTGA TGCAGAGTCT
51951 TGCTCTGTCA CCCAGGCTGG AGTACAGTGG CATGATCTTG GTCACTGCAA
52001 CCTCTGCCCC CAGGTTCAAG TAATTCTCCT GCCTCAGCCT CCCAAGTAGC
52051 TGGGATTACA GGCATGTGAC ACCACGCCCA GCTAATTTTT GTAGTTTTAG
52101 CAGAGATGGG GTTTCACCAT GTTGATCAGG CTGGTCTTGA ACTCCTGTCC
52151 TCAGGTGATC CACCCACCTC GGCCTCCCCA AAAGTGCTTG GATTACAGGC
52201 ATGAGCCAGG GCCTTGACTC TTTATCCAGC TTACCATTCT GTGTCTTTTG
52251 ATTTGGGCAT TTAGCCCATT TAATTGAAGA ATAATATCTT TATGTGTGAA
52301 TTTGATCCTG TCATCATGAT GCTAGCTAGT TATTTTGTAG ATTTGTTAGT
52351 GTAGTTGCTT CATAGAGTCA TTGGTCTGTG TACTTCAGTG TGTTTTTGTA
52401 GTGGCTGCTA ATGATTTTCC CTTTCATATT TAGTGCTTTT CTCAGGAGCT
52451 CTTACAAGGC AGGCAGGCCA GGTGGTGACA AATTCCCTCA GTATTTGCGT
52501 GTCTGAAAAG GGTTCTATTT CTCCTTCACT TATGAAGCGT GGTTTAGCCA
52551 GATATGAAAT TTTGGGTTAG AAATTCTTTT CTTTAAGACT GTTGAATATT
52601 GGCCCCCAGT CTCTGCTGGC TTATAGGGTT TCCACTGAGA TGTTTGCTGT
52651 TAGTCTGATG GACTTCCCTT TGTAGGTGAC CTGGCTTTTC TCTCTGCGCT
52701 GCCCTTAACA TTTTTTCCTT CATTTCTACC TGGAGAATCT GATGACTATA
52751 NNNNNNNNNN NNNNNNNNNN NNNNNNNNNN NNNNNNNNNN NNNNNNNNNN
52801 CTAAATTATT ACATTCAATG AAATGTAATA ATTGACAAAA TTTTATTTTA
52851 TTTTATTATT ATTATACTTC TAGGGCACAT GTGCACAGCA TGCGGGTTTG

FIGURE 3W

52901 TTACTTATGT ATACATGTGC CATGTTGGTG TGCTGCACCC ATTAACTGGT
52951 CATTTACATT AGGTATATCT CCTAATGCTA TCCCTCCCCC CTACCCCCAC
53001 CCCATGACAG GCCCCAGTGT GTGATGTTCC CCTTCCTGTG TCCAAGTGTT
53051 CTCACATTGT TCAGTTCCCA CCTATGAGTG AGAACATGTG GTGTTTGGTT
53101 TTTTGTCCTT GCGATAGTTT GCTGAGAATG ATGGTTTCCA GCTTCATCCA
53151 TGTCCCTACA AAGGATATGA ACTCATCCTT TTTATGGCTG CATAGTATTC
53201 CATGGTATAT ATGTGCCACA TTTTCTTAAT CCAGTGTATC ATTGATGGAC
53251 ATTTGGGTTG GTTCCAAGTC TTTTTTTTTT TTCATTGTTA TTTTTTCCAG
53301 ACTTTTTTTT TTTTATTATA GGTTCCAAGT CTTTGCTATT GTGAATAGTG
53351 CCGCAATAAA CATATGTGTG CATGTGTCTT CATAGCAGCA TGATTTATAA
53401 TCCTTTGGGT ATATACCCAG TAATGGGATT GCTGGGTCAA ACGGTATTTC
53451 TAGTTCTAGA TCCCTGAGGA ATCGCCACAC TGACTTTCAC AATGATTGAA
53501 CTAGTTTACA GTCCCACCAA CAGTGTAAAA GTGTTCCTAT TTCTCCACAT
53551 CCTCTCCAGC ACCTGTTGTT TCCTGACTTT TTAATGATTG CCATTCTAAG
53601 TGGTATGAGA TGGTATCTCA TTGTGGTTTT GATTTGCATT TCTCTGATGG
53651 CCAGTGATGA TGAGCATTTT TTCATGTGCC TGTTGGCTGC ATAAATGTCT
53701 TCTTTTGAGA AGTGTCTGTT CATATCCTTT GCCCACTTTT TGATGGGACT
53751 GTTTGTTTTT TTCTTGTAAA TTTGTTTAAG TTCATTGTAG ATTCTGGCTA
53801 TCAGCTCTTT GTCAGATGAG TAGGTTGCGA AAATTTTCTC CCATTTTGTA
53851 GGTTGCCTGT TCACTTTGAT GGTGATTTCT TTTGCTGTGC AGAAGCTCTT
53901 TAGTTTAATT AGATCCCATT TGTCAATTTT GGCTTTTGTT GCCATTGCTT
53951 TTGGTGTTTT AGACATGAAG TCCTTGCCCA TGCCTATGTC CTGAATGGTA
54001 TTGCCTAGGT TTTCTTCTAG GGTTTTTATG GTTTTAGTCT AACATGTAAG
54051 TCTTTAATCC ATCTTGAATT AATTTTTGTA TATGGTGTAA GGAAGGGATC
54101 CAGTTTCAGC TTTCTACCTA TGGCTAGCCA GTTTTCCCAG CACCATTTAT
54151 TAAATAGGGA ATTCTTTCCC CATTGCTTGT TTTTGTCAGG TTTGTCAAAG
54201 ATCAGATAGT TGTAGATATG CGGCATTATT TCTGAGGGCT CTGTTCTGTT
54251 CCATTGATCT ATATCTCTGT TTTGGTACCA GTACCATGCT GTTTTGGTTA
54301 CTGTAGCCTT GTAGTATAGT TTGAAGTCAG GTAGCGTGAT GCCTCCAGCT
54351 TTGTTCTTTT GGCTTAGGAT TGACTTGGTG ATGTGGGTTC TTTTTTGGTT
54401 CCATATGAAC TTTAAAGCAG TTTTTTCCAA TTCTGTGAAG AAAGTCATTG
54451 GTAGCTTGAT GGGGATGGTA TTGAATCTAT AAATTACCTT GGGCAATATG
54501 GCCATTTTCA TGATATTGAT TCTTCCTACC CATGAGCATG GAATGTTCTT
54551 CCATTTGTTT GTATCCTCTT TTATTTCATT GAGCAGTGGT TTGTAGTTCT
54601 CCTTGGACGA GGTCCTTCGC ATCCCTTTTA AGTTGGAGTT CTAGGTATTT
54651 TATTCTCTTT GAAGCAATTG TGAATGGGAG TTCATTCATG ATTTGGCTCT
54701 CTGTTTGTCT GTTATTGGTG TATAAGAATG CTTATGATTT TTCCACATTG
54751 ATTTTTGTAT CCTGAGACTT GTTGTAGTTG CTTATCAGCT TAAGGAGATT
54801 TTGGGCTGAG ATGATGGGGT TTTCTAGTAT ATACAATCAT GTCATCTGCA
54851 AACAGGGGAC AATGTGACTT CTTTTCCTAA TTGAATGCCC TTTATTTCCT
54901 TCTCCTGCCT GATTGCTCTG GCCAGAACTT CCAACACTAT GTTGAATAGG
54951 AGTGGTGAGA GAGGGCATCC CTGTCTTGTG CCAGTTTTCA AAGGGAATGC
55001 TTCCAGTTTT TGTCCATTCA GTATGATATT GGCTGTGGGT TTGTCATAGA
55051 TAGCTCTTAT TATTTTGAGA TACATCCCAT CAATACCTAA TTTATTGAGA
55101 GTTTTTAGCA TGAAAGGTTG TTGAATTTTG TCAAAGGCCT TTTCTGCATC
55151 TGTTGAAATA ATCATGTGGT TTTTGTCTTT GGTTCTGTTT ATATACTGGA

FIGURE 3X

55201 TTACATTTAT CGATTTGCAT ATGTTGAACC AGCCTTGCAT CCCAGGGATG
55251 AAGGCCACTT GATCATGGTG GATAAGTTTT TGATGTGTTG CTGTATTCAG
55301 TTTGCCAGTA TTTTATTGAG GATTTTTGCA TCAATATTCA TCAAGGATAT
55351 TGGTCTAAAA TTCTCTTTTT TTGTTGTGTC TCTGCCAGGG TTTGGTATCA
55401 GGATGATGCT GGCCTCATAA AATGAGTTAG GGAGGATTCC TTCTTTTTCT
55451 ATCGATTGGA ATTTGGGCAC TCTTAAAAAG TTTTATTACT CCAACGTATA
55501 AGCAACATCA GCAGAATCCT ACTTTATTAT GAGACCCAAT CATAGAATAC
55551 AGTGTTGTTA AAACATCCTA GTTGCATTAG TGTTGCATTC AGGTAAAAGA
55601 ATAGGCCTTT AATATAGACG GAAGAGTTTA TGCTTACATC ATAGGAAAAC
55651 AATGACTGGT TCAAGCCTAC CATATGTCAT GGTTGGGCTG TGATTCCTAG
55701 GTGAGTCTAA AGAGGAACTG GCTTTTGGTC TGTGTGGTAG TGGTGGTGGT
55751 GATGTTTTGC TCATACAAAA AACTTTTAAT GCCCACAAAT AAGTTCAACC
55801 TACTTTGGCT ACTGTACTTA ATAAATATAA TAAATATATT AATTTGTTTA
55851 GATGAATGTG ATGATGATTA ATTAATTCTC CTTCCTATTG CAATCAACTC
55901 CCCAGTAACA AAGCTGCTAA AATTTCACTT TTTTTTTTTG AGACAGAGTC
55951 TCACTCTGTT GGCCAGGCTG CAGTGCTGTA GCACAGTCTT GGCTCACTGC
56001 AACCTCTGCC TCCCTGGTTC AAGCGATTCT CCTGCCTCAG CCTCCTGAGT
56051 AGCTGGGATT ACAGGCACCT GCCACCACAG CCAGCTAATT TTTTGTATTT
56101 TTAGTAGAGA CGGGGTTTCA CCATGTTGGC CAAGCTGGTC TCGAACTCCT
56151 GACCTCGTGA TCCACCCGCA CCAGCCTCCC AAAGTGCTGG GATTACAGGA
56201 ATGAGCCACC GCATCCAGCC CACATTTGTT ATTTTTAATG TCATCTTCTA
56251 TTCTCTTTGT ATAATTTGAA ACTATATTTT CAACTGGGAA CATGGATGAG
56301 CTGCTTTAAA TTGGTAAGTT TGAAGCATAA GCTTGAAGTC AGTGAAAATA
56351 TGAAAGATGA TGAGGGAAAT TTGTAACACT TCAACGTTTA TTTTTTTCCT
56401 CAACCTCCCT GAAAAGAATC TAATAGAAAA GATGATAGGA TTATGCCAAT
56451 TACAATTAGC TAATGTATAA GAAGTAGAAA TAAATCTAAA AGATACAGAC
56501 TATTAAACAC ATGTTTAAAA TATGGTACAC AAAGATACTG AATAAATTAA
56551 CACAGTCCTG GAATTATAAT AGGATTTTGT CAGTCTTAGG TGGTAAATTG
56601 TGCACACTCT TTAGGAGAAA TGAAGCAAAT ATAGAAAACA TGACCTCAAA
56651 GAGCAATTTT TTGATGGACA GTGGCTTCCT GTTCCTATTT TAATGACCAA
56701 TTAGGTGCTA TATGAGAATA TCAAGGTGTT TTTACAAATG TATTTTATTG
56751 TAAAGTATAA GACAAGCATT CACAAGTGTT AAAGCATAGA AACATACATA
56801 TAAAACCCAA TGAATTATCA CACCAGAACA TCTGTGTAAT ACCACCTTGG
56851 CTGGCACTCT AGAAACTCAC TTTGTGCTCA TTACCAGTCA TTAGGTTTTC
56901 CATCCTCCTC AAAAGAATCT CTGGCCTTTC TTTTTACAAT GGGTATTTTG
56951 CTTGTTTTTG AACGTTATAT AAATGAAATC ATATAAGAGG AATTAATTGC
57001 TCAGTGTTCT GTTTATGGAA TTCACCAATG TTTTTGATGT AGCTTCAGCC
57051 TATTCATTTT CATTATTGTA TAGTATGTTA ATGTGCTTCT ATATGCACGG
57101 TATGTATGCA TTCTACTATT GATGGTCATT TGGATCATAT GCAATTAGAA
57151 GCTACTACAA GTAATAATGC TGTGAACATT TTTCTATATG TCTTTTGGTA
57201 TACATATGCA TTTCTCATAC CGATGAATGA AATTATCAAT TGCTGAGTCA
57251 TAGGACATGC ATATTTTCAG TTTTGGTAGA TAATGCCAAA TAGATTTCCA
57301 AAATTGGGGT ACATATTTAC ATTCCCACCA ATAAAGTGTG AGAACTTATG
57351 TTTTTTTGCA TCCTTACTAA CACTTGGTAA TTCCATTCTT TTAACATTAG
57401 CCATTCTCTT AAGGTATGTA ATTATATCTT ATTGTTTTAA TTTATATTTC
57451 TTGATTACCA ATGAAATTGA GTAACTTTGC ATATGCCTTT GGCCATTTGG

FIGURE 3Y

57501 ATATTCTCTT CTAGGAAGTG CCTACCAAAG TCATATTTTT AATGAGCTTT
57551 TATTGATTTG TAGAAGTTCT TTACATGTTA TGGAAATAAG TCCTTTGTTA
57601 GTTTTATGTG TTTTAAATAT CTTCTCACTA TTGTGGGTTC TGATTTCACT
57651 CTCATAATGG TATTTTTTTG ATGTGGCTAC AGATTCCAGC AGAGTCTGCT
57701 AAGAGGCTGA TACCTTTATT CTTTAGGCAA ATTTTTCTAT GTTATTTATT
57751 TCCATTATAT GTTTTAGTAT ATATAGAAGC AGACCCATAT CTTGATCTTC
57801 CATAATCTTG GCTGAAGTTT GTATTTCACT GCTCTATGGT TTCAGTGGCT
57851 ATCATAAAAA TAAACATCCA TCAACACAGG AGAAATATTC TATTAACTTA
57901 GACAATTCTG CCAGGTGCTG TAGCTCACAC CTATAAACCC AGTTACTTAG
57951 AAGGCTGAGG TGAGAGAATT GCTTGAGCCC AGGAGTTCAG GGTTACAGTG
58001 ATCATGCCAT TGCACTCCAG ACTGTGTGAC AGAACAAGAC AGCATCTCTA
58051 ATAAAAATAA CAATTTTTAA CAGGAAGATT TTTTCTGATT TTGATAGTAC
58101 TGCAATTTAC ATGAAATATG TAATACTATT TTAAGGTGTC TATTTTTAAT
58151 AGACATGAAA AATGGGTGTT GAATTACACA TTTGGAAAAT TTACTGTATT
58201 GAAACATAAT CTTAATCCCT TTTTAAGATC TTAAAAATAT GTTAGTAGGA
58251 TGGTTATGAA AAATCTTTTG TGAAAATAAC CTAATACCTA TAAAATCATT
58301 TCTATTTTAA AGAATGAAGG CCTGATACAG GGAACCATAC GTTATCTTGA
58351 ATCAAAATAA AATATTTCTT GTCGCTGAAT AGATGACCCT ATTTCAATAA
58401 ATTATTATTT TCTTTACCAT TGCTGCTATC ATTGTGTTTT AGGGAAGCCT
58451 TTTGAATACC TGACACCCTA TCTCACACTT TCAAATACTC CTTATTCATA
58501 ACTGTGAGGG TGTTATAACC ACATGTTTAC TTACAAATAG TATTTTAAAG
58551 GTGTGTAGTG AGTAAGCCTC ATGCTTTATA AAAGGAAACA CTAATAAGCC
58601 TTAAAATTAA CACTCATGTA CATAGCAATT GAGATTTGGG GGTTGGATGC
58651 ATGGTATTAT AGACATCCAG ATTACTGATG AAGAGTGAAC TGAAATAAGT
58701 CTTTGGAAAC AGTGATGAGA GAAAATGTTT CAGAGACATG GGGACCCTAA
58751 TACCAATGTG GAAGCATGGC TGCTATGAGA TGTGACCTCT GAGAAGTGAT
58801 TGGGTAGTCA GAACTGGTTG TCATGCAACA CAAAATGACT ATGTCTGCTC
58851 ACACTGGGTC AGTCTAATGG GAATATTTAA TTGATTTCTT AGTGTAACTC
58901 TAGAATCACA AATTGTGCTT TTTTTTAAAT GGCTATTCAA AGTACTGATA
58951 TTTTTTCTAG ACCAACTAGT CTGAGAGATA ACAGGCTAAT TAAAAATGCA
59001 GTTGACCCTT GAACAATATG GGTTTGAACT GTGCAGGTCC ACTTACACAT
59051 AGACTTTTAC ATTTATATGT ATATTATGTA GTTTTTGTAT ATTATGTATT
59101 TTTATATTAA AAATGTATGG GCCAGGCGCA GTGGCTCATG CCTGTAATCC
59151 CAGCCTTTTG GGAGGCCTAG AAACACAGAT CACTTGAGGC CAGGAGTTGG
59201 AGACCATCAT GGCCAACATG GCAAAACCTC CTCTCTGCTA AAAATACAAA
59251 AATTAGCTAG ACATGGTGAT GCGCACCTGT AGTCCCAGCT ATTTGGGAGC
59301 CTGGAGCAGG AGAACTGCTT GAACCCAAGA GGTGGAGGCT GCAGTGAGCC
59351 AAGACAGTGC CACTGCACTC CAGCCTGGAT GGCAGAAAGA AACTGTCTCA
59401 AAAAAAATTA TGTGTATATA TATATACTTT TTTTTTAGAT TTGTGACATT
59451 TTGAAAAAAC TCACAGATAA ACTGCATAGC CTAGAAATAT AAAAAAATTA
59501 GGAAAAAAGT ATGTCATGAA TGCATAACAT ATAGGTAGAT ACTAGTCTAT
59551 TGTATCACAT ACTACCATAA AATCTACACA AATCTATTAT AAAAGTTGAA
59601 ATTTATCAGG CCTTATGTAC ACAAACACTT ATAGATTGTG CATGGTGTCA
59651 TTGGCAACTG AGAGAAATGT AAACAAGTGC AAAAAATGCA GTATTAAATC
59701 ATAACTGCAT ACAGTTTACT GTTGTACTTA ATGTACTACT GTAATAATGT
59751 TGTAGCCACT TGCTGTTGCT ATTGTGTGAG TGCAAGTGTT TCCAGTATCC

FIGURE 3Z

59801 ACTTAAAACA CCTTGTGATG CTAATCACGT CTACCTGAGC AGTTCATCTC
59851 TTCAGTAAAC AGCATATTGC CGTAAAAAGA ATGATCTCTC ATGGTTCTCA
59901 CATATTTTTC ATCATGTTTA GTATAATATT GTGAACCTTG AATATAACCA
59951 CGGAACCCGT ATGAAGTGCC ACAGTGATGC TCGAAGTGCT CCCAAGAAGC
60001 AGAGAAAAGT CATAACATTA CAAGACAAAG TTGAATTGCT TGACATGTAC
60051 TGCAGATTGA GGTTTGCAGC AGTGGTTGCC CACCGTTTCA GGCAGATAAC
60101 ATAAAAAGAT GCAGAAACTT ATCAACAAAT ACAGTAAAGT ACTGTAAGTG
60151 TATTTTCTTT CATTTATGAT TTTTGTAAGA GAAAGGATAT CTGCTTGAAC
60201 AGGTTTTTAA AGCAGACGAA AGTGCCCAAT TCTGGGGGGA AAATGCCACA
60251 AAGGAAGAGA ACATCAGTAT TTAAAGCAGA AAGGAATAGG CTAACTACTG
60301 TTTTTTGGCA ATTGCCGCTA GGTTTATGAT CAAGACTACC CTTATCTATA
60351 AAACTACTAA CCCTAGATCC TTGAAAGGAA AAGATGAGTA CTGCCTGCCA
60401 GTCTCTTGGT TGTACTAAAA GGCCTGGACA ATGAGAATCC TTTTTCTACT
60451 TTGGTTCTAT CGATGCTTTG TCCCTGAAGT CAGGAAGTAC CTTACCGGTA
60501 AGGAAATGCC TTTGAAAATC CTTTCAATGT TGGACAATGC CTCTGGCCGT
60551 GTAGAAACCC AGGAGCTAAT GTTCATGAAG GTGTTAAAGT GATCTACTTG
60601 CCCCAAAACA CAAAACTTAT AATCAGCTTC TAGATCAGGT TTTGTAAGGA
60651 CCTTTAAGGT TCATTACACA TGGTACCCTA TGGAAAGCAT CGTCAATAAT
60701 GTGGAAGAGA ACCCCAATAG AGAAGACATC ATGAAACTCT AGATGGATTA
60751 CACCATTAAA GATGCCTTCA TTGCTACAGA AAAATCCATG AAAGCCATCA
60801 AGCTTGAAAC CACAAATTCC TGCTGGAGAA AACTGTGTTC CAGTGTGCAT
60851 GACATCACAA GATTTACAAC ACAGCCAATC AAGGAAATTA TGAAACAGAT
60901 TGTGAATATG GCGAAAAAGG TGGGGGTAAA AGGTATCAGG ATATGGATCT
60951 TGGAGAAACT CAACAGCAAA CAGAAACCAT GTCAGAGGAA TTAATAGAAG
61001 ATGACTCGAT GAAGATGAGT ATTTCTAAAC CAGCGCCAGA AGATAAGGAA
61051 GAAAACATTG AAAAAGCAGT GCCAGAAAAC AAATTCACAT TAGACAATCT
61101 GGCAGAAGAG TTACAATTAT TCAAGACTAG GTTCAACTTT TTTTACAACA
61151 TGGACCCTTC TATAATATGT GCACTGAAAC TAAAATAAAT GGTGGAAGAA
61201 GGATCGCATC TCATGGAAAC AGTTTTAGAG AAATGAAAAA GCGAAAAGGT
61251 CAGAAATTAC AATTTATTTC CATAAAGTTA CATCAAGTGT GTCTGCCTCT
61301 CTTGCCTCCC CTTCTACCTT TTCTGCCTCT GCCACTCCTG AGATAGCAAG
61351 ACCAACCCCT CCTCTTCCTC CTCCTCAGCA TACTCAACAT GAAGACAATG
61401 AGGATCAAGT CCTTTATATA ATCCATTTTC ACTTAATGAG TAGTAAATAT
61451 ATTTTCTCTT CTTTGTGATT TTCTTGTTTT CTCCAGTTTA TTGTAAAAAT
61501 ACAGTACATA ATACACATAA TATACACATT ATGTGTTAAT TGACTATGTT
61551 ATCATTAAGG CACCTGGTCA ACAGTAGGCT ATTAGTAGTT AAGTTTTGAG
61601 GGAGTCAAAA GTTATATACA GATTTTCAGC TGTGTGGGAG ATCAGCACCT
61651 TTAAGACCTG TGTTATTCAA GAGTCAACTG TAGTTGCTTT TTTTTCTTTT
61701 CTACCTTGAA CATCTTCCTG CAGATGCTCC ATCATCTTCC TAGCTCTAGT
61751 TTCTTATCTC TAATGGAGGT AAAGCAGGAA AGTTCTTACT TCACTGCTAC
61801 TGTGGCAAGT TAATGTCACA CTCCTTAGGC TTAGCAAGAA TTTGAGTTTA
61851 TTCATTCTCT CCTGGAGGTT TTCTCACCTG CACTCTTTTC TGCGTTACTA
61901 TTTATTCCTC TTCATCCCCT AGGCATTCAG TTATAATGAT AGAGTCTCTC
61951 TGCTGAAATA TTCTCAGTGC TCTGTGGCAG CCCAAGATGA CTCTATATTC
62001 CACACCCTCT CTCTCTCTTC TCCCCGCTCC CCTCTCATGT GTGTGGCTTA
62051 TGTATGATTC ACAGAAGACA CACACACACT CAGATTGAGT GCTCTGGTAA

FIGURE 3AA

62101 ATACTGAAAG TGTGTGTTAT TGAATGCAGC AATGTCAGCC ATCAGCAGCT
62151 AGGCTGACTT TATGTTTCTC AGGTAAGAAT CATACCCCTA CTGCCATCCC
62201 TTTTAAGGAG AATAAGTAAA TGTCAGACTC ATGTTACAGC TCTTTCCGAA
62251 GAACTCTAAA ATGTGTCTGT TTCATCTCAT GATCCTTTAT AGCCAGCCTC
62301 TGTGTGGGTG AAAAATTAGA GTCACATAAC TAGGTTTTTA GAGCATGGTT
62351 TGCAAATTCT GCATATAATC TTATATCCCA TGTGGAAATA AATATCTGTT
62401 CTTGGTGCTT CATCTGAAAC ATTCATTTTA CCAATCTATT ACCCTGTAAT
62451 GAAATTACTA ATTAGAATTG ATAATATTAT ATTATTTCAA TTATGTAAAT
62501 GAATTAAAAT CTAGAAATTT CAATGAATAG ATTGTGCATG ACATTCAAAT
62551 ACTATGAACA CAATTTTAAA GTTCAACTAA AAATGGAAAA TATTATTGAG
62601 CTTCAAGGAG ACTGGAGACA TAAATTTGGA ACAGAACTAC CAAACTTGTC
62651 ATAATTTCAT AAGATAGATT ATCTGAATAT GGATTCATCT GAACTATAAC
62701 AAAGATAAAG AGGAAGAAAA GTGTCTGTGA TTCAGAAATT CACAATGGTA
62751 AGCATTTTGT GAATCTGTTC TCTTAAGCTA AATGTCATAG TAACCAAGGC
62801 TTGTGTACTT CATGACAGCA AGATTACATA TTAAAATGGA AGTTTTTCAA
62851 TTCACTTCTG TCATTGTACT TGTAATGCTG GCATGATAAA TATATATTCT
62901 CAACATATTT GTAAAATATT GTCCAGAAAG TGTCTAAAAA ATAGAGTGCT
62951 TTTGGAGAGG GCCTGCAAAA GGAGAGTATT TTCACTGATT ATTAGGAACT
63001 ATCTCTTTAA GCCCTGGTTA ATTAGTATGT GAGTTATTAA GGCAATATAA
63051 GTAATATAGC TAATAATGCA AAGATAGAAG TTTGCTAAGG AATTTGTTGT
63101 TTCCAGTTAT GATTCTACAA GGGCTTTCCT CAGATAGCAT AATGATTTAA
63151 ATTTGATTTT CTTAACTAAT TATTTGTTGA AAATACAGTC CATATTCCAA
63201 ATGGAAATAC CTTATTTGTC TATTTCTGAT TATAACAGTA ATAAATGTTC
63251 TTTGGAATTC CAGTGCTATT GAAAATTAGG CTAGCCAGAT CTTCTTTCTC
63301 TTAACACAGT TCTCATTGAC CACCCTACAA CATCCAACAT TATTGACTTC
63351 TTATTCTTTT TAAATTCTTT TCTACTTTGT TCCTGGTTAT ACTACTCTCT
63401 CCGTGAGATG TATGTTCCAT GAAGGCAGAG GCTTTTTTTC TGTTTATATC
63451 TGTCTTATTC ACTACTTAGT ATGGTATCTG ACAAAAGAAA GGTGTTCATT
63501 AAATGTTTGT GTAATGTATT AATCCTTTTA CATATTTATT CCTTTTCCGA
63551 TTCTTTTGTT AACTTATTTT CCTTCTGCCA AATCTTAAAC CTTATTACTT
63601 CTCCAGTGTT GAGTCTTCTT CTCTCTCAAG ACTTTCATTT TGAGTCATCA
63651 TCATCATTGT AATCATGTGA TATCTTTAGT TAAATGTTAT CTATGTCTCT
63701 ATCTCTGTCC CTGCTCTCTC TTCCAGAATC CAATCTCAAA TCTCCAACTG
63751 CCTTATGACC TTCTTCATAT GATGGTCCCT TAGTCACCTC AAAGTTAGCA
63801 TATGCAAAAG TTATCTTTGG AGCACCCAAC CTACAATGCT GGCTCTCATT
63851 CTGACAACTC TCTTTTAATT AATGGCATGA TTATTCTACC TGCTTCAATT
63901 TGTAAAGCTC TCTATTTCTG GTAGGTAATT CTATATCATC ATTATAACCA
63951 TCACCCCCTA TCTCTAATAT AATCATCAGT AATATTATGT GATTCTTTTT
64001 TTTTTTTTGA GACGGAGTCT CGCTCTGTCA ACCAGGCTGG AGTGCAGTGG
64051 CGCGCGATCT CGGCTCACTG CAAGCTCCGC CTCCTGGGTT CACACCATTC
64101 TCCTGCCTCA GCCTTCCGAG TAGCTGGGAC TACAGGCACG CCCGCACCAG
64151 GCCGGCTAAT TTTTTGTATT TTTAGTAGAG ACGGGGTTTC GCCATGTTAG
64201 CCAGGATGGT CTCGATCTCC TGACCTCGTG ATCCGCCCTT CTCGGCCTCC
64251 CAAAGTGCTG GGATTACAGG CGTGAGCCCC CGCGCCCGGC CAATATTTAT
64301 GTGATTCTTT ATTGCTTGAA AAGTATTTTT ACATCTATAA TTTCCTCTTT
64351 TGGGGCTTGG TCCAATCTTC TGGGAGACTA ATTCTGGCAG GTAGAAATAT

FIGURE 3BB

64401 AAGGAGGCCA ATATCAGTAC ATTGCTTATT CACCATTGCT AGCGTCTTAC
64451 TCCTGGGTTT ACTCTGACTT TGGTCCCCAG CTCTCCAGTG CTATTATTTC
64501 TTTGCTTCTT TCTGTTATCC ATATTCCTGT CTTGCAACCA AGTTTCCCTT
64551 TAATGAGATA TTCTATTTCA CTCCAGTTTT CCTATGATGG AACCACTTTG
64601 CTAGACAAAG CCTGCGCATT TGGACTTGTG CTCATTACAT GATGCAAACT
64651 AGTGTGATAA ACCTAGTTAT TGTATTTTAT TAACTTCTTA CAAAACAGTA
64701 TTCATGACTC ACTTGTTCCT TTACTTCTGC CTGCAGATCT GCTTTTTGGA
64751 ATTTCATTTT TGTACTACTG ACCCTTGGAT TTGCTTACAA AACTAAATTA
64801 CTGTTTTTTT CTTGAGCTTT TGAATTTTTG ATATTGACTG CTTCCAGTTT
64851 GGTCCACACT AATTTCAACC AGTCATCAAT TATTAAAGAT ATAATCCTCA
64901 TTTAAAATGT TATATATCTC TATATATTTT AAATATGTAG TATAATTTTA
64951 TATATGCTTA TTTTTATTTG TATATATAAA TATATACATA TTATTTACCA
65001 TATATTATAT ATACATGCAT AGGAAAGGAC TCTTTCTGGT TCCCTAGTAT
65051 TGGAATTTTT GCTTTTCTTC TCTCTGGTAT TTTTTCATCC TTGTTTGATT
65101 CAGACAACCT GGCTATTGTT TTACTGCTTA CCCGGGATCT TAATGCTTCA
65151 GGTTCGGCTG GATTCCAGCT TTTCCTTGGT TTTAATTCTA ATTCATATAT
65201 ATATATATAT ATATATATAT ATATATATAT ATATATGTAT AATCTACATC
65251 TGCATCAAAT CCCTCTCTAG AGCATGCAGT GGATTTCAGA CCTGGGATTT
65301 CATCTTGAAC TTCAGCTACT GAGGATATTT TCTTGCATTA TTCTATTTCT
65351 AAATTATTCT ATTAGAATAA TTCTATTAGA ATTATTCTAT TTCTATATTA
65401 TTGTATTTCT AAATCCATTG CCTAAACCAA ACCATTAATT TTGTCTCAGT
65451 AATCCTGGAT CTTTTTCTTT TACCATATAG TCAAAAATAT TATGTCCTTA
65501 ATGCTGGTGT GGCCTGACTT AATCCCACCT CTTCTTGTGA AAACCTCCTT
65551 GACCGTGTAG CCTTCATTTG TTTTTACACC TCTTTACCCT TATAGCACTA
65601 AGCACCAGAC ATGTTAGTGC TTAATTATTA TTGTCTTACA TTGTCTGTTA
65651 TTATGTATTC ATCTTATTTT TAAAACCAGA TTATAAGCAA TTTAAGAACA
65701 ATAAATATGG TATAGCATTT ATGTGAACTG GAATAGATAC TATCCTACAG
65751 TTAATGAATT GACCAAGCAA CTATTCAAAG TACAGCCAGG CTGAAGACGG
65801 CAGTATGTTG TTTTTTTAAA AGATACTTTA TTTGCTCAAT AAATCTAGGA
65851 AGAAATCAGC CTCACATTTT TTTGAACTGC AACTTCTTTG CTTGCCATCA
65901 TTTAATTAGT TGCCGAGTTA AAGGACCCTC TTGGCTAATA AGATAGCAAA
65951 ATTGTCATGG ATTCTCATGA ATCTCAATAT AATTGAACTT ACAATTCATC
66001 TAAATTATTC CACTTTGTTT TTTATACTAT TTGCAGTAAT TTCATTCCAC
66051 TTGAATAATA AGGGAATGTT TTCTCATGTT CTGTAAATAT ATTATTTGAG
66101 GATATTTTAC TTTTTTTCTA TATTTATGTA TTGGTCTGTT TTCATGCTGC
66151 TGATAAAGAC ATACCTGAGA CTGGGTAATT TATAAAGAAA AAGAGGTTGA
66201 ATGGATCACA GTTCCATATG GCTGAGGAGG CCTCACAATC ATGGCGGGAA
66251 GCAAAAGGAA GGCACATCTT ACATGGCAGC AGACAAGAGA GAATAAGAGC
66301 CAAGCAAAAG GGGTTTCCCC TTATAAAACC ATCAGATCTC ATGAGACTTA
66351 TTCACTACCA CGGGAACAGT ATGGGGAAAC TGTCCCCATG ATTCAATTAT
66401 CTCTCACTGG GTCTCTGCCA CAACACATAA GAATTATGGG AGCTAAAATT
66451 CAAGATGAGA TTTGGGTGAG GACACAGCCC AACCATACCA ATTTCTTTCT
66501 ATAGAATATA CATTTAAAAA TTGACATAAG TGTGCTAAGT GCTCTGCACA
66551 TTTCAGCTCC CAAGGAATGC ATATTGTAGG AACTAAAGCA AAAAAAAAAA
66601 AAAAATAACA ACAACCAGGG CAGTTTTATT GAGTTCAGTA AAGAATATGT
66651 TTCCCTATAT TTTAATAACC ACATCTATTC TTATCTGATT TACTTTAAGA

FIGURE 3CC

66701 ATCTATTTTC CTCTTTAATG CAGTTAACTA ATACTATTTC TTATACAATG
66751 GCAGTTTGAA ATATTAATCC AAACATTTTT ACAATTTTTC CATCCATTTT
66801 CATAACATGC CAGTGTTATA TTTAGTTTAA TAGGCTAAGG TTACCTTTCA
66851 TATTGATGGA TTTACTCTGA ACTTCTAGCT GCTCTTAAGG TAGTTGTGAG
66901 GTTTTTTTTT TTTCCTGTTA TTGTAATTAC AGTTACAGAA TAAGACTGGA
66951 AACTTTGAGC AAGTTTATTT TCTGTTTTTA AAAAAAACCC AGAAACAAAC
67001 AAGCTGACAT GTTGATGAGA TATATTTTAT TACCCTACTT TACCCAGAAA
67051 GCTATGCATA AAGTTCATAC AACAAGATAA AATTTTAAAA AAAAGCCAAA
67101 AGTGTACAAA ATACATCTTG GCTTCATCTT TTAAATAAAT TAATATTTGT
67151 TAAACCTTTG ATATTTACTG AGGATATAGC AGTGAATAAA ACAAACATGG
67201 TTTCTGCCCT TATATTTCAT CCATTCTAGC AAAAAGATAG ATGCAAAATC
67251 AATTATTGCA CAATTAATTA TTAGTTGCAA TTGTGATAAG TAGATCAAGA
67301 GATGTAGGGT GCTATAAGTT AGGATAGCAG GGGCCTGATT TGTTTGTATA
67351 TGAATATGCT TAGATGTGGA TATGTATGTG TTCATATGTC TGTTTTACAA
67401 AGATGATTAG GTAGGTGTGC CAAAGTATAC TACATTTAAG CAGAGAGTAG
67451 ATGTCTAAGA CAGCTACAAG ATTCTGAGGT AGGGAAGAGC ATGATATTTT
67501 TAAGAGTCTT AAAGAAGGCT AATGTACCTA GACTGTAATA GCAAGGGAAA
67551 GACTGGCAGA AGATGAGGCT AATGAGTTAG GCAAGAGTTA CCACAGATAT
67601 TTATTTACAC AGAAATATGA CACTATATTA TCATTGTGTG TTTATTTTTC
67651 ACCTTTGCCC TCTGAAATAC TCTCAATTAT GACTTAGTTG TAATCTAATT
67701 ATTTCAATAA CTTATTAATT GGTTTATTTT CATATATGAA ATGATTAATA
67751 TTATAGATTT CAGTAATTGC TCTATAGCTG TTACTGATTT ACTCATTCTT
67801 TTGTGTTTTA AAAAGTTTAA AACATACCAG ATGTTTTATT GAACTAACAT
67851 TGAATTCATG ATTTTTTTTT ATGACTAAGG CTTCCTCATC ATTCAATAAA
67901 GTTTTATAAT TTTTATCACA AATATGCTAC ATAATTTTGC TGGATTTATT
67951 CCTAATATTA TATTTTTCTT CTAAGGTAAA TGAATTTTTT TCTGGCTAGA
68001 CTAATAGTTT TTGCTGCCCT ATAGGAATAG TATGGATTTT CTTTTTAAGA
68051 CCTAGTAAAG ATTTCTAGGT AAAAATCATA TAATCTGTAC AAAATATAAT
68101 GAAAAAGGAA ATAATGAAAG CAAAATCCCA AGAATTCTTT TTTCCCCCCT
68151 CAAAGAATGC GTTGAAGAAT GGGCAAATAA AATCGGGAAT ATTTAGAGGT
68201 AGGAAGGTGG TGAAAAGGTT CACAAAGAAG TTTCAATTTC AACAAAAAGC
68251 TTTTAATTCA AAGATTTTTC TTTCTTTTTC TGAGAGTGAT CAGAACATGA
68301 AGATGGCTGT TGGGAGACAA ATCTCCATGT ATCCTTTATG TTCCCAAACA
68351 TCTTTTGGGC AAAGGCACTA AGTGCCTTTG TGCCTGTCTG TCTTTACAAG
68401 TATGTTTATA TCGTGAACAC ACTAGGAAGA TATAGATAGT GTCTCTCTCT
68451 GGAGCAAAGG GTAGGTTTTT TATCTTTATA CAGTAAAGAT AATGTCTCCT
68501 TATGGGGCAA CAATCAGTGA GGATTATTGT CCATTATGAA AGACCTGAGT
68551 TCCTTACCTT GGTTCTCCCC TGTCACATAT CCCGCTACAT GTGCAGCATC
68601 TCCTGGCCCT TTGCACACCC TTCTGTGGGA GTTGGGGCTC AGAATGCAAC
68651 ACAAATGATG ATACTCTAGG TACTACTATT CTGTGCATAA TAAACCATCT
68701 TTTGTCTCTG ACTCAAGAGT CTCATGGCTT TTGCTAGCAT CCATAAAACT
68751 GGCAGGGCAA ATCCTGATAC CCTTCACAAT TCTTGGCAGT TTTGGCAGTG
68801 AGGAAGGGAT ACTGACAGAG ACATGGCTTT TGGAAAAAGA AGGATGATGG
68851 CCTCACAGCT AATTAATAGA CTTTGAAAGA AGTCCATTGG TATTGGTAGC
68901 AAACTTGTGG ACCAAATTGT CTAGTAAGCA GAGCAATAAA TATTCTTCTA
68951 CTCTATTGCT CATTAATGAG GAGGATTTGG GGAGGTAGTT GCAAGCTGAG

FIGURE 3DD

69001 AACCAGGCAA CAGATATGAT TTAACTGTCC TTTAGGCAGG GAGATTACAG
69051 TCTGGCAGTA GTCTCAGGTT CACCTATTGT AACAATTAGT ACTTAGATTC
69101 ATTTGGGCTG TGGGGTGGGG AGAGAGGAAC AAGTTTGCAT TTTCTTTTTT
69151 TGTTGTTGTT GTTTTGTTTT GTTTTGTTTT GTTTTTCAGA CAGAGTCTCA
69201 CTCTGTCGCC CAGGCTGGAG TGCAGTGGCG CGATCTCAGC TTACTGCAAG
69251 CTCCGCCTCC CGGGTTCACG CCATTCTTCT GCCTCTGCCT CCCGAATAGC
69301 TGGGATTACA GGCGCCTGCC ACCACGCCTG GCTAATTTTT TGTATTTTTA
69351 GTAGAGACGG GGTTTCACCG TGTTAGCCAG GATGGTCTCG ATCTGCTGAC
69401 CTCGTGATCC GCCCGCCTCA GTCTCCCAAA GTGCAGTGTT GGGATTACAG
69451 GCGTGCGCCA CCGCGCCCGG CCGCATTTTC TTTCAGACAA CAATTTTAGA
69501 GATACATACC TACAGTGAGC ATGAGAGGAA AATTTATGAC TATTATGTAC
69551 AGAAACCAGG CAAATTATTA GAACTTTGGC TGATTTTCTT GGAAAATGAG
69601 TGAGGTGGGT CATGGAATGT TGGTAATAGA AGAATGGCCA AAACTGGGAT
69651 ATCTTTTTTG CTCAGACTCT CCTACCATCA TGCCAACTTG TAATCCATCT
69701 GGAGATGACA GTAGAAAGTC TTGGAATTTT CTGTAATGGG TTCTATCTGC
69751 TGTAAAATAA CTTTGGCCCT TTTATGGAGA TTTCTCTGGA AGAGACAAAA
69801 TCAAGGGGAA ACTATAGATG AGGCATTAAT TAGTATTGCA CTCTTACAGC
69851 CCCAGATTGG TTTCATAATG CTAATATAAG TGACCCCCTG GAGAATGAAA
69901 AGGTCATCAA AGAAATTTAG ATAAATTCTT GTGGTCAGCC TGAAGTTCTA
69951 GAAAAGTTCT TTCACCCTTA TGTTGGAACC AGGCAAGAAC TTAATAAATG
70001 TTGTATTGAT AGTAGGGCAG CAGGTACATC TATCTAGTCT GAGGATGTTG
70051 TTGCTGTTAC AGCCAATTAG TTTATTCTAG ACACACCATG TGACCCTTGA
70101 AACTAATCTA TGTTATGTAT TCAGATTTCT GAACCATTCA CAGTCAGAGA
70151 GTCATGCACT TTTTAATCCC CAAAGCCATA CAACAATTGG CTGATAATCA
70201 AGGTATGTGA TAGACCTTCC ACATTTCCTA TCATCCATCG GCATCTGGTA
70251 TTGTTAAATG TTGGAAGGGC TTCTTCAAAA ATTAAAAAAA GTTTCCAACT
70301 CTGCCTCTCT CACCTCCTTC TGGTGCACAC ATATAAGTAA GATGGTTTGG
70351 TCACTGAATG TGGCTTCTGC AGAAACTGAT CATCTCCTCT CAGCCTCTAT
70401 GTGGATAATA AGATGAAAGG GTTAAGATTT TATATAAACT TATATTGAAA
70451 AATCAGTGTT CCACCATGAC CATTTCTGGG CATAATGCGT TATTCTTTCT
70501 TATTACAGAA ACCTCAGGCC AGCCTGATTG GTACATCCTC CAAATGGTAG
70551 TCCAGCTAAA GGGAGGCCTC AGGAATTTTT ATTTAATTCT TGTATAGCTA
70601 ACTGGATATG CTTGTTGGCT TCATTTGGTC CTACATTGTA AGAGTAGTAA
70651 CCATTTAGTT GAGTACACAG CTTGCCAAGA CCCCCTGCAA TTGCCCAAAT
70701 GTACCATTAA TGTAGGGGAC ATAATGAGTC TCTGTAAATT TTATAAAAAT
70751 GCCCTTTTCT CCCTTATTCT GACCCTTCCC AACAAAAGAT TTGGGTATGA
70801 TAGAGGATGG TTAGAAAAAA AGTGAAATTA TAGCTACCGG AATGGAACAC
70851 ACTCTGCATT TCAGGTGCAG GAGTAAAATC AATGATCTTT CAGAACTTCC
70901 CCTGGAGCCT CCCACATAAA GAAAAGTCCT TGGTGTGAGT CTCTCAAACT
70951 GTGGTAAATG CTTTAAATGT AATTTCCTTC TGGCTTAACA TTCTTCATCA
71001 GATGTCTCTG CCTGCATTTT GATCATCATT GCTTTTAACC TTGAGGAGAA
71051 GTTTATTAGA AACATCAGGG AAAGATCCTT TATCGCCTAC ACACACACAC
71101 ACACACACAC ACACACACAC ACACACACAA AACCTATTAA CACCTTTGGG
71151 TGTCTTCTTT ACCCCTCTTT CTATAACCAT CAATCACTCA TTCCATGGGG
71201 TGGATGAATG CCATGTAGTG GCTTGCATGG ATAAATAGAT CAGATTGGAC
71251 TGACTGTCCC CAAGCAGTTT CTCTAAAAAA CAGCAATAAT CTCAATTATC

FIGURE 3EE

71301 TGAACTGAAC TGAGAACCCC AAGGCCAACT AGCTGGCCTG GAGGCCCTGT

71351 TGGAGACATT GCCAATCTGT TTCTTCTAAC TGACATCGGT CCATTTTTGG

71401 GGTCACAGTC ATCGTAAATA ACATGTTCTT TCTAGGACCA TTGTGTGAAC

71451 CCTTAAGACT ATATGTCTTT TTTTTTTTTT TTGAGACGGA GTCTTGCTCT

71501 GTCACACAGG CTGGAGAGCA ATAGCGCAAT CTTGGCTCAC TGCAACCCCC

71551 ACCTGCTGGG TTCAAGCAAT TCTTCTGCCT CAGTCTCCTG AGTATCTGAG

71601 ACTACAAGCA CGTGCCACCA TGCCCAGCTA ATTTTTTGTA TTTTTAGTAG

71651 AGATGGGATT TCACCATGCT GGCCAGGCTG GTCTTGAACT CCTGACCTTG

71701 TGATCCGTCC ACCTCGGCCT CCCAAAGTGC TGGGATTACA GGCATGAACC

71751 ACTGCGCCCG GCCAAGACTG CATGTCTTAT GTCCAAATCA TGCATTATTT

71801 TCCCTCCCTA TCCAAAATAT AGTGACTTGA ACCACAGGGA TGGTCATAAG

71851 AGACCTTTGA ATGTTTAAGC AAACACCACC AGTAGATTAT GTAAGCTTCA

71901 GACGATTTCG GAGAGAACTC CAAAATCTAC ACTTGGCTAT GAGGATGAGC

71951 TTCCTGGAGG GATAATTGAC TTATTAGTTT TGTGTGCCCT ACAGGCAGTT

72001 ATCCCTACAA TGGTAATCAT CAAATTAGAA AAATTGGTGA GAAATTTGCC

72051 CCTGAATTTA ATCTAAAAGA TTAATGATAC AATTCCAGTC TTCTTTAGCC

72101 TCAGTTCATG GACTAACGTT TTTATGGATG ATAGGATTGC CCTCAGCTAC

72151 CTCCTTGTGG TCCAAGGAAG AGACTGTGCA ATTGCTTATA TATCCTGCTG

72201 TACCTGATCT AATGCCTCCG GCCAAGTGGA AAGGTTAATA TAGAAACTTA

72251 AGGAGAAAGT CACATGGCTT TGTAAGGGAA ACCTTTATGG TTTGGGGGAT

72301 TTATTCAGTT TGTTGGGTTC AGCAGCTGAA TACATCAGCA GTGTGGTTGA

72351 GGTATATACT GTAGATTGGT CCCATCCTTC TGCTTTGAGT CCTGTTGATA

72401 GTGACCTTAA GTAAAGACAT GTATGAGACA AAGTGGATGA ACTTTTTTCC

72451 AGCATCTGTT GGTTAGATTT ATCCGTGACT GATGGCGTAT TTATGGGAAA

72501 ATTAGTCAGA GAAAAGATGA TGTCAAGACA AGCTGTGGCT ATTGTTGATG

72551 ACTGTTCTCA GTTGATTCTG CTGTCACTAT ATCAGAAGCG AAGAGAAAGA

72601 GTATGAAGCA AACAGACAGA AAACTATGGA AGAAATAATT GAAGACAGTT

72651 GTGGTGGCTC ATGCCTGTAA TCCCAGCACT TTGGGAGGCT GAGGCAGGCA

72701 GATCACTTGA GGTCAGGAGT TTGAGACCAG CCTGGCCAAC ATGGCAAAAC

72751 CCCATCTCTA CTAAAAATAC AAAAATTAGC TGGGTGTGGT GGTGCATGCC

72801 TGTAATCCCA GCTACTTGGG AGGCTGAGGC AGGAGAATCA TTTGAACCTG

72851 GGAGGCAGAG GTTGTAGTGA GCAGAGATCA CACCACTGCA CTCCAGTGTG

72901 GGTGACAGAG TGAAAGAAAG AAAAGAAAGA AAAGGAAGAA AAAGAAAGAA

72951 AGAAAGAGAG AGAGAGAGAG AGAAAGAAAG AAAGAAAGAA AGAAAGAAAG

73001 AAAGAAAGAA AGAAAGAAAG AAAGAAAGAA AGGAAGGAAG GAAAGAAATG

73051 AAAGAAAAGA AAGAAAAGAA GAAAGAAAAT TTCTGGAAAA AAAAAAACCC

73101 CATAAACTTA CACATTGAAG AAGCTCAGGG TTCCCACAGG ATAAATGCTA

73151 AAATAAACAA ACACCAAAAC AAAACCCCAA ATCCCAAAAT TATTAAAAAG

73201 TATCATAACC AAGCTTCTGA AAACTAAAAA CAAAGAAAAT ATTCTAATAG

73251 TAGCCAGAGA AAAATGCAAC AATGATTCCA ATGATTGCAG ATTTCTCATT

73301 AAGAAATATG AGGGCTAAAA GGAAATGGAA CAGCATTTGA GAATGCTGAA

73351 AGAACATTTA GTCCAGGATT CTATATCCAC TGACATATTC TTTAGGCATG

73401 AAAGTTAAAT AAAGGCATTC TCAGACAAAG GGAAACTGAC ATCATACTTA

73451 TTCATGAAAG ACTGTTTTCC CCCTGTGACC AGGAACAAAG TAAGCCTGGC

73501 CACTCTCATC ACTGCCACTT AATATCGTAC TGGAATTCTA GCCAGTATAA

73551 TAATAAATAA ATAAATAGAG AAAGAGCTTG GAAAGGAAAA AATAAAATGG

FIGURE 3FF

73601 TTCATATTCA CATATATATG ATCTCTACCT GGAAAATTCC GTGGAACCTA
73651 CAAAAAAATT AGAAATAATA AGTAAGTTTA ATAAGGTTGA AGGATACAAG
73701 GTCACATGAA AATAAATCAC ATTTCTCTAC ACTAGCATTA AAAATTGGAA
73751 ACAAATTAAA AAATATAATA GCCTCAAGAA ATGAAATATC TAGGTATAAA
73801 TTTAACAAAG CAGGTAGAAG ATCTGTGTTC TGGAAATTAT AAAACCTGAT
73851 GGAAGTAAAT ATTTTGAAAT GAAAGAAGAC CTAAATAAAT GAAGATACAC
73901 ATAGTTTCCA TGGGTTGGAA AAATCATTAC ACTTAAGGTA CTATTCTCCC
73951 TAAATTGATC CATAGATTTA GTGCAATATC AATCAAATTC CAAGCAGGAA
74001 TTTTGTAGAT ACAGAAAAAC TTGTTCTAAA ATGTATATCA AAAGGCAAAA
74051 AGATTAGAAT AGCCAAACAG TTTTGAAAAA GAAGAGCAAA GTTGGGAGAC
74101 TCATACCATC TGACTTTAAG AATTACTCTA AAGCTATAGT AATCAAAAAA
74151 GTGTGGTATT GTCAAAGGAA TAGACAAAGC AATGAACTAA ATGTTTGTGT
74201 TCCCCCAAAA CTCATAGGTT GATATTCTCA CCCCAATATG ATGGTATTAG
74251 GAGATCGGGC CTTTGGGATG AAATTAGGTC ATGAGGGTGA AGCCCTTATG
74301 ATTGGGATTA GTGCCCTTAT AAAATGAACC TGCTCTCTCA GCCTTTTCCA
74351 CCATGTGATA TTACAAGGAG AAAACAGCAG TTTGCAACCC AGAATAAGTC
74401 CTTCACTAGA ACCTAACCAT GTTGGCACCC TGATTTCAGA CATCCAGGCT
74451 TCAGAACTGC AAGAAATAAA TTTCTGTTGT TTATAAGCCA CTCAATCTAT
74501 GGTACTTTGT TATAGTATCC TGGACTGACT GAAATATAGG CCTAGATCAA
74551 TGGGACATTT TAGAAAGTCC AGAAAAACAG TCCAAACAAA TATAACTAAT
74601 TGATTTTTGA AAACGGCACA AACCATGAAG AATATACTTT TTCTGTGTCT
74651 TTTATTTGGG TCTTTTCCAT AAATGGTATG ATATTGGAAC AATTTAACAT
74701 CCATATGCAA AAAATAAAAA AAAAACCCTT GAATTAAACC TCATATCTTA
74751 TACCAAAATT AACTCAAAAT GGACCATAGC TTCAAGATGT AAAATATAAT
74801 ATATGAAACT TTAGAAGAAA ACATAAAAGA AAATCTTTGT GACCTTTAGG
74851 CAGAGAGTTT TCAAATTTGA TACCAAAGCA TAATTTATAA CACACACACA
74901 CAAATCAGAA TTTATCAAAA TTTAAAACTT TTCCTCAGTG AAAGACACTG
74951 CTAAAAGAAT ATAAAGTCAA ACTATAAATG GGGAGAAAAG ACAAATATTG
75001 CAAATCATAT GTTCAAAAAA TGTCGTGTAT CCAGAATGTA TAAAGAAGTC
75051 TCAAAACTCG ACAGTAAGGA ACAGACAACC CAATAAAAAT AAGCAAAATG
75101 TTTTCATAAA CACTTTGCCA GAGAATAAAT ATGGATGTCA AATAAACTCA
75151 GGAAAAATTG TCAACAATAA CCATTATAGA AATGTAAAGT AACACCACAA
75201 TGAAATACCA CTACATAGAA TGGCTACAAA ACAACTGATA ATACCAAGTG
75251 CTGGTGAAGA TTCAGAACAA CTGCAACTCT CTTGCATTGC TCCTGGGAAT
75301 GCAAAATGGT ACAGCCATTC TGGAAAGCAG TTTGGCAGTG TCTCAGAAAG
75351 CTGAACATAA ACTTATCATA TGACTAGCAA TCCTACTTCT AGGTATTTAC
75401 CCTAGAGAAA TAAAATTTAT GTTTACACCA AAGCCTACAC AAGAATACTT
75451 ATAGCAGTTG TATTTATAAT TGGGCCAAGC ACTAGAAACC CAAATGTCCT
75501 CCAGCAGGTG AATGCATAAG CAAAGAGTGG TACATTCCTG CAATGGACTG
75551 TTACTCAGCT ATGAAAAAGA ATGAACTACT AATACACACA ATGACAGATA
75601 AATCTCAAAA TCTCAAAGGC ATTTGCTAAG TGAATAAAGC CAGTCTCAAA
75651 AGGTTATATG CTGCGTTTCC ACTTACATGA CATTTTGCAA AGGCAAAGCT
75701 AGCAGCAGAG ACCAGATCAG TGGTTGCTGG GGGCTACAAA AGGGAGGTAG
75751 GAATGACTAC AAAGGAGGAT CACAAGGGAG TTTTTTTGGT GAATAACATT
75801 CTGCATAGTT TTAGTATAAA TGAATTTTAT CATGATCTAC TCTTCTGAAT
75851 ATTACCCATA AAATATACCA TATATGATGA GAGAAAATGA GTATATGTGT

FIGURE 3GG

75901 CTGAGAAATA GAAATAGTCT CCATGAGTGT TAAAAATAAT CCAAAATAAT
75951 AATCATATTT TATTTATTAT TTATTATATG TATACATTAA TATATACATT
76001 TTACATATTT ATTTTCCCCA ATTATACTGG ACTTCATGTA ATGATGAATT
76051 TGGTTTTAGT TCCTGAGTTT GATTTGGATG AGTGTTGCAG TGGGGAGCAG
76101 GGGAGGTGTG AGCTTGGGGT GGTGCGAGCT TGGGGTGGTG CTGAAGGCAG
76151 TGACTGGGAC ATTTTAAGCT CAGGGTCGTG GTAATACATG TTCATGGTAA
76201 TACATGTCTC TGATTTTTTA GACACCCCAT CACAGAGGGT ACAGTTTATT
76251 CTTGGAACCG AGGATGATGA CGAGGAACAC ATTCCTCATG ACCTTTTCAC
76301 AGAACTGGAT GAGATTTGTT GGCGTGAAGG TGAGGACGCT GAGTGGCGAG
76351 AAACAGCCAG GTGAGGATTT TTGTTAAAGG GTGAAGGTAT ACTAAAGAAT
76401 TTTCATGTTA CTAGAAAAAG AGATTTCTAA TGCAACAATT TTGCAAACAT
76451 CTATGATTGC TGCTGATTTT AGAAGTTGCT CATCTAGCCT GAGCATATCC
76501 TATAACGGGA TATGGGTCAG AAAGAAATCT GAAGGCAGTA ATTACAGTAA
76551 ACGGTGATGC AGAGCCAGCA ACAGCTGCAG TCTTAAAGAT AAACAGTAAC
76601 ATAATTTGTG TGTCATCAAC AAAACAAAAG AAATCTAAAA GTAGTTTATT
76651 TCTATTTTTT CAGCTGCTGG CTTGCACCTA AATTTATGAT AGTATATGAT
76701 AACTTGAAAG TGGGCTTTTT TTAAAAGAAA GGGCAAATAT TATGATAAAA
76751 TGCTTTATGT ACAGTCCTGG ATTTCATGTG CTCTTTCATG AGGATAAAAA
76801 TAATTTGTAA TATGTTTCTA GGATATGCAT ACATTTAAGC ATAGTGGTTT
76851 TTAAAAATAT CTTTTAAAAT CACTTTTTCT ATCATTTGTA ATTAAGATTT
76901 TTACATTGCT ATATAATTGA TAGAGTTCTG TAAAGTTGGA ATTAAATTTT
76951 GTGTTTACTT TTCATTCATT CTTTCTGATT TGCTCAGTTA ACAAACATTT
77001 ATGGAGTGTC CATTATGTGC CAAGTGCAAT GGATATGGCA CAACAACAAA
77051 AATCTTAGAT CTTGCCTTTA GGGATCTTGC AGTCTAATTT AGACAAGAAA
77101 ACAAAGTTGT AAATGCTGTA TAATGAAAGC TGTGATACAG GTGTGCACAA
77151 GAAACTGTGG GCACACCCAG GGTTGTCATT TACCCACTTT TTCACAAATT
77201 TTAATGTGAC TACCAATCAC CTGGAATATT GTTTAAAATG TAGACTTAGT
77251 AGGCCTCAGG CATAGTCAGA CCATGAGGAT GTCGTGTAAA ATGTTTTGGG
77301 TTTGAGAACC AAACTTTGAG TAGCAGTTAT CTAAACCACG AGGTGAAAGA
77351 GAGGATCAGG GTAGCTTCCC TGGAGGAGGC GATTCTTGAG CTAGCTCTTG
77401 TGAGTTGGGT TGGAGTTAGC TAGGCAGAAA AGCAGAGGGG ACAGTATTCT
77451 AGGCAGAGAT AGCAGGACGT GCTTAAATAT ATCATTGACA CAGGTTTAGT
77501 GTTTATTTAT TTATTTATTT ATTTGTCTGA GACAGAGTCT CACTCTGTCC
77551 CCCAGGGTGG AGTGCAGTGA CGAGATCTTG GCTCATTGCA ACCTCTGCCT
77601 CCCTGGTTCA AGCCATTCTC CTGCCCCAGC CTCCCTAGTA GCTGAGACCA
77651 CAGTCATCTG CCACCGCGCC CAGCTAATTT TTGTATTTTT AGTAGAGACA
77701 GGGTTTCACC ATGTTGGCCA GGCTGGTCTC GAACTCCTGA CCTCAAGTCC
77751 TCTACCTGCC TCAGCCTCCC AAAGTGCTGG GATTGCAGGT GTGAACCACC
77801 ATGCCCCTGC TGACACAGGT TTTATTGTTT TGTTAGGCTA TCTCTTCCAC
77851 TGTAGGACAG CATTATTATT AGAAAGACTT TATCTTAAGC ATATTTATTA
77901 GTGGTCCTCA GATTGCAATT GCTGTCTGAA AGCCACAGTA ATTCCATTGG
77951 ATCATGTTAA ACTTGTAGCT GCATTTATTC ATTGACTTTA CTCAGTGTAG
78001 AAATAAATGC TCAATTATGA AAAAGAATGT TGTGAATAAC AATGGCCCAG
78051 TTAATTCTTG TTTGATATAT TTTCAGTGGT CTTTACAGCT CTCCTTTATT
78101 TAAAAAACAC TAAAAACGAG ACAACCAAAA TGGTTACCAA CTAGTTTATC
78151 CTTATTAACA TTTTAAAGTA AATAAAACTA ATAACTGCCA GTATTTAAAA

FIGURE 3HH

78201 TTCACAAGGT ATAGGATGGC AGAAAAGTAA AAATACTTCT CTATGCTTAT
78251 TCACAGTATC TCTTTTCAAA AGTAATCACT GTTAATCTTT TCTGTGCATC
78301 TTTCCCCCAA AATTTAATAG CTAAATCTGC GTGTAAATAT ATGCCCTTTT
78351 AAATTTACAC AATAGGGATT ATATAATATA CAGTGTTCAT ATCTTATCTT
78401 TTCCACTTCA TATATTTGGA ACATTTTCCA TATCAGCAAT TCAAATTTAT
78451 ATCATCTATT TGATGATTGC ATTGCATTCA ATTATATGGA TGAACTTTCA
78501 TTTATTTATT TATCAGTTAG TCTTGATAGA CATTTAGGTT ATTTATTTTT
78551 TTCCATAAAA ACCACTGCAG TGATTGCTCA CACAAATATT TTGTCATTAT
78601 TTTGTAGGTA TTTCTGTAAA GTGAATTTCT AACAATGGCA ACATATGTAG
78651 CAAAGAGAGC AGACATTTTT TCCTTTGATA AATACTGTAA ACTTACCTTC
78701 ATAAAATGTT TTTCTAATTT ACACTTCTAT CAACAGTGTA TGAGAGTGCT
78751 TATTTCCTCC ACATCCTTTC ACAGTAAATT ATCAAACTGC TTAAAATGTC
78801 TTTTCCAGTT TTATAAATAA AACATAAATC TCATTGTTTT AATTTGATTA
78851 TTCAAATTAT TAGTGAGGTA CAACATCTTT TCCTATGTTT TTATTTTTTT
78901 CATGTGAACG AACTATTCAT TTCCTTTATT TATTTTATAT AAATCATTCA
78951 TTATTTTCTT TATTTGCCTT TTGGAACACT TTAAATTGGT GGCATGTTAT
79001 TCAGTATGAA CTAACCTTTT TAATAAAATA ATTTACATAA GTTTCCTCAT
79051 GATGTTTTGT ATTGTAATAC TTTAAATATA GACTTAAATT TAAAATAGTT
79101 TTTATTTAAC CTGGTACATA TTAAGATTAA GAGACTTCTA CCTTACTTTT
79151 TGTCCCAACT GCATCAAAAA CTACGTAGTA GTTTTAAAAA TGTGTAATAT
79201 ATGTGCTCAT CTTCTTTATT TGGTGACAGA AAGGGAATAT AAGATCATTT
79251 TTTCCACAGA TTAGTGATAT AACTTGCTCT TTTATGATTT TGATAAGTTA
79301 AAGTTCCTCC CTCCCTGTTT AAGACCAGAA GCATCTGTCT GCCACGAGTT
79351 ACAAGGAACA GATGTTCCTA TGTGACTTGA AGGAAGGCGA TCTGGTGATT
79401 GTGATGACTA GACAGCTCTG GTTAGTTAGA GTCTCTTTAA CCTATTGCTA
79451 AGAAGTATTT TGTTGAAGCA TTTATTTTAG AGTTCCTTCT TTACCCTCAT
79501 ACTACATAAT AGAGCTGAAA AGTAAAATTG GAATATATAT TTGGGCAAGA
79551 GTAACTCACT TATTCTTACA GTGATTGGTG ATTTTTCATC TTACAGATCA
79601 AATAGTGACC CATTCATTTT AACCAATAAT TTCTTGTAAC TTGCCCACTC
79651 TCATAAAGCT AGGAGATTGC AGAAGCGATA CTAGAATATA GCACTCTCAC
79701 TTTGTTACAG TTGAGCAGGT AGGTTTTTGT TATGCTCTAA TGGATTAACT
79751 CAATAACATG TTTGTCCTAA ACCATCAAAA TATATTGCTG TTGATTTATA
79801 AAGAATAAAA AGATAGTCCA TTTAATTATA CACATTCTCT AATATTATTA
79851 GATGGACCTA TGTTTGTAGC CAAGCTTCTA GAATCTAATG CATGCTATAG
79901 CTGTTTGAGC TTCAGGGAGA CATCTGATGA GCAATGGAAA TAATAACAGA
79951 TATTGAAGGG GAGGGTAGAT GAATTTTAAC AGAGACACAA TGATTCAGGG
80001 AAGGGCAGAA CATATTTATT GAGGATTTCG AAAAGTAACA GGTTTTAAAG
80051 TGGCAGAAGT AATTTTGTTC TGATTGCCCT AATTCATCTA AAAACACTAA
80101 TTTTTGTTAA TTCATGACTC CATCTGATTT TTCACATGCA ATTTAATTCT
80151 AGAAAATCAT TAGCATCACC ATTTAAAGCA CTTCTTTCTT TTGATTAGTA
80201 TTCCAGATGG GATTAATAAT TTTCTACCCT CACAGCAGAA ACAAAAAGAT
80251 ATTTTATCAG CTCATTCCAC CTGTCACGTA TCACATCTTG CATAATTTAT
80301 GCCCACTGTC ATTGCCAAGT AAAACTTAAG CAAAGTTTTA GGTTTTGAAG
80351 CTAAATTTTT GAATCATAAT TATTTAATAA ATGTTCGTAA AAACCAGCTG
80401 GTCACTTTTA AAAACCCTAA AAGAAGCCAT ATGAAGAGAC TAATGAAATC
80451 AACACAATTA CAATGTCCTG CTTATAAATA ACATGTAATG TTATTAATAG

FIGURE 3II

80501 AAAAGTGAGC AAAGCTACCA CAGCTGTGCA GTTGTGGCGA CAACATGTTT
80551 GACTCACTGT AGTTACCCTT TATAAAAGCT TCCCACTAAT GAACTCAGAA
80601 GAGGCAAAGC AGGGGGTAGC GTTAGGCTTC TGATACATAC ATACATGGCA
80651 GAATAGAAAA GGATTATTAC ATCAGAACAA TTTTATTGAT GCTGTGAAGG
80701 CATTTGATCT TCAAAATTAG TAATGGTTTA AGTCATCTGG ATTTTTTACG
80751 GGAAAATAAT GTGGATTAAG AACAGGTGTG AAAATAATAT GGATTAAGAA
80801 CAGTTAATGT CTATAAACAC TAGGTTTGGA TGTATATCAT TTCCCCTTAA
80851 GATGACTATA GGTATTCTTT GATTACATGT TATTCTCTAG CTCCACCCCA
80901 GCCATGTCCC CCAACTATCC TAAAAGAGGA TGTTTTTTTC TTGAGACATC
80951 CATTATTTCC CCGAAGGCTA TAATTTTGGA TGATATAATA ACTCCTTTTG
81001 GATGATAGAC TTACTCTTTT TTTGTTTGGG TAGAATGAGA GGATTAAAAA
81051 TCTTAGAAAA GTTAAACTGA GTTAGTGAGA ATAGAACACC CAGAAAGAGT
81101 TAAGTTCTCT AGAAAAAACC TTCTCTAGAA GCACCTAATT GGCAGAATAA
81151 TTTTATTCTG TATATTTTAA TAGGAGTATT GTAGAGGAGA TTATAATAAA
81201 CTTAATCCTC AAAGAATTCA TGAAACACCT ATTTAATGTT GCTTAGTGGA
81251 AAGAGACTCC AATGTGCTAA TCTTGGATGA AAACAGATCC AGACATACTG
81301 AAGGAAATGA AAATAATCTT CTCAGGGTTT AAATCCACCC CTCTCTCCCC
81351 ACAGAAAAGG TCGTGCAATT GGCCAACAGT TTTATTTATT TATTTTTTAG
81401 CATTATCCCT CACATCTCAT TCATGCTTTG AAACTCTTGT TTGCCTTGGT
81451 TTGCTGTTCA AACAAATGTC AGCAGAGTTT ATTTGAAAAC TGGAACAAAT
81501 TGCAGCACTT TAGGTCATTA ACTGCAATCA GGCATTTTGC AACTGACAGT
81551 ATATTCAGTG ATTACAAATC TTGAAACAGT GTCTGGTGTG CTCCCAGATC
81601 TGTTCATGTC TATCTTTGAA GGATGAAATG GGATTTAAAA GAACAGAAAA
81651 GAGAGATATA GTTATGTATT TATGTGTATG TATTATTTTT AATAGTCTCT
81701 TTAACAATAT TCATTTAAAT ATCTCTTAAA GAATTGGCAT CATTCTGGAG
81751 CTGGCATAGA GCACTGAATC TTGAAATGTT TAGTATCTTT AGTAACTTGA
81801 TATTTGTAAC ATGTGGGCAC CTTTTTATGG AAAGTACCTT CTGCCTCCTC
81851 CTATAATACT CATAAAACCT ATGGGTACAT CAAACCATCC ATGCATATAA
81901 CTTATATTTG GTCATCTTAA CTAACAAACT GTTTGGAACT CCCTGAAGTT
81951 CCAAACTCTC TGAAAAGAAC TCCATTCTTT TCTCAGAGAA TTAAGCCCTC
82001 AACTTGAAGA AAATTATTCT AAAGGAAGGA AGAATAATTG GATTTTTTAA
82051 AATGTCATTT CAGACACATA AATCACTGGA ACGGAATAGA GAACTAAGAA
82101 ATAGACCAGC ACAAGTAAAG CTTACTGATT TTTGACAAAA GACAAAAACT
82151 ATTAAATGAA GGAAAAATAA TCTTTTTGAA AAATAATGTT GGAGCAATTA
82201 GACACCTACA GGCAAAAAAT TAGCCTTGAT ATAAACCTCA CCATGTACAT
82251 AAAAATTAAT TTAAAATAGT TTATAGATTT AAATTTGAAA CATAAAGCCA
82301 TGAAATTTTT AGAAGAAAAT ATTAGATAAA ATCTTCAGGA CCTAGGGCTA
82351 GGTGGCAAGT TTTTAGACAT AACACCAAAA GCGCAATTCG TAAAAGGAAA
82401 TATTTATAGA TTGAACTTTA CCAAAATTAA AATGTTTGTG CTGTGAAAGA
82451 TTCTGTTAAG TGGATGAAAA GGCAAGCTAC AGACAGAAAG TATTTGTAAA
82501 CCAGATATTC AACAAAAGTG TTATATGTAG AACATATAAA GAACTCTCAA
82551 AGTTCAACAG TATGAAAATA AATCAACTAG AAAAGTGGGC AAAAGGCACA
82601 AACAGACATT TCACCAAAGA AGAGATACAT ATGGCGAATA GCACATGGAA
82651 AAATGTTCAA TATCATTAGT CATCAGGAAA ATGCAAATTA GAACTGCTCT
82701 GAGATATTAC TGCATACCTA ATAGAATAGT AAAAATGAAA AAATAGTCAT
82751 AATAACAAAT GTTGGTGAGG ATTTGAAAAA ACTAGATCTT TCATACATTG

FIGURE 3JJ

82801 CTGGTGTGAA TGTAAAATGG TAGAGCCACT TATGGAAAAC AGTTTGACAG
82851 TTTCTGATAA AACTAAACAT GCATTTACTA TATGATCCAG CAATTGGACT
82901 CTTGGGCATT TATCCCAGAG TAATGAAAAC ATGTTCACAC AAAGACCTCT
82951 GCATGAGTGT TCACAGCAAA TTTATTTGTA ATGGCAAAAC CTGCAAACAA
83001 CCTGAATGTC CCCCATGGGT GACTGATTAA ACAAACTGAT ACATCCATCT
83051 TTATAATGGA ATATTACTCT GCAATAAAAA GGAACAAACT ACTGATACAC
83101 ACAATAACTT GAATGTATAT CAAGGGCATT ATGCTTAGTA AAAAAGTGTC
83151 AATCTCAAAA GGTTGCAAAC TATATGATTC CATTTATATA ACACCGTCAA
83201 AATAACAAAA GTATGGTGAT GAAGAATAGA TTAGTGGTTT CCAGGGGACA
83251 GAAATAGAGT GAGGATTGAG AATATAAAGG TGCAGCACAA GGGATTTCTT
83301 TTGTGGTGAT GGAACAGCTT CGTATGTTGA TTGTGGTAGA GGTTACATCT
83351 ATCTATACAT GGGATAAAAA TGCATAGAAT GGAGGCAGGG CATGGTGGCT
83401 CATGCCTGTA ATCCCAGCAC TTTGGGTGGT CAGCTAAGGC AGGAGGATTA
83451 CTTGAGGCCA GGAGTTCAAG ACCAGCCTGG GTAACATAGT GAGACCCCCA
83501 TCTCTATTAA AAAAATACAA AAAAAAAAAA GCCAGACATA GTACCTGGCT
83551 ATGTAGTCCC AGCTACTTGG AAGGCTGAGG TGGAAGGATC ATCTGAACCC
83601 AGGAGGTTGT GGCTGCAGTG AGCTGTGATT GCACCACAGC ACTCCAGTCT
83651 GGATGACAGA GTGAGACTAT GTCTCAAAAA AGTTTTTTTT AATGCATAGA
83701 ACTGCACACA CACACACATA CACACACACA CACACAGCAA CACACAGAGC
83751 CCACATCTTA TCAGTATTCT TTTTTTTTTT CTTTCCAACT TTTATTTTAG
83801 GTTCAAGGGG TATATGTGCA GGGTTGTTTC ATGGGTAAAT TGTGTGTTAC
83851 AGGTTTGGTG TACAGATAAT TTTGTCAGCT GTTAGGTAGT TTTTCAATCC
83901 TCCCATTCCT CCACCTTACC TGATAGATAT TTTTTGTCAC TGAATAGGTA
83951 GTTTTCGATC ATCCCACTCT CCACCCTCAA CTAGGCCTCA GTGTCTGTTG
84001 TTCCCTTCTT TGTAGTCCAT GTGTATGAAT GTTTAGCTCC CACTTGTAAG
84051 AACTTGCAGT ATTTAGTTTT CTGTTCCTGC ATTAGTTCAC TTAGGATAAT
84101 GGCCTCTAGC TCTATTCATG TTGCTGCAAA GGCCATTATC TCATTTTTTA
84151 TAGCTGCATA TTATTGCATG GTGTATATGT ACTACATTTT CTTTATACAG
84201 TCCACCACTG GTAGGCACAT AGGTTGATTC CATGTCTTTG CTATTGTGAA
84251 TAGTGCTGCA ATGAACATAC ATGTGCATGT GTCTCTATGG TAGAACGATT
84301 TATATTCCAT TGGTTATATA CTGAGTAATA GGATTGCTGG GATGAATGAT
84351 AGTTCTGTTT TAAGTTCTTT GAGAAATGTC CAGACTGCTT TCCACAGTGG
84401 CTGAACTAAT TTACATTCCC ACCAGCAATG TATAAGCATT CCCCTTCCTC
84451 TGCAACCTCA CCAGCTTCTG TTATTTTTTG ACTTTTTAGT AATAGCCATT
84501 CTGACTGGTG TGTGATGGTA ACTCATTGTA GTTTTGGTTT AGATTTCTGT
84551 AATGATTAGT GATACTGAGC ATTTTTTCAT ATGCTTGTTG CTACTTGTAT
84601 TAGTATGTCT TCTTTTGAGA AGTGTCTGTT AATATCTTTT GCCCACTTTT
84651 TAAATAGGGT TGTTTGTTTT TTGCTTGTTG ATTTATTTGA GTTCCTTAAA
84701 GATTCTGGAT ATTAAACCTT AGTCAGATGC ATAGTTTGCA AACATTTTCT
84751 CCTACTCTGT AGGTTGTTTA CTCTGTTGAT AGTTTCTTTT ACTGTGCAAA
84801 AGCTCTTTAG GTCAATTAAA TTCCACTTGT CAATTTTTGT TTTTGTTGCA
84851 ATTGCTTTTG GCATCTTCAT CATGAAGTCT TTTCTTTGGC TGATGTCCAG
84901 AATGGTATTT CCTGGATTTT CTTCTAGAGT TTTTATAGTG TTTTTGGCCT
84951 TACATTTAAG TCTTTAATTC ATCTTGAGTT GACTTTTGTA TATGGTGAAA
85001 TGTAGGGGTC CCGTTTCAAT CTTCTGCATA TGGCTAGCCA GTTATCCCAG
85051 CAGCATTTAT TGAGTAGGGA GTCCTTTCCT CATTGCTTAT TTTTATTGGC

FIGURE 3KK

85101 TTTGTTGAAG ATCAGATGGT TCTACATATG TGGCTCTATT TCTGGGTCCT
85151 TTAACCTGTT CCATTGGTCT ATGTGTCTGT TTTTATACTG ATACCATGCT
85201 GTTTTGGTTA CTGTAGCCTT GTAGTATAGT TTGAAGTCAG GTAGTGTGAT
85251 GCCTCCAGCT TCATTCTTTT TGTTCAGGAT CACTTTGGCT ATTTGGGATC
85301 TTTTTTGGTT CCATATGAAT TTTAGAATTT TTTTCTAATT TTGAAAAATG
85351 TGCACTTTTT TCTAATTTTG TAAAAATGTT ATTGGTAGGT TGATAGGAAT
85401 AGCACTGAAT CTGTAAATTG CTTTGGGCAG TATGCCATTT TAATTTTGAT
85451 TTTTTTCCTA TCCATGAGCA TGGAATGTTT TTCCATTTGT TTGTGTCATC
85501 TCTGATTTAT TTCAGCAGTG TCTTGTAATT CTCGTTGCAG AGATCTTTTA
85551 CGTCCCTGTT TAGTTGTATT CCTAGGTATT TTATGATTTT CATGGCTATT
85601 GTGAATGGGA TTGCATTCTT GATTTAGCTC TCAGCTTGAA TGTTATTGGT
85651 GTATATAAAC ATATACCATT TGCATATTGA TTTTTGTATC TTAAAACTTT
85701 GCTGAAGTTG TTTAGCAGAT CTAGGAGCCT CAAGCAGAGA TTATGGTTTT
85751 CCTAGGTATA GTATCATATC ATTTGCGAAG AGAGATGATT TGACTTCCTC
85801 TTTCTCTATC TGGATGGCTT TTATTTTTTA TTCTTTTCTG CTTCTCTGGT
85851 TAGGACTTCC AGGACTTATG TTGAATAAGA ATGGTGAGAG TGGGCATCCT
85901 TGTCTTGTAC CAGTTTTCAA GGAGAATGCT TTCAGCTTTT GCCCATTCAG
85951 TATGATGTTG GCTGTAGGTT TGTTGTAGAT AACACTTATT ATTTTGTGGT
86001 GTACACCTTC AATGCCTAGT TTTTTGCGGG TTTCAAACAT GAGGGGATGT
86051 TTAATTTTAT CAAAAGCCTT TTCTGCATCT TCTGAGATGA TCATGTGGTT
86101 TTTGTTTTTA GTTCTGTTTA TGTAATAAAT AACATTTATT GATTTGCATA
86151 TGTTGAACCA AACTTGCCTC CCAGGAATAA AGCCTATTTG ATCATGGTGG
86201 ATTAGCTTTT TGATGTGCTG CTGGATTTGG TTTGCTAGTA TTTTGTGGAG
86251 GATTTTTGCA TCTATGTTTA TCAGGGGTAT TGGTCTGAAG ATTTTTGTTG
86301 TGAATCTGCC TGGTTTTAGT ATGAGAATGA TGCTGGCCTC ATAGAATGAA
86351 TTGGACAGGA GCCCCTCCTC CTTGTTTTTT GGAATAGTTT CAGTATCCGT
86401 TCTTCTTTAC ACATCTGGTA GAATTTGGCT GTGACTCCAT CTGATCCAAG
86451 GCTTTTTTCT GGTTGATAGG TTTTTTTTAT TACTGATTCA AGTTTGGAAC
86501 TCATTATTGG TGTGTTCATG GTTTCAATTT CTTTCTGGTT AGGCCAGGTA
86551 CACGGCTCAC ACCTCTAATT CCAGCACTTT GGGAGGTTGA GGTGGGTGGA
86601 TCACTTGAGC CCAGACATTT GAGACCAGCT TGGCCAAAAT GGCAAAACCC
86651 TGTCTCTACT AAAAATACAA AAAAATTAGC TAGACACAGT GGTGTGCACC
86701 TGTAGTCCCA GCTACTTGTG ATGTGAGGCA GGAGAATCAC TTGAGTGCAG
86751 GAACAGAGGT TGCAGTGAGT CAAGATTGTG CCACTGCACT CCAGTCTGGG
86801 TGACAGAGCA AGACTCTGTC TCAAAAAAAT AAAATAAAAT AAAATAAAAA
86851 TAATTTATTT CTGGTTTAAT CTTGGGCAGT TGAATATTCC CAGGAATTTA
86901 TCCATTTCTT CTAGCTTTTC TAGTTTGTGA GCACAGAGGT GTTCATAATA
86951 GTCTCTTAGG GTTTTTGTAT TTCTGTCGGG TTAGTAGTAA TGTCTCCTTT
87001 GTTTTCTGAT TGTGTTTATC TTTATCTTCT CCCTTTTAAA AAATTAGTAT
87051 AGCTAATAGT ATATCAATGT TATTTATTCT TTCAAAGAGC CAAGTCTTGG
87101 TTTTGTTGAT CTTTTGTGTG ATTTTTCTCA TCTCCATTTT ATTCTGTTCA
87151 GCTATATTTT GGTTATTTCT TTTCTTCTGT TATATTTGGG ATTGGTTGGC
87201 TTTTGTTTTT CAAATTCCTT CAAGTGTAAT GTTAGGTTGT TAACTTAAGT
87251 TGTAAGTTTT TCTTTTTTAT GTCGACATTT AGCAGTATAA ACTTTCCTCT
87301 CAACACTGCT TTTGCCCTGT CCCAGAGATT CTAGTATGTT GTATCTTTGT
87351 TTTCATTAGT TTCAAGGAAT TTCTCGGTTT CTACAGTTAC TTCATTGTTT

FIGURE 3LL

87401 ACCCAAATCA TTCAGGAGTA GGTTGTTTAG TTTCCATGTA ATTGTATGCT
87451 TTTGAGAGAT CTTCTTGATA TTGATTTATA TTTTTACTGC ATTGTGTTCT
87501 GAGAGCATGT TTGGTATGAT TTTGGTTTTG TAAAATTTGT TGAGAATTGC
87551 TTTATGGCTA AGTATGTGGT CAATTTTAGA ATATGTGCCA TCTGCAGATG
87601 AAAAGAATGT ATATTCTGTT TTTGTTGGGT GGAGTGTTCT GTAGATGTCT
87651 GTTAGGTTCA TTTGGTCAAG TGTTAAGTTT AGGTCCCAAA TATCTCTTGT
87701 TAGTATTCTG CCTCAGTGAT CTGTCCAATG CCATCAGTAG GGTGTTGAAG
87751 TCTTCCATGA TTATATTGCC ATTATCTAAG TCTCTTCCTA AGTCTCTAAG
87801 AACTTGTTTT ATGAATCTGG GTGTTCCAGT ATTGGGTGCA TATATATTTA
87851 GGATAGTTAA GTCTTCTTGT TTAATTGAAC ACTTTATTTT TATGTAATCC
87901 TCTTCTTTTT ACTTTCTGAA TGTTTTTGGT TTAAAGTCAT TCTTTTCTGA
87951 AATAAAAACA GCAACCCCTT TTTAGCATTC TTAAAATTTA AAATTTTACT
88001 TTCAAAGGAG CCAAGATGAA ATGATTTAGA TGCTTTGTCA CTTATTTAGT
88051 CATCTTCACT GTTATCCAGA AGTAAATTTT AACTATAAAT TTTATTATAA
88101 GAAAGGGTTT TATCATTCTA TATAGATCAA GAGGCCCAGG AGTATTTTAA
88151 AAGTGAATTT GTTATTAATG TTATTACAGC TTACAAACAA TATTATTGTA
88201 TGGGTAAGTT TATAGAGTTA CACTTAAGTA GTTAAGAAAC AATATGATTT
88251 TTTAGTAATG TACGAAGACT TTTCAGGATT TTGTACTTGA GTATAATTTT
88301 TGGAGATTAC ATTTAATTCA GTTTATTTAT TTGTTCTTTT GAGGCAGGAT
88351 CTCACTCTAT CAGCCAGGCT AGAGTGCAGT GGCGTTATCA TGGCTCACTC
88401 CAGCCTCGAT CTCCTGGGCT CAAGCAATCC TGCCATCTTA GCCTTCTGAG
88451 CAGCTGGGGC TACAGGCATT CACCTCTACA CCTGGTTAAC ATTTTTTATT
88501 TCTTGCAGAG ACGTCATCTC ACTGTTACCC ATCGCCTCAC TGTTACAACA
88551 TTTTAGAATC AATTGTATAA ACAGGGATGA CAGAAAGTAC CATAGTTCTA
88601 GAAACCTTAA TTGAGGACAT TTTCCATAGA GAAAAACCTG TATTTCCTTA
88651 AATAGCATTA CACCCTTTTA AAACTCTAGG TTTTCTTTAC CACCAAATAG
88701 ACTAGAAAGT AAATTTCCAA TTTAACAAAG TTCTTCAGTC AAAATAACAC
88751 CAGCATACAT GCTATTATAT AGTCTCCCTT CCTTTTGCTC TTTTTATCTG
88801 AAATCCACAG CATATGTCAG TAGATTATAA TTTAATTAGA AGATTTAATA
88851 AAAGTTGTAT CCACTCCCCT GATGCCACTT CCTTATGGAA AGTTTCATTA
88901 TAGCCCTTCC ACAGAATAGT ATGTTTGAGT CTTATTCACA AAGGAAAACC
88951 ATCTATTTTT ATCTAGCACA GTAGGCAATA AAGAAAACAA ATTGGAATAA
89001 TATAAAAGAA AAAGTGAGAA CAAAGAACAT TTTGCAACTT AAGATTGGCT
89051 CCAGACATGG ATGAAAATTA AATGTTAAAT CAGTTGTTTC TGCTATAAGC
89101 ATTAGCATAA GATCTTTGAA CTGAAAAGGA CTATAAATTC AATTCAAATT
89151 ACTATATTAT GGTGGGAAAT GGGCACAGAC TCTGGAGAAA AACAAAATTT
89201 TAAAAAAAAC TTAGAGTTGG ATCCTGGCTT GACAAGGTCA CTGGCTAGGT
89251 GATCTTTGGA AAATTATTTA ATGTGTTTAA TTTGTCTCAT CATTTTACCT
89301 GTGAGAAAAC TGACCCAGAG AAGTTAAAAG ACTTTCCTTT TATTACATGG
89351 TGGTTTAGCT GTATAGAAAA AATATAAATG TCTTTTTATT CTCAACTAGT
89401 TGAAGACACT TTATGTAATA CTATTCCATT AAAATGTCTG CCAAGAGGTT
89451 GTTCCTTTGT GATATTGAAA TCATAATGTG ACTATGGCCT TATTCTCATA
89501 TCTGACAAGA AATAGTAATT TATATTTATT AAAATCATAT TTACTTTCAC
89551 CATTAATTCT GATTAGGATT TTTATGCTGA TATGATTAAC GAAAATGGTG
89601 ATCTATGTCA GTTGGGATAG GCTAAATTAT GCTATAAAAA ATACCCTGCA
89651 ATCTCAGTGG CTTAAACCCA TTTATTTATG GCTCACAATT CATGTCCATC

FIGURE 3MM

89701 ATGAATCATT GGGGTTTTGC TCATCTGTTC ATTGTATTAA ATAGTGACTT
89751 AGAAACCTCA GCTGATAGAT CAGTCTTCAC CTTGAACTTT GCTTGTTGCA
89801 TGTCAAGGAA AGGATGAGCT CCAGAGGATA TCCTCTTGCC AATTAAATAC
89851 TCCAGTCTGA AAGTGACACA CACATAATTT CTGTTCCCAC CTCATTTCCA
89901 GATTTAATCA CAGACACATG GACTCACCCA ATTAAAAGGG AGCCAGGTAG
89951 TGATGTTCTA CACTTTCCTA GGAAGAGAGG GAGAACCAGT TATGACATGA
90001 TATGACCATC ACATGATCTA TGAGGTATTA TGGCCCTGTT TAGGACTGAA
90051 AAACTTTAGG AATAACTAAT ATGAAAACTT TCTGTGTAGA CAAAAATGTT
90101 CTATAAAATT CCCAGCCTTG AAGAGATATA CTGTTGGTGA TTTGTGGCTT
90151 AAATGTAAGT TTTTTCAATA TGGCATATCT ATTCTTACCT GATTGTAAAT
90201 TTTGGCAGGT ATAAGTATTC TTTTCTATTG GCTTCCTTTT CACTTTCTGA
90251 CATTTTTTTT TCTTTTTGCT TCCTAAACAC TAAAAACAGA TCCATAGCTT
90301 TCCTGATCTC TCTTACTACT CTGCACATTA ATCATTCTGA CTGTCTCTTT
90351 TGGTTAGTTA CTTTTGGCTA ATCCACTTGA TTCCCTAACT AGTTACTCCC
90401 ACATATTTGT TGTGTGTTGA AGGTGGATCA TTTTATTACA CAAAATAGTA
90451 AGATAATATA ATATAGAGGA TTTGAATGAT ATTGCTTGGA GAGAGAAATT
90501 GGGGTCAAAA ATGACTAAGG AGAAAAGGAA TGAGGGAAAT GGTGGAGATG
90551 GAGGTAGGCA AGAAGATTTA GGCTAAGGTT CATTAGAAAT GGTGAAACTA
90601 AATTGGTCAT CTATTAGGAT TAGAGACCAA ATTCCTAAAC GGATAAGAAT
90651 TAAGTGGCTT GTGCCAGAGC AATAAAATCA CTGGTTTCTC TTTATCTGTT
90701 CCATTTATCT TGCTTATAGA CAATCTAGGT ATTACTATTC ATTTCAGTCC
90751 AAGAAGACAG TGGTCCCCCA TTTGACATCA TGACATCAAG GTTCTTCTCT
90801 GATTATCCAT CCTGGCAGAA ACACCCAGGG ATGGGGTCTG AGCTCAATTC
90851 TCACATATTC AGTCCCTAGG AAGTGACTGC TATCACTAGC TTTCATCCAA
90901 GCAAGCCTAA CAAGGATTTT TCCTATGCAA CAGGCCCCTA ATTATGCTAG
90951 CCTCCCTCAA GATCTTATAA GAAAATTACC AAGAGACTAA AATATTCAGG
91001 TTTAAGACCT CCCACTAAGG AAAAATAAGT ATTCTTTCAT TTTCTTTTTC
91051 AATTACCATT AACTTTCCAT GAAGTATACA CTCTTTATTA GTGCTACATA
91101 AGATTTTCTC TGACCACTGG TTAAACAATT ATATTTAAAT ATTTCTTCAG
91151 AGTTAGACAA GTTAACAAAA TAACATGAGT TTTCCTTTTT TTCAATTATT
91201 TTTTAATTGC AAAAAGAATA TGAGTTAAAT GGAATTAAAA TGAAATAAGC
91251 CAAATGGCTT AGACTAGCTT TTATATACTT CCAAAACCTA TGAACCAAGA
91301 CACAATATGA CTATTTTTCT ATTTCAACCT TTTATTTTTG GTATAAAGGA
91351 TCATTAACCT ACAATATAAT ATAAACTGTG CTGATAATAT TTGTTTGTAT
91401 AGGTGGTTGA AGTTTGAAGA AGATGTGGAA GATGGAGGAG AAAGGTGGAG
91451 CAAGCCTTAT GTGGCTACTC TTTCATTGCA CAGCTTGTTT GAATTGAGAA
91501 GTTGTATTCT GAATGGAACT GTGTTGCTGG ACATGCATGC CAACACTTTA
91551 GAAGAAATTG CAGGTATATC TTTTCCCCCT TAGTGTATTT TATAGGTACA
91601 GCTAATTTTT TGTTACTCTC TTTTCCTTAT AATTCAATAT ACGTATGAAC
91651 TTTGGAAAAC TAATTCTCAT AATCACTGCA TAAGGTCTTA AAAGTCATTT
91701 TCTTTTACCC TGTTATTTGA GATAAAAGAA GTTGAATCTC AGAGAAATAT
91751 GCTCTAGTTT GGCAGTGCCA AGTCTAGGAC AAGAACCTAG ATATCTTGAT
91801 TCCCATTCAC CATTTATTTT CATTATCATA TTTAGACTCT CACCATTAGA
91851 AAATTAAAGG AAAAAACCTT AGAGCTAGAT ACTTATTTTC AATATTCAAA
91901 CATATGAAAT AACCAAATGA AAAAATTTCA ATATACAGAA AAATGTTGGT
91951 TTAGAATGGA CACAGAAAGG TACGGCCATT CATTTTAAAC TTAATTAAAA

FIGURE 3NN

92001 CCCTTGAATT CCAGAGGAAG CCAAGTGATA CAGTTAGGAT TCGTTTTGTA
92051 ATTCAATACT ATAAACTGAT GAATGATTAG TATTATAATT CAATGATATC
92101 TTATAATACA GACAGGTATA TTTAGGAAAT GTTATTATTA CAGAAATTGA
92151 GTCAAAGAAC TCCTGTATCT TTTGACCAGA AGGCAAACAT ATTTTAGTAA
92201 AAACAAAATA ATACAAAAAG ACAGAAATGA ATTTTGAAAG AGTATAAATG
92251 AAATAATTGA TGGAGGTTTT AAAAACACAA ACAAAGAAAA GAGGCAGTTG
92301 AAAAGTTATT AGTTTGGGAA AAAATAAAAT TCATTCCATA TGATTTGTAT
92351 TTGTGAAGTG AAAAAACTTA ATATCTTAAT CATATTGTAG AGATGAAAAA
92401 CTATATGTGT GTTTTTAATC ATGTATATGA AAATAATATA TTAGAAAAAT
92451 AACATATCTA CTTTAATCTG CAGAACAGCC CCATGAAGTA GATGTCATTC
92501 TCATTTTCCA ATCACAAAAT AGAAACTCTA AAATTGTCAT GGCCTAGATT
92551 TCACCCAAGG GCCCCTGACT TTAAGCCTAG TGTTTTTTCT ATTACACTAC
92601 AACTGCTGTC TGAAGAAAAA GAAATGTCTT GAAGTGAATG TCACCCAAAT
92651 TTTGATGGCA CATTTATCAC CTTAAAAATT ATTGATTTAG TCATTGGTGC
92701 TGATAGGCAC TGCAGTATGT GTGAAAAGAA AAGTAAGTAC TGAAAGATAC
92751 TTTGGCTTGA AATATTAAGC AAAAACTCCA AAAATACTAA AACACACACA
92801 CACACACACA CACACACACA CACACACACA CACACCACAC TGCCCCAAAT
92851 AGGAAAGATA AGCGGTCCTC TTCTGTTTCA TGTAACACCT ATAAAGAGAT
92901 TATTCTTTAA GTTACATAGC TAGAGCCTGA AAGACTTTAT AAAGTTAAAC
92951 ATAAATGTAT AATTTTCAGA AATATCCAGG CTACTGTAGC TGCACTAAAT
93001 CAAGAGAAAA TAGAGAAAAT GATTAACTCA GAAATAAGCA AACTCCCTAA
93051 GAATGCTGAA ATAGTTAGCT ATCCAGCTCA ATTTCTTAGC TTTACATTAT
93101 ATGGTCTTGC TAATACCCAA TAAACATTTT TATATTTTAA TTAGGAATGA
93151 AACAGCAGGC TTTTCACAGT ACTTTCAAGT ATGGGAAGCT CTTAAGTTTG
93201 TAATTATCTT TTTAATGCTC AAACCTGGTT CTTAGTATTA TTATTGTTAT
93251 CCTTATTTAA TAAAGAAAAA AACTAAGATT TAAAAGGTTA AAGGCCTTGC
93301 TCTAAGGCGT TTATTTCTGC CGCTTAAATC GATGATGGCG CTACCTTTAA
93351 AAATAGATTA ATCCAAATAC ATTTTGAAAT GGGAAACAAA ACTGTCACAT
93401 TCTACCACCT GGCAAAATTA GCCTCAGAAC ATACCCTTTA TACTTTTACC
93451 AGTCTTCACA TTTCTTAAAT TATGTAATTT CTAATGCTTT CCTCAGAAAG
93501 TTATTCCTAT GAAGAAATTT TCTCCCAGTA ATTTGACTAA AACACTTCAT
93551 TTTATCACTT TAGTTCACTT TCATTGTCCA AAATTATGCA AATTTTTCCT
93601 AACTCTGTCC CTGTTTCCCA AGCTCAATTC TGTAGAATAT GTGAAGGTTA
93651 ACTGGGTTAA ATCTAGCCTT TTCAAGCAAA TTACATTCTC TAAGTCTACC
93701 CTTACAGTGA AAGTAGTTCA GTTGACGTCT TGATACCCTA AATAGCTTTT
93751 TAGTATTCTT TCTGCTCTTC TAATTAGTGT GTATCTTTCT GACTTTGAAG
93801 TAGCCCAACC TGAATGTCCC ATTTTTCAGT GTAGAACAGC CTGTAAAATG
93851 ACATTTAGAA TGTGTCAGTG GTTTAATGCT AACATCACAA AGAAAAATAT
93901 GATTACAAAT ATTTGTGTTG ATCATTATTA CTTTAGATTC CTTTACTGTC
93951 ATTACTAAGA AGAGATTTCC TCTCATTGAA AACTATAATT TGGCTAAATT
94001 TAAAAGTTAC TTATTTATCC CCTCAATATA AACTCATTAA AATATTTTCT
94051 CTCTATAGTT TGTAATTATT TTCTTATTTT TTACTTCTCC TATTTTCATT
94101 TTATAAAAAT TGAGGGGCAT TACTAAGTTT GTAATAAATA AGCATGCTTT
94151 CCGTTTTTAA GACTTCTAAC TTTGCAAAGT ATTTCCACAT AATTATGTTT
94201 TATTATCATA ACAACATATA AAGTAGGAAA GAGACTATTT CACCATAAAC
94251 AGATAAATAG AAAGTTCTTT ATCAAAGATG ACCTTTGCAG AAATAAAAAT

FIGURE 3OO

94301 AATTTTTTTA TTAACCTATA ATCATAATAT TTGGGGATGG GATCTCCTAT
94351 GTTGCCCAGG CTGGTCTTGA ACTCCTGGGT TCAATTGATC CACCTGCCTC
94401 AGCTTCCCAA AGTGCTAGGA TTACAGGCAT GAGTCACTGT GCCCAACCAT
94451 AATTTTTGTT TTATTCTGTT TCATGATCAT TTGTGGCCAT AGTGATTAAC
94501 AATCAGCCCT GAAACTTTTT CCTCAGCTCT TATTTACCAT GATTTTTCTC
94551 TGTTAGCCAT AATTCACATA CATTAGTCAC TAGTTTCAGT TTTACAAACG
94601 CTAAGTGTAA GAGCTTACCT TTAAGGGTTC TAATCCCTAG TACTTTGTGA
94651 ATACACAGGC TTTACAGTAT TGATGTTTTT CAGACATTTC CTACTAGATG
94701 AATATGACCC AGATATTGTT TTGTAATGAT CAAGGATTTT TATATCAATG
94751 TTTTGATATG TTTTTAACAG ACTCGGATAA TTCCTTAAGA GATTTTTGTA
94801 GACTTAGTAG CAGAAAATCC CATTTGTATC TGGCAGATCT GTCAAGAATT
94851 TCTGATATAA TTAAAGTAGG ATTTTCTTTT GGCTAAGTTA ATTTAAAATA
94901 TATCTGTTTC CCAATGTTTC AGGAAACTCA ATAAATTTAA ACTTTATCCT
94951 TCAAAATATT ACTTAACCTT TTCAAATCCA AAATTCTCCA GATATATCTT
95001 CTTACCACAA TTTACTCTGA TATGGAGATT AATTGTATTG AATATGCTTC
95051 TGAATTATAT TCATATAAAT TACAGGGAAT TTTATGGTCT ATGTTAATCT
95101 CTTTGAAATT AAGCATTATA AAGATTAATG ATGGAAATAT CCTCTCTGCA
95151 GTGTGTGTAT ACTTTAACCT AATTCTGTCA ATGAGAGTTA GGAAGAAATT
95201 AAAACCAAAC CAAAGTTGGT ACCATGGACA GATTATCAAT CATAGCTCCC
95251 AACTCATTTA AACAACCTTT GTTGTTTAAA ATCTTTCATT GAAGGAAGAA
95301 TCTACAGTTT GCTCCACTGA ATGTAATCTG TAGAGTTGGG AGTATAGGAA
95351 TAACCATATA TTTTTTAACC TGCCTATACT GTGACAATCC TTGGTCTGAA
95401 AAGTAAGTAT TCTATTACAG TTTACATCTT TAGTACACAC ATCCCTGTTA
95451 GTGCTGGCAA CCAAACCACA GAATTTAGGA ACTTCGTATC ATATTCCCCC
95501 CCACCTCTCC CAATATCTTT TAAAGTTAAG ACAATGGGTT TTCAAAGCAT
95551 TGATATGATG ATCTTCAAAA AGGCAGAGAT TTATGTAGAA TCTGCAATAT
95601 GTCATAACCT CTAGGGGCTT TCATTCAAGA TACATTATGA TAAAATAGTT
95651 ATCTGATAGG ATGAAAAACA ATTTTTCATT TTTCTGAGGC CTTTTTCCAC
95701 AAGTGCTACT AGTTTTTCTT TTCTTTTCTT TTCTTTTTTT TTTTTTTAGA
95751 CGAAGTCTCG CTCTGTCGCC AGGCTGGAGT GCAGTGGTGC GATCTCAGCT
95801 CACTGCAGCC TCCGCCTCCT GGGTTCAAGC AATTCTCCTA CTTCAATCTC
95851 TTGAGTACCT GGGACTACAG GCACACGGCA ACATGCCCAG CTAATTTTTT
95901 TGTATTTTAG TAGAGACGGG GATTCACCAC GTTGGACAGG GTGGTCTCAA
95951 AGTGCTACTA GTTTTTCTAG AGTCTGCTTA GTGTTAGCAG AGTGTGACCT
96001 ATTTGTCCTT TTTTTCTTTT CTTTTCTTTT CTTTTTTTTT TTTTTTTTTT
96051 TTTTTGAGGC GGAGTCTTGC TTTGTCTCCC AGGCTGGAGT GCAGTGGCGC
96101 AATCTCGGCT CACTGCAAGC TCCGCCTCCC GGGTTCACGC CATTCCCCTG
96151 CCTCAACCTC CCGAGTCGCT GGGACTACAG GCGCCCGCCA CCACGCCCGG
96201 CTGATTTTTT GTATTTTTAG AAGTGACGGG GTTTCACCGT GTTAGCCAGG
96251 ATGGTCTCTA TCCCCTGACC TCGTGATCCG CCCGCCTCGG CCTCCCAAAG
96301 TGCTGGGATT ACAGGCGTGA GCCACCGCGC CTTTTCTCTT ATCACCCAGA
96351 TCCTGGGGCA GAATAGACTG TATTATGTAG GCATAATAGC TTGCTGAGAT
96401 TGCAGGACTT CACTCTGGAC CCAACGTCAT TATGGTCCGT TATTCTTTCA
96451 CACTTTTCAA ATTAATACTA ATATGTATTG TAGTGGTGAA AAGAACAATG
96501 TAAGTGATTA CTAATTCAGA TTCCTTTTGG TACTTAAATG TCACCCTAGT
96551 ATAAATTATA TTCTTAAGCA AAATGAGTAA TTTTTTCCAG ACAAGTAGAT

FIGURE 3PP

96601 ATAATTTGAT ACAGTTATAC TTTGGAGAAG TTTGCTGTGT ATTTCTCTGT
96651 AACTAATGAA CAGATGAGTG TGTTTTTTAA TATTTACTTT TCTTTACATA
96701 ACTGTTTCAA ATAAAAATCT TATCTTTGAA AAACTGTGAA GATAGTGACC
96751 TATGGCTTTT TTAGTGTTCG AGCCTGGAAA CATTGTGCTT TAATAGAAAT
96801 TAAAAATAAT AAACATATGT AGGGTTTATT ATGTGATTAC TTTTGATTCT
96851 GACTAGAATA TTGAACTGGG AATTCATATC ATGGCTTATA TTTGGAACTG
96901 CTTTACAATA ATATCATATT GATATTCTAA TAACCTACTT TACAACTTCC
96951 ATTATGAAGT ATATGCATAT TTTATATACA TTTTTCCATC TTAGCAAGGT
97001 TTCAGTGTAA TGTCATATAC GTTGACAATT TATTATTTCC TTTATTTCAG
97051 ATTAACCCAG GGGTATTATA ACTACTGATC TCCAAAGAAC TGAAAAATAG
97101 ATTTAAATAT TATTCTATAG TATCACACAT TTTCAGAATT GGAAGGGACC
97151 TTTGAGGTAA TTATAGTGAC TGACTTTCAA ACATTCCAGG TATATAATAT
97201 GGGTAACTTC CAAATATTCT TTCTACCTCT TTCCATTGTA AACACAAAAA
97251 TGATAGAGCA CACTATATCC CACGTGCCAC ATATGGCCGA CTGCCTGATT
97301 TTGTAGGGCA TTTGAGCTAA GAATGGTGAT TATATTTTAA ATGGTTGAAA
97351 AATAATAAAA AAGAAGTTAA TATGTTGTGA TGTGAATATT ATATGAAATT
97401 CAAGTTTCAG CATCCTTAAA AAAGTTTCAT TGGAGCATAA CCAGGCTCAT
97451 TTGTGTACAT GTTGCCTGTG GCTGCTTTCT TGCTACAAAG GCAAAATTCA
97501 GTATTTGTGA CAGAGATCAT ATGGCCTACA ATGCCTAAAA TATTTGTTAT
97551 CTGGCTCTGG ACAAAAAGAG CTTGTCTTTC TCTGGTTTAG AGAATTAACT
97601 CTAGAGTGAA GCGCAGTTCT TGATTAGCCT GTCAGTCATA TGAATACCAT
97651 CTCCTTTGCC AGTGATTGGT TCAAGATGGG CAGGGCTATG TCAGTTAGAC
97701 TTAGGATAAT TTTTCCTGGC CAGGTGAAAA ATAACTCATC TAAGAGAAAG
97751 TCACAAAAAA ACAATATATT TCTCACTGGA TATGAACAAA AATATATATT
97801 TCCTTGTTGC TGCTGGAAGC CACCTTATGA CCATAAGGAA AATCAGCCTG
97851 AGGTTAAAGC TTACCCTAGA GGAGGAGGAA GTTAACAAAA TCACAGAGAA
97901 GCAGAATTAT AGCCAACCTA ACTTTGATCT TTCTATTTAT GTGAGCCAAT
97951 AAAATTGTTT TATGTAGTTT AATTTGGGTT TTCTGCTATT GATAAGCCCA
98001 GCTTTGTCTC TACTTGATAA GCTGTCACAA AATATGAACA TATTGAAACC
98051 ACCACAAATT TCAAACCAGG AACCCATAAT CTACATTATG AAAATTACAA
98101 AGAAAATCTT GTTCTGGGAA ATATTTACTG ATAGCCTCAA TATTCCAATC
98151 AGTGCATCAG GTGCCTTATG TCATTAGTCT TGGCACCAAT ATATGATATA
98201 GATATTATTA TCTCCATTTT ACAAATAAGG ACACTTAGGT TATTCAACTT
98251 TGCAAAGTTG TCTAGCTAGA ATGTCATAAA GTGGCCCAAA TCTGTCTCCT
98301 AGTTCATTTC CATTTCACAC TGAAGGAAAA CATTGTTGGT AAGGGAGCAT
98351 TCTGCTAACT TTGAAACCTT TATTGTACTC AAAAAGGCAG TGGAAGGCAG
98401 CTCATTGTAA TCTGCTTTAC ATAAGATGTT AATGCCTAAA AAACAATTAG
98451 AGTTAATGTT TGATAATCAG AAAGCAGATT AATTACACAA ACATCCATTG
98501 ATGTGATCTT TATATCACTA AGAAACTTAA AATACCTTTA CTTATCTATT
98551 TTACTGACAT TTTTGATACT ATGTATGGTA AATAATCTGC TTAATTATAG
98601 ACTTCTGAAA TCTCACCTTC CAGTCTTTGT TTTGCAGGTA TAGAATATCT
98651 TTTTAATCTA ACATTCTCAA GGGAGTGTGT TTCCAGCAAA GTTTGAGAAA
98701 GGGCTGATTT TCTATCCATA TGAAACAGAA TTGTTTACTC TCCAAATTCA
98751 GTAACTATAT CACTTCATAG GCCTCTTTGC ATCAGATTTT CACAGATAGA
98801 CTTTTGTTCA CTTAATGGGG AAACAAGGAA ATTAGTCTGT ACTAGAAAAT
98851 GGGAAAAAAA TTAAAATATA AGTATAAAAC CAATTTTCAA ATTCAAACAC

FIGURE 3QQ

98901 GTTATGAATT GTGAATTCAA ACACATTATG AATTTTCAAA TTCAAACACA
98951 TTATGAATTT TGATATTATC TCTACAGCTA TTCCTCCCAT CAGTGTGGAT
99001 AATAAATAAA TAAAGAACTT TCTTCTCAAT GCAACTATTC CCATTTGAAA
99051 AATAATACTT CATAAGAATT ATATATTTAA ATAGAATGGT TTATAATGAA
99101 AATTTGCCCA AATCTTTCTT ATTCAACATT TCTACAATGG AAGATAAATT
99151 TCCATTTATA ACAGCATGCT TAGAGATTTT TTAAAGAAGT TATTTCTATT
99201 TCAAGATGAA TAATATTGTT TAGGGCTTGC ATATTTGGAC TCAGTGGTTC
99251 ACGGCTGGCA CACGTTCTAG AGGAAAGCTG TGCTTATCTT CTTCCGGCCT
99301 TTTCTCTTCA GATATGGTTC TTGACCAACA AGTGAGCTCA GGTCAGCTGA
99351 ATGAAGATGT ACGCCATAGG GTCCATGAGG CATTGATGAA ACAGCATCAT
99401 CATCAGAATC AGAAAAAACT CACCAACAGG ATTCCCATTG TTCGTTCCTT
99451 TGCTGATATT GGCAAGAAAC AGTCAGAACC AAATTCCATG GACAAAAATG
99501 GTAAATGTTT ATTTATTGTG CTCTTTATGT CTACTATAGG TCTCTGACAT
99551 ATCAAAGCGC TTCTAAATCT TTTAAAACTT GTTTTATTTG AAAATGATTT
99601 TTTGAAATTC AGATTATTGT AGAATTCTTT TCACATGAGT ATATATTCTT
99651 ATTATCAAGC ATCAAGTTGT AAAAATTTTA GAAAAGAACT TAAGTTTCCT
99701 GAAAGGTTCA GGAAAAAAAT GCAAAGAAAA CTAATATTTA ATAAAAAAAC
99751 TTTTAGATTT GGCTGCAGAA AACATAAACA GAGCATCTGT GGCATACCAA
99801 ATAAGGTCCT AGTCTCTGTC CTGTAGCTTA AAAATGTAAT GCAGGGCTTT
99851 GACTTACGCC ATAGATGGTC TTTTAGTTTA AAGGAATCAT GATCATCATC
99901 TAGTGTTTGT GGAAAAAAGA TATTGGTTTC ATGTTGCTCA TAGTCAACAA
99951 ATTCCATTAG AGAAAATGAT TGAAAAGACC AGCCAGTGCA TTGTTTGTGG
100001 CTTTACATAC ATTATGGCTG ATTCCGGTTC AAGGGCTCAT TGCTGTTTGT
100051 AATGCAGCAT CTTCAACATC CATGGAGCCA CCCCACTTAC TATCTTCATA
100101 AACCAACATA GATGACCACC ATTGTTTCCT AGCAATCAAC TTACTATGAT
100151 TTATGCTTCA GACTATTTTG TCTTTCCTGT ATTTTTTGTT CTCTCCTTGC
100201 GTTTATTTAA CCCCTCATCA TTTGCAATAA GGAAGTTGCT TAGGAATCTC
100251 CTGTTATCAT CCATCCTTTC TATTAGTCTC ATGAGAGAAA ATGAAGTTAC
100301 CATGAAGATG ATATGAATTT GTTAAACTTC TGTAGGCTTT AAAAGTTTCC
100351 AGTTCTAGGC CGGGCGCAGT GGCTCACTCC TGTAATCCCA GCACTTTGGG
100401 AGGCCGAGGC GGGCGGATCA AGAGGTCAGG AGATCGTGAC CATCCTGGCT
100451 AACACGGTGA AACCCCGTCT CTACTAAAAA TACAGAAAAA TTAGCCGGGC
100501 GTGGTAGTGG GTGCCTGTAG TCCCAGCTAC TCGGGAGACT GAGGCAGGAG
100551 AATGGTGTGA ACCTGGGTGG CGGAGATTGC AGTGAGCCGA GATCGCGCCA
100601 CTGCACTCCA GCCTGGGCTA CACAGCTAGA CTCTGTCTCA AAAAAAAAAA
100651 GTTTCCAGTT CTAAAAGATA AAAATTAATG AAAAGTATTT TCAAATGCTT
100701 TACTGGAAAG ACTGATTTCC ACGAATGGAT GAAAGCACAT GTAATGACAG
100751 CGTGAAATAT CATGTAATCT CACCCTTATT TTCAAAAGCT TCAGAGATGC
100801 CTTAAATAAA ATGTATGAAA ATTAGTTTTC TTCAGATTTG CTTCATATTA
100851 ATCAGTTTTC ATGCTACTGT ATCAAATATA CATAAAAATA TAGGGTAAAT
100901 GCTTTATTAA ATAGATAAAG ATGATTAGAT GTAATTTTGT CTCAGAATGT
100951 AGAACCAGTT CTTAATGACA AAATCATTTT TGAGATAGTT GATTTTTAGG
101001 GCTTTTCAAT GACTGAATAT AAGTCATTTT TGTTACATAC AAGAGTCTAT
101051 AGATGTGCAC ACTTAAGTTC AATAAAATTA TTATGAATAC TTTATGGTGA
101101 ATACCAACTT GTGTTTGTAG ATTCCACTGA ACATTCTGAG GAGATATAAC
101151 TTGCTTTGAA TCAAATCATA TATTTAAAAC ATATTTATAT TCTAAATCAC

FIGURE 3RR

101201 AATTTGCTTT AAAATATGTG ATACATAAGA TAACAAAACT TGAGGCTTTT
101251 ATATTCTAAG AGATGTATTA CAAATGCAGT GCTTTTGTTA TGCTTATAAT
101301 GCTAGTATTT ATTTGGTATG GTAGTGTTAA AATAGACTCA GTTATTTACT
101351 AATTTTGGCT ATGGGATTAT GTCTACATGA TTCCAAAAAC TTTATTAGAA
101401 TTAACTTCCT AAGAATGCAT GCAGATTTTA TAAAAATGAA CTTTTACCTT
101451 CATAACTTTT GCTAGAAATC AGATAAGATA TATGTCTTTA AGAAAGAGGT
101501 ATGTTTCTTC AAAGAGGCAA GGATCTTGCA TTTTGAACTA GTTAAAATTT
101551 ATACCTTAAA TTTCATTGGA GATAATGTTT ACTATAACAA TAATTTCATT
101601 GCATTTTTTT TTCAGGCAAG AGACTACAGA ATTTATTGGA GCAATGATTT
101651 ATTGTAATAT GCAGATCTAG GCACACTGTT TGTTACTGCT TTAAACTTCT
101701 ATTAAACATT AGAAGAGATG TTAGAATTAT AACTGTGAAT CACAAATCTA
101751 CATATAGTCA CAAGGTTTTC TGAGAGCCTG CTTTTTGTCT TATTTAGGAA
101801 ATGGTTTAGT TTTCCCAAAA ATCAGAATCT GAGTGGTTCT AAAGTGATTC
101851 TGTCACCATC TGTACAATCA GCCTTTATCT GAACACATAC AAATCTTTTC
101901 GAGGCATACG TAAGGGCAAT AAAAACTTGG AAACATTTCT AATAAGATTC
101951 ATATACCCAA TTAAGTATTG TTGTAGAGTA TGCTGTCAGA AGTGGTTTTC
102001 TAAGCCTAAG CTTATAACAC CTCCTTATGA CTCTGTTTTG CTTCCTCACA
102051 CACTTTGCAT AATTATGTGT GTTGAGAATT CTGAAAATAT GTATAGACTT
102101 CACCAATTTA GAAGTAAATC TCCTACCCAA AAGTGAAAAA AAGTACAAAA
102151 GACCTTTACT GCTAAGGTTC TTAATCTACT TATGAACTCT AAAGCCTGAC
102201 AAACTCTAGA TATATAAACA AATTGAAATT AATAGCCGTA AATGTAAATT
102251 GGAAATTCTG TTTTAAATAT GCAATCAAGA TTTAAATTTT TGTGCAATAG
102301 TTCAGAGAGA TGCAAAAGGA TTTCAAAACA TCAAAAAAGT AAAGGTAATA
102351 CTATTAATTT TTAAAAATCT CCTTAGTAAA ATCCATTATG CAAAAAGATT
102401 GACTTTTTTA AAAAAAAAGA TTATAGAATA GAAATTAAAT AGAGCAAAGA
102451 TTTTTCCAGA AACTTTAAAA CAGAACACAT TTTCCTCCCT AAGCATAGTG
102501 GTAGAAATAA GTCCCCGTTT CTTGTTTAAT GTGCTAAAAT TATCTCAAAA
102551 AGGGGATCCT CTAGAGTCGA NNNNNNNNNN NNNNNNNNNN NNNNNNNNNN
102601 NNNNNNNNNN NNNNNNNNNN TCCCGGAAGC AGAGCGGGAG AAAGAAGGCC
102651 CCGTTTCGGG GTGAATGTGC GAAAAGGAGC GCAAAAACAA AGTGAAGCTG
102701 ATGTAGATAA ACCTGAAAGA GTCAGATAGA AGAAAGTTAG TACGTCCTGA
102751 AGTGACTTGT GTCTTGAGCA TGTTACCTTG TGAGTACTCT CCGGGGTTAA
102801 ACATTCAGAC ACTGTATTTC AAACGGGGTC TTCCCCATTT TAAAGATTAG
102851 ATTAATAAAA TAGTGCATTT CCTTGCTCTT CTCCTTCCCA AGTCTACCAT
102901 TCTTTGTCCA TTCCTTTTTT AGTGATTTGT GATAATTTGT CAATCTCATC
102951 TCTAAACACA CTAGTTCACT CGTTTGAATA ATTTTTTTCT TCGTATTCCG
103001 CATTCTCTTC AGGGCTAATG TGAAGGATGC TATGGATTCA CCATGCATTT
103051 TTAATGCCAC CATGCTGTGT TTAACTTTCA CTTTTCATTA AGCATCAAAA
103101 CTGTGAGAAT TAAATGTCTG ATTCTGATGT TTCAATAAAA AGTGACAGTT
103151 ACATTTGGCA AAACAACAGC AAAAATAATA GAAAAATAAT ATCTACTTTG
103201 ACATTAGTAC CCTGAAAAGG GTATGGGTGG TAAAGCACTC AAAATAAATG
103251 TATCGAAAAT ATTAAAATAA TTATTTGAAT TAGGAAGATT TTCTAAAACT
103301 AAAAATAAAA CTTTTAAGGG ATCTAGAAGA CAAATTTTAT CAGTATCTGT
103351 ATTTATCATT TAGGTCATGT ATTCAATTAC CTTTTGAGAC ATTGGGATTA
103401 TAAATCTATT ATAAAATATT ATTATCCTTA TGATAATTTT TATATTTTTG
103451 AAGATAATTT GGGATTATTA GTTTTCTTAA GTATAGGATG TCTTTATTCT

FIGURE 3SS

103501 GCTCTATCCT TTACTAATAA TTTCTAACTC TGTTCGTTTT CCTTCACATA
103551 TCTTTTGTCT CTCCTAATCT GAATACTTTC CAGTTGTACC TTTTATTTAG
103601 GATCTCAAAA GGAGTTACAG TGCAGAAAGT CTCTAACTAC TGTTCAACGC
103651 CATAAGTTAC TGAAAAGCAG TTAGATTTGG GAGCCTGGGA CATAAAGTTC
103701 ACTCTTTAGG CCTGGGTAGA TTTCAGCCCT TAAAGCAATG TACACATATG
103751 TATTGTGCAT AATATTTATT TATGGTTTTG GAAATCAGAC CTATTACATT
103801 GTAGTTACTT CTTTTACAAA TGCTGTACTT TTAATTTTCA GATGCATGCT
103851 GTCTTTACGT ATTTAGATAT ATATGCTTTC TTGCTTTTTT AATACAATGG
103901 TCTCATAAAT AAGATATCCA GGATTTAAAA TTTATCCCTC ATAATGTTCT
103951 ACCTTTGAAG AAAAAATAAA GCTAGAATAA TAATTCTTGA GATTGCTTGA
104001 AAGAAAACTT ATTAAAAGAT TTGTGTATAT TAAATAATTA AACATTGTTT
104051 AATAAATATG ATATTTTCCA CCGCTCCAAG AAAATCAAGA TGACATTGTT
104101 GACACAACTG ATGGGCCTGC CCAGAGGCTA TATTGTCATT ACAGTTTTGG
104151 AATGTCAAGA CTAGATTTTA AGAGCAAACA TAATTCTAGT ATGAAGTGTT
104201 TGAATTTGTT ATTTCTTATA TTGCATTAAT TATTTTCAGG CATACTAATT
104251 TTTCTCCGAG TTTAATTGTT TGCATACTTC TCATGTTTTT GAAGTGTAGC
104301 TCACCTAATC AGCATTTTCT AAATATTTAG CCCTTCTTTC TTCATGTTTT
104351 CTATTCCCAT GAATAAATGT ATTGTTACAC ATGTATGTAA CTTTGTCATT
104401 CATCTTTATA TTTCTTTATT TTGCTCTGTC TTGTGTCTGT CTCTAACAGG
104451 CTCATCTCAT CTCTGTACCT CCCTCATCTC CTACCCTTTG GGTACTCTAA
104501 ATGCGTTGAA GGTTTCTGAG GTAGTGTAAA CCAGCTTGGT CTCTAGGTTA
104551 ATAGTAATGT ACCTCCATGT CTTCATCCCA GTTTCCTTCT AGTGCACGTG
104601 ATTTACAGTG GATTAAGCAG TAGAAAATAA TGATACATTT ATGCAATATA
104651 TTCTATTGAT ACGAATTTGG CCAACTATAA ATTTAAAAGT TGCTAAGCTG
104701 CTGTTTTATA ATACATATGT GCATACTTAA AGAAGAAGAG AACTATAGCT
104751 AAAGACAAAT GAGTTAATAT AATACTCAAC AGGGTTTTTG AGAATATACC
104801 TTTTTTTCCA ATAATGAAGT GTTTTAAAAT ACTGCTATTA ATTAAAGTCA
104851 TGAAATAGTA CTTTTGATGT AATCTCATGT TCCTTCCTTT ATGATAAAGA
104901 AACTGTATGA TAAAGAAAAT GACTTTACCA GTCTCACAAT ACACTTAGTG
104951 AAAAATTTAT GGTGTAACAA GCAGAAAAAC AGCTTCATTT TTCTAGTTAG
105001 TATTTACTCA AAATACTCTC AGTTTTCTCC TATGCTAGCC CCATATCTAT
105051 TATAATTTGC CCTAGAAAAA TTCATGGTCT ATAATAACTT TTTATCTGAC
105101 ACATATGATC CCTACATGAA GACTCAAAGA AAAAAAAATG AATTTGTAAC
105151 TCAAAGAAAA GTAATTCAAA CAGGTGCTAA TATGAATACT ATATAATATA
105201 TATCTTAATT GGTAAGATAT CAAACAAATA TTAGAAATTT TGATTTAAGG
105251 TGAAGAACTG TTGAGCTTAA CAAGTCATAA AAATGTATTT AGTAAATAGC
105301 AGAGGAGATA TTAGGTTTCT CAAATGTTTC CATTTACGTT TAAATAGTCA
105351 CAGATACCAG TTAACCTTAG TGATATCTAC TTTTCATCAG TTTTTTAATA
105401 ACTTACCATG AATATAATAG ATTACTCAAT GTCTTTTTTT CATAGTCATC
105451 CTCATGCCTC AAAATTTTCT AGGTATTATA AAAACAGAAA TAATTGAACA
105501 TTGCAATGAC ATTCATTTAT AGGAAATAAT ATGGGTAGTG ATCAGTGGAC
105551 AAAGGTAATA TAAAGAAACA GGTAAAAAGC ATTTGTTTGT AAGTACTGTG
105601 GTATAGCACT TTAAAAAAAT TACAGTATAC AATTAGCATT CATAAAGCTT
105651 CCACACATAT ATGAGTGCTA AATCCTAAAC TTATACTAAT TTTTTTCCGT
105701 GAGGGAAAAA TATCCTAGCA AATTCTTTGT TATTCTATTA GGAAAATTTT
105751 TACTTCTGGC TGAAGGTAAA ATTCTGTACC TGAAAATTGC CATTCTGTGA

FIGURE 3TT

105801 ACCATTATTG CCTTAGACAT CAGCAAGAAA ATAAGAGATG CCCTTCCAAA
105851 ATCTGAATTT ATTGATTCTT CTTATGTAAT AGTATTTCAG TTAATGAAAT
105901 TAATTTTGAA ATTTAATCCA TCATCTTCTT TTGAAAGATG GTAATAATTG
105951 GCATAAACTA AATAATTGGC ATAGAGAAAA ATATATTTAA ACAATGATTA
106001 CAATTGATAA TAGAACTATA AAATCATTTT TAATTTATGA GGTTTCAATT
106051 AGTTCTATAT ACTATAATTC ATGCTTGAAT ATTGGTTTTA TATATACAGC
106101 AAATAAAATG TTAAGCTTTT TAAAAGACTT CTATTTTTTC AAAATAACCC
106151 AAATCAAACT TGTTAGCTTA ATTTTTAAAT AGTATCTATA CATCGTTCTA
106201 TATACTACCA AGTTGTGAAA ACTGCCTTGA GGATATACAC ATTTAATGTA
106251 CATTGTTTCA ACTTTAACAA ATTAACTTAC ATTTTTAGAA ATAATAGACA
106301 AGAAATAACA AGATTTGAAG TGCTACTTAA ACTTCGCAGG ACTTTTGATG
106351 TGATTAAATA TATTTAATTA TGAATATTAA CGCCTATCAT TTAACTACTG
106401 CTCTGAAATA TAAACGATAT ACAATTTGTG GTCTTTATGT CTATGTCATA
106451 GGCTAGTAGT TTTTATGGCT TTTTATATTA GCATACATTC TATACACATA
106501 CCTAGAATCT AGGACTAGCA AGAAGTTTAC TGTCATCTGA TGTGTCTGCT
106551 GCTAGTTAAA CTCTCAACTA GGTCATTATC AACATCACTT AAAATATTTA
106601 TAAAAATAGT TTCTAAATCC CTTCTTCATT ATCAACCTTA TAAAGTAATA
106651 TTTTCTAAAA TTGTTCTTGT TTTAGAACAA GAATAGCATA CAACAATCTC
106701 AAAATATATT ATTATAATTA TTACATAAAA TATTAATTAT TAATTACTGT
106751 AATTATTTAC AAGGAGAAAT ACAAGTATTA ATATTTTAAA CATACTACCT
106801 GAGCTGAAGG TAATTTATGA AATGCTCTGC TTAAAGTATA CAAATGAAAA
106851 CATAAGGTAT TCAATTTCTT CAAATGTTAA GTTCCGCATA TTTTCTATCC
106901 AATTCAAAAT TTAATCTCTT CAAAGTTAAT GACTTTGCAC TGGGTTGACT
106951 TTTGTTTTGT ATGTGTTTGG TGATAGAACT AAATAATTGT TCTTCCATGT
107001 AGATTTATAC CACACGAAAT GAATTATTAT AAGAAAGCAG ATATGTGTTT
107051 ATTTAATTTA TCCATGACTT GAGTTTCACC ACTCAATTTT ACAGAACATT
107101 CAATAAATTT AGTTTTAAAT ATATCTAATG TTCTAACTCA TTAAAATATG
107151 GAGAAATGAT GTGAAACTGG TGATTGAAGA CATCTGTTGG TAGCACAAAT
107201 GCATTATGTA AAAGATTTTT TTAAAACTAC AGTTATTATT TTGAGAATGG
107251 TAAATTGAAT GGCTGCTAAT GAACAGTTCA CAGTCATAGC TGCACATTGT
107301 GGTTAGAAAT GGGAGAATGA GAATAATTTA TGTAGCTTGT GTGACATTTA
107351 TCTGAAGTTT ATATATTTCC CTAGAATATG CTATACTCAG AATTTGTGAA
107401 CATGGTTTGA GGTGAACTTA TTTTAAAAAG TCATTTTATT TTCATCTTCT
107451 CCAAATATAT TCTTTTACAT TTTTTAATGA AAGTAGTGAA ATCCTTAAGT
107501 TCTAGAAGAA TATTAAGCCT ATTACTTTCT GGCATTATAA CAACTTTAAA
107551 CCATAAAATT ACTCCTATTA ATAAATGACC CCTGCTTGAG AGGCTTACTA
107601 GTCCAAAAAG CAAACTTATA GTAATATTTG AAAGTAAATA ATTAGTATTT
107651 TTAACCACAG TTGGTAATTT CTAGGTAACA AAGAATAAGT GGGTTTTCAG
107701 GAGAGAATTT AAGGGAAAGC GTTTTTGTGG GGTTTTTTTG CATTTACACT
107751 GGGAGTTTAG AGAATTTCAG TCAGAGACTG AAGTGATTAG AGATGACACT
107801 AAAGGTGAAT TTAGAATAAA ATTGGGATTT AGGTAGGTAG AGAGAAGAGC
107851 CAGACAGAGA GAGTATTTCT AACATCTACA ACTGACGTGA ATAAAAGCAG
107901 TATTTTGAGT CATTGAGTTA TTATCATAAA TATGAGCAAG GCTTCAGAGT
107951 TGAGTTGTCT TTATTCATTT CACAGAAAAA AAAAAGATGG GGAGATGTTT
108001 AATTTTCATT GCATTGCTAA CTATGAACAA ATTTCATATG ACTTACTGCA
108051 AACAATGTTT CATATTTAGT GAATGATGGA ATTTAACCTT TTCTAGCCAT

FIGURE 3UU

108101 TGCCACACTC CCAGAGCTAC TATCCACTTA ATTCTCATCA TCTTCCCTAT
108151 AATAGGGAAA AGAACTACAA GATAATTTTG TTTTAATTTA CTGTTAATGC
108201 AAAACTAATA CAATTCAAGT TTTTATCTTT TCTCACATCA CAGACTAGTA
108251 CCAGTATGCT TATATAATAG AATAGTCAGA GGCATAAAAT CATATCCATA
108301 GTGTTCATAC TGTGTGAAAT AAAGGTATTT CTAACTGAAC CCCCTTATAT
108351 AGAAAACTGT AAGAGTTATG GCCAAAGAAA TTTTTTTCAT TGGTTTGGCT
108401 TTTTAGATGC AATAGAACCT AAAAATATAC TGTGTAATTT TCAGATAAAT
108451 ATCCGTCCTT TTTAATGCTT TACATTTTAA ATTCTTCAGG CTGAGCTTAC
108501 ATCTTAACAG ATGTCTATCT TGTCTTTTTA TATACGCCAT TAGTTTTGGT
108551 TGGAATCTAG AAATCAATGA TGCTTCAAAA TCCTGGTAAC ATTTACATAT
108601 TTTGTAGATA ATCCTTATTG AAAATAATCT TTTAGAGTTT TTATCTGAAA
108651 ATATGTTTAT TTTTTACTGA ATTCTCCCAT TTCTACCTGT TACTGATAAT
108701 AAGAATGTTT GTATTAATAT AGATTTATTT ATATTGACCC TTCATTCTTA
108751 CATCATAAAT TTATTAAGAA ACCTGTTAGT CTAGTTTAAT TGAAGTGCCT
108801 ATTTCACTCA GTATGTCTAC AACTATGTAA GTAATTGTTT GTATTCTGTC
108851 ACAACAATCT CTTTTAGCAG GTCAGGTTGT TTCTCCTCAG TCTGCTCCAG
108901 CCTGTGTTGA AAATAAAAAT GATGTTAGCA GAGAAAACAG CACTGTTGAC
108951 TTTAGCAAGG TGAGCTTTTC TCCCTCTCAT CTAAGTAAGT TGCTAAATTA
109001 CTACTAGAAA TTACTACCCA TTTTAAGAGG TGTTGACACA ATATTTTGCA
109051 TGCGCTTTTT GTTTCTTGTC AAAGCTTGAT ATTGTTACAG AAAATGTTAG
109101 CATTAAGTCC ACATGTAACA TTTTGCCTAT TCAAAAAAAA AAAAAAAACT
109151 GAACCTGTGA GTTTTATGCA TAGTATTCAT GTTTCAGCCA CTTGGTATAA
109201 TGTTATCTCT TCCAATAAAA AGAATAACTG GGCTTCACAG GGAATTTAAC
109251 AGAAGTTTAA TCTATTTTTG TTTGTTTGTG TTTGTTGTTC TTTGTTTGTT
109301 TGTTTGAGGC AGAGTCTCGC TCTGTCACCC AGGCTGGAAT GCAGTGGTGC
109351 AATCTTGGCT CACTGCAACC TCCGCCTCCT GGGTTCAAGC AATTCTCAAG
109401 CCTCAGCTTC CCGAGTAGCT GGGATTACAG GCGTGCACCA CTATGTCTGA
109451 CTAATTTTTG TATTTTTAGT AGAGACGGGG TTTCACCATC TTGGACAGGC
109501 TGGTCTCGAA CTCCTGACCT CAGGTGATCC GTCCGCCTCA GCCTCTCAAA
109551 GTGCTGGGAT TACAGGCGTG AGCCACCCCG CCCGGCCAAG TTTAATCTAT
109601 TGTTTAAAAA CTTTGGCTAG TTTGTGTTCA AAATCACTTT TCTTCTATTT
109651 GTGGGAAAGC AAATCATAAT ATAAAACTGA ATTGTTAATG TAATTAAGGA
109701 AAAGTCATTA CTGTAAGGAA ATCCTAGAAG GACACAGCAA AACTGAGCAG
109751 AGTTTTAAAT AAAAACATAT TAAGAACTGA CTGTGTTGAG GGATACATCT
109801 AATTGGAGAC AACTGAAGTG AAATCATTAA CTTGAATGTA TTCTTAGAAA
109851 ATGAGTCAGT GACAATGATG TGATTTTGAT TAGCAAATTC CTGACATTGT
109901 ATATGTGCCA TTGCAAGCTA TGGCAAAGTA ACAATTGAGT GGAAAAGAGG
109951 AGTTTCTAGC CGGGTGTGGT GGCGCGTGCC TGTGGTTCCA GCCACTTGGG
110001 AGGCTGAGGT GGGAGGATTG CTTGAGCCTA GGAGGCAGAG ATTGCAGTGA
110051 GCTGAGGTCG TGTCACTGCA CTCCAGCCTG GGTGACAGAG TGAGACCACA
110101 TCTCAAAAAA AAAAAAAAAA AAAAAAAAAA GACAATGCAA AAGAGAAGGA
110151 GTTTGAATAC TTGGTGAAAA TACGGCAGGT TAACAATTCT CTTTATCTGA
110201 GTGGCTGAAA TAGAAGTAAC TCAGAGTAAT ATTTTAATAA AGCCCTTAGC
110251 ACTGGCAATA ATTATAGTAG TGGGAGGAGG TGGGAATGGA TGGAAGCAGT
110301 AGAGGAAGTA GCCTGAATCA AGGTTCTGAA AAGATTAATA GTGATCAGCT
110351 CCTTGGACCT GTTTCAGAAT CCCTCTGACA ATGCCTAAAT AATCTAGATC

FIGURE 3VV

110401 TAGTTACGTG CATGCTCTCC CTCTGGTGCC TGGCGGAGTC TCCGTGGGAG
110451 CATGGTGTAC CAGCTTAAGT CTGTTAATTA TGCGTGCAGG GACTGGGAGG
110501 CCAACAAAAG GGGCATACTA GTCCATGTGG GATGAAACAA AGGCATGAAA
110551 AAGGACCTCC ACACCAGCAA GAGAGAGAGG TGAGGGCATA CTCGGGCTCT
110601 ATTTCTACAG TGGTTCAAAG CTCATTTCAC TGTATGGAGG CATGTGATTC
110651 AAACATTAAG CCAGTTGAAA TGTATTCCAT CTGCCACTCT AAGAACTATC
110701 TTTTTAAAGC ATTGCATCTT CATTCATCTG CAAGTTGGAA AAAGTTGTCA
110751 CAAACTGCCA TACATTTAAT TTCTGATATT CTTAATTTGA AATGATCTTA
110801 AAAGCAATAA TGTAACGAGC TGCATATTTA TGTATAAATG CATTAACAAC
110851 ATAAAGAAGG CATATTTAAC ATCCTCAGAA ACAATCATTA TAAAGCACAT
110901 AGCTCCTCCT TTCAAATAAA TTGTGATTTA ACTTTTTAAA AATAATATAA
110951 CCTTTATACA CTGATTGTGT ATCTCCATAT CATGTTGCTT TTGGTTGTGT
111001 GACCTGCCTT TGCAGCCTTC AAGAATACTT CATCACATAT GAAAGAAAAT
111051 GAAGATTGCC AGTTGTAGGC AGTAGTCTCA TCTTCTGGTC CCCCCTCAAA
111101 CAGTTAAAAC TATGGAAGAG TCAAACTTCG ATTTCCTTTC TTTTAATCCT
111151 TTTCTTTCTC TTCACATTTG CGATCACTGG CCCGTTTCAT CTTTTAATAG
111201 GCAAGTTAAA TTTCTAGAGC CCTCTACTTA GTGTCAGCTG TTGTTCATAG
111251 CATGGCACAC TGGAAAGTCT CTTGTTCATA GCATGGCACA CTGGAAAGAA
111301 TGTGGCTTTT GAGAAACAGC ATGAGATCTT GAATCCCAAC TCTGGCATTA
111351 TAAACTAGCT GATCTTGGAG AAGTTCTCTA AAGTTCAGCC TTCTCATTTG
111401 CAAAGTAAGA AAACTATTTA CAATTTCGTT GTGAAGATTT AATGAGCTAA
111451 TATAGAGGGA GGTGCTGGAA CAGTGCTTGA CTTGTAGCAG GTATTTAATA
111501 AAAGGTGGTT ACACTTATTA GTGTGGTTAT TAGTAGTAGT AGAGATAATA
111551 GTGTCAGAAA TGAAACACCA GACCATAATT GAATGTTTTG GTCTCCACTG
111601 GGTCTTTAGT GCCTTGAATA GTATTTGGTA TATATTTGTT GAATGAATCC
111651 TTCAAGATTC AAAATAATGT AAGCCCAGTT TTGGAATTTA AAAAAGACTA
111701 AGTAAGATTT TTTACTTTAA AGTCTGAGAG GGCAGAAAAG TAGAGTTTGA
111751 AAAGAGCAAT TGTGATCTAT CACTATGGAA ACAAATTTTA GTGCCAGATT
111801 TTGCAGGTGC ATGAGTTGAT ATTTTTTAGC CTTATGATTT TAGTTTAGTA
111851 GTGAATTTAT CAGAATTCAC CTAGTCTCCA GGTTAGTTCT CTGTTTTAAT
111901 ATTTTAAGTC TTAATATACA GATTCCAAAA CCCCAGAATC TTAATATGCA
111951 GATTCCAAAC ATTTTGAGGT GTTAAGAAAA AAAAGGTCTT TATTCATCTT
112001 ATATGATTTG ATCATATTTA TTCCATCTAC ATTCAACCTA CATATTTGTA
112051 ACCCTTCCAG TGGATAGACG TATCAAACTT ACTTAAGGAA TGATTAGGAA
112101 AATAACTGGA ATTATCAGGT TTTAGCTTCC CATAATACTT TTAAAAAGCA
112151 GATGTGTCAA AGCAATATTT GTTTTTGTTT TTCAAGCTGA CAGTGGAACG
112201 TAGGTATTTT ATGTTGGTGG TGTTTTCTTT TACTTCAAAT GACCCAGAGA
112251 TGGCTTCACA TAATTTTCTA CATAGAAAGA ACTTCCGTCT GCATCTAGCT
112301 TTAGTGTATG AAACATATTA GAGAGAGTTG TATTATTTAA TCCTAGAACT
112351 GTAGGAAACC TTAGACATCT CCTCATTTAG TCAGCAAGAA AGCTGAATTA
112401 TAGAGTGATT AAGAGAGCTG CTCAAGATCA CTGGCGAGTT AGTGTCAAGA
112451 CACCATTTCT TCCCAGAGAA TCCCTATGAA GTTTCTTGTA CTTTCTATAA
112501 GGGGCTGAAG GCTTAAATTT TCTCCTTAAA TTTCCATCTG TTTTTCCTTT
112551 AACTCTTAGC GTGTAGTTTG CCCAGACACT TCCAATTTCA CCTTGGTCTT
112601 CTATCTAATC TCATTCCTTG TTCCCTAGAA ATGTAACTGT TTCTCATCCA
112651 CAGATTAAGT ATCAAAGGCC CAGAAAGAAA TCTTTCCACT ACCAGCATAA

FIGURE 3WW

112701 AGGTGAGGTC TGGGCAGCCC AGAAGCATGA GTGTAAATAC AGACCCAGAA
112751 GAGTATAGCT CGATTTCTTC AAGATCCTAT TCAGAGGACC AGAAACTTCC
112801 AGGATTTCCT TCTTGTCCAT TCCAAGTGTT TGTGTTCACT TGACAGTTTT
112851 CTTAGGGATG TAGTTCAACC TAGATTCTCT AGAGCTGCTT TACATATTTA
112901 TAATTTTATA AGAGGTCACA TTCAGGTCTT TAAACATAAT ATTTTATTAT
112951 ATTAAAAGTT GCTTAGGGGG CCAAGGGCAT GGTGGCTGAC ACCTGTAATC
113001 CCAGCATTTT GAGAGGCCAA GTCAGGAGGA TCACTTGAGC TTAGGAGTTC
113051 GAGATCAACC TAGGCAACAT GGTAAGACCT CATCTCTACA AAATCTAGAA
113101 AAAATCAGCC AGGCATGGTG GCGCACCTGT AGTCCCAGCT ACTCAGAAGG
113151 CTGAAATGGA AGGATCAGGA TGGCTTGAGC CAGGAAGTTC GAGGCTGCAG
113201 TGAGCTGGGA TCGCACCACT GCACTCCACT CTGGATGACA CAAGGAGACC
113251 CTGTCTCAAA AACTTAACCA AACCAAAAAA GATAGTTGGT TTGTCAAATA
113301 AGTTTCTTCA TGAAGTATAT AGTACACAAA CACAAAATAT AGGGTTGCCC
113351 CACGAATAAT ATAATATGTA ACTATACATA ATATAGGAAT AATATAATTA
113401 GATAATATAT AATCGATTAC TTCCCAAAGT ATATGATTAC TCCAAGAATA
113451 ATGTAATGTA ATGAGTATAA TACAATGGCT ACCCCAGATA TGTGCTATAG
113501 TACTATAACT TATTCCATTT GAAGTCAAAA GATGAATTTG CTTATCCTGA
113551 ATTTAAATTC TGTATATTTT AATGTTTTTT CTAAATAACA GGTATCAATG
113601 ATATATTAGG TATTTTGTAA ATTTAAAGAT CATATGTAAT GACCATATAT
113651 TTTCTTTTAC AAAATTTAAC TATTTTAACA TACTATGTAC TTCTTGATTT
113701 AATTAAATTT CATCTTTAAA CAGTTATTTC TATAATCACC AGTTGCCCGA
113751 GGCACAGACT TTCATAGTTA AGACAATGGC ATTTGTCAAG CAATAAATGA
113801 GTTTATAGAA TTTTCAAGGT GGAATTTAAA TTTCAGGTAT TATCAATATA
113851 ATTCATATTA TCAATTATGG ATTTTAAAAA AAGATGTTTT CTCATTTTAA
113901 ATTTTGTTCA GTATATTTAT ATTGTATCAT TGTTCTTTCC ATTGAGAGAG
113951 AAAACTTAAC TGTTTATTCT TTTAGTAACA GAAAGGATTA TGAGATTTAT
114001 TATGTTTTCC TCACAGAGCT GATAGTATAT GGGAAATCTT CTATTCCCTC
114051 CTTGGGAATT TTGGCATTAC AATAAAAATG TAAAGCATTA CTAATTTAAA
114101 GCATCTTAAA TGTGTACATT TCTCCTAACT AGATAAATAC CTACAAAAAT
114151 ACCACAATAA ATCCCATGAA ATTTAACCTT ACTTATTATA GTAAATAAAT
114201 ACTTTTGCTA TCTATAAACT AAAAGATCAG ATTCCACAAA AGCAAAATAT
114251 TTGCTGTATA ATCCAGTGTA CATTAATTAT GAATTTACAA ATTTATATTT
114301 GGAGTACATT TGTAGCTTAA AAATTTTGGA TGTATAATAT TTGTTAGATA
114351 TTTTTATAGG CAGTTTTGCT TTGTTAAATC ATTCTTCCTT TCCTTTAAAA
114401 TAAAATAATG ATTCTATTTA ATATTTTTGA TGGAGTACTG TAGGATATTT
114451 TTATATTTAA TCCTTGTGAA AGAACATATG CTTCCTATAC TAGGTTATAT
114501 ATTTTGTGGT ATCCTTATTC TTTGGAAAGA TTAATTAGTT ACAAAACTTA
114551 CAAATAGCTG TACTATCATC TTGATTTCAG AAAGCAACAT ATTTAATGTA
114601 GTCACTAAGT ATTACTATGG ATTTTTTCAT TTTAAATTTT TGAGAAAAAT
114651 ATTCTCAAAT CATTAAACCT GCAAAAGAAC TATCTAGGCT AAAAAAAATC
114701 TTCTCAGCCC CACTCATATT TGCCAGAGCT CATTCCTCTC TCGGCTATTC
114751 TCACTTTGAT CTTTGGCCCT CATTTCATTA ACATCAGAGC ATAAGATCAA
114801 TTACTAGAGC AGATAAATTC TTACTCCCCT AAAAACAGAG TTTCATAAAA
114851 AGCTACTCAA GTGAATTAGA AACAAGACAT AGATCTTGTA CAATTTACAT
114901 TAAAGTCACT GCTTGTCTTT CACTGAGGCC CTATGCATAA AAATTGATAT
114951 TTATTGTTAA GGATATTTTG CATTCATTTT TTAGACTTCA CCCTTTATTC

FIGURE 3XX

115001 TTAGCATTTC TTCTCGTTAA TGATCACTTT TGCTTTGTGT ACATTCATTT
115051 CGATCACAAA CATCTCATGT CAGAAATTCA ACTATAGCTC TTCAGTAACT
115101 CCAAATGTTA ATATTTTTTT CTTATTTTTT TCTACTGTGT CATATCTAAA
115151 TTCTCAGATG AAAAACCAAT ATTGAAGAAT TACCAGGCCA AGTATATAAT
115201 GTGAAGAATA TAGAACAACT AGAAAAGAGA AGAAGGTTAA AGTCATAATT
115251 TATACTGTAA AGAGAAACAG GATTATATTT CTTTTGACAT AAGCATATTT
115301 GAGTATCAAT TAAAATGTAT TATGTACAAA AATTAGGTAA TGTAGTATAA
115351 AATATTAAAT CTGTTGGCAA ATGCTAATTA AATTATGGTT AAAGAATAGT
115401 TATTTAACTG AACTCACATA CTTTTCCCTG TCTAAAATTT CAAGATTGTT
115451 GAGGCTGGAG AAACTTCTTT TAAAAATAAT AAATAGAAGT ACCAGAGTAC
115501 TCAGCTTATT GATGACAAGT TAAAATAATC CACAAGTAAA GAAAAAAGGT
115551 TATTATAGAA AAAGGGCAAA TGAGATGTTT AACTGTGTGT ATTTATTTAA
115601 ACTATATTTA TTCATGGATT ACTATATGTG AAGCACTGTG CAAGAATATG
115651 ATTTACCAGA TTTTTCCAAT TTTGATTTAT CATATTTACC TGGTGATGCT
115701 TGCAGGTTGA TCTGCATTTT ATGAAAAAGA TTCCTCCAGG TGCTGAAGCA
115751 TCGAACATCT TAGTGGGAGA ACTGGAGTTC TTGGATCGAA CAGTAGTTGC
115801 GTTTGTCAGG TTGTCTCCAG CTGTATTGCT TCAAGGACTG GCTGAAGTCC
115851 CAATCCCAAC CAGGTAAAAA GTATAAAAGC GTCTTTTGTA TTTTTCTTAA
115901 ACCATCTTTT CATGGAAAGA AAATGAGGAT TCAATGTAAT TTTCTGTTAG
115951 AGTTTTGACT AGAAACTAAT GTGAAATCCA CAAAACTACT ATTAATTTTT
116001 GTTTGTGGAG GAGGGGAAAA GTGCTTTAAA AATTATTCTC TTCTTTCCTC
116051 CCTTCTCTCA AACTTCTGCT TCATTTTAGG CACATTCCTC ATCTCAAGGT
116101 ACCCTGAAGC CATATGAATC CTTTTTTTTT TTTTTTTTTT TACATTTTTG
116151 GTAAAAGAAG TGGTAACATG TTAGCTTTTT CTCAAAGATT GCATTAAATT
116201 GTCTGCTATA GAAAGAAAGG ATCCTGTGCA TGAGTGCGGT CAAACTCAAA
116251 AACAGCAAAG TTACTAAGGT TTGCTTACAC TTGAATAAGA AGGCCTTCAA
116301 AATGCATGTA AGTGCCATCG TTAGGATAGC GTCAAATATA TGTTTCAATC
116351 CTAGGCACAG TGGGCTTCCG ACACACAGGG TCTGTAGAAA CACTGGTAGA
116401 AGTATTATCG CAGTGTGGTT GGATGTGAGT TAAAGGTACA AATTTAATTT
116451 GATGATCAGA ACTTGTTTCT CATTTAACAA TAAAATAACA ACTTAGGGAT
116501 AATACAAACT GAATTATGCT TTTCTCATTT TTTAGAATAA GGCTATCCAT
116551 TACTAAAACT GTAAAAAAAA GAAAAAGATA AAAAAAAGAA AGGAAACACA
116601 GAATATTGAC TTTAGCACAT TAATTTCCAA GCAATTTACC CAGGAACCTT
116651 GTTTTCTTCC ATACTTCTAC CATCAGTGTG ATTCCAAAAT GCAGATAGCC
116701 TTTTACTCTA GTCCTATTCC CACAGCAAAA CATGTATATT TAGGGCCCCG
116751 TTCCCATATG GCTGGTGCCC TTTGTTTGAT GCTACAGCTA TCTCAAAAGC
116801 TGTTAGTGCG CCTCCTCTTC CAAACATTGA ATACCTTAGC CAAGTTACTT
116851 GATGAAAAGT TCAGGTACTG TATCAACTGT AGAATATATG TCCTCTATGA
116901 ATCTTTGGCC TTAACTCAAA ATATAGCAGA TTACATAACT CCATGCTTTG
116951 ATTATGGATA AAATATTCTA CAACTATGGA ACAGCACAGC CAGGAGAGGC
117001 CTCATTTTTT AAGAGCTCAG CTGACTGGAA CGGGATTCAG TGGTTAAGTA
117051 CCTATGTCTG ACTATGGTTT GGGGGAGGAA TCTAGTTACT GTTCAGATTA
117101 TAGAAAGAAG TCTATGTTTA TCCTGTTTGA GAGTTACTGA GATGACTGAT
117151 ACACATCAAC TTTTATGTAC AAAGGGAAAG GATGAACTGA GCACATTAAA
117201 GTGGCATCTG ACTGTGTGAT TCAGGCTATA TGTTTTCTAT GGACAACCTG
117251 TAACCTATTC AAGGTTTCTG GGAGTCTGGG ATTTATATCT AAGATGTTAA

FIGURE 3YY

117301 ACTTGCTAAT GGTAGAGTTA CTATTATAGC AGTTTAAAAT TTCTTTTCAG
117351 TCCTCCAAGC AGTGCATTTG TGTTCCACCA CTTAGGAAGG TGTCTGGTGA
117401 ACTATGAGCA AATGATGGCT ATTTACGACA ATGATAGTGC TTGTATTTCA
117451 AAAGAAGGAA AAGAAAAATT CCCATGAGTA GAAAAAAGCC GTGATGGGGT
117501 TATATACCCT TACTGTGAAA ACTGTCAGGT TTAAGTGACC TTATTTCATA
117551 CTGAGATAGC AAAATATGTG TAGAGAACAA CGGAGAAAAA AATTAGGGCC
117601 ACTGTAGAGC AACTGTATGA GAAAAGATTT AAAGACAAGA CTATTTAGTT
117651 AGGAAAGGTG AAAAATGGAA GATTAGTTGG ACAAACAAAA TAAAGAAAGC
117701 CATTCAGGGT TTCTTATTAT CCTTTTTTTG GGAAGACAAA AGGCATCCTA
117751 TTAATACGAT GGCAACACAT AGTAGAAAGG TCAGAAAATA ATCTTTTAGA
117801 TCTTTAAAAA TAGCCCATGG AATGGAAACC TGAAAAATAG CAAGATGTAC
117851 ATAGGTTAGG AAGTTTCTTA AAAAGCTATT ATAGTTGATA AAGCACCTGC
117901 TACCGAATTA AACCATTCCT GTTTTTAATG TATACTGGAC ATTTCTACAT
117951 AGTAGAAATT GGCTTGGGTT CAGTTGTCAC TGGCACACAC AAAAAATATT
118001 GTCATATCCT CTACAATTGT GTAATATTTG CCTCATGTAA AAACATGTAC
118051 AATCTCTAAA GATTACAACT AAATGAGGAG TAGAATTATA GTAACTATTT
118101 TAGTACACCT TGTGAAGTCA TTAGTCTTCA TACTTAACAG CATAAACCAT
118151 TTAACAAATT AACACCACAG AATGATATGG CAGAATATAG GGCATTCTTT
118201 AATTTTCAAA ATTTCCCAGA AGGATTGACC TTCTCAGAGA CAGGGCAATT
118251 ACCAGTCTGC TAAAGTTAGA GTATCTATTG ATTTCTTTAA AAGCACCACT
118301 TGTGATGATG AATTTGCCAA ATGTTCGACC TAATATAGAT GGAATATTAT
118351 AGTGCAGATG CTATTTTTAT TCCTCAGCAT TATAAATAAT AGATCATTAA
118401 CTCCCCATTT TCTTCTACGT GGCTGATCTT TGATTCCTGA CAATAATTTT
118451 TTATAATGAA AATTGCACAT ACACCTACTG TTTTTTGACT CTATATTTTC
118501 TCTGTTTTGC TACTGTGTTA CCTTTGTCCC CTTTGAACTA TTCGCCATTT
118551 TGCATACAAG TGAGTTTTCT TCCTTCCAAT TTAGAAAGGT CTAATCAGAT
118601 TTTACTTTTC CCACTTTCCT TCTCTAAGGA TCATAGAATC CTTAAAATTC
118651 CCAATAACAA CTGCACATGC TGTACAGATA ACTAAACGGA GAAACACTGT
118701 GATAAAAAAA AAAAACACGG AAAACCATGC ATTCCCATTG CTTGAGGATC
118751 TTAAGCATAA GGGTCAATCA TGGTAAAATT TTTCAAAATA ATAATGAACT
118801 ATGAAAAACT ATGGAAGTAT TTGCCATCAC AATCTCCATT TTCAGTAATT
118851 CCTTTGAGAT GAGTGATTCT GTATTACTAA AATTATTTTT ATATTTCTAC
118901 CTTAAAACAT TTTTTTTCTT CTTAATTACA GATTTTTGTT CATTCTTCTG
118951 GGACCCCTGG GAAAGGGTCA ACAGTACCAT GAGATTGGCA GATCAATTGC
119001 AACCCTAATG ACAGATGAGG TATTTATTCA AGTTCTTTGG GAACATTTTC
119051 CCCCATTAGG TATACCTAAA ACTTTTGGAG GTCCTCTTTT CATGACAGTT
119101 TGTTGTGAAT CAGATTTCTC TGTATTGAAT CCCATTCTCC CATGCTTCTG
119151 CTATAAAATC TCCTTTAGAA AAATGTTTCC CAAAGGGATA ATAAATTAAC
119201 ACCCATGAAT ATAATATTTT AAAACTTCAT AGTGTAAAGA AATTTTTTCA
119251 GTGACACTTA GAATATATTA TTAATATTCC CTTTATGGTA TATGTGCTAC
119301 CAAAGTAAGC ACCATTGTTA ATATCAATGG AAATCTTGTT TTGAGTAAAG
119351 AATTTCGAAG TCTAAAGAAA AAACAATAGC AGTTTATCTG AATAGTATAC
119401 ATGACACCAA AATGCATGCA ACATCTATCA ACTCTCTACA GTTGCCTGAA
119451 TGTAGATATT TTTAACCTGG GAGTCTGGGG ACTATTAGAG AAGCTGTAGA
119501 TAGATTTCAA GGAGCTTGTG ATTTCTGTAA CAGAGCATGT AAATTTTTCT
119551 ATGTAAAAAA TTTGTATGTA GATTTTTTGG GACTGGAAAA AGCTTTCATC

FIGURE 3ZZ

119601 AGCTCTTCAA AGAAGTGTAT GTCTCAAAAA TATAAGATCT TTAAAGTAAG
119651 AACATAAAAA GTAGCATCAT ACCACTATTT TCCTTTACTT GGGTTCTCCA
119701 ACACATTATG GAAATTTGTT GTTATTGTTA ACGGGAAGAG CAGATGCAGT
119751 AGATCACAGA AGGGGCATTA AATCAAAATT CAGTTGTAAA TGAACAAATG
119801 GGATTATATA CTTCTAGATT TCATCTAAAT AATTTAATAA TGTTTTTATT
119851 GAAATACATG GCTGCAGATA TTTGAAAATT CTGTAAAAAG AGCCAATTAG
119901 TATTGTATAT TACTTTTTCT ATGTTTACAA TAGCTAAAAT TTGAACTTGT
119951 TTTGGGGGTT AAATATTATA AATTCTTCAA TCTGTCCAAA TTATGTTTTA
120001 TAGTGTTATA TGAATTAGTT TTTGATATTT ATGCACAAGA AAGCAAAAGC
120051 AAGAAGAAAA ACATTTTTTC CCTCAGTTTT CAAAAGGAAC CAACTTAATG
120101 AGTGTATTAG TTTACAACGA CTGCCATAAG AAACTACTAC AAATTGGGTG
120151 GTTTAAAATG ACAGTAGTTT GTTTTCTAAC ATTTTTGAGG CTAGAAGTTT
120201 GAAGTCAAGG TGTCAGCAGG GCCACAATCC CTTCGAAGTC TCTAGGGGAG
120251 GATCCTTCCT TGTCTCTTCC ATATTCTGGT GGCTCTTGGT CTTCCCTGGC
120301 TTGTGGCAAT AGACCTTTGT TCTCTGTCTC CATCTTCACA TGGCTTTCTC
120351 CCAGTTGTCT CTGTGTGTCT TCTTATTTTC TGTTATGAAG ACAGACATTT
120401 GTCATTTGAT TTAGGGCCCA TCCTAAATCC ATCCAAATCA TTGGATTTAG
120451 GGCCCATCCT AATTCAGGAT AATTTCATCT TGAGATACTT ACCTTAATTA
120501 CATCTGCAAA AATCCTTATT TCAAATAAGG CCACATTCTG CGGCTCCAGG
120551 TTGATGTGTA TTTTGGGAGG AAATTATTCA ATCCACTGTA ATGAATAACT
120601 TATTCTATTT AGGAAATTTG TGAGAAGACA GGAGGATGAA AAAAATAACT
120651 TAATGAGGGC CATACACCTG ATTTAGCAGA ACTCTCTCTG AGAAAACACT
120701 CACAGTATAA AAGCTCTTAG TATTTCTATA TTGATTTGTA TTGTTATTCT
120751 ATGATTTAAG TATTATCACT TTCACATACA TTTGTTTAAT ATTTTGTTAT
120801 ATTTCAGACA AAAAATGTTT CCCCATCTAA GAAATTAGGG CAATATTTTA
120851 AGATATCTGT GGGGCATGAG ACACGTGATA ATGTGAGAGG ATCCTACTAT
120901 GTCATGGGAA GTACATGTAT ATCAATGTAT CTCTCTTCTC TTCATCCTCT
120951 ACTTCCCCAA TTGGGAATCA AGATTTTTCT CGACAGAAAG ATGTCAGTTC
121001 CAAAGTTTTC TTGACTAACC AAGTGGACAC AGAACAGGGA AACATCCATG
121051 TTCTATAAAT TTCAGATTTA GGATGAGAAC AGAGAAGGGG CTTCCACCTA
121101 TTTCTTTGAT TAGTGAGAGC TACCTAATTT GAGAATAAGC ATCAATCACA
121151 TAATAAAGAC TGAAATTTGA GCATAAGCAT CAGTCATCTA TTTTTTCAAT
121201 TATTTAGACT TGAAAGTTTC AGAGCATGGC TTTAGGTAAT CATTGTAGAT
121251 TATGGGATAG AGAAGCAGAA ACTCAACCAG AAAGCTACTC TAAAAGATAA
121301 GAGCCATTAG TTATAATAGG ACATGTTAAT TACAACAGGA CATTGATTGA
121351 ATATCAAAGA ATGTTTAAAT ATTTTTTAAA AGAGAAAACA GATTTGTATT
121401 TCTCAAAGCC TCGGTGAGGC AATTGTTCTG CTTATCTAAT TGCTTTGAAG
121451 GCTATTGAAT AATTGTACTA GGCCAGGTGT AATGGCTTAC ATCTGTAATC
121501 CCAGCACTTT GGGAGGCCAA GGTGGATGGA TCACCTGAAG TCAGGAGTTC
121551 GAGATCAGCC TGGCCAACAT GGTGAAACCT CGTCTCTACT AAAAATACAA
121601 AAATTAGCTG GGTGTGGTGG CAGGTGCCTG TGGTCCCAGC TACTTGAGAG
121651 GCTGAGAGGG GAGAATCACT TGAACCTGGG AAGTGGAGAT GGCAATGAGC
121701 CAAGATTGCA TCACTGCACT CCAGCCTGGG TGATGGAGCG AGACTCTGTC
121751 TCAAAAATAA ATAAATAGAT AAATAAATAA GAAAGAAAAA GAAAAAAGAA
121801 AAGAACAATT GTACTCATTA AGAATAGAAT TTAATATGTT GATTCATAGT
121851 TTACTTTGGT TAAAAAAAAT AGTGCATTGG AGTGCATTAT CAAACATAAA

FIGURE 3AAA

121901 TTCCATGAGA ACAGTTAGCA TTTTAGCATT CAGTATTCGT TTTTATGACC
121951 TGATTCTTCC AAGTGCTCAA ATAAATATCC ATTGAGCTAA GTTCTGTTTT
122001 CTTTCCCTTC TCTGTACTTG GAACACTTTC TAGGTAGACT GTCTTCCTTT
122051 TGTATTTTTA GACTTATTAT GAGTGTCTGA CCCTCAGTCA GGGTTCAATA
122101 AATCTTTAGA ACATGAATCA ATTACTGAAT ATTCTAGACA TCATACCAAT
122151 ATTCTATCTT GAATCAAGCC AATAATTTAT TTTCTTCATT TCTGTTGAGC
122201 TTTGCTAGAG ATAAATCATA TGATTATGCT TATCAACACT GCTACCAATG
122251 TGTTGATCCC TTCACATTCT CAAAAATTAC TAAGCACCCC AAAGAACTTT
122301 TGTGTATGTA GATATGTTGG TATTTACCAT AGGAGAACTT AAAACTGAGA
122351 AATTTAAAAA GTATGTGTTA ATGAATTCAT TTAAAAATAA TAATAGAACG
122401 GGTTCAGTGG CTCACACCTG TAATCCCAGA ACTTTCAGAG CCTAAGGCGA
122451 GTGGATCACT TGATGTCACA AGTTTGAGAC CAGCCTGGGC AGCATGGTGA
122501 AGCCCTGTCT CTACCAAAAA ATTCAAAAAA ATTTAGCTGC ATATAATCCC
122551 AGCTGCTCAG CTACTTGGGA GGGTGAGGTG GGCGGATCAC TTGAGCCAGG
122601 GAGGTGGAGG TTGCAGTGAG CTGAGATGGC ACCACTGCAC TCCAGCCTGG
122651 GCAATAGAGC CAGACCTTGT CTCAAAATAA ATACATAAAT AACAATAGTA
122701 AAGCCATTAC ATATTAACAT AAATAATACA TTTTAATGAA AACAAANNNN
122751 NNNNNNNNNN NNNNNNNNNN NNNNNNNNNN NNNNNNNNNN NNNNNNAGTT
122801 TGTATTGAGT ATCAAACCAG AAATGGAAAC AAATGGTCTA AAAGTAAAAT
122851 AGAATATTTG AAAGCAGAAT TTTCCTGGCA ATTTTGGGAC ATTTGGTCAC
122901 TGTAATTTAG GCCAGCATAA AGAATAATAT AGGAGTCCTT AATCTCAAAT
122951 ACTTGTATCA TTTCATCCCA AGTAAAATTT AAAGTGTCAG AAATATTTAT
123001 ATTATATTCA GTGTAAATTA ATTTTTTCTC TTCATCCTTA TTTTTATTTT
123051 CCCCACTTAC TATATTAAGT ACGTAATTCC TGAGTATGAT AAGATAAATT
123101 AGGTTATGCT GCAGGAATAA CCAACTAAAA TATTAATGGC TTAAAACAAT
123151 AAGGATTTAT TTCTATCATG CTAAACTTTC ATCAAGATGT AGGAGAGAGG
123201 CTCTGCTCAT TATAATCACT TAGGCCCCCT GTGCTTATAG AAGCTCTAGC
123251 TGGACCTGTG TTTTCTCAGT CACTAAACCA GAAAAAAAGC AATGTGATAA
123301 GTCACACATT GGTACTCATA ACTTCCATTC AAAACTGACA TATGTACACC
123351 CAAGTAGAAT ATACCTGATC CAAATAGCAA AGAAGGCAAA GAAGTACAAT
123401 CTTACCATGT GGTCTAGAAG AAAACCTGGA ATATCTGTGA ACAGCCTAAA
123451 TGGCTAACAT AGCACATGTG TGCGGAGGGG AGGTGGAAGG GACAAGTATG
123501 AAATGTAACT CATACTTTGA GTGGAAATGA ACTTTCTGCA CTGTGTAGAT
123551 ATAATATATA GTTGGCCCTC TGTATCTTCA GGTTCTGCAC CCTTGAACTT
123601 AACTAACTGC AAATCAAAAA TATTTGAAAA GTCAGGGTGC AGTAGCTCAC
123651 ACCTATAATC CCAGCACTTT GGGAGGCCAA GGTGGAGGAT GGTTTGGGGC
123701 CAGGAGTTCA AGACCAGCCC AGGCAACATA GCAAGACTCT GTCTCTACAA
123751 GAAATTTTTT AAAAATTAGC CAGGTTTTGT GGTACACACC TGTAGTCCCA
123801 GCTACTTGGA AGACAGGAGC TTAAGCAGGA GCTTAAGCCT AGGAGTTCAA
123851 GGCTGCAGTG AGGTATGACT GTGCCACTGC ATTCCAGCCT GCATGACAGA
123901 GTGAGACCCT GCCTCTAAAA ACAAAAATCA AAAATATTCG AGGGGGGGAC
123951 AATAAAAAAT AACAATGTTA CAATAAAAAT AATATGCATA AAAATTATAC
124001 AGTATAATAA ATATATAGCA TATACATTGT ATAGATATTA TAATAATCTA
124051 GAAATGATTT AAAGTACAGA TGCTCCTCAA CTTTCAATGG GGGATTATGT
124101 CCCCCCATTG AAAATATCAT AAGTGGAAAC TATGTTTTTG ACTTATGATA
124151 TTTTCAACTT ATGATAGGTT TATCCAGACT TAACCCCACT GAAAGTTGAG

FIGURE 3BBB

124201 GAGCCTACTC AATGCATGTC ACTTTTGCAC CATCATAAAG TCAAAAGATT
124251 GTAAGAGAAA CCATAGAAAG TAGGGGATCC TCTAAATATA GGAGTATATG
124301 CATAGGTTAT GTGCAAATAC CACTCCATTT TATGTAAGGA ACTCAAGTAT
124351 CCATAGATTT TGGTATCTGC AGGGAATCCT GGAACCAATC CCTCAAAGAT
124401 ACTGAGGAAT GACTATATAT CCAGAAAATA CTAACATAAC CTTAGTATTA
124451 TTTTCAAAAT GGAAACAAAA TTAACCTTTT AAATTAATTT ATTTATGCCA
124501 GGGTATAAAT ACTGCTGAAA TTTCCAACAC ATTTTACAAA TTTTTATTTC
124551 TATTTGTAAG CAAAGGCTTC CTCCAGAAAC TGATTTTCCC ATACATAAAT
124601 AACTTTTGCC TAATTCTAGT TTAATGAGCT TCCTTTCATC CTCCTTTTTC
124651 TTTCCCTTAC TCCTTCCCTC TAGAAATTTC AACATTCATC TGACATCATA
124701 AGACAAATAG TTACCTATAT GGATCCATAA AATAAATTAT AATATTTTAC
124751 AACATAAACT TCTTTAGAGT CAGAGCTGTC TATTTCTTCA AATTGTTATA
124801 ATCACATGTG AGATAACTGA GTTGAAAACA CTGAACACAT TAATATTTTA
124851 TAATTATTTT TAAGCTATAA ATAATATTTC TATTTCTTCT AAAGGTATTT
124901 CATGATGTTG CCTATAAAGC TAAAGATCGT AATGACTTGG TATCAGGAAT
124951 TGATGAGTTT CTGGATCAGG TTACTGTTCT CCCTCCTGGA GAATGGGATC
125001 CAAGCATTCG AATAGAGCCT CCCAAAAATG TTCCTTCCCA GGTATGTATA
125051 TTTGAAGACA TTCTTTGAAA TTGAATTTTT TTTTGTCTTT TAAATGCATG
125101 TTTTATTTTA TTTTATTTAT TTATTTATTT ATTTTATTAT TATTATACTT
125151 TAAGTTTTAG GGTACATGTG CACAATGTGC CGGCTAGTTA CATATGTATA
125201 CATGTGCCAT GCTGGTGTGC TGCACCCATT AACTCGTCAT TTAGCATTAG
125251 GTATATCTCC TAATGCTATC CCTCCCCCCT CCCCCCACTC CACAACAGTC
125301 CCCAGAGTGT GATGTTCCCC TTCCTGTGTC CATGTGTTCT CATTGTTCAA
125351 TTCCTATCTA TGAGTGAGAA CATGTGGTGT TTGGTTTTTT GCCCTTGCGA
125401 TAGTTTACTG AGAATGATGA TTTCCAATTT CATCCATGTC CCTACAAAGG
125451 ATGTGAACTC ATCATTTTTA TGGCTGCATA GTATTCCATG GTGTATATGT
125501 GCCCCATTTT CTTAATCCAG TCTATCATTG TTGGACATTT GGGTTGGTTC
125551 CAAGTCTTTG CTATTGTGAA TAGTGCCGCA ATAAACATAC ATGTGCATGT
125601 GTCTTTATGG CAGCATGATT TATAGTCCTT TGGGTATATA CCCAGTAATG
125651 GGATGGCTGG GTCAAATGGT ATTTCTAGTT CTAGATCCCT GAGGAATCGC
125701 CACACTGACT TCCACAAGGG TTGAACTAGT TTACAGTCCC ACCAACACTG
125751 TAAAAGTGTT CCTATTTCTG CACATCCTCT CCAGCACCTG TTGTTTCCTG
125801 ACTTTTTAAT GATCACCATT CTAACTGGTG TGAGATGGTA TCTCACTGTG
125851 TTTTTGATTT GCATTTCTCT GATGACCAGT GATGATGAGC ATTTTTTCAT
125901 GTGTCTTTTG GCTGCATAAA TGTCTTCTTT TAAGAAGTGT CTGTTCATAT
125951 CCTTTGCCCA CTTTTTGATG GGGTTGTTTG TTTTTTTCTT GTAAATTTGT
126001 TTGAGTTCAT TGTAGGTTCT GGATATTAGC CCTTTGTCAG ATGAGTAGGT
126051 TGTGAAAATT TTCTTCCATT TTGTAGGTTG CCTGTTCACT CTGATGGTAG
126101 TTTCTTTTGC TGTGCAGAAG CTCTTTAGTT TAATTAGATC CCATTTGTCA
126151 ATTTTGGCTT TTGTTGCCAT TGCTTTTGGT GTTTTAGACA TGAAGTCCTT
126201 GCCCATGCCT ATGTCCTGAA TGGTAATGCC TAGGTTTTCT TCTAGGGTTT
126251 TTATGGTTTT AGGTCTAACA TTTAAGTCTT TAATCCATCT TGAATTAATT
126301 TTTGCCTGAG GTGTAAGGAA GGGATCCACT TTCAGCTTTC TACATATGGC
126351 TAGCCAGTTT TCCCAGCACC ATTTATTAAA TAGGGAATCC TTTCCCCATT
126401 GCTTGTTTTT GTCAGGTTTG TCAAAGATCA GATAGTTGTA GATATGCAGC
126451 GTTATTTCTG AGGGCTCTGT TCTGTTCCAT TGATCTATAT CTCTGTTTTG

FIGURE 3CCC

126501 GTACCAGTAC CATGCTGTTT TGGTTACTGT AGCCTTGTAG TATAGTTTGA
126551 AGTCAGGTAG TGTGATGCCT CCAGCTTTGT TCTTTTGGCT TAGGATTGAC
126601 TTGGTGATGC AGGCTCTTTT TTAGTTCCAT ATGAACTTTA AAGTAGTTTT
126651 TTTCCAATTC TGTGAAGAAA GTCACTGGTA GCTTGATGGG GCTGGCATTG
126701 AATCTATAAA TTACCTTGGG CAGTATGGCC ATTTTCACGA TATTGATTCT
126751 TCCTATCCAT GAGAGAATAA AATACCTAGG AATCCAACTT ACAAGGGACG
126801 TGAAGGACCT CTTCAAGGAG AACTACAAAC CACTGCTCAA TGAAATAAAA
126851 GAGGATACAA ACAAATGGAA GAACATTCCA TGCTCATAAA TGCATGTTTT
126901 ACAATAGCAT AACCCATCAA GAAGATTCAA ATGATTTAAA GGATAGCCTC
126951 TAAGGCAGAA GGGGCATGAA GTTACAAGAT CTTTCTTAGT ACTACCTAAC
127001 ACACATTACT GAGAAACTTG GCAGTTTGAT GACAACCTAC TAATCAAACA
127051 GTGCCATATG CCTGGAAAGA TTTTAGCCCC TACTTAAAAC ATATTATCCA
127101 AGAGGAATAT TAAAATTTTA ATAACAACAT TAAATATGGC CTAAGAGAAA
127151 GCGCATTACT GTCCTTGTAT GTTTTGATAC ATCACTTTGA AATTGGCAAG
127201 CATTAGGAAA ATTCAAAGAC ATGACTTAAT CATATTATAT AGAAAACTCC
127251 ATATTTATTA CTGCTAATCA CAGGAAATAT TGGGAAGATT TTAAAATTAT
127301 AATTCTTATA TTTGTATTGC TTTTTTGTGA ATGTATGATA TAAAGATTTT
127351 TTAAATTTTG TTTATGAACA TCTAATGTAT ATTTTACCCA TCATACAATC
127401 CAGAAAGATA GAAATATAAA GCATTGCTAT TTTTTAGGGT CATTTTTTAA
127451 ATTGCAGGCA TGAGTATTAA GAGTGATGAC CAAATATTTG TTAAGCTCAC
127501 TCCTCATACT GCCACCTCTA TGCCTACTGA ATCTGCCTCC CACAACCCTC
127551 CCAAATTGTT GTGTACTTAG TCTTGCCTTT GCGCCTTGCC CTGTGGAGTT
127601 CAGCCTTGCC TGACTCTGCT ACCCTATTGG AAGCGGCAGA TGGTCTAATT
127651 GACCCAGCCC TGGAATTAGA AATTTTCCTG CTTTGCCAGA GGTGGGCAAA
127701 TGAGCAGTTG TACCACTCAA CCATGAGTAC TTAAAAAGGG TATCTCAATT
127751 TCACTGTCAA TTTAAAGAAA CTATATGGAT ACCTCATTTT TATATTTTCA
127801 TTTTGAAATC ATTTCATAAT TATTAAAGAC TATTTCCTTT TCTCAAAACT
127851 TACCATTTTG TGATTATGTA ACTGCTACCA CATATTTCAG TTGATCTACT
127901 ATTAAAATAA AAAGTTGCCT AATAATTAAT TGTAGGGTTT ATAGATTGTC
127951 TCATTTCTGT ACTTGTAGAA TACATCTTTG TACTAATGAT ATTAGAAAAG
128001 GCAATATAAT GCTTCCTGAG TATGTAGAAA CTCTTTAATT AATGTTATTT
128051 GGAGAAATGC AGCAAAATAT TAATACATTC AGAATGAGGC TTTAAAATTC
128101 ACTGTAATAC CCATTAGCTA TTGAAACATT GAAGTTAAGT GTTTTTGAAA
128151 ACACCTTTGT GAACAATAAT GTTTTTGAGG CAAGTTGAGT GATGGGAGGC
128201 CAATATTGTT TATGATTTTA TGACACCCTT TAAAATCGAA TTAATTATTG
128251 GATTCTGGGT ATTGAGAGGC AGTCATAGAA AGAACATCAA ATTAAGAATC
128301 AAAGCATCCG AGTTCTGCAA TTATCTATAT GTATGACCTT GAACAAATGT
128351 TTTAACCTCT CTGTTGATGT TCTGTATCAG CACTGTCCAA CAGAGTTTTC
128401 TGCAATAATG GAAATATTCT ACGTCTATGC TATCCAGTAA TCAAGCCACT
128451 AGTAAGCATT AGAAATGTTG CCATTGTAAC TAAAGATCAG AATTTTTCAT
128501 TTTAATTACC TTAAATGTAA ATAGACATAT GTAGTTTGTG GCTATCATAT
128551 TAGACAGCAT AGTTCTATAC AACAAATTTG AAATTACAGA TATGCTCTAT
128601 GCTTCTTTTC AACATTCATG TTTTAAAAAT ATATGTTGTA ATTGAATAAT
128651 AGATAGCATG AGGCTATGTT TTCTATTAGA CGGAGTGAAA TGAGTTAATA
128701 TACATTAAAC ATTCTGACCT CATACTCTTT CAAATTTTTT CACCATTGGG
128751 ATCATTTCCA TCTTTTTTAT TCATTTGAAA TGTGCAAATC CCAGCATTTT

FIGURE 3DDD

128801 AAATATTTTT TCCCTTTCAG TTAAGAGAAG AATAACCTGT CACCTCCAGG
128851 GATAACCCTG AAAATGTTCA TTAGAACTTT GCATCAGTCA TTAAAATCAC
128901 TCCCTTTTGT GTACCCTCAA CTTATTTGCT CTTCTCTCAT GTCGTGTACT
128951 TGCTTGGCAA AACCACAACC CTGTGAGAAT CCAACACTTT ACTCTGTACC
129001 GCACTGATGA ACTGAAGCTG AAGGAAAACA TGTAACCACA CTAACTGGTC
129051 TCACATAAAT TCATGACCAC ATACCTCAAG TGAGCCCTTT GTGTTGCAGG
129101 TTCATCATAC TACACTTTCC TAGTCCAATC ATTCTCACTT GATGACTATT
129151 TCACACTTAT TCTTCTCTCC TCAAGCCTTC AGCACATCCT TTCTGACCCT
129201 CACTCTCATA TGCTGATGTG CCTTTTATTT CCCTAAGAAA TTTGAAACAA
129251 TCAAAAAAGA ACTTCTATAG ATTGCTACAT GCATCCACAT ACTCTGCCTT
129301 CCTGTTCATT ACTATTGATG AAATAGCCAA AGTCAGCCTT CTACTTGTGC
129351 ACTAGAAAGA ACCTATCTCT TCACATCTAC TCAAGAGCAC AACTCTACCA
129401 ATTCTCCTCT TTCTCTTCTA TATCATCAAA TCTTTTTTTC TGTATTTTAT
129451 CACTTTTATT AGCATACAAT ACTATTAAAT TTACCAATCT TAAATAAAAG
129501 AACTCTCTTG ATACCACTAC CCAGCCTGCC ACTCTTATTC ATTCCCTTTT
129551 ATAACAAAAT GCCACAGAAG AGTTCTCTGT GCTACTTGTC TCCAGTTACT
129601 CTCCTCCAAT TCTCTTTTAA CATTCACTCC AAGAGGCTTT TGCCCCTACC
129651 ATTTCACTAA AATACATACG AGAACAATGA TCTCCACCAT GCTAAGTCCC
129701 ATGGTCAATT CTCAGCCTGC ATTTTATCTA ATCTATCAAT GAACAGCATT
129751 TAAGAGTTGA TGACTCCCTT TTCCTTAATA TATGTTCTTT ACTTGGCTCC
129801 CAAAACATCA CCTTCTGTTA GTTTTGTCAT TATAAAATAG AGTTAATTTA
129851 TCTAGTCAGT AGTATTTTCC CAGAAGACCA CATAATAATG CTTGCTTTCT
129901 GAGACCTGTG AAAGCTATGA ATTGTTTTCC TAGGTGATTG GGAAGTAGGT
129951 ATTGAGGGAA ACTCTTAAAT CCCTTTATTA ATGTATCCTA TTTACCTGTA
130001 AAGACAGTTC CTTCATCAGT TGACAGATGC TTCTCTTTTA TCTTTGAACT
130051 TTAGTCTTAC TGCGTCCATC CATTTGCCTG GGAAAATTGT TAAAATATTA
130101 AGCAATAAAC TTTCTTATAT TGAGCATTTT TCAAAACCTT TTTTATGTTT
130151 TAAACCTGTA TCATTCTATC TAAATGTCTC ATGGTAAGTG AGATCAGTTT
130201 ATAAGTCACT TTTGTTTTTC ATGTTTACAC TAATTCTATT TTGGAATGGT
130251 GGTCAAGTAA AAATCATAAT TTCACCACTT AAGATTTTTC CTATTATCCT
130301 TTGAAGTGCT TTTGAACACA TTGGTGTGCT CTAAGATCAC CATAGGTAGG
130351 ATTTTAGGTA GAACTTTCTG ATTTTTTAAG AAATCATATT CACCAACAAA
130401 AGCAGGTGGA ATAGACCATG GGAAAACAAT ACTTACCTGA ATCTCTACTA
130451 ATTTGTCATT GGTTAAATTA GAAGCCTCCT TTTACAACAG TCTTTGGCAC
130501 TCTATGAGTT AGAAAGACCT ATATTGTAAA CTATTTACTG GGTAGAAAAA
130551 CACCAGCTGG AATTACACAG AGAAATATAC TTTAAAAATA GTGATGATGG
130601 TTACTGTTCT TTGAACAGTT AAACTATGCC ACGCATATAA CACCACCATA
130651 CTTAACACCT CCTCACGCCA ACCTACCCAC ATCCTGATCT CTCTCTTTGC
130701 CCCTTCCCTT ACTTCATTTT TCTTCATAGC TCCCATCTGT ACCTGATATT
130751 ATAAGGTTAT TGTCTCTTCA CTAACAGAAT GCTTTTTCTT GCCCACCTTT
130801 GCAGCTCTAG CATTCATTAC AATGAATGGC ATACACTAGG CACTCAGTTT
130851 TAGTTGAAAG AATAAATAAG TGCCCATCAC CTCATTTAAT TCTCTTAGTC
130901 ACACTATAAG ATAGATACTG TTGTTACCCC CAGTAAACAA AGGAAGAAAC
130951 TAACACTTTA AAAGGCTAAA TAACTTCCTG GAGGTCAAGC AACAAGTAAG
131001 TACAGAGCCT GGGTTCTCAG CTATTGTGCA TATTGCTTCA AGGAAAAATG
131051 AACTGTTATT ATTATTTACA ATTAACACCT GAAATTAAAA CAAAACAAAA

FIGURE 3EEE

131101 CACATGAACA AAAAACTCTC CACAGGAGAA GAGGAAGATT CCTGCTGTAC
131151 CAAATGGAAC AGCAGCTCAT GGGGAAGCAG AGCCCCACGG AGGACATAGT
131201 GGACCTGAAC TCCAGCGAAC TGGAAGGTTA GTGAAAATCA CTTCTATGGG
131251 ACTTCAAGGA CCAAATGACA TACCATTCTT CTCTGTCAGA AATTGCTATT
131301 TTGGGATCTA ATTTATTGTA TACTTTTAAT ACCTGCTTTT TGAGGGTGAA
131351 AATGCCAATT AGTTTGATTT CTCTGAAGTT ACTAATGATT GTCATTACTG
131401 TTAAACTAAA ACAGTGGATA CACCCTTCCA TTATACTTTA CCTAGTCTTT
131451 CATTTTGCTG TGCATAAAAT GCATTCTCAG ATTCTTAGAA TGAAAAGGAA
131501 AACCGTCAAT TGACCCTTCC AAAAGAACCC ATTGAAAGCT TCAAGTTGAA
131551 GATAGAAATA AAACTAAATA CCAACAACTC AGTCTTGTAG GCCCTATCTC
131601 ATTAAATGCA AGTAGGATGT ATATAGTGGT ATTTTTTATT TTTATGGCTG
131651 TGATTTGAAA GAGCTATATG ATTTATTTTT CTAATCACAC ATCTTTGAAG
131701 AGATGAAAGC TTCAATTTAT TTCTTAAAAT GGTGCTTCAT GGTTTTTTTG
131751 ACAGCTTGTC TCTCTCTAAG CAATGTGTGA GCAGAAAATC AGAAACCCTT
131801 GGGTGGGTCT CTCTTCAGGG AATATGTGTA TAGCCTCCAT TATAATTAAA
131851 GGCAGTTGCA AAGGCTTTGC AGGATTGGTG CTCCCCTCCC CTCAAGGCCA
131901 TTTTCTGTAC TGCTTGCAAT GTGTCCTCTA AGCTGACTTT CCAGTTCCTG
131951 AGCACTCTGC ATTTTAATTC TGTGTTCTTT CCCTTTATCT ATGTGTTGTC
132001 TCTGAGGAAA TGTCCTTTAA TGTCTTCCTC AGGCTTGATA CCTAATTTGA
132051 GATGGTTCAA ACAATTTTTT CCTTTTCCCT TCACTGGAAG CTTTGTTACT
132101 CATTCTGTTT GCTTTCATAC TTTCAAATGC TGTCTTTTTA TTTTTGGTGG
132151 TATTTTTTTT CTCTTTCTCA GGTGTAACAT GCCACATAGC TTAGATTTTT
132201 TTCGAAGTTC ACTTTTCCTT ACTGCTTCCT AAATCCTCCC AGGTCACCAA
132251 TATCCGGTAT CTTCGCTTCT CCAGAGTTCT TCCACAGATT CTGTTGCTGA
132301 CATGACTTGA AGTATCCATT ACTCATCTGC TCTCCTGGAG TTGCTGGTGT
132351 ACATCTGGGC TGCTCTTGCA CTGTTCTCTG TAATGAACTC CCACTTCCGG
132401 ATTTAGATTT TTACTGCTAA AAGCACATTT ATTACACAGT ACTATAACAA
132451 CTATTCAGAC TAATGTATGC TCTAATAAGT AATTGATTAG AATCAATGGT
132501 CTAATATAAA GTGCTTTCAA AACTATAAAT ATTAATTACT AATTAATAGC
132551 TCATAACCAC CTCAAATTCT TTTTGGGATT AGGTGGGATA TAAATCATAA
132601 ATGAATGCCT AAATAGACTG GTAGAGTAAA TCTGTTTTGA ATTGTGACTT
132651 TGATAAGTTA ACAAATTATT CAGAAATGAT CCCTAAAATA AAAAAAAGTG
132701 CATATGTTTT ACCAAACATG GGTAGAGAAG CCTAAGGTGA TCTTTATGTG
132751 TACAAATATT TCACAGGTTC TCTGCAAGCT TCTCTGAGTT TCAAATGTCC
132801 TTTTATTCAA TTGAAGTTTC ATTCTTCTCA ACCCTCTCCT ACTCCATAGC
132851 TCTCTAATGG AAGCAATCAC AGGAAAATAT AGTGATCTTA TACCTGCATA
132901 ATAGTAGAAG AGTTATTAAT AGGTAACTAT TACAGATAAA TCAGATCAGG
132951 GAAATTACTT GGTAAAATAT TTTAATTATT CATAATATGT ACATCTTTTA
133001 TTTCAAATTC TAAGGAGAAT TTATTTCTAA AAAGGACAGT CCTTTCTGAG
133051 ATGATTCTAG GACTGCCAAA TGAATATTCC TATGCATAAA ATAAATAAGA
133101 AAAATGAAAC AGTTTTTTAT GATCCAAGTA TACTCAGCAT GCTGGCAGTA
133151 TATTGGAGCA TAATAAGATT TTTCACCACT GACATTAACC TTCATGTAGG
133201 AACTTATTCA TAGTCTTATT CATTTTTGCT ATCACATCAT TATTCCATGG
133251 AGCAAAACTT ACAGTAGCCA AATGTTAAGT CTGCGTATTG TTATTAAATG
133301 TTCATAAAAT GAGAATACCT ACTTATTAAT GCTCTCATTT CTTATAGATT
133351 TAAAAAAAGA TCTCAAATTT CAAGCATAAT TTCACAGTTT AATACTTTTC

FIGURE 3FFF

133401 CCCCAAAATA ATTATCTTTC AAGTGTTTCA ACATGGTTTT GAATATATTT
133451 GGAGTAAATG AATTTATACC AAGTAAGGTC ACTATTGTCT TGTGAATCAC
133501 AGATGCTGGG ATATGTTAAC GCAATAGTGG ATCAAAATTA CATTTATCTA
133551 GTTTTATTAT TATAAGGACT CCCTCCTAGT TTTCTAAAAA TGAAAACAGC
133601 TCTGAAACCT ATCTGTCTCT ACTAAGTATT GCTGCCATCC AAAAGGACAT
133651 TTAGATGTCT TCCTGCAACA ATATCTGGTG AGGGATTTTT GTTTGTTTGT
133701 TTTTTGGCCG AGAGAGTAGG TAACTGGAGC CATGGTTAAA CATTGCTTTT
133751 TCTCTCTAGG GTGATGCTCA CTACTGGAGT ATACAAAAGC CAGCTAACCC
133801 TCCCTCCCTC ACTTCCTGCT ATGCTAAATG GAATTAAACA TTTAGAAATA
133851 CTGCCAATGA TTGAGGGTTG TAGGCCTGAG TTTAGGAGGA GTAGGTTGAC
133901 GTAGAAATGG CACAGAGATT AGAGTAATCC TTGAATCTCA TTATTTGGAT
133951 TATGATTGGT AAACAGCTCT GAACCTTGTT TAAGAGAACC TGGGATTTTT
134001 GGTGGTTGAC ACGATATTGG GTTAGGAATT GAGGTAACGA ACGTAGTTGT
134051 GCAGTGCCTC CCTGTAGATT GTTATAAGAC AATGCAGCAG GTTAATGTGT
134101 GTCTCACCTC TGCTGATGGA AAACGTATAC TGTGACCTGG CAACAAAGCA
134151 AATGAGCATT TTGACTTGTG TGTTTTTTAT ATTTGGGTTT CACTATTGTG
134201 TTTTCCCCCC TGTCTTAGGA TTTTTGGGGG ACTTATTTTA GATATCAAAA
134251 GAAAAGCTCC ATACTTCTGG AGTGACTTCA GAGATGCTTT CAGCCTGCAG
134301 TGCTTAGCAT CTTTTCTATT TCTCTACTGC GCGTGTATGT CTCCTGTCAT
134351 CACGTTTGGA GGACTGCTGG GAGAAGCAAC TGAAGGGCGT ATAGTATGTA
134401 TTATGCTTTT CTCTGAACTT TGAAACATAA TCCATTTTTA AGATTCATAG
134451 TTAGATAAGT GAGCATTTAA TTTTGGATTC TTTTCTGAGG AGAGATTTGA
134501 GATATGGTCT GGCAGATACA CCTTATATGA ATTTCCTGGA TGGCTAGTGG
134551 AACTGGTAAT CTGGGAGTGG AATGTCTCAG AATAACTAGT TCTGAGTCTT
134601 ACAAAAGGTT CTCATCTGAT GCCTTGCCCT CAGCGCCCCC AATCCTAAGC
134651 TAGGTTTAGT CTCCATTCTT GTCTCACAAG AGGTCCATTT GCTATGTACC
134701 CGGGCCATGT TTCTGTCCAG ACACTAATCC TGAATACATT TAAACCTTTT
134751 GTAAGGCAAC AGAGACGTGA GATAGGAAAG TGAAGAGAAC ACTCCTACCT
134801 TTGCTACTAT GCATTTTCTT CTTGCTGTCA GCCCCTTTAG TCATCCTTCT
134851 ACCCCACGTC TTGCCCAGGG TTGCTAGACT TTTCAGGGTG AAGCACAAAG
134901 CACATATCCA TGTATTTTAA ATGTCTTCTC CTTAGCTACA ATGGCCTCCT
134951 GTACAGCTTA GGTAATTGAA CCATTTATAT CTCTACACAG AGTGCAATTG
135001 AATCTCTCTT TGGAGCATCC ATGACCGGGA TAGCCTATTC TCTCTTTGGT
135051 GGACAGCCTC TTACCATATT AGGCAGTACA GGACCAGTTT TGGTGTTTGA
135101 AAAGATTTTG TTTAAATTTT GCAAGTAAGT GTTATGTACT TTTTGGCCCT
135151 TAGCCTCTTC CTTTTTTCTT TACTGTATTT ATACTTCTCC CAACATCACT
135201 TTTGGAGGTC TGTTGATAGA GACAGAATTG CCTGATTTGT TTCAGTTTAT
135251 CATTTTTGCT TCATCATGGG AATAGAGGAA AAGTAAAATA TTTATGTATA
135301 TTTTTATGTA ATATTTTTAA AAAGTAAGAC TCAGTTATAA GCATCGATAA
135351 ATCCCTTTTG ATTTTGTCCC TTTAGATGTT CCCTTTAGAC CGGTGGTCTG
135401 CAACCATTTT GGCACCAGGG ACTGGTTTCA TGGAAGACAA TTTTTCCACA
135451 AAGAGGGTTG AGGGGATGGT TTTGGAATGA AACTGTTCAC CTCAGATCAT
135501 CAGGCATTAG ATTCTCATAA GGAGCACACA ATCTAGATTC CTCACATGCA
135551 CAGTTCACAA TAGGGCTTGT GCTCCTATGA GAATCTAACG TCCCCACTGA
135601 TCTGACAAGA GTCTGAGCTC AGGCGGTAAT GCTCACTCGC CTGCCACTCA
135651 CCTCCTGCTG TGCAACCCTT TTCATAACAG GCCATGGACC AGGGGTTGGG

FIGURE 3GGG

135701 GACCCCTGCT TTAGACAGTC TTGAGTTTAG ATACTCATGG GATGTGAAGC
135751 TTATTTACTT TCACTTCCTG AATGAGGTTT ATTTTCATTT GCTTAAAATG
135801 ATAGCAAGCT GTTAAATGAC CTTCTTTTCA CTGTTCTTTC CTTTTCCTCC
135851 TCCCAGAGAA TATGGGCTGT CATACCTATC TTTAAGAGCT AGCATTGGAC
135901 TTTGGACTGC AACTCTATGT ATCATACTTG TGGCCACAGA TGCTAGTTCC
135951 CTTGTCTGCT ACATCACTCG GTTTACTGAA GAAGCTTTTG CTTCCCTGAT
136001 TTGCATCATT TTCATTTATG AGGCCCTGGA GAAGTTGTTT GAACTCAGTG
136051 AAGCATATCC AATCAACATG CATAATGATC TGGAACTGCT GACACAATAC
136101 TCGTAAGTAC CATTTCCCCT GCTGGCCTTG GGGCTTTTCT TTTGACAAAT
136151 ATTGCTATTG TTACAAGAAA TATGAGGAAA TTACTCAGCA GAGAATGTGC
136201 CTTAAGTTGA TTCATGACCT AAATCCTGAC TCTCAGAGTC GAACAGGATT
136251 TTAAAAGTTA TTTAATCGGC CACTCATCTG CTACTTGCAT TCTCATTATA
136301 CCATCTCTGC CAAGAGTATC TTTTTAAAGT TCTATTTGTC CAGTGTTCTC
136351 TAAAATAAGT AGATAAGGAA CCAATTCCAT TTTAATATAC ACGAATTTTA
136401 CCTTAGCGAA ATATATGTTA TTTGGCGTTA TTTCAGGGTC TTTTTAATTT
136451 ACAATAATCC AAAGAAACAT AGTAATGAAA ATATAAGATT TCAAATTTAG
136501 AGCAATAAGG TAAAATAAAC TTATTGGGTC TAAATCTTAG TAGATGTTTG
136551 AAAGTGTGGT AAAAACATAA ATCACTGAAT GAAAATTTAA TTTTGGTTTT
136601 GGCACTTGTG ACATTTTGAT GGAAATACTC AGATATTAGT TGTTGAAGTT
136651 GATGTTACAG TCCGGGATTG AAGATGTGAT TGGATCTATT GCTTTTTCTA
136701 GTTTTGGTGT ATCAACAGTC TGAAATGTCT CTAAGGCTTT GTCTGCAGAC
136751 TATATGTGGC CATTAAATGA CCCCATTATT TAATTGTAGA ATTTTTTATT
136801 GTGCTTATAT GCAGTTTTTT ATACTGCAAA TATCTGAAGC AATATGTTCT
136851 TTAGGAGACA GTTATAATCT CTGCATCAAC CACCAATCAT TTCCCTATAA
136901 ACTGCTTAGA TATGGCCTTG AACCCTTTTA ATATTTTTTA ATCTTTATTT
136951 ACTATCAGAA GTTTAAATTG TTGAAATCAG ACCAAAATAG TGCAATGTTA
137001 TAATTTTGTT AAGAATGACG AAATGTTGGG AGGCCGAGGC GGGCGGATCA
137051 CGAGGTCAGG AGATCGAGAC CATCCTGGCT AACACAGTGA AACCCCGTCT
137101 CTACTAAAAA ACACAAAAAA ATTAGCCAGG CGTGGTGGCG GGCGCCTGTA
137151 GTCCCAGCTA CGCGGGAGGC TGAGGCAGGA GAATGGCGTG AACCCGGGAG
137201 GCGGAGCTTG CAGTGAGCTG AGATCGCGCC ACTGCACTCC AGCCTGGGCG
137251 ACAGAGCGAG ACTCCGTCTC AAAAAAAAAA AAAAAAAAAA AAAAAAGAAT
137301 CACGAAATGA TATTATGTTG AAAATAATGT GAGTTTTAGT ACTTTCACTT
137351 TTATATTATA TTTAGAGATA ACTTTAAACA ACTGACCCCT ATTTTTGAAC
137401 AAGAAAAATC AAAGTGGAAA TATAAAATAA TTTTCCCATT AAAAGCAAAT
137451 AGTGAGAATA TTGTAAACAG GGCTAAGAAA GGACTGAGCA TAGGTGTCAG
137501 GGACACTCAG AAAACAGGCA AATGGGAAGA ACAGTTTGAT CAAAACCAGG
137551 GATAACATTG ATACACGCCT TTTCATTTAT CCTTACCTGA AAGAGAATCT
137601 CACTGAATTT GGATATCCTT GCTGGGATAT GTAATTATCT CTGGTTGGAT
137651 TTTCAAATCT ACTACATGCC AGGCACTATA CTAGGTGCTA GGAAAACCAT
137701 GGTGAATCAT ATTCTGTCCT CAGTGAGCTT CCAGTTTAGT AGGGAATGTA
137751 GATAAACAGA CAGCATAAGG AAATGAGTGC CGGGTTAAGA GGTTGGTACA
137801 GAATGCTATA GCAGCACATC AGGAGAGCAC CTAACCCAGA TTTGAGGTTC
137851 AGAGAAGGCT TCCTGGAGGA AATAATGTAG AATAAAAATG CAGTAGAAGT
137901 TAGGAAGGTG CTAAGGAATA GGGCAGAAAA GTAGTTCAGT CAAAGGGCAT
137951 TCACAGGACT AGATGCAAGA GATGCATTCA TGCTTTAAAA TATTTGTCTG

FIGURE 3HHH

138001 AAGTTATATA GATAGTGGTA AAACAAGAAA TGGAATCCAG GTTTTATTAC
138051 TGATATAATT TTCAGTACAC TGATGAATAC AGATAAACTC TCCAAAAGAA
138101 ACTATGTAAA ACAAATAAAA CAGGTAAAAT CAGAACTATT CTGTTTCAAG
138151 TGGTAGGAAG GCACCCATTG CCTACCCTCT CAGCTGTTCT TTGAACCTTC
138201 ATGGTAGCTT CTTAGGTACT TCAGACTGAG GAACATAGTT TAAAGTCCCT
138251 TGGTCTAGAA AGGAAAAAGA TTGGAAAAGC AAGGTCTGAG CCCTGAACAA
138301 TTTTCACAGC TCTAAAGTAG AATGAGAAAA ATGCAACCAA TAGGCAAAAA
138351 ATAAATAAAT AAAAATAAGA AAGAAGCATC AGAAAAAGAG GAAACTATGG
138401 ATAATGTCAG GTCGCAGAAG GCAAGAAACA AGAAATGTAT CACAAAGTCT
138451 TTAGAGAGGA CAGTGGCATG GACATCAAAC AGAATAAGGA AAAGTGTTTG
138501 AAAAGAGATA CCTGGTAGCT TTAAAAAATT CTCAGCAAAC TATTGCAAGG
138551 ACAAAAAACC AAACACCGCA TGTTCTCATT CATAGGTGGG AACTGAACAA
138601 TGAGAACACA TGGACACAGG AAGGGGAACA TCACACACTG GGGACTGTTG
138651 TGGGGTGGGG GGAGGGGGGA GGGATAGCAT TAGGAGATAT ACCTAATGCT
138701 AAATGACGAG TTGATGGGTG CAGCACACCA ACATGGCACA TGTATACATA
138751 TGTAACAAAC CTGCACGTTG TGCACATGTA CCCTAAAACT TAAAGTATAA
138801 TAATAATAAA ATTAAAAAAA AAAAACAACT GGTATTGGGT TGGGAAAGGA
138851 GGCAGAATGG GAAGCCAGTT TGCAAAAACT AACAAGGAAG TGGGTGGTAA
138901 AGAAATGGAG AAAGCTGCAT AGGCCAGTTG GTGTCAAAGA AAGTGGGAAA
138951 CAGAATGCCT TTTGAGGAGG GCAATGAAAT CGTAAGATTG ATAATTTGTG
139001 ACAGAGAAGG ACTATGTGTG TTTGAAAATG GGAGAATAGA GACTGGGGAG
139051 AGGAAGGCAG CAATGATGAA AAGAGTCGAT AAACGTGGGA TTGCAACCTC
139101 CCAGGAGTCA CAAAATAGTA AACTCAAGAG AATAAGTCAA ACAAATGCTC
139151 AAAAGGTAAT TTAACAACAA GAATAGCTTT AAATAAACGT GAACCCAAAC
139201 TGACATGAAA ATAGCAGGAA AATGACGAAA AAAAAAAATT CGCCAAAAAA
139251 GACAGTGACA CAAACAGTGC ACACAACACA CAAGAGCGAG AAGAGCAGAA
139301 TGGAGGAGGA CAAGACAAGG CCGGTGCTCA GTGAGAGACG CACCGTATGA
139351 CACCTAGCAG AGGAAGCGAA GAGGGTAGAA GTGCTGANNN NNNNNNNNNN
139401 NNNNNNNNNN NNNNNNNNNN NNNNNNNNNN NNNNNNNNNN NNNNNNNNNN
139451 NNNNNNNNNN NNTCTGAGGC ATGGCTGTGA CACCCTCTTT GGGCTCTGCA
139501 GTTCCTGGTG TCTCCAAGCT TCTGGTGCCA CCACGTTCCC CAGAGCCTGC
139551 AGTGTAAGTG GCTTGCAGTA TGCCTGGTCC AGCCACAGCC TTGCACAGAG
139601 CTGGTTCCTG TGCCAGTGTC TGGAACTGCC TGCCCCACCA CAGCAGCCAG
139651 CATGCCTGAC TGTGCACAGT GGCCAGACCA TATGCTTGCT CACTTATGCA
139701 CCCCTCACCT CTGTGCCTTT GGCAGCGCTG GGATCCAGGC TGGTAGCACG
139751 AGCTGAGCAC AACCTGCCAG GCCTAGTGGG CAGAATGAGC CAGAGGGCCC
139801 AAGCAAAACT CAGGCAAAGG CACCACTGGC CACAAAGGCT TCTGGCTGGA
139851 AGAATGACAC CCCGGGGACC TCATGACAGT AATAACTTGG CTTAAAAGGC
139901 TGGGATAGGG ATCTATGACA TTAACCCAAT TAGTGGCCTT GGGTAAGTCC
139951 CTAAGAACAA CCTCTAGAGA CAATGTCTTA ACTCAAGAAA AAAAAAGTAG
140001 GAAGAATATG GAAAATACAT AGGGAATAAG AAGTCTGGAA GTATTGTATT
140051 AATACCAAAC TTATAGTACT TAAAGGACAA AATAAAGGGT TGCAAAAGAG
140101 TTCACCTTGT TGGTGAAGGA AACCTTGTAC TTTTTATTCT CTGCATATTT
140151 TGAATTGTTC AACTTGCACT GTATGCCTGC ATTATTTTGT AATTTCTTTC
140201 TAAAGATGAA TTTTGTGTTG GGAAATTCAA GTCCTGTGAC AAACCATAGT
140251 ATGAGCTAAT CTGGGGGAGG TGGTGCTCTT CAAATTAGTT TCCATGTAAC

FIGURE 3III

140301 AAAATTTATT TTCAAATTCA GGAAAAGAGC AACCTACAAA ACTCAGGAGT
140351 AAAATGGGCA AAATGTTCAA GGAATAATAA GTAGGTTTAC TGTTCTGTTC
140401 ATACATGTGC TTACTCATTC ACTCACTTAG CTCATTCCTT CAACATCCAT
140451 TGATCTTCCT TGTGTATGTC AGTGCTGATG GTATAAAATG AATACAATAT
140501 GGTCCCTACT CTGAAAGACC TTAGTGATTA TCAGACAGTG TCTGGAGATG
140551 TCCTTTGGAC ATGATATCCA CTCAAATAGT ATTTGTTGAA TTAATAAATG
140601 AGGAGAGAGG CTAGAGGATA CACAGTTAAA TAATTGCAAT GTGATATAAC
140651 AAGCACTATA CAAGGTGTCT GTATAATGGC CTAAGAGAAG AAGTAACAGA
140701 GTGCCCTGGA GAGCTCAGAA GCATTCATAG AAAAAGGAAA CCTGAACTTA
140751 TCTCTCCATT TCTGTTGTAC CTGCCACATG AGTTTATTGT ATGTGGCATA
140801 CCTATGTTTC TTTCTCTCTC TCTCTTCATT GTACCTGTGA ATTCCCACAT
140851 GCAGATCATC ACTAGATCTG AGAGTAGTTA CGCAGAGTAG AATGGACCTC
140901 TGGGGACCAA TTGGCAGAGA GCCTTAAAAG TTCTAATAAG TTTTATCTGG
140951 TACAAAGGCC ATCATGGATC ATGACAAGGC TCTGGGAAGA ATTATGTGAC
141001 AATAGGTTAG AAGGTGATCA CAGGAAGCAG AGCAAGGAGC AATACCCTAG
141051 GCATAGAATG TTTAAGTCCT GACTACTGGC TGAGACAATG GTAATGGGAA
141101 GAAAGCAAAA AAACTAAAAA TGGAAAAAAT GAAAAACAAA AATTATCCAG
141151 GATTGATTCA CTTGTTCAAC AAGTAATTGT GGAACAGTGT CTAATTTCTA
141201 GGAGCTATTA TGAAAACTTT GCCTATATGA CTTCATTTGA ACCTCACAAG
141251 AACCTTGTGG GACAAGTATT ATCCCTGCTT TACAAACAAT CAATCTGAGG
141301 CTCCAACAGG TTAAATAATC TTCTCAATAT CACATATACA ATAAACGGTA
141351 AATGGGGTAA ACCCAGGACC ATTTTGTCTT AAAGCTCATA AACTTTCTGA
141401 CATATTAAAG TAAAAATAAT AGCAAATGAT TGCGATGATT ATAACTCCTT
141451 AAAGGTAGGG ACTACGATAT ATGTCTATGT ATCTCCAGTA GGACTTAGCA
141501 CAGTAATCTG TATAAAATAA TTTCAAATTG TTAAATCAGT CAGTTGTCAT
141551 AAGGCTGCCT GCTATGGGCC AGGTGCTTGC TTAAAAAAAA TGAATGCATA
141601 GACAGGATTC CTTCATGGAA CTTATAGTCT GTTGAAAGAA TCAGACATTA
141651 AATATTACAC AAAATTACAT TATACAAATG ACGTAAGTGC TATCATATAA
141701 AAGTATAGGA TGCCAAGACA GTGAGAAATA TTTCCAAACT TATATATTTA
141751 GAGGCTAAGG AGAGGATATG TCTATTTGAA TGAAGATAAA TTTGAGATGA
141801 GAAAAAGTTT AAGAATTTAA TGGAGAGAGT ATTTAAATTT TTAGTGTTAG
141851 CTAATTGTGG TGGTGTTTTA CAAAGCTACG ATGCATATTT TTGAAAAGCT
141901 ATTTTCCTCA TAATATATTA TGGTTATATA CTTAGTGATA TCTTAGAAAA
141951 GTATAAGTAC TAAGCAAACC TCTTCAAATA ATAAGCTCAA AATATGGAAA
142001 TAGGTGTATT CATAAAAGGA TTGTCTCTAT ATTATTTAAA TAGTCATCTT
142051 AATAGTAACA ATTTAATTAA ATGATTAATA ATCCAAGAAT AAGTTATGTT
142101 GTATCCCTTA CAAATAATGG TTCTGAAGGG TAATGTAGCA ATAGGAAAAT
142151 GCTTGCATTC TAGTGCTATG TAAAAAAGGA ATAAAAATAT TGTATGCTCA
142201 TAAAAACATG TTGAAAATAT ACATAAGAAC TACTGAAAGA AGTATACCAA
142251 AAATTTGTAG CAATTATGGT AGAAAGACTA TGAGAGATAC CTTTTTCTTT
142301 TTTTATTTTG TAAATATTCT GTAGTGTGAT TTTATTATCA TTGCAATTAA
142351 AAATACTTTC TGAAATAGAA AAAGAATAAT CATAAAAACA CATTTGGCTT
142401 CTATGGATAG ATCCTGATTT TCTGATTGTA TGTTTTGTAT TAATACCTGA
142451 CTTGGTACAT AGCACTCTGG GAGATAATCA AGTCAATAAA AAGACCTGAA
142501 AAATAAATGA ATCACAAACC ATAACTGTTT AGTGCACACA GGAAGGTACT
142551 ATTAATAACT ACAAAGGCAA AAGGAGAGCA TCTGCAACCC AAGGACTAAA

FIGURE 3JJJ

142601 ATTAGTAATA ATGTTGAAGG GAGTTCTACC AAATTATGTT TTCCAGAAGA
142651 CAGCGCAGGC TCTTCTTGTG TAAGGAAGAC AGATCACCTC CATTAGCCTT
142701 GAAACAAAAG CAAAGACTTC TGGATGAGGG CATTTAATTA TAATGTTTAT
142751 GTAATCACTC TGTAGCCATT TATATAAACA AGATCGCTTA GAGCACTTGC
142801 TTTTCTGTGG GCAGTAAAGG GTACTAAAAG ATGTATTTTA TAAAAAGTGT
142851 ATTTTAAGCC AAATAATTCA GCACCACAAG TGAAAATTAT TGGCATTTTA
142901 TACTGGTGTT TTTAAACATG TAGAGAAGTG CAGATACAAC CCTTTTTCTG
142951 CTTTATGATT GTTGGACTTT TCAGTCTATG AGCTTGTGAT AGTAACAATA
143001 ATAAATAACC AAAATGAGAT ACCTAACAAT CTCTATTTAC TTATGTCAGG
143051 GCCCATTCTA GGACTTTTAT GTATATTAAT TCATTTAATT TTATAATAAC
143101 CCCTAGAAAG GACATGAACT CAGAAGCTGG AAACCATCAT TCTCAGCAAA
143151 CTATCGCGAG GACAAAAAAC CAAACACTGC ATGTTCTCAC TCACAGGTGG
143201 GAATTGAACA ATGAGAACAC ATGGACACAG GAAGGGGAAC ATCACACACC
143251 GGGGCCTGTT GTGGGGTGGG GGGAGTGGGG AAGGATAGCA TTAGGAGATA
143301 TACCTAATGT TAAATGATGA GTTAATGGGT GCAGCACACC AACATGGCAC
143351 ATGTATACAT ATGTAACAAA CCTGCACATT GTGCACATGT ACCCTAAAAC
143401 TTAAAGTATA ATAATAAAAA AAAGAAAAAA AAATAACCCC ATGAGGTTGA
143451 TTATTATCAT TATCTTCACT TTATACATAA GGAAACTGAA ACATAGAGTG
143501 ATTAAATGGC TTGTCCAAGG TTGCTCAGCT AAATGCTTGG ATTTGAATGA
143551 ACATAGGAAA CCTGGCTGGA GACCTCAGTG TTCTAAGCAT ACACTATGCT
143601 ATGCATCAAA AGAAACGTTT TGCATTAATA CTCCATCTTA TTGCCAGAGT
143651 CACTAGAAAT TATTTTTGAT GAGATTAACA AAAAAGCTTG TTCCAGACTC
143701 ATATTCTATC TCCTCACAGT GCTATTTCCA TGTTTCTTTT CTCTTTCTTT
143751 CTTCTTTTTT CTTTTTCATT TATCTTCTTT AACTTTTTGT AGTTTTAGAA
143801 ATAAGTTCAC CAATACAGAG GAAGACAGGA AAATGGGATT TTTTTCTCAC
143851 ATTTTTCTTG ATTGATTTAT TTAGCATATC TATTTTTGAT ATGTAAGAAC
143901 ATAAGAAGTA AGTAGTCAGA AGTCTTCTTT GAGCCACCAA GAGTTGGTAC
143951 GGAGATATCA AATGTCCTTA CACAACTGGG CAGCCTCTGA GAACTGTCTG
144001 CTGAGATTTT AGATGTCAGA GGTGCAGACT CAAGAAAGAA CAATATTTGC
144051 TTGGGTATAC ATGATATCTG TGATTTTATA CATATATAAA TACAAATAAA
144101 TCTTTAACTT ATTTATTTTT AAATTTGAAT TTATTTATTT ATGTCATATA
144151 TAAATCTTGT ATATTAAAAA CATATTTTCC ACTTTGGAAT TGATTTATAG
144201 GTGAGTAATG TCATAACCTA GAGATAGCTT TGACAGGGAG GCACGTAGGT
144251 AACTAACGTC CACTTGTAGA CTCAACTCTT CAAAAAATGT CTCTCCTATG
144301 ACATTGGTAC ATCAAATTTC TAACTTAGCA TTTTCAAAAA GTCACGGTTA
144351 AAATGTAAGT ACACTACCAG GAATGGAGTA ACACATGCCA TTGTATTCAC
144401 TAACACAGTA TAACCACTTT GGAAAGCAGA GACCATGTTC TTGAGGGAGT
144451 AGTAAAGCAA AATGAATGGA GAAGCCATAT CATCAGGTTT CGATGGGGTT
144501 ATAGGAAACT GGACAGTGGG GCTGAGGAAA ATGTGGATGG TGTAGTTTTC
144551 ATGATAGGAG GGCAGAGCTA CAGGTGTTTT GGAAGAATAC CTTATAGGAG
144601 AGAAGTCTTG AAAGTGGAAG CTAGCAAACT ACACGGTGAA ATGTAGATTA
144651 CTTCATTTGT TCTGGAGTCA TCTCACTCTT CTGGCTATCT TGATAGAAAC
144701 AGCACCAAGT CACATATTGA GGCAGCATAC AATAGCTAAA AGAGTAGGAG
144751 TTTCCATCTG GTCCTGGACT CTTTTTGGTT GGTAAGCTAT TGATTATTGT
144801 CACAATTTCA GAGCCTGTTA TTGGTCTATT CAGAGATTCA GCTTCTTCCT
144851 GGTTTAGTCT TGGGAGGGTG TATGTGTCGA GGAATTTATC CATTTCTTCT

FIGURE 3KKK

144901 AGATTTTCTA GTTTATTTGC GTAGAGGTGT TTGTAGTATT CTCTGATGGT
144951 AGTTTGTATT TCTGTGGGAT CGGTGGTGAT ATATATCCCC TTTATCATTT
145001 TTTATTGTGT CTATTTGATT CATCTCTCTT TTCTTCTTTA TTAGTCTTCC
145051 TAGCGGTCTA TCAATTTTGT TGATCCTTTC AAAAAACCAG CTCCTGGATT
145101 CATTAACTTT TTGAAGGGTT TTTTATGTCT CTATTTCCCT CAGTTCTGCT
145151 CTGATTTTAG TTATTTCTTG CCTTCTGCTA GTTTTCGAAG GTGTTTGCTC
145201 TTGCTTTTCT GGTTCTTTTA ATTGTGATGT TAGGGTGTCA ATTTTGGATC
145251 TTTCCTCCTT TCTCTTGTGG GCATTTAGTG CTATAAACTT CCCTCTACAC
145301 ACTGCTTTGA ATGTGTCCCA GAGATTCTGG TATGTTGTGT CTTTGTTCTC
145351 GTTGGTTTCA AAGAACATCT TTATTTCTGC CTTCATTTCA TTATGTACCC
145401 AGTAGTCATT CAGGAGCAGG TTGTTCAGTT TCCATATAGT TGAGCGGTTT
145451 TGAGTGAGTT TCTTAATCCT GAGTTCTAGT TTGATTGCAC TGTGGTCTGA
145501 GAGACAGTTT GTTATAATTT CTGATCTTTT ACATTTGCTG AGAAGAGCTT
145551 TACTTCCAAC TATGTGGTCA ATTTTGGAAT AGGTGTGGTG TGGTGCTGAA
145601 AAAAATGTAT ATTCTGTTGA TTTGGGGTGG AGAGTTCTGT AGATGTCTAT
145651 TAGGTCCGCT TGGTGCAGAG CTGAGTTCAA TTCCTGGGTA TCCTTGTCAA
145701 CTTTCTGTCT CGTTGATCTG TCTAATGTTG ACAGTGGGAT GTTAAAGTCT
145751 CCCATTATTA TTTTGTGGGA GTCTAAGTCT CTTTGTAGGT CACTCAGGAC
145801 TTGCTTTATG AATCTGGGTG CTCCTGTATT AGATACATAT ATATTTAGGA
145851 TAGTTAGCTC TTCTTGTTGA GTTGATCCCT TTACCATTAT GTAATGGCCT
145901 TGTCTCTTTT GATCTTTGTT GGTTTAAAGT CTGTTTTATC AGAGACTATG
145951 ATTGCAACCC CTGCCTTTTT TTGGTTTTTT TTTTTTTTTT TTTTTTTGGT
146001 AGATCTTCCT CCATCCCTTT ATTTTGAGCC TATGTGTGTC TCTGCACGTG
146051 TGATGGGTTT CCTGAATACA GCACACTGAT GGGTCTTGAC TCTTTATCCA
146101 ATTTGCCAAT CTGTGTCTTT TAATTAGAGC ATTCAGCCCA TTTACCTTTA
146151 AGGTTAATAT TGTTATGTGT GAATTTGATC CTGTCATTAT GATGTTAGCT
146201 GGTTATTTTG CTTGTTACTT GATGCAGTTA CTTCCTAGCA TCGATGGTCT
146251 TTACAATTTG GCATGTTTTT GCAGTGGCTG GTACCAGTTG TTCCTCTCCA
146301 TGTTTAGTGC TTCCTTCAGG AGCTCTTTTA GGGCAGGCCT GGTGGTGACA
146351 AAATCTCTCA GCATTTGCTT GTCTGTAAAG TATTTTATTT CTCCTTCACT
146401 TATGAAGCTT AGTTTGGCTG GATATGAAAT TCTGGGTTGA AAATTCTTTT
146451 CTTTAAGAAT GTTGAATATT GGCCCCCACT CTCTTCTGGC TTGTAGAGTT
146501 TCTGCTGAGA GATCCGCTGT TAGTCTGATG GGCTTCCCTT TGTGGGTAAC
146551 CCAACCTTTC TCTCTGGCTG CCCTTAACAT TTTTTCCTTC ATTTCAACTT
146601 TGGTGAATCT GAAAATTATG TGTCTTGGAG TTGGTATTCT CGAGGAGTAT
146651 CTTTGTGGTG TTCTCTGTAT TTTCTGAATC TGAATGTTGG CCTGCCTTGC
146701 TAGATTGGGG AAGTTCTCCT GGATAATATC CTGCGGAGTG TTTTCCAACT
146751 TGGTTCCATT CTCCCGGTCA CTTTCAGGTA CACCAATCGG ACGTAGATTT
146801 GTTCTTTTCA CATAGTCCCA TATTTCTTGG AGGCTTTGTT TGTTTCTTTT
146851 TATTCTTTTT TCTCTAAACT TTCCTTCTCA CTTCATTTCA TTCATTTCAT
146901 CTTCCATCAC TGATAACCTT TCTTCCAGTT GATCACATCA GCTCCTGTGG
146951 CTTCTGCATT CTTTACGTAG TTCTCAAGCC TTGGTTTCAG CTCCATCAGC
147001 TCCTTTAAGC ACTTCTCTGT ATTGGTTATT TCAGGACATA GGCATGGGCA
147051 AGGACTTCAT GTCTAAAACA CCAAAAGCAA TGGCAACAAA AGCCAAAATT
147101 GACAAATGGG ATCTAATTAA ACTGAAGAGC TTCTGCACAG TAAAAGAAAC
147151 TACCATCAGA GTGAACAGGC AACCTACAAA ATGGGAGAAA ATTTTCGCAA

FIGURE 3LLL

147201 CCTACTCATC TGACAAAGGG CTAATATCCA GAACCTACAA TGAACTCAAA
147251 CAAATATACA AGAAAAAAAC AAACAACCCC ATCAAAAAGT GGGCAAAGGA
147301 CATGAACAGA CACTTCTTAA AAGAAGACAT TTATACAGCC AAAAAACACA
147351 TGAAAAAATG CTCACCATCA CTGGCCATCA GAGAAATGCA AATCAAAACC
147401 ACAATGAGAT ACCATCTCAC ACCACTTAGA ATGGCAATCA TTAAAAAGTC
147451 AGGAAACAAC AGGTGCTGGA GAGGATGTGG AGAAATAGAA ACACTTTTAC
147501 ACTGTTGGTG GGACTGTAAA CTAGTTCAAC CATTGTGGAA GTCAGTGTGG
147551 CGATTCCTCA GGGATCTAGA ACTAGAAATA CCATTTGACC CAGCCATCCC
147601 ATTACTGGGT ATATACCCAA AGGACTATAA ATCATGCTGC TATAAAGACA
147651 CATGCACACG TATGTTTATT GTGGCATTAT TCACAATAGC AAAGACTTGG
147701 AACCAACCCA AATGTCCAAC AGTGATAGAC TGGATTAAGA AAATGTGGCA
147751 CATATACACC ATGGAATACT ATGCAGCCAT AAAAAATGAT GAGTTCATGT
147801 CCTTTGTAGG GACATGGATG AAATTGGAAA TCATCATTCT CAGTAAACTA
147851 TCGCAAGAAC AAAAAACCAA ACACGGCATA TTCTCACTCA TAGGCGGGAA
147901 TTGAACAATG AGAACACATG GACACAGGAA GGGGAACATC ACACTCTGGG
147951 GACTGTTGTG GGGTGGGGGG CGGGGGGAGG GATAGCTTTA GGAGATATAC
148001 CTAATGCTAA ATGACGAGTT AATGGGTGCA GCACACCAGC ATGGCACATG
148051 TATACATATG TAACTAACCT GCACATTGTG TACATGTACC CTAAAACTTA
148101 AAGTATAATA ATAACAGAAT AAAAAAAGTA TAATATATAA TAAAAATATC
148151 TTGAAAATTA AAAAAAAAAA CAAACTTCTC AATGGCTGTC CCTCTCATTC
148201 AAGAGCAAAA ATAAAATCAT AACAATCCTT GAAAGCAAAA AAAAAAAAAA
148251 AAAAAGTAGG AGTTTCAGGT TGGGACAGAC CTGGATTCAA GTTTATTTCT
148301 ATCAGTGTAG CCTTGGATAA GTTATCAAAC ATTTAGTTCC TCCCATCTAT
148351 AAAATGTAGC AATTAAACTA TTAAACTAGA AAATCCACTA TATGCCATGC
148401 GTATAGCAAC TGTATGCACG CCATACCTAT AGGCATAGAT ATACAGTAGC
148451 TACAGAAAAC ATATATGTAT GTATATACAC ATATACATTT GTACATGGAG
148501 GTATTCACAT ATCTACGATA GTGCTATCTT TCTCCCTCGT TATGTTACTT
148551 CTGCAAGAAA CTTGCCATAT TTTCTCTATT TTATATTTTT GTTTCTTATG
148601 TATGGATTTA CTTTTAACAA ATTTTCAAAA TATGCAAATA ACTTTCTGTT
148651 AAACTATAGT ACTGGCCCTT TTATTTCTGA GGTAAACTAA CTGACCATCT
148701 TAGGGAATTC TATTTGTTAG CAACCAAAAA AAAAGGATGT TTGCCACTTA
148751 ATAAACAGAT TCAGACAATA TATTACTAAT TTACTTCAAC GAGAAAGAGA
148801 CTCTTGCTTC TAGTGAATGA TATTACACAG TTTGTTTTGT TTTGTTGATA
148851 GCACTACTGT GCAATGGTCA CCTGTGATAC AATTATTTGA ATTCATGACA
148901 ATGCTGGGTT AGGAACCGAG GCAGATCCAC TATGCTTCTT TATGTTCAGA
148951 TGTTTTAAAT CAGAATTATA GGACTATATC TATGTGCCTA GGCAAATATC
149001 TAAAATAATT ATTCCATTCT CTGCTAACAG CTTAAACACG TGTTGTAATT
149051 CTAACAGACT TTAGAGAGCA TATGGCAGTT TCAACAAGTC ACACATATTT
149101 TTACATGCAC CTAAGCTAGG GACCCCTGAC CAATGAGTTG AGCATCATCT
149151 ATCAGGATGC TCCCGATAGA TGACAGATCT TCAACCAGCC AGCTAGGTCA
149201 TTTCTGCTTC CTCAATTCCA CATGTTTAGT TAGTTGGGAT TCCCAGTCGG
149251 GAGGCAAAGC AGGTAGCATT TGGGCCCTCC CCTTACTGTG CTCAGTTCAG
149301 TTTATTGATG GAAACATCTC CAAGGATCTT AAAACTTTAA AATAGAAAAT
149351 ATCTCTTCCT CACAAAGTTG GAAGCCCTGA ACCTGAGCCT TAAGAGATTT
149401 ATTTTTACAT TTGTTTTCAA ATTCTCACAA TTTATACAGA AAAAAAAATC
149451 AGAGTATCCA TTCTGGTTTT TAATTTTTTT ATTTCTTGCC ATAGTATTAT

FIGURE 3MMM

149501 ATATCAAGAA TATTTATAAG AAGGAAGTAG TTAATACATA TTTGTTATCT
149551 AAGTATAATT TGGGACACTA TATAAATCTT TTAGTTTGTG AGTTACTTCT
149601 GTACCCTGTC ATCTCCTAAG CTACCTGGTC TTTCTTGGAA TAATAAATAT
149651 ACATACCTTT TAGGACCAAG ATCTATAGTT TCACAATATT CATAGCCATC
149701 TGGTTCTGCT ACAGGGTAAA TTTAGACTGG AAATAAGGTA ATATTAAGTA
149751 AGAGAAGCTT CGTTTGTTTA ACCTACCTCC CAAAGGCTCC ATTTGTAAAG
149801 AGTGCAGACC AGAAATCACA TGCACTGCTG GATTCTTTCC ATGAGAAAAG
149851 CCTGTGTTGA GCTTTAGTTT CTTCATTTTC TTTAAACAGA ACAAAAATCT
149901 CTCCTACCAC TCAAAGGAGT GATTTGCAGA TTTAATGCAA TTATATCAAA
149951 GTAGTTTATA ACCCATAAAA CACAAAGTTA TATGACCGTT ACTTTGTATT
150001 GAACATCCAT GAAACTCTAG GAATAGTACT AGAAGCTTTA TACACCATTA
150051 TATATAGAAT GGTGTCTCTT TTAATTCTCA AGAAATCCTG TCCAGTTGTT
150101 ATAATTATAC TTACTGAATA AATTATATTA ATTTATATTA TAATTATATT
150151 AATTAGTTAT ATAATGAATT CATAGAAACT CAGGGGTTGG GTGATTTGCT
150201 AAGATCAATA GCTAGAAAGG GGCAGAATCA GTATTCAACT CAATATTACC
150251 TCCAAATGGA AGTAATTCAG TATTAGTGAG TATTACTAAT TATAGAAGTA
150301 ATACTTCTCC TTTCTACTCA GAGCTAACAC AACAGCATTA TCTAATGTTG
150351 TTAAATGGTA GGTGGAATTA AAAATTGTAG GTAAGATTAA GAAAGGAGGG
150401 AAATCACTGA ATAACCTGCC CTTCCAGCAA AGTTGACAAA GTAGATAAGA
150451 TCTCTGGTAA GATCTAATCT TCATCTCATT CTGCCACATG TTTTTGTTTT
150501 GTTTTGTTTT GTTTTGTTTT GTTTTATTTT GTTTTTTAAG ACGCGTCTCG
150551 CTCTGTGGCC CAAGCTGAAG TGCAGTGGCA CAATCTTGGC TCACTGCAAC
150601 CTCTGCTTCC CAGTTCAAAC AATTCTCCTG CCTCGGCCTC CTGAGTAGCT
150651 GGGATTACAG GCGTGCACCA CCACGCCTGG CTAATTTTTG TATTTTCAGC
150701 AGAAAGGGGG TTTCACCATA TTGGCCAGGC TAGTCTCCCC ATGTTTTTTA
150751 TCGAAGTCCC TGTGTTCTCA ATATCCTGAG ATGATTGGCT GATTGGCTGT
150801 TGCCACAGCC ATTGGCTTCA GCCACTCTTC TGGCCTGGAC ATCATCCAGT
150851 GCATGTCAAA GACAGGACTC TGGCCTAGCT TCTTTTGGGG ACTTTCTACC
150901 ACAGAATGAG CAAAGGTGAT GTTCGGAACA AAATACCTAT ACGTTTCATC
150951 CAGCTGCAAA TAATCAGCTC CAGCTTCTGG AGTTACTTGG TACCTAAATT
151001 GGCCAGGTTG CTGTTGAGGA TGAATGGGCC AATCTTACAG CTGAACACCA
151051 TGATACTGGT TCCCAGGAGC CAAGCATTGC CCCAATCCAG CCTTTTTTTA
151101 TTTATTTTAA AAATGTGTTA ATACTTTTTA AATCTTTAAG TAGTGACTAA
151151 TTTTCTTTTA AATAAAGATT GTTTTCCTCC AGGATGCATC AGAGTAAAAG
151201 CATAAAATGG AGCTTTAAAA AAATTAATTT AGAATCAGTT GTGTCTTCAG
151251 TTTACTAATC CACGCTTCAA ATGAGTAGAA CTTACAATTT GCTCTGGTTT
151301 TGTTACTTGG GTGGGTAAGA TAACTTAGAA GAGCGACAGG GATTTTGCTA
151351 AAATATAAAA ATGGGATAGT TTTAAATCTC TATTGTTGTT ACCGTTGGCA
151401 GTAATATAAA GGAGATCAAA GAACTAATGT GTTTGTTCCC AACCTACCTT
151451 TAAATAAAAT TGTTTTATAG ATGTTATAAA AGTATACCTA TATACACTTT
151501 ATGTACACAC ACATGCATTT CATGTATATA TCCACTATAA TGCTAGTTCT
151551 CTCTTATTAT AACACTCCTG CAAGAAATTT GCCATATTTT CCCTATTTTG
151601 TGTTTTAGTT TCCTTTTTGT CATTAATAAA TATACTAGGT TTTCAGAGTA
151651 TGAAAATGTT TTCCCATCAA ACTCTTATGG TGTTGGGCCT TTTTTTTCTG
151701 AGATAAAGTA ACAGAGAAAT CAATTTGGGA GAATCTTCTC ATTAAGGGAG
151751 CATACTACTC CTTACTAGTG AACTGGCTTA CAGACTGAGG TTGGCAGGTT

FIGURE 3NNN

151801 CAGATATGTA TGAGCAGAAC AGTAGCAAGA CATTTGCAGA CCTATGATCC
151851 TTGCTTGTTC ACCTAATTCT TTTTACCTAA CACTGCCACT ACTGTAAAAC
151901 CAAAGCAAGA CATTCAGAAA AAGACATTGC AGACCAAATT GACACTTTGA
151951 GGGAGGCTAC CATGGGTATA ATGTATAAGC CTCCATTTGG AGCAGGATCC
152001 AAGATCAATA TGGATACATT AGATTCTACT TTTTAAAATA AGCACTCATC
152051 TCATTTCAGA CTATGGACAT GCTACTGAGC TTTACTATCC TTAATCCTTA
152101 GTCTAGTACC TCGGTATCTT CATTAAGTAT GAAAGGTTAT TTCTATTAGG
152151 ACTTGCCTCT GAGTCCCAAA CTGGGACTCA GGATCAGATC ATGGAGGAAC
152201 ATGAAACTCT TATGTGGATG ATGACATGGA TTGGGCATCT GTGGTGGTTC
152251 TGGAACTTCA GGATTCACCT GATCTGCCTC CTACTTATCT TTGGAAAAAT
152301 GTAAAGTATA GGATCTTTCT ACCACAATCT TTACTACTGT AGGGAGTTTG
152351 ATCCACTGAC TCTTTTCAAA AGACCTCTCA GTGTTCAAGT ACTTTTCTTT
152401 AATGCCATTT CTTGAGAGTT GGAGCTACAG TTGCTCTAGA TGTGTCTAGG
152451 TCTGATCTTT TCTCCCCATA CTCCTTGAGC CCCTGATAAC CACCATTCTA
152501 CTTTCTATTT CCATGAGTTC AGTCTTTTTA GATTCCCCAT ATAAGTGAGA
152551 TCACAAGGTA TTGGTCTTTC TGTGCCTGGC TTATTCCACT TAACATAATG
152601 TCCTTGAAAT TCATCCAAAT TGTCAAAATG ACAGAATTTT GTTCCTTTTT
152651 AAGGCTGAAA AGTATTCCAC AATGTATATA TGCCACTTAT CTTTCTTTCT
152701 CTTTCTTTCC TGCCTGTTTT TCTTTCTTTT CTTCTTTCTT TCCTCTTTCT
152751 TTCTCTTTCC CCTTCCTTCT TTTCTTTCTT TCTTTCTTTC TTTCTTTCTT
152801 TCTTTCTTTC TTTCTTTCTT TCTTTCTTTC TTTCTTTCTT CTTTCTTTCT
152851 CCTTCCTTCC TTTCTTTTTC TTTCTCTTTC TTTGTTTCTT TTTTCTTTAT
152901 TTCTCTCTCT TTTCTCTTTT TTCTTTCTAT TCTTTTCTTT CTCTTTCTCT
152951 CTCTTTCTCT CTTTGTTTCT CCCTTCCCTT CCCTTCCCTT TCCTCTTTCT
153001 TTTACAGGCT CTCACTCTGT CACCCAGTGA GTACAGTGGC ACAATCATAG
153051 CTCACTGCAG CCTGGAACTC CTGGGCTCAA GCAATACTTC TGCCTCAGCC
153101 TCCCGAGTAA CTAGGACAAC ATGCACATGC CACCACATCT GCCTAATTTA
153151 AAAAATTTGT TATAGAGACA ACATTCTTGC TATGTTGCCC AGATTGTTCT
153201 CAAAGGTCTG GCTTCAAGCA ATCCTCCTGC CTTGGCCTCC CAAAATGCAG
153251 GGATTACAGG CATGAGCCCC CACACTCAGC CTCAATGCCA TGTTTGACTT
153301 ATCCTTTCGT CCATTGATGG GCACTTAGGT TGATTCCATA TCTTGGCTAC
153351 TGTGAATAAA TGCTACAGTG AACATGGGAA TGCAGATATC TCTTCCATTT
153401 ACTGATTTAA TTACCTTTGG GTACATATCC AGTAGTGGAA TTGATGGATC
153451 ATATGGTAGG TCTATTAATT TTTTGAAGAA ACTCCGTACT GTTTTCCATA
153501 TGGCTGTACT AATTTATATT CCCATCAACA ATGTGAAAAG TTTCCCTTTC
153551 TCCACCTCCT CGCCAACACT TGTTCAGACA CTTTCATCTT TAAAAAAAAA
153601 TTAATTTTTA ATTTTGTGCA CACAGTAAGT GTGTATATGT ATGGGGTGCA
153651 TGAGATATTT TGATACCGGC ATTTTGATGT GTAATGATCA CATCAGAGTA
153701 AATGAGATAT CCATTACCTC AAGCGTTTGT TCTTTCTTTC TGTTACAAAC
153751 AATCCAATTT TGCTCTTTAA ATTATTTTAA AATGTTCAAT CCATTATTGT
153801 TGACTGTAGT CACCCTGTTG TGTTATCAAA TACCAGATCT TATTCATTCT
153851 ACCTAACTAT ATTTTTGTAC CCATTAACCA CCCCCACTTG CCTGCCCACC
153901 CCTCATTACC CTTCCCAGCC TCTGATAACC ATCATTATAC TTTTTATCTA
153951 CATGAGGTCG ATTATTTTAA TTTTTAGCTC CCACAAATAA GTGAAAACAT
154001 GCAAAGTCTG TCTTTCAGTG CCTGGCTTAT TTCACTTAAT ATAACGACCT
154051 TCACTTCTAT TCATGTTGAC ACAAATGACA GGATCTCATT CTTTTTATGG

FIGURE 3OOO

154101 CTGAATAGTA TTTCATCATA TATATGTACC ACATTTTCCT TATTCATTCA
154151 TCTGTTGGTG AATACTTAGG TTGCTTCGAA ATCTTGGCTA CTGTGAGTAG
154201 TTTTCATCTT TTCGATAATA ACCATTCTTA TAGATGTGAG GTAGTATCTC
154251 TGTGGTTTTA ATTTGCATTT CTCTGATCAT TGGTGATTTG AGCATTTTTT
154301 CACATACCAT TGGCTATTTG TATGTCTTCT TTTGAGAAAT GTCTATTCAG
154351 ATACTTTGCC CATTTTTAAC CTTGTTTTTT TTCTTACAGT TGTGTTGAGT
154401 TCCTCGTATA TTTTAAACAT TAATCTCTTA TCAGATTTAT GGTTTGTAAA
154451 TATTTTATCT CATTCCATAG GTTGTATATT CACTCTGCTG ATTATTTTCT
154501 TGGCTATGCA GCTTTTTAGT TTGATGTAAT CTCATTTGTC TATCTTTGCT
154551 TTCCCAGTCT GTGATTTGGG GTTAAATCCA AAAAAAAATT ATGCAGACAA
154601 ATGGCAATGT TTTCTTATAG TGGTTTTAGG TATTTAATCC TTTTTTAAAT
154651 ATGGTGTGAG ATAAGGGTCT GATTTCATTC TTCCACATGT GGATATTCAG
154701 TTGTCCCAAC ACCATTTGTT GAAGAGACTG TCCTTTCCCC ACTGTGTGCT
154751 CTCAGCATCT TTGTCGAAAA TCATTTGACC TTAAATACAT GGATTTATTT
154801 CGGGTTGTCT ATTCTGTTCA CTGGCCTCTG TGTCTATTTT TATGCCAGTG
154851 CCATGCTGCC TTGTAATACA GCTTTGTGGT GTATTTTGAA GTTTGATATT
154901 GTGATACTTC CAGGTTTGTT CTTTTTGCTC AAGATTTATT TGGTTATTTG
154951 TTTTTTGTGG TTATACAAAG TTTAGGATTG CTTTTTTCTA TTTTTGTAAA
155001 AAATGTCATT GGCATTTTGG CAGGGATTAT ATTGAATCTG TTGATAGCTT
155051 TTGTTAGTAT GGATATTTTA AATATCAGTT CTTCCAATCC ATAAACACAG
155101 GATATTTTTC CTTTTATATG TGTCCTCTAC AATTATTTCA TCAATGTTTT
155151 ATAGTTTTCA GTGTACAGGT CTTTCACCTC CTTTGGATTA AATTTATTCC
155201 TAAGTATTTG AAATTTATTT TGGTAACTAT TGCAAACAGG ATTGTTTTCT
155251 TGATTTTATT TTTCAGATAG TTTGTTGTTA GGGTGTTAAA GTGCTACCCA
155301 TTTTTATGTG CAAATAAGGA TAATTTTCTT TCTTTCTTTC TTTCCAATTT
155351 GGATGCCTTT TATTTCTTTC TTTTGCCTAA TGGCTATGAC TAGAACTTCC
155401 AGTACAATGT TGACTAAAAG TGGCAAGAGT AGGCATTCTT GTCTTATTCC
155451 TGATCTTGCA GGAAAACCTT TCAACTTTTC ACCATTGAAT AAGATATTAG
155501 CTGTGGGTTT ATCACATGTG GTCTTTATTG TGTTGGGGTA CATTCCTTCT
155551 ATGTTTAATT TCTGAGAGTT TCTATCATGA AAGAATGTTG AATTTTGTCA
155601 AATGCTTTTT CTGTGTCTGT AGAGATGATC ACATGGTTTT TGTTCTTTAT
155651 TATATTAATG TAGTGTATCA CATTTATAGA TTCGTAAATG TTGAATCATC
155701 CTTGCATCTT TGGGATATAT CTCACTTGAT CATGATGAAT TATTCTTTTA
155751 CTGTGTTGTT GCATTTAATT TGCTGGTATA TTTTGAAGGT TTTTGCATTT
155801 ATGTTCATCA GGGATATTGA CCTATAATAT TTTCTTGTAA TGTTCTTGTC
155851 TGGCTTTGGT ATCATTGTAA TGCTTTCCTC ATAAAATGAG TTTGGATGTA
155901 CTTCTCTTCT TCAATTTTTT GAAAGAGTTT CAGAGGAACT GGTATTATTA
155951 GTTCTTCATT AAATGGTTGA TGATTTCAGC ACTGAAGCCA TCAGGTCGTG
156001 GGCTTTTCTT TCTTGGGAGA GGCTTTTGGT AATTGATTCA ATCTCCTTAC
156051 TTATTATTGG TCTGTTCAGA TCTTCTATTT CTTCCTGATT CAACCTTAGT
156101 AGGTTATATG TGTCTAGGAA TTTATCCATT TTTTTCTAGG TTATTCAATA
156151 TGTTGGATAA TAATTGTTTA TAGCGTTCTT TTATAATCCT TTGCATTTCT
156201 GTAGTGTATT TTAATGTCTC CTCTTTCATT TCTGATTTTA TTTGTTTGAA
156251 TTTTCTTTCC TTTATTCTTG GTCTAGCTCA ACATTTGTTG ATTTTGTTAT
156301 TATTTCAAAA CACCAACCTT TAGTTGAGCT GTTCTATTGT TAGATAGAAT
156351 AGAATAGAAT GTTCTATTTC AACAATAAAA TGTTGAGCAG TTCTATTGTT

FIGURE 3PPP

156401 TTTCTACTTT GTATTTCACT TATTTCTGCT CTGATTATTA TTTTCCTCCT
156451 TTTAGTAACT CTGTGCTTAG TTTCTTCTTA TTTTGTGTGT CTTAAGGTAC
156501 AATGTTATAG GTTGTTTGAG ATCTTTCTCC CTTTTTGATG TAAGTGTTTA
156551 TTGCCATGAA CTTTCCTCTT AGAACTCTTA CTGTTGCAAT CTACAAAAGT
156601 ATTTGTTTTT GGCAAGTTGT GTTTCCATTT TCATTTGTCT CAATACATTG
156651 TTAAATTTAT CTTTTAACTT CCTCATTGTC CCACTGGTTG TTGAGGAGTA
156701 TGTTGTTTAA TTTCCACATA TTTCTGCATT TTCCAAAATT CTTCCTGTTA
156751 TTGATTTCTA GTCGCATACC ATTGTGTTAA AAAAAAGATA CTCAATATGG
156801 TTTAAAGTAT CATTTCAGTT AATGATCTGG ACCTTAAATG ATGGCAGCAT
156851 AATCAATGTT AATCACAAAC CAAAGGCTAT TTAGTGTTAT TATTTTAATA
156901 TGCAATATAC TTACCAGGCC CCCCAGCACT CAGTCTGCAC AGTCTAGACC
156951 CTGCCTATCT CAGATCCATA CCCCATCTCT TCCTCCACCC CTTCTGTTTC
157001 AACCAAATTA ACACTGTTTA TTCTCTGTAG TTCCCCACCC TCACTGCCGT
157051 GCCCACACTA TGTCTTACCA AATTCTGTCC CTCTTTTAGA TCTCAGTTTT
157101 CCTTGAACAC CCAGACTCAA GGTGTGGATG CCTATTTGTT TATCTTTTTA
157151 GTAGCCCAGA CTTTTTTATA GTACATTTTA CAGATGTAGT CAAATAATTG
157201 TGTAATTGGC TACTTAAGAT TTCTCTCCTG CATTTAAAGA AAGCCCCGAG
157251 ATTATATCTA TCTTGTCCAA CTTAGCATGC TGTCTTGCAT GACAATCATT
157301 AACTTTTTAT TGAGTTAATT AAGCATTGTG CAGAATGCCT AGATGCCTAA
157351 GCTTTCAATG TTACCAAACA TGTGGAACAA AACTTACTGC AATCTAGGTT
157401 CCCCTGAAAA CATAGCCTAA GGTGGAGGCT TACTTGAAGG TTACCGTACC
157451 TTAAGGAGGA GAAGTAAAGA ACAGGAAGTT ACTGTTATAG AGTGAATTTT
157501 TCTCCATACC CCACCCAAAT TCATATGCTG AAGCCCTGTT GACTAAAGAA
157551 AAAAAAAATC AAGCTTTTAA AGTATCAGGC CAGGTACGGT GGCTCATGCC
157601 TATAATCCCA GCACTTTGGG AGGCTGAAGC AGGCAGATTG CTTTAGGCCA
157651 GGAGTTAGAG GCCAGCTGGC AACATGACAA AACCCCGTCT GTACTAAAAA
157701 TACAAAAATT AGCCAGGCAC GATGGCGATC ATCTGCAGTC CTAGCTATTC
157751 GGGAGGCTGA GGCACGAGAA TCGCTTGAAC CTGGGAGGCG GAGGTTGCAG
157801 TGAACCGAGA TCATGCCATT GCACTCCAGT CTGGGGGACA GAGAGAAACC
157851 CTGTCTCCAA ATAAATAAAT TAATTAATGA ATTAATTAAA TAAAGAAAAG
157901 TTAGCTTTAT TTGGAAGTCT GAGGACTATG GACCAAGGCC TATTGCCTGG
157951 GATCAGTTCT GTTAGACCAT TCCAATGCAG CAATTGAGTT CACAGTTTGT
158001 ATACAAATGG TGAGGATTCA TTACATGCAA AATCACATCC GAGTTCGTGT
158051 ATAAGAGTTG ATATTTATAG ATTATTATTA TTATAGATTA TATTATAGAT
158101 TATACATTAT TATCGATAAT AATCTATTAT CGATAATAAT AATCTATAAC
158151 CTATAACATG CTAGGCTGCC TTCTGCTGTT GAAAATAATC CAAATATCTT
158201 GGGCATATAA TTATCATTGA GAAGGGCATG ATATGTACAA GAGAAGTATT
158251 CAACTGGTTT CCCCATGATC GCAAACCTTT GGAGCTTATA GAAGAGAAAA
158301 AAAAAAAAGA GAGACAAAGC AAATATAAAA GAGATTTTGA GATAATTTGT
158351 ACACTCTGAA ATGAGAAAGC AAACTTAGGG CTGACACAAG AAGAACTAAT
158401 TATTTTTTTC AAGTACATTT TATTGTTATC AAAATAGTCC ATACATATCC
158451 TAGGGAAAAA AAACCCCACA AATAGTACAG GAAGATTATA ATTTAAAGCA
158501 CCAGTTCACT CAAAGGCAAC ATTTTTAACA AAATTTTTTA AAATTATTTT
158551 TAGTGATCCC TCTAAATTTC TAAATAATAT GCTTATATTT TTTTCTTGTT
158601 TTACCCATGT TAAGTGTGAC AAATTTACTT TTTGCTCTTA TAAATATGGA
158651 TTTAGCTAAT TTTATTTTTA TTTTATTTTA TTGAGACCAG TCTCGCTCTG

FIGURE 3QQQ

158701 TCGCCAGGCA GAGTGTGCAG TGATGCAATC TCTGCTCACT GCAACCTCTG
158751 TCTCCCAGGT TCAAGTGATT CTCCTGCCTC AGCCTCCTCA GTACCTGGGA
158801 GTACAGGCAC TTGCCACCAT GCCTCCCTAA TTTTTGTGTT TTTAGTAGAG
158851 ATGGGGTTTC ACCATGTTGG CCAGGATGGT CTCGATCTCT TGACCTTGTG
158901 ATCTGCCTGC CTCTGCCTCC CAAAGTGCTG GAATTACAGA TGTGAGCCAC
158951 TGCACCTGTC CAGATTTAGC TAATTTTCTA CACTTATCCC CAACCTTCCT
159001 CTTCACTCTA CCTCCCTTTT CAATACGATA ATATCACATC TTAAGTTCCA
159051 TCATCCCTGT AACCTCTGTA GCTATAAGTA TATAGCCACA ATTAACATAT
159101 GTAGATTTCC ATTTCTGATT CTATCAGCCA TAGGTAACTG TCTTTACATT
159151 CCACTTTGTA AGAGGAGATG AATAATTCTC ACCTTTCCTC CCAACTCTGT
159201 GTTCCTCCTT CTACCTCCCC ACCCCCAACT CCGTTGTAGC GGCTATTAAC
159251 ATATATTATT TTGTAACCAT GGGTAAGTGT TAAGTAATTT GCCTAAAGAT
159301 TGATTCTAAA AAATTTAAAA ATATAGAAAT CTATAAAATT CTGTAAATTT
159351 TAGATTTTCT ATAATTATAG AATGTAAAAA TATAGATTTT CTATAAACAT
159401 AGAATGTAAA ATTCTATAAA AATATAGAAA TCTTTATGTA ATTATAACTG
159451 TGTAAGTATT ATTTACTGTA GAACCAAGTA ATGTGCAATG CTTCCTTCTC
159501 CATGGCTCCA GTGTCATGAC ATCTATAGTA CTTTACAAAT AATGTTATGA
159551 GTATATACTT CCAGAATGGT GGTAAAAGAA GCTCTGCAGA CCCTCTCCCC
159601 AGTGAAACAA CCATACTGGT AAAAGTAATT TTAAAAGGCA ATCATGAAAA
159651 GTCTCTGGAA ATTTTCTTAA GGGTATACAG CAAATGAAGA AACATTTATT
159701 CCAAAAAGTG TACTAAATCT TGGTAAGAAC AATGAGTCCA AGGCACCTAA
159751 GTCACAACCC ACTTCCCTTC CTCTCCTCCC AGCTCAGCAT GACAGAAGCT
159801 TAACTCTGGA CAAGAACACA GGGCTTCCTC AGCTTCCAGT TGAGGCCAAC
159851 TGTATGTTCC CAAGAGGAGA AGACCAACAG CGTTTCTTGT CTCCCTTCAC
159901 CCTTCCCCTC CAGAAGCTAA ATTCTGGCTA GATGAATCCA AGATATTGGG
159951 GCTCCCTTCT CTCACCCAGC TCCTACTGGT AGGGTGGAGG TTCAACCTCA
160001 GGCCTGGAAC ACTGAGAATA GTATGGGTTC CCAATTATTA ATGAGACTCT
160051 GATTATTGCC CATGCTCAGC TCCCTGCTCC TACAGCAGAG GAGTCACTTA
160101 CAGAGAAACA CAATGCTGTC CCCATCCCTA GCTCTGAAGC CGCGCGTCAG
160151 AGATTTTCCC CAGTGGGAGC ACTGAAGCTC TTTGCAAAGG AACTGACTTT
160201 ATTTGAAGCA GAGTAAAGGG AAGTTCAAGA TAAAGGTATT CTCAAAAATA
160251 ATGTAAGTTC TGGTGGAAAG CAATTAAGGG GAGGTTGGTA GCTTCGTGAA
160301 AGAGACAAGC TAAACCAGAT TAGCTAGTGT ATGAGAGAGA ATCAGGAAAA
160351 GAGATAGCTA AGAAGAGCCC TCCTGGGTCA GAACAAACCT CAAGCACTGA
160401 CCACAGCAGG CAGGGCACTG TGGCTTACAC CTGTAATCCC AGCCCTTTGG
160451 GAGGCTGAGG TGGGAGGATT ACTTGAGCGC AGGAGTTTGA GATTAGCCTG
160501 GGCAACATAA CAAGACTCTG TCTATATTTT AAAAACAAAA AACAAAAGGC
160551 TACCACAGCA AAAAGGCTGG AATTTAGTTG GAGCAGACCC CCAGAGCAAT
160601 TTATGTCCCA GGACATTGTA AAAAATAACA GAACAATCTA GAACAGAATA
160651 GCTGGGTATA TGTGATAAGC CTTAGAGCAA CCACTAAGAA AATAACTCGA
160701 AAAATACATA GTGAAGGAAA GAAAACAACA ATGTTCCTAA CATCACAATC
160751 AAATGAATTC TCCTTTTCAA CATTTCACCA GAGGCTCAAA ATCATTCCAC
160801 GTTTAAAATT TTTTTCTCTT TATAATGTCT ACTGAAAAAG TAGCAAAATC
160851 TACTGAGGAG AGCTTTATTT CTAAAAGGGA GTATCACAAC CTGCAAGTGG
160901 GAAATGGAGC CTCTGGTTAA AACTGAAAAG CAGGTGCTTC GAAGGAGGAA
160951 AAATGAGACA GGAATTCATA CTAAATGGAT TGGTTTAGCA TACATATTCA

FIGURE 3RRR

161001 ACCGGCTATT GGAGGAGCTA TGAATATTCA TGAAGGGGCA CACGTGTAGT
161051 AAGCTAACAT GTCTATTACA TATGTCCCAT GTTCACTTTG GGGTGGAAAA
161101 AGCATTTAAA TATACTAAAA TTAAGCTCTA TATGTCAAAA GGTTAAGCAG
161151 AGGACATGAA GGGACTCAGC ATACAGTCTC TGTAAACTGG CCAGAACCAC
161201 TCCATGTTCA GTGTTCTCTT ATTGGGAAGG AATGCTAGCC AGTTGCTGTG
161251 TCGAAACTAC AAAAAGCAAG GGGCAGCGTA ACATGGTTGG TTGAAATCAG
161301 CCATGGAGCA AGTCTTTCAA AAGAGCTTGT TTCTGTTTAA CCCTTAGGAA
161351 CGAAAGCCTA CTGGTGGTTA ACAAGGTAGG GGGTGTTACA GGGTGTGGCT
161401 GACCTACTGT TCCATCATAG ACAGGAGCTC AGTTTTTAAG GTTTCTCTGG
161451 GGTCTCCAAG TGAGCCTCCC TGGAGAATCC TCCAATTTCC CTAGTGAGAG
161501 CAAGAACCAT ATCTGTCTAT ACTGCCCAAC TCAGTTGTTT TTGCAATAAT
161551 AGACAATAAC TCTTTAAAGA ATGAATAAGT GGTGGTGAAA TGAAACAGAG
161601 TAAGTTCCTG ATGTAGAAGG CAGAAGGGAG ACTGTTGCTT AGGCAGACCA
161651 AGTAGAAACT ATACGATATT TTCTATAGTA ATAACCTTAG AAATGGCAAT
161701 TCGGTTCTAT AGTTCAATTA ATATCACTAA AAGAGCTGTC CAATGAACTT
161751 ACAAGTTATG TGGTATATGT GGGTTAATCT GGGAGACCAA CCACCATTTA
161801 TGAAATTCTT CTCTATGAAA ATGCTTTATG AAGGGCAAAT AGCAAGTTTA
161851 CAAATGAATT TTTGGAAAAC AAACTGTAAA TTGAGGTTAA CTTCTAAGGC
161901 TGTTAATTTG TGGGTATCTT TGTCTATATC TTCTTCTCAC TGATATATCC
161951 TCAGGTAGCT AGAGTTCTCC TTTCAACTAG CCTTAATTTT GAATTATATG
162001 CCAGTTATAA ATCATCTTCA GAATATGAAT TAAATACCCC TTTAATTTTA
162051 ATTGATATGA TTTTACAATA TTAACTACAT AGTAACAATG GATTTGGATA
162101 TTTATCATTT TTCTATTTGA TTTATAATTT AGGGCCAAAT GGGTGTCATA
162151 AGGGGCTCTC ATTCCAGGAA ACACTGTAGA GTAGTCTAGT ATCCTAACAG
162201 TCTATCCATC TTGATTTTTG AAAATAGTCT GTTGTGGAGT AGTTTAGGAT
162251 AACCTAACTA CTTGTCTGTC AAATAGAGGA ATGCTGTGAC TGGAGAAAAT
162301 GGAGCCGTTA TACATTAGTC TTCGGTACAG TCACAAAAAG CTACTTATTT
162351 CACAAAAGAC ACTATTTTGC CTTTTCAGGT GTAACTGTGT GGAACCGCAT
162401 AATCCCAGCA ATGGCACATT GAAGGAATGG AGGGAATCCA ATATTTCTGC
162451 CTCTGACATA ATTTGGGAGA ACCTAACTGT GTCAGTAAGT AAAACACTGA
162501 AAAATAAGTC ATACCTAAGA GCTTTTGTTG ACATTTTGAC TCAATTATTG
162551 CCATTACAGT AAAATTTTTT TGAATGCATA ATATAAAACT AATAGTTGTG
162601 TTTTAATTTT AATTTCATCA TTTCAGATGC TCATCAGTAA ACTGGGGTTA
162651 TCTTTCATTA TTAAGGTTGT TCTAATAGAA GACCAGAATT GCTCAAATAG
162701 CTCACTTATA CAGAAATATG TGACCGAGAT GGACTGAAAG CACATTAAAT
162751 ATGAGTGGTG TTGACCTAAA TGAAACCATA TGGCAGAACT AAGTCTGCCT
162801 TCTGTGTAAA GAACTCAGAA TGCTCTTACT TTACTCTGTA ATGCTGCTCC
162851 AGCTGTTCCG GATCTGCTGG GGGGAAAGGG ATGTTTCTAA TATTCTAGTG
162901 TCAATACTAA AGTCTTTGGG AGGAACAAAT ATCACTTTTC TTCACAAAAT
162951 TCTGGCACCT CCCTCAACAA GATCTTTCTT TTTTCCATTT TATTCTTATC
163001 TCCCACTCAA GAAAGAGCAT GGCAACATAT TTTTCACCTA TAACAGTTCA
163051 ATCCTGTGCC ATTGTCTTAT TTCCTTTGAC TTTTCTCTAC TTTGTGATTT
163101 CTTTTTTCTC ATACCTGCAT TTCTCTATTT TTCTGAATCT ATTCTGTGCC
163151 TCCTTTCCTA TCAATACTTG CATTCTATGC TTCTGGTTCA ATAAAATCTT
163201 GTAATTTGAA AATGTGTTCT ACTTTAAATA AATATTAAAA TCTGAGTAGC
163251 CCTACTTTCT TTTCTATTCT TCCCAGCTAT AAACATTACA GGTTCAAACC

FIGURE 3SSS

163301 TTCTACCACT TTACCTACCC ATATAGGCTC AAGTTTTATT ATGACTATCA
163351 GCACAAAACT ATTGAGTTCT AGTTCATTTG ATCAAATGCA TACTATTTTA
163401 GTAAGTTGTC TAGTTAGTGA GCATAGAAAT CTTTTTTGGT GTACAGATGC
163451 TATAAAACTC TAAACATGAT TCTTGTAAAG AGCATATGAT CTATTGACTA
163501 TATTCTTGAT TTTCTCTATT GAATATGTTC TTTCAAAATT GAAATCAAAT
163551 TACTTACTCT TTATTTAAAA TTCTATCTTG ACCTATATTT TACTACTTCT
163601 ATTCTTACCC TAGCTGTGTT CTGTAGAATA AGCCTTCAGT TACTCTTATT
163651 GTTTTCTTTT GTTATTGTTA ACATTTATTC TGTTCCACCT ATTTTTCCCT
163701 AGAAAAATAA CATTGCCAGT CTGCTTCCAC TCAAAGAGCC ATTTAAACTG
163751 AACAATAAAA GAATTGATGA GCTGATCAAG AAAAAACACT ATAGTTATTC
163801 AGAATTTAGA CATGGGGTCA TGATTAATGA AATCATTAGT GGGTCTTCTG
163851 TCTACACTTT CTTTGGTAAA CTATATTATG TTTACAGAGC CTCTTGATGT
163901 CTTCTTCAAT ATGAAAACCC AAATGATCCC ATCTCTAAGT TATATAACAT
163951 GATAATTTAC TCTATATGTG TTTTGTATTA TGTGAATAAT TTAATACTAA
164001 ATAATAATAT TCCTTCTATG TATTAGCAAA TCTTGAATTT TGAGAGTTCT
164051 AAGAAGCAGA CATACAGCAC AGTTATCAGG CTAGCTGTGA GTTAGATACC
164101 CTGAGTTTTG AGGTCAAGTA GAATAGTGAA AAATATTTTG CAATTAAAGC
164151 AAATACAGCA TTGTGGGGTT GTTGGTTTTT TTCTCTTTTT TTTTGTCATT
164201 TTAAAAAGTT TTGTACTAGG TGTTAACATT TGAGCAGAAA GTTTCATATT
164251 ATTTTTCATT AGTTAAAAGC AGTTTTTGCA ATGGATAATT GCTAAACTTG
164301 ACCAGAAACA GTCTTTATCA CCAGAGGGAA TACTATATAA TGAAAACAAT
164351 CTTGTAATTT TTAAGTCAAA AAAAGACCAT TAAAATTTTT GTCTAATTGT
164401 TATGCTGAAT TTTTTCCTCA ATATATTCAT AATGTCATCA AAAATATTTT
164451 ATTAATAAAG CACTGAACTA GTGGCTATCA CAACTAATTT TGTTAAAATA
164501 GTGACATAAC ATTTAATTTA CATATTATTT GTTTGGCAGG TCCTGTAATG
164551 TTTTATTGAG TTGTTTGTTA CATATCTCAT GAATTATAAT TTATACCTTG
164601 CCAACTCAGC AAGGGCAAAG AACTTTAGTT TTCTCTGATT CTCCCAAACT
164651 GCTCTATGCA TAGTAAGTGT CAAACATTTG ATAGAAGTAC TTAATGTCTG
164701 TTTGAAACAG TTTCATCTTA CTATTTAATG CAAATATTTA TGGCAAACTG
164751 GAGTACTTAA GTTTGTGTGT ATATATATAT ATATATATAT ATATATATAT
164801 ATATCTCTCT ACATATATAT GCGTGTCGAT ATCGCGAAAA ACCGTCTCTA
164851 TATGATACTC TCGCGCAACG TCGAAGAGTA AGCAGGCGCA GCTCAACCAG
164901 CACGAGGTGT CGCAGTCACT ACCTCGCATA CCTTGCGTGT NNNNNNNNNN
164951 NNNNNNNNNN NNNNNNNNNN NNNNNNNNNN NNNNNNNNNN TATACTATAG
165001 GAGCCAAGTA GCAAAGCATA TGTATGACAC GCAGGATCGA CTCTACGAGG
165051 ATCCCCCTTA GGCAAGATTT AAAATATTCA TAAGCAGTTA ACCAGCATTT
165101 GGTGTTTCAG TGCCTGAATT ACATATTTAG CTTGTACATA TATAAGGGGC
165151 AGGACACTAA TGCCAACTTT AATTTCTTAT TCTAACTTAA TTTTTGCCAA
165201 CTTATAGAAT TGCTGAAACT TAGAATGTGT TTGAAGAGTA ATTAGTAGAA
165251 ATCAGTTTGT CAACAAGCAT TTTTTGAGTA CCCATTGTAA CTGAAACCAT
165301 ATGTTAGACT CAAAAAACGA GAGCAGGATT TGGATTTGGT TTTCATTTCT
165351 AAATTTCAGG ACTTACTCTG TGTGTATGTG TGCATGTATG TATGTGTGCA
165401 TGTGTGAGTG CCTCTGTGTG TGTATTGGGG ATACAATTAG TATAAATCTG
165451 AAAATAATTG TTGAATTTAG CAGGTCACAA TTTTTCTCTT TTAAAATTAG
165501 CATTTTGTTT CCTCCCAAAG AGAAAATAAA TAACATTTTC AAATATGCTT
165551 TGAATTAATG TAATTAGGCA GACCATTGGC AAATTATAGA GTGTAAGACA

FIGURE 3TTT

165601 GCTAAGGAAC CCTTTAAATG TCATCTATGT TCTTAAGAAT TGAGAACAAG
165651 ATCCCGCCAA ATGACTTTTA TACCTGCAGA AATGACAAAA GATGCTCACA
165701 AATTTATAGA TAATGTGTTT ATCATGGAAC TTTTAGCTCC TTTTTCTATG
165751 TAGCAATTTT GCTACCCATT ATATTGCTTA ATAATTGCTC TGCTAGCATT
165801 TCTGGACAGG TGCAGAAGAG GATGAAAAAC ACAAGGATTC ATTTTTGCCA
165851 CCTTATCTAT TTTTAAAGCA TTTTGAAAGA AGGAAAATTA AAACTTTAAT
165901 TAAGGCCTGG GGGATTTTTC TGTGGTTTTT CAATTAGCCA AGTTGCTGTG
165951 CTCTGTATTA GCTTAACATG AATAATTGGA ATTTAACTTT GCCTATCAAG
166001 GAAGATGTTT GCAGTTAAAT TAGAAAAGGA GACAGATTCT TTAAGACAAT
166051 AATAAGGTGT ATTAACTATA TTTCTCAAGA CTCTCAGGCT TAGGGTAGCT
166101 AGCAACTCCA AGTAGATTTT ACTAGTTGTT TGTTTTCAGA TGACAGTGTA
166151 GCTATTTGTA ATTTATTCTA CAATCTTTGG AGTGTATTTA CTTTTTGCTC
166201 TACAAAGATT TCAGGCCTAA AGTTGGGCAG ACTCTGTGTT TGTGATCAAT
166251 CTATCAGTTC ATATTTGTCT CCAAGATCTC TCTGCAATTC AATTTATGTT
166301 CAGGGCAAGA ATATCTCAAG GACTAATGAG ATCACTGGAT CATTTAAACC
166351 ATTATTTCCT GTTTTGAAAT GTAAAAATAC TTTAGTAATC TAATTTTTAA
166401 ATAAGATAAA CCAAAGTAAG TTTAAAATAA CTTTTTTTCA TTCAAAATAT
166451 TTGTTTGAAA TGCTCAGTTT TTCCTGGAGG AAAAAAATTT TTTTGACTTT
166501 GCTGCCACCT CATGGCTAAG GCAGTAATTA GAAATAGTTC TTCAGGCTCT
166551 TACAGAACTA CAGTTGCAGA AGAAAAAATA ATCCATGGAG AAGTCATAGT
166601 AAATATGAGC TTTGCCTTGC TCATGTAGTA ATTTTATTTC ATTTGTTCTT
166651 TAGTCCAAGT TCGATAGTCC CATCTTTGAC TTACAAGTTC ATTTCAGTCA
166701 TTGTATGTCA TAGTTTTCTT GTTGCCTTTC TCATCTTTCT TGGCAGCTTT
166751 TGGACTAGAT AATTCTACAA AGTCATTGTT CTTAGTCAAT AAGCAATAAT
166801 AATCTCACTG CAGAAATCGT GTTTGTATCA CAGCTCTGCG GCCACCCACC
166851 AGTGGTGAGG CCACAACAAA TTATTTAACC CCTTTATGCT TCAGTTTCCT
166901 CAGACATGGA ATATTAATAA TAGCATGAAC ATATTTTATG GTATTGGTGT
166951 GAAAAGTAAT TTAAATGATG TATTTAAATA GCTGGGCATA GTGTCTGACC
167001 TTAGTAACCA ATCACTATTA CATATGTCAT ATTTTCAATA TATCTCGTGT
167051 TAGGAACTTA GTAGATATTA GATTTAATAC ATACTAATTA ATTGGTAAAT
167101 CAATCGTTTT ATACATTTAA ATTTAAAAAG CAGTTCATGT TCAAATTTTT
167151 CATAAACCTT TGCATATTTC TCACCACCCA TCCAAGTTGA ACTTGAAACT
167201 CGTAATGTAA TGCCTGCTAA ATCATTGTGA GAGCCATAAA GGAAAAGCCT
167251 CAGCATCTGA ACTACAATTG ATCAGAAGGT GTTAGTTTTC TGCAAGAAAT
167301 GTGTCCGGTT TTTTCTTAGT AGCTCCATTT GTTTTACTTC CTCTGGCAGG
167351 AATGCAAATC ATTGCATGGA GAGTATGTTG GACGGGCCTG TGGCCATGAT
167401 CACCCATATG TTCCAGATGT TCTATTTTGG TCTGTGATCC TGTTCTTTTC
167451 CACAGTTACT CTGTCAGCCA CCCTGAAGCA GTTCAAGACT AGCAGATATT
167501 TTCCAACCAA GGTACTTAGA CTATTTCTTG ATCTAAATGT AAAATAACAT
167551 AGGACAAAAG AAAGAGTAAT TGATGTAATA AAAGGAGCCA CTGAAAGGCT
167601 TTTGTGTGAG TGAGCTGCCA GGTTAGTTGT GGAGTGAGAT GAGGGGCTGA
167651 AGAGAAAGAA TTTGTGATGC AGGTGCTGGG AGTGCATATG CAGGCTTTTC
167701 TCCTAACTGC AAACCCCACG GATCAACTCC TACTTTCCTA CTGACGTTTT
167751 TGGAAATTCA CAGCACACAC TGCATTACTG ATTGTCACTT TTTTGCCCAG
167801 TGAACAGTGG GAACTATTCC AGCCTGACAG ATACCTCAGA GGAGCCTATG
167851 TTACATTCTC TAATTGGGGA AGCCCCGGCA AGACTCATTG GAACAATATT

FIGURE 3UUU

167901 CTCTTTTTCA ATGTTTAAAC CGTCAGTCCC TCCCCCTAAC CCACCACGTT
167951 TGCATCTGCA TATTTGGAAA GGAAAGTAAA CAGAGAAACA GCTTAGTTCA
168001 ATATTTAACA CTGCAAAGTA ACACCTATAA TGTCTGATTC CGCCAAAAAA
168051 AATTTAAAAA AAGGAAAAGA AACAAGGAAA CAAGCTTCTG AGGGATGAGC
168101 TATAGATTAT GATCAAAATT CCACTCTGGA AAAATATTTC AAGAACTGTT
168151 CCTTCCGAAG GGGGCTTCTT TTTTGTCACC ACTTTCTTCT ACTAAAGGTG
168201 GAAGATTCAT TTATTTCCCC AAAAATCTTA GTCTGATTAA TACAAAAACA
168251 TTTTTCTAAG CTGAAACAAT AATCTTAAGC ATTTTGTGTA TGCTTGTGTG
168301 TATGTCATAA AGGCATCTTA AAATAAACTA GATCTGGATA ATAATTATAT
168351 GTGAATATTT GCTCAGAATT GGCTTTATAA ATGAGAAATG GCTTTAAAAA
168401 TTGGCTCACA TAGAATAAAT TTTAAATTTG CCCACTCTGT TGTGTACATT
168451 CCCAACTGTC ATGCTTATAT TCTAGATAAA CTAAAACATT ATGTTTCTTT
168501 GATAAGAACA GATAATTTTA TTTTATGATG CTTCAAGTTT ATCATATTAA
168551 AGTGTTACCT GTGTGAAAGA GATCCCTAAA ATCCAGCCAA ATTCTGCCCA
168601 TGCTACCTTA TTCTGCATTC TGAATATTCA CATGCATGGG TTCATCATAA
168651 AGTTAGATTT TAAATAAACA TTGAAAACAG CACAACCACG ATGTAGCTAT
168701 TCCATAATGC CTCATTCTGG AAAGGTTGAG TGTGTACCAA TCTTAACGAC
168751 AGTGATACAT AAATATATAT TCAGGTTCTG ACAGAGCTAA TGGTAATCTT
168801 ATAGTATGCA TAAAATATAA TATTATGATA TTATGTCATA AAGTGTTTAT
168851 AAAGTGTGAC TCTAGATTAT GTTCCTGAGT ATTCCTTGAT ATTTATAGCT
168901 ACTTTAAGTG ACAAGTGTTT TCATTATTTT TAGGTTCGAT CCATAGTGAG
168951 TGACTTTGCT GTCTTTCTTA CAATTCTGTG TATGGTTTTA ATTGACTATG
169001 CCATTGGGAT CCCATCTCCA AAACTACAAG TACCAAGTGT TTTCAAGGTA
169051 CTTACTATCT CTCTCCCTCT TCCCATCTCT CTCGGTCTAA TCTTCATTTA
169101 GATGATACCT ATAACTCTAG TACTTAGGAT TTTCATGAAA ATATGAAGAA
169151 TTTAGATTAG AAGACCAGTA AATGAAATGC ACACAGCATG GCTAAAATTT
169201 AGGTCTAATA TTTAAAAATA TAAGAATTAC AAAATATAAA TAATTATAAA
169251 TATAAAACTT GCTTGAAAAA AATTTCCTGT CAATTCTGCC AGTTGAAATA
169301 CCTATATATA ACATTCTTAA AAGATAAGGA AGCATTTGAA ACTAAGAGAA
169351 AAGGATTATC TTGGCAGAAT TGTACAGTGA ATAAGGCTTG GAAAACAGAT
169401 AAAAATAGAT TGGGAATAGA ATTCTGACCG TGTTACTAAT GGGGTACAGT
169451 TTGAATATTC CTTATCCAAA GTGCTTGGGA TCGGAAGTGT TTCAGAGTTC
169501 ATTTTTTTTT CAAATTTTGA AATATTTGCA AACACATAAT GAGATATGTT
169551 TGGGGTGGGG CCCAAGTCTA AATACAAAAT TTATGTTTCA TATATACCTT
169601 ATACATATAA CCTGAAGGTA ATTTTATACA CTATTCTTAA TAATATATGT
169651 GACCTATCAC ATGATGTGAG GTGTGAATTT TCCGCTTGTG GCATCATGTG
169701 AGCGCTCAAA AGTTTCAGAT TTTGGATCAT TTCAGATTTC AGCTTTTCAA
169751 ATTAGGGGCA CCCCTTTGTT TTCTCTGTCA AACAGGGCTG GGGACTTCTA
169801 TATAGGGCTC TTGTCAGGAT GAAATTTTGA GAATCATCTC AGACAGCAGC
169851 CATGTTTGGA ATCCTTCCCT GAGCCTCTGC TGTGACCAAG TATCTTTTTT
169901 ATCATTTTCA CTCAATAGCC TCTGCACATC AAAAATAACA GTTACAATAC
169951 CATAATGATG TATTTTGTTT AGATGTCTGT CTCTGATTCT AAACTGAAAG
170001 AAGCCTCTGA TTTATCTTTG TATCTCAGTT CTAGCACAGT GGTCAATGTG
170051 TCAATATGCT ATTTGTAAAT TTCAATACAT TTTCCAATAG TAAATAGTAA
170101 ATATTAATAT CATTTTATTT AATACAGGTA TTGATTAATA ACACAGATTT
170151 TTCAACAAGT CTGTCAGAGT TTAAATCCCA TCTCTACCAC GTACTAGCTT

FIGURE 3VVV

170201 TGGGATCTTG GGCAAGTTAC TGGATCTCTC TGTGCCTCAA TTTTCTTATC
170251 TGTGTCATCT TTAGAGTGTT GTGAAGAAAA AAAAAATGAG TTAAAATATT
170301 TAAAGCACTT AAAATGGTTT TAAGTGATTT ATGAGTATTA TTATTATTTA
170351 TTATAGGCCA CTCAGCTCCT CTGTTTATAA TTAGGGCTTT CCTAGTAGCA
170401 TCTGTAAGAC CTAATTTGAT CAAGTATTCA TTAATCCAGT TCATAACTAT
170451 GCACATTCTT TACTTTATAC AGCCCACTAG AGATGATCGT GGCTGGTTTG
170501 TTACGCCTTT AGGTCCAAAC CCATGGTGGA CAGTAATAGC TGCTATAATT
170551 CCAGCTCTGC TTTGTACTAT TCTAATTTTT ATGGACCAAC AGATTACAGC
170601 TGTCATCATC AACAGGAAAG AGCATAAGCT AAAGGTATAT TTTAACATCC
170651 ATTTTAATGT AAATAATTAT GACAACTGAT ATCAACTGAT GTTCATTTGA
170701 CTTCTATATT CTGTATTCAT TTGCACAGTG AAATATATAA AATAATGTTT
170751 TTAGATGTAT AATTTTTATT GTCTTACAAG ATACTTGGTC TTACAATGAG
170801 ATGAGAATTT ACTTATTTGT AGCACTTGGC TGAGCTCACG TCTGAGAACT
170851 CACCTCCAAG GCATAAAATA AAAAACTGTC AAAGTTTTAA CTTTTCCATA
170901 CTTAACATAT TTTAATGAAA TAACAATCTG TTCTGGTGAA GTACAACCAT
170951 ACCAACTTGT CTTACATCTG AGATTCCTCT ATTCCTCTAT TTAACCCTAA
171001 ATGTATCTAT TACATTGAAT TCATTATCAG AATAAATTAC AACTTCAACT
171051 ATTTCTCATT TTCTTTAATT ATTTTTCTGT CTGCCTGTAA CAACAAAATC
171101 CAGACATAAA CGTCACAGTT TAGAAGTGAC ATCTTTGAGT TTTATTGCAG
171151 ATTTCACTGT CTCTTTTATA AAAAGAATAA CTATAGATGT GTCTTAGTTA
171201 CATTCTGACC TTGCCATTTT GCAATTGTGA ATAATCGAAA TTGTTCACTG
171251 GTATGCAATT TGCCTGAGAT ATGTAATGTA AGCACTGTCA CTTACTTACA
171301 GGAATATGTT AAATAAAATC GATGAAATCA TTAAATGGTT AAAAATAATC
171351 TGCATCAAAC CTTGTAAAAA CATAACATGC ACAATCTTGT TTTTGTTTTG
171401 GTATCGTGGG GTAGTTGCCA GCTATTTTCA CATACCCTTT AAACTCTAGG
171451 AGAAAAAATC ATTGTCAGAG CAACAGAAAT CATGCTTTAT AGAATTTTTT
171501 TATAGGAATG TTAGAAAGAT GAAAAATATC TCTGATTAAA CTCTGATGCA
171551 ATATATTGGG TCAATGCAAA AGTAATTGCA GTTTTTGCCA TTACTTTTAA
171601 TAATAATAAT TACATAAATG TAAGAAAGCA CACTTATTTG CAATAAATCT
171651 TATGAAGAAG GAATTTTGAG TATATGGTGG AGAGAATGTG TGTCTATCTT
171701 AAAGCAAAGG ACATTTTTCA TTCTCTTTGT AGAACGTAAG TTAAGAATTC
171751 TCACAACTTT ATGTATTTTA TTAAATGATA CATTTTAAAA AATCAACTAA
171801 AAAACCTGTT TTAGGAAGAA AGTAAGCCAT ATAATTATTA TTTACCTTTC
171851 AAAAAGATTT TTTTAGCCTT TATAATTAGG CAGAAATTCT AGTGTGTTCA
171901 CTGAAAAATT ATCCTCTGTA AGGGCCATCA GTTAAATGGA TTCAGGCAGC
171951 ATTTTTTTCT TATTGTAAGT GGAATCATAT TAAAACAAAG TGTGGAAGTG
172001 AAATGTGTGC TGAGATTGAT ATTACCTTCC TGGCCATTCT GAATCTTTGC
172051 CCTTTCAACC TTATAAATCA CATGACACTT GCTCTTACTC CTTGTTCTTC
172101 ATGAGCCCTT GACATTCACA GCCTTTGTAA AGCTCCACAT TGACAAATAC
172151 ACTAATTTCC CCCTTCACAT ATACTGTGGA ATAACAAAAA TGTAGTAAAG
172201 CATTCTTTAA GTGGTCCTTT CAAGTACTTG CATTTATAGA ATTAAATGCA
172251 GAACTAGAAC TATTTTTGTC ACTGAAATAA ACCTGAGGCT ACATTACTAA
172301 ATCTGTTTTA TTGTGCAAAT AAATGATTAT GTAGTCAAAA GTTGTGTATT
172351 TTTGCCCCTT ACTACTCTGG ATTTAGTAAA TGATACAGCA AATCTGGCTT
172401 AATCATAAAC TCTGCTATAT GGCCACAGGC AGAAGAGTCA GCCTGTTCTT
172451 GGCCACTGTG AATCTGAACT CTCCATCCTC CTTCTTAGAT ATGAATACTT

FIGURE 3WWW

172501 TTAAAGCAAA TTTCTTCCAG TGAAGATGTA TTTCATCTAC ATTGAACCCC
172551 TATTGGGCCT ATAACTCTTG TCTCCTATAA GCTTCTATAG AGTGTGGTCT
172601 GATGCTACTG GTTTTCCCGT TAACAACAAC AAAATCACCT TCTCAGAATG
172651 TTATTTACTC AGAGTAACGG TTTGTTCCAT AGTCCTTCTC CCCGCCTGTT
172701 GCTTCATTGA AATGTTTGCA AAGTCTCCTG GCTTTGACTT GAACCACATT
172751 TTCACTAAAA GATGTGTTTC TTGAGTATAT CACCAGACCA CAAGCTAACC
172801 ACTTGTGAAA GCATTTTCAG CTTTTACTAA TTTTCTTTTC TCACTTGAAA
172851 ACCCATTTTT GCCTTGGTTG GAGCATTCCC CGAAATTGTT TAATGAATCA
172901 TGTTTTGTAG TTTATGTATC AAACACTTGG TAGACTCCAC ATCATGTATC
172951 TAAGTCTACA TACACCCAAG TCAACTCAGA ATTCCTCATT TCATTCTTTA
173001 TCTCTCCCAA ACATATTTTA GATCTTTTTA CTTTTTCTTC ACCTCTATTG
173051 CCAGAACTAG TAGCTGGTTT TCTTTTAGAT GATATTTCTC CTGCTGATAA
173101 AAATGTTTTT ATTGGCCAGG CACAGTGGCT CACGCCTGTA ATCCCAGCAC
173151 TTTGGGAGGC CGAGACAGGT GGATCACGAG GTCAGGAGTT AGAGACCAGC
173201 CTGGCCAACA TGGTGAAACC CCATCTCTAC TAAAAACACA AAGATTAGCT
173251 GGGCGTAGTG GCGGGCACCT GTAATCCCAG CTACTCAGGA GGCTGAGGCA
173301 GGAGAATCGT CTGAACCTGG AAGGCAGAGG TTGCAGTGAG ATGAGATCAT
173351 GCCATTGCAC CCTGGCCTGG GCGACAGGGT GAGACTCCGT CTCAAAAAAA
173401 AAAAATGTTT TTATCATTTC ATGAGTGTCA CTATGTACAC AATAAAGCTG
173451 TGTTGCACTG CATAGGTGAC TTACTACTCC CGAAGAATGG GGGAGCTCAA
173501 AATCAGTAAA CCTCGAACTC ATTGCATCCT ATGATCCTTT GGATGGCTCC
173551 AGAGTGAAAG AAGAGGCAAA TACAAAAATT TGAGAATGTG AAGTATCATG
173601 TATATTATAC ATAAATGTAC ATATAAATCC ATACTCTCTC TAGCATTTGT
173651 TTGTTTGTTT CTCCCTTAGA GAAGTGGATT AGGCATAAGT TAACTGAATC
173701 CTTTTGAAAA GCATTAAAAA TATCTACTTG GGTTTTTTAA AGCACATTCT
173751 CTAAATGTGA AAAGAGAGAT AAAATCTTAT AAAAAAGAAA GTTTCTGTTA
173801 AGATACAACT GTGGGCTTTT CTACATGTTT CTGTAGACAG TTCAGGCTTC
173851 TTTTGACATC ATTTTTAATA AACAGCAATA CAATCCCGGA TCACTTGAGT
173901 AAATGAATGC ATTTGCAACA TTCATTTGGC ACCATATTCT CTTGATGATT
173951 ATGGCATTTG ATATGTTCTT TTTTGCCCTC TTTGTCAGCC TGGTTCTTCA
174001 TGTCAATCTA TAGTCTTTTA TGTGGTTAAC TTGACAGATG CAGGAAATTG
174051 CTGCCAAGCT TTGAAATGAA TTTTTTCAGC AGTGGCATCT GGGTATCAGA
174101 TGGTCCTCTT GGCTGGCCTC TTGTCTTGCT GCATGTTGGT TTTAGTGGGG
174151 TCTGGTGTAG CATCACCTGT TGCTATGCTC CCTTTTCCTC CCATATGTCC
174201 ATTTCCTGTG ATTCATGGAT GAATGTGAGA ATAAAAGCTC TAGCTCTGTC
174251 TTTATTTGAG AAAAAAATCT ACAGAAATAT GTTAGAAGGT GTAGAGTTCT
174301 CTGTCTGACA AAGGGATACT TCTCTTTGGC TGGCATGCCT ATCAGCTAAT
174351 AATTTTGTTA CAAAGTCCAA GTTTTTAAAG ACATTTTAAA TGAAAGGCAA
174401 GAAGGATACT GGTTAGTTAG GGGAAGAGCA AGAACTGCTT TATTTATTTC
174451 CTTTGGTTTA CGTTAAATCA AGATGCTGCC ATTGTTGTAC AGCATAATTA
174501 GGGGAAATTA TATTTTTGTT TTTGTTATAT ATTTATATAT TACAAAACTA
174551 GCTTTATAAA TTTAGAAAAG AAATTATTTC CTCTGAAAGA ATTATTTTGC
174601 CTACTTCCTG CAATTCAGAA TCCCACTGTT TACATTTGTA TCATATTTTT
174651 AAAACATTCA ATAAGAGCTA TTGGAAATCA CTATCGCGAC AAAGATCTCC
174701 CTCATATTAT TGAGATGTAG TGAATGTGGA CTCTGAGAAA GTCCAGGTGT
174751 GCTAAAAAGT ACAAGCCTGA CTCTCAAGGC CCCCTGTCTT CTGCCCTCCT

FIGURE 3XXX

174801 CTGATGCTCA TCTCACAGCC ACCAGCTCCT CTTCCATCTT TTGATTTCTC
174851 TTAGCAGTAC CATAATTTTG CAAAATAGCT CCAAGGGGGC ACCATTCACA
174901 TTGTACTCCC TCAGAGGCAG AGGCTTAAGT ATGAGGTCCT TCCCTGTTCT
174951 ACATCCTTCT CACTCCAGAG TTGCTAGGAC AAAACACTTC TCAAACTGCT
175001 TAAGACATTG TCCTTTAAAG GGACCAAAAT CTGAGTTCTA TTCTATGGAA
175051 TTACATCTTC CAAAATGTTT TGCAAAAGGG CCAAGGGATG ATATTATGGT
175101 CCTGGCAAAA CTGTTTCCTA TGCTTTTTTG GTTATGCTGA CACCAGGCAG
175151 TTTCTCTTCC TACTCTTCAA CTCTTACTAA TCAAATTCTT TCTTGAGTTA
175201 CTTGCAAAGA AAAGTTTCCA GAGTCATATT CATTCAGGAA ATTGAGTTAG
175251 ATATTTTGGT AAATTGTAGT ATTGCCCCAG TAAGCTGAAT CAATGAAGGG
175301 TACCATTGCT TTGGTGTCAA CATAGGAGGA ACAGGTCCTT AGGCACATAA
175351 CTCTCATTGT CTCCTCACTA TCATCTCTTG CACTTTTATA ATTTGGAAAG
175401 GATGAGCAGA AAGGAAAGAA AGTACAACTG ACTTTAAGAA CCTTCTTACT
175451 AAGAAAACAA GAAAACAAAA TCACAGAGAA AAGACTACCA TGACAAATAT
175501 GCAACAAATA CTCAGTGTGT TTCACACTCC AGGCTATAAG AGCTCTCATA
175551 CTGACTACAA ACTGCTTGAA GTTATATAAA ACTACCTCTA AAAAAGACTA
175601 TTATTCTCCT AGAAGAATTG GTAATTTCTG CTCATGGTCA TAATAACAAA
175651 TTTAACTGCT GTATTTATTT TAAAATTACA CTTACTAAAT TTGATTCTGA
175701 AATGTTTGAT GCGTATTTTA TTTTCAAAAA AGTCAATTTG TAACTTTTAT
175751 TGATTGCTTA TTGTGTGCCA ATGATTGTGC TAAAAACTAG AGGAAATACT
175801 GAGAAATTAT ATAAGTTATC TGATCTTAAG AAACATATTA ATAGTTTTAT
175851 TAAGGAGCCT TGAAACCTAA TGAGTACAAA AGAAACATTT ATTGTTTAAC
175901 CACTAGAATA TAATAGTACC TAACATTTTA CTGATTGCTT TCTATTCAAC
175951 AGATATTATT CCAAATGATT TACAACATCA ACTAATTTAA TTATCACAAC
176001 AGCCCAGTGA GGTGCCTTCT ACTATCATCA TCATCGTTTT TCAGATAGGG
176051 AAAAAGAGGC ACAAGAGCTT AAGTGATTTA TTGGTTGAGC TAGCATTTCA
176101 TTCCAGGCAG TCTGACTCCA GAACTTATAT TCTTAACCAC TTTATTATAC
176151 TGCCTCTCAT AAAGCAGTCA CTAAAAATTA AAAATAAAAG GTGGAACATA
176201 AAATAGGCCA TCCCTTTGGC TGCTTCTGAG GCTCTACACT TCGATTCCTG
176251 CAGGGTATGG AGGGAGTGCT CTTCCCCATC TTTGATTTCC CTCCTCAGAG
176301 AGCACCCTGT CTGCAAGAGG GCAGTTTTCA CACACCCCAT TGCACCTATT
176351 TTTCCTCCTT TACATTTCCT ACCTGGTCCT AGGAGGCACT TAGTTTGCAA
176401 CACCTGGAGA TCAGTGACAG TGGAGTAGCA TAACAGAGGA AATAGAAAAC
176451 AAAAAACCGT GATTTCTAAG GAGGGGCTTA ATTTGTCTAG TGCTGAAACT
176501 GAAGCAAATT AGAACAAGAT AGCACTATAT TAAGGAGAAA ATGACTATAC
176551 AGGGGAGCTT AGGCTCCATG ATATTATTTT TTCTAATAGA AGTCACCCAA
176601 TGAGACAAAC GAGGGCAATT GGAAACTGAG TGTTTGTTTA AGAGTTACTC
176651 CAGGAGATCT GATATGAAGG GCTTGTTGAG TATCATCAGG AAGTGGTTTC
176701 TATTCGCAAT CAGGCCACCC TTAGCCCTGT TATTGACACA GTTTCTTTCT
176751 CTCTTTCTTT CTTTTTTAAA CAGAAAGGTT GTGGGTACCA TCTGGACCTA
176801 TTAATGGTGG CTGTCATGCT CGGTGTATGC TCCATCATGG GCCTGCCATG
176851 GTTTGTGGCT GCCACAGTCC TCTCCATCAC TCATGTCAAT AGCCTAAAAC
176901 TGGAATCAGA ATGCTCAGCT CCAGGAGAAC AACCCAAATT TCTCGGCATT
176951 CGGGAGCAAA GGGTTACTGG GCTTATGATT TTTATTCTTA TGGGTTCATC
177001 AGTCTTTATG ACCAGTATTC TGAAGGTAAC AAAATCTGTC TTTATGAACT
177051 TGAGAGAAAG AATACATTTA TCATCATTTA AGATTTTCAT TTGAATCTGA

FIGURE 3YYY

177101 GCCATAAATT TGCAAATATT GTGTGGCATG TGATGAAAGT GATGAATTTC
177151 TGAACCATGT TTATATAATT CTTCATAACC TAAGGGAGGG AAATTACGTC
177201 CTATATTTTA AAACCCTTAA ATACATAAAA ATTTAGTCTG GCAAAGTAAA
177251 ATTTGATGAG TAAATTATTG TAACAATTTT GAATCGGTGA TCAAGCTATG
177301 GGAAAAAGTC ACTCATTGTT TCTGACTGAC TTGTGACCCG AATCCATTAC
177351 AGGCATTCAT AAAGATTCTA TTTTCTTGTC AGTGGATAAA TATATTAGCA
177401 GTTAATATTA CTTACTATTA ATAAGAGATA GAGGTGAAGG GATGAGCCTG
177451 GTTATAGTCA CATACGCAGT TTTCCATTTT AAGTGCTCTG TAAAACCACT
177501 GTCTGGACAT CATCATTGCA TATAGTGATT TTTTTTTCAC ACAAAACTTG
177551 AAATCTATTT TTAAGAGGAT TAACTAGTAA TTATTTTGTC ATGTAATTTT
177601 GTCAGATATT TCCAAGGTGT GTCAATTGCG CTATAAATTA CAACACATTT
177651 TATTTGCCTA TAATTTGACA TTTTAATTAA ATTATTTAAT GATTTACACT
177701 AGTTTACTTG TATTTGATCA TTAACACAAG TACCTTTGCA AGAATTAATC
177751 TCTGTTATAT AAGTAATTAT GTTATAGACA TAAGATGATG TGAACTATTC
177801 CAATAAAAAG AGAAAATCTG AATTATCCAT ATATTTACAA ATACCTGGTA
177851 TAATACAGGA AACACATCTA AATGTTAGCT TCATTTTTAA TCCACCTTTA
177901 ATCCAAATAT CTTATCTTTG TAAAGCAAAA TTCAAGTTGT CTCCAAAGTA
177951 GCATAATAAT AATATTATTG TTCATTATAT ACTACATGGT TTTTAAAAAT
178001 AGATTTTGAC CTATTAAATA ATTATAACAA CCCTATTGTT ATCATCTCCT
178051 TTTAGATATT GGGAAACTAA GGCACAGAGA GCTTAAGTAA CTTACCTAAG
178101 GTTACACAGC TAAAAATGCT AGAGCTGGAA CTTGAATCCT TGTCTTCTGA
178151 ATCTGTACTA TACTGTTTCT ATTCAAAAAT GCCTTTTTTC CCTGTTTTTT
178201 TCTTTGATAA ATGCAAAACC ACAATCTATT TGAAAATGAT TTCTGCCTTT
178251 TCTCCAATTG TTCTTTTACA GTTTATTCCC ATGCCAGTGC TATATGGAGT
178301 GTTTCTTTAT ATGGGTGCTT CATCTCTAAA GGGAATTCAG GTAAATTACT
178351 TACAGTACTA CAGGCACATC TGTGATGACT GACCTTAAGG TCTACTGATA
178401 AGTCATGTGA CAGCTGAGAA AATGCCACCA CCTGAGGAAC AGCTTTTAGA
178451 CCACAATTAA ATTTCTTCAA ACTTGTCAGA GTTACAAAAG TTAAAGAAGA
178501 TTCTCTCCAG CATCTAAGGT TCATAATCTT ATGGTAATTT TCTTTATCAT
178551 AAGTATATTA AAACTGTAAG AGGCTTAGAT TTTACAGCAT TTTTAGAAAA
178601 ATCATAGTAG TATATTTCAA TATATATCCA AATATTTATA ATATTTGACA
178651 CTTTAATCAT GTGTATGGAC ATCTATTGGT AAGAATAGGA AAAGTCTTTA
178701 TGCACGAAGA TGTTCATTGT AACACATACT ATTAAAATAT TGGAAACAAC
178751 CCAATTCTCT AACTGCAGTC AAATAATTAG GTAACCTATG GTATATTCAC
178801 TGAAAATTGA TAATTATAGG AACCACAAAA GTAACATGGC AAAAATGCTT
178851 ACAACATAAT ACAAAGTAAG AAACTATTGA CCATAGGTTT ATAAAGCTAT
178901 GAGTTTGAGC TGGGTTGTGA AGGAAGGTGT AGAAATAAGA ACAATTTGTT
178951 GAGATAGTGA TATCCCGGGG GTTTTCCCCC TTGTTTTGTT TGTTTTACTG
179001 TTATATTTAT AGGATTATTT TTAAAATTAG ACTAAAATAA AGATATAAGC
179051 AGTTTCAAGT ATAAGGGGAA CTTTATGAAT TATTTAAGTA AGTATTGGTT
179101 AAATAAATAT TTTAGGCATG AATTTGGCAA CAGATCAGCC AGATGGTTCT
179151 GGTTCAGGAT GTCCCATGTG GTCACTGTCA GGGTGTGGAC AAGGTCCACA
179201 GCATCTGAAG GTTTGATAGT GCTGGAGGAT CTGCTTGCAA AATGGCTATT
179251 CCACAACTGT GGGCATGAGG GCATCAGTTC TTTTCTACCT GTTGGTAGGA
179301 TGACTCAGTC TTTTGCCACA GTGGCCTCTC CATGGAATCC TTAGTGTGTC
179351 CTCAAACCAT GGAATGTGAC TCCTTCAGAG TGAGCAATAT AAAAGAGAGA

FIGURE 3ZZZ

179401 GAGAGAGATA GAGGAGAAAG GAGAGAAGAG AATGAGAAAG AAGATGAAGT
179451 GCTTTTTGAC TTAGTCTTCA AAGTCATACA TGGTCTTTCC ATGTTTTCTA
179501 TTTGTTAGAG GCTATCCACT ACTAAGTCCA GCTTGCACCC AAGTGAAGGG
179551 AAAAGGGAGA CTATCTCTTG AAGAGAAGAG TATCAAAGAA TTTGTAGACA
179601 CATTTTAAAA CCTCCACAAG TGTATTCTAA ATTTTTACAG AAGCTGTAGG
179651 CAAATTCTTC CCACGTATTT CTTTGATGAT ACTGTTATTG GTTGAATAGT
179701 GAGTGTTTCC TGAAAATTTA TGTCCACCTG GAGTCTCAAA ATGTGACCTT
179751 ACTTGGGAAA TAGACTATTT GCCTATGTAA TTAGATATGG GTTTCAAGAC
179801 AAGATAATCA TNNNNNNNNN NNNNNNNNNN NNNNNNNNNN NNNNNNNNNN
179851 NNNNNNNNNN NTTGAGTGTG GTGTGGCTCA TGCCTGTAAT CCCAGCACTT
179901 TGGGAAGCCG AGTGGGCGGA TCATGAGGTC AAGAGATCGA GAACATCCTG
179951 GCCAGCATGG TGAAACCCCA TCTCTACTAA AAATATAAAA ATTAGCTGGG
180001 CATGGTGGTG GGCGCCTGTA GTCCTAGCCA CTTGGGAGGC TGAGGCAGGA
180051 GAATTGCTTG AACCTGGGAG GCGGAGGTTG CAGTGAGTGG AAATTGCACC
180101 ACTGCACTCC AGCCTGGGAG GCAGAAAGAG ACTCTGTCTC AAAAAAAAAA
180151 AAAAAAAAAA AAAGAAGAGG GGAGAACACA GAGAGACACA GGACAGGGAA
180201 GAAGGCTATA TGAAGATGTA GGAAGGCCAG GCACGGTCAG CTCACACTTC
180251 TAATGCCAGA CCAAGGCGGG TGGATCACCT GAGGTCAGGA GTTCGAGACC
180301 AGCCTGACCA ATATGGCAAA ATCTAGTCTC TACTAAAAAT ACAAAAATCA
180351 GACGGGTGTG GTGGTGCATG CCTGTAATCC CAGCTACTCA GGAGGTTGAG
180401 ATAGAAGAAT TACTTGAACC CGGGAGGTGA AGATCGCATT GAGCCGAGAT
180451 CATGCTACTG CACTCCAGCC TGGACGACAG AGGGATACTC TGTCTCAAAA
180501 AAAAAGAAAA AAAAAAAAGG GAGAAAGAGA TTAGAGTTTT GTTGCCATAA
180551 ATCAAGGGTG CTAGGAGCCA CCTGGAGCTG GAAGGGGCAA GGAAGTTTTC
180601 TCCCCTAAGA CCTTCAAAGG GAGTGTGGCC CTGGCAATAT CTTGCTTTAG
180651 GCTTCTGGCC TCCACAAGTG TGGAAGAATA TATTTCTATT GATTTAAACC
180701 ACCAAGTTGT GGTAATTTGT TAGGACAGTC CTAGCAAACT AATAGATTTC
180751 TACTTAAATT GTCCCTTGAA AAGTCTTGTT TTATAATTTA ACATTATTTA
180801 GCCCAACACT CCAATGTTCT TGAAAAAGAG ACTAGAGACT TATTCATCAT
180851 ATAGTATTTT GTCAACTGAA AAGCAAAAAT AAATTGCAGC TTTTTCTATA
180901 ACACAGCTAG ACTCACTGAT GTTCATAGCA TATAAGAGAA TAGTTAACCT
180951 GCAGGACAGG CAGCACGGGA TCTCTGTTCC TGAGCAAATG ACTAACCAGC
181001 TTCTGACTTT GGGAGAAAAA GCAGAACTTA GGCCTTAAGA CAATACTGGC
181051 TGCCAGTCTG GGGGAAACTT AAGTATGAAG TCATTGCAGG TCACGGAACA
181101 CCCAAAGTTG ATAGTATGAC TGACTCTTCA TCCTGACACT GGGAAAAATG
181151 AACTGGGAGA GGGAGATGGT TGAGCCATGT TATATGTTTT AATTTTACTC
181201 AAATTAGATT TAATTTGCTC ATTTAAAATT TCATGTATGA AAAGTGTAGT
181251 TTGATAGAAT TTGTTTAGTA AGCCATTAGG GAAGAATATG GAAGAGGTTT
181301 TGTTTATTTG TTTTTCTTTT TCCCTTTTTT TTTTTTTTGC CTTTGGCAAA
181351 AGTTCCATGA GTACTAATTT CATCTGTAAG TGAAAAGCAT TTATTATTAG
181401 GCCCCAGGCT CACATAAATA CAGCAGCAGA GTTTAAGAAA CAATGTAAAA
181451 TCATTTTGAT GATAGGTTTC AACAGATTTT CTCCTCTAAT TCCACATGAT
181501 TTTATACTCA TGAGATTTAG AATTGAACAA GAACGTCAAG TTTTGGAATT
181551 ATTTGGGGTG TGAATCTTTT AAATGAAAAT TGAAGAAAAC GTTATCAAAA
181601 GCCCATGAGT TAAATATAAT GAGTTTTAAA GAACACAAAT GAAACATCAA
181651 TCTGGGGCAC ATGTTGATGA ACAGGGTCTC ACACTGAGAA ACAGTGTTCG

FIGURE 3AAAA

181701 TGAAAATTTA AGTGAGCCCC AAGAGCAGGG AGCTGAAATT CCTATTTGGA
181751 ATTGTAGCTA ACTGGGTGGG GAAATGTGAT ATTGATACTA GGATATAATA
181801 AAAACCAAAT GTAAAACTCA GAATACATTT ATCATGATGA TGATTATTAT
181851 TTAAACATAT GCTAAATATA ATCAGTTCCA GCAGCATGTT ACTGTCTTAC
181901 CCTATTGAAG GAATCTATGT TACCTGCTTG TTTGGCAATA TTAAGAAACT
181951 TATTATCTGG GCTTCTCACT GTGAAACATG GCAGAAAAAA CAGATCACAG
182001 TGTTCTCATG AATGCTGTTT CTGCATTCAG ATATATACCC ACATCTATAT
182051 TCATTCCAAC ACTTCAGGAA TCCAAAGTAA AGCAAATGTG CCATTTAAAC
182101 AATAACAATT GAAGCACCCA CACACTGAAG TACACTTATG CAATAACATA
182151 GCTTCACAAA TGGAGAAATG GTGGCTGGGA AAAACTAGTT CTATAGAAAA
182201 GGAAATATTC CATTGTAAGC CAGAAGATTT TATTTTATTT CTTTCCTATT
182251 CCTACCTCTA CCATGCACCA AGTTTTTGTT TATTTAATGA CTTTTAAGTT
182301 TAAATAATAT TTAGGAAATA GAAATTTTAA AACTTAATGA CATGTACATG
182351 GACAGAATGG AGAGACATTA TTCAGGAATG AGTTCAGCAC TTAGTAGCCT
182401 GCATAGAATG TTTCAATAAT ATTTTTGGAA TATATAAATG AATATGAATA
182451 AATGAATGGT CAGGGAATGA ACTAATATAT GTATGATTCT TATTTAGATA
182501 ACTGAGGAAA GGAAGGCCAT GTCATGCCAT AAGACATAGA ACACAGAAGG
182551 GAAGATAGGT TTATGTTGAG TTTGAGATTC CTATTATGTA TACAAGCAGG
182601 TCTTGGTAAA ACAGGGTGTT TTGACTCTAA CATTTTGACT CAATGGACAA
182651 CTGTTCCTTT GCATATTAAT ATGACACATT TGATGAGAAT TGCCTACAGT
182701 TTTTAAAATA AGTTAGTTAA GAAATAAAAT CTAATATTAC TTTTTGAAAA
182751 TGCATAATGG ATGTTACTGT AGAGATGGCA TGAAATAAAA CAGTGACTGA
182801 CAGTGATTGA AACCATTATT TTCTAAATAA TCGCCTCTAG TTGGAAACAC
182851 TGAAAATTGC AAAAATTGGC CGAAGAACAA TAAACCAAAT AATCTATATA
182901 AAATAAAACT ATCATGCAGT ATGATTTGTT AGTAAATAAA ATGTGATTAA
182951 AGATTTAAGC TTCCTGTGTG CATTTAATTT ATAAAATTCA AAAAAAGAAA
183001 AATTGGTTTG CTTGATTAAA AAAGCCCTCA AAGTCAAAGC TGTAACATAA
183051 TAGTATGAAG TACTATAACA ATAGTGTTAT GTAATACTAT GTACTATCTT
183101 TATGGCAAGA TTGAAACAAA TAACATTGAT TGAGATGAAA ATAATTTTAA
183151 TAAAATACAA CTGAAAATAT ATAAATGACG TGACAGTGCT GTATATAAAG
183201 TTAATCAAGA AATTAAATAG AGTTAACAAA ATTTGCTCTG GAACATACTT
183251 TATTAACAAA ATTTATTTAG GTTAAATTTT TATGGTTAAG ATGTTTGTGT
183301 CCATAAAGAC AGCATCTAAA CTTTTGTTGG GGATTAAAGG GACAAAGTCA
183351 AAACAGCAGA GTCAAAATAA GGAGGTTAAA ATACCGTACT TAGCAGCTGG
183401 ATAAGGGTCT AGAACTCAGG AGAGAGCTAA GGCAGAGACG TAGGTCCGTG
183451 AATCATTAGC AAGTCTGTGA AAGTCAAAGC CATGGGTATG GATGAACTAT
183501 TCCAGGAGAA AAGAAAACAG AGAATGAGAG TCCAGGAATC CCAATGTTGA
183551 GGGGCAAATA AAGGAAGAGA TTGTGTTGTG ACAATGAAAA AGAAGATGGT
183601 TAATTATGTT TTGCTTCACA GGGCTCCACT CTTCAAGGTA GCAATATTTA
183651 ACATTGGCTT TCTATTTTTA AACTCTTCTA AATTGTAACC CGTCTCCATA
183701 TTCAAGAAAA TGTGGGCTAT TGTTTAACTG AAATTGTAGT GTTTCAGAGG
183751 GTAAGCATAA CAATCCCATT GTCTTGATGC CGAGATATCA ACTTAGTGTT
183801 ATCCAGGTAT GTCATTTAAC CCAAAATTGT GGACCATATT AAACATCAAC
183851 TTGTCCTACT TTTATTGTTG TCTTACACCT AAAAACAATT TAGTCTGTTT
183901 AATCTTTTAG TTCTTTGATA GGATAAAGCT CTTCTGGATG CCGGCAAAAC
183951 ATCAACCAGA TTTTATATAC CTAAGGCACG TACCGCTTCG AAAAGTGCAT

FIGURE 3BBBB

184001 CTCTTCACAA TTATTCAGAT GAGTTGCCTT GGCCTTTTGT GGATAATAAA
184051 AGTTTCAAGA GCTGCTATTG TCTTTCCCAT GATGGTATGA AACTTCTGTC
184101 AACTATTTTT CTCTTTCTCT GATTTGCTGG TCTCTTTGGA AACATAAACA
184151 CATGAATTGA AACTGGAACA ACAGAGTCAT TTTGAACAAT TATTGGAAAA
184201 TATAAGTTTT GGCACTGAAA GTGTGACTAA GATAGGGTTT AAGAATGCCT
184251 ATGAATTTCA GTGATTCCTA TTAGTTTTGT CTCTATCACT CTGAATGTTT
184301 GTGGTAGTCT GAATTAATTG AAGCTGGATG GAAAAATGCA TTCTTCCAAA
184351 ATTTAACATT AAAGATACTA GCAAATATGA AAAATTAGGA TTTTTAAAAT
184401 AACATTGTAT TAAATGTTTC AGGCAAGTTT CAAATACTTC AAAAACTATA
184451 GTGAATTTGA ATGACTAAAT AATTTCATAA TTATTAGTAT AGATAAGAAT
184501 GTTCTCGTGT TCATTTAATA TAGTATAAAC TATTAACTAC ATGTATTTAA
184551 GGAAACATAG TCAAATACAT TTTATAGGTT TTTTAAAATA GCTTATTTAA
184601 TAGACTCCCA TATTGGTTAA AATCATAGTC ATTATTGTGG TGATGTAGTA
184651 AGAAAAGAAA ATGAAGGAAG CAGAAGACTA GACAATGTTT TATACATATA
184701 TATCTTTAAT TTTTACTTTA ATCTCAGGCC TAATAGAAAT TGTTTCTACC
184751 AAAAACCATA CAGGCAAATC TACACCTCTC ATTTTAATTT TTTTTCCACT
184801 TTAAACTAGT TTATTATTTA CTTCAGGTGT TAGCCCTGGT ATTTGTAAGA
184851 AAGTTGATGG ACTTGTTGTT CACGAAGCGG GAACTCAGCT GGTTGGATGA
184901 TTTGATGCCC GAGAGTAAGA AAAAGAAACT GGAAGATGCT GAAAAAGAAG
184951 TAAGAGCAAA ATCAATGTTT TATAAAGAAA GAAAAAAGGA ACATAGTAAT
185001 ATTTCTTTGC AAAACTAAAT TATTGTTTTT ATCTTTAGAC AGTTTTGTCT
185051 TTAGACAGTG ATCACTAACA ACCACAAGTA GACTAGTTTG GAAGTTTAAT
185101 GTTTAAAATC ATAAAGATTT GAACAGAGAG AGAATGAAGA TCTTATAGGA
185151 GGAAACCAAA TCCTAATGAA ATATGGAAAT ACTTTGTACT AAAATACCCT
185201 CCAAATTGTA AGGCTCATTT TTCTGATTCC TCTCCTATGG ATGGCAGAAA
185251 CTTGCTAATA CTTAACTATT TCCAAATTAT GATCATGCAG TGATTGTTTT
185301 TTTGTTACAT ATGTGAGAAC AAAAAGAAGA GACATTATTA CTGTTGGTAT
185351 TTTCCTAGGG AACAGAGTTT TAATCAAAAT ATTCTAATGA ATAATTATTT
185401 ATTCTTGAAA TAGGTGAAAT GTTTAGTAGG AAAAATGTTG ATCTGATTTG
185451 CTTTCAAAGT GATTTAAGAT TGAGTAGATG TTGCAGAAAC TTCTGGAATT
185501 TATTTTTACA GGCTACTTAT TTATTTTATT CTATTTTATA TGGTATAACA
185551 ATGTATTATA AGTTTCGTGG CATATTTAAA GTTTATATGT AAGCCTGAGT
185601 CTATTTTGAA AGCACTTAAT CAACATTTTT TTAAGTATAT AAAAACTACA
185651 AAGAGTGTAA ATGAGGGAAA AATAACTAGC GTAACATTTA GCAGGATGAT
185701 TGAGCCCATA CAATGTAAAA CACAACAAAG TTTTCACATA AATAGAAATG
185751 AGATTGAAAT AAAATATTTG ATGAGAATTA TACTATTTTT CTCTATAAGT
185801 AGTCAGTAAA TGTATTCAAC TTTCTATTTC CTCAAACCAT AGATATATTT
185851 CCTATTTCCT TTGGGGAATT CATTTGCAGA TGTTTCAGAG GTCTTAGTCA
185901 TTTAATGAGG TCAGATCAGG CCATAAATCA AATGAGGTTT TTTCTTTCTC
185951 AGAAATTTAT ACCAATATGG TTACATAATG TGTAATTGGT AATTCCCTTA
186001 CTCTACATGG TGTTCTATCA CTAACAATGG ATTCCCACAG ATAGAGATTC
186051 ATCATGATGA TGTGTCTTAA TCCTGTAAGA ATGTTTCAAT TTTTCCAAAT
186101 ATTGTAGAAG GCAATACTTA GACTCATACT TCTAGTAATA TTAATGTTAA
186151 CACAAAAAAT GATATTATAC AATTGTTATT ATTTATTTTT CTGTTTGATA
186201 TATTTTTATT TAAATATTAG TGCTTTTTTA AAAAATAATA CTTTGAGTCA
186251 GGCGCAGTGG CTCATGCCTG TAATGCTAGC AGTTTGGGAG GCTGAGGCGG

FIGURE 3CCCC

186301 GCAGATCACG AGATCAGGAG ATAAGACCAT ATTGGCTAAC ATGGTGAAAC
186351 CCCGTGTCCA CTAAAAATAC AAAAATTAGC TGGGCATGGT GGTGCACACC
186401 TGTAGTCTCA GCTACTCAGG AGGCTGAGGC AGGAGGATCA CTTGAACCGG
186451 GAGGTGGACG TTGCAGTGAG CCACTGCACT CCAGCCTGGT GACAGAGCGA
186501 GACTCCGTCT CAAAAAAAAA AAAAACAAAA AACAAAAAAC TTTGACTAGG
186551 ATATTTTGAT AGTCTCTATT TCTTTTTAGG CCTTTAGTAA ACGTTTGCTT
186601 TCATCCTCAG ATACTCTTCA AGAAAATATG GTATAATTTG GCACAAGTTA
186651 AATTTAAATA AAACGGACAC TAGAACACAG AAATTCTAAA ATCTTAAGTT
186701 ATCTATATTT GATGTAAATA AAATTATTGA GATCAAACAC AACACCCAAG
186751 AAGGTTTAAA TTAATTTAAT TTTGATGAAA AAGCTCTTGG CTGTGAGCTT
186801 GCCTTTCAGT CTTTTTGATA ATGTCAGTAC AGCAGACCCT TGAATAATAT
186851 AGCATTGTTA TAATGTTGAT GAGAAAAGAA AAAAAAAATT CCCTGGCCAG
186901 GGCCACTGTC TGTAGGGAGT TTGCACATTC TCCTCATATC TGTGTGGGTT
186951 TTCTCTGGAC ACTTCGGTTT CCTCCCACAT CCCCAAAATG TGCCCATTAG
187001 GTTCATTGGC GTGTCTACAT TGGCTCAGTG TGAGTGAATG TGGGTGTGTG
187051 TGTGAGTGTG TGCTGCAAGG GAATAGCGTC TTGGCCAGTC TTATTTCTCA
187101 TCTTGTACCC TGAGCTGCCA AGATAGGCTC CAGCCACCCT CGACCTTGAA
187151 CTGGAATAAG TGGGTTGGAA AAGGAATGAA TAAATGAATA CAAATGACTG
187201 TAAAATAAAA ATTCATCAAG TATACGATAA TCACACAAAT GTACGACAAC
187251 AATTTGGTAT GAAAATGCTC AGTGAACCCA GCCATATTTG CTATTGTTTT
187301 TGAACTGCTT GGTGGTAAGA TGTGCTCCTT ACAATTTTCA CTTTGCAAAC
187351 ATTTATTCCT GATTTAATCC ACCCCTACTA TGGCCTCAGT CACTCTCTCA
187401 CTCACCAGAA ATTTGGTAAT TCAATATCTT ACTTGCTTTT ATTAACTTTT
187451 CTTACATGTT TGTATAGCTC ACATTTATTT CAATGTTTAA TATTAAAAAC
187501 ATTTTGGGTC TTTAGTTAGA AGTTTGGTGA TGTTTTTGTG ACCAGATATT
187551 GCCATAGGAA TTTAACTCTT GTTTATATCA ATTAGCCTAT GGTAAAATTG
187601 GTTTTATTTA TTCTTAATGT CACAGTCTCC GAGAACCTAT CAATAACTTT
187651 ATGTGAGCAC TTATTGTACT ATTAATTATA CTCAAGCAGT AACTTACATA
187701 TCTAATTTTG CTTTATTTTT CTGCTTTTTT TTGTTAACTG TCTTTACTGC
187751 TTCTGGAAAA AAAAAAAACG AACACAGCCC CAGACATATA ATCATCTCTT
187801 TCACAGTATT CTCCTTAGAT CATACTCATA CCGTGAAACA TTCTTGCCTT
187851 TTAGAAGTTC ACAAAATGAA AAATGATATG TAATCTATTA TGTAATGTTT
187901 AATATTTCTG TGACTGTGAT TCAAAGATAA TTTCAGATTC TCCTTTTATT
187951 TTCTGTGAAA CAGGAGAGAA CAAGTTTAAT AATAATTGTA AATTTATTAG
188001 AATTTGCCAT TCCCACTGCC CAGAACCACT CACATAGCTA TGCATGTATG
188051 GTACTTATAT GTGTGTGTGC CATATGCCCA TTTTGGAATT TATGAATCTC
188101 ATAGGGCAGA GAACATATGT AATCAGTGTC TAATCTTTTT ATATTATATA
188151 CCCACTGTAC TTTAATGGGC ATTTACTGTT CTCTGATTAT GAAGATAAAG
188201 ATTTTAAAAG TAACTAAATA GCACTAAATT TCCTAGAACT CATGCTTTCT
188251 GAAAAGATAC AAAAATGGAT TAAAGATTTC CTGGGGCAAT TTTACTGCTA
188301 AATCCTTCAT ATCCAAGTTA GAGGGAAAAG CCTTGCAGTA CATTAACTAG
188351 GCAGGTTTAT AGATCCTTAA AATCTCAGAT GGGTTAATAT GATGATACTT
188401 TCATGTGATC CTCAGTACAT GGAAAGAAAC AAGAAAATCA ATAATATAGT
188451 CAAGAAATAA TCTATAATTG AACAATAAAA TATAGCTCTG ACTAGTGCAA
188501 AGACAGCTAA TTCTCCATCG AACAGGAAAG AAAATAGGAA GTTTAAAGAG
188551 GTTCGCTTTC TAGCTTAGAA TTAGTATTAA AAGAGTATGG TCACTAAAGA

FIGURE 3DDDD

188601 CATTAGGAAG ATTTAGGAAT AATTATACTA AAAGTTAAAT TCCTGGTTGA
188651 TTTGTTTGCC CGGATCTTGG TATTCTATTT TCTTGAGGCT TACAGACTCA
188701 GTAGAAGGAT GTGATCTTAC TGTGGCATCT TATACTAAGG CCCAGTCTTC
188751 TAAGAGATTG TGTGTTAAGG TGGTAAACGG ACAAGTTCTC CAGAAATGTT
188801 GCATTTCTGC AATTGCTCAA ATTAATTGAG TAACTTTGAT CATGAACTGG
188851 CAAGATGGTA AATAGCAGAA ATGTCTCAGC TCCCTGAGAC TTGAATTTAA
188901 AGTAGGCTCA CCTCTTGTCC TTTTGATGAT AGATACAAGC TTTTACCTTT
188951 AGCCTCCAGG GTTTTCCTAT CAGTAGCCCA TTTCTGGTCT TATGGCACTG
189001 AGAAAACATT CATTTGACCT TAAAATTCAA TAATGAGTTA AGCAGAATAA
189051 ATAGCTACAC AGGCCAGTCC AAGGTCGCAG AGCTTCTGTT CCAAATTTTC
189101 ATGTACTTCA TGCATATGCA TATGCATATG CTTCAGTTTT TAGAAAGAAA
189151 GGATTATAAT CAGGGTAGAA ATGAATATTG GAACCCTGAC ATTTTGCACA
189201 TTGCTCTGTG TAAAGGGAAG ACTGCAGAAT CAAATTCTGG ATGTCCAAAT
189251 GTGCTCAGAG TACCAACATG CCTTCCTTCC TACTTAAATA TTCTCTAGGC
189301 CATTGTACAC ATTTGACAAA AGGCTACTTA CTGTTAAAGG CAGAAAATCC
189351 CAGCAGAATG TTTGCTCCTG GGTAGGAGGA AAGGGGGTTA GTGTTGGATA
189401 AATCCTAGAA ATTCTACTCT GTGGAAGTGA TCATGATAGT GATACTTCTT
189451 GATTTACTGG GGCTTCACTC TTAACATATA CACTATAGGA GAAAACAAAA
189501 AGAGGGCAAA TGGGACCCTG TGATCCCAAT GCAGGATCAT GAAAAAGGTC
189551 AAGAAAAAAG CAATCTAAAA ACAAGTGCAA CTAAACAAAT TACAGAGGAC
189601 GACTTACTGC TAAGATAGGT CAGAATTGGT TATGGATTTG GGAAGCATGG
189651 CCAAATTATT ACANNNNNNN NNNNNNNNNN NNNNNNNNNN NNNNNNNNNN
189701 NNNNNNNNNN NNNAACAAAG TATGCTAGCT ATGGGAAGAT GAGGGCACAG
189751 TACAACTCCC ATTGGAAGGG CACTATAGGT AAGACATAAA TTTAAAAACA
189801 CATCAATTAA AGTAATGAAA TGCATTGTTA TATACTTTAA GAATTTCATA
189851 CTGTGTAGAT CCTCAGAGAG GTTTCTTGAA ATTGTATAAG AGTAGAAAGA
189901 ACGAAGAGTT AGATAACATG GGTCCTACTG CTAAGTTTTG CCAATAATAG
189951 CCGTGTGACT ATAATCAAAT TGCATTAAAT GAAGTGAAGC AGGAAGCTGT
190001 TGTCTGAAGT TTTTCTTGCT CCTGTTTTAT AATGTGTATG AAAAATCCCT
190051 TTCATATTCT CAGAAAGTAG CACCAGAAGA CAGATCAAGG TTCCTTTTTT
190101 GTATAAGTGA CTAGTTATTC ACTAAGTTGA TCACAGGTAA ATGTTTTAAC
190151 TCTGGGAATT TGCCGCTAAA AGTGGAATTT CCAATGACAT AATCTATTTC
190201 TTAAGTGATT CAGTTGTATC AGTCATTTTA GGATATATTT ATGCAATTCT
190251 CCAAAATTTT CTAATCTTCT TTATGTACAA AGACATAGCA AAAGAAAGCA
190301 AACTACTGAA GTTATAAAGA AAACATTTGC AAGCATTTGG CCCAGAATTC
190351 TCCCCTCTCT CTCTCTTCTC TGTCTCCCTC TCAATATAGT TTAGTTTAAA
190401 CGGTTATCTT GTACAATTCT AAGTATCAAT TAGTGCCCAA TTTTATAGTC
190451 TCAAAGTCTT TATGAATAAT TTAAGGTTAT GCCAATAAAA ATACAGAGAA
190501 TACTTTTTTA TGAGAAGGGA ATTTGTCATA GTGTTAAAAA CCAAAATAGG
190551 AGAGAATTTT CTAGATCTTT AGGGTCTGAC TCTAAGATTA TATTCCCTAG
190601 AATTTAAGAA AATGTGATTA CCTCCCTCTT AAGAGGGGGC ACAAGTATAA
190651 GATGTTTTAT CTTTTTTTTC TTTTTTACAA CATTTAAATT TTAAAATCCT
190701 GTTGATTTTT TAGCTGAACC AGCATATTTC CAAGTGTATT AGGTAGAAAC
190751 CTAGTCTTGT GTGATACCAC TCTCGAAAGG GCTGTGTGGT TAAATAAGTT
190801 TGAAAAAATG TGCCAAACTG CATTCCAGTT TGGAGATTCA CAATGCATAT
190851 TAGCAAATGA AACAATCTAA GTAGTACTGC ATTTTAAAAA ATTGTATAGC

FIGURE 3EEEE

190901 TTCGTTCAAT CAAGTATTTA AAAAAATCTT TTGCTCAGAA GACTCTTCCT
190951 CACATAATAT CATGAAAAAT GTCTATTCCA CATGATGCTT TTTTTAAGAA
191001 AGTAGTCAAT CTGGTGCTTT GAATTACCAG GAAACTATCT TTCTAGGAAG
191051 ACCAAAACAG CTGGAGGGTT TAGAGGAACT GAAGAACACA TTTCCAGATT
191101 GGGCAAGAGA GGGAGACCCA AGGTTTTGTT CCTCTTAAAA GTTGCATTTG
191151 TTCCTCTCCT GTGACCTATC ACCAATCAGG GTCATATGAA AAGGCGGCAT
191201 TTGAACAAAG AAGGGGCAAG GTTGCTCCAT GTGAAGGGAC ATGATAAGCA
191251 GAGGGAAGAG CAAGGACAAG GCCCCCAGGC AGCACCATGC CCATTGTGTT
191301 CCAGAACAGT CAGGAGGCTA CTGAAATGGG GCTGGAAAGG AGTGAGCAGG
191351 GATGCAGTGG CAGGAGGTGA AATCAGAGTG AGGTGGGGAC AGAGCCTTTA
191401 GGCCATTATA AGGACTTGGC ATTGACTCTG AGTGACTGGG AGCCACTGCA
191451 AGGTCTGAGC AAAGGAGGGA AGTGATCTGG TTGCTATGAT GTTAGGGGCA
191501 AGCGTTTAAG CAATGGACAT GCGGAACCCA TTCTCTGTAA TTTGAAATGA
191551 ATTAAGAATA CCACAGGCCA ACTCAGTATC TATTCAACTA GAATATTTTC
191601 TTTAGTTTTT TTATTTTTCA CAGATTGTTT TCAATAATTG AGAGAAATAT
191651 TCAATACTTC TTCATTTTTA ATTATCAAAA ATATTGTACA ATAAACAAAA
191701 TGGGGCATAC ACATACAATG GAACATTATC CAGGTTTAAA AAGGAGGAAA
191751 TTCTGACATA TGCTACAACA TGGATGCACC TTGAGGATGT TGTACTAACT
191801 GAAATAAACC AGTCACAAAA AGACAAATAC TGTATGATTC TGCTTATATG
191851 AGGCACTTAG AGAAGTCAGA AACCTAGAGA CAGAAAGTGG AATTATAGTT
191901 GCCAGGGACC GGGAACAAGA GGAAATGGAG AGTTGTGGTT TAGTGGGTAT
191951 GGAGTTCCAG TTTTATAGGA TAAAAAGAGT TCTGGAAATG GATGGTGGTG
192001 ATGGTTGCAC AACATTATGA ATGTATTTAG TAACCCTGAA CTGTACTTTT
192051 AAAAATAGTT AAGGTAGTAA ATTTTATGTT ATGTGTATTT TACCACAATT
192101 TAAAAATTGG GAAAAATATT CTTCATAGAT ATATGATTGC CCTATATTTA
192151 GTTTCTGTCA TTGAAAAACT GCAGTTACTT ATGTAATGTT TATTATTTCA
192201 TTTGGGGAAA CTCCTGTCTA GAGATGATCC ATCTGTGATC AATATATCTG
192251 ATGAAATGTC AAAGACTGCC TTGTGGAGGA ACCTTCTGAT TACTGCCGAT
192301 AACTCAAAAG ATAAGGAGTC AAGCTTTCCT TCCAAAAGGT TTGGATTTTA
192351 AAATAATGAG AATTTATACT AATTCCAATT GTTTTTTGAC ATAAACCATA
192401 AGCAAAAGAA TAATATTAGT TTCCATCAAA TTTAGATATA AAATATTCCA
192451 GAAAATTCTT TCCAAAAGTG GGTAGAAATT GTAATTATTT CAAATGTTGG
192501 TATGTTTTTC ATACCAACTG TGGTATGGGG AACTGTGCTA GAAATGAGTC
192551 ACAATGCATG ACATTTTTGG ACATTCATCT TGGCCTACTG TTTTTCAGTA
192601 TGATTTTATT TTATTCCCTC ATCACCCACT TCCCCCAGGA CCCCTTTAGA
192651 CATCTGGCCA CATTTTGCAC TCCTTTATTT TCCCTTTTTT AGACTGATAT
192701 GCACTGTGTG TATTTTATAT TTATATTTTA TAAATATGCA TAAATATTTA
192751 TATTTAGTAT AGTTCTAGTC CTGACTCCAA CCCCCTGAAA GTCTTCCCTA
192801 AACTTCTTAT CCCAAAACTT TCAACTCCTG AAAGTTCTAT CCATTCTTTC
192851 TTCTCTGTGT GTAAATGTAC AAACAACTCC TGTAGTTGTG GATGGTAGTT
192901 TTAAGTGCAT GCTGGAGGAA GAGTGTGTCC CTAAATATCA ACAGTCATCA
192951 AAGGATTTCC AAGTGAATCT TCTAGGATTT ATAAATAAGA GTTCAAGTCA
193001 CCCAGTCTTC TTAGATGCTG ATCTGAAGAA AGAGGAATTC CTATGTTATG
193051 CTAATATCTC TTTTTGTTAG AGAGTGATTG AGGGAATTGG GACAGTGTTT
193101 ACTATAATTA TAAAGTTCCT TTATTTTCGT AACCTTAAAT TAACTTTTTC
193151 TACTTAATTT TTATATTACA TTTTTGTCAT AAGCTCCCCT TCCTAATCAC

FIGURE 3FFFF

193201 TCTAGAAGCT GATTCCCCAA AGGTAAGACC CTCTCCCTCA AATCTATTCC
193251 TTGGTTGCAT TTCCTTATGT TAAATGGTGT CTTCTAGAAA CCTGGTCAGT
193301 CTATGTCCTC TGTGTGAGTT TTGGGGAGGC AAAAGGCATG GAGAGTGTTG
193351 GGCTCAGATC CAGTAGCAGA CTGAGTTTGA TGATATATCT GTAACAACTC
193401 AGCTCTTTAA GTTAGTCTGA AACTTGAATA AACTTTATTC CTTCCTTGAT
193451 TTATACAGAT GCATCATGTA TAAATCAACA AGTTTCACAG AACTGTAGTT
193501 AGTAATGGCA TCAAATTTCT GGATAGGGAA AATTAAATTT GTCCCTTTAA
193551 GAAATTGAAA AGCTTGCCTG GTGTGGTGAC TCATGCTTGT AATCCCAGCA
193601 TTTTGGGATG CCAAGGTGAG CGGATCACTT GAGGTCAGGA GTTCGAGACA
193651 AGCTTCGTCA ACATGGTGAA ACCTTTTCTG TACTAAAAAT ACAAAAAAAT
193701 TAGCCAGGCG TGGTGGCGGA TGCCTGTAAT CCCAGCTACT TGGAGGATGA
193751 GGCAGGAGGA TCGCTGAGCC CAAGAGGNNN NNNNNNNNNN NNNNNNNNNN
193801 NNNNNNNNNN NNNNNNNNNN NNNNNNNAAA TGCCCTTGAG GTCAATGTGT
193851 TGAGTAATTT GAAACAAACC TGTAAAAAAT TTTCTTCCTG TATTATATGG
193901 ATTCAAAGTC CAAACTTTTC CTCTATTTTT CTTTGGTTCA AGCAAAAGTC
193951 TTGTGACGTG ATATTTTAGC TACTCCTTAA AGTCAAGTGA TACTTTTCAC
194001 CAGAAAAATC TTTTTGTTTT AAAAATATAT ATCCAGATGA CTTCACATAG
194051 TGGGTTGACT CTAGTGAACA ATATAATGTG CTTTAAAGCA GGTCCAATTT
194101 TCAATAGACT ATCCTTTATA TTTAGATATA ACCACTTGTT TCTTATTCTT
194151 TAAATGTACT TTCACTGACG TGAGGTTCAG ACTATTGTGG AATGAAAGTT
194201 TATCCAGCTT TCCTTACCTT TTGATGTGAT CGCATTTGTG GTTTTCCATG
194251 TGAGAAACAT CTTTTGGTTG GTAGTTAATC TCTTTTATCC TCATTACAGT
194301 AGAAACTCTG GCAGAAAGTG TATGACTTAC AGAATTCTAA AACTACTGAT
194351 ACTAATAAGG CTCCCAAAGC CACTTCCTTT TTGTGGTATC TGTTAAAGGC
194401 TTTAAAGCAT CATGACCAGG AACTGTGAAA ATTTAGTACG TGGTAGAGTA
194451 TCCATTGGCA AAAAGAGACC CAAAGAGCAG GTTACTAGGG TCTGAGTCCT
194501 GAGCTGGCAC CCATGCAGCC TTTGACACCC CCCATTCTGA GTTATTTTCC
194551 ATCCTGTGCT GTAATGTGTC AGAGAAGCCT AGAAACCCTT TTTTCATGGA
194601 ATTTTGAATA GAAATTATAT TTTCTCAATT ATATCATTCA CTTTTTGTTG
194651 TCAAAAATAT TTTATCTCGT TTAACTGACA GTAGAATCTA AGAACTAACG
194701 GCAAATTCTG TCTTATCTGG AGGATGTCTA ATTTTGATCC TGATGTCATA
194751 CATGCATGTG ACAAGAGCCT CTGCAGCTTA TTAAATGGGC TGGTGAAAAT
194801 AGGGCTCATT AACGACCACA TTGCATCAGA ATAGGTTAGC AACTGCTACG
194851 TTTTTTAAAC TGATGCCCAA GATCAGTGTG TCTGGAGGTC CTTGGCAATG
194901 TTAGGAAAAG CAGCACTTAG CTTTGCCTTG GTGACAGAGG CTAGTCTCTG
194951 GGACTATCCG CTCTACCCCC CAACACCCAC CCCTGCACTC CCCCACCACC
195001 TTTTTCTATC CCAGATTCTT TCTTTGCTCT GATTGCCTAG GCTTAGGCTC
195051 TCTCATGACT TCTTGGAAAT ATTATTCATA AAAACAACTT TAGCCTGGGC
195101 GTGGTGGCTC AGGCCTATAA TCTCAGCACT TTGGGAGGCC GAGGCGAGCA
195151 GATCACTTGA GCTCGGGAGC TCAAGATCGG CCTGGCCAAC ATGGTGAAAC
195201 CCCATCTCTA CTAAAAATAC AAAAATTAGT TGGGTATGGT AACGCACACC
195251 TGTAATCCCA GCTACTCAGG AGGCTGAGGC AGGAGAATCC CTTCAACCTG
195301 CGACGTGGAG GTTGCAGTGA GCCAAGATTG TGCCACTGCA CTCCAGCCTG
195351 GGCAACAGAG CAACACTCTG TCTCAAAAAA AACAACCACT ATTTTAGTGA
195401 CATTAAAAAG TAATAGTTTC ATAGTTTACT TAGCATCATG ACAGTACCAG
195451 GTCACTTTTT GCCCTCTTGA AATATTACTT CCTTATATTT TAAATTTTAA

FIGURE 3GGGG

195501 CTCCTCAGGG ACAGGGACAC TCTTATCTAT CTTGTACTCC TAGGTCATTA
195551 TGGAGTTCCT GGCATATAAT AGATATGCAA CATATGTTTA TTACAATGAC
195601 AGATAACAGA TGCATAATAC ATGTTTGTTA CAATGAAAGC TTAAAATTGA
195651 TTGGCCTCCA CAAAAGCGAA CTTAACAAGT AATTCCGAAC AATGGATCCT
195701 AGAGGTCTTG AGCTGGTTAT AAAATTTCTG CTTCATAGTT TGCTGAAATC
195751 TAATCTGATA CCAAAACTAT GGTTATGATG AAGAGGGAAA AAAACCCAGA
195801 CATTTAATAG GTTATTGTTT TGTAACCAAA CAACCAAAGC AGAGTCAGGA
195851 GGAAGCACAT CTATGGATCA AGTTGATATT ATGAATCTTT TTATTTATGA
195901 CTTGGTGACT AATAGTGCCA CTTGGCACAC ATTCATTTAT CAAAAGGTTA
195951 TGGAACACCT CCCACGTTTC AAAGTATTGT GCACACAGTA ATTGCACATG
196001 TGTAGAGACC AGTATATCTC TGTCCTACAA TCTCCTACAT ATAGGATCTG
196051 TTATTCTATC TTTCAAAAAA TAAGAGTTCA TTGGAATTGG GAATACCAGC
196101 CTCAGAATTC TGGAATTCTC ACTACAAGAG AGCCTAGAGG CCATCTAGTC
196151 CAAAACCAAT TTTACAGATG AAGAAACCAA GTCTCAGAGA GATTAAATAA
196201 CTAGTCCAAG GTCATGCAGC TCATTCTGAG TTTCTGAAAA CTGAACCTAG
196251 ATCTTCCAAC ACCAAGCCCA GTGCTGCCCT TTTTCATTGA CTTTGTTTGG
196301 CAAAAGAGAC TGGAAGGCAG GTAGAGCTTA AGGAAAAGTT AATTTGGAAA
196351 GCAGGAGAGC ATACACTTGT CATATAAAAG GAACTTAAAG TAGAAGAAAG
196401 TGAGTCATAC AGATAGAGGA GTTAAAAATA CGAGTTAGGG CTCTCAACAC
196451 ATCATGTGCA CACTGTCATC TTTTCTCATG GAAGGAGAAA AGAAAAGGGA
196501 GGAAAGTTGC TTTGCTCTGA CCTGTAAGTA GTATGTGCTG AGAAGTGTGG
196551 CAGGCACAAA CCCGGGCGCC ATAGACACGC GCTCACACCA GCTCTCAGAG
196601 CTGGCAGCGT GCCACAGATG GCAGAAGCTC CGGCACTTCT TACCTGATGG
196651 TGCCGGGTGG TGGTGACAAC TGAGAAGGGC TGTTTCTAGC TTGAATTGGA
196701 GGAAAAACAA TTTAAAAAAC ACACTCTTAG AATGTGTCTA AGTTATTGAC
196751 CACTTAGAAA GTTGTACAGG AGGCCCCATA GAAAAATGGA GTTTTATTAC
196801 TTTATTACTT GGAGAAGAGT TATAAAACCA AGGGTGCGGT CCATTGTCAA
196851 GTGTTTCATA AATTTATATT AAGGGCCGAA GTTAACAGTA AAAATGTATG
196901 GATACTTACA GCCCAGGGCC TCAGTAGCTG GCTATGGGCT GCCCTTTGTG
196951 TCAGCAGTGG GGAGGGTCAC ATAGAAGCCT CAGATGAGGA GGGTTTTGCT
197001 GTGTGCTGCA AGTATCAGGG AGAAAGCATT TCTGCCCTCT CTGGAACATG
197051 GTGTGAACTT CATCCCTGTA ATGATATTGT TTGAATTTTC CATGAAAAAT
197101 TGTCAGCATG AGAGTAAGAA AAGTGTACGA TGGGAAAATA TTGAACCAAA
197151 CAGACAAAAA TGGTAGAGTC ACATGACCAG TTTACTCATT GGTAAAGTTA
197201 ATGAGAGGGT GAGATTAAAC AGAAATTGGT AAAGTTAATG AGAGGGTGAG
197251 ATTAAACAGA GGGTGAGATT AAACTTGGGA ATGAGTTTGT CTGAGGAGTG
197301 AGGTGAAGCA TCATTCCTCT GATGCACAGG GTAAGGGTTT GTCTGTAAAG
197351 AGATAGCACA GGTGTCTGGA GAGCAGCGTG CATGGTAACC TGTCCTCCAG
197401 GCCAGTGGAG CTGTCTGTCT AACCTGGCCA AGGTACAGTC TTCATCAAAG
197451 GTCAGGATCC AGTCCATGCA CAAGGGAGGA GCCATTTGCA GCAGAGCCCA
197501 GAAATGCCTC CTGCGACATC TTGTTTGTGT CATTTACTAG AGTTGGCACT
197551 GTCTTAAGAT GGGGGCATGG CTGACATTTT CAACTATCAT CAGTGAGTCA
197601 CTTGCCCAAA TGAGGACCAT GGTATTAATC TTGCATGTTT TTGGAACTGT
197651 TTAAAAAATG TCTGATTTTT GTTGTTTAGT GTCTGTTTTT GAATTTCCCC
197701 TTCTCTGCAG TTCTTGGTTT CTATCTCACT GAGTGCAGAG GATTTTAATT
197751 GTTGCTGTCT ATCTGTGCTT CGCAGCATGA GAGAGCAATG CCTACGGGCT

FIGURE 3HHHH

197801 CTTGTGGTGC TTTGGGGTTG ACGGGTTTTA TGTCTGAGCA AGCAGATGTC
197851 ATAGTAGCCA TGCTGGATTG CAGTAATAAA TGTGTCCTTT TTTTCCTTCT
197901 GTAGCATTGA AAGCCGAAAA GAGAAGAAAG CTGACTCAGG GAAAGGTGTT
197951 GACAGGGAGA CTTGTCTATG ACTCGATCTT CAATTTATTT TTTACATATA
198001 TATGAGAAGA GTGTCACAAT TATTAATAAA ACTGCTTTGA TCATGTATTG
198051 TAAATTCTGT CCCTCAACCC AAATCCACCT TCATACTGTA AGTAGTGCAA
198101 TACTTGTTTC ATTTCTGTGT TTAAACTTCT GAGCAGTGAG ACATCCCTGT
198151 GAGCAGATAC AATAGCCAAT GCAAGAATCT GTGTGTTCCT TGCTGTACGT
198201 TAGACATTTG TAAACTGGAT TCTGATTGTC AGTTTTATGA GAGCAATAGC
198251 TTCCTTAAAG AGATAAGTCA TATTTACCTA GTTTGTATTT TCCTACTTTA
198301 GTGACCTGAA GATGCCTGAT AATTTCATTC AGAAGAATTT TTGAAAGGTA
198351 GTCTTACTTC TTTTTAGTTT TTATAGCTTA GCATTAGTGA CTTATTTCAA
198401 AAGACCCAAA TCAAAAAGTT AGTTTGAAAG CATTTTTTAA TAATTGTATT
198451 TATGCATTTC CTTGATTTAA TATGATAAAT TTAATACTTA ACAATTTATA
198501 TGTAACTAAA ACTTAAAGTC ATTTGAAAAA TATATAGAAA CCTATTTACA
198551 ACTTGTTAAG GACAATCAGA CATAATGCAG AGTTAAGTAG TATTTGCTTA
198601 AAATTCAAGT TGTGACTAAT GATCAAATAC TAGGCTTGTA CGAAATGCTT
198651 TAGAAAAACT TTGTAACAGT TTTGTGGGAT TTTTCAATAT AAACCTTTAT
198701 CAGAAATATA CTAAGTTTGT CTCCCACTGA CAACAGATGT TTTCCAAATA
198751 AACATATTCT ATACATACTT GTGGAATGCC ACATGGTGAA TCATTGTATA
198801 TGAAATTCCA CTCCTGTACA GTTACTCTGC AGCTAATGGT CATGCACTGC
198851 TTAATGCTGG TCCTGAATCA TGTTCTCATG TTAGACCAAC AGCTCTCCAA
198901 TTGTCATTTT TTTTCTGCAG AGTTTTTTTT TTCCACTTTT AAATTAAATG
198951 CATGTTGTGG AAAAACAGTC TTTTAAAATG AAATTTCAGA TTCCATTTGA
199001 GAAGGTTCTG TAGATATTTC AGTCCATATA AAATAATACA TCTTTACTAA
199051 ACTTATATAA GGGGAGAGAA AGTTATGAAG TTTTGGACAT TACTAAAAGT
199101 ACAGTATTTG ATTTCACTTT CAATGAATGG TGAAGTTAAT AAAACTAAAT
199151 CTCATAATGC TCTTGGTTCC TAAGAATGAG TAGTAATCAT CAACTTTATA
199201 ATACTCCAAT ATTCCGTTTT ATAATAATTC AGAGCCCTGT GGCTTTTACA
199251 CACCGTTAAT TATGTACTCT GTTGGAAGTG CACATGAAAA GTGAAGAAAA
199301 GTTCCTCTTG TGATTAAACT AATGGGAGGA AATAAATCAA CAAAGTCTCC
199351 ATTAAGTTCT ACATTTTGAG ACCTTTTAAA AATTCCCCTC ACAATTCTTT
199401 AAGGAGCCCC CCTTTTTATG GAACATGAGC CTAAAAATTA TAGAAAGAAG
199451 AATTTTAAGT TAATAAAGTT TGTATTTATA AATGCTGAAA AAATACAGAA
199501 ACTTTCTGTT CCAAATGTGT TGCCTTTGTG TATTTTATAA TACAGATACT
199551 ACATTGTAAA CATTTCCATT GTTTTATGAT TTAGCCAGTG ATTCCCCAAA
199601 GCAGCCTCTT AGTGTTTTAA TATATTAATA ACTGTTTTGT TAAAAATGAT
199651 CATAGTGAAT TTAAATCTTC ACATGATCAC CTATTTGAAT AAGCAATCAT
199701 ATCCAATGAA ATTCTGTATT TCTGAGTATT TTTATAGTCA TTTTGTTCTT
199751 GTGTGAATTT TAAAGCTATC CCTATGTTAA TCCTAATATT TTGAAATCAT
199801 ATAAAATATA ATAAAAATGT AGTATTATAT ATTTACTTCT AATTTCAGAT
199851 TCCTGGTCAA AATTACTAAA TATCTTGAAT GTAATTTAGT GCCAAGTTTA
199901 AATAATGTGT AAATGTGACT AGGATATTGT GTTTTTCACA ATTAAGAAAT
199951 GTTATGTGGA AATAAATATT TATCCTAACT TCCTTGCACA TTTTAAATTG
200001 TGATACAAAG TGTCTTGTCT TTTTTCTTTG TTTTAATTAG TAAATCAGTG
200051 TAAAACATTT TGATTGTTTG AATATAATAT TTAAATTTAG ACAGCCCCAA

FIGURE 3IIII

200101 AGCTAAGAAC TCTTGGTGAT GTAAACAATT TATGAGTATG TTTCAAGAGT
200151 AAACAATTTG AACTTTATGA ACAGAAGATT ATGAGAACTA TATAAAGATA
200201 TATTTACTCA TTTTTCCAGA AATGGGTGCA GATGACACGG TTTCTTATGC
200251 TAGGAAAAAC CTCCAAGGTC GTTAGTAGTA GTATTCCTCA TTATTAGAAC
200301 TCTATTTAGA CTTCCGTTTT TAACTTCCAT GGGGAAAGCA TTGCCTAAAA
200351 TTTGTCTCCT CCCTGTTTCT TACAAAAGTC AGATGGGACC ATTATTCTTT
200401 GGTAGCCATC TGGCAGTGTG TTGTGGAGAT AATTGCATTC AGAATTCTAT
200451 CTAACCTACT GCTTGGTATT TTTCTCTTGA CTAGTGAGTT TACTTTGTAA
200501 TTGCTCCTGT TTCACAGCCT ACAATATTGG AAAGTTTTTT TCCTGTATAA
200551 TATAATATAG GAATATATAT ATTCCTATGT ATGTATAGGA TATCCTATAT
200601 ATCCTGTATA GATGAATGTC TCCTTGGTAT AGTTTAAACC CGAGTTTGAA
200651 AGAAACTCTC CACTGATGAT CCAAAAGCAA CTTGTATTTC AACATGATTC
200701 CTAGATCTTT TTGGATTTTT CTTGACTCTT AGAAGTGTGA CTTACCTGTT
200751 TTCTATGGCA CTGACCTACC TCTGTTTTGG TTTAACTTTA GCCTATTAGC
200801 TCCTGGGCAC TTGTCTATTT TACTATCATT GCAAGATTGC TCTCTCATTT
200851 TTCCAATATA TTAATATCTA TCTCATATAT TCACACAATG AAATGAAATG
200901 AGATTACATC CATTTGAAAG TTTTATGAGA GTCATTTGGA TAATATGATG
200951 GTTCTCTAAA TGTCTACATC AAGAGGCTAA TTGTAGTTAG TCCCCTTGAA
201001 GAGGCTTAAT AATCAAAGAT TACTGGTAAT ACTTTATTTT AGAGATCTCC
201051 TTCGATGTTC TTCATGGAAT GCTGTGGCTA ACTGATACAA CTGTCACACC
201101 AATTCCGTTC CTGTTGGTGT ACTGGGTACT ATCATTTCTG CTGGAACTTT
201151 GAAAATAGGA CTATGATCCT TGCTTCTAAG GGCAGGGTGG ATACATAGCT
201201 GTAAATAATG TGATATGTGC TGAGTTGGCC ATATGAGTAA AGCCATTTTT
201251 TGAATAGGGC AGAGTTTGAC GAAAACATTA TAGTAGAGGT AGCACGTGAA
201301 TTAGAATGGA AATGGGGAAG GAAATGTACT CCAGATGTTG AAGGAACCCC
201351 TGCCTACTAG GCCTCTGGTC TAATGAAGTA TGACCAGAAT GACTCCATCT
201401 TGAAGTGAAG AGCTAGAACA CTCTTAAGGC ACCTATAAGA TTAATGCTTG
201451 TGGTCTGAAA ATAGCCACTT TCCAAGCTGG CTACAACCTA TTATTACAGA
201501 ATATTTATGA CCATACAGAG CATCTCCCAC CATGCCTGCA GAATGTCCCT
201551 ATGTCCTAAG AATTCAGCCC TCCTTACTTA GAGATAACGT TAATGAACAA
201601 GCTTAGGTTA AAAGATTAAG GGTCATGTAA TATCAATGAC ACTGAAGGCC
201651 CCTGCCTTTA GTGAGCACAT AGACACATTC CAAGTTTAAT TGTAGCTCTT
201701 TGTAACTCCT TATAAAAGTA GAGGCGCTAA CAAAGGACAG GGCATTCCTC
201751 CTTTTGCTTT CAGAGGATAT CCCACACTGT AACGAAACGG TTTCTGAAAA
201801 ACTTACTTCT TCCACTATGC TCTGTGGCTT TCCTTGAATT CTCTCCTTTG
201851 CAAGATCCAA GGACCCATTT TTGGGGTCTG GATCAGGACC CCTTTTCCAG
201901 CAACACCGGA ACTACAAAGA TTCTCAAACC TATGTCGGTA TTGAAATAAA
201951 GATGAAATTT AAAAGTAAAG CTATATGGCA TAACTAGAGC CTGGCATATT
202001 T (SEQ ID NO:3)

FEATURES:
Start: 3016
Exon: 3016-3096
Intron: 3097-11617
Exon: 11618-11690

FIGURE 3JJJJ

| | |
|---|---|
| Intron: | 11691-37943 |
| Exon: | 37944-38090 |
| Intron: | 38091-76221 |
| Exon: | 76222-76360 |
| Intron: | 76361-91402 |
| Exon: | 91403-91563 |
| Intron: | 91564-99311 |
| Exon: | 99312-99500 |
| Intron: | 99501-108867 |
| Exon: | 108868-108959 |
| Intron: | 108960-110489 |
| Exon: | 110490-110579 |
| Intron: | 110580-115705 |
| Exon: | 115706-115863 |
| Intron: | 115864-118931 |
| Exon: | 118932-119019 |
| Intron: | 119020-124894 |
| Exon: | 124895-125041 |
| Intron: | 125042-131125 |
| Exon: | 131126-131226 |
| Intron: | 131227-134218 |
| Exon: | 134219-134393 |
| Intron: | 134394-134990 |
| Exon: | 134991-135124 |
| Intron: | 135125-135856 |
| Exon: | 135857-136102 |
| Intron: | 136103-162378 |
| Exon: | 162379-162484 |
| Intron: | 162485-167349 |
| Exon: | 167350-167511 |
| Intron: | 167512-168933 |
| Exon: | 168934-169047 |
| Intron: | 169048-170472 |
| Exon: | 170473-170634 |
| Intron: | 170635-176773 |
| Exon: | 176774-177025 |
| Intron: | 177026-178271 |
| Exon: | 178272-178340 |
| Intron: | 178341-183910 |
| Exon: | 183911-184084 |
| Intron: | 184085-184826 |
| Exon: | 184827-184949 |
| Intron: | 184950-189728 |
| Exon: | 189729-189778 |
| Intron: | 189779-192221 |
| Exon(incomplete) | 192222-192336 |

FIGURE 3KKKK

Stop:

CHROMOSOME MAP POSITION:
Bac Accession #: AC008063.2
Chromosome: 2

ALLELIC VARIANTS (SNPs):
DNA

| Position | Major | Minor |
|---|---|---|
| 2180 | T | C |
| 4693 | T | C |
| 13759 | T | C |
| 17580 | T | A |
| 17701 | G | A |
| 18151 | A | C |
| 21076 | A | C |
| 22984 | T | C |
| 25961 | - | T |
| 25962 | - | A T |
| 29242 | A | T |
| 29249 | C | T |
| 34940 | A | C |
| 35122 | A | G |
| 35888 | G | A |
| 37779 | G | A |
| 40997 | G | C |
| 45222 | T | C |
| 45890 | A | G |
| 49199 | A | G C |
| 61696 | A | G C |
| 63810 | G | C |
| 64061 | C | T |
| 64186 | T | G |
| 65909 | G | A |
| 66361 | C | T |
| 68545 | C | T |
| 70223 | A | T |
| 72117 | C | G |
| 74720 | A | - |
| 77206 | G | A |
| 77426 | A | G |
| 78935 | C | T |
| 89179 | A | G |
| 90081 | T | C |
| 96033 | T | C |
| 96808 | A | C |

FIGURE 3LLLL

| | | |
|---|---|---|
| 102300 | A | T G |
| 105400 | A | G |
| 105494 | C | T |
| 105494 | T | C |
| 105911 | A | T |
| 110376 | T | C |
| 111250 | G | A |
| 111990 | T | C |
| 112748 | A | G |
| 112783 | A | G |
| 114256 | G | A |
| 118703 | - | T |
| 120414 | A | G |
| 127435 | - | T |
| 127929 | G | A |
| 130083 | G | A |
| 131381 | G | A |
| 132580 | C | T |
| 133900 | T | C |
| 143073 | A | G |
| 143157 | T | C |
| 148401 | T | C G |
| 153365 | G | A |
| 156875 | T | C G |
| 159594 | A | T |
| 160577 | G | A |
| 161658 | G | A |
| 165461 | A | T |
| 166267 | G | T |
| 169684 | A | G |
| 171916 | T | C |
| 173389 | G | A |
| 173435 | G | T |
| 174462 | G | A |
| 176313 | - | T G |
| 177082 | G | A |
| 177358 | C | A |
| 178098 | A | G |
| 178537 | A | C |
| 181240 | - | A |
| 181325 | - | T |
| 181730 | C | G |
| 185615 | C | T |
| 185975 | A | G |
| 188447 | T | C |
| 190645 | G | C |

FIGURE 3MMMM

| | | |
|---|---|---|
| 190708 | T | G |
| 191287 | A | T |
| 194488 | G | A |
| 201885 | A | G |

Context:

DNA
Position

2180
TGTGGTAAAAGAAAACAGTACTCAAACTTTAATAAATAAGACACAGTGAAAATCCATAGT
AAAAATGCCAACAACTTACATAGGTTTCATTACTAGACTTAACCGTGCAGTTTTAGCATT
TGATAATACCACATTATCTTTTGCATGTAAATTCTTTAGAAGAAGATATTAAATAAAAAG
ATAAAATGTATGTTGGTATGAAGAATCTGAAACATAAATGAAATCCCTGAAAATTAAAAG
GTGAATATGTATTTACCTATTTACTATTTACACAACTATCAAAGATTGCCAAAATAAAAA
[T,C]
CCTGTATAGGCGCTCATCATTTTGATGGGTGGATAAGTCGTGATACCCATAGTTTGGAAG
GAAGATTCCTTCAAGAGAGTACAATTTTTGCTTGGTAAATCTTTTGCATGTTAAACTTTTT
AGAAGAAGAAATTAAATAAAAATATAAAATGTATGTTGGTATGAAGAATCTGAAACATAA
ATGAAATTCCTGAAAATTAAAGGGTGAATATGTATTTACCTATTTACTATTTATACAACT
ATCAAAGATTGCCAAAATAAAAATCCTTTTTAGGCACTCATCATTTTGATGGGTGGATAA

4693
TTTATATGTTATTCAGGCTACTTAGCCAGCTTATATTCTTATTAGTAGGGAAGATTGGCA
TATTCTTAAGCTTGATTAATTTTGAAATGATTTGAATATACCTTTTAATTGCAACAAAAT
ATGTCTAATCTGTTAGAATTTATTTCCAGTATTTGCATGTATTAGTCATTATGAGTACAT
TCTGTTTCTTGGCATTGCTTTGGGATTCCTCTTGGTATTGGTTTCACAGCATTCTGCTAT
TTTTCACTGTATTCCTGACCTTTCAAGAGAACCAAACTGTAAAGATTTTTAGTTACTTTC
[T,C]
GTTAGTGGCATTTAAATGAGGATATCGATAATTTTGTAAGGTGGAAAAAAATTACTATTT
TAGAATTGTCATTTCTGTCACAAATCAGAGAAATTTTTCTCTATTACTATTTCAAAATAT
ACTACAATAAAAAGCAAAGACTGGTTAGAATGTAGTTAAATGCAATGTCAATCTTTCTTC
TTGCATGGCAGGATAATCTTGATCTTTGGAATGATAAAACTGATTGTAAACTTGCCCAGT
AATGATTGGTCATCTTCCTTACAAAGGCTGCCTTCGTTTATACTATTTTACATGCATTTC

13759
AATATATGTGGCTCCATCTTGGTTCACACTGCTACTCAGTGTACTACAAATCACAGTGAG
TTTGAATGCCATTCATATTACTGCAAACGACATTTTATTTATTTTTATTGCCAGTGCATA
TCCATCATGCCAGAACAAGAAAATAAGAGAAAAATGAACTTTGATTGTCATGCTTTTATA
GCACAGTGGAGTGTGAATTATTTTATTTAATTAGATGACAAAATATGTATTTATTATGTA
AAGACTCTATAGCTATGCTAAAAGAATAGAATATATCTCCACATAACCAGATTAATCACT
[T,C]
ATCACAATATTCCTGACTCACAAGAAGACAACAGTCATAAATATTAGAAGGCTTAAAATG
GAATCTCTCATTATAGCAGAGTTTTCCTACAAAACAAAAAGGACAGTGAGACTTCAACCA
ATGTACATTTCTGAATGGCTCACTTGTTAGCCAAGTATGCCCTTATAAGACTGTGGCACT
CTAAACAGGGCTTTCACAATGTCCACCCACACAATACCTGCCTTAATGAAAAGCTCAGTA
CCAGTTTCAGGCAATTTAAAAATCTTAGCCTTTATTATATTGAAATTAAGTCGAATTATT

17580
AAAAATCAACAAAACATGAAAAATGAGAGCAAGAGAGGAAAAAATGCACAAAATAATTAC
AAGGCTAACAGAAAACAGTACATGACAATAATAAATCCTTCTCTATCAATAATTACTTTA
AAACTAAATAAATTATACTTCCCAATCAAAGACATAGGGTGGTTGAATGGATTAAATGTA
TAATGGAATCACATGCTGTTATCAAGAGACTCCCTTTAGAATTTAGGCTCAATGTGAAAG
AATGGAAAAAAAAATTCCACGAAAATGTTAATGAAAAACGAGCAAGAGTGACTATACTTA
[T,A]
ATCAGATAAAATAGACTATAAGTCAAAACTCTCTCAAAAGACTGAGAAAGACATCTTATA

FIGURE 3NNNN

ATGATAAAAGGATCAATTCACCAGGAATATATAACAATTGTAAGTAGTTATGCACCCAAC
GATTAAGCACCTAAACATATAAAGCAAACATTGACAAAACTGAAGAGAGAAACAGGCAGC
AACACAATAATAGTAGGATATTTCAATACCTCATTTTGAATGATGGGTAAAACATATTAT
CCATTACCCACGGGCAAAACAGAGCAAAAGGAAATAAAGGACTTCAACAACCTTATAGAA

17701 AACTAAATAAATTATACTTCCCAATCAAAGACATAGGGTGGTTGAATGGATTAAATGTAT
AATGGAATCACATGCTGTTATCAAGAGACTCCCTTTAGAATTTAGGCTCAATGTGAAAGA
ATGGAAAAAAAAATTCCACGAAAATGTTAATGAAAAACGAGCAAGAGTGACTATACTTAT
ATCAGATAAAATAGACTATAAGTCAAAACTCTCTCAAAAGACTGAGAAAGACATCTTATA
ATGATAAAAGGATCAATTCACCAGGAATATATAACAATTGTAAGTAGTTATGCACCCAAC
[G,A]
ATTAAGCACCTAAACATATAAAGCAAACATTGACAAAACTGAAGAGAGAAACAGGCAGCA
ACACAATAATAGTAGGATATTTCAATACCTCATTTTGAATGATGGGTAAAACATATTATC
CATTACCCACGGGCAAAACAGAGCAAAAGGAAATAAAGGACTTCAACAACCTTATAGAAA
AAAATGGACCCAATAGACATGAACATTTCACTCAATAGCAGCATAATACACATTCTTCTC
AAGTGCAGCCAGAATATTCTCCAGAATAGATCACATATTAAGCTGAAAAGTATGTTTTAA

18151 GAAATAAAGGACTTCAACAACCTTATAGAAAAAAATGGACCCAATAGACATGAACATTTC
ACTCAATAGCAGCATAATACACATTCTTCTCAAGTGCAGCCAGAATATTCTCCAGAATAG
ATCACATATTAAGCTGAAAAGTATGTTTTAAAAAATTTAAAGTGATCAAAATTGTACCAAC
TATTATTTCTGACTACAATGGAATGTGAAAGTAGAAATCAATAGCCATGGAAAAACTGAA
AATATTATAAATATGTGGACATTAAACAAAACACTCTTGAACAACTAATGGGTCAGAAAG
[A,C]
ATTCAAAAGAGACATTAGAAAATATCTTGAGAGACATGAAGATGAAAACATAATATACCA
AAACTTATGGTATACAGCCAAAGCACTATTAAAAGATAAGTTTATAATGATAAAAGTCTA
TATGAAAAAAGAAGACAGATCTCAAATTTGCAACCTAATTATACATTTGAAGGGACTAGA
AAAAAAAAACACACTAGACCCAAAGTTAGCTGATAGGAAGAACTAGCAAAGATCAGAGCA
GAAATAAACAAAATAGATAATAGAAAACAATAGGAAAAAATCAATGAAATTGGGTTTTTT

21076 CCACTGCTAGTCTGATGGAATTTCCTTTACAGGTGACTTGACTGTTCTCTCTAACTCTCT
TTAAGATTTTTTCTTTAGCATTGACCTTGGTTAGTCTGATGACTATATGCCTTGATGATG
TTCATCTTATATAGTATCTTGCAAGTGTTTTCTGAATTTCTTTTATCTGGATGTCTACCT
CCCAACAAGATCAGGGAAATTTTTCTGAATGATTCCTTTAAATATGTTTCCAAATTGCTT
ACTTTTCCTTCTTTCTCAGCAATACCTATAAGCTATAGGTTTGGTCAATTTACCCCCTAT
[A,C]
CCATCTTTCTCAAATATTTTGTTTATTTTTAAAATGCTTTTCTATTTATTTTTGTCTGAC
TGGATTAATTTGAAAGACCAATGTTTAAGCTCTGAAATTCTTTCTTCTACTTGGTCTAGT
CTTTTGTTAATGTTTTCAATTGTACATTGAAATTACTTTTGTGAATTTTTTTATTTTCAG
AAGTTCTATTTTTATAAATATAGCTATCTTGTCTTTCATTTTCTGAGTTGTTCTTCTGGT
TTCTTTGTATTGGTTTTCAACATTCTCTTGGATATCATTGCACTTCTTTAGAATCCGTAT

22984 AGAGTTCCCAAATTGCCACCAACTGCATTGCCTGGGATTTCAAGGGCAGAGGGGTTCTCT
GACAATTTGTCAGTCAGCAGTTAGTCACAGGAGTGAGGGGAGCAGAGAAGCACCCCAACC
TATCCTTTACATGGGACTCTGAGTTCCTCAGGAGTCAGTGTCTGCCAGACTTTTGCTGCT
TTCCTTGTCTGCACCCCAGTTTCTTCCCATGGGCTCTCTGAAAGCTCGTGGCTCTCTTCC
CTCAGCTTTCCATTTGGATCATGACCATTCAACTGTAACTTTGATCTTTCTACAAACTGG
[T,C]
GTCTGACATCTCTAGTCAGCCATCTTGAAAAAAAAAAGCTACATTAAAGTTATAAAAATA
AAAGTAATTGCACTGTGATGTTACAAAGGCTACTATATCACTAGGTGACAAGAATTTTTC
AGCCCTATTATAGTTTTATGGTACCACTATTTTATATGCGATCCATCATTTGACTGAAAC
ATCATTATGTATGACTGTACATAACAAATTGCGAATAGAATTAGAAAGTGCTTTCTACTT
CTGGAAATCAATGTTGTCTTCACAGAGACAGAGGTGGGCTTTGAAGGATAAATAGGAGTT

25961 AGAACTGTGTATTTGTGCGTATATGTATATATAATGTTTTCAACCAATCACTATTTCAGA

FIGURE 3OOOO

GAAAAAATGGATGAAAATAAACTTGTATTCATTACATTAAATATAATCCTATACATATTA
AGAGGAAATTTTACAGCAGGAAATTGTTCCTTTAATCATTATTTTTCTTGAAAATTATTT
AATACTTTTAAGACAAACCACGGATGACCAAAGTCTCTTAATATTTACCACATAGATTTA
TATTAACACTATATTTTTGTTTTAAGTTTTCTAGACATCTGAGACTTAAATATGTTCTTA
[-,T]
TTAAAGACTTTAATAGTATGGCAGTTGTACCATGAAGGTGGCATAGTGAAGGAGATCAAC
TTAGTCTACTTTTTGACTAAATTCTTAAATCTCTATTTCAGCTGTCTTCCCCCTAGAACT
ATAGCTTAAAAGCTCCTCAGCTGCATACAGCACATAGCCTTCACAGGTTATCGCCTTTCT
ATAGAGTCCTCTCACAATATAAACAGGTGTAGCTACCAATTAGGACATGTCTCAAGAAAT
TGTTAACACTCACCAATATTAATTAAGTGCTAATAGGGTACTGAGCCAAACACTGAGGGT

25962 GAACTGTGTATTTGTGCGTATATGTATATATAATGTTTTCAACCAATCACTATTTCAGAG
AAAAAATGGATGAAAATAAACTTGTATTCATTACATTAAATATAATCCTATACATATTAA
GAGGAAATTTTACAGCAGGAAATTGTTCCTTTAATCATTATTTTTCTTGAAAATTATTTA
ATACTTTTAAGACAAACCACGGATGACCAAAGTCTCTTAATATTTACCACATAGATTTAT
ATTAACACTATATTTTTGTTTTAAGTTTTCTAGACATCTGAGACTTAAATATGTTCTTAT
[-,A,T]
TAAAGACTTTAATAGTATGGCAGTTGTACCATGAAGGTGGCATAGTGAAGGAGATCAACT
TAGTCTACTTTTTGACTAAATTCTTAAATCTCTATTTCAGCTGTCTTCCCCCTAGAACTA
TAGCTTAAAAGCTCCTCAGCTGCATACAGCACATAGCCTTCACAGGTTATCGCCTTTCTA
TAGAGTCCTCTCACAATATAAACAGGTGTAGCTACCAATTAGGACATGTCTCAAGAAATT
GTTAACACTCACCAATATTAATTAAGTGCTAATAGGGTACTGAGCCAAACACTGAGGGTG

29242 GTTTGGAATATACACCCATGAAATCATTACTAGCATCAAAGCCACAGATATATCTATCAC
CTCCCAAAGCTTCCTAATGCCTTTATTATTATTACTATTATTTTTATTATTATTAGTATG
TGTGTGTGTGGTAAGAACACAACATAAGATTCAACCTCTTGGAAGATTTTAAGTATACAA
TGCAGTATTGTTAGCTATAGGCACTATGCTGTGTAGTAGATCTCTAGAACCTATTTATCG
GAAAGTTACTTTTTTGAACCTCAATTTCATTATTTGTAAGTTGGGGAAAATAGTCCATAG
[A,T]
TTGCAGCGATTTTGTGAAGATTAAATGAGAAAATATAAATAAAACACTTAGCATAGTAGA
TGGTACATTGTAGATTTTCTATAAAGGCTAGTTTCTTTTTTTTAACTCTAAACTCTTATA
GCTATCTTAAGTGCCAAATGAATCGGCATTTATTTATATTCTGCCTTGGATGTTGCTTGC
CTTCTCTAGTATCCTCAGCTTGTACCTTTATGCAGGTTCTTATACATAATTTGTTGTTCC
TATCAACATTGATCACAATGTAGTATCAATACTTTCTGATTCTTGGTTCTTAATTTGCCT

29249 ATATACACCCATGAAATCATTACTAGCATCAAAGCCACAGATATATCTATCACCTCCCAA
AGCTTCCTAATGCCTTTATTATTATTACTATTATTTTTATTATTATTAGTATGTGTGTGT
GTGGTAAGAACACAACATAAGATTCAACCTCTTGGAAGATTTTAAGTATACAATGCAGTA
TTGTTAGCTATAGGCACTATGCTGTGTAGTAGATCTCTAGAACCTATTTATCGGAAAGTT
ACTTTTTTGAACCTCAATTTCATTATTTGTAAGTTGGGGAAAATAGTCCATAGATTGCAG
[C,T]
GATTTTGTGAAGATTAAATGAGAAAATATAAATAAAACACTTAGCATAGTAGATGGTACA
TTGTAGATTTTCTATAAAGGCTAGTTTCTTTTTTTTAACTCTAAACTCTTATAGCTATCT
TAAGTGCCAAATGAATCGGCATTTATTTATATTCTGCCTTGGATGTTGCTTGCCTTCTCT
AGTATCCTCAGCTTGTACCTTTATGCAGGTTCTTATACATAATTTGTTGTTCCTATCAAC
ATTGATCACAATGTAGTATCAATACTTTCTGATTCTTGGTTCTTAATTTGCCTGCCCATT

34940 CTATTCTCTTGCTTTATCTGATAATATAGATAAGGGTGTCACCTGTAATCATTGTTACCA
TATTTCTTGAGGCCATTTTCTTATTCTCATTTAACTTTTCTACTTGTTTCTTCTTTATTT
GTATTTTTCTCTGTTTTTAATCTTGCTCTTTTTATCATTTCTGTCTCTTTATATCCTACT
TACCTCTTAATCTTTTTGCCCAACTTCTCTCTTAATATATATATATATTTTTGCTCTTTACT
ATTTCTCTTATCTTTCTATTTCAAAATTACACTGTCTGCTGTTTTCTCCAACTCCCCACA
[A,C]
CTCACCTTAGGTGTAGTTGGGACTATGCAATATGCCATCACACAGGTAGTACTAATTTTG

FIGURE 3PPPP

ACAGGTAGCATCTCTACTTCAAACAAAGAAAGCTTTAACCAAAAAGGAATTACAGGAGAG
AAGACAGTATTCTCCCCAACTGATGCTAACATTGCCACCTACACTTTTGACGCTTTCTTC
AACAGTTAAGACGTAGCAACTTATTACTTCCCCAAATTCCCTGTGCTCTGTTGATCTGTC
TTAAACTCTAAAGGGAGAGAAAGTAGGTTTGTTCATTAGCTGTGGACTTAAAATGTGAC

35122 CCTCTTAATCTTTTTGCCCAACTTCTCTCTTAATATATATATATTTTTGCTCTTTACTAT
TTCTCTTATCTTTCTATTTCAAAATTACACTGTCTGCTGTTTTCTCCAACTCCCCACAAC
TCACCTTAGGTGTAGTTGGGACTATGCAATATGCCATCACACAGGTAGTACTAATTTTGA
CAGGTAGCATCTCTACTTCAAACAAAGAAAGCTTTAACCAAAAAGGAATTACAGGAGAGA
AGACAGTATTCTCCCCAACTGATGCTAACATTGCCACCTACACTTTTGACGCTTTCTTCA
[A,G]
CAGTTAAGACGTAGCAACTTATTACTTCCCCAAATTCCCTGTGCTCTGTTGATCTGTCTT
AAACTCTAAAGGGAGAGAAAGTAGGTTTGTTCATTAGCTGTGGACTTAAAATGTGACTT
AACTTTTTTGAACCTTTTGTTTCGTGAATGATAAAAAAACACTTTCTGAATGATATAGCT
ACTAATATTTTCATTTTATAGATAAAGTGAAAGATAAAGTACTTTTTTTAAAGGTTGCAT
AAATATAAGTGACACACACTGATATGAATGTAAGCATTTGACTCAATCCCAGAGATCATG

35888 TATAATCAGGTACTTGAACCAATTATAATTTTTCACTTGCCTGCATGAATCCATACAGGA
CAAAAACCTGAATATAGAAACTATCTTTCAGCTTTCGGTTTGCCAGAGGATTAATCTATA
ATTATTTTTAGGATTATAAAAGATTTACATCCGTTCTTAAAATATACATAATATCGGATT
TTTTTCCAGCAATAGAGGAATAACTAATTCTATAGTTTCATGCCAATCTCACCTCCAGTC
CTTCTAGAATTTGGAGGTAATTTAACCCCGTGTATAAAAAATAAATATTTTCTTTTTTGC
[G,A]
TTTTATTGAAAAAATCACGTAATTTAAGTACAAATATATCCACTAAAGTAGGCAAATTTA
TTTTAGTAGAATTCAGTTATCCCTTTCAAAGAAACACTATCAGCCTAAGTGTTATACATT
GGATATTTTAGAAATCTTACAATTTCAATTACATGTCTTCTGAAACTCATTATTGTAAGG
CTTTGTTTTAGGCTTTCCTTGCTGTATTAGTTGACTGGGGCTGCCAGAAAAAAATACCAC
AGGCTGGGCAGCTTAAACTACAGAAATGTATTTTCTCACAGTTCTGGAGGCTGGGACACC

37779 TAGGAAAACAGAAAAACCTCTGTGGAATTTGGCATTAACATAGACCTTAGCGAAACCTGT
TTTATTAGAGACAGTGATTTTTTAAAAACACTTAACTGTGAAGGGAAGGGATTTGATGAG
ATAACACAATTGTCTGAAGGTAGAGAGAATAAAAAACAATTTTTTTTCTAATGAGAAGAG
TATAATTAAGCATGGGGAACAGACACATAGAGATTATAAAGGAAGTGATGATTGCAAAAT
ATTTAACCAAATAATTAGTATTATACATGTTTGTGATAGAGCTATGGTACACTTAATTAG
[G,A]
TAAAATGCCAAAAGACAGTGCCACGCTCCAAGCTTTATGTATCATAAACATCAAAAATGA
CTTGCTGAATTAAATTAAATTGAGTCTCCATTAACATGTAAATCATCATATCTGTGCCCT
GGAATAATTCAGAGTTTAATTTGTGGGTTTGCTTCCTTATGAAGGTCATCGAACACTATT
TATTGGAGTACATGTGCCCTTGGGAGGAAGAAAAAGCCATCGACGTCACAGGCATCGTGG
TCATAAACACAGAAAGAGAGACAGAGAAAGAGATTCAGGATTAGAGGATGGAAGGGAGTC

40997 CATGTGAGAATTCAAGATGAGATTTGGGTGGGGACACAACCAAACCATATCAAATGTGAA
CCTTTTACTATTGTGAATGCTCTCTCATTGAAAGCATATTCAGAATACCACAATAAGTGT
TTTCGTAGTTGTTAAAAGGTTCTGAATGCCATGAGAGCCCATGTACATGACATAACTGAG
AACCTGGCTCTCAGTTCCTTGACCATCCCATCTCTTATGACCTTCTCTGTCATTGCACTT
TGTTCACCTTCTCAACCATATTCACTCCATCCCTGAAGTCACTAATTCATTTATCTTTCT
[G,C]
TCTGACCACAGCTTCACTCCTTTCTTGCTGTGCAGCTACTTAACCCCTCTACTTTTCTTC
TATCCATAAGTTTGTCTTTATTTGTTTATCCTAGTCTGATTGCATAGCATGCAGTCTTAG
GAATACTTTAGCATTACTAGTATTCCATTTGTATTACTAGTAGTCTATTTAGTAATACTA
GTATTCTAAATATCTTAGGTTCTAAGTTTTAGTTTTCTTCATACCTTTACTGCCTCTTTT
ATTTTCATTTTTAATAGGAAGCAGCATTTTATTTAAAATGTTTTTAATAGATTTCTTAAA

45222 GGGTTCCTCCATTTTTCCATTTTCTCCTTGCCTCCACAAGCAGATATACTCTGCTGGAAA

FIGURE 3QQQQ

TCATCATTCAACAAGGCAGATTGTAACCATTATGAAGTTATGACTCAAGGAGACCTTCAA
CATCTCCTCCTAATTTCATTGTGTATCTTTTTTGACATTTGAAATAATTATTTTTCAACT
TTCTTCGCCTTCTTCATCATTCTCCAACATCCTCTCTTTTCACCATTACTTGATAGTAAT
CTTGCTTTGTACTTCAGAGGGAAAATATATCATCAGAAAGAACTCACTTTACTTTCTTCC
[T,C]
GTTAAAAAGTTATAGCTGAAACCTTTCTTCCTATTAAACGGTTAAAACTGCAAGAAAATA
AGGAAGTTTTCTTTTCCTTTATGTTTATTTTCTATTCCCTCTCACCACTCTGGAAACTTA
TGCCATTTCTAATTTAATTGACCTCTTCCTCTTGAAATGAATTTTTCTTATCATCTTTGA
AACATGATAGAGTCTCCACCATTTTAAGCAGTTCTCCAACCTCCTGCAAACCCACCTTTA
GTCATTCAGATATGTAAGTTAACTGCATATAAATGTTCTGGGTAGCAATTTTACTTTTAA

45890 TATAGTCTCTCTATTTTTATTTTTTAGGTTTATGTATTTTAATCCTGAATGTTTATAGAC
ATTTTTCTGTGTCCCTTAATGAAGAAAATTGCTAAGATTGACCTAATGGTAGGTGTATTA
AAAAACTTTTCCATCCCGCATACACGAATAGTTTTCCACCTAGGGAACATTTTCCTATTA
TGTTTCATTCTGTTCCATTTACTTTGATCTCTTTGTGAAGACTTTCTTTGCTCATATCCC
TCTACTTTCTTCAAACATTTTAACTACATATATCTTTCATTTTTTTTTAACTTTGAATTT
[A,G]
GGGGTACATGTGCAGGTTTGTTACATGAGTATGTTGTATGATGCTGAGGTTTGGGGTACA
GATGGTCCTATCACGCAGGTAGTGAGCACAGAGTATAGTCAATTTTACAACCCTTGTTCC
CTACCCTCCTTCCCAGCTCCGGTGATTCCAAGTGCCTATTGTTCCCATCTTTATGTCCAT
GAGTACCCAATGTTTATCTCCCATTTATGAGTAACAACATGCAGTATTTGGTTTTCTGTT
CCTGAGTTAATTTGCTTAGAGTAATGGCCTCCAGCTGCATTCATGTTACTGCAAAAGGAT

49199 AAAGTGCCTACTTCTCCTTCCGCCATGATTGTAAGTTTCCTGAGGCCTCTCCAGGCATAT
GGAGCTGTGAGACAATTAAACTTCTTTCCTTTATAAATTACCCAGCCTCAGGGAAGCTCT
TTATCACAGTGGTGAAACAGACTAATAACAGTAACGTATATGAATCTTAAAATTTGACGC
CAAGCGATGCTCTAGAACATTGCTTATCAAACCCTTCTGGCACATTGGGAATCACTTGAG
AAGCTTTAAAAAAATTATTGATGCTAGGCTTCAACCTCGAAGGATTTTTATTTAATTAAT
[A,G,C]
TTGGGTGTTTCCCTAGGCACTGGTATTTTTAAAAAGTACCCCAAATTATTTAATAACCAC
TTAAATAATTGACCAAGAATCAGATTCTGAGAAGCTTCTGCCTCTCAATTTGGTGAAACT
TGGAAATAAGTCGGGTGGCCCAGATTCTCCCTCTTATTTTTTGCCACTATTTTTGGATGC
CACCTACCTTTTTCCTTCTTCAATCATCTGAGTATCTTCAGTGACATTTAGACCTAAATG
TGGTTTATCAGTGACAAATGTTTGGCACTTGGTGGTTTCTAAGCAATGGAATTTTCTAGA

61696 CAATGAGGATCAAGTCCTTTATATAATCCATTTTCACTTAATGAGTAGTAAATATATTTT
CTCTTCTTTGTGATTTTCTTGTTTTCTCCAGTTTATTGTAAAAATACAGTACATAATACA
CATAATATACACATTATGTGTTAATTGACTATGTTATCATTAAGGCACCTGGTCAACAGT
AGGCTATTAGTAGTTAAGTTTTGAGGGAGTCAAAAGTTATATACAGATTTTCAGCTGTGT
GGGAGATCAGCACCTTTAAGACCTGTGTTATTCAAGAGTCAACTGTAGTTGCTTTTTTTT
[A,G,C]
TTTTCTACCTTGAACATCTTCCTGCAGATGCTCCATCATCTTCCTAGCTCTAGTTTCTTA
TCTCTAATGGAGGTAAAGCAGGAAAGTTCTTACTTCACTGCTACTGTGGCAAGTTAATGT
CACACTCCTTAGGCTTAGCAAGAATTTGAGTTTATTCATTCTCTCCTGGAGGTTTTCTCA
CCTGCACTCTTTTCTGCGTTACTATTTATTCCTCTTCATCCCCTAGGCATTCAGTTATAA
TGATAGAGTCTCTCTGCTGAAATATTCTCAGTGCTCTGTGGCAGCCCAAGATGACTCTAT

63810 TGTAATGTATTAATCCTTTTACATATTTATTCCTTTTCCGATTCTTTTGTTAACTTATTT
TCCTTCTGCCAAATCTTAAACCTTATTACTTCTCCAGTGTTGAGTCTTCTTCTCTCTCAA
GACTTTCATTTTGAGTCATCATCATCATTGTAATCATGTGATATCTTTAGTTAAATGTTA
TCTATGTCTCTATCTCTGTCCCTGCTCTCTCTTCCAGAATCCAATCTCAAATCTCCAACT
GCCTTATGACCTTCTTCATATGATGGTCCCTTAGTCACCTCAAAGTTAGCATATGCAAAA
[G,C]
TTATCTTTGGAGCACCCAACCTACAATGCTGGCTCTCATTCTGACAACTCTCTTTTAATT

FIGURE 3RRRR

AATGGCATGATTATTCTACCTGCTTCAATTTGTAAAGCTCTCTATTTCTGGTAGGTAATT
CTATATCATCATTATAACCATCACCCCCTATCTCTAATATAATCATCAGTAATATTATGT
GATTCTTTTTTTTTTTTTGAGACGGAGTCTCGCTCTGTCAACCAGGCTGGAGTGCAGTGG
CGCGCGATCTCGGCTCACTGCAAGCTCCGCCTCCTGGGTTCACACCATTCTCCTGCCTCA

64061 TTCTTCATATGATGGTCCCTTAGTCACCTCAAAGTTAGCATATGCAAAAGTTATCTTTGG
AGCACCCAACCTACAATGCTGGCTCTCATTCTGACAACTCTCTTTTAATTAATGGCATGA
TTATTCTACCTGCTTCAATTTGTAAAGCTCTCTATTTCTGGTAGGTAATTCTATATCATC
ATTATAACCATCACCCCCTATCTCTAATATAATCATCAGTAATATTATGTGATTCTTTTT
TTTTTTTTGAGACGGAGTCTCGCTCTGTCAACCAGGCTGGAGTGCAGTGGCGCGCGATCT
[C,T]
GGCTCACTGCAAGCTCCGCCTCCTGGGTTCACACCATTCTCCTGCCTCAGCCTTCCGAGT
AGCTGGGACTACAGGCACGCCCGCACCAGGCCGGCTAATTTTTTGTATTTTTAGTAGAGA
CGGGGTTTCGCCATGTTAGCCAGGATGGTCTCGATCTCCTGACCTCGTGATCCGCCCTTC
TCGGCCTCCCAAAGTGCTGGGATTACAGGCGTGAGCCCCCGCGCCCGGCCAATATTTATG
TGATTCTTTATTGCTTGAAAAGTATTTTTACATCTATAATTTCCTCTTTTGGGGCTTGGT

64186 CTACCTGCTTCAATTTGTAAAGCTCTCTATTTCTGGTAGGTAATTCTATATCATCATTAT
AACCATCACCCCCTATCTCTAATATAATCATCAGTAATATTATGTGATTCTTTTTTTTTT
TTTGAGACGGAGTCTCGCTCTGTCAACCAGGCTGGAGTGCAGTGGCGCGCGATCTCGGCT
CACTGCAAGCTCCGCCTCCTGGGTTCACACCATTCTCCTGCCTCAGCCTTCCGAGTAGCT
GGGACTACAGGCACGCCCGCACCAGGCCGGCTAATTTTTTGTATTTTTAGTAGAGACGGG
[T,G]
TTTCGCCATGTTAGCCAGGATGGTCTCGATCTCCTGACCTCGTGATCCGCCCTTCTCGGC
CTCCCAAAGTGCTGGGATTACAGGCGTGAGCCCCCGCGCCCGGCCAATATTTATGTGATT
CTTTATTGCTTGAAAAGTATTTTTACATCTATAATTTCCTCTTTTGGGGCTTGGTCCAAT
CTTCTGGGAGACTAATTCTGGCAGGTAGAAATATAAGGAGGCCAATATCAGTACATTGCT
TATTCACCATTGCTAGCGTCTTACTCCTGGGTTTACTCTGACTTTGGTCCCCAGCTCTCC

65909 ACATGTTAGTGCTTAATTATTATTGTCTTACATTGTCTGTTATTATGTATTCATCTTATT
TTTAAAACCAGATTATAAGCAATTTAAGAACAATAAATATGGTATAGCATTTATGTGAAC
TGGAATAGATACTATCCTACAGTTAATGAATTGACCAAGCAACTATTCAAAGTACAGCCA
GGCTGAAGACGGCAGTATGTTGTTTTTTTAAAAGATACTTTATTTGCTCAATAAATCTAG
GAAGAAATCAGCCTCACATTTTTTTTGAACTGCAACTTCTTTGCTTGCCATCATTTAATTA
[G,A]
TTGCCGAGTTAAAGGACCCTCTTGGCTAATAAGATAGCAAAATTGTCATGGATTCTCATG
AATCTCAATATAATTGAACTTACAATTCATCTAAATTATTCCACTTTGTTTTTTATACTA
TTTGCAGTAATTTCATTCCACTTGAATAATAAGGGAATGTTTTCTCATGTTCTGTAAATA
TATTATTTGAGGATATTTTACTTTTTTTCTATATTTATGTATTGGTCTGTTTTCATGCTG
CTGATAAAGACATACCTGAGACTGGGTAATTTATAAAGAAAAAGAGGTTGAATGGATCAC

66361 AGGGAATGTTTTCTCATGTTCTGTAAATATATTATTTGAGGATATTTTACTTTTTTTCTA
TATTTATGTATTGGTCTGTTTTCATGCTGCTGATAAAGACATACCTGAGACTGGGTAATT
TATAAAGAAAAAGAGGTTGAATGGATCACAGTTCCATATGGCTGAGGAGGCCTCACAATC
ATGGCGGGAAGCAAAAGGAAGGCACATCTTACATGGCAGCAGACAAGAGAGAATAAGAGC
CAAGCAAAAGGGGTTTCCCCTTATAAAACCATCAGATCTCATGAGACTTATTCACTACCA
[C,T]
GGGAACAGTATGGGGAAACTGTCCCCATGATTCAATTATCTCTCACTGGGTCTCTGCCAC
AACACATAAGAATTATGGGAGCTAAAATTCAAGATGAGATTTGGGTGAGGACACAGCCCA
ACCATACCAATTTCTTTCTATAGAATATACATTTAAAAATTGACATAAGTGTGCTAAGTG
CTCTGCACATTTCAGCTCCCAAGGAATGCATATTGTAGGAACTAAAGCAAAAAAAAAAAA
AAAATAACAACAACCAGGGCAGTTTTATTGAGTTCAGTAAAGAATATGTTTCCCTATATT

68545 AAAAGCTTTTAATTCAAAGATTTTTCTTTCTTTTTCTGAGAGTGATCAGAACATGAAGAT

FIGURE 3SSSS

GGCTGTTGGGAGACAAATCTCCATGTATCCTTTATGTTCCCAAACATCTTTTGGGCAAAG
GCACTAAGTGCCTTTGTGCCTGTCTGTCTTTACAAGTATGTTTATATCGTGAACACACTA
GGAAGATATAGATAGTGTCTCTCTCTGGAGCAAAGGGTAGGTTTTTTATCTTTATACAGT
AAAGATAATGTCTCCTTATGGGGCAACAATCAGTGAGGATTATTGTCCATTATGAAAGAC
[C,T]
TGAGTTCCTTACCTTGGTTCTCCCCTGTCACATATCCCGCTACATGTGCAGCATCTCCTG
GCCCTTTGCACACCCTTCTGTGGGAGTTGGGGCTCAGAATGCAACACAAATGATGATACT
CTAGGTACTACTATTCTGTGCATAATAAACCATCTTTTGTCTCTGACTCAAGAGTCTCAT
GGCTTTTGCTAGCATCCATAAAACTGGCAGGGCAAATCCTGATACCCTTCACAATTCTTG
GCAGTTTTGGCAGTGAGGAAGGGATACTGACAGAGACATGGCTTTTGGAAAAAGAAGGAT

70223 AAATTCTTGTGGTCAGCCTGAAGTTCTAGAAAAGTTCTTTCACCCTTATGTTGGAACCAG
GCAAGAACTTAATAAATGTTGTATTGATAGTAGGGCAGCAGGTACATCTATCTAGTCTGA
GGATGTTGTTGCTGTTACAGCCAATTAGTTTATTCTAGACACACCATGTGACCCTTGAAA
CTAATCTATGTTATGTATTCAGATTTCTGAACCATTCACAGTCAGAGAGTCATGCACTTT
TTAATCCCCAAAGCCATACAACAATTGGCTGATAATCAAGGTATGTGATAGACCTTCCAC
[A,T]
TTTCCTATCATCCATCGGCATCTGGTATTGTTAAATGTTGGAAGGGCTTCTTCAAAAATT
AAAAAAAGTTTCCAACTCTGCCTCTCTCACCTCCTTCTGGTGCACACATATAAGTAAGAT
GGTTTGGTCACTGAATGTGGCTTCTGCAGAAACTGATCATCTCCTCTCAGCCTCTATGTG
GATAATAAGATGAAAGGGTTAAGATTTTATATAAACTTATATTGAAAAATCAGTGTTCCA
CCATGACCATTTCTGGGCATAATGCGTTATTCTTTCTTATTACAGAAACCTCAGGCCAGC

72117 ATATAGTGACTTGAACCACAGGGATGGTCATAAGAGACCTTTGAATGTTTAAGCAAACAC
CACCAGTAGATTATGTAAGCTTCAGACGATTTCGGAGAGAACTCCAAAATCTACACTTGG
CTATGAGGATGAGCTTCCTGGAGGGATAATTGACTTATTAGTTTTGTGTGCCCTACAGGC
AGTTATCCCTACAATGGTAATCATCAAATTAGAAAAATTGGTGAGAAATTTGCCCCTGAA
TTTAATCTAAAAGATTAATGATACAATTCCAGTCTTCTTTAGCCTCAGTTCATGGACTAA
[C,G]
GTTTTTATGGATGATAGGATTGCCCTCAGCTACCTCCTTGTGGTCCAAGGAAGAGACTGT
GCAATTGCTTATATATCCTGCTGTACCTGATCTAATGCCTCCGGCCAAGTGGAAAGGTTA
ATATAGAAACTTAAGGAGAAAGTCACATGGCTTTGTAAGGGAAACCTTTATGGTTTGGGG
GATTTATTCAGTTTGTTGGGTTCAGCAGCTGAATACATCAGCAGTGTGGTTGAGGTATAT
ACTGTAGATTGGTCCCATCCTTCTGCTTTGAGTCCTGTTGATAGTGACCTTAAGTAAAGA

74720 TGTTGGCACCCTGATTTCAGACATCCAGGCTTCAGAACTGCAAGAAATAAATTTCTGTTG
TTTATAAGCCACTCAATCTATGGTACTTTGTTATAGTATCCTGGACTGACTGAAATATAG
GCCTAGATCAATGGGACATTTTAGAAAGTCCAGAAAAACAGTCCAAACAAATATAACTAA
TTGATTTTTGAAAACGGCACAAACCATGAAGAATATACTTTTTCTGTGTCTTTTATTTGG
GTCTTTTCCATAAATGGTATGATATTGGAACAATTTAACATCCATATGCAAAAAATAAAA
[A,-]
AAAAACCCTTGAATTAAACCTCATATCTTATACCAAAATTAACTCAAAATGGACCATAGC
TTCAAGATGTAAAATATAATATATGAAACTTTAGAAGAAAACATAAAAGAAAATCTTTGT
GACCTTTAGGCAGAGAGTTTTCAAATTTGATACCAAAGCATAATTTATAACACACACACA
CAAATCAGAATTTATCAAAATTTAAAACTTTTCCTCAGTGAAAGACACTGCTAAAAGAAT
ATAAAGTCAAACTATAAATGGGGAGAAAAGACAAATATTGCAAATCATATGTTCAAAAAA

77206 TTGCTATATAATTGATAGAGTTCTGTAAAGTTGGAATTAAATTTTGTGTTTACTTTTCAT
TCATTCTTTCTGATTTGCTCAGTTAACAAACATTTATGGAGTGTCCATTATGTGCCAAGT
GCAATGGATATGGCACAACAACAAAAATCTTAGATCTTGCCTTTAGGGATCTTGCAGTCT
AATTTAGACAAGAAAACAAAGTTGTAAATGCTGTATAATGAAAGCTGTGATACAGGTGTG
CACAAGAAACTGTGGGCACACCCAGGGTTGTCATTTACCCACTTTTTCACAAATTTTAAT
[G,A]
TGACTACCAATCACCTGGAATATTGTTTAAAATGTAGACTTAGTAGGCCTCAGGCATAGT

FIGURE 3TTTT

CAGACCATGAGGATGTCGTGTAAAATGTTTTGGGTTTGAGAACCAAACTTTGAGTAGCAG
TTATCTAAACCACGAGGTGAAAGAGAGGATCAGGGTAGCTTCCCTGGAGGAGGCGATTCT
TGAGCTAGCTCTTGTGAGTTGGGTTGGAGTTAGCTAGGCAGAAAAGCAGAGGGGACAGTA
TTCTAGGCAGAGATAGCAGGACGTGCTTAAATATATCATTGACACAGGTTTAGTGTTTAT

77426 AAAGCTGTGATACAGGTGTGCACAAGAAACTGTGGGCACACCCAGGGTTGTCATTTACCC
ACTTTTTCACAAATTTTAATGTGACTACCAATCACCTGGAATATTGTTTAAAATGTAGAC
TTAGTAGGCCTCAGGCATAGTCAGACCATGAGGATGTCGTGTAAAATGTTTTGGGTTTGA
GAACCAAACTTTGAGTAGCAGTTATCTAAACCACGAGGTGAAAGAGAGGATCAGGGTAGC
TTCCCTGGAGGAGGCGATTCTTGAGCTAGCTCTTGTGAGTTGGGTTGGAGTTAGCTAGGC
[A,G]
GAAAAGCAGAGGGGACAGTATTCTAGGCAGAGATAGCAGGACGTGCTTAAATATATCATT
GACACAGGTTTAGTGTTTATTTATTTATTTATTTATTTGTCTGAGACAGAGTCTCACTCT
GTCCCCCAGGGTGGAGTGCAGTGACGAGATCTTGGCTCATTGCAACCTCTGCCTCCCTGG
TTCAAGCCATTCTCCTGCCCCAGCCTCCCTAGTAGCTGAGACCACAGTCATCTGCCACCG
CGCCCAGCTAATTTTTGTATTTTTAGTAGAGACAGGGTTTCACCATGTTGGCCAGGCTGG

78935 ATGGCAACATATGTAGCAAAGAGAGCAGACATTTTTTCCTTTGATAAATACTGTAAACTT
ACCTTCATAAAATGTTTTTCTAATTTACACTTCTATCAACAGTGTATGAGAGTGCTTATT
TCCTCCACATCCTTTCACAGTAAATTATCAAACTGCTTAAAATGTCTTTTCCAGTTTTAT
AAATAAAACATAAATCTCATTGTTTTAATTTGATTATTCAAATTATTAGTGAGGTACAAC
ATCTTTTCCTATGTTTTTATTTTTTTCATGTGAACGAACTATTCATTTCCTTTATTTATT
[C,T]
TATATAAATCATTCATTATTTTCTTTATTTGCCTTTTGGAACACTTTAAATTGGTGGCAT
GTTATTCAGTATGAACTAACCTTTTTAATAAAATAATTTACATAAGTTTCCTCATGATGT
TTTGTATTGTAATACTTTAAATATAGACTTAAATTTAAAATAGTTTTTATTTAACCTGGT
ACATATTAAGATTAAGAGACTTCTACCTTACTTTTTGTCCCAACTGCATCAAAAACTACG
TAGTAGTTTTAAAAATGTGTAATATATGTGCTCATCTTCTTTATTTGGTGACAGAAAGGG

89179 TTCCTTATGGAAAGTTTCATTATAGCCCTTCCACAGAATAGTATGTTTGAGTCTTATTCA
CAAAGGAAAACCATCTATTTTTATCTAGCACAGTAGGCAATAAAGAAAACAAATTGGAAT
AATATAAAAGAAAAAGTGAGAACAAAGAACATTTTGCAACTTAAGATTGGCTCCAGACAT
GGATGAAAATTAAATGTTAAATCAGTTGTTTCTGCTATAAGCATTAGCATAAGATCTTTG
AACTGAAAAGGACTATAAATTCAATTCAAATTACTATATTATGGTGGGAAATGGGCACAG
[A,G]
CTCTGGAGAAAAACAAAATTTTAAAAAAAACTTAGAGTTGGATCCTGGCTTGACAAGGTC
ACTGGCTAGGTGATCTTTGGAAAATTATTTAATGTGTTTAATTTGTCTCATCATTTTACC
TGTGAGAAAACTGACCCAGAGAAGTTAAAAGACTTTCCTTTTATTACATGGTGGTTTAGC
TGTATAGAAAAAATATAAATGTCTTTTTATTCTCAACTAGTTGAAGACACTTTATGTAAT
ACTATTCCATTAAAATGTCTGCCAAGAGGTTGTTCCTTTGTGATATTGAAATCATAATGT

90081 CTTGAACTTTGCTTGTTGCATGTCAAGGAAAGGATGAGCTCCAGAGGATATCCTCTTGCC
AATTAAATACTCCAGTCTGAAAGTGACACACACATAATTTCTGTTCCCACCTCATTTCCA
GATTTAATCACAGACACATGGACTCACCCAATTAAAAGGGAGCCAGGTAGTGATGTTCTA
CACTTTCCTAGGAAGAGAGGGAGAACCAGTTATGACATGATATGACCATCACATGATCTA
TGAGGTATTATGGCCCTGTTTAGGACTGAAAAACTTTAGGAATAACTAATATGAAAACTT
[T,C]
CTGTGTAGACAAAAATGTTCTATAAAATTCCCAGCCTTGAAGAGATATACTGTTGGTGAT
TTGTGGCTTAAATGTAAGTTTTTTCAATATGGCATATCTATTCTTACCTGATTGTAAATT
TTGGCAGGTATAAGTATTCTTTTCTATTGGCTTCCTTTTCACTTTCTGACATTTTTTTTT
CTTTTTGCTTCCTAAACACTAAAAACAGATCCATAGCTTTCCTGATCTCTCTTACTACTC
TGCACATTAATCATTCTGACTGTCTCTTTTGGTTAGTTACTTTTGGCTAATCCACTTGAT

96033 CTTTTTTTTTTTTTTAGACGAAGTCTCGCTCTGTCGCCAGGCTGGAGTGCAGTGGTGCGA

FIGURE 3UUUU

TCTCAGCTCACTGCAGCCTCCGCCTCCTGGGTTCAAGCAATTCTCCTACTTCAATCTCTT
GAGTACCTGGGACTACAGGCACACGGCAACATGCCCAGCTAATTTTTTTGTATTTTAGTA
GAGACGGGGATTCACCACGTTGGACAGGGTGGTCTCAAAGTGCTACTAGTTTTTCTAGAG
TCTGCTTAGTGTTAGCAGAGTGTGACCTATTTGTCCTTTTTTTCTTTTCTTTTCTTTTCT
[T,C]
TTTTTTTTTTTTTTTTTTTTTTGAGGCGGAGTCTTGCTTTGTCTCCCAGGCTGGAGTGCA
GTGGCGCAATCTCGGCTCACTGCAAGCTCCGCCTCCCGGGTTCACGCCATTCCCCTGCCT
CAACCTCCCGAGTCGCTGGGACTACAGGCGCCCGCCACCACGCCCGGCTGATTTTTTGTA
TTTTTAGAAGTGACGGGGTTTCACCGTGTTAGCCAGGATGGTCTCTATCCCCTGACCTCG
TGATCCGCCCGCCTCGGCCTCCCAAAGTGCTGGGATTACAGGCGTGAGCCACCGCGCCTT

96808 TTACTAATTCAGATTCCTTTTGGTACTTAAATGTCACCCTAGTATAAATTATATTCTTAA
GCAAAATGAGTAATTTTTTCCAGACAAGTAGATATAATTTGATACAGTTATACTTTGGAG
AAGTTTGCTGTGTATTTCTCTGTAACTAATGAACAGATGAGTGTGTTTTTTAATATTTAC
TTTTCTTTACATAACTGTTTCAAATAAAAATCTTATCTTTGAAAAACTGTGAAGATAGTG
ACCTATGGCTTTTTTAGTGTTCGAGCCTGGAAACATTGTGCTTTAATAGAAATTAAAAAT
[A,C]
ATAAACATATGTAGGGTTTATTATGTGATTACTTTTGATTCTGACTAGAATATTGAACTG
GGAATTCATATCATGGCTTATATTTGGAACTGCTTTACAATAATATCATATTGATATTCT
AATAACCTACTTTACAACTTCCATTATGAAGTATATGCATATTTTATATACATTTTTCCA
TCTTAGCAAGGTTTCAGTGTAATGTCATATACGTTGACAATTTATTATTTCCTTTATTTC
AGATTAACCCAGGGGTATTATAACTACTGATCTCCAAAGAACTGAAAAATAGATTTAAAT

102300 TATAGACTTCACCAATTTAGAAGTAAATCTCCTACCCAAAAGTGAAAAAAAGTACAAAAG
ACCTTTACTGCTAAGGTTCTTAATCTACTTATGAACTCTAAAGCCTGACAAACTCTAGAT
ATATAAACAAATTGAAATTAATAGCCGTAAATGTAAATTGGAAATTCTGTTTTAAATATG
CAATCAAGATTTAAATTTTTGTGCAATA
[A,T,G]
TTCAGAGAGATGCAAAAGGATTTCAAAACATCAAAAAAGTAAAGGTAATACTATTAATTT
TTAAAAATCTCCTTAGTAAAATCCATTATGCAAAAAGATTGACTTTTTTAAAAAAAAAGA
TTATAGAATAGAAATTAAATAGAGCAAAGATTTTTCCAGAAACTTTAAAACAGAACACAT
TTTCCTCCCTAAGCATAGTGGTAGAAAT

105400 CACATATGATCCCTACATGAAGACTCAAAGAAAAAAAAATGAATTTGTAACTCAAAGAAA
AGTAATTCAAACAGGTGCTAATATGAATACTATATAATATATATCTTAATTGGTAAGATA
TCAAACAAATATTAGAAATTTTGATTTAAGGTGAAGAACTGTTGAGCTTAACAAGTCATA
AAAATGTATTTAGTAAATAGCAGAGGAGATATTAGGTTTCTCAAATGTTTCCATTTACGT
TTAAATAGTCACAGATACCAGTTAACCTTAGTGATATCTACTTTTCATCAGTTTTTTAAT
[A,G]
ACTTACCATGAATATAATAGATTACTCAATGTCTTTTTTTCATAGTCATCCTCATGCCTC
AAAATTTTCTAGGTATTATAAAAACAGAAATAATTGAACATTGCAATGACATTCATTTAT
AGGAAATAATATGGGTAGTGATCAGTGGACAAAGGTAATATAAAGAAACAGGTAAAAAGC
ATTTGTTTGTAAGTACTGTGGTATAGCACTTTAAAAAAATTACAGTATACAATTAGCATT
CATAAAGCTTCCACACATATATGAGTGCTAAATCCTAAACTTATA

105494 TAATATATATCTTAATTGGTAAGATATCAAACAAATATTAGAAATTTTGATTTAAGGTGA
AGAACTGTTGAGCTTAACAAGTCATAAAAATGTATTTAGTAAATAGCAGAGGAGATATTA
GGTTTCTCAAATGTTTCCATTTACGTTTAAATAGTCACAGATACCAGTTAACCTTAGTGA
TATCTACTTTTCATCAGTTTTTTAATAACTTACCATGAATATAATAGATTACTCAATGTC
TTTTTTTCATAGTCATCCTCATGCCTCAAAATTTTCTAGGTATTATAAAAACAGAAATAA
[C,T]
TGAACATTGCAATGACATTCATTTATAGGAAATAATATGGGTAGTGATCAGTGGACAAAG
GTAATATAAAGAAACAGGTAAAAAGCATTTGTTTGTAAGTACTGTGGTATAGCACTTTAA
AAAAATTACAGTATACAATTAGCATTCATAAAGCTTCCACACATATATGAGTGCTAAATC

FIGURE 3VVVV

CTAAACTTATA

105494 TTTAAGGTGAAGAACTGTTGAGCTTAACAAGTCATAAAAATGTATTTAGTAAATAGCAGA
GGAGATATTAGGTTTCTCAAATGTTTCCATTTACGTTTAAATAGTCACAGATACCAGTTA
ACCTTAGTGATATCTACTTTTCATCAGTTTTTTAATAACTTACCATGAATATAATAGATT
ACTCAATGTCTTTTTTTCATAGTCATCCTCATGCCTCAAAATTTTCTAGGTATTATAAAA
ACAGAAATAA
[T,C]
TGAACATTGCAATGACATTCATTTATAGGAAATAATATGGGTAGTGATCAGTGGACAAAG
GTAATATAAAGAAACAGGTAAAAAGCATTTGTTTGTAAGTACTGTGGTATAGCACTTTAA
AAAAATTACAGTATACAATTAGCATTCATAAAGCTTCCACACATATATGAGTGCTAAATC
CTAAACTTATACTAATTTTTTTCCGTGAGGGAAAAATATCCTAGCAAATTCTTTGTTATT
CTATTAGGAAAATTTTTACTTCTGGCTGAAGGTAAAATTCTGTACCTGAAAATTGCCATT

105911 TTAAAAAAATTACAGTATACAATTAGCATTCATAAAGCTTCCACACATATATGAGTGCTA
AATCCTAAACTTATACTAATTTTTTTCCGTGAGGGAAAAATATCCTAGCAAATTCTTTGT
TATTCTATTAGGAAAATTTTTACTTCTGGCTGAAGGTAAAATTCTGTACCTGAAAATTGC
CATTCTGTGAACCATTATTGCCTTAGACATCAGCAAGAAAATAAGAGATGCCCTTCCAAA
ATCTGAATTTATTGATTCTTCTTATGTAATAGTATTTCAGTTAATGAAATTAATTTTGAA
[A,T]
TTTAATCCATCATCTTCTTTTGAAAGATGGTAATAATTGGCATAAACTAAATAATTGGCA
TAGAGAAAAATATATTTAAACAATGATTACAATTGATAATAGAACTATAAAATCATTTTT
AATTTATGAGGTTTCAATTAGTTCTATATACTATAATTCATGCTTGAATATTGGTTTTAT
ATATACAGCAAATAAAATGTTAAGCTTTTTAAAAGACTTCTATTTTTTCAAAATAACCCA
AATCAAACTTGTTAGCTTAATTTTTAAATAGTATCTATACATCGTTCTATATACTACCAA

110376 GCCTGGGTGACAGAGTGAGACCACATCTCAAAAAAAAAAAAAAAAAAAAAAAAAAGACAA
TGCAAAAGAGAAGGAGTTTGAATACTTGGTGAAAATACGGCAGGTTAACAATTCTCTTTA
TCTGAGTGGCTGAAATAGAAGTAACTCAGAGTAATATTTTAATAAAGCCCTTAGCACTGG
CAATAATTATAGTAGTGGGAGGAGGTGGGAATGGATGGAAGCAGTAGAGGAAGTAGCCTG
AATCAAGGTTCTGAAAAGATTAATAGTGATCAGCTCCTTGGACCTGTTTCAGAATCCCTC
[T,C]
GACAATGCCTAAATAATCTAGATCTAGTTACGTGCATGCTCTCCCTCTGGTGCCTGGCGG
AGTCTCCGTGGGAGCATGGTGTACCAGCTTAAGTCTGTTAATTATGCGTGCAGGGACTGG
GAGGCCAACAAAAGGGGCATACTAGTCCATGTGGGATGAAACAAAGGCATGAAAAAGGAC
CTCCACACCAGCAAGAGAGAGAGGTGAGGGCATACTCGGGCTCTATTTCTACAGTGGTTC
AAAGCTCATTTCACTGTATGGAGGCATGTGATTCAAACATTAAGCCAGTTGAAATGTATT

111250 ACCTTTATACACTGATTGTGTATCTCCATATCATGTTGCTTTTGGTTGTGTGACCTGCCT
TTGCAGCCTTCAAGAATACTTCATCACATATGAAAGAAAATGAAGATTGCCAGTTGTAGG
CAGTAGTCTCATCTTCTGGTCCCCCCTCAAACAGTTAAAACTATGGAAGAGTCAAACTTC
GATTTCCTTTCTTTTAATCCTTTTCTTTCTCTTCACATTTGCGATCACTGGCCCGTTTCA
TCTTTTAATAGGCAAGTTAAATTTCTAGAGCCCTCTACTTAGTGTCAGCTGTTGTTCATA
[G,A]
CATGGCACACTGGAAAGTCTCTTGTTCATAGCATGGCACACTGGAAAGAATGTGGCTTTT
GAGAAACAGCATGAGATCTTGAATCCCAACTCTGGCATTATAAACTAGCTGATCTTGGAG
AAGTTCTCTAAAGTTCAGCCTTCTCATTTGCAAAGTA

111990 AAAAAAGACTAAGTAAGATTTTTTACTTTAAAGTCTGAGAGGGCAGAAAAGTAGAGTTTG
AAAAGAGCAATTGTGATCTATCACTATGGAAACAAATTTTAGTGCCAGATTTTGCAGGTG
CATGAGTTGATATTTTTTAGCCTTATGATTTTAGTTTAGTAGTGAATTTATCAGAATTCA
CCTAGTCTCCAGGTTAGTTCTCTGTTTTAATATTTTAAGTCTTAATATACAGATTCCAAA
ACCCCAGAATCTTAATATGCAGATTCCAAACATTTTGAGGTGTTAAGAAAAAAAAGGTCT
[T,C]

FIGURE 3WWWW

TATTCATCTTATATGATTTGATCATATTTATTCCATCTACATTCAACCTACATATTTGTA
ACCCTTCCAGTGGATAGACGTATCAAACTTACTTAAGGAATGATTAGGAAAATAACTGGA
ATTATCAGGTTTTAGCTTCCCATAATACTTTTAAAAAGCAGATGTGTCAAAGCAATATTT
GTTTTTGTTTTTCAAGCTGACAGTGGAACGTAGGTATTTTATGTTGGTGGTGTTTTCTTT
TACTTCAAATGACCCAGAGATGGCTTCACATAATTTTCTACATAGAAAGAACTTCCGTCT

112748 AGACACCATTTCTTCCCAGAGAATCCCTATGAAGTTTCTTGTACTTTCTATAAGGGGCTG
AAGGCTTAAATTTTCTCCTTAAATTTCCATCTGTTTTTCCTTTAACTCTTAGCGTGTAGT
TTGCCCAGACACTTCCAATTTCACCTTGGTCTTCTATCTAATCTCATTCCTTGTTCCCTA
GAAATGTAACTGTTTCTCATCCACAGATTAAGTATCAAAGGCCCAGAAAGAAATCTTTCC
ACTACCAGCATAAAGGTGAGGTCTGGGCAGCCCAGAAGCATGAGTGTAAATACAGACCCA
[A,G]
AAGAGTATAGCTCGATTTCTTCAAGATCCTATTCAGAGGACCAGAAACTTCCAGGATTTC
CTTCTTGTCCATTCCAAGTGTTTGTGTTCACTTGACAGTTTTCTTAGGGATGTAGTTCAA
CCTAGATTCTCTAGAGCTGCTTTACATATTTATAATTTTATAAGAGGTCACATTCAGGTC
TTTAAACATAATATTTTATTATATTAAAAGTTGCTTAGGGGGCCAAGGGCATGGTGGCTG
ACACCTGTAATCCCAGCATTTTGAGAGGCCAAGTCAGGAGGATCACTTGAGCTTAGGAGT

112783 TTCTTGTACTTTCTATAAGGGGCTGAAGGCTTAAATTTTCTCCTTAAATTTCCATCTGTT
TTTCCTTTAACTCTTAGCGTGTAGTTTGCCCAGACACTTCCAATTTCACCTTGGTCTTCT
ATCTAATCTCATTCCTTGTTCCCTAGAAATGTAACTGTTTCTCATCCACAGATTAAGTAT
CAAAGGCCCAGAAAGAAATCTTTCCACTACCAGCATAAAGGTGAGGTCTGGGCAGCCCAG
AAGCATGAGTGTAAATACAGACCCAGAAGAGTATAGCTCGATTTCTTCAAGATCCTATTC
[A,G]
GAGGACCAGAAACTTCCAGGATTTCCTTCTTGTCCATTCCAAGTGTTTGTGTTCACTTGA
CAGTTTTCTTAGGGATGTAGTTCAACCTAGATTCTCTAGAGCTGCTTTACATATTTATAA
TTTTATAAGAGGTCACATTCAGGTCTTTAAACATAATATTTTATTATATTAAAAGTTGCT
TAGGGGGCCAAGGGCATGGTGGCTGACACCTGTAATCCCAGCATTTTGAGAGGCCAAGTC
AGGAGGATCACTTGAGCTTAGGAGTTCGAGATCAACCTAGGCAACATGGTAAGACCTCAT

114256 TTAACTGTTTATTCTTTTAGTAACAGAAAGGATTATGAGATTTATTATGTTTTCCTCACA
GAGCTGATAGTATATGGGAAATCTTCTATTCCCTCCTTGGGAATTTTGGCATTACAATAA
AAATGTAAAGCATTACTAATTTAAAGCATCTTAAATGTGTACATTTCTCCTAACTAGATA
AATACCTACAAAAATACCACAATAAATCCCATGAAATTTAACCTTACTTATTATAGTAAA
TAAATACTTTTGCTATCTATAAACTAAAAGATCAGATTCCACAAAAGCAAAATATTTGCT
[G,A]
TATAATCCAGTGTACATTAATTATGAATTTACAAATTTATATTTGGAGTACATTTGTAGC
TTAAAAATTTTGGATGTATAATATTTGTTAGATATTTTTATAGGCAGTTTTGCTTTGTTA
AATCATTCTTCCTTTCCTTTAAAATAAAATAATGATTCTATTTAATATTTTTGATGGAGT
ACTGTAGGATATTTTTATATTTAATCCTTGTGAAAGAACATATGCTTCCTATACTAGGTT
ATATATTTTGTGGTATCCTTATTCTTTGGAAAGATTAATTAGTTACAAAACTTACAAATA

118703 CCCCATTTTCTTCTACGTGGCTGATCTTTGATTCCTGACAATAATTTTTTATAATGAAAA
TTGCACATACACCTACTGTTTTTTGACTCTATATTTTCTCTGTTTTGCTACTGTGTTACC
TTTGTCCCCTTTGAACTATTCGCCATTTTGCATACAAGTGAGTTTTCTTCCTTCCAATTT
AGAAAGGTCTAATCAGATTTTACTTTTCCCACTTTCCTTCTCTAAGGATCATAGAATCCT
TAAAATTCCCAATAACAACTGCACATGCTGTACAGATAACTAAACGGAGAAACACTGTGA
[-,T]
AAAAAAAAAAAACACGGAAAACCATGCATTCCCATTGCTTGAGGATCTTAAGCATAAGGG
TCAATCATGGTAAAATTTTTCAAAATAATAATGAACTATGAAAAACTATGGAAGTATTTG
CCATCACAATCTCCATTTTCAGTAATTCCTTTGAGATGAGTGATTCTGTATTACTAAAAT
TATTTTTATATTTCTACCTTAAAACATTTTTTTTTCTTCTTAATTACAGATTTTTGTTCAT
TCTTCTGGGACCCCTGGGAAAGGGTCAACAGTACCATGAGATTGGCAGATCAATTGCAAC

FIGURE 3XXXX

120414 ACAACGACTGCCATAAGAAACTACTACAAATTGGGTGGTTTAAAATGACAGTAGTTTGTT
TTCTAACATTTTTGAGGCTAGAAGTTTGAAGTCAAGGTGTCAGCAGGGCCACAATCCCTT
CGAAGTCTCTAGGGGAGGATCCTTCCTTGTCTCTTCCATATTCTGGTGGCTCTTGGTCTT
CCCTGGCTTGTGGCAATAGACCTTTGTTCTCTGTCTCCATCTTCACATGGCTTTCTCCCA
GTTGTCTCTGTGTGTCTTCTTATTTTCTGTTATGAAGACAGACATTTGTCATTTGATTTA
[A,G]
GGCCCATCCTAAATCCATCCAAATCATTGGATTTAGGGCCCATCCTAATTCAGGATAATT
TCATCTTGAGATACTTACCTTAATTACATCTGCAAAAATCCTTATTTCAAATAAGGCCAC
ATTCTGCGGCTCCAGGTTGATGTGTATTTTGGGAGGAAATTATTCAATCCACTGTAATGA
ATAACTTATTCTATTTAGGAAATTTGTGAGAAGACAGGAGGATGAAAAAAATAACTTAAT
GAGGGCCATACACCTGATTTAGCAGAACTCTCTCTGAGAAAACACTCACAGTATAAAAGC

127435 TATGGCCTAAGAGAAAGCGCATTACTGTCCTTGTATGTTTTGATACATCACTTTGAAATT
GGCAAGCATTAGGAAAATTCAAAGACATGACTTAATCATATTATATAGAAAACTCCATAT
TTATTACTGCTAATCACAGGAAATATTGGGAAGATTTTAAAATTATAATTCTTATATTTG
TATTGCTTTTTTGTGAATGTATGATATAAAGATTTTTTAAATTTTGTTTATGAACATCTA
ATGTATATTTTACCCATCATACAATCCAGAAAGATAGAAATATAAAGCATTGCTATTTTT
[-,T]
AGGGTCATTTTTTAAATTGCAGGCATGAGTATTAAGAGTGATGACCAAATATTTGTTAAG
CTCACTCCTCATACTGCCACCTCTATGCCTACTGAATCTGCCTCCCACAACCCTCCCAAA
TTGTTGTGTACTTAGTCTTGCCTTTGCGCCTTGCCCTGTGGAGTTCAGCCTTGCCTGACT
CTGCTACCCTATTGGAAGCGGCAGATGGTCTAATTGACCCAGCCCTGGAATTAGAAATTT
TCCTGCTTTGCCAGAGGTGGGCAAATGAGCAGTTGTACCACTCAACCATGAGTACTTAAA

127929 GGAAGCGGCAGATGGTCTAATTGACCCAGCCCTGGAATTAGAAATTTTCCTGCTTTGCCA
GAGGTGGGCAAATGAGCAGTTGTACCACTCAACCATGAGTACTTAAAAAGGGTATCTCAA
TTTCACTGTCAATTTAAAGAAACTATATGGATACCTCATTTTTATATTTTCATTTTGAAA
TCATTTCATAATTATTAAAGACTATTTCCTTTTCTCAAAACTTACCATTTTGTGATTATG
TAACTGCTACCACATATTTCAGTTGATCTACTATTAAAATAAAAAGTTGCCTAATAATTA
[G,A]
TTGTAGGGTTTATAGATTGTCTCATTTCTGTACTTGTAGAATACATCTTTGTACTAATGA
TATTAGAAAAGGCAATATAATGCTTCCTGAGTATGTAGAAACTCTTTAATTAATGTTATT
TGGAGAAATGCAGCAAAATATTAATACATTCAGAATGAGGCTTTAAAATTCACTGTAATA
CCCATTAGCTATTGAAACATTGAAGTTAAGTGTTTTTGAAAACACCTTTGTGAACAATAA
TGTTTTTGAGGCAAGTTGAGTGATGGGAGGCCAATATTGTTTATGATTTTATGACACCCT

130083 TGTTCTTTACTTGGCTCCCAAAACATCACCTTCTGTTAGTTTTGTCATTATAAAATAGAG
TTAATTTATCTAGTCAGTAGTATTTTCCCAGAAGACCACATAATAATGCTTGCTTTCTGA
GACCTGTGAAAGCTATGAATTGTTTTCCTAGGTGATTGGGAAGTAGGTATTGAGGGAAAC
TCTTAAATCCCTTTATTAATGTATCCTATTTACCTGTAAAGACAGTTCCTTCATCAGTTG
ACAGATGCTTCTCTTTTATCTTTGAACTTTAGTCTTACTGCGTCCATCCATTTGCCTGGG
[G,A]
AAATTGTTAAAATATTAAGCAATAAACTTTCTTATATTGAGCATTTTTCAAAACCTTTTT
TATGTTTTAAACCTGTATCATTCTATCTAAATGTCTCATGGTAAGTGAGATCAGTTTATA
AGTCACTTTTGTTTTTCATGTTTACACTAATTCTATTTTGGAATGGTGGTCAAGTAAAAA
TCATAATTTCACCACTTAAGATTTTTCCTATTATCCTTTGAAGTGCTTTTGAACACATTG
GTGTGCTCTAAGATCACCATAGGTAGGATTTTAGGTAGAACTTTCTGATTTTTTAAGAAA

131381 GAAATTAAAACAAAACAAAACACATGAACAAAAAACTCTCCACAGGAGAAGAGGAAGATT
CCTGCTGTACCAAATGGAACAGCAGCTCATGGGGAAGCAGAGCCCCACGGAGGACATAGT
GGACCTGAACTCCAGCGAACTGGAAGGTTAGTGAAAATCACTTCTATGGGACTTCAAGGA
CCAAATGACATACCATTCTTCTCTGTCAGAAATTGCTATTTTGGGATCTAATTTATTGTA
TACTTTTAATACCTGCTTTTTGAGGGTGAAAATGCCAATTAGTTTGATTTCTCTGAAGTT
[G,A]

FIGURE 3YYYY

CTAATGATTGTCATTACTGTTAAACTAAAACAGTGGATACACCCTTCCATTATACTTTAC
CTAGTCTTTCATTTTGCTGTGCATAAAATGCATTCTCAGATTCTTAGAATGAAAAGGAAA
ACCGTCAATTGACCCTTCCAAAAGAACCCATTGAAAGCTTCAAGTTGAAGATAGAAATAA
AACTAAATACCAACAACTCAGTCTTGTAGGCCCTATCTCATTAAATGCAAGTAGGATGTA
TATAGTGGTATTTTTTATTTTTATGGCTGTGATTTGAAAGAGCTATATGATTTATTTTTC

132580 TTCCACAGATTCTGTTGCTGACATGACTTGAAGTATCCATTACTCATCTGCTCTCCTGGA
GTTGCTGGTGTACATCTGGGCTGCTCTTGCACTGTTCTCTGTAATGAACTCCCACTTCCG
GATTTAGATTTTTACTGCTAAAAGCACATTTATTACACAGTACTATAACAACTATTCAGA
CTAATGTATGCTCTAATAAGTAATTGATTAGAATCAATGGTCTAATATAAAGTGCTTTCA
AAACTATAAATATTAATTACTAATTAATAGCTCATAACCACCTCAAATTCTTTTTGGGAT
[C,T]
AGGTGGGATATAAATCATAAATGAATGCCTAAATAGACTGGTAGAGTAAATCTGTTTTGA
ATTGTGACTTTGATAAGTTAACAAATTATTCAGAAATGATCCCTAAAATAAAAAAAAGTG
CATATGTTTTACCAAACATGGGTAGAGAAGCCTAAGGTGATCTTTATGTGTACAAATATT
TCACAGGTTCTCTGCAAGCTTCTCTGAGTTTCAAATGTCCTTTTATTCAATTGAAGTTTC
ATTCTTCTCAACCCTCTCCTACTCCATAGCTCTCTAATGGAAGCAATCACAGGAAAATAT

133900 CCGAGAGAGTAGGTAACTGGAGCCATGGTTAAACATTGCTTTTTCTCTCTAGGGTGATGC
TCACTACTGGAGTATACAAAAGCCAGCTAACCCTCCCTCCCTCACTTCCTGCTATGCTAA
ATGGAATTAAACATTTAGAAATACTGCCAATGATTGAGGGTTGTAGGCCTGAGTTTAGGA
GGAGTAGGTTGA
[T,C]
GTAGAAATGGCACAGAGATTAGAGTAATCCTTGAATCTCATTATTTGGATTATGATTGGT
AAACAGCTCTGAACCTTGTTTAAGAGAACCTGGGATTTTTTGGTGGTTGACACGATATTGG
GTTAGGAATTGAGGTAACGAACGTAGTTGTGCAGTGCCTCCCTGTAGATTGTTATAAGAC
AATGCAGCAGGT

143073 TATAAACAAGATCGCTTAGAGCACTTGCTTTTCTGTGGGCAGTAAAGGGTACTAAAAGAT
GTATTTTATAAAAAGTGTATTTTAAGCCAAATAATTCAGCACCACAAGTGAAAATTATTG
GCATTTTATACTGGTGTTTTTAAACATGTAGAGAAGTGCAGATACAACCCTTTTTCTGCT
TTATGATTGTTGGACTTTTCAGTCTATGAGCTTGTGATAGTAACAATAATAAATAACCAA
AATGAGATACCTAACAATCTCTATTTACTTATGTCAGGGCCCATTCTAGGACTTTTATGT
[A,G]
TATTAATTCATTTAATTTTATAATAACCCCTAGAAAGGACATGAACTCAGAAGCTGGAAA
CCATCATTCTCAGCAAACTATCGCGAGGACAAAAAACCAAACACTGCATGTTCTCACTCA
CAGGTGGGAATTGAACAATGAGAACACATGGACACAGGAAGGGGAACATCACACACCGGG
GCCTGTTGTGGGGTGGGGGGAGTGGGGAAGGATAGCATTAGGAGATATACCTAATGTTAA
ATGATGAGTTAATGGGTGCAGCACACCAACATGGCACATGTATACATATGTAACAAACCT

143157 AGCCAAATAATTCAGCACCACAAGTGAAAATTATTGGCATTTTATACTGGTGTTTTTAAA
CATGTAGAGAAGTGCAGATACAACCCTTTTTCTGCTTTATGATTGTTGGACTTTTCAGTC
TATGAGCTTGTGATAGTAACAATAATAAATAACCAAAATGAGATACCTAACAATCTCTAT
TTACTTATGTCAGGGCCCATTCTAGGACTTTTATGTATATTAATTCATTTAATTTTATAA
TAACCCCTAGAAAGGACATGAACTCAGAAGCTGGAAACCATCATTCTCAGCAAACTATCG
[T,C]
GAGGACAAAAAACCAAACACTGCATGTTCTCACTCACAGGTGGGAATTGAACAATGAGAA
CACATGGACACAGGAAGGGGAACATCACACACCGGGGCCTGTTGTGGGGTGGGGGGAGTG
GGGAAGGATAGCATTAGGAGATATACCTAATGTTAAATGATGAGTTAATGGGTGCAGCAC
ACCAACATGGCACATGTATACATATGTAACAAACCTGCACATTGTGCACATGTACCCTAA
AACTTAAAGTATAATAATAAAAAAA

148401 AAGTATAATAATAACAGAATAAAAAAAGTATAATATATAATAAAAATATCTTGAAAATTA
AAAAAAAAAACAAACTTCTCAATGGCTGTCCCTCTCATTCAAGAGCAAAAATAAAATCAT

FIGURE 3ZZZZ

AACAATCCTTGAAAGCAAAAAAAAAAAAAAAAAAAGTAGGAGTTTCAGGTTGGGACAGAC
CTGGATTCAAGTTTATTTCTATCAGTGTAGCCTTGGATAAGTTATCAAACATTTAGTTCC
TCCCATCTATAAAATGTAGCAATTAAACTATTAAACTAGAAAATCCACTATATGCCATGC
[T,C,G]
TATAGCAACTGTATGCACGCCATACCTATAGGCATAGATATACAGTAGCTACAGAAAACA
TATATGTATGTATATACACATATACATTTGTACATGGAGGTATTCACATATCTACGATAG
TGCTATCTTTCTCCCTCGTTATGTTACTTCTGCAAGAAACTTGCCATATTTTCTCTATTT
TATATTTTTGTTTCTTATGTATGGATTTACTTTTAACAAATTTTCAAAATATGCAAATAA
CTTTCTGTTAAACTATAGTACTGGCCCTTTTATTTCTGAGGTAAACTAACTGACCATCTT

153365 GAACTCCTGGGCTCAAGCAATACTTCTGCCTCAGCCTCCCGAGTAACTAGGACAACATGC
ACATGCCACCACATCTGCCTAATTTAAAAAATTTGTTATAGAGACAACATTCTTGCTATG
TTGCCCAGATTGTTCTCAAAGGTCTGGCTTCAAGCAATCCTCCTGCCTTGGCCTCCCAAA
ATGCAGGGATTACAGGCATGAGCCCCCACACTCAGCCTCAATGCCATGTTTGACTTATCC
TTTCGTCCATTGATGGGCACTTAGGTTGATTCCATATCTTGGCTACTGTGAATAAATGCT
[G,A]
CAGTGAACATGGGAATGCAGATATCTCTTCCATTTACTGATTTAATTACCTTTGGGTACA
TATCCAGTAGTGGAATTGATGGATCATATGGTAGGTCTATTAATTTTTTTGAAGAAACTCC
GTACTGTTTTCCATATGGCTGTACTAATTTATATTCCCATCAACAATGTGAAAAGTTTCC
CTTTCTCCACCTCCTCGCCAACACTTGTTCAGACACTTTCATCTTTAAAAAAAAATTAAT
TTTTAATTTTGTGCACACAGTAAGTGTGTATATGTATGGGGTGCATGAGATATTTTGATA

156875 CTCTTACTGTTGCAATCTACAAAAGTATTTGTTTTTGGCAAGTTGTGTTTCCATTTTCAT
TTGTCTCAATACATTGTTAAATTTATCTTTTAACTTCCTCATTGTCCCACTGGTTGTTGA
GGAGTATGTTGTTTAATTTCCACATATTTCTGCATTTTCCAAAATTCTTCCTGTTATTGA
TTTCTAGTCGCATACCATTGTGTTAAAAAAAAGATACTCAATATGGTTTAAAGTATCATT
TCAGTTAATGATCTGGACCTTAAATGATGGCAGCATAATCAATGTTAATCACAAACCAAA
[T,C,G]
GCTATTTAGTGTTATTATTTTAATATGCAATATACTTACCAGGCCCCCCAGCACTCAGTC
TGCACAGTCTAGACCCTGCCTATCTCAGATCCATACCCCATCTCTTCCTCCACCCCTTCT
GTTTCAACCAAATTAACACTGTTTATTCTCTGTAGTTCCCCACCCTCACTGCCGTGCCCA
CACTATGTCTTACCAAATTCTGTCCCTCTTTTAGATCTCAGTTTTCCTTGAACACCCAGA
CTCAAGGTGTGGATGCCTATTTGTTTATCTTTTTAGTAGCCCAGACTTTTTTATAGTACA

159594 TAAAGATTGATTCTAAAAAATTTAAAAATATAGAAATCTATAAAATTCTGTAAATTTTAG
ATTTTCTATAATTATAGAATGTAAAAATATAGATTTTCTATAAACATAGAATGTAAAATT
CTATAAAAATATAGAAATCTTTATGTAATTATAACTGTGTAAGTATTATTTACTGTAGAA
CCAAGTAATGTGCAATGCTTCCTTCTCCATGGCTCCAGTGTCATGACATCTATAGTACTT
TACAAATAATGTTATGAGTATATACTTCCAGAATGGTGGTAAAAGAAGCTCTGCAGACCC
[A,T]
CTCCCCAGTGAAACAACCATACTGGTAAAAGTAATTTTAAAAGGCAATCATGAAAAGTCT
CTGGAAATTTTCTTAAGGGTATACAGCAAATGAAGAAACATTTATTCCAAAAAGTGTACT
AAATCTTGGTAAGAACAATGAGTCCAAGGCACCTAAGTCACAACCCACTTCCCTTCCTCT
CCTCCCAGCTCAGCATGACAGAAGCTTAACTCTGGACAAGAACACAGGGCTTCCTCAGCT
TCCAGTTGAGGCCAACTGTATGTTCCCAAGAGGAGAAGACCAACAGCGTTTCTTGTCTCC

160577 CAAGCACTGACCACAGCAGGCAGGGCACTGTGGCTTACACCTGTAATCCCAGCCCTTTGG
GAGGCTGAGGTGGGAGGATTACTTGAGCGCAGGAGTTTGAGATTAGCCTGGGCAACATAA
CAAGACTCTGTCTATATTTTAAAAACAAAAAACAAAAGGCTACCACAGCAAAAAGGCTGG
AATTTA
[G,A]
TTGGAGCAGACCCCCAGAGCAATTTATGTCCCAGGACATTGTAAAAAATAACAGAACAAT
CTAGAACAGAATAGCTGGGTATATGTGATAAGCCTTAGAGCAACCACTAAGAAAATAACT
CGAAAAATACATAGTGAAGGAAAGAAAACAACAATGTTCCTAACATCACAATCAAATGAA

FIGURE 3AAAAA

TTCTCC

161658 CTACTGGTGGTTAACAAGGTAGGGGGTGTTACAGGGTGTGGCTGACCTACTGTTCCATCA
TAGACAGGAGCTCAGTTTTTAAGGTTTCTCTGGGGTCTCCAAGTGAGCCTCCCTGGAGAA
TCCTCCAATTTCCCTAGTGAGAGCAAGAACCATATCTGTCTATACTGCCCAACTCAGTTG
TTTTTGCAATAATAGACAATAACTCTTTAAAGAATGAATAAGTGGTGGTGAAATGAAACA
GAGTAAGTTCCTGATGTAGAAGGCAGAAGGGAGACTGTTGCTTAGGCAGACCAAGTAGAA
[G,A]
CTATACGATATTTTCTATAGTAATAACCTTAGAAATGGCAATTCGGTTCTATAGTTCAAT
TAATATCACTAAAAGAGCTGTCCAATGAACTTACAAGTTATGTGGTATATGTGGGTTAAT
CTGGGAGACCAACCACCATTTATGAAATTCTTCTCTATGAAAATGCTTTATGAAGGGCAA
ATAGCAAGTTTACAAATGAATTTTTGGAAAACAAACTGTAAATTGAGGTTAACTTCTAAG
GCTGTTAATTTGTGGGTATCTTTGTCTATATCTTCTTCTCACTGATATATCCTCAGGTAG

165461 CTTTAATTTCTTATTCTAACTTAATTTTTGCCAACTTATAGAATTGCTGAAACTTAGAAT
GTGTTTGAAGAGTAATTAGTAGAAATCAGTTTGTCAACAAGCATTTTTTGAGTACCCATT
GTAACTGAAACCATATGTTAGACTCAAAAAACGAGAGCAGGATTTGGATTTGGTTTTCAT
TTCTAAATTTCAGGACTTACTCTGTGTGTATGTGTGCATGTATGTATGTGTGCATGTGTG
AGTGCCTCTGTGTGTGTATTGGGGATACAATTAGTATAAATCTGAAAATAATTG
[A,T]
TGAATTTAGCAGGTCACAATTTTTCTCTTTTAAAATTAGCATTTTGTTTCCTCCCAAAGA
GAAAATAAATAACATTTTCAAATATGCTTTGAATTAATGTAATTAGGCAGACCATTGGCA
AATTATAGAGTGTAAGACAGCTAAGGAACCCTTTAAATGTCATCTATGTTCTTAAGAATT
GAGAACAAGATCCCGCCAAATGACTTTTATACCTGCAGAAATGACAAAAGATGCTCACAA
ATTTATAGATAATGTGTTTATCATGGAACTTTTAGCTCCTTTTTCTATGTAGCAATTTTG

166267 CATGAATAATTGGAATTTAACTTTGCCTATCAAGGAAGATGTTTGCAGTTAAATTAGAAA
AGGAGACAGATTCTTTAAGACAATAATAAGGTGTATTAACTATATTTCTCAAGACTCTCA
GGCTTAGGGTAGCTAGCAACTCCAAGTAGATTTTACTAGTTGTTTGTTTTCAGATGACAG
TGTAGCTATTTGTAATTTATTCTACAATCTTTGGAGTGTATTTACTTTTTGCTCTACAAA
GATTTCAGGCCTAAAGTTGGGCAGACTCTGTGTTTGTGATCAATCTATCAGTTCATATTT
[G,T]
TCTCCAAGATCTCTCTGCAATTCAATTTATGTTCAGGGCAAGAATATCTCAAGGACTAAT
GAGATCACTGGATCATTTAAACCATTATTTCCTGTTTTGAAATGTAAAAATACTTTAGTA
ATCTAATTTTTAAATAAGATAAACCAAAGTAAGTTTAAAATAACTTTTTTTCATTCAAAA
TATTTGTTTGAAATGCTCAGTTTTTCCTGGAGGAAAAAAATTTTTTTGACTTTGCTGCCA
CCTCATGGCTAAGGCAGTAATTAGAAATAGTTCTTCAGGCTCTTACAGAACTACAGTTGC

169684 AGGCTTGGAAAACAGATAAAAATAGATTGGGAATAGAATTCTGACCGTGTTACTAATGGG
GTACAGTTTGAATATTCCTTATCCAAAGTGCTTGGGATCGGAAGTGTTTCAGAGTTCATT
TTTTTTTCAAATTTTGAAATATTTGCAAACACATAATGAGATATGTTTGGGGTGGGGCCC
AAGTCTAAATACAAAATTTATGTTTCATATATACCTTATACATATAACCTGAAGGTAATT
TTATACACTATTCTTAATAATATATGTGACCTATCACATGATGTGAGGTGTGAATTTTCC
[A,G]
CTTGTGGCATCATGTGAGCGCTCAAAAGTTTCAGATTTTGGATCATTTCAGATTTCAGCT
TTTCAAATTAGGGGCACCCCTTTGTTTTCTCTGTCAAACAGGGCTGGGGACTTCTATATA
GGGCTCTTGTCAGGATGAAATTTTGAGAATCATCTCAGACAGCAGCCATGTTTGGAATCC
TTCCCTGAGCCTCTGCTGTGACCAAGTATCTTTTTTATCATTTTCACTCAATAGCCTCTG
CACATCAAAAATAACAGTTACAATACCATAATGATGTATTTTGTTTAGATGTCTGTCTCT

171916 AAATGTAAGAAAGCACACTTATTTGCAATAAATCTTATGAAGAAGGAATTTTGAGTATAT
GGTGGAGAGAATGTGTGTCTATCTTAAAGCAAAGGACATTTTTCATTCTCTTTGTAGAAC
GTAAGTTAAGAATTCTCACAACTTTATGTATTTTATTAAATGATACATTTTAAAAAATCA
ACTAAAAAAACCTGTTTTAGGAAGAAAGTAAGCCATATAATTATTATTTACCTTTCAAAAA

FIGURE 3BBBBB

GATTTTTTTAGCCTTTATAATTAGGCAGAAATTCTAGTGTGTTCACTGAAAAATTATCCT
[T,C]
TGTAAGGGCCATCAGTTAAATGGATTCAGGCAGCATTTTTTTCTTATTGTAAGTGGAATC
ATATTAAAACAAAGTGTGGAAGTGAAATGTGTGCTGAGATTGATATTACCTTCCTGGCCA
TTCTGAATCTTTGCCCTTTCAACCTTATAAATCACATGACACTTGCTCTTACTCCTTGTT
CTTCATGAGCCCTTGACATTCACAGCCTTTGTAAAGCTCCACATTGACAAATACACTAAT
TTCCCCCTTCACATATACTGTGGAATAACAAAAATGTAGTAAAGCATTCTTTAAGTGGTC

173389 TCCTGCTGATAAAAATGTTTTTATTGGCCAGGCACAGTGGCTCACGCCTGTAATCCCAGC
ACTTTGGGAGGCCGAGACAGGTGGATCACGAGGTCAGGAGTTAGAGACCAGCCTGGCCAA
CATGGTGAAACCCCATCTCTACTAAAAACACAAAGATTAGCTGGGCGTAGTGGCGGGCAC
CTGTAATCCCAGCTACTCAGGAGGCTGAGGCAGGAGAATCGTCTGAACCTGGAAGGCAGA
GGTTGCAGTGAGATGAGATCATGCCATTGCACCCTGGCCTGGGCGACAGGGTGAGACTCC
[G,A]
TCTCAAAAAAAAAAAATGTTTTTATCATTTCATGAGTGTCACTATGTACACAATAAAGCT
GTGTTGCACTGCATAGGTGACTTACTACTCCCGAAGAATGGGGGAGCTCAAAATCAGTAA
ACCTCGAACTCATTGCATCCTATGATCCTTTGGATGGCTCCAGAGTGAAAGAAGAGGCAA
ATACAAAAATTTGAGAATGTGAAGTATCATGTATATTATACATAAATGTACATATAAATC
CATACTCTCTCTAGCATTTGTTTGTTTGTTTCTCCCTTAGAGAAGTGGATTAGGCATAAG

173435 CCTGTAATCCCAGCACTTTGGGAGGCCGAGACAGGTGGATCACGAGGTCAGGAGTTAGAG
ACCAGCCTGGCCAACATGGTGAAACCCCATCTCTACTAAAAACACAAAGATTAGCTGGGC
GTAGTGGCGGGCACCTGTAATCCCAGCTACTCAGGAGGCTGAGGCAGGAGAATCGTCTGA
ACCTGGAAGGCAGAGGTTGCAGTGAGATGAGATCATGCCATTGCACCCTGGCCTGGGCGA
CAGGGTGAGACTCCGTCTCAAAAAAAAAAAATGTTTTTATCATTTCATGAGTGTCACTAT
[G,T]
TACACAATAAAGCTGTGTTGCACTGCATAGGTGACTTACTACTCCCGAAGAATGGGGGAG
CTCAAAATCAGTAAACCTCGAACTCATTGCATCCTATGATCCTTTGGATGGCTCCAGAGT
GAAAGAAGAGGCAAATACAAAAATTTGAGAATGTGAAGTATCATGTATATTATACATAAA
TGTACATATAAATCCATACTCTCTCTAGCATTTGTTTGTTTGTTTCTCCCTTAGAGAAGT
GGATTAGGCATAAGTTAACTGAATCCTTTTGAAAAGCATTAAAAATATCTACTTGGGTTT

174462 ATCACCTGTTGCTATGCTCCCTTTTCCTCCCATATGTCCATTTCCTGTGATTCATGGATG
AATGTGAGAATAAAAGCTCTAGCTCTGTCTTTATTTGAGAAAAAAATCTACAGAAATATG
TTAGAAGGTGTAGAGTTCTCTGTCTGACAAAGGGATACTTCTCTTTGGCTGGCATGCCTA
TCAGCTAATAATTTTGTTACAAAGTCCAAGTTTTTAAAGACATTTTAAATGAAAGGCAAG
AAGGATACTGGTTAGTTAGGGGAAGAGCAAGAACTGCTTTATTTATTTCCTTTGGTTTAC
[G,A]
TTAAATCAAGATGCTGCCATTGTTGTACAGCATAATTAGGGGAAATTATATTTTTGTTTT
TGTTATATATTTATATATTACAAAACTAGCTTTATAAATTTAGAAAAGAAATTATTTCCT
CTGAAAGAATTATTTTGCCTACTTCCTGCAATTCAGAATCCCACTGTTTACATTTGTATC
ATATTTTTAAAACATTCAATAAGAGCTATTGGAAATCACTATCGCGACAAAGATCTCCCT
CATATTATTGAGATGTAGTGAATGTGGACTCTGAGAAAGTCCAGGTGTGCTAAAAAGTAC

176313 TGCCTTCTACTATCATCATCATCGTTTTTCAGATAGGGAAAAAGAGGCACAAGAGCTTAA
GTGATTTATTGGTTGAGCTAGCATTTCATTCCAGGCAGTCTGACTCCAGAACTTATATTC
TTAACCACTTTATTATACTGCCTCTCATAAAGCAGTCACTAAAAATTAAAAATAAAAGGT
GGAACATAAAATAGGCCATCCCTTTGGCTGCTTCTGAGGCTCTACACTTCGATTCCTGCA
GGGTATGGAGGGAGTGCTCTTCCCCATCTTTGATTTCCCTCCTCAGAGAGCACCCTGTCT
[-,T,G]
CAAGAGGGCAGTTTTCACACACCCCATTGCACCTATTTTTCCTCCTTTACATTTCCTACC
TGGTCCTAGGAGGCACTTAGTTTGCAACACCTGGAGATCAGTGACAGTGGAGTAGCATAA
CAGAGGAAATAGAAAACAAAAAACCGTGATTTCTAAGGAGGGGCTTAATTTGTCTAGTGC
TGAAACTGAAGCAAATTAGAACAAGATAGCACTATATTAAGGAGAAAATGACTATACAGG

FIGURE 3CCCCC

GGAGCTTAGGCTCCATGATATTATTTTTTCTAATAGAAGTCACCCAATGAGACAAACGAG

177082 TGGGTACCATCTGGACCTATTAATGGTGGCTGTCATGCTCGGTGTATGCTCCATCATGGG
CCTGCCATGGTTTGTGGCTGCCACAGTCCTCTCCATCACTCATGTCAATAGCCTAAAACT
GGAATCAGAATGCTCAGCTCCAGGAGAACAACCCAAATTTCTCGGCATTCGGGAGCAAAG
GGTTACTGGGCTTATGATTTTTATTCTTATGGGTTCATCAGTCTTTATGACCAGTATTCT
GAAGGTAACAAAATCTGTCTTTATGAACTTGAGAGAAAGAATACATTTATCATCATTTAA
[G,A]
ATTTTCATTTGAATCTGAGCCATAAATTTGCAAATATTGTGTGGCATGTGATGAAAGTGA
TGAATTTCTGAACCATGTTTATATAATTCTTCATAACCTAAGGGAGGGAAATTACGTCCT
ATATTTTAAAACCCTTAAATACATAAAAATTTAGTCTGGCAAAGTAAAATTTGATGAGTA
AATTATTGTAACAATTTTGAATCGGTGATCAAGCTATGGGAAAAAGTCACTCATTGTTTC
TGACTGACTTGTGACCCGAATCCATTACAGGCATTCATAAAGATTCTATTTTCTTGTCAG

177358 AAGAATACATTTATCATCATTTAAGATTTTCATTTGAATCTGAGCCATAAATTTGCAAAT
ATTGTGTGGCATGTGATGAAAGTGATGAATTTCTGAACCATGTTTATATAATTCTTCATA
ACCTAAGGGAGGGAAATTACGTCCTATATTTTAAAACCCTTAAATACATAAAAATTTAGT
CTGGCAAAGTAAAATTTGATGAGTAAATTATTGTAACAATTTTGAATCGGTGATCAAGCT
ATGGGAAAAAGTCACTCATTGTTTCTGACTGACTTGTGACCCGAATCCATTACAGGCATT
[C,A]
ATAAAGATTCTATTTTCTTGTCAGTGGATAAATATATTAGCAGTTAATATTACTTACTAT
TAATAAGAGATAGAGGTGAAGGGATGAGCCTGGTTATAGTCACATACGCAGTTTTCCATT
TTAAGTGCTCTGTAAAACCACTGTCTGGACATCATCATTGCATATAGTGATTTTTTTTTC
ACACAAAACTTGAAATCTATTTTTAAGAGGATTAACTAGTAATTATTTTGTCATGTAATT
TTGTCAGATATTTCCAAGGTGTGTCAATTGCGCTATAAATTACAACACATTTTATTTGCC

178098 TTCCAATAAAAAGAGAAAATCTGAATTATCCATATATTTACAAATACCTGGTATAATACA
GGAAACACATCTAAATGTTAGCTTCATTTTTAATCCACCTTTAATCCAAATATCTTATCT
TTGTAAAGCAAAATTCAAGTTGTCTCCAAAGTAGCATAATAATAATATTATTGTTCATTA
TATACTACATGGTTTTTAAAAATAGATTTTGACCTATTAAATAATTATAACAACCCTATT
GTTATCATCTCCTTTTAGATATTGGGAAACTAAGGCACAGAGAGCTTAAGTAACTTACCT
[A,G]
AGGTTACACAGCTAAAAATGCTAGAGCTGGAACTTGAATCCTTGTCTTCTGAATCTGTAC
TATACTGTTTCTATTCAAAAATGCCTTTTTTCCCTGTTTTTTTCTTTGATAAATGCAAAA
CCACAATCTATTTGAAAATGATTTCTGCCTTTTCTCCAATTGTTCTTTTACAGTTTATTC
CCATGCCAGTGCTATATGGAGTGTTTCTTTATATGGGTGCTTCATCTCTAAAGGGAATTC
AGGTAAATTACTTACAGTACTACAGGCACATCTGTGATGACTGACCTTAAGGTCTACTGA

178537 TGATTTCTGCCTTTTCTCCAATTGTTCTTTTACAGTTTATTCCCATGCCAGTGCTATATG
GAGTGTTTCTTTATATGGGTGCTTCATCTCTAAAGGGAATTCAGGTAAATTACTTACAGT
ACTACAGGCACATCTGTGATGACTGACCTTAAGGTCTACTGATAAGTCATGTGACAGCTG
AGAAAATGCCACCACCTGAGGAACAGCTTTTAGACCACAATTAAATTTCTTCAAACTTGT
CAGAGTTACAAAAGTTAAAGAAGATTCTCTCCAGCATCTAAGGTTCATAATCTTATGGTA
[A,C]
TTTTCTTTATCATAAGTATATTAAAACTGTAAGAGGCTTAGATTTTACAGCATTTTTAGA
AAAATCATAGTAGTATATTTCAATATATATCCAAATATTTATAATATTTGACACTTTAAT
CATGTGTATGGACATCTATTGGTAAGAATAGGAAAAGTCTTTATGCACGAAGATGTTCAT
TGTAACACATACTATTAAAATATTGGAAACAACCCAATTCTCTAACTGCAGTCAAATAAT
TAGGTAACCTATGGTATATTCACTGAAAATTGATAATTATAGGAACCACAAAAGTAACAT

181240 ATAGTTAACCTGCAGGACAGGCAGCACGGGATCTCTGTTCCTGAGCAAATGACTAACCAG
CTTCTGACTTTGGGAGAAAAAGCAGAACTTAGGCCTTAAGACAATACTGGCTGCCAGTCT
GGGGGAAACTTAAGTATGAAGTCATTGCAGGTCACGGAACACCCAAAGTTGATAGTATGA
CTGACTCTTCATCCTGACACTGGGAAAAATGAACTGGGAGAGGGAGATGGTTGAGCCATG

FIGURE 3DDDDD

TTATATGTTTTAATTTTACTCAAATTAGATTTAATTTGCTCATTTAAAATTTCATGTATG
[-,A]
AAAGTGTAGTTTGATAGAATTTGTTTAGTAAGCCATTAGGGAAGAATATGGAAGAGGTTT
TGTTTATTTGTTTTTCTTTTTCCCTTTTTTTTTTTTTTGCCTTTGGCAAAAGTTCCATGA
GTACTAATTTCATCTGTAAGTGAAAAGCATTTATTATTAGGCCCCAGGCTCACATAAATA
CAGCAGCAGAGTTTAAGAAACAATGTAAAATCATTTTGATGATAGGTTTCAACAGATTTT
CTCCTCTAATTCCACATGATTTTATACTCATGAGATTTAGAATTGAACAAGAACGTCAAG

181325 AACTTAGGCCTTAAGACAATACTGGCTGCCAGTCTGGGGGAAACTTAAGTATGAAGTCAT
TGCAGGTCACGGAACACCCAAAGTTGATAGTATGACTGACTCTTCATCCTGACACTGGGA
AAAATGAACTGGGAGAGGGAGATGGTTGAGCCATGTTATATGTTTTAATTTTACTCAAAT
TAGATTTAATTTGCTCATTTAAAATTTCATGTATGAAAAGTGTAGTTTGATAGAATTTGT
TTAGTAAGCCATTAGGGAAGAATATGGAAGAGGTTTTGTTTATTTGTTTTTCTTTTTCCC
[-,T]
TTTTTTTTTTTTTTGCCTTTGGCAAAAGTTCCATGAGTACTAATTTCATCTGTAAGTGAAA
AGCATTTATTATTAGGCCCCAGGCTCACATAAATACAGCAGCAGAGTTTAAGAAACAATG
TAAAATCATTTTGATGATAGGTTTCAACAGATTTTCTCCTCTAATTCCACATGATTTTAT
ACTCATGAGATTTAGAATTGAACAAGAACGTCAAGTTTTGGAATTATTTGGGGTGTGAAT
CTTTTAAATGAAAATTGAAGAAAACGTTATCAAAAGCCCATGAGTTAAATATAATGAGTT

181730 AGTTTAAGAAACAATGTAAAATCATTTTGATGATAGGTTTCAACAGATTTTCTCCTCTAA
TTCCACATGATTTTATACTCATGAGATTTAGAATTGAACAAGAACGTCAAGTTTTGGAAT
TATTTGGGGTGTGAATCTTTTAAATGAAAATTGAAGAAAACGTTATCAAAAGCCCATGAG
TTAAATATAATGAGTTTTAAAGAACACAAATGAAACATCAATCTGGGGCACATGTTGATG
AACAGGGTCTCACACTGAGAAACAGTGTTCGTGAAAATTTAAGTGAGCCCCAAGAGCAGG
[C,G]
AGCTGAAATTCCTATTTGGAATTGTAGCTAACTGGGTGGGGAAATGTGATATTGATACTA
GGATATAATAAAAACCAAATGTAAAACTCAGAATACATTTATCATGATGATGATTATTAT
TTAAACATATGCTAAATATAATCAGTTCCAGCAGCATGTTACTGTCTTACCCTATTGAAG
GAATCTATGTTACCTGCTTGTTTGGCAATATTAAGAAACTTATTATCTGGGCTTCTCACT
GTGAAACATGGCAGAAAAAACAGATCACAGTGTTCTCATGAATGCTGTTTCTGCATTCAG

185615 GAGAACAAAAAGAAGAGACATTATTACTGTTGGTATTTTCCTAGGGAACAGAGTTTTAAT
CAAAATATTCTAATGAATAATTATTTATTCTTGAAATAGGTGAAATGTTTAGTAGGAAAA
ATGTTGATCTGATTTGCTTTCAAAGTGATTTAAGATTGAGTAGATGTTGCAGAAACTTCT
GGAATTTATTTTTACAGGCTACTTATTTATTTTATTCTATTTTATATGGTATAACAATGT
ATTATAAGTTTCGTGGCATATTTAAAGTTTATATGTAAGCCTGAGTCTATTTTGAAAGCA
[C,T]
TTAATCAACATTTTTTTAAGTATATAAAAACTACAAAGAGTGTAAATGAGGGAAAAATAA
CTAGCGTAACATTTAGCAGGATGATTGAGCCCATACAATGTAAAACACAACAAAGTTTTC
ACATAAATAGAAATGAGATTGAAATAAAATATTTGATGAGAATTATACTATTTTTCTCTA
TAAGTAGTCAGTAAATGTATTCAACTTTCTATTTCCTCAAACCATAGATATATTTCCTAT
TTCCTTTGGGGAATTCATTTGCAGATGTTTCAGAGGTCTTAGTCATTTAATGAGGTCAGA

185975 ACTAGCGTAACATTTAGCAGGATGATTGAGCCCATACAATGTAAAACACAACAAAGTTTT
CACATAAATAGAAATGAGATTGAAATAAAATATTTGATGAGAATTATACTATTTTTCTCT
ATAAGTAGTCAGTAAATGTATTCAACTTTCTATTTCCTCAAACCATAGATATATTTCCTA
TTTCCTTTGGGGAATTCATTTGCAGATGTTTCAGAGGTCTTAGTCATTTAATGAGGTCAG
ATCAGGCCATAAATCAAATGAGGTTTTTTCTTTCTCAGAAATTTATACCAATATGGTTAC
[A,G]
TAATGTGTAATTGGTAATTCCCTTACTCTACATGGTGTTCTATCACTAACAATGGATTCC
CACAGATAGAGATTCATCATGATGATGTGTCTTAATCCTGTAAGAATGTTTCAATTTTTC
CAAATATTGTAGAAGGCAATACTTAGACTCATACTTCTAGTAATATTAATGTTAACACAA
AAAATGATATTATACAATTGTTATTATTTATTTTTCTGTTTGATATATTTTTATTTAAAT

FIGURE 3EEEEE

ATTAGTGCTTTTTTAAAAAATAATACTTTGAGTCAGGCGCAGTGGCTCATGCCTGTAATG

188447 TATACCCACTGTACTTTAATGGGCATTTACTGTTCTCTGATTATGAAGATAAAGATTTTA
AAAGTAACTAAATAGCACTAAATTTCCTAGAACTCATGCTTTCTGAAAAGATACAAAAAT
GGATTAAAGATTTCCTGGGGCAATTTTACTGCTAAATCCTTCATATCCAAGTTAGAGGGA
AAAGCCTTGCAGTACATTAACTAGGCAGGTTTATAGATCCTTAAAATCTCAGATGGGTTA
ATATGATGATACTTTCATGTGATCCTCAGTACATGGAAAGAAACAAGAAAATCAATAATA
[T,C]
AGTCAAGAAATAATCTATAATTGAACAATAAAATATAGCTCTGACTAGTGCAAAGACAGC
TAATTCTCCATCGAACAGGAAAGAAAATAGGAAGTTTAAAGAGGTTCGCTTTCTAGCTTA
GAATTAGTATTAAAAGAGTATGGTCACTAAAGACATTAGGAAGATTTAGGAATAATTATA
CTAAAAGTTAAATTCCTGGTTGATTTGTTTGCCCGGATCTTGGTATTCTATTTTCTTGAG
GCTTACAGACTCAGTAGAAGGATGTGATCTTACTGTGGCATCTTATACTAAGGCCCAGTC

190645 GAATTCTCCCCTCTCTCTCTCTTCTCTGTCTCCCTCTCAATATAGTTTAGTTTAAACGGT
TATCTTGTACAATTCTAAGTATCAATTAGTGCCCAATTTTATAGTCTCAAAGTCTTTATG
AATAATTTAAGGTTATGCCAATAAAAATACAGAGAATACTTTTTTATGAGAAGGGAATTT
GTCATAGTGTTAAAAACCAAAATAGGAGAGAATTTTCTAGATCTTTAGGGTCTGACTCTA
AGATTATATTCCCTAGAATTTAAGAAAATGTGATTACCTCCCTCTTAAGAGGGGGCACAA
[G,C]
TATAAGATGTTTTATCTTTTTTTTCTTTTTTACAACATTTAAATTTTAAAATCCTGTTGA
TTTTTTAGCTGAACCAGCATATTTCCAAGTGTATTAGGTAGAAACCTAGTCTTGTGTGAT
ACCACTCTCGAAAGGGCTGTGTGGTTAAATAAGTTTGAAAAAATGTGCCAAACTGCATTC
CAGTTTGGAGATTCACAATGCATATTAGCAAATGAAACAATCTAAGTAGTACTGCATTTT
AAAAAATTGTATAGCTTCGTTCAATCAAGTATTTAAAAAAATCTTTTGCTCAGAAGACTC

190708 CTTGTACAATTCTAAGTATCAATTAGTGCCCAATTTTATAGTCTCAAAGTCTTTATGAAT
AATTTAAGGTTATGCCAATAAAAATACAGAGAATACTTTTTTATGAGAAGGGAATTTGTC
ATAGTGTTAAAAACCAAAATAGGAGAGAATTTTCTAGATCTTTAGGGTCTGACTCTAAGA
TTATATTCCCTAGAATTTAAGAAAATGTGATTACCTCCCTCTTAAGAGGGGGCACAAGTA
TAAGATGTTTTATCTTTTTTTTCTTTTTTACAACATTTAAATTTTAAAATCCTGTTGATT
[T,G]
TTTAGCTGAACCAGCATATTTCCAAGTGTATTAGGTAGAAACCTAGTCTTGTGTGATACC
ACTCTCGAAAGGGCTGTGTGGTTAAATAAGTTTGAAAAAATGTGCCAAACTGCATTCCAG
TTTGGAGATTCACAATGCATATTAGCAAATGAAACAATCTAAGTAGTACTGCATTTTAAA
AAATTGTATAGCTTCGTTCAATCAAGTATTTAAAAAAATCTTTTGCTCAGAAGACTCTTC
CTCACATAATATCATGAAAAATGTCTATTCCACATGATGCTTTTTTTAAGAAAGTAGTCA

191287 GCTTTTTTTAAGAAAGTAGTCAATCTGGTGCTTTGAATTACCAGGAAACTATCTTTCTAG
GAAGACCAAAACAGCTGGAGGGTTTAGAGGAACTGAAGAACACATTTCCAGATTGGGCAA
GAGAGGGAGACCCAAGGTTTTGTTCCTCTTAAAAGTTGCATTTGTTCCTCTCCTGTGACC
TATCACCAATCAGGGTCATATGAAAAGGCGGCATTTGAACAAAGAAGGGGCAAGGTTGCT
CCATGTGAAGGGACATGATAAGCAGAGGGAAGAGCAAGGACAAGGCCCCCAGGCAGCACC
[A,T]
TGCCCATTGTGTTCCAGAACAGTCAGGAGGCTACTGAAATGGGGCTGGAAAGGAGTGAGC
AGGGATGCAGTGGCAGGAGGTGAAATCAGAGTGAGGTGGGGACAGAGCCTTTAGGCCATT
ATAAGGACTTGGCATTGACTCTGAGTGACTGGGAGCCACTGCAAGGTCTGAGCAAAGGAG
GGAAGTGATCTGGTTGCTATGATGTTAGGGGCAAGCGTTTAAGCAATGGACATGCGGAAC
CCATTCTCTGTAATTTGAAATGAATTAAGAATACCACAGGCCAACTCAGTATCTATTCAA

194488 TGGAATGAAAGTTTATCCAGCTTTCCTTACCTTTTGATGTGATCGCATTTGTGGTTTTCC
ATGTGAGAAACATCTTTTGGTTGGTAGTTAATCTCTTTTATCCTCATTACAGTAGAAACT
CTGGCAGAAAGTGTATGACTTACAGAATTCTAAAACTACTGATACTAATAAGGCTCCCAA
AGCCACTTCCTTTTTGTGGTATCTGTTAAAGGCTTTAAAGCATCATGACCAGGAACTGTG

FIGURE 3FFFFF

AAAATTTAGTACGTGGTAGAGTATCCATTGGCAAAAAGAGACCCAAAGAGCAGGTTACTA
[G,A]
GGTCTGAGTCCTGAGCTGGCACCCATGCAGCCTTTGACACCCCCCATTCTGAGTTATTTT
CCATCCTGTGCTGTAATGTGTCAGAGAAGCCTAGAAACCCTTTTTTCATGGAATTTTGAA
TAGAAATTATATTTTCTCAATTATATCATTCACTTTTTGTTGTCAAAAATATTTTATCTC
GTTTAACTGACAGTAGAATCTAAGAACTAACGGCAAATTCTGTCTTATCTGGAGGATGTC
TAATTTTGATCCTGATGTCATACATGCATGTGACAAGAGCCTCTGCAGCTTATTAAATGG

201885 TAACGTTAATGAACAAGCTTAGGTTAAAAGATTAAGGGTCATGTAATATCAATGACACTG
AAGGCCCCTGCCTTTAGTGAGCACATAGACACATTCCAAGTTTAATTGTAGCTCTTTGTA
ACTCCTTATAAAAGTAGAGGCGCTAACAAAGGACAGGGCATTCCTCCTTTTGCTTTCAGA
GGATATCCCACACTGTAACGAAACGGTTTCTGAAAAACTTACTTCTTCCACTATGCTCTG
TGGCTTTCCTTGAATTCTCTCCTTTGCAAGATCCAAGGACCCATTTTTGGGGTCTGGATC
[A,G]
GGACCCCTTTTCCAGCAACACCGGAACTACAAAGATTCTCAAACCTATGTCGGTATTGAA
ATAAAGATGAAATTTAAAAGTAAAGCTATATGGCATAACTAGAGCCTGGCATATTT

FIGURE 3GGGGG

ISOLATED NUCLEIC ACID MOLECULES ENCODING HUMAN CARBONATE TRANSPORTER PROTEINS, AND USES THEREOF

FIELD OF THE INVENTION

The present invention is in the field of transporter proteins that are related to the sodium bicarbonate cotransporter subfamily, recombinant DNA molecules, and protein production. The present invention specifically provides novel peptides and proteins that effect ligand transport and nucleic acid molecules encoding such peptide and protein molecules, all of which are useful in the development of human therapeutics and diagnostic compositions and methods.

BACKGROUND OF THE INVENTION

Transporters

Transporter proteins regulate many different functions of a cell, including cell proliferation, differentiation, and signaling processes, by regulating the flow of molecules such as ions and macromolecules, into and out of cells. Transporters are found in the plasma membranes of virtually every cell in eukaryotic organisms. Transporters mediate a variety of cellular functions including regulation of membrane potentials and absorption and secretion of molecules and ion across cell membranes. When present in intracellular membranes of the Golgi apparatus and endocytic vesicles, transporters, such as chloride channels, also regulate organelle pH. For a review, see Greger, R. (1988) Annu. Rev. Physiol. 50: 111–122.

Transporters are generally classified by structure and the type of mode of action. In addition, transporters are sometimes classified by the molecule type that is transported, for example, sugar transporters, chlorine channels, potassium channels, etc. There may be many classes of channels for transporting a single type of molecule (a detailed review of channel types can be found at Alexander, S. P. H. and J. A. Peters: Receptor and transporter nomenclature supplement. Trends Pharmacol. Sci., Elsevier, pp. 65–68 (1997).

The following general classification scheme is known in the art and is followed in the present discoveries.

Channel-type transporters. Transmembrane channel proteins of this class are ubiquitously found in the membranes of all types of organisms from bacteria to higher eukaryotes. Transport systems of this type catalyze facilitated diffusion (by an energy-independent process) by passage through a transmembrane aqueous pore or channel without evidence for a carrier-mediated mechanism. These channel proteins usually consist largely of a-helical spanners, although b-strands may also be present and may even comprise the channel. However, outer membrane porin-type channel proteins are excluded from this class and are instead included in class 9.

Carrier-type transporters. Transport systems are included in this class if they utilize a carrier-mediated process to catalyze uniport (a single species is transported by facilitated diffusion), antiport (two or more species are transported in opposite directions in a tightly coupled process, not coupled to a direct form of energy other than chemiosmotic energy) and/or symport (two or more species are transported together in the same direction in a tightly coupled process, not coupled to a direct form of energy other than chemiosmotic energy).

Pyrophosphate bond hydrolysis-driven active transporters. Transport systems are included in this class if they hydrolyze pyrophosphate or the terminal pyrophosphate bond in ATP or another nucleoside triphosphate to drive the active uptake and/or extrusion of a solute or solutes. The transport protein may or may not be transiently phosphorylated, but the substrate is not phosphorylated.

PEP-dependent, phosphoryl transfer-driven group translocators. Transport systems of the bacterial phosphoenolpyruvate:sugar phosphotransferase system are included in this class. The product of the reaction, derived from extracellular sugar, is a cytoplasmic sugar-phosphate.

Decarboxylation-driven active transporters. Transport systems that drive solute (e.g., ion) uptake or extrusion by decarboxylation of a cytoplasmic substrate are included in this class.

Oxidoreduction-driven active transporters. Transport systems that drive transport of a solute (e.g., an ion) energized by the flow of electrons from a reduced substrate to an oxidized substrate are included in this class.

Light-driven active transporters. Transport systems that utilize light energy to drive transport of a solute (e.g., an ion) are included in this class.

Mechanically-driven active transporters. Transport systems are included in this class if they drive movement of a cell or organelle by allowing the flow of ions (or other solutes) through the membrane down their electrochemical gradients.

Outer-membrane porins (of b-structure). These proteins form transmembrane pores or channels that usually allow the energy independent passage of solutes across a membrane. The transmembrane portions of these proteins consist exclusively of b-strands that form a b-barrel. These porin-type proteins are found in the outer membranes of Gram-negative bacteria, mitochondria and eukaryotic plastids.

Methyltransferase-driven active transporters. A single characterized protein currently falls into this category, the Na+-transporting methyltetrahydromethanopterin:coenzyme M methyltransferase.

Non-ribosome-synthesized channel-forming peptides or peptide-like molecules. These molecules, usually chains of L- and D-amino acids as well as other small molecular building blocks such as lactate, form oligomeric transmembrane ion channels. Voltage may induce channel formation by promoting assembly of the transmembrane channel. These peptides are often made by bacteria and fungi as agents of biological warfare.

Non-Proteinaceous Transport Complexes. Ion conducting substances in biological membranes that do not consist of or are not derived from proteins or peptides fall into this category.

Functionally characterized transporters for which sequence data are lacking. Transporters of particular physiological significance will be included in this category even though a family assignment cannot be made.

Putative transporters in which no family member is an established transporter. Putative transport protein families are grouped under this number and will either be classified elsewhere when the transport function of a member becomes established, or will be eliminated from the TC classification system if the proposed transport function is disproven. These families include a member or members for which a transport function has been suggested, but evidence for such a function is not yet compelling.

Auxiliary transport proteins. Proteins that in some way facilitate transport across one or more biological membranes but do not themselves participate directly in transport are included in this class. These proteins always function in conjunction with one or more transport proteins. They may provide a function connected with energy coupling to transport, play a structural role in complex formation or serve a regulatory function.

Transporters of unknown classification. Transport protein families of unknown classification are grouped under this number and will be classified elsewhere when the transport process and energy coupling mechanism are characterized. These families include at least one member for which a transport function has been established, but either the mode of transport or the energy coupling mechanism is not known.

Ion Channels

An important type of transporter is the ion channel. Ion channels regulate many different cell proliferation, differentiation, and signaling processes by regulating the flow of ions into and out of cells. Ion channels are found in the plasma membranes of virtually every cell in eukaryotic organisms. Ion channels mediate a variety of cellular functions including regulation of membrane potentials and absorption and secretion of ion across epithelial membranes. When present in intracellular membranes of the Golgi apparatus and endocytic vesicles, ion channels, such as chloride channels, also regulate organelle pH. For a review, see Greger, R. (1988) Annu. Rev. Physiol. 50: 111–122.

Ion channels are generally classified by structure and the type of mode of action. For example, extracellular ligand gated channels (ELGs) are comprised of five polypeptide subunits, with each subunit having 4 membrane spanning domains, and are activated by the binding of an extracellular ligand to the channel. In addition, channels are sometimes classified by the ion type that is transported, for example, chlorine channels, potassium channels, etc. There may be many classes of channels for transporting a single type of ion (a detailed review of channel types can be found at Alexander, S. P. H. and J. A. Peters (1997). Receptor and ion channel nomenclature supplement. Trends Pharmacol. Sci., Elsevier, pp. 65–68.

There are many types of ion channels based on structure. For example, many ion channels fall within one of the following groups: extracellular ligand-gated channels (ELG), intracellular ligand-gated channels (ILG), inward rectifying channels (INR), intercellular (gap junction) channels, and voltage gated channels (VIC). There are additionally recognized other channel families based on ion-type transported, cellular location and drug sensitivity. Detailed information on each of these, their activity, ligand type, ion type, disease association, drugability, and other information pertinent to the present invention, is well known in the art.

Extracellular ligand-gated channels, ELGs, are generally comprised of five polypeptide subunits, Unwin, N. (1993), Cell 72: 31–41; Unwin, N. (1995), Nature 373: 37–43; Hucho, F., et al., (1996) J. Neurochem. 66: 1781–1792; Hucho, F., et al., (1996) Eur. J. Biochem. 239: 539–557; Alexander, S. P. H. and J. A. Peters (1997), Trends Pharmacol. Sci., Elsevier, pp. 4–6; 36–40; 42–44; and Xue, H. (1998) J. Mol. Evol. 47: 323–333. Each subunit has 4 membrane spanning regions: this serves as a means of identifying other members of the ELG family of proteins. ELG bind a ligand and in response modulate the flow of ions. Examples of ELG include most members of the neurotransmitter-receptor family of proteins, e.g., GABAI receptors. Other members of this family of ion channels include glycine receptors, ryandyne receptors, and ligand gated calcium channels.

The Voltage-gated Ion Channel (VIC) Superfamily

Proteins of the VIC family are ion-selective channel proteins found in a wide range of bacteria, archaea and eukaryotes Hille, B. (1992), Chapter 9: Structure of channel proteins; Chapter 20: Evolution and diversity. In: Ionic Channels of Excitable Membranes, 2nd Ed., Sinaur Assoc. Inc., Pubs., Sunderland, Mass.; Sigworth, F. J. (1993), Quart. Rev. Biophys. 27: 1–40; Salkoff, L. and T. Jegla (1995), Neuron 15: 489–492; Alexander, S. P. H. et al., (1997), Trends Pharmacol. Sci., Elsevier, pp. 76–84; Jan, L. Y. et al., (1997), Annu. Rev. Neurosci. 20: 91–123; Doyle, D. A, et al., (1998) Science 280: 69–77; Terlau, H. and W. Stühmer (1998), Naturwissenschaften 85: 437–444. They are often homo- or heterooligomeric structures with several dissimilar subunits (e.g., a1-a2-d-b $Ca^{2+}$ channels, $ab_1b_2$ $Na^+$ channels or $(a)_4$-b $K^+$ channels), but the channel and the primary receptor is usually associated with the a (or al) subunit. Functionally characterized members are specific for $K^+$, $Na^+$ or $Ca^{2+}$. The $K^+$ channels usually consist of homotetrameric structures with each a-subunit possessing six transmembrane spanners (TMSs). The al and a subunits of the $Ca^{2+}$ and $Na^+$ channels, respectively, are about four times as large and possess 4 units, each with 6 TMSs separated by a hydrophilic loop, for a total of 24 TMSs. These large channel proteins form heterotetra-unit structures equivalent to the homotetrameric structures of most $K^+$ channels. All four units of the $Ca^{2+}$ and $Na^+$ channels are homologous to the single unit in the homotetrameric $K^+$ channels. Ion flux via the eukaryotic channels is generally controlled by the transmembrane electrical potential (hence the designation, voltage-sensitive) although some are controlled by ligand or receptor binding.

Several putative $K^+$-selective channel proteins of the VIC family have been identified in prokaryotes. The structure of one of them, the KcsA $K^+$ channel of *Streptomyces lividans,* has been solved to 3.2 Å resolution. The protein possesses four identical subunits, each with two transmembrane helices, arranged in the shape of an inverted teepee or cone. The cone cradles the "selectivity filter" P domain in its outer end. The narrow selectivity filter is only 12 Å long, whereas the remainder of the channel is wider and lined with hydrophobic residues. A large water-filled cavity and helix dipoles stabilize $K^+$ in the pore. The selectivity filter has two bound $K^+$ ions about 7.5 Å apart from each other. Ion conduction is proposed to result from a balance of electrostatic attractive and repulsive forces.

In eukaryotes, each VIC family channel type has several subtypes based on pharmacological and electrophysiological data. Thus, there are five types of $Ca^{2+}$ channels (L, N, P, Q and T). There are at least ten types of $K^+$ channels, each responding in different ways to different stimuli: voltage-sensitive [Ka, Kv, Kvr, Kvs and Ksr], $Ca^{2+}$-sensitive [$BK_{Ca}$, $IK_{Ca}$ and $SK_{Ca}$] and receptor-coupled [$K_M$ and $K_{ACh}$]. There are at least six types of $Na^+$ channels (I, II, III, $\mu$1, H1 and PN3). Tetrameric channels from both prokaryotic and eukaryotic organisms are known in which each a-subunit possesses 2 TMSs rather than 6, and these two TMSs are homologous to TMSs 5 and 6 of the six TMS unit found in the voltage-sensitive channel proteins. KcsA of *S. lividans* is an example of such a 2 TMS channel protein. These channels may include the $K_{Na}$ ($Na^+$-activated) and $K_{Vol}$ (cell volume-sensitive) $K^+$ channels, as well as distantly related channels such as the Tok1 $K^+$ channel of yeast, the TWIK-1 inward rectifier $K^+$ channel of the mouse and the TREK-1

$K^+$ channel of the mouse. Because of insufficient sequence similarity with proteins of the VIC family, inward rectifier $K^+$ IRK channels (ATP-regulated; G-protein-activated) which possess a P domain and two flanking TMSs are placed in a distinct family. However, substantial sequence similarity in the P region suggests that they are homologous. The b, g and d subunits of VIC family members, when present, frequently play regulatory roles in channel activation/deactivation.

The Epithelial $Na^+$ Channel (ENaC) Family

The ENaC family consists of over twenty-four sequenced proteins (Canessa, C. M., et al., (1994), Nature 367: 463–467, Le, T. and M. H. Saier, Jr. (1996), Mol. Membr. Biol. 13: 149–157; Garty, H. and L. G. Palmer (1997), Physiol. Rev. 77: 359–396; Waldmann, R., et al., (1997), Nature 386: 173–177; Darboux, I., et al., (1998), J. Biol. Chem. 273: 9424–9429; Firsov, D., et al., (1998), EMBO J. 17: 344–352; Horisberger, J. D. (1998). Curr. Opin. Struc. Biol. 10: 443–449). All are from animals with no recognizable homologues in other eukaryotes or bacteria. The vertebrate ENaC proteins from epithelial cells cluster tightly together on the phylogenetic tree: voltage-insensitive ENaC homologues are also found in the brain. Eleven sequenced *C. elegans* proteins, including the degenerins, are distantly related to the vertebrate proteins as well as to each other. At least some of these proteins form part of a mechano-transducing complex for touch sensitivity. The homologous *Helix aspersa* (FMRF-amide)-activated $Na^+$ channel is the first peptide neurotransmitter-gated ionotropic receptor to be sequenced.

Protein members of this family all exhibit the same apparent topology, each with N- and C-termini on the inside of the cell, two amphipathic transmembrane spanning segments, and a large extracellular loop. The extracellular domains contain numerous highly conserved cysteine residues. They are proposed to serve a receptor function.

Mammalian ENaC is important for the maintenance of $Na^+$ balance and the regulation of blood pressure. Three homologous ENaC subunits, alpha, beta, and gamma, have been shown to assemble to form the highly $Na^+$-selective channel. The stoichiometry of the three subunits is $alpha_2$ beta1, gamma1 in a heterotetrameric architecture.

The Glutamate-gated Ion Channel (GIC) Family of Neurotransmitter Receptors

Members of the GIC family are heteropentameric complexes in which each of the 5 subunits is of 800–1000 amino acyl residues in length (Nakanishi, N., et al, (1990), Neuron 5: 569–581; Unwin, N. (1993), Cell 72: 31–41; Alexander, S. P. H. and J. A. Peters (1997) Trends Pharmacol. Sci., Elsevier, pp. 36–40). These subunits may span the membrane three or five times as putative a-helices with the N-termini (the glutamate-binding domains) localized extracellularly and the C-termini localized cytoplasmically. They may be distantly related to the ligand-gated ion channels, and if so, they may possess substantial b-structure in their transmembrane regions. However, homology between these two families cannot be established on the basis of sequence comparisons alone. The subunits fall into six subfamilies: a, b, g, d, e and z.

The GIC channels are divided into three types: (1) a-amino-3-hydroxy-5-methyl-4-isoxazole propionate (AMPA)-, (2) kainate- and (3) N-methyl-D-aspartate (NMDA)-selective glutamate receptors. Subunits of the AMPA and kainate classes exhibit 35–40% identity with each other while subunits of the NMDA receptors exhibit 22–24% identity with the former subunits. They possess large N-terminal, extracellular glutamate-binding domains that are homologous to the periplasmic glutamine and glutamate receptors of ABC-type uptake permeases of Gram-negative bacteria. All known members of the GIC family are from animals. The different channel (receptor) types exhibit distinct ion selectivities and conductance properties. The NMDA-selective large conductance channels are highly permeable to monovalent cations and $Ca^{2+}$. The AMPA- and kainate-selective ion channels are permeable primarily to monovalent cations with only low permeability to $Ca^{2+}$.

The Chloride Channel (ClC) Family

The ClC family is a large family consisting of dozens of sequenced proteins derived from Gram-negative and Gram-positive bacteria, cyanobacteria, archaea, yeast, plants and animals (Steinmeyer, K., et al., (1991), Nature 354: 301–304; Uchida, S., et al., (1993), J. Biol. Chem. 268: 3821–3824; Huang, M.-E., et al., (1994), J. Mol. Biol. 242: 595–598; Kawasaki, M., et al, (1994), Neuron 12: 597–604; Fisher, W. E., et al., (1995), Genomics. 29:598–606; and Foskett, J. K. (1998), Annu. Rev. Physiol. 60: 689–717). These proteins are essentially ubiquitous, although they are not encoded within genomes of *Haemophilus influenzae, Mycoplasma genitalium,* and *Mycoplasma pneumoniae.* Sequenced proteins vary in size from 395 amino acyl residues (*M. jannaschii*) to 988 residues (man). Several organisms contain multiple ClC family paralogues. For example, Synechocystis has two paralogues, one of 451 residues in length and the other of 899 residues. *Arabidopsis thaliana* has at least four sequenced paralogues, (775–792 residues), humans also have at least five paralogues (820–988 residues), and *C. elegans* also has at least five (810–950 residues). There are nine known members in mammals, and mutations in three of the corresponding genes cause human diseases. *E. coli, Methanococcus jannaschii* and *Saccharomyces cerevisiae* only have one ClC family member each. With the exception of the larger Synechocystis paralogue, all bacterial proteins are small (395–492 residues) while all eukaryotic proteins are larger (687–988 residues). These proteins exhibit 10–12 putative transmembrane a-helical spanners (TMSs) and appear to be present in the membrane as homodimers. While one member of the family, Torpedo ClC-O, has been reported to have two channels, one per subunit, others are believed to have just one.

All functionally characterized members of the ClC family transport chloride, some in a voltage-regulated process. These channels serve a variety of physiological functions (cell volume regulation; membrane potential stabilization; signal transduction; transepithelial transport, etc.). Different homologues in humans exhibit differing anion selectivities, i.e., ClC4 and ClC5 share a $NO_3^- > Cl^- > Br^{31} > I^-$ conductance sequence, while ClC3 has an $I^- > Cl^-$ selectivity. The ClC4 and ClC5 channels and others exhibit outward rectifying currents with currents only at voltages more positive than +20 mV.

Animal Inward Rectifier $K^+$ Channel (IRK-C) Family

IRK channels possess the "minimal channel-forming structure" with only a P domain, characteristic of the channel proteins of the VIC family, and two flanking transmembrane spanners (Shuck, M. E., et al., (1994), J. Biol. Chem. 269:

24261–24270; Ashen, M. D., et al., (1995), Am. J. Physiol. 268: H506–H511; Salkoff, L. and T. Jegla (1995), Neuron 15: 489–492; Aguilar-Bryan, L., et al., (1998), Physiol. Rev. 78: 227–245; Ruknudin, A., et al., (1998), J. Biol. Chem. 273: 14165–14171). They may exist in the membrane as homo- or heterooligomers. They have a greater tendency to let $K^+$ flow into the cell than out. Voltage-dependence may be regulated by external $K^+$, by internal $Mg^{2+}$, by internal ATP and/or by G-proteins. The P domains of IRK channels exhibit limited sequence similarity to those of the VIC family, but this sequence similarity is insufficient to establish homology. Inward rectifiers play a role in setting cellular membrane potentials, and the closing of these channels upon depolarization permits the occurrence of long duration action potentials with a plateau phase. Inward rectifiers lack the intrinsic voltage sensing helices found in VIC family channels. In a few cases, those of Kir.1.1a and Kir6.2, for example, direct interaction with a member of the ABC superfamily has been proposed to confer unique functional and regulatory properties to the heteromeric complex, including sensitivity to ATP. The SUR1 sulfonylurea receptor (spQ09428) is the ABC protein that regulates the Kir6.2 channel in response to ATP, and CFTR may regulate Kir1.1a. Mutations in SUR1 are the cause of familial persistent hyperinsulinemic hypoglycemia in infancy (PHHI), an autosomal recessive disorder characterized by unregulated insulin secretion in the pancreas.

ATP-gated Cation Channel (ACC) Family

Members of the ACC family (also called P2X receptors) respond to ATP, a functional neurotransmitter released by exocytosis from many types of neurons (North, R. A. (1996), Curr. Opin. Cell Biol. 8: 474–483; Soto, F., M. Garcia-Guzman and W. Stühmer (1997), J. Membr. Biol. 160: 91–100). They have been placed into seven groups ($P2X_1$–$P2X_7$) based on their pharmacological properties. These channels, which function at neuron-neuron and neuron-smooth muscle junctions, may play roles in the control of blood pressure and pain sensation. They may also function in lymphocyte and platelet physiology. They are found only in animals.

The proteins of the ACC family are quite similar in sequence (>35% identity), but they possess 380–1000 amino acyl residues per subunit with variability in length localized primarily to the C-terminal domains. They possess two transmembrane spanners, one about 30–50 residues from their N-termini, the other near residues 320–340. The extracellular receptor domains between these two spanners (of about 270 residues) are well conserved with numerous conserved glycyl and cysteyl residues. The hydrophilic C-termini vary in length from 25 to 240 residues. They resemble the topologically similar epithelial $Na^+$ channel (ENaC) proteins in possessing (a) N- and C-termini localized intracellularly, (b) two putative transmembrane spanners, (c) a large extracellular loop domain, and (d) many conserved extracellular cysteyl residues. ACC family members are, however, not demonstrably homologous with them. ACC channels are probably hetero- or homomultimers and transport small monovalent cations ($Me^+$). Some also transport $Ca^{2+}$; a few also transport small metabolites.

The Ryanodine-Inositol 1,4,5-triphosphate Receptor $Ca^{2+}$ Channel (RIR-CaC) Family Ryanodine (Ry)-sensitive and inositol 1,4,5-triphosphate (IP3)-sensitive $Ca^{2+}$-release channels function in the release of $Ca^{2+}$ from intracellular storage sites in animal cells and thereby regulate various $Ca^{2+}$-dependent physiological processes (Hasan, G. et al., (1992) Development 116: 967–975; Michikawa, T., et al., (1994), J. Biol. Chem. 269: 9184–9189; Tunwell, R. E. A., (1996), Biochem. J. 318: 477–487; Lee, A. G. (1996) *Biomembranes,* Vol. 6, Transmembrane Receptors and Channels (A. G. Lee, ed.), JAI Press, Denver, Colo., pp 291–326; Mikoshiba, K., et al., (1996) J. Biochem. Biomem. 6: 273–289). Ry receptors occur primarily in muscle cell sarcoplasmic reticular (SR) membranes, and IP3 receptors occur primarily in brain cell endoplasmic reticular (ER) membranes where they effect release of $Ca^{2+}$ into the cytoplasm upon activation (opening) of the channel.

The Ry receptors are activated as a result of the activity of dihydropyridine-sensitive $Ca^{2+}$ channels. The latter are members of the voltage-sensitive ion channel (VIC) family. Dihydropyridine-sensitive channels are present in the T-tubular systems of muscle tissues.

Ry receptors are homotetrameric complexes with each subunit exhibiting a molecular size of over 500,000 daltons (about 5,000 amino acyl residues). They possess C-terminal domains with six putative transmembrane a -helical spanners (TMSs). Pulative pore-forming sequences occur between the fifth and sixth TMSs as suggested for members of the VIC family. The large N-terminal hydrophilic domains and the small C-terminal hydrophilic domains are localized to the cytoplasm. Low resolution 3-dimensional structural data are available. Mammals possess at least three isoforms that probably arose by gene duplication and divergence before divergence of the mammalian species. Homologues are present in humans and *Caenorabditis elegans.*

$IP_3$ receptors resemble Ry receptors in many respects. (1) They are homotetrameric complexes with each subunit exhibiting a molecular size of over 300,000 daltons (about 2,700 amino acyl residues). (2) They possess C-terminal channel domains that are homologous to those of the Ry receptors. (3) The channel domains possess six putative TMSs and a putative channel lining region between TMSs 5 and 6. (4) Both the large N-terminal domains and the smaller C-terminal tails face the cytoplasm. (5) They possess covalently linked carbohydrate on extracytoplasmic loops of the channel domains. (6) They have three currently recognized isoforms (types 1, 2, and 3) in mammals which are subject to differential regulation and have different tissue distributions.

$IP_3$ receptors possess three domains: N-terminal $IP_3$-binding domains, central coupling or regulatory domains and C-terminal channel domains. Channels are activated by $IP_3$ binding, and like the Ry receptors, the activities of the $IP_3$ receptor channels are regulated by phosphorylation of the regulatory domains, catalyzed by various protein kinases. They predominate in the endoplasmic reticular membranes of various cell types in the brain but have also been found in the plasma membranes of some nerve cells derived from a variety of tissues.

The channel domains of the Ry and $IP_3$ receptors comprise a coherent family that in spite of apparent structural similarities, do not show appreciable sequence similarity of the proteins of the VIC family. The Ry receptors and the $IP_3$ receptors cluster separately on the RIR-CaC family tree. They both have homologues in Drosophila. Based on the phylogenetic tree for the family, the family probably evolved in the following sequence: (1) A gene duplication event occurred that gave rise to Ry and $IP_3$ receptors in invertebrates. (2) Vertebrates evolved from invertebrates. (3) The three isoforms of each receptor arose as a result of two distinct gene duplication events. (4) These isoforms were transmitted to mammals before divergence of the mammalian species.

The Organellar Chloride Channel (O-ClC) Family

Proteins of the O-ClC family are voltage-sensitive chloride channels found in intracellular membranes but not the plasma membranes of animal cells (Landry, D, et al., (1993), J. Biol. Chem. 268: 14948–14955; Valenzuela, Set al., (1997), J. Biol. Chem. 272: 12575–12582; and Duncan, R. R., et al., (1997), J. Biol. Chem. 272: 23880–23886).

They are found in human nuclear membranes, and the bovine protein targets to the microsomes, but not the plasma membrane, when expressed in *Xenopus laevis* oocytes. These proteins are thought to function in the regulation of the membrane potential and in transepithelial ion absorption and secretion in the kidney. They possess two putative transmembrane a-helical spanners (TMSs) with cytoplasmic N- and C-termini and a large luminal loop that may be glycosylated. The bovine protein is 437 amino acyl residues in length and has the two putative TMSs at positions 223–239 and 367–385. The human nuclear protein is much smaller (241 residues). A *C. elegans* homologue is 260 residues long.

Sodium Bicarbonate Cotransporters

The novel human protein provided by the present invention is related to the family of sodium bicarbonate cotransporters, and shows a particularly high degree of similarity to the mouse sodium bicarbonate cotransporter isoform kNBC-3.

The sodium bicarbonate cotransporter provides the primary mechanism for transporting bicarbonate across the basolateral membrane in the kidney. At least three sodium bicarbonate cotransporter isoforms are located in the kidney and these may be functionally altered in various pathophysiologic states. For example, sodium bicarbonate cotransporter isoform 1 may be stimulated by metabolic acidosis, potassium depletion, and glucocorticoid excess and may be inhibited by bicarbonate loading or alkalosis. Sodium bicarbonate cotransporters are activated by cystic fibrosis transmembrane conductance regulator (CFTR) and play an important role in bicarbonate secretion in pancreatic duct cells. Furthermore, sodium bicarbonate cotransporters may play an important role in acid-base disorders such as proximal renal tubular acidosis (Soleimani et al., *Kidney Int* 2000 February;57(2):371–84).

The sodium-driven chloride/bicarbonate exchanger plays an important role in regulating intracellular pH in a wide variety cells by transporting extracellular sodium and bicarbonate into cells in exchange for intracellular chloride and H(+), thereby raising intracellular pH (Wang et al, *J Biol Chem* Nov. 10, 2000;275(45):35486–90).

Transporter proteins, particularly members of the sodium bicarbonate cotransporter subfamily, are a major target for drug action and development. Accordingly, it is valuable to the field of pharmaceutical development to identify and characterize previously unknown transport proteins. The present invention advances the state of the art by providing previously unidentified human transport proteins.

SUMMARY OF THE INVENTION

The present invention is based in part on the identification of amino acid sequences of human transporter peptides and proteins that are related to the sodium bicarbonate cotransporter subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate transporter activity in cells and tissues that express the transporter. Experimental data as provided in FIG. 1 indicates expression in humans in the testis, brain (adult and fetal), placenta, and bone marrow.

DESCRIPTION OF THE FIGURE SHEETS

FIGS. 1A–1D provide the nucleotide sequence of a cDNA molecule that encodes the transporter protein of the present invention. In addition structure and functional information is provided, such as ATG start, stop and tissue distribution, where available, that allows one to readily determine specific uses of inventions based on this molecular sequence. Experimental data as provided in FIG. 1 indicates expression in humans in the testis, brain (adult and fetal), placenta, and bone marrow.

FIGS. 2A–2G provide the predicted amino acid sequence of the transporter of the present invention. In addition structure and functional information such as protein family, function, and modification sites is provided where available, allowing one to readily determine specific uses of inventions based on this molecular sequence.

FIGS. 3A–3GGGGG provide genomic sequences that span the gene encoding the transporter protein of the present invention. In addition structure and functional information, such as intron/exon structure, promoter location, etc., is provided where available, allowing one to readily determine specific uses of inventions based on this molecular sequence. As illustrated in FIG. 3, SNPs, including insertion/deletion polymorphisms ("indels"), were identifed at 87 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a transporter protein or part of a transporter protein and are related to the sodium bicarbonate cotransporter subfamily. Utilizing these sequences, additional genomic sequences were assembled and transcript and/or cDNA sequences were isolated and characterized. Based on this analysis, the present invention provides amino acid sequences of human transporter peptides and proteins that are related to the sodium bicarbonate cotransporter subfamily, nucleic acid sequences in the form of transcript sequences, cDNA sequences and/or genomic sequences that encode these transporter peptides and proteins, nucleic acid variation (allelic information), tissue distribution of expression, and information about the closest art known protein/peptide/domain that has structural or sequence homology to the transporter of the present invention.

In addition to being previously unknown, the peptides that are provided in the present invention are selected based on their ability to be used for the development of commercially important products and services. Specifically, the present peptides are selected based on homology and/or structural relatedness to known transporter proteins of the sodium bicarbonate cotransporter subfamily and the expression pattern observed. Experimental data as provided in FIG. 1 indicates expression in humans in the testis, brain (adult and fetal), placenta, and bone marrow. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known sodium bicarbonate cotransporter family or subfamily of transporter proteins.

Specific Embodiments

Peptide Molecules

The present invention provides nucleic acid sequences that encode protein molecules that have been identified as being members of the transporter family of proteins and are related to the sodium bicarbonate cotransporter subfamily (protein sequences are provided in FIG. 2, transcript/cDNA sequences are provided in FIGS. 1 and genomic sequences are provided in FIG. 3). The peptide sequences provided in FIG. 2, as well as the obvious variants described herein, particularly allelic variants as identified herein and using the information in FIG. 3, will be referred herein as the transporter peptides of the present invention, transporter peptides, or peptides/proteins of the present invention.

The present invention provides isolated peptide and protein molecules that consist of, consist essentially of, or comprising the amino acid sequences of the transporter peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the transporter peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated transporter peptide can be purified from cells that naturally express it, purified from cells that have been altered to express it (recombinant), or synthesized using known protein synthesis methods. Experimental data as provided in FIG. 1 indicates expression in humans in the testis, brain (adult and fetal), placenta, and bone marrow. For example, a nucleic acid molecule encoding the transporter peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the transporter peptides of the present invention are the naturally occurring mature proteins. A brief description of how various types of these proteins can be made/isolated is provided below.

The transporter peptides of the present invention can be attached to heterologous sequences to form chimeric or fusion proteins. Such chimeric and fusion proteins comprise a transporter peptide operatively linked to a heterologous protein having an amino acid sequence not substantially homologous to the transporter peptide. "Operatively linked" indicates that the transporter peptide and the heterologous protein are fused in-frame. The heterologous protein can be fused to the N-terminus or C-terminus of the transporter peptide.

In some uses, the fusion protein does not affect the activity of the transporter peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant transporter peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A transporter peptide-encoding nucleic acid can be cloned into such an expression vector such that the fusion moiety is linked in-frame to the transporter peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the transporter peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, N.Y., 1988; *Biocomputing: Informatics and Genome Projects,* Smith, D. W., ed., Academic Press, N.Y., 1993; *Computer Analysis of Sequence Data, Part* 1, Griffin, A. M., and Griffin, H. G., eds., Humana Press, N. J., 1994; *Sequence Analysis in Molecular Biology, von Heinje, G., Academic Press,* 1987; and *Sequence Analysis Primer,* Gribskov, M. and Devereux, J., eds., M Stockton Press, N. Y., 1991). In a preferred embodiment, the percent identity between two amino acid sequences is determined using the Needleman and Wunsch (*J. Mol. Biol.* (48): 444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the transporter peptides of the present invention as well as being encoded by the same genetic locus as the transporter peptide provided herein. As indicated by the data presented in FIG. 3, the gene provided by the present invention is located on public BAC AC008063.2, which is known to be mapped to chromosome 2.

Allelic variants of a transporter peptide can readily be identified as being a human protein having a high degree (significant) of sequence homology/identity to at least a portion of the transporter peptide as well as being encoded by the same genetic locus as the transporter peptide provided herein. Genetic locus can readily be determined based on the genomic information provided in FIG. 3, such as the genomic sequence mapped to the reference human. As indicated by the data presented in FIG. 3, the gene provided by the present invention is located on public BAC AC008063.2, which is known to be mapped to chromosome 2. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a transporter peptide encoding nucleic acid molecule under stringent conditions as more fully described below.

FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3.

Paralogs of a transporter peptide can readily be identified as having some degree of significant sequence homology/identity to at least a portion of the transporter peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a transporter peptide encoding nucleic acid molecule under moderate to stringent conditions as more fully described below.

Orthologs of a transporter peptide can readily be identified as having some degree of significant sequence homology/identity to at least a portion of the transporter peptide as well as being encoded by a gene from another organism. Preferred orthologs will be isolated from mammals, preferably primates, for the development of human therapeutic targets and agents. Such orthologs will be encoded by a nucleic acid sequence that will hybridize to a transporter peptide encoding nucleic acid molecule under moderate to stringent conditions, as more fully described below, depending on the degree of relatedness of the two organisms yielding the proteins.

Non-naturally occurring variants of the transporter peptides of the present invention can readily be generated using recombinant techniques. Such variants include, but are not limited to deletions, additions and substitutions in the amino acid sequence of the transporter peptide. For example, one class of substitutions are conserved amino acid substitution. Such substitutions are those that substitute a given amino acid in a transporter peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant transporter peptides can be fully functional or can lack function in one or more activities, e.g. ability to bind ligand, ability to transport ligand, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al, *Science* 244:1081–1085 (1989)), particularly using the results provided in FIG. 2. The latter procedure introduces single alanine mutations at every residue in the molecule. The resulting mutant molecules are then tested for biological activity such as transporter activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the transporter peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a transporter peptide. Such fragments can be chosen based on the ability to retain one or more of the biological activities of the transporter peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the transporter peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in transporter peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the transporter peptides of the present invention also encompass derivatives or analogs in which a substituted amino acid residue is not one encoded by the genetic code, in which a substituent group is included, in which the mature transporter peptide is fused with another compound, such as a compound to increase the half-life of the transporter peptide (for example, polyethylene glycol), or in which the additional amino acids are fused to the mature transporter peptide, such as a leader or secretory sequence or a sequence for purification of the mature transporter peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a transporter-effector protein interaction or transporter-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, transporters isolated from humans and their human/mammalian orthologs serve as targets for identifying agents for use in mammalian therapeutic applications, e.g. a human drug, particularly in modulating a biological or pathological response in a cell or tissue that expresses the transporter. Experimental data as provided in FIG. 1 indicates that the transporter protein of the present invention is expressed in humans in the testis, brain (adult and fetal), placenta, and bone marrow, as indicated by PCR-based tissue screening panels. A large percentage of pharmaceutical agents are being developed that modulate the activity of transporter proteins, particularly members of the sodium bicarbonate cotransporter subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the testis, brain (adult and fetal), placenta, and bone marrow. Such uses can readily be determined using the information provided herein, that known in the art and routine experimentation.

The proteins of the present invention (including variants and fragments that may have been disclosed prior to the present invention) are useful for biological assays related to transporters that are related to members of the sodium bicarbonate cotransporter subfamily. Such assays involve any of the known transporter functions or activities or properties useful for diagnosis and treatment of transporter-related conditions that are specific for the subfamily of transporters that the one of the present invention belongs to, particularly in cells and tissues that express the transporter. Experimental data as provided in FIG. 1 indicates that the transporter protein of the present invention is expressed in humans in the testis, brain (adult and fetal), placenta, and bone marrow, as indicated by PCR-based tissue screening panels. The proteins of the present invention are also useful in drug screening assays, in cell-based or cell-free systems ((Hodgson, Bio/technology, 1992, September 10(9) ;973–80). Cell-based systems can be native, i.e., cells that normally express the transporter, as a biopsy or expanded in cell culture. Experimental data as provided in FIG. 1 indicates expression in humans in the testis, brain (adult and fetal), placenta, and bone marrow. In an alternate embodiment, cell-based assays involve recombinant host cells expressing the transporter protein.

The polypeptides can be used to identify compounds that modulate transporter activity of the protein in its natural state or an altered form that causes a specific disease or pathology associated with the transporter. Both the transporters of the present invention and appropriate variants and fragments can be used in high-throughput screens to assay candidate compounds for the ability to bind to the transporter. These compounds can be further screened against a functional transporter to determine the effect of the compound on the transporter activity. Further, these compounds can be tested in animal or invertebrate systems to determine activity/effectiveness. Compounds can be identified that activate (agonist) or inactivate (antagonist) the transporter to a desired degree.

Further, the proteins of the present invention can be used to screen a compound for the ability to stimulate or inhibit interaction between the transporter protein and a molecule that normally interacts with the transporter protein, e.g. a substrate or a component of the signal pathway that the transporter protein normally interacts (for example, another transporter). Such assays typically include the steps of combining the transporter protein with a candidate compound under conditions that allow the transporter protein, or fragment, to interact with the target molecule, and to detect the formation of a complex between the protein and the target or to detect the biochemical consequence of the interaction with the transporter protein and the target, such as any of the associated effects of signal transduction such as changes in membrane potential, protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for ligand binding. Other candidate compounds include mutant transporters or appropriate fragments containing mutations that affect transporter function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) transporter activity. The assays typically involve an assay of events in the signal transduction pathway that indicate transporter activity. Thus, the transport of a ligand, change in cell membrane potential, activation of a protein, a change in the expression of genes that are up- or down-regulated in response to the transporter protein dependent signal cascade can be assayed.

Any of the biological or biochemical functions mediated by the transporter can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the transporter can be assayed. Experimental data as provided in FIG. 1 indicates that the transporter protein of the present invention is expressed in humans in the testis, brain (adult and fetal), placenta, and bone marrow, as indicated by PCR-based tissue screening panels.

Binding and/or activating compounds can also be screened by using chimeric transporter proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a ligand-binding region can be used that interacts with a different ligand then that which is recognized by the native transporter. Accordingly, a different set of signal transduction components is available as an end-point assay for activation. This allows for assays to be performed in other than the specific host cell from which the transporter is derived.

The proteins of the present invention are also useful in competition binding assays in methods designed to discover compounds that interact with the transporter (e.g. binding partners and/or ligands). Thus, a compound is exposed to a transporter polypeptide under conditions that allow the compound to bind or to otherwise interact with the polypeptide. Soluble transporter polypeptide is also added to the mixture. If the test compound interacts with the soluble transporter polypeptide, it decreases the amount of complex formed or activity from the transporter target. This type of assay is particularly useful in cases in which compounds are sought that interact with specific regions of the transporter. Thus, the soluble polypeptide that competes with the target transporter region is designed to contain peptide sequences corresponding to the region of interest.

To perform cell free drug screening assays, it is sometimes desirable to immobilize either the transporter protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of transporter-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a transporter-binding protein and a candidate compound are incubated in the transporter protein-presenting wells and the amount of complex trapped in the well can be quantitated. Methods for detecting such complexes, in addition to those described above for the GST-immobilized complexes, include immunodetection of complexes using antibodies reactive with the transporter protein target molecule, or which are reactive with transporter protein and compete with the target molecule, as well as enzyme-linked assays which rely on detecting an enzymatic activity associated with the target molecule.

Agents that modulate one of the transporters of the present invention can be identified using one or more of the above assays, alone or in combination. It is generally preferable to use a cell-based or cell free system first and then confirm activity in an animal or other model system.

Such model systems are well known in the art and can readily be employed in this context.

Modulators of transporter protein activity identified according to these drug screening assays can be used to treat a subject with a disorder mediated by the transporter pathway, by treating cells or tissues that express the transporter. Experimental data as provided in FIG. 1 indicates expression in humans in the testis, brain (adult and fetal), placenta, and bone marrow. These methods of treatment include the steps of administering a modulator of transporter activity in a pharmaceutical composition to a subject in need of such treatment, the modulator being identified as described herein.

In yet another aspect of the invention, the transporter proteins can be used as "bait proteins" in a two-hybrid assay or three-hybrid assay (see, e.g., U.S. Pat. No. 5,283,317; Zervos et al (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the transporter and are involved in transporter activity. Such transporter-binding proteins are also likely to be involved in the propagation of signals by the transporter proteins or transporter targets as, for example, downstream elements of a transporter-mediated signaling pathway. Alternatively, such transporter-binding proteins are likely to be transporter inhibitors.

The two-hybrid system is based on the modular nature of most transcription factors, which consist of separable DNA-binding and activation domains. Briefly, the assay utilizes two different DNA constructs. In one construct, the gene that codes for a transporter protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a transporter-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the transporter protein.

This invention further pertains to novel agents identified by the above-described screening assays. Accordingly, it is within the scope of this invention to further use an agent identified as described herein in an appropriate animal model. For example, an agent identified as described herein (e.g., a transporter-modulating agent, an antisense transporter nucleic acid molecule, a transporter-specific antibody, or a transporter-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The transporter proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the testis, brain (adult and fetal), placenta, and bone marrow. The method involves contacting a biological sample with a compound capable of interacting with the transporter protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered transporter activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the transporter protein in which one or more of the transporter functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and transporter activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the testis, brain (adult and fetal), placenta, and bone marrow. Accordingly, methods for treatment include the use of the transporter protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the transporter proteins. Antibodies can be prepared from any region of the peptide as described herein. However, preferred regions will include those involved in function/activity and/or transporter/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the transporter protein of the present invention is expressed in humans in the testis, brain (adult and fetal), placenta, and bone marrow, as indicated by PCR-based tissue screening panels. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the testis, brain (adult and fetal), placenta, and bone marrow. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the testis, brain (adult and fetal), placenta, and bone marrow. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the testis, brain (adult and fetal), placenta, and bone marrow. Thus, where a specific protein has been correlated with expression in a specific tissue, antibodies that are specific for this protein can be used to identify a tissue type.

The antibodies are also useful for inhibiting protein function, for example, blocking the binding of the transporter peptide to a binding partner such as a ligand or protein binding partner. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a transporter peptide or protein of the present invention (cDNA, transcript and genomic sequence). Such nucleic acid molecules will consist of, consist essentially of, or comprise a nucleotide sequence that encodes one of the transporter peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the transporter peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the transporter proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the gene provided by the present invention is located on public BAC AC008063.2, which is known to be mapped to chromosome 2.

FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, New York (1989), 6.3.1–6.3.6. One example of stringent hybridization conditions are hybridization in 6× sodium chloride/sodium citrate (SSC) at about 45 C, followed by one or more washes in 0.2× SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, including insertion/deletion polymorphisms ("indels"), were identifed at 87 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the gene provided by the present invention is located on public BAC AC008063.2, which is known to be mapped to chromosome 2.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the transporter protein of the present invention is expressed in humans in the testis, brain (adult and fetal), placenta, and bone marrow, as indicated by PCR-based tissue screening panels.

Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in transporter protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a transporter protein, such as by measuring a level of a transporter-encoding nucleic acid in a sample of cells from a subject e.g., mRNA or genomic DNA, or determining if a transporter gene has been mutated. Experimental data as provided in FIG. 1 indicates that the transporter protein of the present invention is expressed in humans in the testis, brain (adult and fetal), placenta, and bone marrow, as indicated by PCR-based tissue screening panels.

Nucleic acid expression assays are useful for drug screening to identify compounds that modulate transporter nucleic acid expression.

The invention thus provides a method for identifying a compound that can be used to treat a disorder associated with nucleic acid expression of the transporter gene, particularly biological and pathological processes that are mediated by the transporter in cells and tissues that express it. Experimental data as provided in FIG. 1 indicates expression in humans in the testis, brain (adult and fetal), placenta, and bone marrow. The method typically includes assaying the ability of the compound to modulate the expression of the transporter nucleic acid and thus identifying a compound that can be used to treat a disorder characterized by undesired transporter nucleic acid expression. The assays can be performed in cell-based and cell-free systems. Cell-based assays include cells naturally expressing the transporter nucleic acid or recombinant cells genetically engineered to express specific nucleic acid sequences.

The assay for transporter nucleic acid expression can involve direct assay of nucleic acid levels, such as mRNA levels, or on collateral compounds involved in the signal pathway. Further, the expression of genes that are up- or down-regulated in response to the transporter protein signal pathway can also be assayed. In this embodiment the regulatory regions of these genes can be operably linked to a reporter gene such as luciferase.

Thus, modulators of transporter gene expression can be identified in a method wherein a cell is contacted with a candidate compound and the expression of mRNA determined. The level of expression of transporter mRNA in the presence of the candidate compound is compared to the level of expression of transporter mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate transporter nucleic acid expression in cells and tissues that express the transporter. Experimental data as provided in FIG. 1 indicates that the transporter protein of the present invention is expressed in humans in the testis, brain (adult and fetal), placenta, and bone marrow, as indicated by PCR-based tissue screening panels. Modulation includes both up-regulation (i.e. activation or agonization) or down-regulation (suppression or antagonization) or nucleic acid expression.

Alternatively, a modulator for transporter nucleic acid expression can be a small molecule or drug identified using the screening assays described herein as long as the drug or small molecule inhibits the transporter nucleic acid expression in the cells and tissues that express the protein. Experimental data as provided in FIG. 1 indicates expression in humans in the testis, brain (adult and fetal), placenta, and bone marrow.

The nucleic acid molecules are also useful for monitoring the effectiveness of modulating compounds on the expression or activity of the transporter gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in transporter nucleic acid expression, and particularly in qualitative changes that lead to pathology. The nucleic acid molecules can be used to detect mutations in transporter genes and gene expression products such as mRNA. The nucleic acid molecules can be used as hybridization probes to detect naturally occurring genetic mutations in the transporter gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the transporter gene associated with a dysfunction provides a diagnostic tool for an active disease or susceptibility to disease when the disease results from overexpression, underexpression, or altered expression of a transporter protein.

Individuals carrying mutations in the transporter gene can be detected at the nucleic acid level by a variety of techniques. FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3. As indicated by the data presented in FIG. 3, the gene provided by the present invention is located on public BAC AC008063.2, which is known to be mapped to chromosome 2. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al, *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a transporter gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant transporter gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al, *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the transporter gene in an individual in order to select an appropriate compound or dosage regimen for treatment. FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control transporter gene expression in cells, tissues, and organisms. A DNA antisense nucleic acid molecule is designed to be complementary to a region of the gene involved in transcription, preventing transcription and hence production of transporter protein. An antisense RNA or DNA nucleic acid molecule would hybridize to the mRNA and thus block translation of mRNA into transporter protein.

Alternatively, a class of antisense molecules can be used to inactivate mRNA in order to decrease expression of transporter nucleic acid. Accordingly, these molecules can treat a disorder characterized by abnormal or undesired transporter nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the transporter protein, such as ligand binding.

The nucleic acid molecules also provide vectors for gene therapy in patients containing cells that are aberrant in transporter gene expression. Thus, recombinant cells, which include the patient's cells that have been engineered ex vivo and returned to the patient, are introduced into an individual where the cells produce the desired transporter protein to treat the individual.

The invention also encompasses kits for detecting the presence of a transporter nucleic acid in a biological sample. Experimental data as provided in FIG. 1 indicates that the transporter protein of the present invention is expressed in humans in the testis, brain (adult and fetal), placenta, and bone marrow, as indicated by PCR-based tissue screening panels. For example, the kit can comprise reagents such as a labeled or labelable nucleic acid or agent capable of detecting transporter nucleic acid in a biological sample; means for determining the amount of transporter nucleic acid in the sample; and means for comparing the amount of transporter nucleic acid in the sample with a standard. The compound or agent can be packaged in a suitable container. The kit can further comprise instructions for using the kit to detect transporter protein MRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et aL. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides that cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the transporter proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the transporter gene of the present invention. FIG. 3 provides information on SNPs that have been found in the gene encoding the transporter protein of the present invention. SNPs, including insertion/deletion polymorphisms ("indels"), were identifed at 87 different nucleotide positions. Changes in the amino acid sequence caused by these SNPs can readily be determined using the universal genetic code and the protein sequence provided in FIG. 2 as a reference. SNPs outside the ORF and in introns may affect control/regulatory elements. SNP positioning in exons, introns, or outside the ORF can readily be determined based on the genomic features given in FIG. 3.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified transporter gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al, *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterotransporter. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11 d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al, *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840 (1987)) and pMT2PC (Kaufman et al, *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2$^{nd}$, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as transporters, appropriate secretion signals are incorporated into the vector. The signal sequence can be endogenous to the peptides or heterologous to these peptides.

Where the peptide is not secreted into the medium, which is typically the case with transporters, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a transporter protein or peptide that can be further purified to produce desired amounts of transporter protein or fragments. Thus, host cells containing expression vectors are useful for peptide production.

Host cells are also useful for conducting cell-based assays involving the transporter protein or transporter protein fragments, such as those described above as well as other formats known in the art. Thus, a recombinant host cell expressing a native transporter protein is useful for assaying compounds that stimulate or inhibit transporter protein function.

Host cells are also useful for identifying transporter protein mutants in which these functions are affected. If the mutants naturally occur and give rise to a pathology, host cells containing the mutations are useful to assay compounds that have a desired effect on the mutant transporter protein (for example, stimulating or inhibiting function) which may not be indicated by their effect on the native transporter protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA that is integrated into the genome of a cell from which a transgenic animal develops and which remains in the genome of the mature animal in one or more cell types or tissues of the transgenic animal. These animals are useful for studying the function of a transporter protein and identifying and evaluating modulators of transporter protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the transporter protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the transporter protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, transporter protein activation, and signal transduction, may not be evident from in vitro cell-free or cell-based assays. Accordingly, it is useful to provide non-human transgenic animals to assay in vivo transporter protein function, including ligand interaction, the effect of specific mutant transporter proteins on transporter protein function and ligand interaction, and the effect of chimeric transporter proteins. It is also possible to assess the effect of null mutations, that is mutations that substantially or completely eliminate one or more transporter protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:

(a) a nucleotide sequence that encodes a protein comprising the amino acid sequence of SEQ ID NO:2;

(b) a nucleotide sequence consisting of SEQ ID NO:1;

(c) a nucleotide sequence consisting of SEQ ID NO:3; and (d) a nucleotide sequence that is completely complementary to a nucleotide sequence of(a)–(c).

2. A nucleic acid vector comprising a nucleic acid molecule of claim 1.

3. A host cell containing the vector of claim 2.

4. A process for producing a polypeptide comprising SEQ ID NO:2, the process comprising culturing the host cell of claim 3 under conditions sufficient for the production of said polypeptide, and recovering said polypeptide from the host cell culture, wherein said isolated nucleic acid molecule encodes a polypeptide comprising SEQ ID NO:2.

5. A vector according to claim 2, wherein said vector is selected from the group consisting of a plasmid, virus, and bacteriophage.

6. A vector according to claim 2, wherein said isolated nucleic acid molecule encodes a polypeptide comprising SEQ ID NO:2 and is inserted into said vector in proper orientation and correct reading frame such that a polypeptide comprising SEQ ID NO:2 may be expressed by a cell transformed with said vector.

7. A vector according to claim 6, wherein said isolated nucleic acid molecule is operatively linked to a promoter sequence.

8. An isolated polynucleotide consisting of a nucleotide sequence set forth in SEQ ID NO:1.

9. An isolated polynucleotide consisting of a nucleotide sequence set forth in SEQ ID NO:3.

* * * * *

SEQUENCE LISTING

<160> NUMBER OF SEQ ID NOS: 4

<210> SEQ ID NO 1
<211> LENGTH: 5735
<212> TYPE: DNA
<213> ORGANISM: Human

<400> SEQUENCE: 1

```
cggccgcgtc gacgtgattt gatatcttga tgatggctta aacagatact gatggacaga     60

tctgttgttt gatatttttt tcactagccc tgaagatgct gagacataga gatggctgtg    120

attatctttt gtaagacagg aaatgcagtc tttaggggtt tctggaaata gaaaggtcat    180

gcagtctgga acctgtgagc cttttcaatc tctaagtcat cagagaaatg atgaagaagc    240

agttgtggat agaggtggaa ctcgttctat tctcaaaaca cactttgaga aagaagattt    300

agaaggtcat cgaacactat ttattggagt acatgtgccc ttgggaggaa gaaaaagcca    360

tcgacgtcac aggcatcgtg gtcataaaca cagaaagaga gacagagaaa gagattcagg    420

attagaggat ggaagggagt caccttcttt tgacacccca tcacagaggg tacagtttat    480
```

-continued

```
tcttggaacc gaggatgatg acgaggaaca cattcctcat gaccttttca cagaactgga    540
tgagatttgt tggcgtgaag gtgaggacgc tgagtggcga gaaacagcca ggtggttgaa    600
gtttgaagaa gatgtggaag atggaggaga aaggtggagc aagccttatg tggctactct    660
ttcattgcac agcttgtttg aattgagaag ttgtattctg aatggaactg tgttgctgga    720
catgcatgcc aacactttag aagaaattgc agatatggtt cttgaccaac aagtgagctc    780
aggtcagctg aatgaagatg tacgccatag ggtccatgag gcattgatga aacagcatca    840
tcatcagaat cagaaaaaac tcaccaacag gattcccatt gttcgttcct ttgctgatat    900
tggcaagaaa cagtcagaac caaattccat ggacaaaaat gcaggtcagg ttgtttctcc    960
tcagtctgct ccagcctgtg ttgaaaataa aaatgatgtt agcagagaaa acagcactgt   1020
tgactttagc aagggactgg gaggccaaca aaaggggcat actagtccat gtgggatgaa   1080
acaaaggcat gaaaaaggac ctccacacca gcaagagaga gaggttgatc tgcattttat   1140
gaaaaagatt cctccaggtg ctgaagcatc gaacatctta gtgggagaac tggagttctt   1200
ggatcgaaca gtagttgcgt ttgtcaggtt gtctccagct gtattgcttc aaggactggc   1260
tgaagtccca atcccaacca gatttttgtt cattcttctg ggacccctgg gaaagggtca   1320
acagtaccat gagattggca gatcaattgc aaccctaatg acagatgagg tatttcatga   1380
tgttgcctat aaagctaaag atcgtaatga cttggtatca ggaattgatg agtttctgga   1440
tcaggttact gttctccctc ctggagaatg ggatccaagc attcgaatag agcctcccaa   1500
aaatgttcct tcccaggaga agaggaagat tcctgctgta ccaaatggaa cagcagctca   1560
tggggaagca gagccccacg gaggacatag tggacctgaa ctccagcgaa ctggaaggat   1620
ttttggggga cttattttag atatcaaaag aaaagctcca tacttctgga gtgacttcag   1680
agatgctttc agcctgcagt gcttagcatc ttttctattt ctctactgcg cgtgtatgtc   1740
tcctgtcatc acgtttggag gactgctggg agaagcaact gaagggcgta taagtgcaat   1800
tgaatctctc tttggagcat ccatgaccgg gatagcctat tctctctttg gtggacagcc   1860
tcttaccata ttaggcagta caggaccagt tttggtgttt gaaaagattt tgtttaaatt   1920
ttgcaaagaa tatgggctgt catacctatc tttaagagct agcattggac tttggactgc   1980
aactctatgt atcatacttg tggccacaga tgctagttcc cttgtctgct acatcactcg   2040
gtttactgaa gaagcttttg cttccctgat ttgcatcatt ttcatttatg aggccctgga   2100
gaagttgttt gaactcagtg aagcatatcc aatcaacatg cataatgatc tggaactgct   2160
gacacaatac tcgtgtaact gtgtggaacc gcataatccc agcaatggca cattgaagga   2220
atggagggaa tccaatattt ctgcctctga cataatttgg gagaacctaa ctgtgtcaga   2280
atgcaaatca ttgcatggag agtatgttgg acgggcctgt ggccatgatc acccatatgt   2340
tccagatgtt ctattttggt ctgtgatcct gttcttttcc acagttactc tgtcagccac   2400
cctgaagcag ttcaagacta gcagatattt tccaaccaag gttcgatcca tagtgagtga   2460
ctttgctgtc tttcttacaa ttctgtgtat ggttttaatt gactatgcca ttgggatccc   2520
atctccaaaa ctacaagtac caagtgtttt caagcccact agagatgatc gtggctggtt   2580
tgttacgcct ttaggtccaa acccatggtg gacagtaata gctgctataa ttccagctct   2640
gctttgtact attctaattt ttatggacca acagattaca gctgtcatca tcaacaggaa   2700
agagcataag ctaaagaaag gttgtgggta ccatctggac ctattaatgg tggctgtcat   2760
gctcggtgta tgctccatca tgggcctgcc atggtttgtg gctgccacag tcctctccat   2820
```

-continued

```
cactcatgtc aatagcctaa aactggaatc agaatgctca gctccaggag aacaacccaa   2880
atttctcggc attcgggagc aaagggttac tgggcttatg atttttattc ttatgggttc   2940
atcagtcttt atgaccagta ttctgaagtt tattcccatg ccagtgctat atggagtgtt   3000
tctttatatg ggtgcttcat ctctaaaggg aattcagttc tttgatagga taaagctctt   3060
ctggatgccg gcaaaacatc aaccagattt tatataccta aggcacgtac cgcttcgaaa   3120
agtgcatctc ttcacaatta ttcagatgag ttgccttggc cttttgtgga taataaaagt   3180
ttcaagagct gctattgtct ttcccatgat ggtgttagcc ctggtatttg taagaaagtt   3240
gatggacttg ttgttcacga agcgggaact cagctggttg gatgatttga tgcccgagag   3300
taagaaaaag aaactggaag atgctgaaaa agaagaagaa caaagtatgc tagctatgga   3360
agatgagggc acagtacaac tcccattgga agggcactat agagatgatc catctgtgat   3420
caatatatct gatgaaatgt caaagactgc cttgtggagg aaccttctga ttactgccga   3480
taactcaaaa gataaggagt caagctttcc ttccaaaagc tccccttcct aatcactcta   3540
gaagctgatt ccccaaagca ttgaaagccg aaaagagaag aaagctgact cagggaaagg   3600
tgttgacagg gagacttgtc tatgactcga tcttcaattt attttttaca tatatatgag   3660
aagagtgtca caattattaa taaaactgct ttgatcatgt attgtaaatt ctgtccctca   3720
acccaaatcc accttcatac tgtaagtagt gcaatacttg tttcatttct gtgtttaaac   3780
ttctgagcag tgagacatcc ctgtgagcag atacaatagc caatgcaaga atctgtgtgt   3840
tccttgctgt acgttagaca tttgtaaact ggattctgat tgtcagtttt atgagagcaa   3900
tagcttcctt aaagagataa gtcatattta cctagtttgt attttcctac tttagtgacc   3960
tgaagatgcc tgataatttc attcagaaga atttttgaaa ggtagtctta cttcttttta   4020
gtttttatag cttagcatta gtgacttatt tcaaaagacc caaatcaaaa agttagtttg   4080
aaagcatttt ttaataattg tatttatgca tttccttgat ttaatatgat aaatttaata   4140
cttaacaatt tatatgtaac taaaacttaa agtcatttga aaaatatata gaaacctatt   4200
tacaacttgt taaggacaat cagacataat gcagagttaa gtagtatttg cttaaaattc   4260
aagttgtgac taatgatcaa atactaggct tgtacgaaat gctttagaaa aactttgtaa   4320
cagttttgtg ggatttttca atataaacct ttatcagaaa tatactaagt ttgtctccca   4380
ctgacaacag atgttttcca aataaacata ttctatacat acttgtggaa tgccacatgg   4440
tgaatcattg tatatgaaat tccactcctg tacagttact ctgcagctaa tggtcatgca   4500
ctgcttaatg ctggtcctga atcatgttct catgttagac caacagctct ccaattgtca   4560
tttttttct gcagagtttt ttttttcca cttttaaatt aaatgcatgt tgtggaaaaa   4620
cagtctttta aaatgaaatt tcagattcca tttgagaagg ttctgtagat atttcagtcc   4680
atataaaata atacatcttt actaaactta tataagggga gagaaagtta tgaagttttg   4740
gacattacta aaagtacagt atttgatttc actttcaatg aatgtgaagt taataaaact   4800
aaatctcata atgctcttgg ttcctaagaa tgagtagtaa tcatcaactt tataatactc   4860
caatattccg ttttataata attcagagcc ctgtggcttt tacacaccgt taattatgta   4920
ctctgttgga agtgcacatg aaaagtgaag aaaagttcct cttgtgatta aactaatggg   4980
aggaaataaa tcaacaaagt ctccattaag ttctacattt tgagaccttt taaaaattcc   5040
cctcacaatt ctttaaggag cccccctttt tatggaacat gagcctaaaa attatagaaa   5100
gaagaatttt aagttaataa agtttgtatt tataaatgct gaaaaaatac agaaactttc   5160
tgttccaaat gtgttgcctt tgtgtatttt ataatacaga tactacattg taaacatttc   5220
```

-continued

```
cattgtttta tgatttagcc agtgattccc caaagcagcc tcttagtgtt ttaatatatt   5280

aataactgtt ttgttaaaaa tgatcatagt gaatttaaat cttcacatga tcacctattt   5340

gaataagcaa tcatatccaa tgaaattctg tatttctgag tatttttata gtcattttgt   5400

tcttgtgtga attttaaagc tatccctatg ttaatcctaa tattttgaaa tcatataaaa   5460

tataataaaa atgtagtatt atatatttac ttctaatttc agattcctgg tcaaaattac   5520

taaatatctt gaatgtaatt tagtgccaag tttaaataat gtgtaaatgt gactaggata   5580

ttgtgttttt cacaattaag aaatgttatg tggaaataaa tatttatcct aacttccttg   5640

cacattttaa attgtgatac aaagtgtctt gtctttttc tttgttttaa ttagtaaatc    5700

agtgtaaaac aaaaaaaaaa aaaaaaaaaa aaaaa                              5735

<210> SEQ ID NO 2
<211> LENGTH: 1129
<212> TYPE: PRT
<213> ORGANISM: Human

<400> SEQUENCE: 2

Met Gln Ser Leu Gly Val Ser Gly Asn Arg Lys Val Met Gln Ser Gly
 1               5                  10                  15

Thr Cys Glu Pro Phe Gln Ser Leu Ser His Gln Arg Asn Asp Glu Glu
            20                  25                  30

Ala Val Val Asp Arg Gly Gly Thr Arg Ser Ile Leu Lys Thr His Phe
        35                  40                  45

Glu Lys Glu Asp Leu Glu Gly His Arg Thr Leu Phe Ile Gly Val His
    50                  55                  60

Val Pro Leu Gly Gly Arg Lys Ser His Arg Arg His Arg His Arg Gly
65                  70                  75                  80

His Lys His Arg Lys Arg Asp Arg Glu Arg Asp Ser Gly Leu Glu Asp
                85                  90                  95

Gly Arg Glu Ser Pro Ser Phe Asp Thr Pro Ser Gln Arg Val Gln Phe
            100                 105                 110

Ile Leu Gly Thr Glu Asp Asp Asp Glu Glu His Ile Pro His Asp Leu
        115                 120                 125

Phe Thr Glu Leu Asp Glu Ile Cys Trp Arg Glu Gly Glu Asp Ala Glu
    130                 135                 140

Trp Arg Glu Thr Ala Arg Trp Leu Lys Phe Glu Glu Asp Val Glu Asp
145                 150                 155                 160

Gly Gly Glu Arg Trp Ser Lys Pro Tyr Val Ala Thr Leu Ser Leu His
                165                 170                 175

Ser Leu Phe Glu Leu Arg Ser Cys Ile Leu Asn Gly Thr Val Leu Leu
            180                 185                 190

Asp Met His Ala Asn Thr Leu Glu Glu Ile Ala Asp Met Val Leu Asp
        195                 200                 205

Gln Gln Val Ser Ser Gly Gln Leu Asn Glu Asp Val Arg His Arg Val
    210                 215                 220

His Glu Ala Leu Met Lys Gln His His His Gln Asn Gln Lys Lys Leu
225                 230                 235                 240

Thr Asn Arg Ile Pro Ile Val Arg Ser Phe Ala Asp Ile Gly Lys Lys
                245                 250                 255

Gln Ser Glu Pro Asn Ser Met Asp Lys Asn Ala Gly Gln Val Val Ser
            260                 265                 270

Pro Gln Ser Ala Pro Ala Cys Val Glu Asn Lys Asn Asp Val Ser Arg
        275                 280                 285
```

-continued

```
Glu Asn Ser Thr Val Asp Phe Ser Lys Gly Leu Gly Gly Gln Gln Lys
    290                 295                 300

Gly His Thr Ser Pro Cys Gly Met Lys Gln Arg His Glu Lys Gly Pro
305                 310                 315                 320

Pro His Gln Gln Glu Arg Glu Val Asp Leu His Phe Met Lys Lys Ile
                325                 330                 335

Pro Pro Gly Ala Glu Ala Ser Asn Ile Leu Val Gly Glu Leu Glu Phe
            340                 345                 350

Leu Asp Arg Thr Val Val Ala Phe Val Arg Leu Ser Pro Ala Val Leu
        355                 360                 365

Leu Gln Gly Leu Ala Glu Val Pro Ile Pro Thr Arg Phe Leu Phe Ile
    370                 375                 380

Leu Leu Gly Pro Leu Gly Lys Gly Gln Gln Tyr His Glu Ile Gly Arg
385                 390                 395                 400

Ser Ile Ala Thr Leu Met Thr Asp Glu Val Phe His Asp Val Ala Tyr
                405                 410                 415

Lys Ala Lys Asp Arg Asn Asp Leu Val Ser Gly Ile Asp Glu Phe Leu
            420                 425                 430

Asp Gln Val Thr Val Leu Pro Pro Gly Glu Trp Asp Pro Ser Ile Arg
        435                 440                 445

Ile Glu Pro Pro Lys Asn Val Pro Ser Gln Glu Lys Arg Lys Ile Pro
    450                 455                 460

Ala Val Pro Asn Gly Thr Ala Ala His Gly Glu Ala Glu Pro His Gly
465                 470                 475                 480

Gly His Ser Gly Pro Glu Leu Gln Arg Thr Gly Arg Ile Phe Gly Gly
                485                 490                 495

Leu Ile Leu Asp Ile Lys Arg Lys Ala Pro Tyr Phe Trp Ser Asp Phe
            500                 505                 510

Arg Asp Ala Phe Ser Leu Gln Cys Leu Ala Ser Phe Leu Phe Leu Tyr
        515                 520                 525

Cys Ala Cys Met Ser Pro Val Ile Thr Phe Gly Gly Leu Leu Gly Glu
    530                 535                 540

Ala Thr Glu Gly Arg Ile Ser Ala Ile Glu Ser Leu Phe Gly Ala Ser
545                 550                 555                 560

Met Thr Gly Ile Ala Tyr Ser Leu Phe Gly Gly Gln Pro Leu Thr Ile
                565                 570                 575

Leu Gly Ser Thr Gly Pro Val Leu Val Phe Glu Lys Ile Leu Phe Lys
            580                 585                 590

Phe Cys Lys Glu Tyr Gly Leu Ser Tyr Leu Ser Leu Arg Ala Ser Ile
        595                 600                 605

Gly Leu Trp Thr Ala Thr Leu Cys Ile Ile Leu Val Ala Thr Asp Ala
    610                 615                 620

Ser Ser Leu Val Cys Tyr Ile Thr Arg Phe Thr Glu Glu Ala Phe Ala
625                 630                 635                 640

Ser Leu Ile Cys Ile Ile Phe Ile Tyr Glu Ala Leu Glu Lys Leu Phe
                645                 650                 655

Glu Leu Ser Glu Ala Tyr Pro Ile Asn Met His Asn Asp Leu Glu Leu
            660                 665                 670

Leu Thr Gln Tyr Ser Cys Asn Cys Val Glu Pro His Asn Pro Ser Asn
        675                 680                 685

Gly Thr Leu Lys Glu Trp Arg Glu Ser Asn Ile Ser Ala Ser Asp Ile
    690                 695                 700
```

-continued

```
Ile Trp Glu Asn Leu Thr Val Ser Glu Cys Lys Ser Leu His Gly Glu
705                 710                 715                 720

Tyr Val Gly Arg Ala Cys Gly His Asp His Pro Tyr Val Pro Asp Val
                725                 730                 735

Leu Phe Trp Ser Val Ile Leu Phe Phe Ser Thr Val Thr Leu Ser Ala
            740                 745                 750

Thr Leu Lys Gln Phe Lys Thr Ser Arg Tyr Phe Pro Thr Lys Val Arg
        755                 760                 765

Ser Ile Val Ser Asp Phe Ala Val Phe Leu Thr Ile Leu Cys Met Val
    770                 775                 780

Leu Ile Asp Tyr Ala Ile Gly Ile Pro Ser Pro Lys Leu Gln Val Pro
785                 790                 795                 800

Ser Val Phe Lys Pro Thr Arg Asp Asp Arg Gly Trp Phe Val Thr Pro
                805                 810                 815

Leu Gly Pro Asn Pro Trp Trp Thr Val Ile Ala Ala Ile Ile Pro Ala
            820                 825                 830

Leu Leu Cys Thr Ile Leu Ile Phe Met Asp Gln Gln Ile Thr Ala Val
        835                 840                 845

Ile Ile Asn Arg Lys Glu His Lys Leu Lys Lys Gly Cys Gly Tyr His
    850                 855                 860

Leu Asp Leu Leu Met Val Ala Val Met Leu Gly Val Cys Ser Ile Met
865                 870                 875                 880

Gly Leu Pro Trp Phe Val Ala Ala Thr Val Leu Ser Ile Thr His Val
                885                 890                 895

Asn Ser Leu Lys Leu Glu Ser Glu Cys Ser Ala Pro Gly Glu Gln Pro
            900                 905                 910

Lys Phe Leu Gly Ile Arg Glu Gln Arg Val Thr Gly Leu Met Ile Phe
        915                 920                 925

Ile Leu Met Gly Ser Ser Val Phe Met Thr Ser Ile Leu Lys Phe Ile
    930                 935                 940

Pro Met Pro Val Leu Tyr Gly Val Phe Leu Tyr Met Gly Ala Ser Ser
945                 950                 955                 960

Leu Lys Gly Ile Gln Phe Phe Asp Arg Ile Lys Leu Phe Trp Met Pro
                965                 970                 975

Ala Lys His Gln Pro Asp Phe Ile Tyr Leu Arg His Val Pro Leu Arg
            980                 985                 990

Lys Val His Leu Phe Thr Ile Ile Gln Met Ser Cys Leu Gly Leu Leu
        995                 1000                1005

Trp Ile Ile Lys Val Ser Arg Ala Ala Ile Val Phe Pro Met Met Val
    1010                1015                1020

Leu Ala Leu Val Phe Val Arg Lys Leu Met Asp Leu Leu Phe Thr Lys
1025                1030                1035                1040

Arg Glu Leu Ser Trp Leu Asp Asp Leu Met Pro Glu Ser Lys Lys Lys
                1045                1050                1055

Lys Leu Glu Asp Ala Glu Lys Glu Glu Glu Gln Ser Met Leu Ala Met
            1060                1065                1070

Glu Asp Glu Gly Thr Val Gln Leu Pro Leu Glu Gly His Tyr Arg Asp
        1075                1080                1085

Asp Pro Ser Val Ile Asn Ile Ser Asp Glu Met Ser Lys Thr Ala Leu
    1090                1095                1100

Trp Arg Asn Leu Leu Ile Thr Ala Asp Asn Ser Lys Asp Lys Glu Ser
1105                1110                1115                1120

Ser Phe Pro Ser Lys Ser Ser Pro Ser
```

-continued

1125

<210> SEQ ID NO 3
<211> LENGTH: 202001
<212> TYPE: DNA
<213> ORGANISM: Human
<220> FEATURE:
<221> NAME/KEY: misc_feature
<222> LOCATION: (1)...(202001)
<223> OTHER INFORMATION: n = A,T,C or G

<400> SEQUENCE: 3
gccttgggag ctgtgagaaa taaatatttg ttgttgtggc attttgttat agcagcccaa 60
atggactaag atacactctt ttggctctct cttcattcag tccaagggtg ttctgctagg 120
ttttggctac tcttcatttc ttttatcaaa tatttgttaa ggcttattag ggcctaaagt 180
ctagaggcat tctgctttac tattatgacc atatcttaat aacactggta tgagtaacat 240
actgtatgag taaataattt gttttagagc aatggttttc taaaaatggg agatcatagt 300
ttttagtaat taattgtgtt aaattactat taagagggtc aagtaataga tgttaagtaa 360
ttttttggat taaatagatc ttatcaacta gataatagag agattaagag ctgctttgca 420
ctcaggtttc atgtttttat tgcaaagatc aattgtgctt acaagaaaac actgaaggaa 480
attggggatt atatatacta attaataaca tccagagaat gataaaaata tcagtgtttg 540
tattcttgct gtgacaaaat acctgaagga aaagttcaat tttcttattt ttcattattg 600
attcatttaa taactttgat atgtaatagt ataggagatt aggaatgaac cttgcttgat 660
gtttcgcttt tcctcatttc tcacattcaa tccctgaatt ctatcttttt tcaataagat 720
gtgtatctgg atctattcat ttctcttcat tcctattgcc acttctttgg ttcaggccat 780
catcatcccc tgattgaaat tatttaacat tctcctgatt tgtctcccgt cctccagttt 840
tgttttactc aattgattgt ctatagagta gccgggatat tttaaacctg attatgctga 900
cagtttgtca tttccctaag ggtaaagctc acactcttta aatggctcct gacgcttacc 960
gtgactgggc ctcacttctc atctcttccc tctgttctta cactttatgg tctaacctat 1020
gttgtatttg ccattccttg aatgtgacta gatcagaatc ttctgtttta acagtacttc 1080
cctaaggaaa tcttttctga tccctagatt agggtaggat gccttgctac ggctttcatg 1140
tcaactttta attcttcagt tataacaaaa catgcttgtt tgatttatct gctttctgtg 1200
atggcaggtt ttgtgttgtt tgttatggag tccctagcac ctatatagta cctgacacat 1260
agtaagaatt caatattttc tacaggaaag aatgaatata gaaagagaga cgatgtagct 1320
taggaaggct ttattgagaa gataggtctt aaaggatgag tacctatttt gattataata 1380
agagggtaaa tactacatag atggaaatat ttgtttacat gtgatttttc attcagatgt 1440
gttatagtat acatacagca gaataccaag ctctgtgtct ccaacctgtg cagttagagt 1500
cagtagtttt tctaaaagta taatttggat cagcccagtt tcttaagact cattgtgact 1560
agtctccatc aaatgttgtg agtgaaagaa gggaaactat tcacaggtaa ataaagtgtt 1620
catagagtcg tgaattcagg ctattcataa tgtgagggct gtttcaggat aatatgttgc 1680
acttggtgtc ttaattttga atgtagttga attgactata atcttagtct tttttttttt 1740
tggtttgtgt tttctttagt tataaaacac aacctttttgt cacacggtaa agagaaagca 1800
tttccaatta taatttttga gatattgatt ctatattaga acactttatc aatcttaaag 1860
ttccctgatt ctgctatgtt gtggtaaaag aaaacagtac tcaaacttta ataaataaga 1920
cacagtgaaa atccatagta aaaatgccaa caacttacat aggtttcatt actagactta 1980

-continued

```
accgtgcagt tttagcattt gataatacca cattatcttt tgcatgtaaa ttctttagaa   2040
gaagatatta aataaaaaga taaaatgtat gttggtatga agaatctgaa acataaatga   2100
aatccctgaa aattaaaagg tgaatatgta tttacctatt tactatttac acaactatca   2160
aagattgcca aaataaaaat cctgtatagg cgctcatcat tttgatgggt ggataagtcg   2220
tgatacccat agtttggaag gaagattcct tcaagagagt acaattttgc ttggtaaatc   2280
ttttgcatgt taaacttttt agaagaagaa attaaataaa aatataaaat gtatgttggt   2340
atgaagaatc tgaaacataa atgaaattcc tgaaaattaa agggtgaata tgtatttacc   2400
tatttactat ttatacaact atcaaagatt gccaaaataa aaatcctttt taggcactca   2460
tcattttgat gggtggataa gtgatgatat tcagagtttg gagggaaaat tcctttaaga   2520
gagtataatt ttgcttggta agtcataaag cctaaagctt agtcacatat agagaaagct   2580
gcctaataat taagagttga cattttaaca tggtatttgc aacagacaca ttggatactt   2640
aattaaatgg aaaactgctt atttttaaag gactgaaaaa attcaactct ccttggcaaa   2700
tgaagtcttc atagtatcag aaatggggaa atctgaagga tgtggctcat tctctgtttc   2760
gatgatgcag aattgctcta agcagtaagc ttacagtttt cagacagcat cagcaaatac   2820
aactgtgtca gtctctctta gtatggggtg tttgtaactg cacaggggag atgataaata   2880
gtatatgtga tttgatatct tgatgatggc ttaaacagat actgatggac agatctgttg   2940
tttgatattt ttttcactag ccctgaagat gctgagacat agagatggct gtgattatct   3000
tttgtaagac aggaaatgca gtctttaggg gtttctggaa atagaaaggt catgcagtct   3060
ggaacctgtg agccttttca atctctaagt catcaggtat gacctcatga attatgatga   3120
taatattaga atgtagggtg cttgcttttt ctagttctta ctcattgaaa atatattcat   3180
taatgtaatt gtttattgtc agactttcct taggatattt gaacaagtaa gatttatggc   3240
agctaaacaa tatgattatt agaaatgtgt gtgtatgtgt gtgcctgtgt gtgtgtatgt   3300
gtttaaattt gtgtttactt tagctttttg ggggagaggg cggtaaagga agagattctt   3360
tgaatgtgat taaaagcaag gtttggggca cttcagattt ttccagatta agcctgaata   3420
gagtcaatct ttatatttta cttcaagtga taaaaatagt ataaatcgat caaactgata   3480
aggatacatc gtagctagct gcttacagat actgatatat tgcaaatatt tttattattt   3540
ggaatttctt aaccatagaa actgatgctg ctaccattgt agtgtgctac atagcaaagg   3600
aagtttggtg aatagaatca tctttgtcag catctgacct ataaactaat ttcctgaaat   3660
ttatgttgca ttatctgaac tgttgtaaag acactggttt taatcatttc tcagatctat   3720
tgaaatattg atgctcttgg tgcttttaag gtagatatat actaacgtat tgttcataga   3780
agaaaggaga ctataaatct gtttttcaca aagaaagctt gtgacattta agcttgttga   3840
agattttttg acccagagag cttcgtcctt tgcttacttt cattttcaaa ctgaaaatac   3900
ttgactatgt taaacatgca aatgatttgg atttcgatgt ccattttgta ctgaaactct   3960
gccatttatt ttaaactatt ttcacccatc aagttatata taatgcattt aactttgatt   4020
tgttacagca tgtcctcaga attatatact tggataagaa actacctata tttgacattc   4080
agattttgaa ggaaatatat ttcatttttc aaaatattgt acatgcttct gcctcaatgt   4140
tagagaactt ttcaggtact ccatattaaa tgatcaaaaa gagagaaata tattgcagca   4200
gttctcaaca gcaagatggt tttgtcttta tgattctgta gcctgattgt aatttaatgc   4260
cttatcaggg tgaaatgaca tagattaaaa aaatgaatat atttaaggaa gtctgaaaca   4320
```

-continued

```
atgaattgat tcagttaagg ggtttctcct ttttaattaa aaacacattc tgcctactga   4380
tattgactat aatttatatg ttattcaggc tacttagcca gcttatattc ttattagtag   4440
ggaagattgg catattctta agcttgatta attttgaaat gatttgaata taccttttaa   4500
ttgcaacaaa atatgtctaa tctgttagaa tttatttcca gtatttgcat gtattagtca   4560
ttatgagtac attctgtttc ttggcattgc tttgggattc ctcttggtat tggtttcaca   4620
gcattctgct atttttcact gtattcctga cctttcaaga gaaccaaact gtaaagattt   4680
ttagttactt tctgttagtg gcatttaaat gaggatatcg ataattttgt aaggtggaaa   4740
aaaattacta ttttagaatt gtcatttctg tcacaaatca gagaaatttt tctctattac   4800
tatttcaaaa tatactacaa taaaaagcaa agactggtta gaatgtagtt aaatgcaatg   4860
tcaatctttc ttcttgcatg gcaggataat cttgatcttt ggaatgataa aactgattgt   4920
aaacttgccc agtaatgatt ggtcatcttc cttacaaagg ctgccttcgt ttatactatt   4980
ttacatgcat ttcattatac atcataaagg ttttaaaggt aagctgccta taaaaactat   5040
ttgagtaatt cttcaattca gtaaacatag taaaggctga gcattggatg atactgtatg   5100
tatttggtgt tatgaggaat gcagaaaaga aaaagtcatt tccggctttc aaggagatta   5160
gtgaatatat gcaatgaatt gtgttcacat tttgaattga tttttgatag gcagtatgct   5220
acaatcagtt ttaacttaat ctataagctg atgaatccta gaaggagtta catgtaacct   5280
tttttcctca tgtaaatttc ttgatattag ataaatgaag gcttaggtca aactgtatca   5340
ttatgcatcc cataacttta ttgaaaattg cattaaagac ttttagagtg catagtttct   5400
cgtatagggc tttataaact gtgaatcagt aaaatagcaa aatagctttg catgttgtat   5460
aagccatcat tgtcagtatg agactgaagg tgcacccagt ccactggcag gaggcagaag   5520
tgtcagctca acatagagac ttgatcaatc ctgtctaatt ccaggctcag tgtgggtaat   5580
taagtattat ggaaggggtt ttgactttat agggataaaa cttggaaata aagagtagca   5640
agtatggaag tgtctgttac taactaggtc atttggagag tcctttgaat aaaatggggg   5700
aataggattt acctcaggtt ctgagaaagc ggatcaggac caactaatta tggaagtgga   5760
ccttagctgc tgcttggtga acagtcaggc attactctct tctctttcat tccaatatgt   5820
ttgctgaaag ttgcaggaag gtgggtggag aagatgcaaa gcccttgttt ccccagaatc   5880
ccaaactgga acacgctgcc tgatagtgcc tccaaagtgc ctgtttcctt gtattagagc   5940
aatagaaaat tgatttgcaa attcttctgg tttgtaatgg ctggctgcag taagaggctt   6000
gtgcaatggt tcagtgtctg gactgccatg ttctctgggt tcaaatctta gctatgctac   6060
ttactggctg catgatcttg gcttgtttcc tgatgtgtaa tatagggata ataatggcac   6120
ctacctcaaa gagttgtggt aaacattaag tgagttaatg tatgtgaaac acttataaga   6180
gtacctgaca tatatcaaac atattattgt caacatcctt tgtcgacaga ctttgttata   6240
gacattctaa gaggttggat gggctattgg caagactttg taacagtcat catgcagttt   6300
agttttgttc cctctccctt aatctcttta tcaaataaga aattcagcca aaaatatatg   6360
ctacactgaa atatagttat aaaaatgcaa acaaagaaca acatgctata tctgattcaa   6420
ttctaacatt tactgacaat aagaattgtg acttgatgaa agattttgtg tttaaacttt   6480
acatctacct gctaggctga tccaaactct cttagaattc tatgtgtgca gattctttgc   6540
ttctctgtat tacaccaact actttattca tgactgaaag attactagga ctttgggaaa   6600
atttaacagc aacttaaggt ctttcttgtt tattgtttaa gactaaaatt aaggggtaaa   6660
aaaaagcctt tctttaaagg cttaaaaaaa ataatagggg caaatttacc tagcatagat   6720
```

-continued

```
ttagtgatac ttagtcatca aaaatgtcca agacaaaaaa ttttaccgaa agtcaaacac   6780
aacttgtttt taataatttt atttcttggc atttttattc tagatgaaac actaaatgaa   6840
atatattata aatagaatgc tacatatata agtagaacaa ttcaagttcc catttgatag   6900
agtataatat tttgaattgc tggtgattat ttaatgtaaa aacatttatc tgcttaaaat   6960
tctcaataaa cttcaaagag aagtgagtaa tatgatattt ggattaaatt tacatgctta   7020
aatatggcat tttattacat ctctgaattt cacttctctt ctctgaagaa atttcctcag   7080
tgtgctgctg tttcccccaa attggcagag tcagttgaat ctcagaataa tgcaattttt   7140
aaaaacaaat atacaaaatc ctacaatgtt ctagaaagaa ttgtactggg caaggatata   7200
aaagtctgta ggtctctgcc ttcaggaggt cacaggtaat gggttgtaac tacaaaatac   7260
aagtaactat ggcagaatat gaaagtagtg aatgccatga ggtagtcttg aagactggcc   7320
aacatagaga gaaaaggtca tttcaggcag aggaaacaac atcattaaag gtagggaggc   7380
agaaagcaaa taatagaata gttcattttg gctatagcct agtgggataa cttagactta   7440
ccacaggaaa ggtttgttgg gaccagataa gtgtagaatc ttgaatgcta gactatgatt   7500
tctaaactga gaacatttct ttgctgatgt acgtattcct ggaaaaaata aaataaaaaa   7560
aacaaaagag cagtacctat attttgaagt cattttcaga gctctaaccc tcttgagact   7620
ttgagaatga aaattaaatt cctgagtaga tttagtagtt agtagacaag gtagggggta   7680
gaaacaaact gaaggatttt aataaaattt tctatcaaaa ttgcacatga gagcatttct   7740
cagtctatcc acaagcactc aaaagtccta gatttcagat cctaagagac ctcctgcttg   7800
tccgtgatgt aaactccatt ttattggtac gtaatctgat ttagctttgg ctttgttttt   7860
gacatttcct aaagcaagga caatctagtg ggatcatttt aatacaatga atactcatgt   7920
tactatggtg aatagttgga taaaaaggac tttgtcttag ggaaaattgg aaattaaaat   7980
tgccattttg aatcacggaa gtcgctgaat attttacctt tgttctctgt tcatttaaaa   8040
atcataaagt aaaccatgtt tgcaaatact tttaatatcg ccttcttcta ctccatacac   8100
cagaggcatt ttagtattgc atgaggttag taaaaaagct ggataccttc caagagcaga   8160
tttcctttag atgtgacagc tgggatgtga cttttggtat cagatgcagg aagacgtcat   8220
ttgtacatgg taattgtgaa aaaattggaa cttattactc tcagtataaa tgatccataa   8280
aaagtatgtc agaagtaaaa ctcctggaat tctacaggga gagttaaaat aaaaccagac   8340
acaggtgctc atctgactct atttttagaa caataggaga ctcatataac tgagaatgct   8400
ctgtacttcc tgtataaatc tacattattt gaaagtcgta ttttctagaa gttcctgtga   8460
agttgtactt attaatcttt gcaacttcac attgcctagg aaagagccat tcacctggta   8520
ggaacccaac aaattttcag tgcttgtctt agaatcatag tcccatttct gaaagaaacc   8580
ttgaatatca ttgggcttca agttgttcta aaaatgttta agcatttaaa catggttttc   8640
tttctcaaaa agcaaataga aggcatttag aggaaaagga ccctttcttc accttaagac   8700
ttttaaaaat ggcaatatgg gaagattaat aagaagaata agttaaggga gaattcaata   8760
ttcctccatg aaactactct ttctaaaagg caacagagac tggttccagt gaagcatatt   8820
atgatgtgtg gcgtgtaaat gtatatcatt atccctactc atctttttcc ccaaattcaa   8880
tttaatactc ataagaattt attgaggcta ctgtataaca tggaggaaag ctgtatacca   8940
cagtagcaag gagctagggc tccagagcgg gactcctgtg ttatgatccc atatcttcca   9000
ctttactggc aatttttatc ttaggaagtt acttaatctc tcttttcttc agtgttttca   9060
```

-continued

```
tctgtgaaat gaggacacta atacgttaat ctctagagtt gtaatgaaaa tcaaataaaa   9120
taataaatta atacttcaaa cagtgcctag agtgtttgat acagtgccta gcttttggtt   9180
attataatta tccccactga actaggtaaa tgctacaaat atgtatgtgt atatttgtgt   9240
gtatacacac aaatatgcat atatgtacac acacatactg tacatcctat gtaaacacaa   9300
ttttagtatg tatgtatgtc tatacatacg tatacattct accttaagta tatatagtat   9360
actgaaaaag aaatttagta gtttgcccaa gatcaaaatt gcctgcaaag gataggacaa   9420
tttgagtttc aaacccagaa agtctagctc tacagctgtt ggccttaact actgtttcat   9480
actgtttaga gtataaacac ctgaattaga tagccatgta taaattagca tattctaaat   9540
gccaaattga gactaaagac atgaaggtaa actgaaacta ctgtgaaaga cttaatggaa   9600
gaattgtgac ttttatttga ttttaagttc tgggatacat gtgcaggata cgcaggtctg   9660
ttacataggt aaatgtgtgc caaggtggtt tgctgcacct atcaacccat cacctaggta   9720
ttaagcccag catgcattag ctatttttcc ttatgctctc cctcttctca cacacccctc   9780
agcagacccc agtgtgtgtt tttcccctgc ctgtgtccat gtgttctcat ctttcagctc   9840
ccagtgagaa catgtggtat ttggttttct gttcctgcgt tagtttgcag atgataatgg   9900
cttccagctc catccatatc cctgtaaaag acatgatcta attcctttct atggccacat   9960
agtattccag ggtgtctatg taccacattt tctttatcca gcctatcatt gatgggcatt  10020
tgggttgatt ccatgccttt gatattgtta atagtgctgc aatgaatata cgcacgcatg  10080
tatctttata atagaatgat ttatattcct ttgagtgtat acccagtaat agggtcaaat  10140
ggtatttctg gtgcaggtct ttgaggaatt gccacactgt tttctacaat gtgtgaacta  10200
atttacattc ccaccaaaaa tgtaaaagtg tttctgtttc tccacagccc tcgctagcat  10260
ctgttgtttc ttgacttctt tataatcacc attctgactg gcatgagatg gtatcttatt  10320
gtggttttaa tttgaatttc tctaataatc agcaatatta agctttctct aaatatgttt  10380
tttggctgct tatatatctt cttttgagaa gtgtctgttc atgtcctttg cccacttttt  10440
gatgggtttt tttttttct tgtaaatttg tttatgttcc ttgtagagtc tggatactag  10500
gcctgtgcca gatggatgga ttgcaaaaat ctcccattct gtaggttgtc tgttttctct  10560
gatgatagtt tcttttgctg tgcagaagtt ctttagttta attagatccc atttgtaaat  10620
ttttgctttt gttgcaattg cttttgatat ttttgtcatg aaatctttgc ccgtgcctat  10680
gtcctgaatg gtattgccta gattttcttc tagggttttt ataattttgg gttttacatt  10740
taagtcttta ctccatcttg agttaatttt tgtaaaagat gtaaggaaaa ggtccatttt  10800
caattttctg cactatttat taaataggga atcctttctc cattgcttgt ttttgtcagg  10860
tttgttgaag atcagacaat tgtaaatgta tggtcttatt tctgagttct ctattctgtt  10920
ccattggtct atgtgtctgt ttttgtacca ataccatgct gctttggtta ctgtagcctt  10980
gtagtacagt ttgaagttgg gtagggtgat gttgccagct ttattctttt ttctttagga  11040
ttgtcttgac tataccagct cttttctggt tccatatgaa ttttaaaatt ttttttctaa  11100
ttctgtgaag aatgtcattg gtagtttaat cattgaatct ataaattact ttgggcagta  11160
tggccatttt catgatgttg attcttctta tccatgagtg tggattgttt ttcgatttgt  11220
ttgagtcatc tctgatttcc ttgagcagtg gtttgtagtt ctccttgaag aggtccttca  11280
cattccttgt tagctgtatt ctaggtattt tattctcttt gtagcaattg tgaatgggag  11340
ttcattcatg atttggcttt atgcttgtct gttgttggtg tataggaata cctgtgattt  11400
ttgcatgttg attttttatc ctgagatttt gctgaagttg cttatctgct taagaagctt  11460
```

-continued

```
ttgggctgag atgatggggt tttctaggta tgggatcatg tcatgggcaa agacaatttg  11520
atttcttctc tttctatttg aatacgcttt atttatttct ctttgcctga ttgccctggc  11580
ccagaacttc caatactatt tgaataggag tggtgagaga gcatccttgt cttgtgccag  11640
ttttcaaggg gaatgcttcc agcttttgcc catgcagtat gatattggct gtgagtttgt  11700
cataaatggc ttttattatt ttgaggtatg ttccttcaaa cctagtttat ttagagtttt  11760
taagacgaag ggatgttgaa ctttatcaaa gtccttcttc tgcatctaat gagataatca  11820
cgtggctttt ttctttagtt ctgttcatgt ggtgaattat gtatattgat ttgcatacgc  11880
tgaaccaccc ttgcatccca gggatgaagt agacttgatt gcgatggata agctttttga  11940
tgtgctgctg gattcatttt gccagcattt tcttgaagat ttttgcattg atattcatca  12000
gggatattgg cctgaagttt tctttatttg ttatatctct cccaggtttt ggtgtgagga  12060
tgacgctggc ctcataaaat ggtttacaga ggagtccctc ctttccaatt gtttggaata  12120
gtttcagaag aaatggtacc aactcctctt tgtacctctg gtagaattca gctgtaaatt  12180
catctggtcc tgggctgttt tgtttgggag gctattttta ctgcctcaat ttcagaactt  12240
gttattggtt attggttatt gattattctt cagggaatca acttctttgt gggtcagtgt  12300
gaggagggtg tatgtgtcca ggaatttatc catttctcct agattttcta gtttgtttgc  12360
atagaggtgt ttatagtatt ctctgatggt tgtttgtatt tctgtgatat cccctttatc  12420
atttttactg tgtctatttg atttttctct tttttcttct ttattagtct agctagtggt  12480
ctagctattt tattaatttt ttaaaaaaat cacctcctgg attcgttgat tttttgaagg  12540
gttttttttgt gtgtctctct ccttcagttc tgctctgatc ttgcttattt cttgtcttct  12600
gctagctttg ggtttgtttt gctcttggtt ctctgtaaat agttctttca gttgtgatgt  12660
taggatgtgg gtttgagata ttgctagcat tttgatggca gcatttagtg ctataaattt  12720
ccctcttaac actgctttag ctgtgtccca gagattctgg tatgctctct ttgttctcat  12780
tagtttcaaa gaacttcctg atttttgcct taattatttt attcacccag aagtcattca  12840
ggagtgggtt gttcaatttc catgtagttg tgtagttttg agtgagtttc ttaattttga  12900
attctaattt gattgtgcca tggtctgaga gactgttgtg atttcagttc ttttgcattt  12960
gctgaagagt gttttacttc cacttatgtg atcagtttta gagtaggcac catgtagtgc  13020
tgagaagaat gtatattctg ttgtttttgg gtggaaagat ctgtagataa ctatcaagtt  13080
cacttgatgc agagctgact tcaagtcctt tgttgatttt ctgtcgtgat gatgagtcta  13140
atattgacag cagggtgtta ttatctccca ctgttttttt tattattata ctttaagttt  13200
tagggtacat gtgcacaatg tgcaggatag ttacatatgt atacatgtgc catgctggtg  13260
tgctgcaccc attaactcct gcttgagcaa tagtggtatc tcctaaggta aactttcccc  13320
ctcccctaac ccacaacagg gcccaaagtg ggttggtccc ccttcttnnn nnnnnnnnnn  13380
nnnnnnnnnn nnnnnnnnnn nnnnnnnnnn nnnnnnnnnn nnnnnnnnnn nnnnnnnnnn  13440
nnnnnnnnnn nnnnnnnnaa tatatgtggc tccatcttgg ttcacactgc tactcagtgt  13500
actacaaatc acagtgagtt tgaatgccat tcatattact gcaaacgaca ttttatttat  13560
ttttattgcc agtgcatatc catcatgcca gaacaagaaa ataagagaaa aatgaacttt  13620
gattgtcatg cttttatagc acagtggagt gtgaattatt ttatttaatt agatgacaaa  13680
atatgtattt attatgtaaa gactctatag ctatgctaaa agaatagaat atatctccac  13740
ataaccagat taatcactca tcacaatatt cctgactcac aagaagacaa cagtcataaa  13800
```

-continued

```
tattagaagg cttaaaatgg aatctctcat tatagcagag ttttcctaca aaacaaaaag  13860
gacagtgaga cttcaaccaa tgtacatttc tgaatggctc acttgttagc caagtatgcc  13920
cttataagac tgtggcactc taaacagggc tttcacaatg tccacccaca caatacctgc  13980
cttaatgaaa agctcagtac cagtttcagg caatttaaaa atcttagcct ttattatatt  14040
gaaattaagt cgaattattt ttctattatg atcccttttg aaataagctt ttacacattt  14100
ctaatgcttt cttcagagcg gctcatataa atcaatgatt ttttaaaaaa ttctttcatt  14160
tcgatttaat ctattaatac tttagatctc actctcaggg aaaaattact ttattgcatg  14220
taaagtaatt caaatagaat atagtttaca attttcttcc aaattaagct tgagcctgga  14280
taaaaatatt tttaagtgcc caacaatatt tagatattat ttgccatgtt tctattttca  14340
taggaagaga taatatgttt aataaaaaat acatatctaa aaggataatc tgatgttgta  14400
aaattataaa ttctaatttt ctgtcaaaac aaccctgaat gtgaacttat cagaatcttg  14460
tctgtgtgac tgcaacccct cccccaacct taaaaaacat accaccagcc ccactctcca  14520
ccagtgtggc caaaccaagg gaagtgagaa gcaggaacat agctacacag gtcagagcta  14580
aatattaaga gtaaaaatag tatcttgagc tttcagaacc acaaattttc aaagtgagcc  14640
agaggacaga gcagcagctg cattttcaaa cagaagcaac tacatttttc taatcaactg  14700
ctgtgttatg gaacatgaac tgcaggaaat gatggactaa tgtcctttta tgtatcagat  14760
aagcaggagg aagtatcagt ggtgtgcttt acttggtgag tgaatcttga taaacatatt  14820
caataaatat cttccactta tgtcctttaa ttcagtacaa tgctttttaa aaaatattca  14880
acttgtgtgt acatcgacca gaaaatgttc tatataaaaa ctgtattttg cttgggtttc  14940
gagatgaatg tttcataaga tatctatata tgtattaaaa ttatttaaat atgaggaaaa  15000
agaacttgtt tgctgttggc gatgaaatca tgtttaatta tagtactgaa aaaaatgtgc  15060
caagagtaaa caaacttgtt tagtgctgct agtgtttagg tgagaaccat tgcttgaaga  15120
gttggggaca ctgggagcaa catagatggt caatgaaaaa atgacagaag actgatgtca  15180
ccaaagtgtg gagtaggaaa ccttcgtccc caccacaaac acaccaattc aggaacaatt  15240
cacagaaaaa ttccctttgt gggaaatcca gcaactaatt gaagggctcc tgcaccctgg  15300
gtgaatgcaa aatcagatcc atcgaagctg gtgaggatat tcacgacagc tgtctgccaa  15360
aatttctacc cccaacgcaa caccatacaa ttgggaaaag agtctcagct ctcagcttct  15420
cccagaggag gtttgtacat ccaatacccc aacttcgatg gggctaccc aaaggactgg  15480
cttctgtctt ctctgtctta aagtgctaat ggtgtggaat tatctagcca cctgggggag  15540
aatagagatg gtggcttaga ttggtagcca ccatagcttt tcctccctag ctcagagcat  15600
agagcaagca aacaaaatcc ccacctttca gcttctccct ggggatggaa agagttggta  15660
catacattaa actttctggg ggttttccaa aggattggct gaaatcccaa agaattcagt  15720
ctcactcatc ctggtgcact cacaagacct ggcaaaccct agacacctgg ggctacaaga  15780
aatacacaag caaataagtt gaacaagcat gaggtttaag aagctttaga atctcttcct  15840
ggacttattg gtggggatct tccatataag gccagctctt tgtgaagact cagagagaag  15900
tctgctttat ctgatgcaaa gacaccaatg catagagtca agtaagatga aaaaacagga  15960
aaatgtgttc caaactaggt aacagaaaaa tctccagaaa ttgactctaa tgaaacaaag  16020
atacacaatt tacctggaaa agaatttaga ataactgtca taaagatgct cactgaggat  16080
aagagaacgt tgcatgaaca aagtgagaat ttcagcaaag agatagaaaa tatcttaaaa  16140
gtaccaaaca ggaatcatga agttgaagaa taaaataatt aaattgaaaa attcactaga  16200
```

-continued

```
gggattcaac aacatactag tatcaagcta aagaaagaat cagtgaactt aaggacaggc  16260
cattggaact tgctgagtca gagaaacaaa aaggacaaaa taatgaaaaa gaataaaaaa  16320
agcttaaagg acttacgaga caccatcaag tggatcaata tatgcattat gagaattcca  16380
gaaggagaag agagaaggaa agaaccagaa gatttattca aagaaataat agctaaaaac  16440
tcccaagtat ggaaaaggaa atgtgtaatc caaggacccc caaaaaggaa aacttagaga  16500
tatcaacact aagacacctt ataatcaaat tgtcaaaagt caatcacaaa gagaaaaagc  16560
aacaagggaa aagttacttg ttcgggtaca agggaaattt cataagagta taagtagatt  16620
tttcttcagc aacttttttg cagatgagaa ggaaatgaga tgatagattc acaatgctgg  16680
gggaaaaagc caaccaggaa acctagacca aatgaaactg tccttcaacc aggaaaacta  16740
gaccaaatga aactgtcatt caatcatgaa agagagataa agtcttttcc agacaaacaa  16800
aaactaagga agttcatcac caccagacct ccctacaaaa aatgctaagg gaacctcctt  16860
aacttgaaat gaaaggacac taaacagcaa caagatagca taagaaagta taaaagtatt  16920
ggtaaaggta aatatataga caaatgcagg accgtaatac tgcaatagtg gtaggtagac  16980
cacttgtaat tcaagtaaaa aagttaaaag acaaagtagc aaaatacttt caataactaa  17040
aatactttta ataagtaaaa ctatgttaat agatacacaa tataaagaaa tgttaactgt  17100
gacaacaata acaaaatgtg tatgggaagg agagtaaaaa gaggcatatt tttgtatgtc  17160
attgaactta agttgttatc aggaaaaaat agactgtcat tactataagg tattatataa  17220
accccatggt atctaatgag aaaataccta tagaaaggta tcaaagattc ccaacaaaaa  17280
aaaatcaaca aaacatgaaa aatgagagca agagaggaaa aaatgcacaa aataattaca  17340
aggctaacag aaaacagtac atgacaataa taaatccttc tctatcaata attactttaa  17400
aactaaataa attatacttc ccaatcaaag acatagggtg gttgaatgga ttaaatgtat  17460
aatggaatca catgctgtta tcaagagact ccctttagaa tttaggctca atgtgaaaga  17520
atggaaaaaa aaattccacg aaaatgttaa tgaaaaacga gcaagagtga ctatacttat  17580
atcagataaa atagactata agtcaaaact ctctcaaaag actgagaaag acatcttata  17640
atgataaaag gatcaattca ccaggaatat ataacaattg taagtagtta tgcacccaac  17700
gattaagcac ctaaacatat aaagcaaaca ttgacaaaac tgaagagaga aacaggcagc  17760
aacacaataa tagtaggata tttcaatacc tcattttgaa tgatgggtaa aacatattat  17820
ccattaccca cgggcaaaac agagcaaaag gaaataaagg acttcaacaa ccttatagaa  17880
aaaaatggac ccaatagaca tgaacatttc actcaatagc agcataatac acattcttct  17940
caagtgcagc cagaatattc tccagaatag atcacatatt aagctgaaaa gtatgtttta  18000
aaaatttaaa gtgatcaaaa ttgtaccaac tattatttct gactacaatg gaatgtgaaa  18060
gtagaaatca atagccatgg gaaaactgaa aatattataa atatgtggac attaaacaaa  18120
acactcttga acaactaatg ggtcagaaag aattcaaaag agacattaga aaatatcttg  18180
agagacatga agatgaaaac ataatatacc aaaacttatg gtatacagcc aaagcactat  18240
taaaagataa gtttataatg ataaaagtct atatgaaaaa agaagacaga tctcaaattt  18300
gcaacctaat tatacatttg aagggactag aaaaaaaaaa cacactagac ccaaagttag  18360
ctgataggaa gaactagcaa agatcagagc agaaataaac aaaatagata atagaaaaca  18420
ataggaaaaa atcaatgaaa ttgggttttt ttttaaaaga taaaattgac aaacctttgg  18480
ctagacttag aaaaaagaga ggattcaaat aaatataaat catatattaa agaggaggta  18540
```

-continued

```
ttaccactga tatcacataa gttaaaaagt tcataagtat ctatgataaa caattatatg  18600
ctaagaaact ctatgacctt aaaaatggat aaattcctag gaacataaaa tctaccaaac  18660
acgaaacaag aagatataga aaatctggac agacaaataa caagcaagaa aattaaatca  18720
gtaataaaag acctccaaac aaagaaaatc ccaggaacag atggcttcac tggtgaattt  18780
taccaaacat ttgaagaaga tttatgtcaa actttttttt atcttgaaga agaggaaata  18840
cctccaaact cattgtatga tgccagcatt accctgatac caaagccaga caaagacact  18900
gcaagataag aaaattacat aataatatct ctgatgaaca tagatgcaaa aattcttaac  18960
aacaaaaact acctagcaag ctgaattcaa cagtacatta aaaagtcata tgatatttat  19020
tataggaagc aatggatacc ctgggctggg gttcattata tacaaatcaa taaatgtgat  19080
gtgccacatt cacagagtaa agaacaaaaa atatattatt atttaacatc gtttcatgat  19140
aaaaactctc aacaaattag ctgtagaagg gatgtagctc aacacaataa aggccatata  19200
tgacaatcct acagtttaca tcatactcaa tgatgaaaag ttgaaagctt ttcctctaag  19260
ttcaggaaca aggcaaggat gtctactctt gctacttcca ttcaacatag tactagaagt  19320
cctaggaaga gcgattaggc aagaaaattt tttcatgtgc agatgagaaa aaatgtatat  19380
tctgtggtcg ttgaatggaa tgttcagtag atgtttatta ggtccatttg gtcaagagtg  19440
cagtttaagt tcagagtttc tttgttagtt ttctgcttta atgatctgtc tagtgccatc  19500
attgggatgt tgaagtcctc cactgttatt gtatatctgt ctgtctcttt tctgaggtct  19560
aatggcattt gctttataaa tctgggtggt caggtattgg gtataaatat atttaggata  19620
gttaaatctt cttgtagaat tgaactcttt gtcattatat aatgttattc tttgtctttt  19680
ttttaactat tattggtata aattctgttt ttttctgatg taagaatagc aacctatgct  19740
ctttttgtt ttccattgtg tgatatacct ttctccactc ctttactttg agcctgtggg  19800
tgtcctttca cattagatgg atctcttgta gtcagcagat gttgagtctt gtttcttaaa  19860
tgcaatttga caatctatat cttcatttag gtcatttctg ttcaaagtta atattgacat  19920
gtgaagtttt gttccaatca tagtactgtt agctaattgc tttgtagtct cagtggtgtg  19980
attgctttat aggatctttg gattttgtac ttatatgagc ttttatgaca ggagagtatt  20040
gtcctatatt cttttatgac ataaaagagt atactctttt ctgttcgaag tttatgcttt  20100
atgacataaa agagtatact catttctgtt caaagttaat attgacgtga aattttgttc  20160
caatcatagt attgttagct agttgctttg cagtctcagt agtgtaattg ctttttagga  20220
tctttgagtt ttgtacttat atgagctttt atgacaggag agtattgtcc tatattcttt  20280
tatgacataa aagagtatac tcttttctgt tcaaagttta tgctttatga cataaaagag  20340
tatactcatt tctgttcaaa gttaatattg acatgtgaag ttttgtccca atcatagtat  20400
tgttagctag ttgctttgca gtctcagtgg tgtaattgct ttataggatc tttgaatttt  20460
gtacttatat gagcttttat gacaggagag tattgtccta tgttctttta tgacataaaa  20520
gagtatactt ttttatgaca aagagtattg tcctttttcc ccacgtttac aacacctttg  20580
agcatttctt atagcaccag tctcatggtg atgaattttc ttaatatttg cttgtttgag  20640
aaagacttta tttctccttt gcttatgaag cttagttagg caggatatac aatttggggc  20700
tataattttt tgtcctcaag aaggctaaaa ataggccccc tatctttttg gcttatatgg  20760
tttctgttga gaaagccact gctagtctga tggaatttcc tttacaggtg acttgactgt  20820
tctctctaac tctctttaag attttttctt tagcattgac cttggttagt ctgatgacta  20880
tatgccttga tgatgttcat cttatatagt atcttgcaag tgttttctga atttctttta  20940
```

-continued

```
tctggatgtc tacctcccaa caagatcagg gaaatttttc tgaatgattc ctttaaatat  21000
gtttccaaat tgcttacttt tccttctttc tcagcaatac ctataagcta taggtttggt  21060
caatttaccc cctataccat ctttctcaaa tattttgttt atttttaaaa tgcttttcta  21120
tttatttttg tctgactgga ttaatttgaa agaccaatgt ttaagctctg aaattctttc  21180
ttctacttgg tctagtcttt tgttaatgtt ttcaattgta cattgaaatt acttttgtga  21240
atttttttat tttcagaagt tctattttta taaatatagc tatcttgtct ttcattttct  21300
gagttgttct tctggtttct ttgtattggt tttcaacatt ctcttggata tcattgcact  21360
tctttagaat ccgtatcttg aattccttat cagtcatttt ttattttgtt taggatccat  21420
tgctagaaat ctagcctgat cctttcaagg tgttaaaaca ctctgtcttt ttgtaccact  21480
ggagttcttg cactgattcc ttcccatgcg aaggagttgt tgcttctaag ttttgaattt  21540
gctattgttt gaatgggact ttatcatgtt tattcttttt tcccttgagg gtatgactgt  21600
ggtgtatgtt gtatgtgatt gtttggcttc ttttctgggg tttctcggtg ccaagactct  21660
gcatgggctc cttggttatg gatagccttt gtgtggtggc tttctcaaat gctgcttgtt  21720
gtagacatgt attgggcata tgagccaaca cactattttc tgtgtgacta ggagagcaga  21780
ggtctcagta aacttatctt gtacactagt actataccct tctgacagta ggttttttat  21840
ttggtggtgc aattcagtct tcagtcaagt aggaggtgct taagagtaag aatccactca  21900
ccctcaggca gtctaatgat gaaggaagac aactgtccta attgaggtta gtgtggggag  21960
cttgtgttgg agtgaactgg tcttggtggt aggggcaggg ggcctgcatt agcccctcat  22020
cctgggcagg caggaatgtg atccgttttc ctatcacacc tttctgtcac agggctcatg  22080
atcttcagca tatagacatt gttctttggc tcccaagctg aagtgtgact gaggtctgga  22140
gaaatgcccc tttggtggct accaccaaaa tgagctcagg gcagagcctc ttcccagagc  22200
ccagagcaaa cagtttttca acttgtctgc ccttcgttgc tgggacactg ccattctgtg  22260
ttgggatggg gagacaggtc ccacctttca tgcatgccta ggtggcattg gctcactttc  22320
aatgaggtgt agctgccacg aagagtgctg gaaaggctgt ctccaagtgc aatcaggtca  22380
gccctcatca ggaaaaagcc tctgctgcat ccacaacagt gcctgcactg agggctagat  22440
ttccatggaa cctgcagctc cccagagacc cgccagtctc ctgtggttgc caaagtcaga  22500
aggggttctg aggtatgttt gcaggggatc ttgtagtgtg gcaacacaag gactaaggtt  22560
ccttggacag ggcactggcc cacaatgagt gcacaaccag tgtggcacct gccatctcag  22620
ttagggcctg aggggagtgt gggcacacca gcacgagctg gccacctgag gctcccaccc  22680
cagagagttc ccaaattgcc accaactgca ttgcctggga tttcaagggc agaggggttc  22740
tctgacaatt tgtcagtcag cagttagtca caggagtgag gggagcagag aagcacccca  22800
acctatcctt tacatgggac tctgagttcc tcaggagtca gtgtctgcca gacttttgct  22860
gctttccttg tctgcacccc agtttcttcc catgggctct ctgaaagctc gtggctctct  22920
tccctcagct ttccatttgg atcatgacca ttcaactgta actttgatct ttctacaaac  22980
tggtgtctga catctctagt cagccatctt gaaaaaaaaa agctacatta aagttataaa  23040
aataaaagta attgcactgt gatgttacaa aggctactat atcactaggt gacaagaatt  23100
tttcagccct attatagttt tatggtacca ctattttata tgcgatccat catttgactg  23160
aaacatcatt atgtatgact gtacataaca aattgcgaat agaattagaa agtgctttct  23220
acttctggaa atcaatgttg tcttcacaga gacagaggtg ggctttgaag gataaatagg  23280
```

-continued

```
agttcaggag gcaaagaagg aaggatctgt tatattctgg gaatggcaaa tatgatgtgg  23340

ataaagcatt gggattgtgt ctgggggcat aaaatgtgac tggatataaa gtttaaatct  23400

ttacataagg taggtcaaat tgtggagaat gaattaatcc ttgaagtcac tctatctgat  23460

aagcacatta ttatctccat ttcacagata aagaaactaa ggtacagaag attaaatgac  23520

ttaaataggt cacctgacta gtaagtcgta tggcagtgat tcaaacccac aaggaagact  23580

tgtacatatt tattgacttt ttcatgatga tttttaaaaa gttgagaata ttctattata  23640

aagcaataaa gaatttgata tttagtaacc atatcacaat agttttacaa atgttttagc  23700

aaaagtttga aagttttata gttagaaaat tcccattgaa ctaagattta ttcccataat  23760

taggaaagcc actctcccat tggagactac ttttattata gcctcatgtt ctcttacttt  23820

aaattatctt ctctgctgta ccacaaaata aaaagtctta taatttcctt atttcaaatg  23880

tttttctttt gaaaaagaac catttatttc tggtattatt agttgattaa tttttgtgca  23940

acttagtagt gttgatatag gatcaatgtc aactggtgga gcaattctaa gggtgtttgc  24000

tccattagta ataaccagtg gagttaatta attacacagg catttgaaat tgtaggtttt  24060

gcctgttaaa cactggatat ttcaggatga gaaatgtgga ggtggactaa tactgaacat  24120

tttatttcag aaaatacagc caatagtaaa tttcagtctt ttattgagct atctttgaca  24180

cctgtgcaca tcttataata aactgttctg tttttcaatg ggtatcctag gaacaagaac  24240

taaataagag acaattattt taaagtcttc aataatagaa tttacttttg tgtgggcaaa  24300

agacacgaac agacacttct caaaagaaga catacatgcg gctgacatag gaaaaaaaag  24360

ctcaacatca ctaatcatta gagaaatgca aatcaaaacc tcaataagat atcatctcac  24420

atcagtcaga atggctatta ttaaaacgtc aagaaacaac agatgctggt gaggttgtgg  24480

agaaaaagga ttcctttaca ctattggtgg aaacgtaaat tagttcaacc attgtggaag  24540

acagtgtggc aattccttaa agacctagag gcagaaatac catttgaccc aacaatgcca  24600

ttaatgtgta tatacccaaa ggaatataaa tcattctatt ataaagatac atgcacgcac  24660

gtgttcattg tagtgctatt cacaatagca aagacatgga accaactaaa atgcccatca  24720

gtgatagact ggataaagaa aatgttgcac atgtataccc tgaaatgcta tgcagccata  24780

aaaaggaaca agatcatgtc ctttgcaggg acctggatgg aactggaagc cattaccctc  24840

agcaaactaa agcagtaaca gaaaactaaa taccacatat tctcacttat aagtgggagt  24900

agaatgatga gaacacatgg acacatgaga ggaaacaaca cacactgagg cctgttggag  24960

ggtaggaggt gggaggaggg agcacatcag gaagaatagc tgatggactc tgggcttaat  25020

acctagatga tgggttgatc tgtgcagcaa accaccgtgg tacacattta cctatgcaac  25080

aaaactgcac atattgccct tgtacatctg aacttcaaaa taaaagttgg agattaaaaa  25140

acgaaattac ttttgttcca gaattaactc tcagatgttc catgtttcat cactttattt  25200

tttcacataa tttgtgtatg tgactcacat caattcattt tgatatataa ttgatttctg  25260

atattttgtt tgtttgaagt gagaggtaac tgggtaatta tctatactct gcttttacca  25320

tgcattttat ttccaggtaa atttgaaaaa tctaaattat ttttctaaat ttgatcatgg  25380

tttatttgac agtttacaag tacttgcagg catgtgtttg catgtggata ataacaaata  25440

actaagaaat cttacaaaag tatagcttca taatttgggg gtcctggtta tacattttac  25500

atctctaagt taggaactca tattgttaat ctcccttcat agttccttat aactaaactc  25560

tgtttagtat gagtttctac ttatcaaagg cataataact cactcactat ttggtatatt  25620

tgctctttaa tgtgacatga catgttttct gtggataagg agaactgtgt atttgtgcgt  25680
```

-continued

```
atatgtatat ataatgtttt caaccaatca ctatttcaga gaaaaaatgg atgaaaataa  25740
acttgtattc attacattaa atataatcct atacatatta agaggaaatt ttacagcagg  25800
aaattgttcc tttaatcatt atttttcttg aaaattattt aatactttta agacaaacca  25860
cggatgacca aagtctctta atatttacca catagattta tattaacact atatttttgt  25920
tttaagtttt ctagacatct gagacttaaa tatgttctta tttaaagact ttaatagtat  25980
ggcagttgta ccatgaaggt ggcatagtga aggagatcaa cttagtctac tttttgacta  26040
aattcttaaa tctctatttc agctgtcttc cccctagaac tatagcttaa aagctcctca  26100
gctgcataca gcacatagcc ttcacaggtt atcgcctttc tatagagtcc tctcacaata  26160
taaacaggtg tagctaccaa ttaggacatg tctcaagaaa ttgttaacac tcaccaatat  26220
taattaagtg ctaatagggt actgagccaa acactgaggg tgctgagcca aatttccatt  26280
tcacattctt cattctccaa ggaggtttag atactggtgc tgtcaatagg gtgcttgagt  26340
tctagaaccc atggggaaaa ataaattact gtggccactt tgcacataaa tgtttaaatt  26400
taaaatatca attgatataa atactgataa taatgaataa atattaaata ataattgaaa  26460
gggatgatgt tcttggtttg ggggataata cccataatct tagcagtacc agaatcattg  26520
caaccctaat aggattaatt ccattttgga atatcagtat tctgagatta ctattttgaa  26580
tgttctcgtt tatattttct tcaagtaaac ttttttgctt cttcattctt tttcagaaat  26640
tttattattt ttaaaattga cagataaaat tgtatgtatt tattatgtac aacatgatgc  26700
tttgaaatat atatatctat gcactgtaga ataactaaat atagctaatt aacatatgcc  26760
ttacctcaca tagttattat ttttgtagtg aaaatactta tccactctca ctatttttca  26820
ggaatacaat atgttattaa ctattgtcac tatgctgtac aatagatctc ttgaacttat  26880
ttctgctgtc aaactagaat tttatatcct ttgactagcc ccttcctcag ccccccaagt  26940
gccccagccc ctagtagcca tcattctact ctctagttct atgtgtttgc ctcctcgttc  27000
tatctttcct cttcctcact acctagtcat tcctagtgcc cacagtgtgt cacaactgct  27060
gaaagcatgg tgaaaaaata tctgttttct tttcttccct tctctctctc ttcttaatgc  27120
gtttcaggtg ggaagataat aaaagaaacc aaaatgattg aaatcattat tagcagaaag  27180
taaaatttta atttcctgct ggtacaataa gcttttgtct gggctctggg gacaaaaaga  27240
ttatgaatat tcttttgtgc cactttcaaa ctgcttctaa atatcttagg tacatttgta  27300
atatgaaaat atggcagcct tattagcaaa ataatttcta attttgagct aaattgtata  27360
agattatgca tgtttttctt ttgcataact caatttgttt cctgtaatga taattgccat  27420
gattgaatta gaagataata tagcataaaa aaattttatg acatcacagt gattaatcca  27480
aaactatcag catcaatgaa gttaataaca atattgttca tgaaaacaaa ggtcatgttt  27540
atgaaattga aacattgttt atatgtgagt ggcctatttt tctcatgcta ctgcactaat  27600
tttatcttag ggtttataaa tatgaatcct aaatattaaa gtagtgctat ttatcgccaa  27660
ctctagtggc cttctgtcct cagccttttt gaattcacaa aattcctgta aactgtggac  27720
tattttcccc aacttacaaa taaagaaatt gaggttcaaa aaagtaactc gccaataaat  27780
aggttctaga tatctactat acagcatagt gcctatagct aaaaatactg tatcgtatac  27840
ttaaaatctt ccaagagggt ggatcttatg ttgtattctt accacgcaca tacaaataat  27900
aataatgata gtaaaggcat tagggagctt tgggatgtga tagatatatt tccatgtgta  27960
agtgctgtaa gagttcacaa gggcataacc caagtgcccc agatatggcc cttctgtatt  28020
```

-continued

```
gaatatacct aaggtagaca cactgaagaa gatggatata tgaaaaagtc taatatacta  28080
gccttattga ggtaaattga tcagttcaca ttgggtatag aacattgtca gcaactagaa  28140
aaagaaaatg aggttgttcc gtctctatgt tcacacgagg catgaggcag cgacgttcta  28200
ataatcctcc tgctcttctc ccttaccctc ctgcctcctc aatagcctta atttgtagca  28260
ttttccaata tctgtggtta aattctttcc ctatggccaa ttttatacca ctgaggtgtt  28320
ttcccctgaa cataaagtta ggaagagatg cgtgtaactg gcactggtga gctggggtaa  28380
gccagctcta gcataccact gctgccaggt tatctaccgt agagtgtaag ccatagtttt  28440
catcaaaagt gtcctgcaaa aaaaaaacat tgaaaaatga gaaacagttt ctgtatgtca  28500
atataagtca atttttattg caatgaatat tgaaggaggt aaaatttttt tttacttcct  28560
gatgaaaaca gatgaagtat gttaatatat gtccctgggc cctctgtgtt tctgtgcctc  28620
ccctcacaag gcatgctatt tttctgtacc tgccaataca tatcttatct tccttacagg  28680
cctctctcct ctgtttttga ctatttcagc ctactccagc ttgtagtgct gtagaaaagg  28740
ctttagattc atttatttat tcaagaaaca cttactgagc ttttaatatg ccaggtactg  28800
agaatataaa catgattaga cagaccatgc tatagctttg attgtatggc tttggggcaa  28860
ttgctttttt tgttttttaa cttactgagg gatgactgac atgtaaaaag ctgtacatat  28920
ttaatgtata caactcaatg agtttggaat atacacccat gaaatcatta ctagcatcaa  28980
agccacagat atatctatca cctcccaaag cttcctaatg cctttattat tattactatt  29040
atttttatta ttattagtat gtgtgtgtgt ggtaagaaca caacataaga ttcaacctct  29100
tggaagattt taagtataca atgcagtatt gttagctata ggcactatgc tgtgtagtag  29160
atctctagaa cctatttatc ggaaagttac ttttttgaac ctcaatttca ttatttgtaa  29220
gttggggaaa atagtccata gattgcagcg attttgtgaa gattaaatga gaaaatataa  29280
ataaaacact tagcatagta gatggtacat tgtagatttt ctataaaggc tagtttcttt  29340
tttttaactc taaactctta tagctatctt aagtgccaaa tgaatcggca tttatttata  29400
ttctgccttg gatgttgctt gccttctcta gtatcctcag cttgtacctt tatgcaggtt  29460
cttatacata atttgttgtt cctatcaaca ttgatcacaa tgtagtatca atactttctg  29520
attcttggtt cttaatttgc ctgcccattg agatattggt cataagttaa cattttccca  29580
ttattttcca ttttgaatca ctttcctggt actttcaatt ttgtatttta tatcctgtcc  29640
atctgtattt tataatttta aattttttct tccaaataaa ttttagcatt cagctattgc  29700
tgtgtcacaa tccatttcca aacgcagtgg cttcaaacag caacatttta tttaggtcat  29760
aattctgtag gttgtgaatt tgggttggac tcagctagtt agttcttcta atgtgaatca  29820
gctggcgccc gcttctacaa tcagctgatg atttcacaac tgaggccggc tggtttgtga  29880
agtcctcagc tggatgactg ccagctaggg cttctctctt catggtctct gatctgatcc  29940
agccagctag gctgggcatg tttacatggt ggcatgactt ccagaagcaa cagcaggtaa  30000
gaacctatgc ataagaaccc ttcaaacctc tgtgtcacat ttgctaatgc cccattgatc  30060
cagattcaag ggttggagga atatattcca actcttgttg gaacaagctg ctaaaatatt  30120
gtggccattt taagagaatc taccacatta tctatgtatt tttcatttgt aaacatctat  30180
acagaaatgc caagtgtttt tatctttgat ttcagatatt ttaattgttt cacagttgaa  30240
tttcataaac tttcctcatg gaaatctgtt tttctcctca gcaacttctc ggtttttcca  30300
ggcaagcctt tctgttctta attactgtaa ttttcagaat gagctacttt ctacatgtgc  30360
acatgtcttt taaattaata taatacaaaa ctaaatctgg aaaattttag ttttacattt  30420
```

-continued

```
ttttgttcat ctcctaacct atttccctga agcaaagtga caggtctgtt cagaatttat  30480
aatttaatta agatgagatt ggggaggtaa ggaagtacca ctttctcttt tgcattcatt  30540
ttttaaggat ctcaggacat atgttgatct attttctttc tcttccttgc aaattaaaac  30600
aaaatgtttt aaaataaatg ttttaaaata atagtgaaat tgcgagcttt gctgattata  30660
aaaatatatg ctctatgtca tcttgccttt tcttccctgc tctaatatga acttcacatt  30720
atcccttcaa ttgctcttct gtttttgctc acgttatctc ctttttctaa atttttcact  30780
cctctgctga tgtaaaacct gcttattgtt taagagcaac tcaagtccta catcctccat  30840
gaaattttca ctgattgccc aggttatcct tgattttact ctattgtgaa ctcctacagc  30900
atttgatggc tggtaccaca cagtaacatt tgcctcatta caggttggta ttgtttaatg  30960
cttttaatgt gtatttttaa tttgtattgt ttgctgctgt tttcattgct gggcttgatt  31020
cgttagccag tttttttttt tactgatttg cactcctggc tctctaagtg ctgtaaatgt  31080
ccaggattaa gctgttttat aatataccaa aattgggagt tctcaagtca ttttttttat  31140
aagaaaacac atatttttag gtttcattca cttattcaag atatattaaa tgcttattat  31200
gtttcaagat taaaaataaa cactatctca agacacaaag ttaatttagt tgctatgttt  31260
tgctcaagac ggtgttataa acttgtaaga aacagtattt ttgaaaatgt gccacagtac  31320
cttctaaact agtaaatctc agttagtggc ccttttgatg agcaacttta ggactttcaa  31380
gatttctact ttctatctag aatagtcata gtcatgaagc cttttgtttt ataatgatta  31440
taaataccct tcccagggtc aggtaactat gaccagcact agtttaacac tgtctttttc  31500
ttttagcaaa acaacacaag gaacaatggc acagtagcct agtaatacct ctttgctata  31560
aacatacact cactcccatc ctctcagtct ctttgtttct ctgttactct cccttagcag  31620
aaattttcca ttggacttct agtgctttga tgtattatga tcaatgatga cttgtgtttt  31680
ctgactctgt tagagtctcc atggaattaa agattatatg cttattcagc ttaatgtact  31740
tgaccttttt gtatgattga cacatctaaa tttctgtagc aactcagtca ttatgcaaca  31800
gctgtgttat attcatttca tgtaaaaagc aaaaacaaaa gacatagagt tctcttcaag  31860
agtagatacc ttgacccctt ccctcccagc taaataaaga atagtttatt aataacatta  31920
ttaatcagtt tccaaatgcg tctcctttcc tcaccgcatt ttataaacat tcagtatact  31980
gtgaccatag tcacatcaag aatcatttca atactgatcc ttattatata attaaaatat  32040
tcaataattc tgagtctgtt gaacataata atagccacac aacttaagtg tcaaacatct  32100
aggatttgtt agcaagattt gtgctcagaa aataatatgt acaaaccttt gatttcttta  32160
atgatgaaac tgtattttgt ctgaattgac atatgtgtct ttaagttaga gagaaaaaac  32220
cttgacattt ttctgtgact tttccttatc aacagctgtg ttctacctgc gtttattttt  32280
ctcagaattc attatgaatt ctgtataggc cttcagaagg cctatacagg ctttctaaca  32340
gagattctat aggaaaaagt tttggttaac tgtttgaagt attagttgaa gaaggcattc  32400
tagataaggt tttacaagac agaagaaaag aatcaattca tttttagttc tgagcctgaa  32460
ttgtggaaac tgtactaact gcagataaac tctgaataaa ttctagtgtt ctctgcttat  32520
ctcaaaaaat cttttctttt aatgatactg ttccatgctc actaatgttt tcaaaacata  32580
ttcatatcta aatggttttg tatttttatt aaattttgga ttttttgcat tacataaagt  32640
taattttgtt gaccatttta tgaatttaag aaatgtccac ttgaaaggac tcgctccttt  32700
aattaaattt ttggccttta tttataaaat aaaaattatt ctttatatgt tcttgaaaag  32760
```

-continued

```
taaatcagat taggattaat aattgtcaag tcattttaga acaatgacat ctatcattaa  32820
atttcttgaa ttttttgcct tctcaactga tagctatccg ggtgaaaaat tcaattatgg  32880
atattggaaa aattgatggt aatattaatc tggaaatgtt atttctgtac tattctttac  32940
aggacctgag ggattctct agttctttag gccagtgtta taatgttagg atttacaaaa  33000
gttggtaata tagagagaaa caggaagaaa atgaaatggg acaggaaaat atcattcctt  33060
cttcttattc cttcctctaa gtcactggca ttgtgaaggg aaaagggaac taacatgtat  33120
tagtgtctac catgtaacag gcattgtctt tcatatttta tatttatcgt attagctcat  33180
gtaatctttg tggaaaatct cctaaatcta ttagtaggtc tttaatatct atgtttattt  33240
attttgtcct gaaaacaaat gaagtttttg gatcaagaca gagaattatt attacttata  33300
gcaataacca ccttggaaag aaggcacaca gttatgcgca caggagggga gccatgaaat  33360
tatgaatctg ggaatttata taggaattac tatataaact ctttatatag taaatggtct  33420
tctcctgtct tctcctttc tgaaagagga agagaaagtt tatctccgtt atatacaata  33480
agcaaatctt taggggagag aatgagaagg tcctggttta aaccctttga aatgtaaacc  33540
agtagctctg ggattttgtt ctcttttgaa atgtaaacac agagctgtag aaaataagtg  33600
tctgcatatc tctgagggtc tctgtctatt cagtccacct ttaatccaga tttcagtttg  33660
tcttgcttta taactcctta accatgcaga agcatgaaaa cattttctct gtagttccac  33720
atcatgaatt ttagcagttt tagtactgtt gctaaaaaat tgtggctatt agcttgtttc  33780
cattcctttc ataaagtgtt tagtagcata atgcattatt aggtctactt tctatctatt  33840
atacttgaaa accatcctct ctatgtaaaa tatctattta ttcaatggat atttattgag  33900
caccaaaaac tgtcaagcat tgttctaggt atttgggata catcagtcga caaatcaaag  33960
atacctgcct tgcttgtatt tacaaacttt ggggttagaa tgcataaaat tgagattatg  34020
gaggggttgt aattattgcc aatgaaaagc ctaggatgaa agatcactgg aagactaaag  34080
tttaaggaat tgaaaggcca gaatatcaaa agaatcatct atatgtgttt tgaaatctta  34140
tgaattaagg cagtatcgaa gagaatgaca gtatgcaaag agctcaaatg gttgagtggg  34200
aattacctgg accttagtgg ataacagcaa ccatgaggca aagtatgtag tgagtaatgt  34260
cgaccatgag atttaaatct gaaggatgtc aggaaggata tggggaaatg gtctgaaaat  34320
gtcagaatgg agcaaagaaa taccactttg cttattccac tcacccaacc agaggtcgca  34380
ggaacaagaa tgacaccttt ccatcttgca taagaactgt gggagagaag cagccatcac  34440
tgagagattg taggggaggc attgtcctcc agagaaagac aggtttatgt ttcagctagg  34500
aaagtaaagg gaacacttag aaaattgatt tttggctcac tggaagggtt tcagcagttg  34560
ggagagaaca aaggtaattt ttaccagctt gtaacttcac atgtattaac tgtgttgcaa  34620
aactaatgaa acttactgtc tattctcttg ctttatctga taatatagat aagggtgtca  34680
cctgtaatca ttgttaccat atttcttgag gccattttct tattctcatt taacttttct  34740
acttgtttct tctttatttg tatttttctc tgtttttaat cttgctcttt ttatcatttc  34800
tgtctcttta tatcctactt acctcttaat ctttttgccc aacttctctc ttaatatata  34860
tatatttttg ctctttacta tttctcttat ctttctattt caaaattaca ctgtctgctg  34920
ttttctccaa ctccccacaa ctcaccttag gtgtagttgg gactatgcaa tatgccatca  34980
cacaggtagt actaattttg acaggtagca tctctacttc aaacaaagaa agctttaacc  35040
aaaaaggaat tacaggagag aagacagtat tctccccaac tgatgctaac attgccacct  35100
acacttttga cgctttcttc aacagttaag acgtagcaac ttattacttc cccaaattcc  35160
```

-continued

```
ctgtgctctg ttgatctgtc ttaaactcta aagggagaga aagtaggttt gttcattagc  35220
tgtgggactt aaaatgtgac ttaacttttt tgaacctttt gtttcgtgaa tgataaaaaa  35280
acactttctg aatgatatag ctactaatat tttcatttta tagataaagt gaaagataaa  35340
gtactttttt taaaggttgc ataaatataa gtgacacaca ctgatatgaa tgtaagcatt  35400
tgactcaatc ccagagatca tgttttaatg aatactctat tgtttctcac ataatataac  35460
ttaatattgt ggtcaataaa ataataaata ggaccagaca catatatgta ttaattcact  35520
tccctttatt tcctttttcc aaaattgagc cttattggta aagggctttt tgtgcatttt  35580
aattgtctat aatcaggtac ttgaaccaat tataattttt cacttgcctg catgaatcca  35640
tacaggacaa aaacctgaat atagaaacta tctttcagct ttcggtttgc cagaggatta  35700
atctataatt atttttagga ttataaaaga tttacatccg ttcttaaaat atacataata  35760
tcggattttt ttccagcaat agaggaataa ctaattctat agtttcatgc caatctcacc  35820
tccagtcctt ctagaatttg gaggtaattt aaccccgtgt ataaaaaata aatattttct  35880
tttttgcgtt ttattgaaaa aatcacgtaa tttaagtaca aatatatcca ctaaagtagg  35940
caaatttatt ttagtagaat tcagttatcc ctttcaaaga aacactatca gcctaagtgt  36000
tatacattgg atattttaga aatcttacaa tttcaattac atgtcttctg aaactcatta  36060
ttgtaaggct ttgttttagg ctttccttgc tgtattagtt gactggggct gccagaaaaa  36120
aataccacag gctgggcagc ttaaactaca gaaatgtatt ttctcacagt tctggaggct  36180
gggacaccta agatcaagat ggctagccag gtgggtctca ttctgaagac ttttctcttg  36240
gctttaggtg gttaccatct ccttgcatca ttgtgttacc tctttgtgtg cttggacaga  36300
gagcaagaga ggtagctctt tggtgtttct tcttttaaga acactaattg gatggatcca  36360
gccccactcc tatggcctca tttaacctta attacctcta taaaggccct atctctaaat  36420
acagtcacat ttggggttgg gactttaaaa tataaacctc gggggacata agccttcatc  36480
cacagtattg ccattataat attttgtgta ctttggcact tgagaaagta agattttttt  36540
taacctagta ttttaatgtt ttctttagag gtttttttccc tgatacaaca ctctcctata  36600
catgatctac ttggtaacac aaatatccct ttgtttgctt gtacttttgc ttcctcataa  36660
atttttctgt agctacaaat gttaactttg ttggataggc tttatttttt agatcaattt  36720
taagtttata aaaatactgc acagaaagtt gagacagttc ccatgtattt cctctccctg  36780
ctgcacacaa tttcttctct tattaacatt ttacattagt gcagtacatt tgttacaatt  36840
gataaaccaa cattaatagg ttattatcaa ccaaagtcca tagtttacat tagggttcac  36900
tctgtgttat acagttctat tggtctggac aaatgtttaa tgacatgtat ctaccattac  36960
attatcaagg atggtttgac ttccctaaaa atgccctgtg ctccacctgt tcatccctat  37020
accttctccc tgaagccctg acaactgctg atatttttac tgtctctata gttttagctt  37080
ttccagaatg tcatacagtt ggaataatac agtatgtagc ttttaaaacc atcttctttc  37140
acctagcaat atgcattaac agttctctca tgtctttttt gtggttgaca gctcatttcc  37200
ttttccagta gtcccacttt atctgtagag gatacgttct aagaccccca aaagatgcct  37260
gaaacctcag atagtactga accctatata tactgtgttt ttcctttaca tacataccta  37320
tgataaaatt taatttataa attaggcaca gtaagagatt aacagtagct aataataaaa  37380
ttgaacaatt ataacaatat gccagagtcg aaactcttgt gccttgggac ttttattaag  37440
tataataggt ggccaatatc aagtgtaaca tatagaaata ggaaaacaga aaaacctctg  37500
```

-continued

```
tggaatttgg cattaacata gaccttagcg aaacctgttt tattagagac agtgattttt  37560
taaaaacact taactgtgaa gggaagggat ttgatgagat aacacaattg tctgaaggta  37620
gagagaataa aaaacaattt tttttctaat gagaagagta taattaagca tggggaacag  37680
acacatagag attataaagg aagtgatgat tgcaaaatat ttaaccaaat aattagtatt  37740
atacatgttt gtgatagagc tatggtacac ttaattaggt aaaatgccaa aagacagtgc  37800
cacgctccaa gctttatgta tcataaacat caaaaatgac ttgctgaatt aaattaaatt  37860
gagtctccat taacatgtaa atcatcatat ctgtgccctg gaataattca gagtttaatt  37920
tgtgggtttg cttccttatg aaggtcatcg aacactattt attggagtac atgtgccctt  37980
gggaggaaga aaaagccatc gacgtcacag gcatcgtggt cataaacaca gaaagagaga  38040
cagagaaaga gattcaggat tagaggatgg aagggagtca ccttcttttg gtaagaatcc  38100
ttctccttgt ttttattaag ttaattattg taatatactt gcttatacaa ttatgattag  38160
gagtaatacc ttatactcat aaaattgttt atacttttat aaaagacttt gggccggttg  38220
gagagaagtg ggagagataa agcttgatct ttgtttttct cttatatatt tgcattgaga  38280
agctgagaat tgatgaagat ttatgatata ggaaatacaa ttgagtaaag ctcaaaaact  38340
cttgataatt tatacaaata atcatcatta ctcaaagtgg tttgaaaatc cagggcaaaa  38400
tgccttaatt tagttcccat ttgcactttt actgatagtg cccaagtttc agtcttagga  38460
tgttgtatta gtccgttttc acactgctga taaagacata cccggactag acaatttacc  38520
aaaataaaaa agaggtttaa ttggacttac agtaccacat ggctggggaa gcctcacaat  38580
tatggtggaa ggcaaggaga agcaagtcat gtcttacatg ggtggcagca ggcaaagaga  38640
gcttgtgcag gaaaactccc ccttataata actatcagat ctcatgagac ttactcacta  38700
tcacgagaaa agcacaggaa agacctgtcc tcattattca attaactccc actgggtccc  38760
tcccacaaca catggaaaat tcaagatgag atttgggtga ggacacagcc aaaccatatc  38820
gttccaccct tgggccctcc caaatctcat gtcctcacat ttcaaaacca atcgtgcctt  38880
cccaacagtc ctccaaggtc ttaacttatt tcagctttaa ttcaaaagtc tatagtccaa  38940
aatctcatct gagataaggc aagtcccttc cacctgtgag cctgtaaaat caaaagcaag  39000
ctagttactt cctagataca actggggtaa aggcattagg taaatacagc cattccaaat  39060
gggagatatt ggccaaaaca aaggggctac aggcccaatg caagtccaaa atccagcaag  39120
gcaatcaaat cttaaagctc cgaaatgatc tccttttact ccatgtctca catgcaggtc  39180
atgctgatgg ttctcatggt cttgggcagc tctgccctcg tggctttgca ggatatagcc  39240
cacctcctgg ctgctttcat gggctggcgt tgagtgtctt gttgcttttc cggacacact  39300
attcaagctg tcagtggatc ttccattctg cagtcaggag gacagtggcc cttttctcac  39360
agctccacta ggtggtgtcc cagtagggac tctgtggggg ctgtaacccc acatttccct  39420
tctgcactgc cctagcagag gttctccatg agggccctgc ccctgaagca aatttctgcc  39480
tgggcatcca ggcatttcca tacatcctct gaaatctagg cagaggttcc taaaccccaa  39540
ttcttgactt ccgtacacct gcaggctcaa caccacatgg aagctgccaa ggcttgaggc  39600
ttgcaccctc tgaagccaca gcctgagctc tacatttgtc cctttcagct atggctggag  39660
cagctgaaac acagggcacc aagtccctag gctgtacaca ggatgggtac cctgtgcctg  39720
actgagaaaa ccactttttc ttcctgggcc tctgggtctg tgatgggagg ggctgccata  39780
aagacctttg acatgccctg gagacatttt ccccattgtc ttggggatta acatttggct  39840
cctcattact tttgtgaatt tctgcatttg gcttgaattt ctcctcagaa aatggaattt  39900
```

-continued

```
tcttttctat tgcactgtca ggctgcaaat tttctgaact tttatccttt gcttccttta  39960
taaaaccgaa tgtctttaac agcatccaag tcacttcttg aatgctttgc tgcttagaaa  40020
tttcttctgc cagataccct aaatcatctc tctcaagttc aaagtttcac agatctctag  40080
ggcaggggta aaacactgcc agtctctttg ctaaaacata acaagagtca cctttgctcc  40140
agttcccaac acgttcttca tctccacctg agaccacctg agattgcctg gaccttattg  40200
tccatatcat tatcaagctt ttggtcaaag ccattcaaca cgtcactagg aagttccaaa  40260
ctttcccaca ttttcctatc ttcttctgac ccctccaaac tgttccaact tctgcctgtt  40320
acccagttcc aaagtcactt ccacatttc aggtatcttt tcagcagcac cccactctac  40380
tggtatcaat ttactatatt aatatgtttt cacactgctg ataaaaacat acctgagact  40440
aggcaattta cagaagaagg aggtttaatt ggacttacag ttccacatga ctggggaagc  40500
ctcacaatca tagcggaaag caaggaggag caagtcacat cttatgtgaa tggcagcagg  40560
taaagagacc ttgtgcagga aaactctgcc ttataataac catcagatct catggactta  40620
ctcactatca tgagaacagc acaggaaaga cctgcccccc atgattcaat tacctcccac  40680
caggtccctc ccacaacatg tgagaattca agatgagatt tgggtgggga cacaaccaaa  40740
ccatatcaaa tgtgaacctt ttactattgt gaatgctctc tcattgaaag catattcaga  40800
ataccacaat aagtgttttc gtagttgtta aaaggttctg aatgccatga gagcccatgt  40860
acatgacata actgagaacc tggctctcag ttccttgacc atcccatctc ttatgacctt  40920
ctctgtcatt gcactttgtt caccttctca accatattca ctccatccct gaagtcacta  40980
attcatttat ctttctgtct gaccacagct tcactccttt cttgctgtgc agctacttaa  41040
cccctctact tttcttctat ccataagttt gtctttattt gtttatccta gtctgattgc  41100
atagcatgca gtcttaggaa tactttagca ttactagtat tccatttgta ttactagtag  41160
tctatttagt aatactagta ttctaaatat cttaggttct aagttttagt tttcttcata  41220
cctttactgc ctcttttatt ttcattttta ataggaagca gcattttatt taaaatgttt  41280
ttaatagatt tcttaaagat gtaaataatc gaattaaact tagtctatat tacttgtatg  41340
aattaattta catttgttc acattcgtga aaaataattt agctaggtat gcaattccaa  41400
attgacaagt attttaactc agcactttga acataatatc tatttattta tcaatttcat  41460
gaagatgtta agaaaggaga taaaaatcta ttgttgctct acagttaatt tggattttat  41520
atttttatga atttaaatca tttcctttat tttggtattt agttttacat ttattatgat  41580
attttcagac acacatatat gccttttatg cttttcttgg ttgatattta atgagaatgt  41640
atattattag ttctttaaaa tgcttaaaca tgtcctattt tctattattt tctctcccac  41700
ttatttaaat tctttcttca aatattcatt aagcatattc ctttcaattt cattttcgat  41760
ttattttgat ccctctttta tattttttca tcattttctc cttgtcctga cattgaagtg  41820
tttattttag ctaattcatt tattcatatt ttagctcata gtttttgcct tgctcatatc  41880
cctttacttt ctttaaacat tttgactaca tgtgtctttc acttctttta ctttggattc  41940
gggggcatgt gtgcaggttt gttacataag tatgttgtgt gatgctgggg tttgggatat  42000
ggatggtcct atcacctagg tagtgagcac agagtatagt tttacaaccc ttgttcccca  42060
ccctccttcc ctgctctggt gattcccagt gcctattgtt cccatcttaa tgtacataag  42120
tacccaatgt ttagccccac ttatgagtga gaacatgcag tatttggttt tctgttcctg  42180
agttaatttt tttaggataa tgatctccag ctgcattcat gttgctgcaa aaggatatga  42240
```

-continued

```
tgtcattctt tttatggcca catagtattc catgatatat atgtaccaca ttttcttcat  42300
ccactttacc ataaggaaac ctagttgatt ccatgtcttt gctatggtga ataacactgc  42360
agtgaacata ccagtgcatg catctttttg gtggaatgat tcatttttct ttgagtatat  42420
acccagtaat gggattgctg ggttgaatgg tagttctgtt ttaatttctt tgataaatct  42480
ccaaactgct ttccacagtg gctgaaccaa tttatattcc caccaacagt gtataagcat  42540
tccgttttct ctgcagcctt gtcagcatct attatttttt gactttttaa tgttcaccat  42600
tctgactggt gtgacatggt atctcattgt ggttttgact tgcatttcat ttgttgactg  42660
cttgtatgtt ttcttttgag aagtgtctgt tcgtgtcctt tgcccatttt tagtagaatt  42720
atttgttttt tgcttgttga tttgtttaaa ttttgcttgt ggattcgggg tatcagacat  42780
tttttgaatg catagtttgc aaatattttc tcccattctg taagctatct gtttagacta  42840
ttgagatttg ctgtgcagag gctctttagt ttaattaggt cccacttgtc aatttttgtt  42900
tttgtttcaa ttgcttttgg agacttagcc attaattctt tgtcaaagtt aatgttggga  42960
agggtatttc ctaagctttc ttctagaatt attataactt aaagtcttac atttaactct  43020
ttaatccaac ttgagttaat ttttgtatat ggtgaaaagt aggtatccag tttcattatt  43080
ttgcatatgg cttgacagtt atcccagcac catttattta atagggagtc ctttctgtat  43140
tagttattct tggtgacttt gttgaagagc agactgttgt aggtgtttga ctttatttct  43200
ggattctcta ttctattcca ttagtgtgtg tgtctgtttt ttgtaccagt acaatgctgt  43260
ttgggttaat gtagccatag agtacagttt gaagtcaggt aatatgatgc ctctgacttt  43320
gttctttttg cttagaattg ctttggctat ttgggctctt ttttgattcc atattaattt  43380
tagaatagtt tttctaattc tgtgaaaaac aacattggtg ttttgataga gatcggtatt  43440
gaattctgta aattgctttg ggcagtatgg ccattttaat gatattgatt cttcctattc  43500
atgagtgtgg aacattttta catttgtttg tgttgtctct gatttctttc agcagtgttt  43560
tgtagttctc cttgtagaaa tctttcacct ctttggttag atgtattaca tttttttgtg  43620
tgcctattgt aaatgggatt gagtttttga cttggctctc tgatacaatg ttattgctgt  43680
acagaaatac tattgacttt tgtacattga ttttgtctcc tgaaactcta ctgaaattgt  43740
caattctagt tgccttttgg tggagtcttt agggttttct atttctaaaa ttataatcat  43800
cagcaaagga gagatagttt gacttcctct cttcctattt gaatgccttt tatttctttc  43860
tcttgcctga ttgctctggc taggtcttcc ttatactatg ttaaatagga gtggtaagag  43920
taggcatcac tttcttgttc tggttctcca ggggaatagt tatagctttt gcccattcag  43980
tatgatttta gctgtgtgtt tttcatagat ggctcttatt gttttgaggt atgtttcttc  44040
aatgactagc ctgttgaggg tattttatca tgaagggatt tgggattctc ttgaaggcct  44100
tttctgtatc tatcgagata accatatggt tttgattttg attctgttta tgcgatgaat  44160
catatctagt gaattgtgta tgtcgaacca accttgcatt ccaggaatga agcccacttt  44220
tctcatagtg aattagattt tgatgtgctg ctgaattcag tttgctagta ttttgttgag  44280
gattttgtgt ctatgttcat cagggagttt agcctgaagt tttctgtttt tgtgtctctg  44340
ccagattttg gtataaggat gatgatgact ttgtataata tgttagtgag aagcctcccc  44400
tcatcctcaa ttttttggaa gagttttagt aggattggta ccagttcttc tttgtaactc  44460
tagtagaatt cagctgtgaa tccgcctggt tcagggcttt ttttggttgg taggtttttt  44520
taaaattacc gattcaattt cagaacttgt tattggctta ttcatgtttt cacattatcc  44580
cttgttcaac cttggatggt tttgtgtttc tgagaactta tccatttcct ctagattttc  44640
```

-continued

```
taatttgttt gcacagaggt gttcataata gtctctgaat atcttttgta tttctgtggg  44700
attgggtgta atgtcatttg tcatttttga ttgtgcttat ttgggtcttc tctttttttg  44760
ttaatctaac tagtagtcta tcaatcttat ttattctttc aaaaaacaaa ctctgtttca  44820
tttatctttg tatggacttt tgcatctcaa tttctttcag ttgttctctg attttagtaa  44880
tctcttttct tctgctagct tttaaagcca tacttatgtt ggggttcctc catttttcca  44940
ttttctcctt gcctccacaa gcagatatac tctgctggaa atcatcattc aacaaggcag  45000
attgtaacca ttatgaagtt atgactcaag gagaccttca acatctcctc ctaatttcat  45060
tgtgtatctt ttttgacatt tgaaataatt atttttcaac tttcttcgcc ttcttcatca  45120
ttctccaaca tcctctcttt tcaccattac ttgatagtaa tcttgctttg tacttcagag  45180
ggaaaatata tcatcagaaa gaactcactt tactttcttc ctgttaaaaa gttatagctg  45240
aaacctttct tcctattaaa cggttaaaac tgcaagaaaa taaggaagtt ttcttttcct  45300
ttatgtttat tttctattcc ctctcaccac tctggaaact tatgccattt ctaatttaat  45360
tgacctcttc ctcttgaaat gaatttttct tatcatcttt gaaacatgat agagtctcca  45420
ccattttaag cagttctcca acctcctgca aacccacctt tagtcattca gatatgtaag  45480
ttaactgcat ataaatgttc tgggtagcaa ttttactttt aaatatctct ccatattgct  45540
ttatttggtt tattcaatat ctggcttcag taactattgc agataagtct atagtctctc  45600
tatttttatt ttttaggttt atgtatttta atcctgaatg tttatagaca tttttctgtg  45660
tcccttaatg aagaaaattg ctaagattga cctaatggta ggtgtattaa aaaacttttc  45720
catcccgcat acacgaatag ttttccacct agggaacatt ttcctattat gtttcattct  45780
gttccattta ctttgatctc tttgtgaaga ctttctttgc tcatatccct ctactttctt  45840
caaacatttt aactacatat atctttcatt tttttttaac tttgaatttg ggggtacatg  45900
tgcaggtttg ttacatgagt atgttgtatg atgctgaggt ttggggtaca gatggtccta  45960
tcacgcaggt agtgagcaca gagtatagtc aattttacaa cccttgttcc ctaccctcct  46020
tcccagctcc ggtgattcca agtgcctatt gttcccatct ttatgtccat gagtacccaa  46080
tgtttatctc ccatttatga gtaacaacat gcagtatttg gttttctgtt cctgagttaa  46140
tttgcttaga gtaatggcct ccagctgcat tcatgttact gcaaaaggat atgatgtcat  46200
tctttttatg gctgcacagt attccatggt gtatatgtac cacattttct ttatccacct  46260
caccctaatg gtacctagtt gattccatgt ctttgctatg gtgaatagca ctaagatgaa  46320
catgcacgta tatgtcagat ttctgatttc tgctctgtat ccttttcctc tgtagtttaa  46380
tgttagtctt ttatattacc atttgattat ctgcagaata aattctgcat tttcctactt  46440
ttattatgag ttttggtttt gctgttgcat ttttagtttt cattaatttc tttcttattt  46500
catcctattt tctttacatt ttagcctgtc ctttcctgaa tactttttat ttttttctgg  46560
ttggtagagt gtatccccag tgatttctgg acgttttcat tttatcctaa agtagacaat  46620
tttcagagct atgcttttcc tttggactgt cagattattt ttactctcca ttgattttta  46680
gtatttttta tggactccta ggttttttcc tttttttctc atttttaaac aaggaaaggt  46740
agattcctac tatatctacc tagctatatc ttaagattgc ttaatgaggc tgctgtcagt  46800
atgctccatg tttccaacag tatgtataat aagcatcaca cttatccaaa tgccctgtac  46860
ttctgccagg ggcagcatag ttgttggtgg cagagtatgt aaagaaaagt actctaggta  46920
tcctgcacca ccatgataaa gaaggatggt tgtccataag aatgggcaga tgggctgaga  46980
```

-continued

```
gtgtaggata tactaagtat cttctgcatt ttcagatgtt gtctctttca tgaaggaacg  47040
tcttagagtg taaaaaaatg acaatttggc atatttttct cattcaagtt ccatctgctt  47100
atagttagca gagatgccct cttagactgc aggaatggat tatctgtagg gctatgcgct  47160
aatgatgagt tttcatcatt ttctagtatt tgagaaaata tatttatatc atcttacaag  47220
tatttcatga gcaaataaaa ataagctgta tttatcattt gtttgttccc tgtgcctctt  47280
ctttattttt ccctaactgg aggcattatg ccagtttttc tagaacagtg gttctcaata  47340
atgactgcat ttgagaattc taaaaccgtg ctaatgctca acccgtacac caaccagaat  47400
ctctgtgcct ggggcctaag catgagtatt ttttgaaaag tacccccagg tgattcttct  47460
gtggagctgt tgatagctcc acagaaggtt gatatccact gttctggaaa ctttgctatt  47520
taaatttagt tcatcagggg tctaatatcc agaatctata aggaacttaa acaactcaac  47580
aagcaaaaat caacgtgatt aaaaagtggg taaagacatg aacagacact tcttaaaaga  47640
agacatataa gcagccaata aacatatgaa gaaatgctca atatcacgaa tcatcagaga  47700
aatgcaaacc aaaaccacaa tgagatacta tctcacacca gtcaaaatgg tgattatcaa  47760
aaagttaaaa aataacagat tctgacaaag ctgcagagaa aagggtatgc ttacacactg  47820
ttggtgggaa tataaattgg ttcagccact gtggaaagca gtttggagat ttctcgaaga  47880
acttaaaaca gaacaactat tgacccagca atgtcattac tgggcatata cccaaaggca  47940
aatgaatcat tctatcaaaa ggcacatgga cacgactgtt aatcacagtg ctattcacca  48000
tggcaaagac atggaatcaa cctaggtgct catcaacagt ggattgaata aagaaaatat  48060
actccatggc atacattgca gccctaaaaa agagcaaaat catgttcttt gcagcaacat  48120
gtatacaact ggaggtcatt atcctaagtg aattaatgca ggaacagaaa accaaatacc  48180
acatgttctc acttataagt gggagctaaa cattgggtag ttgtgaacat aacgatggca  48240
acaatagaca ctggaaacca ccagagagga gagggagggt ggggaactag ggttaaaaaa  48300
gtaactattg ggtactatac tgcccactac ttgggggaca ggatcagtca taccccaaac  48360
ctcagcatca ttcaatatgc ccatataaca agcctgcaca tgtactccct gaatctaaaa  48420
taaaagtaga aattattttt aaaacttacc aaacgtaaag aaagaaacct gtactgctag  48480
cttttaaaag ttatttaata aataaaccta ttttataaca aaaatagtaa aaataaattt  48540
ctacttcaaa gtataaagcc aacaatatta gcattaaatt taaacttgcc agaaatgcag  48600
aatctcaggc ccatccaga cctcttgagt caggacctgt acattaaaaa tatatttagg  48660
taactggtat ggtttggctc tgtgtcccca ccaaaatctc atctccattt ataatcccca  48720
tgtgttgagg gagggacctg taatccccat gtgtccaagg agggaggtga ttggattttg  48780
ggggcggttt ccctcatgct gttctcgtga tggtgagtga tttctcatga gatctgaagg  48840
atttataagg cagtgttccc agctctttgc tcgctcgctc ttctgccgcc ttgtgaagaa  48900
agtgcctact tctccttccg ccatgattgt aagtttcctg aggcctctcc aggcatatgg  48960
agctgtgaga caattaaact tctttccttt ataaattacc cagcctcagg gaagctcttt  49020
atcacagtgg tgaaacagac taataacagt aacgtatatg aatcttaaaa tttgacgcca  49080
agcgatgctc tagaacattg cttatcaaac ccttctggca cattgggaat cacttgagaa  49140
gctttaaaaa aattattgat gctaggcttc aacctcgaag gatttttatt taattaatct  49200
tgggtgtttc cctaggcact ggtattttta aaaagtaccc caaattattt aataaccact  49260
taaataattg accaagaatc agattctgag aagcttctgc ctctcaattt ggtgaaactt  49320
ggaaataagt cgggtggccc agattctccc tcttattttt tgccactatt tttggatgcc  49380
```

-continued

```
acctaccttt ttccttcttc aatcatctga gtatcttcag tgacatttag acctaaatgt  49440
ggtttatcag tgacaaatgt ttggcacttg gtggtttcta agcaatggaa ttttctagat  49500
ttcacttttt tcagtttctc tagtactaat cttctgcctt catccttatt ccacactcag  49560
tttatttgct ataataagta ctcagtcaca cacagagact tcaaccaaac cctaaacacc  49620
atcctatctg atttgggttt tgatattctg catagtgaga atatatgaca tttccatgct  49680
gaaggcatta aagaaaattt ctgcctactt aagaaatagt tattttacgt ggaagcattc  49740
caaagaaaat attttgaaga tatttctgca ggtgcctcaa aattctttgg aattcaactt  49800
ccgaagaagt ataggataga ggagaattta agagagtatc aggtctctct gctatgaagc  49860
tagatatatg ttgttaattg cagtatgaat ctgtgaaatc atggaatcat tagggcccaa  49920
attatgaagc aagcatcaat ttaacaaaac gatttttgga aaaacgtttg aatttgggca  49980
ctcttttttt tattattata ctttaagttt tagggtacat gtggacaacg tgcaggtttc  50040
ttacatacgt atacatgtgc catgtgtggt gtgctgcacc cattaactcg tcatttagca  50100
ttaggtatat ctcccaatgc tatccttccc cccctccccc caccccacaa cagtccccag  50160
tgtgtgatgt tccccttccc tgtgtccatg tgttctcatt gttcaattcc cacctgtgag  50220
tgacaacatg cggtgtttgg ttttttgtcc ttgcaatagt ttgctgagaa tgatggtttc  50280
cagcttcatc catgtcccta caaaggacat gaactcatca ttttttatgg ctgcatagta  50340
ttccatggtg tatatgtgcc acattttctt aatccagtct atcattgttg gacatttggg  50400
ttggttccaa gtctttgcta ttctgaatag tgccgcaata aacatacatg tgcatgtgtc  50460
tttatggcag catgatttat agtcctttgg gtatataccc agtaatggga ttgttgggtc  50520
aaatggtatt tctagttcta gatccctgag gaatcgccac actgactttc acaatgattg  50580
aactagttta cagtcccacc aacagtgtaa aagtgttcct atttctccac atcctctcca  50640
gcacctgttg tttcctgact ttttaatgat tgccattcta agtggtatga gatggtatct  50700
cattgtggtt ttgatttgca tttctctgat ggccagtgat gatgagcatt ttttcatgtg  50760
cctgttggct gcataaatgt cttcttttga gaagtgtctg ttcatatcct ttgcccactt  50820
tttgatggga ctgtttgttt ttttcttgta aatttgttta agttcattgt agattctgga  50880
tattagccct ttgtcagatg agtaggttgc gaaaattttc tcccattttg taggttgcct  50940
gttcactctg atggtagttt cttttgctgt gcagaagctc tttagtttaa ttagatccca  51000
tttgtcaatt ttggcttttt gttgccattg cttttggtgt tttagacatg aagtccttgc  51060
ccatgcctat gtcctgaatg gtattgccta ggttttcttc tagggttttt atggttttag  51120
gtctaacatt taagtcttta atccatcttg aattaatttt tgtataaggt gtaaggaagg  51180
gatccagttt cagctttcta catatggcta gccagttttc ccagcaccat ttattaaata  51240
gggaatcctt tccccattgc ttgtttttct caggtttgtc aaagatcaga tagttgtaga  51300
tatgcagtgt tatttctgag ggctctgttc tgttccattg atctatatct ctgttttggt  51360
accagtacca tgctgttttg gttactgtag ccttgtagta tagtttgaag tcaggtagcg  51420
tgatgcctcc agctttgttc ttttggctta ggattgactt ggtgatgtgg gttctttttt  51480
ggttccatat gaactttaaa gtagtttttt tccaattctg tgaagaaagt cattggtagc  51540
ttgatgggga tggcattgaa tctataaatt accttgtatc tcccactgtt attgtgtggg  51600
agtctaagtc tcttcatagg tctccaagaa tgtgttttat gaatctgggt gctcctgtat  51660
tgggagcata tataattagg acagttagct cctcttgttg aattgaaccc tttaccatta  51720
```

-continued

```
tataatgccc ttctttgtct ttttcgatct ttgttgggtt aaagtctctt ttgtcagaaa  51780
ctaggatttc aactcctgct tttttctgct ttccatttgc ttggaaaatt ttctccctcc  51840
ctttatttga gcctatctgt atcttggcat gtgagatgga tttcttgaat acagcacgcc  51900
aatgagtctt gactcttttt ttttttcttt tttttcttga tgcagagtct tgctctgtca  51960
cccaggctgg agtacagtgg catgatcttg gtcactgcaa cctctgcccc caggttcaag  52020
taattctcct gcctcagcct cccaagtagc tgggattaca ggcatgtgac accacgccca  52080
gctaattttt gtagttttag cagagatggg gtttcaccat gttgatcagg ctggtcttga  52140
actcctgtcc tcaggtgatc cacccacctc ggcctcccca aaagtgcttg gattacaggc  52200
atgagccagg gccttgactc tttatccagc ttaccattct gtgtcttttg atttgggcat  52260
ttagcccatt taattgaaga ataatatctt tatgtgtgaa tttgatcctg tcatcatgat  52320
gctagctagt tattttgtag atttgttagt gtagttgctt catagagtca ttggtctgtg  52380
tacttcagtg tgtttttgta gtggctgcta atgattttcc ctttcatatt tagtgctttt  52440
ctcaggagct cttacaaggc aggcaggcca ggtggtgaca aattccctca gtatttgcgt  52500
gtctgaaaag ggttctattt ctccttcact tatgaagcgt ggtttagcca gatatgaaat  52560
tttgggttag aaattctttt ctttaagact gttgaatatt ggcccccagt ctctgctggc  52620
ttatagggtt tccactgaga tgtttgctgt tagtctgatg gacttccctt tgtaggtgac  52680
ctggcttttc tctctgcgct gcccttaaca ttttttcctt catttctacc tggagaatct  52740
gatgactata nnnnnnnnnn nnnnnnnnnn nnnnnnnnnn nnnnnnnnnn nnnnnnnnnn  52800
ctaaattatt acattcaatg aaatgtaata attgacaaaa ttttatttta ttttattatt  52860
attatacttc tagggcacat gtgcacagca tgcgggtttg ttacttatgt atacatgtgc  52920
catgttggtg tgctgcaccc attaactggt catttacatt aggtatatct cctaatgcta  52980
tccctccccc ctaccccccac cccatgacag gccccagtgt gtgatgttcc ccttcctgtg  53040
tccaagtgtt ctcacattgt tcagttccca cctatgagtg agaacatgtg gtgtttggtt  53100
ttttgtcctt gcgatagttt gctgagaatg atggtttcca gcttcatcca tgtccctaca  53160
aaggatatga actcatcctt tttatggctg catagtattc catggtatat atgtgccaca  53220
ttttcttaat ccagtgtatc attgatggac atttgggttg gttccaagtc tttttttttt  53280
ttcattgtta ttttttccag actttttttt ttttattata ggttccaagt ctttgctatt  53340
gtgaatagtg ccgcaataaa catatgtgtg catgtgtctt catagcagca tgatttataa  53400
tcctttgggt atatacccag taatgggatt gctgggtcaa acggtatttc tagttctaga  53460
tccctgagga atcgccacac tgactttcac aatgattgaa ctagtttaca gtcccaccaa  53520
cagtgtaaaa gtgttcctat ttctccacat cctctccagc acctgttgtt tcctgacttt  53580
ttaatgattg ccattctaag tggtatgaga tggtatctca ttgtggtttt gatttgcatt  53640
tctctgatgg ccagtgatga tgagcatttt ttcatgtgcc tgttggctgc ataaatgtct  53700
tcttttgaga agtgtctgtt catatccttt gcccactttt tgatgggact gtttgttttt  53760
ttcttgtaaa tttgtttaag ttcattgtag attctggcta tcagctcttt gtcagatgag  53820
taggttgcga aaattttctc ccattttgta ggttgcctgt tcactttgat ggtgatttct  53880
tttgctgtgc agaagctctt tagtttaatt agatcccatt tgtcaatttt ggcttttgtt  53940
gccattgctt ttggtgtttt agacatgaag tccttgccca tgcctatgtc ctgaatggta  54000
ttgcctaggt tttcttctag ggtttttatg gttttagtct aacatgtaag tctttaatcc  54060
atcttgaatt aatttttgta tatggtgtaa ggaagggatc cagtttcagc tttctaccta  54120
```

-continued

```
tggctagcca gttttcccag caccatttat taaataggga attctttccc cattgcttgt  54180
ttttgtcagg tttgtcaaag atcagatagt tgtagatatg cggcattatt tctgagggct  54240
ctgttctgtt ccattgatct atatctctgt tttggtacca gtaccatgct gttttggtta  54300
ctgtagcctt gtagtatagt ttgaagtcag gtagcgtgat gcctccagct ttgttctttt  54360
ggcttaggat tgacttggtg atgtgggttc ttttttggtt ccatatgaac tttaaagcag  54420
ttttttccaa ttctgtgaag aaagtcattg gtagcttgat ggggatggta ttgaatctat  54480
aaattacctt gggcaatatg gccattttca tgatattgat tcttcctacc catgagcatg  54540
gaatgttctt ccatttgttt gtatcctctt ttatttcatt gagcagtggt ttgtagttct  54600
ccttggacga ggtccttcgc atccctttta agttggagtt ctaggtattt tattctcttt  54660
gaagcaattg tgaatgggag ttcattcatg atttggctct ctgtttgtct gttattggtg  54720
tataagaatg cttatgattt ttccacattg atttttgtat cctgagactt gttgtagttg  54780
cttatcagct taaggagatt ttgggctgag atgatggggt tttctagtat atacaatcat  54840
gtcatctgca aacaggggac aatgtgactt cttttcctaa ttgaatgccc tttatttcct  54900
tctcctgcct gattgctctg gccagaactt ccaacactat gttgaatagg agtggtgaga  54960
gagggcatcc ctgtcttgtg ccagttttca aagggaatgc ttccagtttt tgtccattca  55020
gtatgatatt ggctgtgggt ttgtcataga tagctcttat tattttgaga tacatcccat  55080
caatacctaa tttattgaga gtttttagca tgaaaggttg ttgaattttg tcaaaggcct  55140
tttctgcatc tgttgaaata atcatgtggt ttttgtcttt ggttctgttt atatactgga  55200
ttacatttat cgatttgcat atgttgaacc agccttgcat cccagggatg aaggccactt  55260
gatcatggtg gataagtttt tgatgtgttg ctgtattcag tttgccagta ttttattgag  55320
gatttttgca tcaatattca tcaaggatat tggtctaaaa ttctcttttt ttgttgtgtc  55380
tctgccaggg tttggtatca ggatgatgct ggcctcataa aatgagttag ggaggattcc  55440
ttctttttct atcgattgga atttgggcac tcttaaaaag ttttattact ccaacgtata  55500
agcaacatca gcagaatcct actttattat gagacccaat catagaatac agtgttgtta  55560
aaacatccta gttgcattag tgttgcattc aggtaaaaga ataggccttt aatatagacg  55620
gaagagttta tgcttacatc ataggaaaac aatgactggt tcaagcctac catatgtcat  55680
ggttgggctg tgattcctag gtgagtctaa agaggaactg gcttttggtc tgtgtggtag  55740
tggtggtggt gatgttttgc tcatacaaaa aacttttaat gcccacaaat aagttcaacc  55800
tactttggct actgtactta ataaatataa taaatatatt aatttgttta gatgaatgtg  55860
atgatgatta attaattctc cttcctattg caatcaactc cccagtaaca aagctgctaa  55920
aatttcactt tttttttttg agacagagtc tcactctgtt ggccaggctg cagtgctgta  55980
gcacagtctt ggctcactgc aacctctgcc tccctggttc aagcgattct cctgcctcag  56040
cctcctgagt agctgggatt acaggcacct gccaccacag ccagctaatt ttttgtattt  56100
ttagtagaga cggggtttca ccatgttggc caagctggtc tcgaactcct gacctcgtga  56160
tccacccgca ccagcctccc aaagtgctgg gattacagga atgagccacc gcatccagcc  56220
cacatttgtt atttttaatg tcatcttcta ttctctttgt ataatttgaa actatatttt  56280
caactgggaa catggatgag ctgctttaaa ttggtaagtt tgaagcataa gcttgaagtc  56340
agtgaaaata tgaaagatga tgagggaaat ttgtaacact tcaacgttta ttttttttcct  56400
caacctccct gaaaagaatc taatagaaaa gatgatagga ttatgccaat tacaattagc  56460
```

-continued

```
taatgtataa gaagtagaaa taaatctaaa agatacagac tattaaacac atgtttaaaa  56520
tatggtacac aaagatactg aataaattaa cacagtcctg gaattataat aggattttgt  56580
cagtcttagg tggtaaattg tgcacactct ttaggagaaa tgaagcaaat atagaaaaca  56640
tgacctcaaa gagcaatttt ttgatggaca gtggcttcct gttcctattt taatgaccaa  56700
ttaggtgcta tatgagaata tcaaggtgtt tttacaaatg tattttattg taaagtataa  56760
gacaagcatt cacaagtgtt aaagcataga aacatacata taaaacccaa tgaattatca  56820
caccagaaca tctgtgtaat accaccttgg ctggcactct agaaactcac tttgtgctca  56880
ttaccagtca ttaggttttc catcctcctc aaaagaatct ctggcctttc tttttacaat  56940
gggtattttg cttgtttttg aacgttatat aaatgaaatc atataagagg aattaattgc  57000
tcagtgttct gtttatggaa ttcaccaatg tttttgatgt agcttcagcc tattcatttt  57060
cattattgta tagtatgtta atgtgcttct atatgcacgg tatgtatgca ttctactatt  57120
gatggtcatt tggatcatat gcaattagaa gctactacaa gtaataatgc tgtgaacatt  57180
tttctatatg tcttttggta tacatatgca tttctcatac cgatgaatga aattatcaat  57240
tgctgagtca taggacatgc atattttcag ttttggtaga taatgccaaa tagatttcca  57300
aaattggggt acatatttac attcccacca ataaagtgtg agaacttatg tttttttgca  57360
tccttactaa cacttggtaa ttccattctt ttaacattag ccattctctt aaggtatgta  57420
attatatctt attgttttaa tttatatttc ttgattacca atgaaattga gtaactttgc  57480
atatgccttt ggccatttgg atattctctt ctaggaagtg cctaccaaag tcatattttt  57540
aatgagcttt tattgatttg tagaagttct ttacatgtta tggaaataag tcctttgtta  57600
gttttatgtg ttttaaatat cttctcacta ttgtgggttc tgatttcact ctcataatgg  57660
tatttttttg atgtggctac agattccagc agagtctgct aagaggctga tacctttatt  57720
ctttaggcaa atttttctat gttatttatt tccattatat gttttagtat atatagaagc  57780
agacccatat cttgatcttc cataatcttg gctgaagttt gtatttcact gctctatggt  57840
ttcagtggct atcataaaaa taaacatcca tcaacacagg agaaatattc tattaactta  57900
gacaattctg ccaggtgctg tagctcacac ctataaaccc agttacttag aaggctgagg  57960
tgagagaatt gcttgagccc aggagttcag ggttacagtg atcatgccat tgcactccag  58020
actgtgtgac agaacaagac agcatctcta ataaaaataa caatttttaa caggaagatt  58080
ttttctgatt ttgatagtac tgcaatttac atgaaatatg taatactatt ttaaggtgtc  58140
tatttttaat agacatgaaa aatgggtgtt gaattacaca tttggaaaat ttactgtatt  58200
gaaacataat cttaatccct ttttaagatc ttaaaaatat gttagtagga tggttatgaa  58260
aaatcttttg tgaaaataac ctaataccta taaaatcatt tctattttaa agaatgaagg  58320
cctgatacag ggaaccatac gttatcttga atcaaaataa aatatttctt gtcgctgaat  58380
agatgaccct atttcaataa attattattt tctttaccat tgctgctatc attgtgtttt  58440
agggaagcct tttgaatacc tgacacccta tctcacactt tcaaatactc cttattcata  58500
actgtgaggg tgttataacc acatgtttac ttacaaatag tattttaaag gtgtgtagtg  58560
agtaagcctc atgctttata aaaggaaaca ctaataagcc ttaaaattaa cactcatgta  58620
catagcaatt gagatttggg ggttggatgc atggtattat agacatccag attactgatg  58680
aagagtgaac tgaaataagt ctttggaaac agtgatgaga gaaaatgttt cagagacatg  58740
gggaccctaa taccaatgtg gaagcatggc tgctatgaga tgtgacctct gagaagtgat  58800
tgggtagtca gaactggttg tcatgcaaca caaaatgact atgtctgctc acactgggtc  58860
```

-continued

```
agtctaatgg gaatatttaa ttgatttctt agtgtaactc tagaatcaca aattgtgctt  58920
ttttttaaat ggctattcaa agtactgata ttttttctag accaactagt ctgagagata  58980
acaggctaat taaaaatgca gttgaccctt gaacaatatg ggtttgaact gtgcaggtcc  59040
acttacacat agacttttac atttatatgt atattatgta gtttttgtat attatgtatt  59100
tttatattaa aaatgtatgg gccaggcgca gtggctcatg cctgtaatcc cagccttttg  59160
ggaggcctag aaacacagat cacttgaggc caggagttgg agaccatcat ggccaacatg  59220
gcaaaacctc ctctctgcta aaaatacaaa aattagctag acatggtgat gcgcacctgt  59280
agtcccagct atttgggagc ctggagcagg agaactgctt gaacccaaga ggtggaggct  59340
gcagtgagcc aagacagtgc cactgcactc cagcctggat ggcagaaaga aactgtctca  59400
aaaaaaatta tgtgtatata tatatacttt ttttttagat ttgtgacatt ttgaaaaaac  59460
tcacagataa actgcatagc ctagaaatat aaaaaaatta ggaaaaaagt atgtcatgaa  59520
tgcataacat ataggtagat actagtctat tgtatcacat actaccataa aatctacaca  59580
aatctattat aaaagttgaa atttatcagg ccttatgtac acaaacactt atagattgtg  59640
catggtgtca ttggcaactg agagaaatgt aaacaagtgc aaaaaatgca gtattaaatc  59700
ataactgcat acagtttact gttgtactta atgtactact gtaataatgt tgtagccact  59760
tgctgttgct attgtgtgag tgcaagtgtt tccagtatcc acttaaaaca ccttgtgatg  59820
ctaatcacgt ctacctgagc agttcatctc ttcagtaaac agcatattgc cgtaaaaaga  59880
atgatctctc atggttctca catatttttc atcatgttta gtataaatatt gtgaaccttg  59940
aatataacca cggaacccgt atgaagtgcc acagtgatgc tcgaagtgct cccaagaagc  60000
agagaaaagt cataacatta caagacaaag ttgaattgct tgacatgtac tgcagattga  60060
ggtttgcagc agtggttgcc caccgtttca ggcagataac ataaaaagat gcagaaactt  60120
atcaacaaat acagtaaagt actgtaagtg tattttcttt catttatgat ttttgtaaga  60180
gaaaggatat ctgcttgaac aggtttttaa agcagacgaa agtgcccaat tctgggggga  60240
aaatgccaca aaggaagaga acatcagtat ttaaagcaga aaggaatagg ctaactactg  60300
tttttggca attgccgcta ggtttatgat caagactacc cttatctata aaactactaa  60360
ccctagatcc ttgaaaggaa aagatgagta ctgcctgcca gtctcttggt tgtactaaaa  60420
ggcctggaca atgagaatcc tttttctact ttggttctat cgatgctttg tccctgaagt  60480
caggaagtac cttaccggta aggaaatgcc tttgaaaatc ctttcaatgt tggacaatgc  60540
ctctggccgt gtagaaaccc aggagctaat gttcatgaag gtgttaaagt gatctacttg  60600
ccccaaaaca caaaacttat aatcagcttc tagatcaggt tttgtaagga cctttaaggt  60660
tcattacaca tggtacccta tggaaagcat cgtcaataat gtggaagaga accccaatag  60720
agaagacatc atgaaactct agatggatta caccattaaa gatgccttca ttgctacaga  60780
aaaatccatg aaagccatca agcttgaaac cacaaattcc tgctggagaa aactgtgttc  60840
cagtgtgcat gacatcacaa gatttacaac acagccaatc aaggaaatta tgaaacagat  60900
tgtgaatatg gcgaaaaagg tgggggtaaa aggtatcagg atatggatct tggagaaact  60960
caacagcaaa cagaaaccat gtcagaggaa ttaatagaag atgactcgat gaagatgagt  61020
atttctaaac cagcgccaga agataaggaa gaaaacattg aaaaagcagt gccagaaaac  61080
aaattcacat tagacaatct ggcagaagag ttacaattat tcaagactag gttcaacttt  61140
ttttacaaca tggacccttc tataatatgt gcactgaaac taaaataaat ggtggaagaa  61200
```

-continued

```
ggatcgcatc tcatggaaac agttttagag aaatgaaaaa gcgaaaaggt cagaaattac  61260
aatttatttc cataaagtta catcaagtgt gtctgcctct cttgcctccc cttctacctt  61320
ttctgcctct gccactcctg agatagcaag accaacccct cctcttcctc ctcctcagca  61380
tactcaacat gaagacaatg aggatcaagt cctttatata atccattttc acttaatgag  61440
tagtaaatat attttctctt ctttgtgatt ttcttgtttt ctccagttta ttgtaaaaat  61500
acagtacata atacacataa tatacacatt atgtgttaat tgactatgtt atcattaagg  61560
cacctggtca acagtaggct attagtagtt aagttttgag ggagtcaaaa gttatataca  61620
gattttcagc tgtgtgggag atcagcacct ttaagacctg tgttattcaa gagtcaactg  61680
tagttgcttt tttttctttt ctaccttgaa catcttcctg cagatgctcc atcatcttcc  61740
tagctctagt ttcttatctc taatggaggt aaagcaggaa agttcttact tcactgctac  61800
tgtggcaagt taatgtcaca ctccttaggc ttagcaagaa tttgagttta ttcattctct  61860
cctggaggtt ttctcacctg cactcttttc tgcgttacta tttattcctc ttcatcccct  61920
aggcattcag ttataatgat agagtctctc tgctgaaata ttctcagtgc tctgtggcag  61980
cccaagatga ctctatattc cacaccctct ctctctcttc tccccgctcc cctctcatgt  62040
gtgtggctta tgtatgattc acagaagaca cacacacact cagattgagt gctctggtaa  62100
atactgaaag tgtgtgttat tgaatgcagc aatgtcagcc atcagcagct aggctgactt  62160
tatgtttctc aggtaagaat catacccccta ctgccatccc ttttaaggag aataagtaaa  62220
tgtcagactc atgttacagc tctttccgaa gaactctaaa atgtgtctgt ttcatctcat  62280
gatcctttat agccagcctc tgtgtgggtg aaaaattaga gtcacataac taggttttta  62340
gagcatggtt tgcaaattct gcatataatc ttatatccca tgtggaaata aatatctgtt  62400
cttggtgctt catctgaaac attcatttta ccaatctatt accctgtaat gaaattacta  62460
attagaattg ataatattat attatttcaa ttatgtaaat gaattaaaat ctagaaattt  62520
caatgaatag attgtgcatg acattcaaat actatgaaca caattttaaa gttcaactaa  62580
aaatggaaaa tattattgag cttcaaggag actggagaca taaatttgga acagaactac  62640
caaacttgtc ataatttcat aagatagatt atctgaatat ggattcatct gaactataac  62700
aaagataaag aggaagaaaa gtgtctgtga ttcagaaatt cacaatggta agcattttgt  62760
gaatctgttc tcttaagcta aatgtcatag taaccaaggc ttgtgtactt catgacagca  62820
agattacata ttaaaatgga agtttttcaa ttcacttctg tcattgtact tgtaatgctg  62880
gcatgataaa tatatattct caacatattt gtaaaatatt gtccagaaag tgtctaaaaa  62940
atagagtgct tttggagagg gcctgcaaaa ggagagtatt ttcactgatt attaggaact  63000
atctctttaa gccctggtta attagtatgt gagttattaa ggcaatataa gtaatatagc  63060
taataatgca aagatagaag tttgctaagg aatttgttgt ttccagttat gattctacaa  63120
gggctttcct cagatagcat aatgatttaa atttgatttt cttaactaat tatttgttga  63180
aaatacagtc catattccaa atggaaatac cttatttgtc tatttctgat tataacagta  63240
ataaatgttc tttggaattc cagtgctatt gaaaattagg ctagccagat cttctttctc  63300
ttaacacagt tctcattgac caccctacaa catccaacat tattgacttc ttattctttt  63360
taaattcttt tctactttgt tcctggttat actactctct ccgtgagatg tatgttccat  63420
gaaggcagag gcttttttc tgtttatatc tgtcttattc actacttagt atggtatctg  63480
acaaaagaaa ggtgttcatt aaatgtttgt gtaatgtatt aatcctttta catatttatt  63540
ccttttccga ttcttttgtt aacttatttt ccttctgcca aatcttaaac cttattactt  63600
```

-continued

```
ctccagtgtt gagtcttctt ctctctcaag actttcattt tgagtcatca tcatcattgt  63660
aatcatgtga tatctttagt taaatgttat ctatgtctct atctctgtcc ctgctctctc  63720
ttccagaatc caatctcaaa tctccaactg ccttatgacc ttcttcatat gatggtccct  63780
tagtcacctc aaagttagca tatgcaaaag ttatctttgg agcacccaac ctacaatgct  63840
ggctctcatt ctgacaactc tcttttaatt aatggcatga ttattctacc tgcttcaatt  63900
tgtaaagctc tctatttctg gtaggtaatt ctatatcatc attataacca tcacccccta  63960
tctctaatat aatcatcagt aatattatgt gattcttttt tttttttga gacggagtct  64020
cgctctgtca accaggctgg agtgcagtgg cgcgcgatct cggctcactg caagctccgc  64080
ctcctgggtt cacaccattc tcctgcctca gccttccgag tagctgggac tacaggcacg  64140
cccgcaccag gccggctaat tttttgtatt tttagtagag acggggtttc gccatgttag  64200
ccaggatggt ctcgatctcc tgacctcgtg atccgccctt ctcggcctcc caaagtgctg  64260
ggattacagg cgtgagcccc cgcgcccggc caatatttat gtgattcttt attgcttgaa  64320
aagtattttt acatctataa tttcctcttt tggggcttgg tccaatcttc tgggagacta  64380
attctggcag gtagaaatat aaggaggcca atatcagtac attgcttatt caccattgct  64440
agcgtcttac tcctgggttt actctgactt tggtccccag ctctccagtg ctattatttc  64500
tttgcttctt tctgttatcc atattcctgt cttgcaacca agtttccctt taatgagata  64560
ttctatttca ctccagtttt cctatgatgg aaccactttg ctagacaaag cctgcgcatt  64620
tggacttgtg ctcattacat gatgcaaact agtgtgataa acctagttat tgtattttat  64680
taacttctta caaaacagta ttcatgactc acttgttcct ttacttctgc ctgcagatct  64740
gctttttgga atttcatttt tgtactactg acccttggat ttgcttacaa aactaaatta  64800
ctgttttttt cttgagcttt tgaatttttg atattgactg cttccagttt ggtccacact  64860
aatttcaacc agtcatcaat tattaaagat ataatcctca tttaaaatgt tatatatctc  64920
tatatatttt aaatatgtag tataatttta tatatgctta tttttatttg tatatataaa  64980
tatatacata ttatttacca tatattatat atacatgcat aggaaaggac tctttctggt  65040
tccctagtat tggaattttt gcttttcttc tctctggtat tttttcatcc ttgtttgatt  65100
cagacaacct ggctattgtt ttactgctta cccgggatct taatgcttca ggttcggctg  65160
gattccagct tttccttggt tttaattcta attcatatat atatatatat atatatatat  65220
atatatatat atatatgtat aatctacatc tgcatcaaat ccctctctag agcatgcagt  65280
ggatttcaga cctgggattt catcttgaac ttcagctact gaggatattt tcttgcatta  65340
ttctatttct aaattattct attagaataa ttctattaga attattctat ttctatatta  65400
ttgtatttct aaatccattg cctaaaccaa accattaatt ttgtctcagt aatcctggat  65460
ctttttcttt taccatatag tcaaaaatat tatgtcctta atgctggtgt ggcctgactt  65520
aatcccacct cttcttgtga aaacctcctt gaccgtgtag ccttcatttg tttttacacc  65580
tctttaccct tatagcacta agcaccagac atgttagtgc ttaattatta ttgtcttaca  65640
ttgtctgtta ttatgtattc atcttatttt taaaaccaga ttataagcaa tttaagaaca  65700
ataaatatgg tatagcattt atgtgaactg gaatagatac tatcctacag ttaatgaatt  65760
gaccaagcaa ctattcaaag tacagccagg ctgaagacgg cagtatgttg tttttttaaa  65820
agatacttta tttgctcaat aaatctagga agaaatcagc ctcacatttt tttgaactgc  65880
aacttctttg cttgccatca tttaattagt tgccgagtta aaggaccctc ttggctaata  65940
```

-continued

```
agatagcaaa attgtcatgg attctcatga atctcaatat aattgaactt acaattcatc  66000
taaattattc cactttgttt tttatactat ttgcagtaat ttcattccac ttgaataata  66060
agggaatgtt ttctcatgtt ctgtaaatat attatttgag gatattttac ttttttttcta  66120
tatttatgta ttggtctgtt ttcatgctgc tgataaagac atacctgaga ctgggtaatt  66180
tataaagaaa aagaggttga atggatcaca gttccatatg gctgaggagg cctcacaatc  66240
atggcgggaa gcaaaaggaa ggcacatctt acatggcagc agacaagaga gaataagagc  66300
caagcaaaag gggtttcccc ttataaaacc atcagatctc atgagactta ttcactacca  66360
cgggaacagt atggggaaac tgtccccatg attcaattat ctctcactgg gtctctgcca  66420
caacacataa gaattatggg agctaaaatt caagatgaga tttgggtgag gacacagccc  66480
aaccatacca atttctttct atagaatata catttaaaaa ttgacataag tgtgctaagt  66540
gctctgcaca tttcagctcc caaggaatgc atattgtagg aactaaagca aaaaaaaaaa  66600
aaaaataaca acaaccaggg cagttttatt gagttcagta aagaatatgt ttccctatat  66660
tttaataacc acatctattc ttatctgatt tactttaaga atctattttc ctctttaatg  66720
cagttaacta atactatttc ttatacaatg gcagtttgaa atattaatcc aaacattttt  66780
acaatttttc catccatttt cataacatgc cagtgttata tttagtttaa taggctaagg  66840
ttacctttca tattgatgga tttactctga acttctagct gctcttaagg tagttgtgag  66900
gttttttttt tttcctgtta ttgtaattac agttacagaa taagactgga aactttgagc  66960
aagtttattt tctgttttta aaaaaaaccc agaaacaaac aagctgacat gttgatgaga  67020
tatattttat taccctactt tacccagaaa gctatgcata aagttcatac aacaagataa  67080
aattttaaaa aaaagccaaa agtgtacaaa atacatcttg gcttcatctt ttaaataaat  67140
taatatttgt taaacctttg atatttactg aggatatagc agtgaataaa acaaacatgg  67200
tttctgccct tatatttcat ccattctagc aaaaagatag atgcaaaatc aattattgca  67260
caattaatta ttagttgcaa ttgtgataag tagatcaaga gatgtagggt gctataagtt  67320
aggatagcag gggcctgatt tgtttgtata tgaatatgct tagatgtgga tatgtatgtg  67380
ttcatatgtc tgttttacaa agatgattag gtaggtgtgc caaagtatac tacatttaag  67440
cagagagtag atgtctaaga cagctacaag attctgaggt agggaagagc atgatatttt  67500
taagagtctt aaagaaggct aatgtaccta gactgtaata gcaagggaaa gactggcaga  67560
agatgaggct aatgagttag gcaagagtta ccacagatat ttatttacac agaaatatga  67620
cactatatta tcattgtgtg tttatttttc acctttgccc tctgaaatac tctcaattat  67680
gacttagttg taatctaatt atttcaataa cttattaatt ggtttatttt catatatgaa  67740
atgattaata ttatagattt cagtaattgc tctatagctg ttactgattt actcattctt  67800
ttgtgtttta aaaagtttaa aacataccag atgttttatt gaactaacat tgaattcatg  67860
attttttttt atgactaagg cttcctcatc attcaataaa gttttataat ttttatcaca  67920
aatatgctac ataattttgc tggatttatt cctaatatta tatttttctt ctaaggtaaa  67980
tgaatttttt tctggctaga ctaatagttt ttgctgccct ataggaatag tatggatttt  68040
ctttttaaga cctagtaaag atttctaggt aaaaatcata taatctgtac aaaatataat  68100
gaaaaaggaa ataatgaaag caaaatccca agaattcttt tttccccccct caaagaatgc  68160
gttgaagaat gggcaaataa aatcgggaat atttagaggt aggaaggtgg tgaaaaggtt  68220
cacaaagaag tttcaatttc aacaaaaagc ttttaattca aagatttttc tttctttttc  68280
tgagagtgat cagaacatga agatggctgt tgggagacaa atctccatgt atcctttatg  68340
```

-continued

```
ttcccaaaca tcttttgggc aaaggcacta agtgcctttg tgcctgtctg tctttacaag  68400
tatgtttata tcgtgaacac actaggaaga tatagatagt gtctctctct ggagcaaagg  68460
gtaggttttt tatctttata cagtaaagat aatgtctcct tatggggcaa caatcagtga  68520
ggattattgt ccattatgaa agacctgagt tccttacctt ggttctcccc tgtcacatat  68580
cccgctacat gtgcagcatc tcctggccct ttgcacaccc ttctgtggga gttggggctc  68640
agaatgcaac acaaatgatg atactctagg tactactatt ctgtgcataa taaaccatct  68700
tttgtctctg actcaagagt ctcatggctt ttgctagcat ccataaaact ggcagggcaa  68760
atcctgatac ccttcacaat tcttggcagt tttggcagtg aggaagggat actgacagag  68820
acatggcttt tggaaaaaga aggatgatgg cctcacagct aattaataga ctttgaaaga  68880
agtccattgg tattggtagc aaacttgtgg accaaattgt ctagtaagca gagcaataaa  68940
tattcttcta ctctattgct cattaatgag gaggatttgg ggaggtagtt gcaagctgag  69000
aaccaggcaa cagatatgat ttaactgtcc tttaggcagg gagattacag tctggcagta  69060
gtctcaggtt cacctattgt aacaattagt acttagattc atttgggctg tggggtgggg  69120
agagaggaac aagtttgcat tttctttttt tgttgttgtt gttttgtttt gttttgtttt  69180
gtttttcaga cagagtctca ctctgtcgcc caggctggag tgcagtggcg cgatctcagc  69240
ttactgcaag ctccgcctcc cgggttcacg ccattcttct gcctctgcct cccgaatagc  69300
tgggattaca ggcgcctgcc accacgcctg gctaattttt tgtattttta gtagagacgg  69360
ggtttcaccg tgttagccag gatggtctcg atctgctgac ctcgtgatcc gcccgcctca  69420
gtctcccaaa gtgcagtgtt gggattacag gcgtgcgcca ccgcgcccgg ccgcattttc  69480
tttcagacaa caattttaga gatacatacc tacagtgagc atgagaggaa aatttatgac  69540
tattatgtac agaaaccagg caaattatta gaactttggc tgattttctt ggaaaatgag  69600
tgaggtgggt catggaatgt tggtaataga agaatggcca aaactgggat atcttttttg  69660
ctcagactct cctaccatca tgccaacttg taatccatct ggagatgaca gtagaaagtc  69720
ttggaatttt ctgtaatggg ttctatctgc tgtaaaataa ctttggccct tttatggaga  69780
tttctctgga agagacaaaa tcaaggggaa actatagatg aggcattaat tagtattgca  69840
ctcttacagc cccagattgg tttcataatg ctaatataag tgacccccctg gagaatgaaa  69900
aggtcatcaa agaaatttag ataaattctt gtggtcagcc tgaagttcta gaaaagttct  69960
ttcaccctta tgttggaacc aggcaagaac ttaataaatg ttgtattgat agtagggcag  70020
caggtacatc tatctagtct gaggatgttg ttgctgttac agccaattag tttattctag  70080
acacaccatg tgacccttga aactaatcta tgttatgtat tcagatttct gaaccattca  70140
cagtcagaga gtcatgcact ttttaatccc caaagccata caacaattgg ctgataatca  70200
aggtatgtga tagaccttcc acatttccta tcatccatcg gcatctggta ttgttaaatg  70260
ttggaagggc ttcttcaaaa attaaaaaaa gtttccaact ctgcctctct cacctccttc  70320
tggtgcacac atataagtaa gatggtttgg tcactgaatg tggcttctgc agaaactgat  70380
catctcctct cagcctctat gtggataata agatgaaagg gttaagattt tatataaact  70440
tatattgaaa aatcagtgtt ccaccatgac catttctggg cataatgcgt tattctttct  70500
tattacagaa acctcaggcc agcctgattg gtacatcctc caaatggtag tccagctaaa  70560
gggaggcctc aggaattttt atttaattct tgtatagcta actggatatg cttgttggct  70620
tcatttggtc ctacattgta agagtagtaa ccatttagtt gagtacacag cttgccaaga  70680
```

-continued

```
ccccctgcaa ttgcccaaat gtaccattaa tgtaggggac ataatgagtc tctgtaaatt  70740
ttataaaaat gccctttttct cccttattct gacccttccc aacaaaagat ttgggtatga  70800
tagaggatgg ttagaaaaaa agtgaaatta tagctaccgg aatggaacac actctgcatt  70860
tcaggtgcag gagtaaaatc aatgatcttt cagaacttcc cctggagcct cccacataaa  70920
gaaaagtcct tggtgtgagt ctctcaaact gtggtaaatg ctttaaatgt aatttccttc  70980
tggcttaaca ttcttcatca gatgtctctg cctgcatttt gatcatcatt gcttttaacc  71040
ttgaggagaa gtttattaga aacatcaggg aaagatcctt tatcgcctac acacacacac  71100
acacacacac acacacacac acacacacaa aacctattaa cacctttggg tgtcttcttt  71160
acccctcttt ctataaccat caatcactca ttccatgggg tggatgaatg ccatgtagtg  71220
gcttgcatgg ataaatagat cagattggac tgactgtccc caagcagttt ctctaaaaaa  71280
cagcaataat ctcaattatc tgaactgaac tgagaacccc aaggccaact agctggcctg  71340
gaggccctgt tggagacatt gccaatctgt ttcttctaac tgacatcggt ccatttttgg  71400
ggtcacagtc atcgtaaata acatgttctt tctaggacca ttgtgtgaac ccttaagact  71460
atatgtcttt tttttttttt ttgagacgga gtcttgctct gtcacacagg ctggagagca  71520
atagcgcaat cttggctcac tgcaaccccc acctgctggg ttcaagcaat tcttctgcct  71580
cagtctcctg agtatctgag actacaagca cgtgccacca tgcccagcta attttttgta  71640
tttttagtag agatgggatt tcaccatgct ggccaggctg gtcttgaact cctgaccttg  71700
tgatccgtcc acctcggcct cccaaagtgc tgggattaca ggcatgaacc actgcgcccg  71760
gccaagactg catgtcttat gtccaaatca tgcattattt tccctcccta tccaaaatat  71820
agtgacttga accacaggga tggtcataag agacctttga atgtttaagc aaacaccacc  71880
agtagattat gtaagcttca gacgatttcg gagagaactc caaaatctac acttggctat  71940
gaggatgagc ttcctggagg gataattgac ttattagttt tgtgtgccct acaggcagtt  72000
atccctacaa tggtaatcat caaattagaa aaattggtga gaaatttgcc cctgaattta  72060
atctaaaaga ttaatgatac aattccagtc ttctttagcc tcagttcatg gactaacgtt  72120
tttatggatg ataggattgc cctcagctac ctccttgtgg tccaaggaag agactgtgca  72180
attgcttata tatcctgctg tacctgatct aatgcctccg gccaagtgga aaggttaata  72240
tagaaactta aggagaaagt cacatggctt tgtaagggaa acctttatgg tttgggggat  72300
ttattcagtt tgttgggttc agcagctgaa tacatcagca gtgtggttga ggtatatact  72360
gtagattggt cccatccttc tgctttgagt cctgttgata gtgaccttaa gtaaagacat  72420
gtatgagaca aagtggatga actttttttcc agcatctgtt ggttagattt atccgtgact  72480
gatggcgtat ttatgggaaa attagtcaga gaaaagatga tgtcaagaca agctgtggct  72540
attgttgatg actgttctca gttgattctg ctgtcactat atcagaagcg aagagaaaga  72600
gtatgaagca aacagacaga aaactatgga agaaataatt gaagacagtt gtggtggctc  72660
atgcctgtaa tcccagcact ttgggaggct gaggcaggca gatcacttga ggtcaggagt  72720
ttgagaccag cctggccaac atggcaaaac cccatctcta ctaaaaatac aaaaattagc  72780
tgggtgtggt ggtgcatgcc tgtaatccca gctacttggg aggctgaggc aggagaatca  72840
tttgaacctg ggaggcagag gttgtagtga gcagagatca caccactgca ctccagtgtg  72900
ggtgacagag tgaaagaaag aaaagaaaga aaaggaagaa aaagaaagaa agaaagagag  72960
agagagagag agaaagaaag aaagaaagaa agaaagaaag aaagaaagaa agaaagaaag  73020
aaagaaagaa aggaaggaag gaaagaaatg aaagaaaaga aagaaaagaa gaaagaaaat  73080
```

-continued

```
ttctggaaaa aaaaaaaccc cataaactta cacattgaag aagctcaggg ttcccacagg  73140
ataaatgcta aaataaacaa acaccaaaac aaaaccccaa atcccaaaat tattaaaaag  73200
tatcataacc aagcttctga aaactaaaaa caaagaaaat attctaatag tagccagaga  73260
aaaatgcaac aatgattcca atgattgcag atttctcatt aagaaatatg agggctaaaa  73320
ggaaatggaa cagcatttga gaatgctgaa agaacattta gtccaggatt ctatatccac  73380
tgacatattc tttaggcatg aaagttaaat aaaggcattc tcagacaaag ggaaactgac  73440
atcatactta ttcatgaaag actgttttcc ccctgtgacc aggaacaaag taagcctggc  73500
cactctcatc actgccactt aatatcgtac tggaattcta gccagtataa taataaataa  73560
ataaatagag aaagagcttg gaaaggaaaa aataaaatgg ttcatattca catatatatg  73620
atctctacct ggaaaattcc gtggaaccta caaaaaaatt agaaataata agtaagttta  73680
ataaggttga aggatacaag gtcacatgaa aataaatcac atttctctac actagcatta  73740
aaaattggaa acaaattaaa aaatataata gcctcaagaa atgaaatatc taggtataaa  73800
tttaacaaag caggtagaag atctgtgttc tggaaattat aaaacctgat ggaagtaaat  73860
attttgaaat gaaagaagac ctaaataaat gaagatacac atagtttcca tgggttggaa  73920
aaatcattac acttaaggta ctattctccc taaattgatc catagattta gtgcaatatc  73980
aatcaaattc caagcaggaa ttttgtagat acagaaaaac ttgttctaaa atgtatatca  74040
aaaggcaaaa agattagaat agccaaacag ttttgaaaaa gaagagcaaa gttgggagac  74100
tcataccatc tgactttaag aattactcta aagctatagt aatcaaaaaa gtgtggtatt  74160
gtcaaaggaa tagacaaagc aatgaactaa atgtttgtgt tcccccaaaa ctcataggtt  74220
gatattctca ccccaatatg atggtattag gagatcgggc ctttgggatg aaattaggtc  74280
atgagggtga agcccttatg attgggatta gtgcccttat aaaatgaacc tgctctctca  74340
gccttttcca ccatgtgata ttacaaggag aaaacagcag tttgcaaccc agaataagtc  74400
cttcactaga acctaaccat gttggcaccc tgatttcaga catccaggct tcagaactgc  74460
aagaaataaa tttctgttgt ttataagcca ctcaatctat ggtactttgt tatagtatcc  74520
tggactgact gaaatatagg cctagatcaa tgggacattt tagaaagtcc agaaaaacag  74580
tccaaacaaa tataactaat tgatttttga aaacggcaca aaccatgaag aatatacttt  74640
ttctgtgtct tttatttggg tcttttccat aaatggtatg atattggaac aatttaacat  74700
ccatatgcaa aaaataaaaa aaaaaccctt gaattaaacc tcatatctta taccaaaatt  74760
aactcaaaat ggaccatagc ttcaagatgt aaaatataat atatgaaact ttagaagaaa  74820
acataaaaga aaatctttgt gacctttagg cagagagttt tcaaatttga taccaaagca  74880
taatttataa cacacacaca caaatcagaa tttatcaaaa tttaaaactt ttcctcagtg  74940
aaagacactg ctaaaagaat ataaagtcaa actataaatg gggagaaaag acaaatattg  75000
caaatcatat gttcaaaaaa tgtcgtgtat ccagaatgta taaagaagtc tcaaaactcg  75060
acagtaagga acagacaacc caataaaaat aagcaaaatg ttttcataaa cactttgcca  75120
gagaataaat atggatgtca aataaactca ggaaaaattg tcaacaataa ccattataga  75180
aatgtaaagt aacaccacaa tgaaatacca ctacatagaa tggctacaaa acaactgata  75240
ataccaagtg ctggtgaaga ttcagaacaa ctgcaactct cttgcattgc tcctgggaat  75300
gcaaaatggt acagccattc tggaaagcag tttggcagtg tctcagaaag ctgaacataa  75360
acttatcata tgactagcaa tcctacttct aggtatttac cctagagaaa taaaatttat  75420
```

-continued

```
gtttacacca aagcctacac aagaatactt atagcagttg tatttataat tgggccaagc  75480
actagaaacc caaatgtcct ccagcaggtg aatgcataag caaagagtgg tacattcctg  75540
caatggactg ttactcagct atgaaaaaga atgaactact aatacacaca atgacagata  75600
aatctcaaaa tctcaaaggc atttgctaag tgaataaagc cagtctcaaa aggttatatg  75660
ctgcgtttcc acttacatga cattttgcaa aggcaaagct agcagcagag accagatcag  75720
tggttgctgg gggctacaaa agggaggtag gaatgactac aaaggaggat cacaagggag  75780
ttttttggt gaataacatt ctgcatagtt ttagtataaa tgaattttat catgatctac  75840
tcttctgaat attacccata aaatatacca tatatgatga gagaaaatga gtatatgtgt  75900
ctgagaaata gaaatagtct ccatgagtgt taaaaataat ccaaaataat aatcatattt  75960
tatttattat ttattatatg tatacattaa tatatacatt ttacatattt attttcccca  76020
attatactgg acttcatgta atgatgaatt tggttttagt tcctgagttt gatttggatg  76080
agtgttgcag tggggagcag gggaggtgtg agcttggggt ggtgcgagct tggggtggtg  76140
ctgaaggcag tgactgggac attttaagct cagggtcgtg gtaatacatg ttcatggtaa  76200
tacatgtctc tgatttttta gacaccccat cacagagggt acagtttatt cttggaaccg  76260
aggatgatga cgaggaacac attcctcatg accttttcac agaactggat gagatttgtt  76320
ggcgtgaagg tgaggacgct gagtggcgag aaacagccag gtgaggattt ttgttaaagg  76380
gtgaaggtat actaaagaat tttcatgtta ctagaaaaag agatttctaa tgcaacaatt  76440
ttgcaaacat ctatgattgc tgctgatttt agaagttgct catctagcct gagcatatcc  76500
tataacggga tatgggtcag aaagaaatct gaaggcagta attacagtaa acggtgatgc  76560
agagccagca acagctgcag tcttaaagat aaacagtaac ataatttgtg tgtcatcaac  76620
aaaacaaaag aaatctaaaa gtagtttatt tctatttttt cagctgctgg cttgcaccta  76680
aatttatgat agtatatgat aacttgaaag tgggcttttt ttaaaagaaa gggcaaatat  76740
tatgataaaa tgctttatgt acagtcctgg atttcatgtg ctctttcatg aggataaaaa  76800
taatttgtaa tatgtttcta ggatatgcat acatttaagc atagtggttt ttaaaaatat  76860
cttttaaaat cactttttct atcatttgta attaagattt ttacattgct atataattga  76920
tagagttctg taaagttgga attaaatttt gtgtttactt ttcattcatt ctttctgatt  76980
tgctcagtta acaaacattt atggagtgtc cattatgtgc caagtgcaat ggatatggca  77040
caacaacaaa aatcttagat cttgccttta gggatcttgc agtctaattt agacaagaaa  77100
acaaagttgt aaatgctgta taatgaaagc tgtgatacag gtgtgcacaa gaaactgtgg  77160
gcacacccag ggttgtcatt tacccacttt ttcacaaatt ttaatgtgac taccaatcac  77220
ctggaatatt gtttaaaatg tagacttagt aggcctcagg catagtcaga ccatgaggat  77280
gtcgtgtaaa atgttttggg tttgagaacc aaactttgag tagcagttat ctaaaccacg  77340
aggtgaaaga gaggatcagg gtagcttccc tggaggaggc gattcttgag ctagctcttg  77400
tgagttgggt tggagttagc taggcagaaa agcagagggg acagtattct aggcagagat  77460
agcaggacgt gcttaaatat atcattgaca caggtttagt gtttatttat ttatttattt  77520
atttgtctga gacagagtct cactctgtcc cccagggtgg agtgcagtga cgagatcttg  77580
gctcattgca acctctgcct ccctggttca agccattctc ctgccccagc ctccctagta  77640
gctgagacca cagtcatctg ccaccgcgcc cagctaattt ttgtattttt agtagagaca  77700
gggtttcacc atgttggcca ggctggtctc gaactcctga cctcaagtcc tctacctgcc  77760
tcagcctccc aaagtgctgg gattgcaggt gtgaaccacc atgcccctgc tgacacaggt  77820
```

-continued

```
tttattgttt tgttaggcta tctcttccac tgtaggacag cattattatt agaaagactt  77880
tatcttaagc atatttatta gtggtcctca gattgcaatt gctgtctgaa agccacagta  77940
attccattgg atcatgttaa acttgtagct gcatttattc attgacttta ctcagtgtag  78000
aaataaatgc tcaattatga aaaagaatgt tgtgaataac aatggcccag ttaattcttg  78060
tttgatatat tttcagtggt ctttacagct ctcctttatt taaaaaacac taaaaacgag  78120
acaaccaaaa tggttaccaa ctagtttatc cttattaaca ttttaaagta aataaaacta  78180
ataactgcca gtatttaaaa ttcacaaggt ataggatggc agaaaagtaa aaatacttct  78240
ctatgcttat tcacagtatc tcttttcaaa agtaatcact gttaatcttt tctgtgcatc  78300
tttcccccaa aatttaatag ctaaatctgc gtgtaaatat atgccctttt aaatttacac  78360
aatagggatt atataatata cagtgttcat atcttatctt ttccacttca tatatttgga  78420
acattttcca tatcagcaat tcaaatttat atcatctatt tgatgattgc attgcattca  78480
attatatgga tgaactttca tttatttatt tatcagttag tcttgataga catttaggtt  78540
atttattttt ttccataaaa accactgcag tgattgctca cacaaatatt ttgtcattat  78600
tttgtaggta tttctgtaaa gtgaatttct aacaatggca acatatgtag caaagagagc  78660
agacattttt tcctttgata aatactgtaa acttaccttc ataaaatgtt tttctaattt  78720
acacttctat caacagtgta tgagagtgct tatttcctcc acatcctttc acagtaaatt  78780
atcaaactgc ttaaaatgtc ttttccagtt ttataaataa aacataaatc tcattgtttt  78840
aatttgatta ttcaaattat tagtgaggta caacatcttt tcctatgttt ttattttttt  78900
catgtgaacg aactattcat ttcctttatt tattttatat aaatcattca ttattttctt  78960
tatttgcctt ttggaacact ttaaattggt ggcatgttat tcagtatgaa ctaacctttt  79020
taataaaata atttacataa gtttcctcat gatgttttgt attgtaatac tttaaatata  79080
gacttaaatt taaaatagtt tttatttaac ctggtacata ttaagattaa gagacttcta  79140
ccttactttt tgtcccaact gcatcaaaaa ctacgtagta gttttaaaaa tgtgtaatat  79200
atgtgctcat cttctttatt tggtgacaga aagggaatat aagatcattt tttccacaga  79260
ttagtgatat aacttgctct tttatgattt tgataagtta aagttcctcc ctccctgttt  79320
aagaccagaa gcatctgtct gccacgagtt acaaggaaca gatgttccta tgtgacttga  79380
aggaaggcga tctggtgatt gtgatgacta gacagctctg gttagttaga gtctctttaa  79440
cctattgcta agaagtattt tgttgaagca tttattttag agttccttct ttaccctcat  79500
actacataat agagctgaaa agtaaaattg gaatatatat ttgggcaaga gtaactcact  79560
tattcttaca gtgattggtg atttttcatc ttacagatca aatagtgacc cattcatttt  79620
aaccaataat ttcttgtaac ttgcccactc tcataaagct aggagattgc agaagcgata  79680
ctagaatata gcactctcac tttgttacag ttgagcaggt aggtttttgt tatgctctaa  79740
tggattaact caataacatg tttgtcctaa accatcaaaa tatattgctg ttgatttata  79800
aagaataaaa agatagtcca tttaattata cacattctct aatattatta gatggaccta  79860
tgtttgtagc caagcttcta gaatctaatg catgctatag ctgtttgagc ttcagggaga  79920
catctgatga gcaatggaaa taataacaga tattgaaggg gagggtagat gaattttaac  79980
agagacacaa tgattcaggg aagggcagaa catatttatt gaggatttcg aaaagtaaca  80040
ggttttaaag tggcagaagt aattttgttc tgattgccct aattcatcta aaaacactaa  80100
tttttgttaa ttcatgactc catctgattt ttcacatgca atttaattct agaaaatcat  80160
```

-continued

```
tagcatcacc atttaaagca cttctttctt ttgattagta ttccagatgg gattaataat  80220
tttctaccct cacagcagaa acaaaaagat attttatcag ctcattccac ctgtcacgta  80280
tcacatcttg cataatttat gcccactgtc attgccaagt aaaacttaag caaagtttta  80340
ggttttgaag ctaaattttt gaatcataat tatttaataa atgttcgtaa aaaccagctg  80400
gtcactttta aaaaccctaa aagaagccat atgaagagac taatgaaatc aacacaatta  80460
caatgtcctg cttataaata acatgtaatg ttattaatag aaaagtgagc aaagctacca  80520
cagctgtgca gttgtggcga caacatgttt gactcactgt agttaccctt tataaaagct  80580
tcccactaat gaactcagaa gaggcaaagc agggggtagc gttaggcttc tgatacatac  80640
atacatggca gaatagaaaa ggattattac atcagaacaa ttttattgat gctgtgaagg  80700
catttgatct tcaaaattag taatggttta agtcatctgg attttttacg ggaaaataat  80760
gtggattaag aacaggtgtg aaaataatat ggattaagaa cagttaatgt ctataaacac  80820
taggtttgga tgtatatcat ttccccttaa gatgactata ggtattcttt gattacatgt  80880
tattctctag ctccacccca gccatgtccc ccaactatcc taaaagagga tgtttttttc  80940
ttgagacatc cattatttcc ccgaaggcta taattttgga tgatataata actccttttg  81000
gatgatagac ttactctttt tttgtttggg tagaatgaga ggattaaaaa tcttagaaaa  81060
gttaaactga gttagtgaga atagaacacc cagaaagagt taagttctct agaaaaaacc  81120
ttctctagaa gcacctaatt ggcagaataa ttttattctg tatattttaa taggagtatt  81180
gtagaggaga ttataataaa cttaatcctc aaagaattca tgaaacacct atttaatgtt  81240
gcttagtgga aagagactcc aatgtgctaa tcttggatga aaacagatcc agacatactg  81300
aaggaaatga aaataatctt ctcagggttt aaatccaccc ctctctcccc acagaaaagg  81360
tcgtgcaatt ggccaacagt tttatttatt tattttttag cattatccct cacatctcat  81420
tcatgctttg aaactcttgt ttgccttggt ttgctgttca aacaaatgtc agcagagttt  81480
atttgaaaac tggaacaaat tgcagcactt taggtcatta actgcaatca ggcattttgc  81540
aactgacagt atattcagtg attacaaatc ttgaaacagt gtctggtgtg ctcccagatc  81600
tgttcatgtc tatctttgaa ggatgaaatg ggatttaaaa gaacagaaaa gagagatata  81660
gttatgtatt tatgtgtatg tattattttt aatagtctct ttaacaatat tcatttaaat  81720
atctcttaaa gaattggcat cattctggag ctggcataga gcactgaatc ttgaaatgtt  81780
tagtatcttt agtaacttga tatttgtaac atgtgggcac ctttttatgg aaagtacctt  81840
ctgcctcctc ctataatact cataaaacct atgggtacat caaaccatcc atgcatataa  81900
cttatatttg gtcatcttaa ctaacaaact gtttggaact ccctgaagtt ccaaactctc  81960
tgaaaagaac tccattcttt tctcagagaa ttaagccctc aacttgaaga aaattattct  82020
aaaggaagga agaataattg gatttttaa aatgtcattt cagacacata aatcactgga  82080
acggaataga gaactaagaa atagaccagc acaagtaaag cttactgatt tttgacaaaa  82140
gacaaaaact attaaatgaa ggaaaaataa tctttttgaa aaataatgtt ggagcaatta  82200
gacacctaca ggcaaaaaat tagccttgat ataaacctca ccatgtacat aaaaattaat  82260
ttaaaatagt ttatagattt aaatttgaaa cataaagcca tgaaattttt agaagaaaat  82320
attagataaa atcttcagga cctagggcta ggtggcaagt ttttagacat aacaccaaaa  82380
gcgcaattcg taaaaggaaa tatttataga ttgaacttta ccaaaattaa aatgtttgtg  82440
ctgtgaaaga ttctgttaag tggatgaaaa ggcaagctac agacagaaag tatttgtaaa  82500
ccagatattc aacaaaagtg ttatatgtag aacatataaa gaactctcaa agttcaacag  82560
```

-continued tatgaaaata aatcaactag aaaagtgggc aaaaggcaca aacagacatt tcaccaaaga 82620
agagatacat atggcgaata gcacatggaa aaatgttcaa tatcattagt catcaggaaa 82680
atgcaaatta gaactgctct gagatattac tgcataccta atagaatagt aaaaatgaaa 82740
aaatagtcat aataacaaat gttggtgagg atttgaaaaa actagatctt tcatacattg 82800
ctggtgtgaa tgtaaaatgg tagagccact tatggaaaac agtttgacag tttctgataa 82860
aactaaacat gcatttacta tatgatccag caattggact cttgggcatt tatcccagag 82920
taatgaaaac atgttcacac aaagacctct gcatgagtgt tcacagcaaa tttatttgta 82980
atggcaaaac ctgcaaacaa cctgaatgtc ccccatgggt gactgattaa acaaactgat 83040
acatccatct ttataatgga atattactct gcaataaaaa ggaacaaact actgatacac 83100
acaataactt gaatgtatat caagggcatt atgcttagta aaaaagtgtc aatctcaaaa 83160
ggttgcaaac tatatgattc catttatata acaccgtcaa aataacaaaa gtatggtgat 83220
gaagaataga ttagtggttt ccaggggaca gaaatagagt gaggattgag aatataaagg 83280
tgcagcacaa gggatttctt ttgtggtgat ggaacagctt cgtatgttga ttgtggtaga 83340
ggttacatct atctatacat gggataaaaa tgcatagaat ggaggcaggg catggtggct 83400
catgcctgta atcccagcac tttgggtggt cagctaaggc aggaggatta cttgaggcca 83460
ggagttcaag accagcctgg gtaacatagt gagaccccca tctctattaa aaaaatacaa 83520
aaaaaaaaaa gccagacata gtacctggct atgtagtccc agctacttgg aaggctgagg 83580
tggaaggatc atctgaaccc aggaggttgt ggctgcagtg agctgtgatt gcaccacagc 83640
actccagtct ggatgacaga gtgagactat gtctcaaaaa agtttttttt aatgcataga 83700
actgcacaca cacacacata cacacacaca cacacagcaa cacacagagc ccacatctta 83760
tcagtattct tttttttttt ctttccaact tttattttag gttcaagggg tatatgtgca 83820
gggttgtttc atgggtaaat tgtgtgttac aggtttggtg tacagataat tttgtcagct 83880
gttaggtagt ttttcaatcc tcccattcct ccaccttacc tgatagatat tttttgtcac 83940
tgaataggta gttttcgatc atcccactct ccaccctcaa ctaggcctca gtgtctgttg 84000
ttcccttctt tgtagtccat gtgtatgaat gtttagctcc cacttgtaag aacttgcagt 84060
atttagtttt ctgttcctgc attagttcac ttaggataat ggcctctagc tctattcatg 84120
ttgctgcaaa ggccattatc tcattttta tagctgcata ttattgcatg gtgtatatgt 84180
actacatttt ctttatacag tccaccactg gtaggcacat aggttgattc catgtctttg 84240
ctattgtgaa tagtgctgca atgaacatac atgtgcatgt gtctctatgg tagaacgatt 84300
tatattccat tggttatata ctgagtaata ggattgctgg gatgaatgat agttctgttt 84360
taagttcttt gagaaatgtc cagactgctt tccacagtgg ctgaactaat ttacattccc 84420
accagcaatg tataagcatt ccccttcctc tgcaacctca ccagcttctg ttattttttg 84480
actttttagt aatagccatt ctgactggtg tgtgatggta actcattgta gttttggttt 84540
agatttctgt aatgattagt gatactgagc atttttcat atgcttgttg ctacttgtat 84600
tagtatgtct tcttttgaga agtgtctgtt aatatctttt gcccactttt taaatagggt 84660
tgtttgtttt ttgcttgttg atttatttga gttccttaaa gattctggat attaaacctt 84720
agtcagatgc atagtttgca aacattttct cctactctgt aggttgttta ctctgttgat 84780
agtttctttt actgtgcaaa agctctttag gtcaattaaa ttccacttgt caatttttgt 84840
ttttgttgca attgcttttg gcatcttcat catgaagtct tttctttggc tgatgtccag 84900

-continued

```
aatggtattt cctggatttt cttctagagt ttttatagtg tttttggcct tacatttaag  84960
tctttaattc atcttgagtt gacttttgta tatggtgaaa tgtaggggtc ccgtttcaat  85020
cttctgcata tggctagcca gttatcccag cagcatttat tgagtaggga gtcctttcct  85080
cattgcttat ttttattggc tttgttgaag atcagatggt tctacatatg tggctctatt  85140
tctgggtcct ttaacctgtt ccattggtct atgtgtctgt ttttatactg ataccatgct  85200
gttttggtta ctgtagcctt gtagtatagt ttgaagtcag gtagtgtgat gcctccagct  85260
tcattctttt tgttcaggat cactttggct atttgggatc ttttttggtt ccatatgaat  85320
tttagaattt ttttctaatt ttgaaaaatg tgcacttttt tctaattttg taaaaatgtt  85380
attggtaggt tgataggaat agcactgaat ctgtaaattg ctttgggcag tatgccattt  85440
taattttgat ttttttccta tccatgagca tggaatgttt ttccatttgt ttgtgtcatc  85500
tctgatttat ttcagcagtg tcttgtaatt ctcgttgcag agatctttta cgtccctgtt  85560
tagttgtatt cctaggtatt ttatgatttt catggctatt gtgaatggga ttgcattctt  85620
gatttagctc tcagcttgaa tgttattggt gtatataaac atataccatt tgcatattga  85680
tttttgtatc ttaaaacttt gctgaagttg tttagcagat ctaggagcct caagcagaga  85740
ttatggtttt cctaggtata gtatcatatc atttgcgaag agagatgatt tgacttcctc  85800
tttctctatc tggatggctt ttatttttta ttcttttctg cttctctggt taggacttcc  85860
aggacttatg ttgaataaga atggtgagag tgggcatcct tgtcttgtac cagttttcaa  85920
ggagaatgct ttcagctttt gcccattcag tatgatgttg gctgtaggtt tgttgtagat  85980
aacacttatt attttgtggt gtacaccttc aatgcctagt tttttgcggg tttcaaacat  86040
gaggggatgt ttaattttat caaaagcctt ttctgcatct tctgagatga tcatgtggtt  86100
tttgttttta gttctgttta tgtaataaat aacatttatt gatttgcata tgttgaacca  86160
aacttgcctc ccaggaataa agcctatttg atcatggtgg attagctttt tgatgtgctg  86220
ctggatttgg tttgctagta ttttgtggag gatttttgca tctatgttta tcaggggtat  86280
tggtctgaag atttttgttg tgaatctgcc tggttttagt atgagaatga tgctggcctc  86340
atagaatgaa ttggacagga gcccctcctc cttgtttttt ggaatagttt cagtatccgt  86400
tcttctttac acatctggta gaatttggct gtgactccat ctgatccaag gctttttttct  86460
ggttgatagg tttttttttat tactgattca agtttggaac tcattattgg tgtgttcatg  86520
gtttcaattt ctttctggtt aggccaggta cacggctcac acctctaatt ccagcacttt  86580
gggaggttga ggtgggtgga tcacttgagc ccagacattt gagaccagct tggccaaaat  86640
ggcaaaaccc tgtctctact aaaaatacaa aaaaattagc tagacacagt ggtgtgcacc  86700
tgtagtccca gctacttgtg atgtgaggca ggagaatcac ttgagtgcag gaacagaggt  86760
tgcagtgagt caagattgtg ccactgcact ccagtctggg tgacagagca agactctgtc  86820
tcaaaaaaat aaaataaaat aaaataaaaa taatttattt ctggtttaat cttgggcagt  86880
tgaatattcc caggaattta tccatttctt ctagcttttc tagtttgtga gcacagaggt  86940
gttcataata gtctcttagg gtttttgtat ttctgtcggg ttagtagtaa tgtctccttt  87000
gttttctgat tgtgtttatc tttatcttct cccttttaaa aaattagtat agctaatagt  87060
atatcaatgt tatttattct ttcaaagagc caagtcttgg ttttgttgat cttttgtgtg  87120
atttttctca tctccatttt attctgttca gctatatttt ggttatttct tttcttctgt  87180
tatatttggg attggttggc ttttgttttt caaattcctt caagtgtaat gttaggttgt  87240
taacttaagt tgtaagtttt tcttttttat gtcgacattt agcagtataa actttcctct  87300
```

-continued

```
caacactgct tttgccctgt cccagagatt ctagtatgtt gtatctttgt tttcattagt  87360
ttcaaggaat ttctcggttt ctacagttac ttcattgttt acccaaatca ttcaggagta  87420
ggttgtttag tttccatgta attgtatgct tttgagagat cttcttgata ttgatttata  87480
tttttactgc attgtgttct gagagcatgt ttggtatgat tttggttttg taaaatttgt  87540
tgagaattgc tttatggcta agtatgtggt caattttaga atatgtgcca tctgcagatg  87600
aaaagaatgt atattctgtt tttgttgggt ggagtgttct gtagatgtct gttaggttca  87660
tttggtcaag tgttaagttt aggtcccaaa tatctcttgt tagtattctg cctcagtgat  87720
ctgtccaatg ccatcagtag ggtgttgaag tcttccatga ttatattgcc attatctaag  87780
tctcttccta agtctctaag aacttgtttt atgaatctgg gtgttccagt attgggtgca  87840
tatatattta ggatagttaa gtcttcttgt ttaattgaac actttatttt tatgtaatcc  87900
tcttcttttt actttctgaa tgtttttggt ttaaagtcat tcttttctga aataaaaaca  87960
gcaacccctt tttagcattc ttaaaattta aaattttact ttcaaaggag ccaagatgaa  88020
atgatttaga tgctttgtca cttatttagt catcttcact gttatccaga agtaaatttt  88080
aactataaat tttattataa gaaagggttt tatcattcta tatagatcaa gaggcccagg  88140
agtattttaa aagtgaattt gttattaatg ttattacagc ttacaaacaa tattattgta  88200
tgggtaagtt tatagagtta cacttaagta gttaagaaac aatatgattt tttagtaatg  88260
tacgaagact tttcaggatt ttgtacttga gtataatttt tggagattac atttaattca  88320
gtttatttat ttgttctttt gaggcaggat ctcactctat cagccaggct agagtgcagt  88380
ggcgttatca tggctcactc cagcctcgat ctcctgggct caagcaatcc tgccatctta  88440
gccttctgag cagctggggc tacaggcatt cacctctaca cctggttaac attttttatt  88500
tcttgcagag acgtcatctc actgttaccc atcgcctcac tgttacaaca ttttagaatc  88560
aattgtataa acagggatga cagaaagtac catagttcta gaaaccttaa ttgaggacat  88620
tttccataga gaaaaacctg tatttcctta aatagcatta caccctttta aaactctagg  88680
ttttctttac caccaaatag actagaaagt aaatttccaa tttaacaaag ttcttcagtc  88740
aaaataacac cagcatacat gctattatat agtctccctt ccttttgctc tttttatctg  88800
aaatccacag catatgtcag tagattataa tttaattaga agatttaata aaagttgtat  88860
ccactcccct gatgccactt ccttatggaa agtttcatta tagcccttcc acagaatagt  88920
atgtttgagt cttattcaca aaggaaaacc atctattttt atctagcaca gtaggcaata  88980
aagaaaacaa attggaataa tataaaagaa aaagtgagaa caaagaacat tttgcaactt  89040
aagattggct ccagacatgg atgaaaatta aatgttaaat cagttgtttc tgctataagc  89100
attagcataa gatctttgaa ctgaaaagga ctataaattc aattcaaatt actatattat  89160
ggtgggaaat gggcacagac tctggagaaa aacaaaattt taaaaaaaac ttagagttgg  89220
atcctggctt gacaaggtca ctggctaggt gatctttgga aaattattta atgtgtttaa  89280
tttgtctcat cattttacct gtgagaaaac tgacccagag aagttaaaag actttccttt  89340
tattacatgg tggtttagct gtatagaaaa aatataaatg tctttttatt ctcaactagt  89400
tgaagacact ttatgtaata ctattccatt aaaatgtctg ccaagaggtt gttcctttgt  89460
gatattgaaa tcataatgtg actatggcct tattctcata tctgacaaga aatagtaatt  89520
tatatttatt aaaatcatat ttactttcac cattaattct gattaggatt tttatgctga  89580
tatgattaac gaaaatggtg atctatgtca gttgggatag gctaaattat gctataaaaa  89640
```

-continued

```
atacccctgca atctcagtgg cttaaaccca tttatttatg gctcacaatt catgtccatc  89700
atgaatcatt ggggttttgc tcatctgttc attgtattaa atagtgactt agaaacctca  89760
gctgatagat cagtcttcac cttgaacttt gcttgttgca tgtcaaggaa aggatgagct  89820
ccagaggata tcctcttgcc aattaaatac tccagtctga aagtgacaca cacataattt  89880
ctgttcccac ctcatttcca gatttaatca cagacacatg gactcaccca attaaaaggg  89940
agccaggtag tgatgttcta cactttccta ggaagagagg gagaaccagt tatgacatga  90000
tatgaccatc acatgatcta tgaggtatta tggccctgtt taggactgaa aaactttagg  90060
aataactaat atgaaaactt tctgtgtaga caaaaatgtt ctataaaatt cccagccttg  90120
aagagatata ctgttggtga tttgtggctt aaatgtaagt tttttcaata tggcatatct  90180
attcttacct gattgtaaat tttggcaggt ataagtattc ttttctattg gcttcctttt  90240
cactttctga catttttttt tctttttgct tcctaaacac taaaaacaga tccatagctt  90300
tcctgatctc tcttactact ctgcacatta atcattctga ctgtctcttt tggttagtta  90360
cttttggcta atccacttga ttccctaact agttactccc acatatttgt tgtgtgttga  90420
aggtggatca ttttattaca caaaatagta agataatata atatagagga tttgaatgat  90480
attgcttgga gagagaaatt ggggtcaaaa atgactaagg agaaaaggaa tgagggaaat  90540
ggtggagatg gaggtaggca agaagattta ggctaaggtt cattagaaat ggtgaaacta  90600
aattggtcat ctattaggat tagagaccaa attcctaaac ggataagaat taagtggctt  90660
gtgccagagc aataaaatca ctggtttctc tttatctgtt ccatttatct tgcttataga  90720
caatctaggt attactattc atttcagtcc aagaagacag tggtcccccca tttgacatca  90780
tgacatcaag gttcttctct gattatccat cctggcagaa acacccaggg atggggtctg  90840
agctcaattc tcacatattc agtccctagg aagtgactgc tatcactagc tttcatccaa  90900
gcaagcctaa caaggatttt tcctatgcaa caggccccta attatgctag cctccctcaa  90960
gatcttataa gaaaattacc aagagactaa aatattcagg tttaagacct cccactaagg  91020
aaaaataagt attctttcat tttctttttc aattaccatt aactttccat gaagtataca  91080
ctctttatta gtgctacata agattttctc tgaccactgg ttaaacaatt atatttaaat  91140
atttcttcag agttagacaa gttaacaaaa taacatgagt tttccttttt ttcaattatt  91200
ttttaattgc aaaaagaata tgagttaaat ggaattaaaa tgaaataagc caaatggctt  91260
agactagctt ttatatactt ccaaaaccta tgaaccaaga cacaatatga ctatttttct  91320
atttcaacct tttattttttg gtataaagga tcattaacct acaatataat ataaactgtg  91380
ctgataatat ttgtttgtat aggtggttga agtttgaaga agatgtggaa gatggaggag  91440
aaaggtggag caagccttat gtggctactc tttcattgca cagcttgttt gaattgagaa  91500
gttgtattct gaatggaact gtgttgctgg acatgcatgc caacacttta gaagaaattg  91560
caggtatatc ttttcccccct tagtgtattt tataggtaca gctaattttt tgttactctc  91620
ttttccttat aattcaatat acgtatgaac tttggaaaac taattctcat aatcactgca  91680
taaggtctta aaagtcattt tcttttaccc tgttatttga gataaaagaa gttgaatctc  91740
agagaaatat gctctagttt ggcagtgcca agtctaggac aagaacctag atatcttgat  91800
tcccattcac catttatttt cattatcata tttagactct caccattaga aaattaaagg  91860
aaaaaacctt agagctagat acttattttc aatattcaaa catatgaaat aaccaaatga  91920
aaaaatttca atatacagaa aaatgttggt ttagaatgga cacagaaagg tacggccatt  91980
cattttaaac ttaattaaaa cccttgaatt ccagaggaag ccaagtgata cagttaggat  92040
```

-continued tcgttttgta attcaatact ataaactgat gaatgattag tattataatt caatgatatc 92100
ttataataca gacaggtata tttaggaaat gttattatta cagaaattga gtcaaagaac 92160
tcctgtatct tttgaccaga aggcaaacat attttagtaa aaacaaaata atacaaaaag 92220
acagaaatga attttgaaag agtataaatg aaataattga tggaggtttt aaaaacacaa 92280
acaaagaaaa gaggcagttg aaaagttatt agtttgggaa aaaataaaat tcattccata 92340
tgatttgtat ttgtgaagtg aaaaaactta atatcttaat catattgtag agatgaaaaa 92400
ctatatgtgt gtttttaatc atgtatatga aaataatata ttagaaaaat aacatatcta 92460
ctttaatctg cagaacagcc ccatgaagta gatgtcattc tcattttcca atcacaaaat 92520
agaaactcta aaattgtcat ggcctagatt tcacccaagg gcccctgact ttaagcctag 92580
tgtttttttct attacactac aactgctgtc tgaagaaaaa gaaatgtctt gaagtgaatg 92640
tcacccaaat tttgatggca catttatcac cttaaaaatt attgatttag tcattggtgc 92700
tgataggcac tgcagtatgt gtgaaaagaa aagtaagtac tgaaagatac tttggcttga 92760
aatattaagc aaaaactcca aaaatactaa aacacacaca cacacacaca cacacacaca 92820
cacacacaca cacaccacac tgccccaaat aggaaagata agcggtcctc ttctgtttca 92880
tgtaacacct ataaagagat tattctttaa gttacatagc tagagcctga aagactttat 92940
aaagttaaac ataaatgtat aattttcaga aatatccagg ctactgtagc tgcactaaat 93000
caagagaaaa tagagaaaat gattaactca gaaataagca aactccctaa gaatgctgaa 93060
atagttagct atccagctca atttcttagc tttacattat atggtcttgc taatacccaa 93120
taaacatttt tatattttaa ttaggaatga aacagcaggc ttttcacagt actttcaagt 93180
atgggaagct cttaagtttg taattatctt tttaatgctc aaacctggtt cttagtatta 93240
ttattgttat ccttatttaa taaagaaaaa aactaagatt taaaaggtta aaggccttgc 93300
tctaaggcgt ttatttctgc cgcttaaatc gatgatggcg ctacctttaa aaatagatta 93360
atccaaatac attttgaaat gggaaacaaa actgtcacat tctaccacct ggcaaaatta 93420
gcctcagaac atacccttta tacttttacc agtcttcaca tttcttaaat tatgtaattt 93480
ctaatgcttt cctcagaaag ttattcctat gaagaaattt tctcccagta atttgactaa 93540
aacacttcat tttatcactt tagttcactt tcattgtcca aaattatgca aatttttcct 93600
aactctgtcc ctgtttccca agctcaattc tgtagaatat gtgaaggtta actgggttaa 93660
atctagcctt ttcaagcaaa ttacattctc taagtctacc cttacagtga aagtagttca 93720
gttgacgtct tgatacccta aatagctttt tagtattctt tctgctcttc taattagtgt 93780
gtatctttct gactttgaag tagcccaacc tgaatgtccc atttttcagt gtagaacagc 93840
ctgtaaaatg acatttagaa tgtgtcagtg gtttaatgct aacatcacaa agaaaaatat 93900
gattacaaat atttgtgttg atcattatta ctttagattc ctttactgtc attactaaga 93960
agagatttcc tctcattgaa aactataatt tggctaaatt taaaagttac ttatttatcc 94020
cctcaatata aactcattaa aatattttct ctctatagtt tgtaattatt ttcttatttt 94080
ttacttctcc tattttcatt ttataaaaat tgaggggcat tactaagttt gtaataaata 94140
agcatgcttt ccgtttttaa gacttctaac tttgcaaagt atttccacat aattatgttt 94200
tattatcata acaacatata aagtaggaaa gagactattt caccataaac agataaatag 94260
aaagttcttt atcaaagatg acctttgcag aaataaaaat aatttttttta ttaacctata 94320
atcataatat ttggggatgg gatctcctat gttgcccagg ctggtcttga actcctgggt 94380

-continued

```
tcaattgatc cacctgcctc agcttcccaa agtgctagga ttacaggcat gagtcactgt  94440
gcccaaccat aatttttgtt ttattctgtt tcatgatcat ttgtggccat agtgattaac  94500
aatcagccct gaaacttttt cctcagctct tatttaccat gatttttctc tgttagccat  94560
aattcacata cattagtcac tagtttcagt tttacaaacg ctaagtgtaa gagcttacct  94620
ttaagggttc taatccctag tactttgtga atacacaggc tttacagtat tgatgttttt  94680
cagacatttc ctactagatg aatatgaccc agatattgtt ttgtaatgat caaggatttt  94740
tatatcaatg ttttgatatg tttttaacag actcggataa ttccttaaga gatttttgta  94800
gacttagtag cagaaaatcc catttgtatc tggcagatct gtcaagaatt tctgatataa  94860
ttaaagtagg attttctttt ggctaagtta atttaaaata tatctgtttc ccaatgtttc  94920
aggaaactca ataaatttaa actttatcct tcaaaatatt acttaacctt ttcaaatcca  94980
aaattctcca gatatatctt cttaccacaa tttactctga tatggagatt aattgtattg  95040
aatatgcttc tgaattatat tcatataaat tacagggaat tttatggtct atgttaatct  95100
ctttgaaatt aagcattata aagattaatg atggaaatat cctctctgca gtgtgtgtat  95160
actttaacct aattctgtca atgagagtta ggaagaaatt aaaaccaaac caaagttggt  95220
accatggaca gattatcaat catagctccc aactcattta aacaaccttt gttgtttaaa  95280
atctttcatt gaaggaagaa tctacagttt gctccactga atgtaatctg tagagttggg  95340
agtataggaa taaccatata ttttttaacc tgcctatact gtgacaatcc ttggtctgaa  95400
aagtaagtat tctattacag tttacatctt tagtacacac atccctgtta gtgctggcaa  95460
ccaaaccaca gaatttagga acttcgtatc atattccccc ccacctctcc caatatcttt  95520
taaagttaag acaatgggtt ttcaaagcat tgatatgatg atcttcaaaa aggcagagat  95580
ttatgtagaa tctgcaatat gtcataacct ctaggggctt tcattcaaga tacattatga  95640
taaaatagtt atctgatagg atgaaaaaca atttttcatt tttctgaggc ctttttccac  95700
aagtgctact agtttttctt ttcttttctt ttcttttttt ttttttttaga cgaagtctcg  95760
ctctgtcgcc aggctggagt gcagtggtgc gatctcagct cactgcagcc tccgcctcct  95820
gggttcaagc aattctccta cttcaatctc ttgagtacct gggactacag gcacacggca  95880
acatgcccag ctaatttttt tgtattttag tagagacggg gattcaccac gttggacagg  95940
gtggtctcaa agtgctacta gtttttctag agtctgctta gtgttagcag agtgtgacct  96000
atttgtcctt tttttctttt cttttctttt cttttttttt tttttttttt tttttgaggc  96060
ggagtcttgc tttgtctccc aggctggagt gcagtggcgc aatctcggct cactgcaagc  96120
tccgcctccc gggttcacgc cattcccctg cctcaacctc ccgagtcgct gggactacag  96180
gcgcccgcca ccacgcccgg ctgatttttt gtatttttag aagtgacggg gtttcaccgt  96240
gttagccagg atggtctcta tcccctgacc tcgtgatccg cccgcctcgg cctcccaaag  96300
tgctgggatt acaggcgtga gccaccgcgc cttttctctt atcacccaga tcctggggca  96360
gaatagactg tattatgtag gcataatagc ttgctgagat tgcaggactt cactctggac  96420
ccaacgtcat tatggtccgt tattctttca cacttttcaa attaatacta atatgtattg  96480
tagtggtgaa aagaacaatg taagtgatta ctaattcaga ttccttttgg tacttaaatg  96540
tcaccctagt ataaattata ttcttaagca aaatgagtaa ttttttccag acaagtagat  96600
ataatttgat acagttatac tttggagaag tttgctgtgt atttctctgt aactaatgaa  96660
cagatgagtg tgttttttaa tatttacttt tctttacata actgtttcaa ataaaaatct  96720
tatctttgaa aaactgtgaa gatagtgacc tatggctttt ttagtgttcg agcctggaaa  96780
```

-continued

```
cattgtgctt taatagaaat taaaaataat aaacatatgt agggtttatt atgtgattac  96840
ttttgattct gactagaata ttgaactggg aattcatatc atggcttata tttggaactg  96900
ctttacaata atatcatatt gatattctaa taacctactt tacaacttcc attatgaagt  96960
atatgcatat tttatataca tttttccatc ttagcaaggt ttcagtgtaa tgtcatatac  97020
gttgacaatt tattatttcc tttatttcag attaacccag gggtattata actactgatc  97080
tccaaagaac tgaaaaatag atttaaatat tattctatag tatcacacat tttcagaatt  97140
ggaagggacc tttgaggtaa ttatagtgac tgactttcaa acattccagg tatataatat  97200
gggtaacttc caaatattct ttctacctct ttccattgta aacacaaaaa tgatagagca  97260
cactatatcc cacgtgccac atatggccga ctgcctgatt ttgtagggca tttgagctaa  97320
gaatggtgat tatattttaa atggttgaaa aataataaaa aagaagttaa tatgttgtga  97380
tgtgaatatt atatgaaatt caagtttcag catccttaaa aaagtttcat tggagcataa  97440
ccaggctcat ttgtgtacat gttgcctgtg gctgctttct tgctacaaag gcaaaattca  97500
gtatttgtga cagagatcat atggcctaca atgcctaaaa tatttgttat ctggctctgg  97560
acaaaaagag cttgtctttc tctggtttag agaattaact ctagagtgaa gcgcagttct  97620
tgattagcct gtcagtcata tgaataccat ctcctttgcc agtgattggt tcaagatggg  97680
cagggctatg tcagttagac ttaggataat ttttcctggc caggtgaaaa ataactcatc  97740
taagagaaag tcacaaaaaa acaatatatt tctcactgga tatgaacaaa aatatatatt  97800
tccttgttgc tgctggaagc caccttatga ccataaggaa aatcagcctg aggttaaagc  97860
ttaccctaga ggaggaggaa gttaacaaaa tcacagagaa gcagaattat agccaaccta  97920
actttgatct ttctatttat gtgagccaat aaaattgttt tatgtagttt aatttgggtt  97980
ttctgctatt gataagccca gctttgtctc tacttgataa gctgtcacaa aatatgaaca  98040
tattgaaacc accacaaatt tcaaaccagg aacccataat ctacattatg aaaattacaa  98100
agaaaatctt gttctgggaa atatttactg atagcctcaa tattccaatc agtgcatcag  98160
gtgccttatg tcattagtct tggcaccaat atatgatata gatattatta tctccatttt  98220
acaaataagg acacttaggt tattcaactt tgcaaagttg tctagctaga atgtcataaa  98280
gtggcccaaa tctgtctcct agttcatttc catttcacac tgaaggaaaa cattgttggt  98340
aagggagcat tctgctaact ttgaaacctt tattgtactc aaaaaggcag tggaaggcag  98400
ctcattgtaa tctgctttac ataagatgtt aatgcctaaa aaacaattag agttaatgtt  98460
tgataatcag aaagcagatt aattacacaa acatccattg atgtgatctt tatatcacta  98520
agaaacttaa aataccttta cttatctatt ttactgacat ttttgatact atgtatggta  98580
aataatctgc ttaattatag acttctgaaa tctcaccttc cagtctttgt tttgcaggta  98640
tagaatatct ttttaatcta acattctcaa gggagtgtgt ttccagcaaa gtttgagaaa  98700
gggctgattt tctatccata tgaaacagaa ttgtttactc tccaaattca gtaactatat  98760
cacttcatag gcctctttgc atcagatttt cacagataga cttttgttca cttaatgggg  98820
aaacaaggaa attagtctgt actagaaaat gggaaaaaaa ttaaaatata agtataaaac  98880
caattttcaa attcaaacac gttatgaatt gtgaattcaa acacattatg aattttcaaa  98940
ttcaaacaca ttatgaattt tgatattatc tctacagcta ttcctcccat cagtgtggat  99000
aataaataaa taaagaactt tcttctcaat gcaactattc ccatttgaaa aataatactt  99060
cataagaatt atatatttaa atagaatggt ttataatgaa aatttgccca aatctttctt  99120
```

-continued

```
attcaacatt tctacaatgg aagataaatt tccatttata acagcatgct tagagatttt  99180
ttaaagaagt tatttctatt tcaagatgaa taatattgtt tagggcttgc atatttggac  99240
tcagtggttc acggctggca cacgttctag aggaaagctg tgcttatctt cttccggcct  99300
tttctcttca gatatggttc ttgaccaaca agtgagctca ggtcagctga atgaagatgt  99360
acgccatagg gtccatgagg cattgatgaa acagcatcat catcagaatc agaaaaaact  99420
caccaacagg attcccattg ttcgttcctt tgctgatatt ggcaagaaac agtcagaacc  99480
aaattccatg gacaaaaatg gtaaatgttt atttattgtg ctctttatgt ctactatagg  99540
tctctgacat atcaaagcgc ttctaaatct tttaaaactt gttttatttg aaaatgattt  99600
tttgaaattc agattattgt agaattcttt tcacatgagt atatattctt attatcaagc  99660
atcaagttgt aaaaatttta gaaaagaact taagtttcct gaaaggttca ggaaaaaaat  99720
gcaaagaaaa ctaatattta ataaaaaaac ttttagattt ggctgcagaa aacataaaca  99780
gagcatctgt ggcataccaa ataaggtcct agtctctgtc ctgtagctta aaaatgtaat  99840
gcagggcttt gacttacgcc atagatggtc ttttagttta aaggaatcat gatcatcatc  99900
tagtgtttgt ggaaaaaaga tattggtttc atgttgctca tagtcaacaa attccattag  99960
agaaaatgat tgaaaagacc agccagtgca ttgtttgtgg ctttacatac attatggctg 100020
attccggttc aagggctcat tgctgtttgt aatgcagcat cttcaacatc catggagcca 100080
ccccacttac tatcttcata aaccaacata gatgaccacc attgtttcct agcaatcaac 100140
ttactatgat ttatgcttca gactattttg tctttcctgt attttttgtt ctctccttgc 100200
gtttatttaa cccctcatca tttgcaataa ggaagttgct taggaatctc ctgttatcat 100260
ccatcctttc tattagtctc atgagagaaa atgaagttac catgaagatg atatgaattt 100320
gttaaacttc tgtaggcttt aaaagtttcc agttctaggc cgggcgcagt ggctcactcc 100380
tgtaatccca gcactttggg aggccgaggc gggcggatca agaggtcagg agatcgtgac 100440
catcctggct aacacggtga aaccccgtct ctactaaaaa tacagaaaaa ttagccgggc 100500
gtggtagtgg gtgcctgtag tcccagctac tcgggagact gaggcaggag aatggtgtga 100560
acctgggtgg cggagattgc agtgagccga gatcgcgcca ctgcactcca gcctgggcta 100620
cacagctaga ctctgtctca aaaaaaaaaa gtttccagtt ctaaaagata aaaattaatg 100680
aaaagtattt tcaaatgctt tactggaaag actgatttcc acgaatggat gaaagcacat 100740
gtaatgacag cgtgaaatat catgtaatct cacccttatt ttcaaaagct tcagagatgc 100800
cttaaataaa atgtatgaaa attagttttc ttcagatttg cttcatatta atcagttttc 100860
atgctactgt atcaaatata cataaaaata tagggtaaat gctttattaa atagataaag 100920
atgattagat gtaattttgt ctcagaatgt agaaccagtt cttaatgaca aaatcatttt 100980
tgagatagtt gatttttagg gcttttcaat gactgaatat aagtcatttt tgttacatac 101040
aagagtctat agatgtgcac acttaagttc aataaaatta ttatgaatac tttatggtga 101100
ataccaactt gtgtttgtag attccactga acattctgag gagatataac ttgctttgaa 101160
tcaaatcata tatttaaaac atatttatat tctaaatcac aatttgcttt aaaatatgtg 101220
atacataaga taacaaaact tgaggctttt atattctaag agatgtatta caaatgcagt 101280
gcttttgtta tgcttataat gctagtattt atttggtatg gtagtgttaa aatagactca 101340
gttatttact aattttggct atgggattat gtctacatga ttccaaaaac tttattagaa 101400
ttaacttcct aagaatgcat gcagatttta taaaaatgaa cttttacctt cataactttt 101460
gctagaaatc agataagata tatgtcttta agaaagaggt atgtttcttc aaagaggcaa 101520
```

-continued ggatcttgca ttttgaacta gttaaaattt ataccttaaa tttcattgga gataatgttt 101580
actataacaa taatttcatt gcattttttt ttcaggcaag agactacaga atttattgga 101640
gcaatgattt attgtaatat gcagatctag gcacactgtt tgttactgct ttaaacttct 101700
attaaacatt agaagagatg ttagaattat aactgtgaat cacaaatcta catatagtca 101760
caaggttttc tgagagcctg ctttttgtct tatttaggaa atggtttagt tttcccaaaa 101820
atcagaatct gagtggttct aaagtgattc tgtcaccatc tgtacaatca gcctttatct 101880
gaacacatac aaatcttttc gaggcatacg taagggcaat aaaaacttgg aaacatttct 101940
aataagattc atatacccaa ttaagtattg ttgtagagta tgctgtcaga agtggttttc 102000
taagcctaag cttataacac ctccttatga ctctgttttg cttcctcaca cactttgcat 102060
aattatgtgt gttgagaatt ctgaaaatat gtatagactt caccaattta gaagtaaatc 102120
tcctacccaa aagtgaaaaa aagtacaaaa gacctttact gctaaggttc ttaatctact 102180
tatgaactct aaagcctgac aaactctaga tatataaaca aattgaaatt aatagccgta 102240
aatgtaaatt ggaaattctg ttttaaatat gcaatcaaga tttaaatttt tgtgcaatag 102300
ttcagagaga tgcaaaagga tttcaaaaca tcaaaaaagt aaaggtaata ctattaattt 102360
ttaaaaatct ccttagtaaa atccattatg caaaaagatt gactttttta aaaaaaaaga 102420
ttatagaata gaaattaaat agagcaaaga tttttccaga aactttaaaa cagaacacat 102480
tttcctccct aagcatagtg gtagaaataa gtccccgttt cttgtttaat gtgctaaaat 102540
tatctcaaaa aggggatcct ctagagtcga nnnnnnnnnn nnnnnnnnnn nnnnnnnnnn 102600
nnnnnnnnnn nnnnnnnnnn tcccggaagc agagcgggag aaagaaggcc ccgtttcggg 102660
gtgaatgtgc gaaaaggagc gcaaaaacaa agtgaagctg atgtagataa acctgaaaga 102720
gtcagataga agaaagttag tacgtcctga agtgacttgt gtcttgagca tgttaccttg 102780
tgagtactct ccggggttaa acattcagac actgtatttc aaacggggtc ttccccattt 102840
taaagattag attaataaaa tagtgcattt ccttgctctt ctccttccca agtctaccat 102900
tctttgtcca ttcctttttt agtgatttgt gataatttgt caatctcatc tctaaacaca 102960
ctagttcact cgtttgaata atttttttct tcgtattccg cattctcttc agggctaatg 103020
tgaaggatgc tatggattca ccatgcattt ttaatgccac catgctgtgt ttaactttca 103080
cttttcatta agcatcaaaa ctgtgagaat taaatgtctg attctgatgt ttcaataaaa 103140
agtgacagtt acatttggca aaacaacagc aaaaataata gaaaaataat atctactttg 103200
acattagtac cctgaaaagg gtatgggtgg taaagcactc aaaataaatg tatcgaaaat 103260
attaaaataa ttatttgaat taggaagatt ttctaaaact aaaaataaaa cttttaaggg 103320
atctagaaga caaattttat cagtatctgt atttatcatt taggtcatgt attcaattac 103380
cttttgagac attgggatta taaatctatt ataaaatatt attatcctta tgataatttt 103440
tatatttttg aagataattt gggattatta gttttcttaa gtataggatg tctttattct 103500
gctctatcct ttactaataa tttctaactc tgttcgtttt ccttcacata tcttttgtct 103560
ctcctaatct gaatactttc cagttgtacc ttttatttag gatctcaaaa ggagttacag 103620
tgcagaaagt ctctaactac tgttcaacgc cataagttac tgaaaagcag ttagatttgg 103680
gagcctggga cataaagttc actctttagg cctgggtaga tttcagccct taaagcaatg 103740
tacacatatg tattgtgcat aatatttatt tatggttttg gaaatcagac ctattacatt 103800
gtagttactt cttttacaaa tgctgtactt ttaattttca gatgcatgct gtctttacgt 103860

-continued

```
atttagatat atatgctttc ttgctttttt aatacaatgg tctcataaat aagatatcca 103920
ggatttaaaa tttatccctc ataatgttct acctttgaag aaaaaataaa gctagaataa 103980
taattcttga gattgcttga aagaaaactt attaaaagat ttgtgtatat taaataatta 104040
aacattgttt aataaatatg atattttcca ccgctccaag aaaatcaaga tgacattgtt 104100
gacacaactg atgggcctgc ccagaggcta tattgtcatt acagttttgg aatgtcaaga 104160
ctagatttta agagcaaaca taattctagt atgaagtgtt tgaatttgtt atttcttata 104220
ttgcattaat tattttcagg catactaatt tttctccgag tttaattgtt tgcatacttc 104280
tcatgttttt gaagtgtagc tcacctaatc agcattttct aaatatttag cccttctttc 104340
ttcatgtttt ctattcccat gaataaatgt attgttacac atgtatgtaa ctttgtcatt 104400
catctttata tttctttatt ttgctctgtc ttgtgtctgt ctctaacagg ctcatctcat 104460
ctctgtacct ccctcatctc ctaccctttg ggtactctaa atgcgttgaa ggtttctgag 104520
gtagtgtaaa ccagcttggt ctctaggtta atagtaatgt acctccatgt cttcatccca 104580
gtttccttct agtgcacgtg atttacagtg gattaagcag tagaaaataa tgatacattt 104640
atgcaatata ttctattgat acgaatttgg ccaactataa atttaaaagt tgctaagctg 104700
ctgttttata atacatatgt gcatacttaa agaagaagag aactatagct aaagacaaat 104760
gagttaatat aatactcaac agggtttttg agaatatacc ttttttttcca ataatgaagt 104820
gttttaaaat actgctatta attaaagtca tgaaatagta cttttgatgt aatctcatgt 104880
tccttccttt atgataaaga aactgtatga taaagaaaat gactttacca gtctcacaat 104940
acacttagtg aaaaatttat ggtgtaacaa gcagaaaaac agcttcattt ttctagttag 105000
tatttactca aaatactctc agttttctcc tatgctagcc ccatatctat tataatttgc 105060
cctagaaaaa ttcatggtct ataataactt tttatctgac acatatgatc cctacatgaa 105120
gactcaaaga aaaaaaaatg aatttgtaac tcaaagaaaa gtaattcaaa caggtgctaa 105180
tatgaatact atataatata tatcttaatt ggtaagatat caaacaaata ttagaaattt 105240
tgatttaagg tgaagaactg ttgagcttaa caagtcataa aaatgtattt agtaaatagc 105300
agaggagata ttaggtttct caaatgtttc catttacgtt taaatagtca cagataccag 105360
ttaaccttag tgatatctac ttttcatcag ttttttaata acttaccatg aatataatag 105420
attactcaat gtcttttttt catagtcatc ctcatgcctc aaaattttct aggtattata 105480
aaaacagaaa taattgaaca ttgcaatgac attcatttat aggaaataat atgggtagtg 105540
atcagtggac aaaggtaata taaagaaaca ggtaaaaagc atttgtttgt aagtactgtg 105600
gtatagcact ttaaaaaaat tacagtatac aattagcatt cataaagctt ccacacatat 105660
atgagtgcta aatcctaaac ttatactaat ttttttccgt gagggaaaaa tatcctagca 105720
aattctttgt tattctatta ggaaaatttt tacttctggc tgaaggtaaa attctgtacc 105780
tgaaaattgc cattctgtga accattattg ccttagacat cagcaagaaa ataagagatg 105840
cccttccaaa atctgaattt attgattctt cttatgtaat agtatttcag ttaatgaaat 105900
taattttgaa atttaatcca tcatcttctt ttgaaagatg gtaataattg gcataaacta 105960
aataattggc atagagaaaa atatatttaa acaatgatta caattgataa tagaactata 106020
aaatcatttt taatttatga ggtttcaatt agttctatat actataattc atgcttgaat 106080
attggtttta tatatacagc aaataaaatg ttaagctttt taaaagactt ctattttttc 106140
aaaataaccc aaatcaaact tgttagctta atttttaaat agtatctata catcgttcta 106200
tatactacca agttgtgaaa actgccttga ggatatacac atttaatgta cattgtttca 106260
```

-continued

```
actttaacaa attaacttac atttttagaa ataatagaca agaaataaca agatttgaag 106320
tgctacttaa acttcgcagg acttttgatg tgattaaata tatttaatta tgaatattaa 106380
cgcctatcat ttaactactg ctctgaaata taaacgatat acaatttgtg gtctttatgt 106440
ctatgtcata ggctagtagt ttttatggct ttttatatta gcatacattc tatacacata 106500
cctagaatct aggactagca agaagtttac tgtcatctga tgtgtctgct gctagttaaa 106560
ctctcaacta ggtcattatc aacatcactt aaaatattta taaaaatagt ttctaaatcc 106620
cttcttcatt atcaacctta taaagtaata ttttctaaaa ttgttcttgt tttagaacaa 106680
gaatagcata caacaatctc aaaatatatt attataatta ttacataaaa tattaattat 106740
taattactgt aattatttac aaggagaaat acaagtatta atattttaaa catactacct 106800
gagctgaagg taatttatga aatgctctgc ttaaagtata caaatgaaaa cataaggtat 106860
tcaatttctt caaatgttaa gttccgcata ttttctatcc aattcaaaat ttaatctctt 106920
caaagttaat gactttgcac tgggttgact tttgttttgt atgtgtttgg tgatagaact 106980
aaataattgt tcttccatgt agatttatac cacacgaaat gaattattat aagaaagcag 107040
atatgtgttt atttaattta tccatgactt gagtttcacc actcaatttt acagaacatt 107100
caataaattt agttttaaat atatctaatg ttctaactca ttaaaatatg gagaaatgat 107160
gtgaaactgg tgattgaaga catctgttgg tagcacaaat gcattatgta aaagattttt 107220
ttaaaactac agttattatt ttgagaatgg taaattgaat ggctgctaat gaacagttca 107280
cagtcatagc tgcacattgt ggttagaaat gggagaatga gaataattta tgtagcttgt 107340
gtgacattta tctgaagttt atatatttcc ctagaatatg ctatactcag aatttgtgaa 107400
catggtttga ggtgaactta ttttaaaaag tcattttatt ttcatcttct ccaaatatat 107460
tcttttacat tttttaatga aagtagtgaa atccttaagt tctagaagaa tattaagcct 107520
attactttct ggcattataa caactttaaa ccataaaatt actcctatta ataaatgacc 107580
cctgcttgag aggcttacta gtccaaaaag caaacttata gtaatatttg aaagtaaata 107640
attagtattt ttaaccacag ttggtaattt ctaggtaaca aagaataagt gggttttcag 107700
gagagaattt aagggaaagc gtttttgtgg ggttttttttg catttacact gggagtttag 107760
agaatttcag tcagagactg aagtgattag agatgacact aaaggtgaat ttagaataaa 107820
attgggattt aggtaggtag agagaagagc cagacagaga gagtatttct aacatctaca 107880
actgacgtga ataaaagcag tattttgagt cattgagtta ttatcataaa tatgagcaag 107940
gcttcagagt tgagttgtct ttattcattt cacagaaaaa aaaaagatgg ggagatgttt 108000
aattttcatt gcattgctaa ctatgaacaa atttcatatg acttactgca aacaatgttt 108060
catatttagt gaatgatgga atttaacctt ttctagccat tgccacactc ccagagctac 108120
tatccactta attctcatca tcttccctat aatagggaaa agaactacaa gataattttg 108180
ttttaattta ctgttaatgc aaaactaata caattcaagt ttttatcttt tctcacatca 108240
cagactagta ccagtatgct tatataatag aatagtcaga ggcataaaat catatccata 108300
gtgttcatac tgtgtgaaat aaaggtattt ctaactgaac cccccttatat agaaaactgt 108360
aagagttatg gccaaagaaa tttttttcat tggtttggct ttttagatgc aatagaacct 108420
aaaaatatac tgtgtaattt tcagataaat atccgtcctt tttaatgctt tacattttaa 108480
attcttcagg ctgagcttac atcttaacag atgtctatct tgtcttttta tatacgccat 108540
tagttttggt tggaatctag aaatcaatga tgcttcaaaa tcctggtaac atttacatat 108600
```

-continued

```
tttgtagata atccttattg aaaataatct tttagagttt ttatctgaaa atatgtttat 108660
tttttactga attctcccat ttctacctgt tactgataat aagaatgttt gtattaatat 108720
agatttattt atattgaccc ttcattctta catcataaat ttattaagaa acctgttagt 108780
ctagtttaat tgaagtgcct atttcactca gtatgtctac aactatgtaa gtaattgttt 108840
gtattctgtc acaacaatct cttttagcag gtcaggttgt ttctcctcag tctgctccag 108900
cctgtgttga aaataaaaat gatgttagca gagaaaacag cactgttgac tttagcaagg 108960
tgagcttttc tccctctcat ctaagtaagt tgctaaatta ctactagaaa ttactaccca 109020
ttttaagagg tgttgacaca atattttgca tgcgcttttt gtttcttgtc aaagcttgat 109080
attgttacag aaaatgttag cattaagtcc acatgtaaca ttttgcctat tcaaaaaaaa 109140
aaaaaaaact gaacctgtga gttttatgca tagtattcat gtttcagcca cttggtataa 109200
tgttatctct tccaataaaa agaataactg ggcttcacag ggaatttaac agaagtttaa 109260
tctatttttg tttgtttgtg tttgttgttc tttgtttgtt tgtttgaggc agagtctcgc 109320
tctgtcaccc aggctggaat gcagtggtgc aatcttggct cactgcaacc tccgcctcct 109380
gggttcaagc aattctcaag cctcagcttc ccgagtagct gggattacag gcgtgcacca 109440
ctatgtctga ctaatttttg tatttttagt agagacgggg tttcaccatc ttggacaggc 109500
tggtctcgaa ctcctgacct caggtgatcc gtccgcctca gcctctcaaa gtgctgggat 109560
tacaggcgtg agccaccccg cccggccaag tttaatctat tgtttaaaaa ctttggctag 109620
tttgtgttca aaatcacttt tcttctattt gtgggaaagc aaatcataat ataaaactga 109680
attgttaatg taattaagga aaagtcatta ctgtaaggaa atcctagaag gacacagcaa 109740
aactgagcag agttttaaat aaaaacatat taagaactga ctgtgttgag ggatacatct 109800
aattggagac aactgaagtg aaatcattaa cttgaatgta ttcttagaaa atgagtcagt 109860
gacaatgatg tgattttgat tagcaaattc ctgacattgt atatgtgcca ttgcaagcta 109920
tggcaaagta acaattgagt ggaaaagagg agtttctagc cgggtgtggt ggcgcgtgcc 109980
tgtggttcca gccacttggg aggctgaggt gggaggattg cttgagccta ggaggcagag 110040
attgcagtga gctgaggtcg tgtcactgca ctccagcctg ggtgacagag tgagaccaca 110100
tctcaaaaaa aaaaaaaaaa aaaaaaaaaa gacaatgcaa aagagaagga gtttgaatac 110160
ttggtgaaaa tacggcaggt taacaattct ctttatctga gtggctgaaa tagaagtaac 110220
tcagagtaat attttaataa agcccttagc actggcaata attatagtag tgggaggagg 110280
tgggaatgga tggaagcagt agaggaagta gcctgaatca aggttctgaa aagattaata 110340
gtgatcagct ccttggacct gtttcagaat ccctctgaca atgcctaaat aatctagatc 110400
tagttacgtg catgctctcc ctctggtgcc tggcggagtc tccgtgggag catggtgtac 110460
cagcttaagt ctgttaatta tgcgtgcagg gactgggagg ccaacaaaag gggcatacta 110520
gtccatgtgg gatgaaacaa aggcatgaaa aaggacctcc acaccagcaa gagagagagg 110580
tgagggcata ctcgggctct atttctacag tggttcaaag ctcatttcac tgtatggagg 110640
catgtgattc aaacattaag ccagttgaaa tgtattccat ctgccactct aagaactatc 110700
tttttaaagc attgcatctt cattcatctg caagttggaa aaagttgtca caaactgcca 110760
tacatttaat ttctgatatt cttaatttga aatgatctta aaagcaataa tgtaacgagc 110820
tgcatattta tgtataaatg cattaacaac ataaagaagg catatttaac atcctcagaa 110880
acaatcatta taaagcacat agctcctcct ttcaaataaa ttgtgattta actttttaaa 110940
aataatataa cctttataca ctgattgtgt atctccatat catgttgctt ttggttgtgt 111000
```

-continued gacctgcctt tgcagccttc aagaatactt catcacatat gaaagaaaat gaagattgcc 111060
agttgtaggc agtagtctca tcttctggtc ccccctcaaa cagttaaaac tatggaagag 111120
tcaaacttcg atttcctttc ttttaatcct tttctttctc ttcacatttg cgatcactgg 111180
cccgtttcat cttttaatag gcaagttaaa tttctagagc cctctactta gtgtcagctg 111240
ttgttcatag catggcacac tggaaagtct cttgttcata gcatggcaca ctggaaagaa 111300
tgtggctttt gagaaacagc atgagatctt gaatcccaac tctggcatta taaactagct 111360
gatcttggag aagttctcta aagttcagcc ttctcatttg caaagtaaga aaactattta 111420
caatttcgtt gtgaagattt aatgagctaa tatagaggga ggtgctggaa cagtgcttga 111480
cttgtagcag gtatttaata aaaggtggtt acacttatta gtgtggttat tagtagtagt 111540
agagataata gtgtcagaaa tgaaacacca gaccataatt gaatgttttg gtctccactg 111600
ggtctttagt gccttgaata gtatttggta tatatttgtt gaatgaatcc ttcaagattc 111660
aaaataatgt aagcccagtt ttggaattta aaaaagacta agtaagattt tttactttaa 111720
agtctgagag ggcagaaaag tagagtttga aaagagcaat tgtgatctat cactatggaa 111780
acaaatttta gtgccagatt ttgcaggtgc atgagttgat attttttagc cttatgattt 111840
tagtttagta gtgaatttat cagaattcac ctagtctcca ggttagttct ctgttttaat 111900
attttaagtc ttaatataca gattccaaaa ccccagaatc ttaatatgca gattccaaac 111960
attttgaggt gttaagaaaa aaaaggtctt tattcatctt atatgatttg atcatattta 112020
ttccatctac attcaaccta catatttgta acccttccag tggatagacg tatcaaactt 112080
acttaaggaa tgattaggaa aataactgga attatcaggt tttagcttcc cataatactt 112140
ttaaaaagca gatgtgtcaa agcaatattt gtttttgttt ttcaagctga cagtggaacg 112200
taggtatttt atgttggtgg tgttttcttt tacttcaaat gacccagaga tggcttcaca 112260
taattttcta catagaaaga acttccgtct gcatctagct ttagtgtatg aaacatatta 112320
gagagagttg tattatttaa tcctagaact gtaggaaacc ttagacatct cctcatttag 112380
tcagcaagaa agctgaatta tagagtgatt aagagagctg ctcaagatca ctggcgagtt 112440
agtgtcaaga caccatttct tcccagagaa tccctatgaa gtttcttgta ctttctataa 112500
ggggctgaag gcttaaattt tctccttaaa tttccatctg tttttccttt aactcttagc 112560
gtgtagtttg cccagacact tccaatttca ccttggtctt ctatctaatc tcattccttg 112620
ttccctagaa atgtaactgt ttctcatcca cagattaagt atcaaaggcc cagaaagaaa 112680
tctttccact accagcataa aggtgaggtc tgggcagccc agaagcatga gtgtaaatac 112740
agacccagaa gagtatagct cgatttcttc aagatcctat tcagaggacc agaaacttcc 112800
aggatttcct tcttgtccat tccaagtgtt tgtgttcact tgacagtttt cttagggatg 112860
tagttcaacc tagattctct agagctgctt tacatattta taattttata agaggtcaca 112920
ttcaggtctt taaacataat attttattat attaaaagtt gcttaggggg ccaagggcat 112980
ggtggctgac acctgtaatc ccagcatttt gagaggccaa gtcaggagga tcacttgagc 113040
ttaggagttc gagatcaacc taggcaacat ggtaagacct catctctaca aaatctagaa 113100
aaaatcagcc aggcatggtg gcgcacctgt agtcccagct actcagaagg ctgaaatgga 113160
aggatcagga tggcttgagc caggaagttc gaggctgcag tgagctggga tcgcaccact 113220
gcactccact ctggatgaca caaggagacc ctgtctcaaa aacttaacca aaccaaaaaa 113280
gatagttggt ttgtcaaata agtttcttca tgaagtatat agtacacaaa cacaaaatat 113340

-continued agggttgccc cacgaataat ataatatgta actatacata atataggaat aatataatta 113400
gataatatat aatcgattac ttcccaaagt atatgattac tccaagaata atgtaatgta 113460
atgagtataa tacaatggct accccagata tgtgctatag tactataact tattccattt 113520
gaagtcaaaa gatgaatttg cttatcctga atttaaattc tgtatatttt aatgtttttt 113580
ctaaataaca ggtatcaatg atatattagg tattttgtaa atttaaagat catatgtaat 113640
gaccatatat tttcttttac aaaatttaac tattttaaca tactatgtac ttcttgattt 113700
aattaaattt catctttaaa cagttatttc tataatcacc agttgcccga ggcacagact 113760
ttcatagtta agacaatggc atttgtcaag caataaatga gtttatagaa ttttcaaggt 113820
ggaatttaaa tttcaggtat tatcaatata attcatatta tcaattatgg attttaaaaa 113880
aagatgtttt ctcattttaa attttgttca gtatatttat attgtatcat tgttctttcc 113940
attgagagag aaaacttaac tgtttattct tttagtaaca gaaaggatta tgagatttat 114000
tatgttttcc tcacagagct gatagtatat gggaaatctt ctattccctc cttgggaatt 114060
ttggcattac aataaaaatg taaagcatta ctaatttaaa gcatcttaaa tgtgtacatt 114120
tctcctaact agataaatac ctacaaaaat accacaataa atcccatgaa atttaacctt 114180
acttattata gtaaataaat acttttgcta tctataaact aaaagatcag attccacaaa 114240
agcaaaatat ttgctgtata atccagtgta cattaattat gaatttacaa atttatattt 114300
ggagtacatt tgtagcttaa aaattttgga tgtataatat ttgttagata tttttatagg 114360
cagttttgct ttgttaaatc attcttcctt tcctttaaaa taaaataatg attctattta 114420
atatttttga tggagtactg taggatattt ttatatttaa tccttgtgaa agaacatatg 114480
cttcctatac taggttatat attttgtggt atccttattc tttggaaaga ttaattagtt 114540
acaaaactta caaatagctg tactatcatc ttgatttcag aaagcaacat atttaatgta 114600
gtcactaagt attactatgg attttttcat tttaaatttt tgagaaaaat attctcaaat 114660
cattaaacct gcaaaagaac tatctaggct aaaaaaaatc ttctcagccc cactcatatt 114720
tgccagagct cattcctctc tcggctattc tcactttgat ctttggccct catttcatta 114780
acatcagagc ataagatcaa ttactagagc agataaattc ttactcccct aaaaacagag 114840
tttcataaaa agctactcaa gtgaattaga aacaagacat agatcttgta caatttacat 114900
taaagtcact gcttgtcttt cactgaggcc ctatgcataa aaattgatat ttattgttaa 114960
ggatattttg cattcatttt ttagacttca ccctttattc ttagcatttc ttctcgttaa 115020
tgatcacttt tgctttgtgt acattcattt cgatcacaaa catctcatgt cagaaattca 115080
actatagctc ttcagtaact ccaaatgtta atattttttt cttatttttt tctactgtgt 115140
catatctaaa ttctcagatg aaaaaccaat attgaagaat taccaggcca agtatataat 115200
gtgaagaata tagaacaact agaaaagaga agaaggttaa agtcataatt tatactgtaa 115260
agagaaacag gattatattt cttttgacat aagcatattt gagtatcaat taaaatgtat 115320
tatgtacaaa aattaggtaa tgtagtataa aatattaaat ctgttggcaa atgctaatta 115380
aattatggtt aaagaatagt tatttaactg aactcacata cttttccctg tctaaaattt 115440
caagattgtt gaggctggag aaacttcttt taaaaataat aaatagaagt accagagtac 115500
tcagcttatt gatgacaagt taaaataatc cacaagtaaa gaaaaaaggt tattatagaa 115560
aaagggcaaa tgagatgttt aactgtgtgt atttatttaa actatattta ttcatggatt 115620
actatatgtg aagcactgtg caagaatatg atttaccaga tttttccaat tttgatttat 115680
catatttacc tggtgatgct tgcaggttga tctgcatttt atgaaaaaga ttcctccagg 115740

-continued tgctgaagca tcgaacatct tagtgggaga actggagttc ttggatcgaa cagtagttgc 115800
gtttgtcagg ttgtctccag ctgtattgct tcaaggactg gctgaagtcc caatcccaac 115860
caggtaaaaa gtataaaagc gtcttttgta tttttcttaa accatctttt catggaaaga 115920
aaatgaggat tcaatgtaat tttctgttag agttttgact agaaactaat gtgaaatcca 115980
caaaactact attaattttt gtttgtggag gaggggaaaa gtgctttaaa aattattctc 116040
ttctttcctc ccttctctca aacttctgct tcattttagg cacattcctc atctcaaggt 116100
accctgaagc catatgaatc cttttttttt tttttttttt tacatttttg gtaaaagaag 116160
tggtaacatg ttagcttttt ctcaaagatt gcattaaatt gtctgctata gaaagaaagg 116220
atcctgtgca tgagtgcggt caaactcaaa aacagcaaag ttactaaggt ttgcttacac 116280
ttgaataaga aggccttcaa aatgcatgta agtgccatcg ttaggatagc gtcaaatata 116340
tgtttcaatc ctaggcacag tgggcttccg acacacaggg tctgtagaaa cactggtaga 116400
agtattatcg cagtgtggtt ggatgtgagt taaaggtaca aatttaattt gatgatcaga 116460
acttgtttct catttaacaa taaaataaca acttagggat aatacaaact gaattatgct 116520
tttctcattt tttagaataa ggctatccat tactaaaact gtaaaaaaaa gaaaaagata 116580
aaaaaaagaa aggaaacaca gaatattgac tttagcacat taatttccaa gcaatttacc 116640
caggaacctt gttttcttcc atacttctac catcagtgtg attccaaaat gcagatagcc 116700
ttttactcta gtcctattcc cacagcaaaa catgtatatt tagggccccg ttcccatatg 116760
gctggtgccc tttgtttgat gctacagcta tctcaaaagc tgttagtgcg cctcctcttc 116820
caaacattga ataccttagc caagttactt gatgaaaagt tcaggtactg tatcaactgt 116880
agaatatatg tcctctatga atctttggcc ttaactcaaa atatagcaga ttacataact 116940
ccatgctttg attatggata aaatattcta caactatgga acagcacagc caggagaggc 117000
ctcatttttt aagagctcag ctgactggaa cgggattcag tggttaagta cctatgtctg 117060
actatggttt gggggaggaa tctagttact gttcagatta tagaaagaag tctatgttta 117120
tcctgtttga gagttactga gatgactgat acacatcaac ttttatgtac aaagggaaag 117180
gatgaactga gcacattaaa gtggcatctg actgtgtgat tcaggctata tgttttctat 117240
ggacaacctg taacctattc aaggtttctg ggagtctggg atttatatct aagatgttaa 117300
acttgctaat ggtagagtta ctattatagc agtttaaaat ttcttttcag tcctccaagc 117360
agtgcatttg tgttccacca cttaggaagg tgtctggtga actatgagca aatgatggct 117420
atttacgaca atgatagtgc ttgtatttca aaagaaggaa aagaaaaatt cccatgagta 117480
gaaaaaagcc gtgatggggt tatataccct tactgtgaaa actgtcaggt ttaagtgacc 117540
ttatttcata ctgagatagc aaaatatgtg tagagaacaa cggagaaaaa aattagggcc 117600
actgtagagc aactgtatga gaaaagattt aaagacaaga ctatttagtt aggaaaggtg 117660
aaaaatggaa gattagttgg acaaacaaaa taaagaaagc cattcagggt ttcttattat 117720
cctttttttg ggaagacaaa aggcatccta ttaatacgat ggcaacacat agtagaaagg 117780
tcagaaaata atcttttaga tctttaaaaa tagcccatgg aatggaaacc tgaaaaatag 117840
caagatgtac ataggttagg aagtttctta aaaagctatt atagttgata aagcacctgc 117900
taccgaatta aaccattcct gtttttaatg tatactggac atttctacat agtagaaatt 117960
ggcttgggtt cagttgtcac tggcacacac aaaaaaatatt gtcatatcct ctacaattgt 118020
gtaatatttg cctcatgtaa aaacatgtac aatctctaaa gattacaact aaatgaggag 118080

-continued

```
tagaattata gtaactattt tagtacacct tgtgaagtca ttagtcttca tacttaacag 118140
cataaaccat ttaacaaatt aacaccacag aatgatatgg cagaatatag ggcattcttt 118200
aattttcaaa atttcccaga aggattgacc ttctcagaga cagggcaatt accagtctgc 118260
taaagttaga gtatctattg atttctttaa aagcaccact tgtgatgatg aatttgccaa 118320
atgttcgacc taatatagat ggaatattat agtgcagatg ctatttttat tcctcagcat 118380
tataaataat agatcattaa ctccccattt tcttctacgt ggctgatctt tgattcctga 118440
caataatttt ttataatgaa aattgcacat acacctactg ttttttgact ctatattttc 118500
tctgttttgc tactgtgtta cctttgtccc ctttgaacta ttcgccattt tgcatacaag 118560
tgagttttct tccttccaat ttagaaaggt ctaatcagat tttacttttc ccactttcct 118620
tctctaagga tcatagaatc cttaaaattc ccaataacaa ctgcacatgc tgtacagata 118680
actaaacgga gaaacactgt gataaaaaaa aaaaacacgg aaaaccatgc attcccattg 118740
cttgaggatc ttaagcataa gggtcaatca tggtaaaatt tttcaaaata ataatgaact 118800
atgaaaaact atggaagtat ttgccatcac aatctccatt ttcagtaatt cctttgagat 118860
gagtgattct gtattactaa aattattttt atatttctac cttaaaacat tttttttctt 118920
cttaattaca gatttttgtt cattcttctg ggacccctgg gaaagggtca acagtaccat 118980
gagattggca gatcaattgc aaccctaatg acagatgagg tatttattca agttctttgg 119040
gaacattttc ccccattagg tatacctaaa acttttggag gtcctctttt catgacagtt 119100
tgttgtgaat cagatttctc tgtattgaat cccattctcc catgcttctg ctataaaatc 119160
tcctttagaa aaatgtttcc caaagggata ataaattaac acccatgaat ataatatttt 119220
aaaacttcat agtgtaaaga aatttttca gtgacactta gaatatatta ttaatattcc 119280
ctttatggta tatgtgctac caaagtaagc accattgtta atatcaatgg aaatcttgtt 119340
ttgagtaaag aatttcgaag tctaaagaaa aaacaatagc agtttatctg aatagtatac 119400
atgacaccaa aatgcatgca acatctatca actctctaca gttgcctgaa tgtagatatt 119460
tttaacctgg gagtctgggg actattagag aagctgtaga tagatttcaa ggagcttgtg 119520
atttctgtaa cagagcatgt aaatttttct atgtaaaaaa tttgtatgta gattttttgg 119580
gactggaaaa agctttcatc agctcttcaa agaagtgtat gtctcaaaaa tataagatct 119640
ttaaagtaag aacataaaaa gtagcatcat accactattt tcctttactt gggttctcca 119700
acacattatg gaaatttgtt gttattgtta acgggaagag cagatgcagt agatcacaga 119760
aggggcatta aatcaaaatt cagttgtaaa tgaacaaatg ggattatata cttctagatt 119820
tcatctaaat aatttaataa tgtttttatt gaaatacatg gctgcagata tttgaaaatt 119880
ctgtaaaaag agccaattag tattgtatat tactttttct atgtttacaa tagctaaaat 119940
ttgaacttgt tttggggggtt aaatattata aattcttcaa tctgtccaaa ttatgtttta 120000
tagtgttata tgaattagtt tttgatattt atgcacaaga aagcaaaagc aagaagaaaa 120060
acattttttc cctcagtttt caaaaggaac caacttaatg agtgtattag tttacaacga 120120
ctgccataag aaactactac aaattgggtg gtttaaaatg acagtagttt gttttctaac 120180
atttttgagg ctagaagttt gaagtcaagg tgtcagcagg gccacaatcc cttcgaagtc 120240
tctaggggag gatccttcct tgtctcttcc atattctggt ggctcttggt cttccctggc 120300
ttgtggcaat agacctttgt tctctgtctc catcttcaca tggctttctc ccagttgtct 120360
ctgtgtgtct tcttattttc tgttatgaag acagacattt gtcatttgat ttagggccca 120420
tcctaaatcc atccaaatca ttggatttag ggcccatcct aattcaggat aatttcatct 120480
```

-continued tgagatactt accttaatta catctgcaaa aatccttatt tcaaataagg ccacattctg 120540
cggctccagg ttgatgtgta ttttgggagg aaattattca atccactgta atgaataact 120600
tattctattt aggaaatttg tgagaagaca ggaggatgaa aaaaataact taatgagggc 120660
catacacctg atttagcaga actctctctg agaaaacact cacagtataa aagctcttag 120720
tatttctata ttgatttgta ttgttattct atgatttaag tattatcact ttcacataca 120780
tttgtttaat attttgttat atttcagaca aaaaatgttt ccccatctaa gaaattaggg 120840
caatatttta agatatctgt ggggcatgag acacgtgata atgtgagagg atcctactat 120900
gtcatgggaa gtacatgtat atcaatgtat ctctcttctc ttcatcctct acttccccaa 120960
ttgggaatca agatttttct cgacagaaag atgtcagttc caaagttttc ttgactaacc 121020
aagtggacac agaacaggga aacatccatg ttctataaat ttcagattta ggatgagaac 121080
agagaagggg cttccaccta tttctttgat tagtgagagc tacctaattt gagaataagc 121140
atcaatcaca taataaagac tgaaatttga gcataagcat cagtcatcta tttttttcaat 121200
tatttagact tgaaagtttc agagcatggc tttaggtaat cattgtagat tatgggatag 121260
agaagcagaa actcaaccag aaagctactc taaaagataa gagccattag ttataatagg 121320
acatgttaat tacaacagga cattgattga atatcaaaga atgtttaaat attttttaaa 121380
agagaaaaca gatttgtatt tctcaaagcc tcggtgaggc aattgttctg cttatctaat 121440
tgctttgaag gctattgaat aattgtacta ggccaggtgt aatggcttac atctgtaatc 121500
ccagcacttt gggaggccaa ggtggatgga tcacctgaag tcaggagttc gagatcagcc 121560
tggccaacat ggtgaaacct cgtctctact aaaaatacaa aaattagctg ggtgtggtgg 121620
caggtgcctg tggtcccagc tacttgagag gctgagaggg gagaatcact tgaacctggg 121680
aagtggagat ggcaatgagc caagattgca tcactgcact ccagcctggg tgatggagcg 121740
agactctgtc tcaaaaataa ataaatagat aaataaataa gaaagaaaaa gaaaaaagaa 121800
aagaacaatt gtactcatta agaatagaat ttaatatgtt gattcatagt ttactttggt 121860
taaaaaaaat agtgcattgg agtgcattat caaacataaa ttccatgaga acagttagca 121920
ttttagcatt cagtattcgt ttttatgacc tgattcttcc aagtgctcaa ataaatatcc 121980
attgagctaa gttctgtttt ctttcccttc tctgtacttg gaacactttc taggtagact 122040
gtcttccttt tgtattttta gacttattat gagtgtctga ccctcagtca gggttcaata 122100
aatctttaga acatgaatca attactgaat attctagaca tcataccaat attctatctt 122160
gaatcaagcc aataatttat tttcttcatt tctgttgagc tttgctagag ataaatcata 122220
tgattatgct tatcaacact gctaccaatg tgttgatccc ttcacattct caaaaattac 122280
taagcacccc aaagaacttt tgtgtatgta gatatgttgg tatttaccat aggagaactt 122340
aaaactgaga aatttaaaaa gtatgtgtta atgaattcat ttaaaaataa taatagaacg 122400
ggttcagtgg ctcacacctg taatcccaga actttcagag cctaaggcga gtggatcact 122460
tgatgtcaca agtttgagac cagcctgggc agcatggtga agccctgtct ctaccaaaaa 122520
attcaaaaaa atttagctgc atataatccc agctgctcag ctacttggga gggtgaggtg 122580
ggcggatcac ttgagccagg gaggtggagg ttgcagtgag ctgagatggc accactgcac 122640
tccagcctgg gcaatagagc cagaccttgt ctcaaaataa atacataaat aacaatagta 122700
aagccattac atattaacat aaataataca ttttaatgaa aacaaannnn nnnnnnnnnn 122760
nnnnnnnnnn nnnnnnnnnn nnnnnnnnnn nnnnnnagtt tgtattgagt atcaaaccag 122820

-continued

```
aaatggaaac aaatggtcta aaagtaaaat agaatatttg aaagcagaat tttcctggca 122880
attttgggac atttggtcac tgtaatttag gccagcataa agaataatat aggagtcctt 122940
aatctcaaat acttgtatca tttcatccca agtaaaattt aaagtgtcag aaatatttat 123000
attatattca gtgtaaatta attttttctc ttcatcctta tttttatttt ccccacttac 123060
tatattaagt acgtaattcc tgagtatgat aagataaatt aggttatgct gcaggaataa 123120
ccaactaaaa tattaatggc ttaaaacaat aaggatttat ttctatcatg ctaaactttc 123180
atcaagatgt aggagagagg ctctgctcat tataatcact taggccccct gtgcttatag 123240
aagctctagc tggacctgtg ttttctcagt cactaaacca gaaaaaaagc aatgtgataa 123300
gtcacacatt ggtactcata acttccattc aaaactgaca tatgtacacc caagtagaat 123360
atacctgatc caaatagcaa agaaggcaaa gaagtacaat cttaccatgt ggtctagaag 123420
aaaacctgga atatctgtga acagcctaaa tggctaacat agcacatgtg tgcggagggg 123480
aggtggaagg gacaagtatg aaatgtaact catactttga gtggaaatga actttctgca 123540
ctgtgtagat ataatatata gttggccctc tgtatcttca ggttctgcac ccttgaactt 123600
aactaactgc aaatcaaaaa tatttgaaaa gtcagggtgc agtagctcac acctataatc 123660
ccagcacttt gggaggccaa ggtggaggat ggtttggggc caggagttca agaccagccc 123720
aggcaacata gcaagactct gtctctacaa gaaatttttt aaaaattagc caggttttgt 123780
ggtacacacc tgtagtccca gctacttgga agacaggagc ttaagcagga gcttaagcct 123840
aggagttcaa ggctgcagtg aggtatgact gtgccactgc attccagcct gcatgacaga 123900
gtgagaccct gcctctaaaa acaaaaatca aaaatattcg aggggggggac aataaaaaat 123960
aacaatgtta caataaaaat aatatgcata aaaattatac agtataataa atatatagca 124020
tatacattgt atagatatta taataatcta gaaatgattt aaagtacaga tgctcctcaa 124080
ctttcaatgg gggattatgt ccccccattg aaaatatcat aagtggaaac tatgtttttg 124140
acttatgata ttttcaactt atgataggtt tatccagact taaccccact gaaagttgag 124200
gagcctactc aatgcatgtc acttttgcac catcataaag tcaaaagatt gtaagagaaa 124260
ccatagaaag taggggatcc tctaaatata ggagtatatg cataggttat gtgcaaatac 124320
cactccattt tatgtaagga actcaagtat ccatagattt tggtatctgc agggaatcct 124380
ggaaccaatc cctcaaagat actgaggaat gactatatat ccagaaaata ctaacataac 124440
cttagtatta ttttcaaaat ggaaacaaaa ttaacctttt aaattaattt atttatgcca 124500
gggtataaat actgctgaaa tttccaacac attttacaaa tttttatttc tatttgtaag 124560
caaaggcttc ctccagaaac tgattttccc atacataaat aactttttgcc taattctagt 124620
ttaatgagct tcctttcatc ctcctttttc tttcccttac tccttccctc tagaaatttc 124680
aacattcatc tgacatcata agacaaatag ttacctatat ggatccataa aataaattat 124740
aatattttac aacataaact tctttagagt cagagctgtc tatttcttca aattgttata 124800
atcacatgtg agataactga gttgaaaaca ctgaacacat taatatttta taattatttt 124860
taagctataa ataatatttc tatttcttct aaaggtattt catgatgttg cctataaagc 124920
taaagatcgt aatgacttgg tatcaggaat tgatgagttt ctggatcagg ttactgttct 124980
ccctcctgga gaatgggatc caagcattcg aatagagcct cccaaaaatg ttccttccca 125040
ggtatgtata tttgaagaca ttctttgaaa ttgaattttt ttttgtcttt taaatgcatg 125100
ttttatttta ttttatttat ttatttattt attttattat tattatactt taagttttag 125160
ggtacatgtg cacaatgtgc cggctagtta catatgtata catgtgccat gctggtgtgc 125220
```

-continued

```
tgcacccatt aactcgtcat ttagcattag gtatatctcc taatgctatc cctcccccct 125280
ccccccactc cacaacagtc cccagagtgt gatgttcccc ttcctgtgtc catgtgttct 125340
cattgttcaa ttcctatcta tgagtgagaa catgtggtgt ttggtttttt gcccttgcga 125400
tagtttactg agaatgatga tttccaattt catccatgtc cctacaaagg atgtgaactc 125460
atcattttta tggctgcata gtattccatg gtgtatatgt gccccatttt cttaatccag 125520
tctatcattg ttggacattt gggttggttc caagtctttg ctattgtgaa tagtgccgca 125580
ataaacatac atgtgcatgt gtctttatgg cagcatgatt tatagtcctt tgggtatata 125640
cccagtaatg ggatggctgg gtcaaatggt atttctagtt ctagatccct gaggaatcgc 125700
cacactgact tccacaaggg ttgaactagt ttacagtccc accaacactg taaaagtgtt 125760
cctatttctg cacatcctct ccagcacctg ttgtttcctg actttttaat gatcaccatt 125820
ctaactggtg tgagatggta tctcactgtg tttttgattt gcatttctct gatgaccagt 125880
gatgatgagc attttttcat gtgtcttttg gctgcataaa tgtcttcttt taagaagtgt 125940
ctgttcatat cctttgccca ctttttgatg gggttgtttg ttttttttctt gtaaatttgt 126000
ttgagttcat tgtaggttct ggatattagc cctttgtcag atgagtaggt tgtgaaaatt 126060
ttcttccatt ttgtaggttg cctgttcact ctgatggtag tttcttttgc tgtgcagaag 126120
ctctttagtt taattagatc ccatttgtca attttggctt ttgttgccat tgcttttggt 126180
gttttagaca tgaagtcctt gcccatgcct atgtcctgaa tggtaatgcc taggttttct 126240
tctagggttt ttatggtttt aggtctaaca tttaagtctt taatccatct tgaattaatt 126300
tttgcctgag gtgtaaggaa gggatccact ttcagctttc tacatatggc tagccagttt 126360
tcccagcacc atttattaaa tagggaatcc tttccccatt gcttgttttt gtcaggtttg 126420
tcaaagatca gatagttgta gatatgcagc gttatttctg agggctctgt tctgttccat 126480
tgatctatat ctctgttttg gtaccagtac catgctgttt tggttactgt agccttgtag 126540
tatagtttga agtcaggtag tgtgatgcct ccagctttgt tcttttggct taggattgac 126600
ttggtgatgc aggctctttt ttagttccat atgaacttta aagtagtttt tttccaattc 126660
tgtgaagaaa gtcactggta gcttgatggg gctggcattg aatctataaa ttaccttggg 126720
cagtatggcc attttcacga tattgattct tcctatccat gagagaataa aatacctagg 126780
aatccaactt acaagggacg tgaaggacct cttcaaggag aactacaaac cactgctcaa 126840
tgaaataaaa gaggatacaa acaaatggaa gaacattcca tgctcataaa tgcatgtttt 126900
acaatagcat aacccatcaa gaagattcaa atgatttaaa ggatagcctc taaggcagaa 126960
ggggcatgaa gttacaagat ctttcttagt actacctaac acacattact gagaaacttg 127020
gcagtttgat gacaacctac taatcaaaca gtgccatatg cctggaaaga ttttagcccc 127080
tacttaaaac atattatcca agaggaatat taaaatttta ataacaacat taaatatggc 127140
ctaagagaaa gcgcattact gtccttgtat gttttgatac atcactttga aattggcaag 127200
cattaggaaa attcaaagac atgacttaat catattatat agaaaactcc atatttatta 127260
ctgctaatca caggaaatat tgggaagatt ttaaaattat aattcttata tttgtattgc 127320
ttttttgtga atgtatgata taaagatttt ttaaattttg tttatgaaca tctaatgtat 127380
attttaccca tcatacaatc cagaaagata gaaatataaa gcattgctat tttttagggt 127440
catttttaa attgcaggca tgagtattaa gagtgatgac caaatatttg ttaagctcac 127500
tcctcatact gccacctcta tgcctactga atctgcctcc cacaaccctc ccaaattgtt 127560
```

-continued

```
gtgtacttag tcttgccttt gcgccttgcc ctgtggagtt cagccttgcc tgactctgct 127620
accctattgg aagcggcaga tggtctaatt gacccagccc tggaattaga aattttcctg 127680
ctttgccaga ggtgggcaaa tgagcagttg taccactcaa ccatgagtac ttaaaaaggg 127740
tatctcaatt tcactgtcaa tttaaagaaa ctatatggat acctcatttt tatattttca 127800
ttttgaaatc atttcataat tattaaagac tatttccttt tctcaaaact taccattttg 127860
tgattatgta actgctacca catatttcag ttgatctact attaaaataa aaagttgcct 127920
aataattaat tgtagggttt atagattgtc tcatttctgt acttgtagaa tacatctttg 127980
tactaatgat attagaaaag gcaatataat gcttcctgag tatgtagaaa ctctttaatt 128040
aatgttattt ggagaaatgc agcaaaatat taatacattc agaatgaggc tttaaaattc 128100
actgtaatac ccattagcta ttgaaacatt gaagttaagt gtttttgaaa acacctttgt 128160
gaacaataat gtttttgagg caagttgagt gatgggaggc caatattgtt tatgatttta 128220
tgacaccctt taaaatcgaa ttaattattg gattctgggt attgagaggc agtcatagaa 128280
agaacatcaa attaagaatc aaagcatccg agttctgcaa ttatctatat gtatgacctt 128340
gaacaaatgt tttaacctct ctgttgatgt tctgtatcag cactgtccaa cagagttttc 128400
tgcaataatg gaaatattct acgtctatgc tatccagtaa tcaagccact agtaagcatt 128460
agaaatgttg ccattgtaac taaagatcag aatttttcat tttaattacc ttaaatgtaa 128520
atagacatat gtagtttgtg gctatcatat tagacagcat agttctatac aacaaatttg 128580
aaattacaga tatgctctat gcttcttttc aacattcatg ttttaaaaat atatgttgta 128640
attgaataat agatagcatg aggctatgtt ttctattaga cggagtgaaa tgagttaata 128700
tacattaaac attctgacct catactcttt caaatttttt caccattggg atcatttcca 128760
tctttttat tcatttgaaa tgtgcaaatc ccagcatttt aaatattttt tccctttcag 128820
ttaagagaag aataacctgt cacctccagg gataaccctg aaaatgttca ttagaacttt 128880
gcatcagtca ttaaaatcac tccctttgt gtaccctcaa cttatttgct cttctctcat 128940
gtcgtgtact tgcttggcaa aaccacaacc ctgtgagaat ccaacacttt actctgtacc 129000
gcactgatga actgaagctg aaggaaaaca tgtaaccaca ctaactggtc tcacataaat 129060
tcatgaccac atacctcaag tgagcccttt gtgttgcagg ttcatcatac tacactttcc 129120
tagtccaatc attctcactt gatgactatt tcacacttat tcttctctcc tcaagccttc 129180
agcacatcct ttctgaccct cactctcata tgctgatgtg ccttttattt ccctaagaaa 129240
tttgaaacaa tcaaaaaaga acttctatag attgctacat gcatccacat actctgcctt 129300
cctgttcatt actattgatg aaatagccaa agtcagcctt ctacttgtgc actagaaaga 129360
acctatctct tcacatctac tcaagagcac aactctacca attctcctct ttctcttcta 129420
tatcatcaaa tcttttttc tgtattttat cacttttatt agcatacaat actattaaat 129480
ttaccaatct taaataaaag aactctcttg ataccactac ccagcctgcc actcttattc 129540
attccctttt ataacaaaat gccacagaag agttctctgt gctacttgtc tccagttact 129600
ctcctccaat tctcttttaa cattcactcc aagaggcttt tgcccctacc atttcactaa 129660
aatacatacg agaacaatga tctccaccat gctaagtccc atggtcaatt ctcagcctgc 129720
attttatcta atctatcaat gaacagcatt taagagttga tgactccctt ttccttaata 129780
tatgttcttt acttggctcc caaaacatca ccttctgtta gttttgtcat tataaaatag 129840
agttaattta tctagtcagt agtattttcc cagaagacca cataataatg cttgctttct 129900
gagacctgtg aaagctatga attgttttcc taggtgattg ggaagtaggt attgagggaa 129960
```

-continued actcttaaat ccctttatta atgtatccta tttacctgta aagacagttc cttcatcagt 130020
tgacagatgc ttctctttta tctttgaact ttagtcttac tgcgtccatc catttgcctg 130080
ggaaaattgt taaaatatta agcaataaac tttcttatat tgagcatttt tcaaaacctt 130140
ttttatgttt taaacctgta tcattctatc taaatgtctc atggtaagtg agatcagttt 130200
ataagtcact tttgtttttc atgtttacac taattctatt ttggaatggt ggtcaagtaa 130260
aaatcataat ttcaccactt aagatttttc ctattatcct ttgaagtgct tttgaacaca 130320
ttggtgtgct ctaagatcac cataggtagg attttaggta gaactttctg attttttaag 130380
aaatcatatt caccaacaaa agcaggtgga atagaccatg ggaaaacaat acttacctga 130440
atctctacta atttgtcatt ggttaaatta gaagcctcct tttacaacag tctttggcac 130500
tctatgagtt agaaagacct atattgtaaa ctatttactg ggtagaaaaa caccagctgg 130560
aattacacag agaaatatac tttaaaaata gtgatgatgg ttactgttct ttgaacagtt 130620
aaactatgcc acgcatataa caccaccata cttaacacct cctcacgcca acctacccac 130680
atcctgatct ctctctttgc cccttccctt acttcatttt tcttcatagc tcccatctgt 130740
acctgatatt ataaggttat tgtctcttca ctaacagaat gctttttctt gcccaccttt 130800
gcagctctag cattcattac aatgaatggc atacactagg cactcagttt tagttgaaag 130860
aataaataag tgcccatcac ctcatttaat tctcttagtc acactataag atagatactg 130920
ttgttacccc cagtaaacaa aggaagaaac taacacttta aaaggctaaa taacttcctg 130980
gaggtcaagc aacaagtaag tacagagcct gggttctcag ctattgtgca tattgcttca 131040
aggaaaaatg aactgttatt attatttaca attaacacct gaaattaaaa caaaacaaaa 131100
cacatgaaca aaaaactctc cacaggagaa gaggaagatt cctgctgtac caaatggaac 131160
agcagctcat ggggaagcag agccccacgg aggacatagt ggacctgaac tccagcgaac 131220
tggaaggtta gtgaaaatca cttctatggg acttcaagga ccaaatgaca taccattctt 131280
ctctgtcaga aattgctatt ttgggatcta atttattgta tacttttaat acctgctttt 131340
tgagggtgaa aatgccaatt agtttgattt ctctgaagtt actaatgatt gtcattactg 131400
ttaaactaaa acagtggata caccccttcca ttatacttta cctagtcttt cattttgctg 131460
tgcataaaat gcattctcag attcttagaa tgaaaaggaa aaccgtcaat tgacccttcc 131520
aaaagaaccc attgaaagct tcaagttgaa gatagaaata aaactaaata ccaacaactc 131580
agtcttgtag gccctatctc attaaatgca agtaggatgt atatagtggt attttttatt 131640
tttatggctg tgatttgaaa gagctatatg atttattttt ctaatcacac atctttgaag 131700
agatgaaagc ttcaatttat ttcttaaaat ggtgcttcat ggttttttttg acagcttgtc 131760 tctctctaag caatgtgtga gcagaaaatc agaaaccctt gggtgggtct ctcttcaggg 131820
aatatgtgta tagcctccat tataattaaa ggcagttgca aaggctttgc aggattggtg 131880
ctcccctccc ctcaaggcca ttttctgtac tgcttgcaat gtgtcctcta agctgacttt 131940
ccagttcctg agcactctgc attttaattc tgtgttcttt ccctttatct atgtgttgtc 132000
tctgaggaaa tgtcctttaa tgtcttcctc aggcttgata cctaatttga gatggttcaa 132060
acaatttttt ccttttccct tcactggaag ctttgttact cattctgttt gctttcatac 132120
tttcaaatgc tgtcttttta tttttggtgg tattttttttt ctctttctca ggtgtaacat 132180
gccacatagc ttagattttt ttcgaagttc acttttcctt actgcttcct aaatcctccc 132240
aggtcaccaa tatccggtat cttcgcttct ccagagttct tccacagatt ctgttgctga 132300

-continued catgacttga agtatccatt actcatctgc tctcctggag ttgctggtgt acatctgggc 132360
tgctcttgca ctgttctctg taatgaactc ccacttccgg atttagattt ttactgctaa 132420
aagcacattt attacacagt actataacaa ctattcagac taatgtatgc tctaataagt 132480
aattgattag aatcaatggt ctaatataaa gtgctttcaa aactataaat attaattact 132540
aattaatagc tcataaccac ctcaaattct ttttgggatt aggtgggata taaatcataa 132600
atgaatgcct aaatagactg gtagagtaaa tctgttttga attgtgactt tgataagtta 132660
acaaattatt cagaaatgat ccctaaaata aaaaaaagtg catatgtttt accaaacatg 132720
ggtagagaag cctaaggtga tctttatgtg tacaaatatt tcacaggttc tctgcaagct 132780
tctctgagtt tcaaatgtcc ttttattcaa ttgaagtttc attcttctca accctctcct 132840
actccatagc tctctaatgg aagcaatcac aggaaaatat agtgatctta tacctgcata 132900
atagtagaag agttattaat aggtaactat tacagataaa tcagatcagg gaaattactt 132960
ggtaaaatat tttaattatt cataatatgt acatctttta tttcaaattc taaggagaat 133020
ttatttctaa aaaggacagt cctttctgag atgattctag gactgccaaa tgaatattcc 133080
tatgcataaa ataaataaga aaaatgaaac agttttttat gatccaagta tactcagcat 133140
gctggcagta tattggagca taataagatt tttcaccact gacattaacc ttcatgtagg 133200
aacttattca tagtcttatt catttttgct atcacatcat tattccatgg agcaaaactt 133260
acagtagcca aatgttaagt ctgcgtattg ttattaaatg ttcataaaat gagaatacct 133320
acttattaat gctctcattt cttatagatt taaaaaaaga tctcaaattt caagcataat 133380
ttcacagttt aatactttc ccccaaaata attatctttc aagtgtttca acatggtttt 133440
gaatatattt ggagtaaatg aatttatacc aagtaaggtc actattgtct tgtgaatcac 133500
agatgctggg atatgttaac gcaatagtgg atcaaaatta catttatcta gttttattat 133560
tataaggact ccctcctagt tttctaaaaa tgaaaacagc tctgaaacct atctgtctct 133620
actaagtatt gctgccatcc aaaaggacat ttagatgtct tcctgcaaca atatctggtg 133680
agggattttt gtttgtttgt tttttggccg agagagtagg taactggagc catggttaaa 133740
cattgctttt tctctctagg gtgatgctca ctactggagt atacaaaagc cagctaaccc 133800
tccctccctc acttcctgct atgctaaatg gaattaaaca tttagaaata ctgccaatga 133860
ttgagggttg taggcctgag tttaggagga gtaggttgac gtagaaatgg cacagagatt 133920
agagtaatcc ttgaatctca ttatttggat tatgattggt aaacagctct gaaccttgtt 133980
taagagaacc tgggattttt ggtggttgac acgatattgg gttaggaatt gaggtaacga 134040
acgtagttgt gcagtgcctc cctgtagatt gttataagac aatgcagcag gttaatgtgt 134100
gtctcacctc tgctgatgga aaacgtatac tgtgacctgg caacaaagca aatgagcatt 134160
ttgacttgtg tgttttttat atttgggttt cactattgtg ttttcccccc tgtcttagga 134220
tttttggggg acttatttta gatatcaaaa gaaaagctcc atacttctgg agtgacttca 134280
gagatgcttt cagcctgcag tgcttagcat cttttctatt tctctactgc gcgtgtatgt 134340
ctcctgtcat cacgtttgga ggactgctgg gagaagcaac tgaagggcgt atagtatgta 134400
ttatgctttt ctctgaactt tgaaacataa tccattttta agattcatag ttagataagt 134460
gagcatttaa ttttggattc ttttctgagg agagatttga gatatggtct ggcagataca 134520
ccttatatga atttcctgga tggctagtgg aactggtaat ctgggagtgg aatgtctcag 134580
aataactagt tctgagtctt acaaaaggtt ctcatctgat gccttgccct cagcgccccc 134640
aatcctaagc taggtttagt ctccattctt gtctcacaag aggtccattt gctatgtacc 134700

-continued

```
cgggccatgt ttctgtccag acactaatcc tgaatacatt taaacctttt gtaaggcaac 134760
agagacgtga gataggaaag tgaagagaac actcctacct ttgctactat gcattttctt 134820
cttgctgtca gcccctttag tcatccttct accccacgtc ttgcccaggg ttgctagact 134880
tttcagggtg aagcacaaag cacatatcca tgtattttaa atgtcttctc cttagctaca 134940
atggcctcct gtacagctta ggtaattgaa ccatttatat ctctacacag agtgcaattg 135000
aatctctctt tggagcatcc atgaccggga tagcctattc tctctttggt ggacagcctc 135060
ttaccatatt aggcagtaca ggaccagttt tggtgtttga aaagattttg tttaaatttt 135120
gcaagtaagt gttatgtact ttttggccct tagcctcttc cttttttctt tactgtattt 135180
atacttctcc caacatcact tttggaggtc tgttgataga gacagaattg cctgatttgt 135240
ttcagtttat catttttgct tcatcatggg aatagaggaa aagtaaaata tttatgtata 135300
tttttatgta atatttttaa aaagtaagac tcagttataa gcatcgataa atccctttttg 135360
attttgtccc tttagatgtt ccctttagac cggtggtctg caaccatttt ggcaccaggg 135420
actggtttca tggaagacaa tttttccaca aagagggttg aggggatggt tttggaatga 135480
aactgttcac ctcagatcat caggcattag attctcataa ggagcacaca atctagattc 135540
ctcacatgca cagttcacaa tagggcttgt gctcctatga gaatctaacg tccccactga 135600
tctgacaaga gtctgagctc aggcggtaat gctcactcgc ctgccactca cctcctgctg 135660
tgcaaccctt ttcataacag gccatggacc aggggttggg gacccctgct ttagacagtc 135720
ttgagtttag atactcatgg gatgtgaagc ttatttactt tcacttcctg aatgaggttt 135780
attttcattt gcttaaaatg atagcaagct gttaaatgac cttcttttca ctgttctttc 135840
cttttcctcc tcccagagaa tatgggctgt catacctatc tttaagagct agcattggac 135900
tttggactgc aactctatgt atcatacttg tggccacaga tgctagttcc cttgtctgct 135960
acatcactcg gtttactgaa gaagcttttg cttccctgat ttgcatcatt ttcatttatg 136020
aggccctgga gaagttgttt gaactcagtg aagcatatcc aatcaacatg cataatgatc 136080
tggaactgct gacacaatac tcgtaagtac catttcccct gctggccttg gggcttttct 136140
tttgacaaat attgctattg ttacaagaaa tatgaggaaa ttactcagca gagaatgtgc 136200
cttaagttga ttcatgacct aaatcctgac tctcagagtc gaacaggatt ttaaaagtta 136260
tttaatcggc cactcatctg ctacttgcat tctcattata ccatctctgc caagagtatc 136320
tttttaaagt tctatttgtc cagtgttctc taaaataagt agataaggaa ccaattccat 136380
tttaatatac acgaatttta ccttagcgaa atatatgtta tttggcgtta tttcagggtc 136440
tttttaattt acaataatcc aaagaaacat agtaatgaaa atataagatt tcaaatttag 136500
agcaataagg taaaataaac ttattgggtc taaatcttag tagatgtttg aaagtgtggt 136560
aaaaacataa atcactgaat gaaaatttaa ttttggtttt ggcacttgtg acattttgat 136620
ggaaatactc agatattagt tgttgaagtt gatgttacag tccgggattg aagatgtgat 136680
tggatctatt gctttttcta gttttggtgt atcaacagtc tgaaatgtct ctaaggcttt 136740
gtctgcagac tatatgtggc cattaaatga ccccattatt taattgtaga atttttttatt 136800
gtgcttatat gcagtttttt atactgcaaa tatctgaagc aatatgttct ttaggagaca 136860
gttataatct ctgcatcaac caccaatcat ttccctataa actgcttaga tatggccttg 136920
aacccttttta atattttttta atctttattt actatcagaa gtttaaattg ttgaaatcag 136980
accaaaatag tgcaatgtta taattttgtt aagaatgacg aaatgttggg aggccgaggc 137040
```

-continued

```
gggcggatca cgaggtcagg agatcgagac catcctggct aacacagtga aaccccgtct 137100
ctactaaaaa acacaaaaaa attagccagg cgtggtggcg ggcgcctgta gtcccagcta 137160
cgcgggaggc tgaggcagga gaatggcgtg aacccgggag gcggagcttg cagtgagctg 137220
agatcgcgcc actgcactcc agcctgggcg acagagcgag actccgtctc aaaaaaaaaa 137280
aaaaaaaaaa aaaaaagaat cacgaaatga tattatgttg aaaataatgt gagttttagt 137340
actttcactt ttatattata tttagagata actttaaaca actgacccct atttttgaac 137400
aagaaaaatc aaagtggaaa tataaaataa ttttcccatt aaaagcaaat agtgagaata 137460
ttgtaaacag ggctaagaaa ggactgagca taggtgtcag ggacactcag aaaacaggca 137520
aatgggaaga acagtttgat caaaaccagg gataacattg atacacgcct tttcatttat 137580
ccttacctga aagagaatct cactgaattt ggatatcctt gctgggatat gtaattatct 137640
ctggttggat tttcaaatct actacatgcc aggcactata ctaggtgcta ggaaaaccat 137700
ggtgaatcat attctgtcct cagtgagctt ccagtttagt agggaatgta gataaacaga 137760
cagcataagg aaatgagtgc cgggttaaga ggttggtaca gaatgctata gcagcacatc 137820
aggagagcac ctaacccaga tttgaggttc agagaaggct tcctggagga aataatgtag 137880
aataaaaatg cagtagaagt taggaaggtg ctaaggaata gggcagaaaa gtagttcagt 137940
caaagggcat tcacaggact agatgcaaga gatgcattca tgctttaaaa tatttgtctg 138000
aagttatata gatagtggta aaacaagaaa tggaatccag gttttattac tgatataatt 138060
ttcagtacac tgatgaatac agataaactc tccaaaagaa actatgtaaa acaaataaaa 138120
caggtaaaat cagaactatt ctgtttcaag tggtaggaag gcacccattg cctaccctct 138180
cagctgttct ttgaaccttc atggtagctt cttaggtact tcagactgag gaacatagtt 138240
taaagtccct tggtctagaa aggaaaaaga ttggaaaagc aaggtctgag ccctgaacaa 138300
ttttcacagc tctaaagtag aatgagaaaa atgcaaccaa taggcaaaaa ataaataaat 138360
aaaaataaga aagaagcatc agaaaaagag gaaactatgg ataatgtcag gtcgcagaag 138420
gcaagaaaca agaaatgtat cacaaagtct ttagagagga cagtggcatg gacatcaaac 138480
agaataagga aaagtgtttg aaaagagata cctggtagct ttaaaaaatt ctcagcaaac 138540
tattgcaagg acaaaaaacc aaacaccgca tgttctcatt cataggtggg aactgaacaa 138600
tgagaacaca tggacacagg aaggggaaca tcacacactg gggactgttg tggggtgggg 138660
ggaggggga gggatagcat taggagatat acctaatgct aaatgacgag ttgatgggtg 138720
cagcacacca acatggcaca tgtatacata tgtaacaaac ctgcacgttg tgcacatgta 138780
ccctaaaact taaagtataa taataataaa attaaaaaaa aaaaacaact ggtattgggt 138840
tgggaaagga ggcagaatgg gaagccagtt tgcaaaaact aacaaggaag tgggtggtaa 138900
agaaatggag aaagctgcat aggccagttg gtgtcaaaga aagtgggaaa cagaatgcct 138960
tttgaggagg gcaatgaaat cgtaagattg ataatttgtg acagagaagg actatgtgtg 139020
tttgaaaatg ggagaataga gactggggag aggaaggcag caatgatgaa aagagtcgat 139080
aaacgtggga ttgcaacctc ccaggagtca caaaatagta aactcaagag aataagtcaa 139140
acaaatgctc aaaaggtaat ttaacaacaa gaatagcttt aaataaacgt gaacccaaac 139200
tgacatgaaa atagcaggaa aatgacgaaa aaaaaaaatt cgccaaaaaa gacagtgaca 139260
caaacagtgc acacaacaca caagagcgag aagagcagaa tggaggagga caagacaagg 139320
ccggtgctca gtgagagacg caccgtatga cacctagcag aggaagcgaa gagggtagaa 139380
gtgctgannn nnnnnnnnnn nnnnnnnnnn nnnnnnnnnn nnnnnnnnnn nnnnnnnnnn 139440
```

-continued nnnnnnnnnn nnnnnnnnnn nntctgaggc atggctgtga caccctcttt gggctctgca 139500
gttcctggtg tctccaagct tctggtgcca ccacgttccc cagagcctgc agtgtaagtg 139560
gcttgcagta tgcctggtcc agccacagcc ttgcacagag ctggttcctg tgccagtgtc 139620
tggaactgcc tgccccacca cagcagccag catgcctgac tgtgcacagt ggccagacca 139680
tatgcttgct cacttatgca cccctcacct ctgtgccttt ggcagcgctg ggatccaggc 139740
tggtagcacg agctgagcac aacctgccag gcctagtggg cagaatgagc cagagggccc 139800
aagcaaaact caggcaaagg caccactggc cacaaaggct tctggctgga agaatgacac 139860
cccggggacc tcatgacagt aataacttgg cttaaaaggc tgggataggg atctatgaca 139920
ttaacccaat tagtggcctt gggtaagtcc ctaagaacaa cctctagaga caatgtctta 139980
actcaagaaa aaaaaagtag gaagaatatg gaaaatacat agggaataag aagtctggaa 140040
gtattgtatt aataccaaac ttatagtact taaaggacaa aataaagggt tgcaaaagag 140100
ttcaccttgt tggtgaagga aaccttgtac tttttattct ctgcatattt tgaattgttc 140160
aacttgcact gtatgcctgc attattttgt aatttctttc taaagatgaa ttttgtgttg 140220
ggaaattcaa gtcctgtgac aaaccatagt atgagctaat ctgggggagg tggtgctctt 140280
caaattagtt tccatgtaac aaaatttatt ttcaaattca ggaaaagagc aacctacaaa 140340
actcaggagt aaaatgggca aaatgttcaa ggaataataa gtaggtttac tgttctgttc 140400
atacatgtgc ttactcattc actcacttag ctcattcctt caacatccat tgatcttcct 140460
tgtgtatgtc agtgctgatg gtataaaatg aatacaatat ggtccctact ctgaaagacc 140520
ttagtgatta tcagacagtg tctggagatg tcctttggac atgatatcca ctcaaatagt 140580
atttgttgaa ttaataaatg aggagagagg ctagaggata cacagttaaa taattgcaat 140640
gtgatataac aagcactata caaggtgtct gtataatggc ctaagagaag aagtaacaga 140700
gtgccctgga gagctcagaa gcattcatag aaaaaggaaa cctgaactta tctctccatt 140760
tctgttgtac ctgccacatg agtttattgt atgtggcata cctatgtttc tttctctctc 140820
tctcttcatt gtacctgtga attcccacat gcagatcatc actagatctg agagtagtta 140880
cgcagagtag aatggacctc tggggaccaa ttggcagaga gccttaaaag ttctaataag 140940
ttttatctgg tacaaaggcc atcatggatc atgacaaggc tctgggaaga attatgtgac 141000
aataggttag aaggtgatca caggaagcag agcaaggagc aataccctag gcatagaatg 141060
tttaagtcct gactactggc tgagacaatg gtaatgggaa gaaagcaaaa aaactaaaaa 141120
tggaaaaaat gaaaaacaaa aattatccag gattgattca cttgttcaac aagtaattgt 141180
ggaacagtgt ctaatttcta ggagctatta tgaaaacttt gcctatatga cttcatttga 141240
acctcacaag aaccttgtgg gacaagtatt atccctgctt tacaaacaat caatctgagg 141300
ctccaacagg ttaaataatc ttctcaatat cacatataca ataaacggta aatggggtaa 141360
acccaggacc attttgtctt aaagctcata aactttctga catattaaag taaaaataat 141420
agcaaatgat tgcgatgatt ataactcctt aaaggtaggg actacgatat atgtctatgt 141480
atctccagta ggacttagca cagtaatctg tataaaataa tttcaaattg ttaaatcagt 141540
cagttgtcat aaggctgcct gctatgggcc aggtgcttgc ttaaaaaaaa tgaatgcata 141600
gacaggattc cttcatggaa cttatagtct gttgaaagaa tcagacatta aatattacac 141660
aaaattacat tatacaaatg acgtaagtgc tatcatataa aagtatagga tgccaagaca 141720
gtgagaaata tttccaaact tatatattta gaggctaagg agaggatatg tctatttgaa 141780

-continued

```
tgaagataaa tttgagatga gaaaaagttt aagaatttaa tggagagagt atttaaattt 141840
ttagtgttag ctaattgtgg tggtgtttta caaagctacg atgcatattt ttgaaaagct 141900
attttcctca taatatatta tggttatata cttagtgata tcttagaaaa gtataagtac 141960
taagcaaacc tcttcaaata ataagctcaa aatatggaaa taggtgtatt cataaaagga 142020
ttgtctctat attatttaaa tagtcatctt aatagtaaca atttaattaa atgattaata 142080
atccaagaat aagttatgtt gtatccctta caaataatgg ttctgaaggg taatgtagca 142140
ataggaaaat gcttgcattc tagtgctatg taaaaaagga ataaaaatat tgtatgctca 142200
taaaaacatg ttgaaaatat acataagaac tactgaaaga agtataccaa aaatttgtag 142260
caattatggt agaaagacta tgagagatac ctttttcttt ttttattttg taaatattct 142320
gtagtgtgat tttattatca ttgcaattaa aaatactttc tgaaatagaa aaagaataat 142380
cataaaaaca catttggctt ctatggatag atcctgattt tctgattgta tgttttgtat 142440
taatacctga cttggtacat agcactctgg gagataatca agtcaataaa aagacctgaa 142500
aaataaatga atcacaaacc ataactgttt agtgcacaca ggaaggtact attaataact 142560
acaaaggcaa aaggagagca tctgcaaccc aaggactaaa attagtaata atgttgaagg 142620
gagttctacc aaattatgtt ttccagaaga cagcgcaggc tcttcttgtg taaggaagac 142680
agatcacctc cattagcctt gaaacaaaag caaagacttc tggatgaggg catttaatta 142740
taatgtttat gtaatcactc tgtagccatt tatataaaca agatcgctta gagcacttgc 142800
ttttctgtgg gcagtaaagg gtactaaaag atgtatttta taaaaagtgt attttaagcc 142860
aaataattca gcaccacaag tgaaaattat tggcatttta tactggtgtt tttaaacatg 142920
tagagaagtg cagatacaac ccttttctg ctttatgatt gttggacttt tcagtctatg 142980
agcttgtgat agtaacaata ataaataacc aaaatgagat acctaacaat ctctatttac 143040
ttatgtcagg gcccattcta ggacttttat gtatattaat tcatttaatt ttataataac 143100
ccctagaaag gacatgaact cagaagctgg aaaccatcat tctcagcaaa ctatcgcgag 143160
gacaaaaaac caaacactgc atgttctcac tcacaggtgg gaattgaaca atgagaacac 143220
atggacacag gaaggggaac atcacacacc ggggcctgtt gtggggtggg gggagtgggg 143280
aaggatagca ttaggagata tacctaatgt taaatgatga gttaatgggt gcagcacacc 143340
aacatggcac atgtatacat atgtaacaaa cctgcacatt gtgcacatgt accctaaaac 143400
ttaaagtata ataataaaaa aaagaaaaaa aaataacccc atgaggttga ttattatcat 143460
tatcttcact ttatacataa ggaaactgaa acatagagtg attaaatggc ttgtccaagg 143520
ttgctcagct aaatgcttgg atttgaatga acataggaaa cctggctgga gacctcagtg 143580
ttctaagcat acactatgct atgcatcaaa agaaacgttt tgcattaata ctccatctta 143640
ttgccagagt cactagaaat tatttttgat gagattaaca aaaaagcttg ttccagactc 143700
atattctatc tcctcacagt gctatttcca tgtttctttt ctctttcttt cttctttttt 143760
ctttttcatt tatcttcttt aactttttgt agttttagaa ataagttcac caatacagag 143820
gaagacagga aaatgggatt tttttctcac atttttcttg attgatttat ttagcatatc 143880
tatttttgat atgtaagaac ataagaagta agtagtcaga agtcttcttt gagccaccaa 143940
gagttggtac ggagatatca aatgtcctta cacaactggg cagcctctga gaactgtctg 144000
ctgagatttt agatgtcaga ggtgcagact caagaaagaa caatatttgc ttgggtatac 144060
atgatatctg tgattttata catatataaa tacaaataaa tctttaactt atttattttt 144120
aaatttgaat ttatttattt atgtcatata taaatcttgt atattaaaaa catattttcc 144180
```

-continued actttggaat tgatttatag gtgagtaatg tcataaccta gagatagctt tgacagggag 144240
gcacgtaggt aactaacgtc cacttgtaga ctcaactctt caaaaaatgt ctctcctatg 144300
acattggtac atcaaatttc taacttagca ttttcaaaaa gtcacggtta aaatgtaagt 144360
acactaccag gaatggagta acacatgcca ttgtattcac taacacagta taaccacttt 144420
ggaaagcaga gaccatgttc ttgagggagt agtaaagcaa aatgaatgga gaagccatat 144480
catcaggttt cgatggggtt ataggaaact ggacagtggg gctgaggaaa atgtggatgg 144540
tgtagttttc atgataggag ggcagagcta caggtgtttt ggaagaatac cttataggag 144600
agaagtcttg aaagtggaag ctagcaaact acacggtgaa atgtagatta cttcatttgt 144660
tctggagtca tctcactctt ctggctatct tgatagaaac agcaccaagt cacatattga 144720
ggcagcatac aatagctaaa agagtaggag tttccatctg gtcctggact ctttttggtt 144780
ggtaagctat tgattattgt cacaatttca gagcctgtta ttggtctatt cagagattca 144840
gcttcttcct ggtttagtct tgggagggtg tatgtgtcga ggaatttatc catttcttct 144900
agattttcta gtttatttgc gtagaggtgt ttgtagtatt ctctgatggt agtttgtatt 144960
tctgtgggat cggtggtgat atatatcccc tttatcattt tttattgtgt ctatttgatt 145020
catctctctt ttcttcttta ttagtcttcc tagcggtcta tcaattttgt tgatcctttc 145080
aaaaaaccag ctcctggatt cattaacttt ttgaagggtt ttttatgtct ctatttccct 145140
cagttctgct ctgattttag ttatttcttg ccttctgcta gttttcgaag gtgtttgctc 145200
ttgcttttct ggttctttta attgtgatgt tagggtgtca attttggatc tttcctcctt 145260
tctcttgtgg gcatttagtg ctataaactt ccctctacac actgctttga atgtgtccca 145320
gagattctgg tatgttgtgt ctttgttctc gttggtttca aagaacatct ttatttctgc 145380
cttcatttca ttatgtaccc agtagtcatt caggagcagg ttgttcagtt tccatatagt 145440
tgagcggttt tgagtgagtt tcttaatcct gagttctagt ttgattgcac tgtggtctga 145500
gagacagttt gttataattt ctgatctttt acatttgctg agaagagctt tacttccaac 145560
tatgtggtca attttggaat aggtgtggtg tggtgctgaa aaaaatgtat attctgttga 145620
tttggggtgg agagttctgt agatgtctat taggtccgct tggtgcagag ctgagttcaa 145680
ttcctgggta tccttgtcaa ctttctgtct cgttgatctg tctaatgttg acagtgggat 145740
gttaaagtct cccattatta ttttgtggga gtctaagtct ctttgtaggt cactcaggac 145800
ttgctttatg aatctgggtg ctcctgtatt agatacatat atatttagga tagttagctc 145860
ttcttgttga gttgatccct ttaccattat gtaatggcct tgtctctttt gatctttgtt 145920
ggtttaaagt ctgttttatc agagactatg attgcaaccc ctgccttttt ttggtttttt 145980
tttttttttt tttttttggt agatcttcct ccatcccttt attttgagcc tatgtgtgtc 146040
tctgcacgtg tgatgggttt cctgaataca gcacactgat gggtcttgac tctttatcca 146100
atttgccaat ctgtgtcttt taattagagc attcagccca tttaccttta aggttaatat 146160
tgttatgtgt gaatttgatc ctgtcattat gatgttagct ggttattttg cttgttactt 146220
gatgcagtta cttcctagca tcgatggtct ttacaatttg gcatgttttt gcagtggctg 146280
gtaccagttg ttcctctcca tgtttagtgc ttccttcagg agctctttta gggcaggcct 146340
ggtggtgaca aaatctctca gcatttgctt gtctgtaaag tattttattt ctccttcact 146400
tatgaagctt agtttggctg gatatgaaat tctgggttga aaattctttt ctttaagaat 146460
gttgaatatt ggcccccact ctcttctggc ttgtagagtt tctgctgaga gatccgctgt 146520

-continued

```
tagtctgatg ggcttccctt tgtgggtaac ccaacctttc tctctggctg cccttaacat 146580
tttttccttc atttcaactt tggtgaatct gaaaattatg tgtcttggag ttggtattct 146640
cgaggagtat ctttgtggtg ttctctgtat tttctgaatc tgaatgttgg cctgccttgc 146700
tagattgggg aagttctcct ggataatatc ctgcggagtg ttttccaact tggttccatt 146760
ctcccggtca ctttcaggta caccaatcgg acgtagattt gttcttttca catagtccca 146820
tatttcttgg aggctttgtt tgtttctttt tattcttttt tctctaaact ttccttctca 146880
cttcatttca ttcatttcat cttccatcac tgataacctt tcttccagtt gatcacatca 146940
gctcctgtgg cttctgcatt ctttacgtag ttctcaagcc ttggtttcag ctccatcagc 147000
tcctttaagc acttctctgt attggttatt tcaggacata ggcatgggca aggacttcat 147060
gtctaaaaca ccaaaagcaa tggcaacaaa agccaaaatt gacaaatggg atctaattaa 147120
actgaagagc ttctgcacag taaaagaaac taccatcaga gtgaacaggc aacctacaaa 147180
atgggagaaa attttcgcaa cctactcatc tgacaaaggg ctaatatcca gaacctacaa 147240
tgaactcaaa caaatataca agaaaaaaac aaacaacccc atcaaaaagt gggcaaagga 147300
catgaacaga cacttcttaa aagaagacat ttatacagcc aaaaaacaca tgaaaaaatg 147360
ctcaccatca ctggccatca gagaaatgca aatcaaaacc acaatgagat accatctcac 147420
accacttaga atggcaatca ttaaaaagtc aggaaacaac aggtgctgga gaggatgtgg 147480
agaaatagaa acacttttac actgttggtg ggactgtaaa ctagttcaac cattgtggaa 147540
gtcagtgtgg cgattcctca gggatctaga actagaaata ccatttgacc cagccatccc 147600
attactgggt atatacccaa aggactataa atcatgctgc tataaagaca catgcacacg 147660
tatgtttatt gtggcattat tcacaatagc aaagacttgg aaccaaccca aatgtccaac 147720
agtgatagac tggattaaga aaatgtggca catatacacc atggaatact atgcagccat 147780
aaaaaatgat gagttcatgt cctttgtagg gacatggatg aaattggaaa tcatcattct 147840
cagtaaacta tcgcaagaac aaaaaaccaa acacggcata ttctcactca taggcgggaa 147900
ttgaacaatg agaacacatg gacacaggaa ggggaacatc acactctggg gactgttgtg 147960
gggtgggggg cggggggagg gatagcttta ggagatatac ctaatgctaa atgacgagtt 148020
aatgggtgca gcacaccagc atggcacatg tatacatatg taactaacct gcacattgtg 148080
tacatgtacc ctaaaactta aagtataata ataacagaat aaaaaaagta taatatataa 148140
taaaaatatc ttgaaaatta aaaaaaaaaa caaacttctc aatggctgtc cctctcattc 148200
aagagcaaaa ataaaatcat aacaatcctt gaaagcaaaa aaaaaaaaaa aaaaagtagg 148260
agtttcaggt tgggacagac ctggattcaa gtttatttct atcagtgtag ccttggataa 148320
gttatcaaac atttagttcc tcccatctat aaaatgtagc aattaaacta ttaaactaga 148380
aaatccacta tatgccatgc gtatagcaac tgtatgcacg ccatacctat aggcatagat 148440
atacagtagc tacagaaaac atatatgtat gtatatacac atatacattt gtacatggag 148500
gtattcacat atctacgata gtgctatctt tctccctcgt tatgttactt ctgcaagaaa 148560
cttgccatat tttctctatt ttatattttt gtttcttatg tatggattta cttttaacaa 148620
attttcaaaa tatgcaaata actttctgtt aaactatagt actggccctt ttatttctga 148680
ggtaaactaa ctgaccatct tagggaattc tatttgttag caaccaaaaa aaaaggatgt 148740
ttgccactta ataaacagat tcagacaata tattactaat ttacttcaac gagaaagaga 148800
ctcttgcttc tagtgaatga tattacacag tttgttttgt tttgttgata gcactactgt 148860
gcaatggtca cctgtgatac aattatttga attcatgaca atgctgggtt aggaaccgag 148920
```

-continued

```
gcagatccac tatgcttctt tatgttcaga tgttttaaat cagaattata ggactatatc 148980
tatgtgccta ggcaaatatc taaaataatt attccattct ctgctaacag cttaaacacg 149040
tgttgtaatt ctaacagact ttagagagca tatggcagtt tcaacaagtc acacatattt 149100
ttacatgcac ctaagctagg gacccctgac caatgagttg agcatcatct atcaggatgc 149160
tcccgataga tgacagatct tcaaccagcc agctaggtca tttctgcttc ctcaattcca 149220
catgtttagt tagttgggat tcccagtcgg gaggcaaagc aggtagcatt tgggccctcc 149280
ccttactgtg ctcagttcag tttattgatg gaaacatctc caaggatctt aaaactttaa 149340
aatagaaaat atctcttcct cacaaagttg gaagccctga acctgagcct taagagattt 149400
atttttacat ttgttttcaa attctcacaa tttatacaga aaaaaaaatc agagtatcca 149460
ttctggtttt taattttttt atttcttgcc atagtattat atatcaagaa tatttataag 149520
aaggaagtag ttaatacata tttgttatct aagtataatt tgggacacta tataaatctt 149580
ttagtttgtg agttacttct gtaccctgtc atctcctaag ctacctggtc tttcttggaa 149640
taataaatat acataccttt taggaccaag atctatagtt tcacaatatt catagccatc 149700
tggttctgct acagggtaaa tttagactgg aaataaggta atattaagta agagaagctt 149760
cgtttgttta acctacctcc caaaggctcc atttgtaaag agtgcagacc agaaatcaca 149820
tgcactgctg gattctttcc atgagaaaag cctgtgttga gctttagttt cttcattttc 149880
tttaaacaga acaaaaatct ctcctaccac tcaaaggagt gatttgcaga tttaatgcaa 149940
ttatatcaaa gtagtttata acccataaaa cacaaagtta tatgaccgtt actttgtatt 150000
gaacatccat gaaactctag gaatagtact agaagcttta tacaccatta tatatagaat 150060
ggtgtctctt ttaattctca agaaatcctg tccagttgtt ataattatac ttactgaata 150120
aattatatta atttatatta taattatatt aattagttat ataatgaatt catagaaact 150180
caggggttgg gtgatttgct aagatcaata gctagaaagg ggcagaatca gtattcaact 150240
caatattacc tccaaatgga agtaattcag tattagtgag tattactaat tatagaagta 150300
atacttctcc tttctactca gagctaacac aacagcatta tctaatgttg ttaaatggta 150360
ggtggaatta aaaattgtag gtaagattaa gaaaggaggg aaatcactga ataacctgcc 150420
cttccagcaa agttgacaaa gtagataaga tctctggtaa gatctaatct tcatctcatt 150480
ctgccacatg tttttgtttt gttttgtttt gttttgtttt gttttatttt gtttttttaag 150540
acgcgtctcg ctctgtggcc caagctgaag tgcagtggca caatcttggc tcactgcaac 150600
ctctgcttcc cagttcaaac aattctcctg cctcggcctc ctgagtagct gggattacag 150660
gcgtgcacca ccacgcctgg ctaatttttg tattttcagc agaaaggggg tttcaccata 150720
ttggccaggc tagtctcccc atgtttttta tcgaagtccc tgtgttctca atatcctgag 150780
atgattggct gattggctgt tgccacagcc attggcttca gccactcttc tggcctggac 150840
atcatccagt gcatgtcaaa gacaggactc tggcctagct tcttttgggg actttctacc 150900
acagaatgag caaaggtgat gttcggaaca aaatacctat acgtttcatc cagctgcaaa 150960
taatcagctc cagcttctgg agttacttgg tacctaaatt ggccaggttg ctgttgagga 151020
tgaatgggcc aatcttacag ctgaacacca tgatactggt tcccaggagc caagcattgc 151080
cccaatccag ccttttttta tttattttaa aaatgtgtta atactttttta aatctttaag 151140
tagtgactaa ttttctttta aataaagatt gttttcctcc aggatgcatc agagtaaaag 151200
cataaaatgg agctttaaaa aaattaattt agaatcagtt gtgtcttcag tttactaatc 151260
```

-continued

```
cacgcttcaa atgagtagaa cttacaattt gctctggttt tgttacttgg gtgggtaaga 151320
taacttagaa gagcgacagg gattttgcta aaatataaaa atgggatagt tttaaatctc 151380
tattgttgtt accgttggca gtaatataaa ggagatcaaa gaactaatgt gtttgttccc 151440
aacctacctt taaataaaat tgttttatag atgttataaa agtataccta tatacacttt 151500
atgtacacac acatgcattt catgtatata tccactataa tgctagttct ctcttattat 151560
aacactcctg caagaaattt gccatatttt ccctattttg tgttttagtt tcctttttgt 151620
cattaataaa tatactaggt tttcagagta tgaaaatgtt ttcccatcaa actcttatgg 151680
tgttgggcct tttttttctg agataaagta acagagaaat caatttggga gaatcttctc 151740
attaagggag catactactc cttactagtg aactggctta cagactgagg ttggcaggtt 151800
cagatatgta tgagcagaac agtagcaaga catttgcaga cctatgatcc ttgcttgttc 151860
acctaattct ttttacctaa cactgccact actgtaaaac caaagcaaga cattcagaaa 151920
aagacattgc agaccaaatt gacactttga gggaggctac catgggtata atgtataagc 151980
ctccatttgg agcaggatcc aagatcaata tggatacatt agattctact ttttaaaata 152040
agcactcatc tcatttcaga ctatggacat gctactgagc tttactatcc ttaatcctta 152100
gtctagtacc tcggtatctt cattaagtat gaaaggttat ttctattagg acttgcctct 152160
gagtcccaaa ctgggactca ggatcagatc atggaggaac atgaaactct tatgtggatg 152220
atgacatgga ttgggcatct gtggtggttc tggaacttca ggattcacct gatctgcctc 152280
ctacttatct ttggaaaaat gtaaagtata ggatctttct accacaatct ttactactgt 152340
agggagtttg atccactgac tcttttcaaa agacctctca gtgttcaagt acttttcttt 152400
aatgccattt cttgagagtt ggagctacag ttgctctaga tgtgtctagg tctgatcttt 152460
tctccccata ctccttgagc ccctgataac caccattcta ctttctattt ccatgagttc 152520
agtcttttta gattccccat ataagtgaga tcacaaggta ttggtctttc tgtgcctggc 152580
ttattccact taacataatg tccttgaaat tcatccaaat tgtcaaaatg acagaatttt 152640
gttccttttt aaggctgaaa agtattccac aatgtatata tgccacttat ctttctttct 152700
ctttctttcc tgcctgtttt tctttctttt cttctttctt tcctctttct ttctctttcc 152760
ccttccttct tttctttctt tctttctttc tttctttctt tctttctttc tttctttctt 152820
tctttctttc tttctttctt ctttctttct ccttccttcc tttctttttc tttctctttc 152880
tttgtttctt ttttctttat ttctctctct tttctctttt ttctttctat tcttttcttt 152940
ctctttctct ctctttctct ctttgtttct cccttccctt cccttccctt tcctctttct 153000
tttacaggct ctcactctgt cacccagtga gtacagtggc acaatcatag ctcactgcag 153060
cctggaactc ctgggctcaa gcaatacttc tgcctcagcc tcccgagtaa ctaggacaac 153120
atgcacatgc caccacatct gcctaattta aaaaatttgt tatagagaca acattcttgc 153180
tatgttgccc agattgttct caaaggtctg gcttcaagca atcctcctgc cttggcctcc 153240
caaaatgcag ggattacagg catgagcccc cacactcagc ctcaatgcca tgtttgactt 153300
atcctttcgt ccattgatgg gcacttaggt tgattccata tcttggctac tgtgaataaa 153360
tgctacagtg aacatgggaa tgcagatatc tcttccattt actgatttaa ttacctttgg 153420
gtacatatcc agtagtggaa ttgatggatc atatggtagg tctattaatt ttttgaagaa 153480
actccgtact gttttccata tggctgtact aatttatatt cccatcaaca atgtgaaaag 153540
tttccctttc tccacctcct cgccaacact tgttcagaca ctttcatctt taaaaaaaaa 153600
ttaattttta attttgtgca cacagtaagt gtgtatatgt atggggtgca tgagatattt 153660
```

-continued tgataccggc attttgatgt gtaatgatca catcagagta aatgagatat ccattacctc 153720
aagcgtttgt tctttctttc tgttacaaac aatccaattt tgctctttaa attattttaa 153780
aatgttcaat ccattattgt tgactgtagt caccctgttg tgttatcaaa taccagatct 153840
tattcattct acctaactat atttttgtac ccattaacca cccccacttg cctgcccacc 153900
cctcattacc cttcccagcc tctgataacc atcattatac tttttatcta catgaggtcg 153960
attattttaa tttttagctc ccacaaataa gtgaaaacat gcaaagtctg tctttcagtg 154020
cctggcttat ttcacttaat ataacgacct tcacttctat tcatgttgac acaaatgaca 154080
ggatctcatt ctttttatgg ctgaatagta tttcatcata tatatgtacc acattttcct 154140
tattcattca tctgttggtg aatacttagg ttgcttcgaa atcttggcta ctgtgagtag 154200
ttttcatctt ttcgataata accattctta tagatgtgag gtagtatctc tgtggtttta 154260
atttgcattt ctctgatcat tggtgatttg agcatttttt cacataccat tggctatttg 154320
tatgtcttct tttgagaaat gtctattcag atactttgcc catttttaac cttgtttttt 154380
ttcttacagt tgtgttgagt tcctcgtata ttttaaacat taatctctta tcagatttat 154440
ggtttgtaaa tattttatct cattccatag gttgtatatt cactctgctg attattttct 154500
tggctatgca gctttttagt ttgatgtaat ctcatttgtc tatctttgct ttcccagtct 154560
gtgatttggg gttaaatcca aaaaaaaatt atgcagacaa atggcaatgt tttcttatag 154620
tggttttagg tatttaatcc ttttttaaat atggtgtgag ataagggtct gatttcattc 154680
ttccacatgt ggatattcag ttgtcccaac accatttgtt gaagagactg tcctttcccc 154740
actgtgtgct ctcagcatct ttgtcgaaaa tcatttgacc ttaaatacat ggatttattt 154800
cgggttgtct attctgttca ctggcctctg tgtctatttt tatgccagtg ccatgctgcc 154860
ttgtaataca gctttgtggt gtattttgaa gtttgatatt gtgatacttc caggtttgtt 154920
ctttttgctc aagatttatt tggttatttg ttttttgtgg ttatacaaag tttaggattg 154980
ctttttteta tttttgtaaa aaatgtcatt ggcattttgg cagggattat attgaatctg 155040
ttgatagctt ttgttagtat ggatatttta aatatcagtt cttccaatcc ataaacacag 155100
gatattttte cttttatatg tgtcctctac aattatttca tcaatgtttt atagttttca 155160
gtgtacaggt ctttcacctc ctttggatta aatttattcc taagtatttg aaatttattt 155220
tggtaactat tgcaaacagg attgttttct tgattttatt tttcagatag tttgttgtta 155280
gggtgttaaa gtgctaccca tttttatgtg caaataagga taattttctt tctttctttc 155340
tttccaattt ggatgccttt tatttctttc ttttgcctaa tggctatgac tagaacttcc 155400
agtacaatgt tgactaaaag tggcaagagt aggcattctt gtcttattcc tgatcttgca 155460
ggaaaacctt tcaacttttc accattgaat aagatattag ctgtgggttt atcacatgtg 155520
gtctttattg tgttggggta cattccttct atgtttaatt tctgagagtt tctatcatga 155580
aagaatgttg aattttgtca aatgcttttt ctgtgtctgt agagatgatc acatggtttt 155640
tgttctttat tatattaatg tagtgtatca catttataga ttcgtaaatg ttgaatcatc 155700
cttgcatctt tgggatatat ctcacttgat catgatgaat tattctttta ctgtgttgtt 155760
gcatttaatt tgctggtata ttttgaaggt ttttgcattt atgttcatca gggatattga 155820
cctataatat tttcttgtaa tgttcttgtc tggctttggt atcattgtaa tgctttcctc 155880
ataaaatgag tttggatgta cttctcttct tcaatttttt gaaagagttt cagaggaact 155940
ggtattatta gttcttcatt aaatggttga tgatttcagc actgaagcca tcaggtcgtg 156000

-continued ggcttttctt tcttgggaga ggcttttggt aattgattca atctccttac ttattattgg 156060
tctgttcaga tcttctattt cttcctgatt caaccttagt aggttatatg tgtctaggaa 156120
tttatccatt tttttctagg ttattcaata tgttggataa taattgttta tagcgttctt 156180
ttataatcct ttgcatttct gtagtgtatt ttaatgtctc ctctttcatt tctgatttta 156240
tttgtttgaa ttttctttcc tttattcttg gtctagctca acatttgttg attttgttat 156300
tatttcaaaa caccaacctt tagttgagct gttctattgt tagatagaat agaatagaat 156360
gttctatttc aacaataaaa tgttgagcag ttctattgtt tttctacttt gtatttcact 156420
tatttctgct ctgattatta ttttcctcct tttagtaact ctgtgcttag tttcttctta 156480
ttttgtgtgt cttaaggtac aatgttatag gttgtttgag atctttctcc ctttttgatg 156540
taagtgttta ttgccatgaa ctttcctctt agaactctta ctgttgcaat ctacaaaagt 156600
atttgttttt ggcaagttgt gtttccattt tcatttgtct caatacattg ttaaatttat 156660
cttttaactt cctcattgtc ccactggttg ttgaggagta tgttgtttaa tttccacata 156720
tttctgcatt ttccaaaatt cttcctgtta ttgatttcta gtcgcatacc attgtgttaa 156780
aaaaaagata ctcaatatgg tttaaagtat catttcagtt aatgatctgg accttaaatg 156840
atggcagcat aatcaatgtt aatcacaaac caaaggctat ttagtgttat tattttaata 156900
tgcaatatac ttaccaggcc ccccagcact cagtctgcac agtctagacc ctgcctatct 156960
cagatccata ccccatctct tcctccaccc cttctgtttc aaccaaatta acactgttta 157020
ttctctgtag ttccccaccc tcactgccgt gcccacacta tgtcttacca aattctgtcc 157080
ctcttttaga tctcagtttt ccttgaacac ccagactcaa ggtgtggatg cctatttgtt 157140
tatcttttta gtagcccaga ctttttttata gtacatttta cagatgtagt caaataattg 157200
tgtaattggc tacttaagat ttctctcctg catttaaaga aagccccgag attatatcta 157260
tcttgtccaa cttagcatgc tgtcttgcat gacaatcatt aactttttat tgagttaatt 157320
aagcattgtg cagaatgcct agatgcctaa gctttcaatg ttaccaaaca tgtggaacaa 157380
aacttactgc aatctaggtt cccctgaaaa catagcctaa ggtggaggct tacttgaagg 157440
ttaccgtacc ttaaggagga gaagtaaaga acaggaagtt actgttatag agtgaatttt 157500
tctccatacc ccacccaaat tcatatgctg aagccctgtt gactaaagaa aaaaaaaatc 157560
aagcttttaa agtatcaggc caggtacggt ggctcatgcc tataatccca gcactttggg 157620
aggctgaagc aggcagattg ctttaggcca ggagttagag gccagctggc aacatgacaa 157680
aaccccgtct gtactaaaaa tacaaaaatt agccaggcac gatggcgatc atctgcagtc 157740
ctagctattc gggaggctga ggcacgagaa tcgcttgaac ctgggaggcg gaggttgcag 157800
tgaaccgaga tcatgccatt gcactccagt ctgggggaca gagagaaacc ctgtctccaa 157860
ataaataaat taattaatga attaattaaa taaagaaaag ttagctttat ttggaagtct 157920
gaggactatg gaccaaggcc tattgcctgg gatcagttct gttagaccat tccaatgcag 157980
caattgagtt cacagtttgt atacaaatgg tgaggattca ttacatgcaa aatcacatcc 158040
gagttcgtgt ataagagttg atatttatag attattatta ttatagatta tattatagat 158100
tatacattat tatcgataat aatctattat cgataataat aatctataac ctataacatg 158160
ctaggctgcc ttctgctgtt gaaaataatc caaatatctt gggcatataa ttatcattga 158220
gaagggcatg atatgtacaa gagaagtatt caactggttt ccccatgatc gcaaaccttt 158280
ggagcttata gaagagaaaa aaaaaaaaga gagacaaagc aaatataaaa gagattttga 158340
gataatttgt acactctgaa atgagaaagc aaacttaggg ctgacacaag aagaactaat 158400

-continued

```
tatttttttc aagtacattt tattgttatc aaaatagtcc atacatatcc tagggaaaaa 158460
aaaccccaca aatagtacag gaagattata atttaaagca ccagttcact caaaggcaac 158520
atttttaaca aaattttta aaattatttt tagtgatccc tctaaatttc taaataatat 158580
gcttatattt ttttcttgtt ttacccatgt taagtgtgac aaatttactt tttgctctta 158640
taaatatgga tttagctaat tttattttta ttttatttta ttgagaccag tctcgctctg 158700
tcgccaggca gagtgtgcag tgatgcaatc tctgctcact gcaacctctg tctcccaggt 158760
tcaagtgatt ctcctgcctc agcctcctca gtacctggga gtacaggcac ttgccaccat 158820
gcctccctaa tttttgtgtt tttagtagag atggggtttc accatgttgg ccaggatggt 158880
ctcgatctct tgaccttgtg atctgcctgc ctctgcctcc caaagtgctg gaattacaga 158940
tgtgagccac tgcacctgtc cagatttagc taattttcta cacttatccc caaccttcct 159000
cttcactcta cctccctttt caatacgata atatcacatc ttaagttcca tcatccctgt 159060
aacctctgta gctataagta tatagccaca attaacatat gtagatttcc atttctgatt 159120
ctatcagcca taggtaactg tctttacatt ccactttgta agaggagatg aataattctc 159180
acctttcctc ccaactctgt gttcctcctt ctacctcccc acccccaact ccgttgtagc 159240
ggctattaac atatattatt ttgtaaccat gggtaagtgt taagtaattt gcctaaagat 159300
tgattctaaa aaatttaaaa atatagaaat ctataaaatt ctgtaaattt tagattttct 159360
ataattatag aatgtaaaaa tatagatttt ctataaacat agaatgtaaa attctataaa 159420
aatatagaaa tctttatgta attataactg tgtaagtatt atttactgta gaaccaagta 159480
atgtgcaatg cttccttctc catggctcca gtgtcatgac atctatagta ctttacaaat 159540
aatgttatga gtatatactt ccagaatggt ggtaaaagaa gctctgcaga ccctctcccc 159600
agtgaaacaa ccatactggt aaaagtaatt ttaaaaggca atcatgaaaa gtctctggaa 159660
attttcttaa gggtatacag caaatgaaga aacatttatt ccaaaaagtg tactaaatct 159720
tggtaagaac aatgagtcca aggcacctaa gtcacaaccc acttcccttc ctctcctccc 159780
agctcagcat gacagaagct taactctgga caagaacaca gggcttcctc agcttccagt 159840
tgaggccaac tgtatgttcc caagaggaga agaccaacag cgtttcttgt ctcccttcac 159900
ccttcccctc cagaagctaa attctggcta gatgaatcca agatattggg gctcccttct 159960
ctcacccagc tcctactggt agggtggagg ttcaacctca ggcctggaac actgagaata 160020
gtatgggttc ccaattatta atgagactct gattattgcc catgctcagc tccctgctcc 160080
tacagcagag gagtcactta cagagaaaca caatgctgtc cccatcccta gctctgaagc 160140
cgcgcgtcag agattttccc cagtgggagc actgaagctc tttgcaaagg aactgacttt 160200
atttgaagca gagtaaaggg aagttcaaga taaaggtatt ctcaaaaata atgtaagttc 160260
tggtggaaag caattaaggg gaggttggta gcttcgtgaa agagacaagc taaaccagat 160320
tagctagtgt atgagagaga atcaggaaaa gagatagcta agaagagccc tcctgggtca 160380
gaacaaacct caagcactga ccacagcagg cagggcactg tggcttacac ctgtaatccc 160440
agccctttgg gaggctgagg tgggaggatt acttgagcgc aggagtttga gattagcctg 160500
ggcaacataa caagactctg tctatatttt aaaaacaaaa aacaaaaggc taccacagca 160560
aaaaggctgg aatttagttg gagcagaccc ccagagcaat ttatgtccca ggacattgta 160620
aaaaataaca gaacaatcta gaacagaata gctgggtata tgtgataagc cttagagcaa 160680
ccactaagaa aataactcga aaaatacata gtgaaggaaa gaaaacaaca atgttcctaa 160740
```

-continued catcacaatc aaatgaattc tccttttcaa catttcacca gaggctcaaa atcattccac 160800
gtttaaaatt tttttctctt tataatgtct actgaaaaag tagcaaaatc tactgaggag 160860
agctttattt ctaaaaggga gtatcacaac ctgcaagtgg gaaatggagc ctctggttaa 160920
aactgaaaag caggtgcttc gaaggaggaa aaatgagaca ggaattcata ctaaatggat 160980
tggtttagca tacatattca accggctatt ggaggagcta tgaatattca tgaaggggca 161040
cacgtgtagt aagctaacat gtctattaca tatgtcccat gttcactttg gggtggaaaa 161100
agcatttaaa tatactaaaa ttaagctcta tatgtcaaaa ggttaagcag aggacatgaa 161160
gggactcagc atacagtctc tgtaaactgg ccagaaccac tccatgttca gtgttctctt 161220
attgggaagg aatgctagcc agttgctgtg tcgaaactac aaaaagcaag gggcagcgta 161280
acatggttgg ttgaaatcag ccatggagca agtctttcaa aagagcttgt ttctgtttaa 161340
cccttaggaa cgaaagccta ctggtggtta acaaggtagg gggtgttaca gggtgtggct 161400
gacctactgt tccatcatag acaggagctc agtttttaag gtttctctgg ggtctccaag 161460
tgagcctccc tggagaatcc tccaatttcc ctagtgagag caagaaccat atctgtctat 161520
actgcccaac tcagttgttt ttgcaataat agacaataac tctttaaaga atgaataagt 161580
ggtggtgaaa tgaaacagag taagttcctg atgtagaagg cagaagggag actgttgctt 161640
aggcagacca agtagaaact atacgatatt ttctatagta ataaccttag aaatggcaat 161700
tcggttctat agttcaatta atatcactaa aagagctgtc caatgaactt acaagttatg 161760
tggtatatgt gggttaatct gggagaccaa ccaccattta tgaaattctt ctctatgaaa 161820
atgctttatg aagggcaaat agcaagttta caaatgaatt tttggaaaac aaactgtaaa 161880
ttgaggttaa cttctaaggc tgttaatttg tgggtatctt tgtctatatc ttcttctcac 161940
tgatatatcc tcaggtagct agagttctcc tttcaactag ccttaatttt gaattatatg 162000
ccagttataa atcatcttca gaatatgaat taaatacccc tttaatttta attgatatga 162060
ttttacaata ttaactacat agtaacaatg gatttggata tttatcattt ttctatttga 162120
tttataattt agggccaaat gggtgtcata aggggctctc attccaggaa acactgtaga 162180
gtagtctagt atcctaacag tctatccatc ttgatttttg aaaatagtct gttgtggagt 162240
agtttaggat aacctaacta cttgtctgtc aaatagagga atgctgtgac tggagaaaat 162300
ggagccgtta tacattagtc ttcggtacag tcacaaaaag ctacttattt cacaaaagac 162360
actattttgc cttttcaggt gtaactgtgt ggaaccgcat aatcccagca atggcacatt 162420
gaaggaatgg agggaatcca atatttctgc ctctgacata atttgggaga acctaactgt 162480
gtcagtaagt aaaacactga aaaataagtc atacctaaga gcttttgttg acattttgac 162540
tcaattattg ccattacagt aaaatttttt tgaatgcata atataaaact aatagttgtg 162600
ttttaatttt aatttcatca tttcagatgc tcatcagtaa actggggtta tctttcatta 162660
ttaaggttgt tctaatagaa gaccagaatt gctcaaatag ctcacttata cagaaatatg 162720
tgaccgagat ggactgaaag cacattaaat atgagtggtg ttgacctaaa tgaaaccata 162780
tggcagaact aagtctgcct tctgtgtaaa gaactcagaa tgctcttact ttactctgta 162840
atgctgctcc agctgttccg gatctgctgg ggggaaaggg atgtttctaa tattctagtg 162900
tcaatactaa agtctttggg aggaacaaat atcacttttc ttcacaaaat tctggcacct 162960
ccctcaacaa gatctttctt ttttccattt tattcttatc tcccactcaa gaaagagcat 163020
ggcaacatat ttttcaccta taacagttca atcctgtgcc attgtcttat ttcctttgac 163080
ttttctctac tttgtgattt cttttttctc atacctgcat ttctctattt ttctgaatct 163140

-continued attctgtgcc tcctttccta tcaatacttg cattctatgc ttctggttca ataaaatctt 163200
gtaatttgaa aatgtgttct actttaaata aatattaaaa tctgagtagc cctactttct 163260
tttctattct tcccagctat aaacattaca ggttcaaacc ttctaccact ttacctaccc 163320
atataggctc aagttttatt atgactatca gcacaaaact attgagttct agttcatttg 163380
atcaaatgca tactatttta gtaagttgtc tagttagtga gcatagaaat ctttttttggt 163440
gtacagatgc tataaaactc taaacatgat tcttgtaaag agcatatgat ctattgacta 163500
tattcttgat tttctctatt gaatatgttc tttcaaaatt gaaatcaaat tacttactct 163560
ttatttaaaa ttctatcttg acctatattt tactacttct attcttaccc tagctgtgtt 163620
ctgtagaata agccttcagt tactcttatt gttttctttt gttattgtta acatttattc 163680
tgttccacct atttttccct agaaaaataa cattgccagt ctgcttccac tcaaagagcc 163740
atttaaactg aacaataaaa gaattgatga gctgatcaag aaaaaacact atagttattc 163800
agaatttaga catggggtca tgattaatga aatcattagt gggtcttctg tctacacttt 163860
ctttggtaaa ctatattatg tttacagagc ctcttgatgt cttcttcaat atgaaaaccc 163920
aaatgatccc atctctaagt tatataacat gataatttac tctatatgtg ttttgtatta 163980
tgtgaataat ttaatactaa ataataatat tccttctatg tattagcaaa tcttgaattt 164040
tgagagttct aagaagcaga catacagcac agttatcagg ctagctgtga gttagatacc 164100
ctgagttttg aggtcaagta gaatagtgaa aaatattttg caattaaagc aaatacagca 164160
ttgtggggtt gttggttttt ttctcttttt ttttgtcatt ttaaaaagtt ttgtactagg 164220
tgttaacatt tgagcagaaa gtttcatatt atttttcatt agttaaaagc agtttttgca 164280
atggataatt gctaaacttg accagaaaca gtctttatca ccagagggaa tactatataa 164340
tgaaaacaat cttgtaattt ttaagtcaaa aaaagaccat taaaattttt gtctaattgt 164400
tatgctgaat tttttcctca atatattcat aatgtcatca aaaatatttt attaataaag 164460
cactgaacta gtggctatca caactaattt tgttaaaata gtgacataac atttaattta 164520
catattattt gtttggcagg tcctgtaatg ttttattgag ttgtttgtta catatctcat 164580
gaattataat ttataccttg ccaactcagc aagggcaaag aactttagtt ttctctgatt 164640
ctcccaaact gctctatgca tagtaagtgt caaacatttg atagaagtac ttaatgtctg 164700
tttgaaacag tttcatctta ctatttaatg caaatattta tggcaaactg gagtacttaa 164760
gtttgtgtgt atatatatat atatatatat atatatatat atatctctct acatatatat 164820
gcgtgtcgat atcgcgaaaa accgtctcta tatgatactc tcgcgcaacg tcgaagagta 164880
agcaggcgca gctcaaccag cacgaggtgt cgcagtcact acctcgcata ccttgcgtgt 164940
nnnnnnnnnn nnnnnnnnnn nnnnnnnnnn nnnnnnnnnn nnnnnnnnnn tatactatag 165000
gagccaagta gcaaagcata tgtatgacac gcaggatcga ctctacgagg atcccccctta 165060
ggcaagattt aaaatattca taagcagtta accagcattt ggtgtttcag tgcctgaatt 165120
acatatttag cttgtacata tataaggggc aggacactaa tgccaacttt aatttcttat 165180
tctaacttaa tttttgccaa cttatagaat tgctgaaact tagaatgtgt ttgaagagta 165240
attagtagaa atcagtttgt caacaagcat tttttgagta cccattgtaa ctgaaaccat 165300
atgttagact caaaaaacga gagcaggatt tggatttggt tttcatttct aaatttcagg 165360
acttactctg tgtgtatgtg tgcatgtatg tatgtgtgca tgtgtgagtg cctctgtgtg 165420
tgtattgggg atacaattag tataaatctg aaaataattg ttgaatttag caggtcacaa 165480

-continued

```
tttttctctt ttaaaattag cattttgttt cctcccaaag agaaaataaa taacattttc 165540
aaatatgctt tgaattaatg taattaggca gaccattggc aaattataga gtgtaagaca 165600
gctaaggaac cctttaaatg tcatctatgt tcttaagaat tgagaacaag atcccgccaa 165660
atgactttta tacctgcaga aatgacaaaa gatgctcaca aatttataga taatgtgttt 165720
atcatggaac ttttagctcc tttttctatg tagcaatttt gctacccatt atattgctta 165780
ataattgctc tgctagcatt tctggacagg tgcagaagag gatgaaaaac acaaggattc 165840
atttttgcca ccttatctat ttttaaagca ttttgaaaga aggaaaatta aaactttaat 165900
taaggcctgg gggatttttc tgtggttttt caattagcca agttgctgtg ctctgtatta 165960
gcttaacatg aataattgga atttaacttt gcctatcaag gaagatgttt gcagttaaat 166020
tagaaaagga gacagattct ttaagacaat aataaggtgt attaactata tttctcaaga 166080
ctctcaggct tagggtagct agcaactcca agtagatttt actagttgtt tgttttcaga 166140
tgacagtgta gctatttgta atttattcta caatctttgg agtgtattta ctttttgctc 166200
tacaaagatt tcaggcctaa agttgggcag actctgtgtt tgtgatcaat ctatcagttc 166260
atatttgtct ccaagatctc tctgcaattc aatttatgtt cagggcaaga atatctcaag 166320
gactaatgag atcactggat catttaaacc attatttcct gttttgaaat gtaaaaatac 166380
tttagtaatc taatttttaa ataagataaa ccaaagtaag tttaaaataa ctttttttca 166440
ttcaaaatat ttgtttgaaa tgctcagttt ttcctggagg aaaaaaattt ttttgacttt 166500
gctgccacct catggctaag gcagtaatta gaaatagttc ttcaggctct tacagaacta 166560
cagttgcaga agaaaaaata atccatggag aagtcatagt aaatatgagc tttgccttgc 166620
tcatgtagta attttatttc atttgttctt tagtccaagt tcgatagtcc catctttgac 166680
ttacaagttc atttcagtca ttgtatgtca tagttttctt gttgcctttc tcatctttct 166740
tggcagcttt tggactagat aattctacaa agtcattgtt cttagtcaat aagcaataat 166800
aatctcactg cagaaatcgt gtttgtatca cagctctgcg gccacccacc agtggtgagg 166860
ccacaacaaa ttatttaacc cctttatgct tcagtttcct cagacatgga atattaataa 166920
tagcatgaac atattttatg gtattggtgt gaaaagtaat ttaaatgatg tatttaaata 166980
gctgggcata gtgtctgacc ttagtaacca atcactatta catatgtcat attttcaata 167040
tatctcgtgt taggaactta gtagatatta gatttaatac atactaatta attggtaaat 167100
caatcgtttt atacatttaa atttaaaaag cagttcatgt tcaaattttt cataaacctt 167160
tgcatatttc tcaccaccca tccaagttga acttgaaact cgtaatgtaa tgcctgctaa 167220
atcattgtga gagccataaa ggaaaagcct cagcatctga actacaattg atcagaaggt 167280
gttagttttc tgcaagaaat gtgtccggtt ttttcttagt agctccattt gttttacttc 167340
ctctggcagg aatgcaaatc attgcatgga gagtatgttg gacgggcctg tggccatgat 167400
cacccatatg ttccagatgt tctattttgg tctgtgatcc tgttcttttc cacagttact 167460
ctgtcagcca ccctgaagca gttcaagact agcagatatt ttccaaccaa ggtacttaga 167520
ctatttcttg atctaaatgt aaaataacat aggacaaaag aaagagtaat tgatgtaata 167580
aaaggagcca ctgaaaggct tttgtgtgag tgagctgcca ggttagttgt ggagtgagat 167640
gaggggctga agagaaagaa tttgtgatgc aggtgctggg agtgcatatg caggcttttc 167700
tcctaactgc aaaccccacg gatcaactcc tactttccta ctgacgtttt tggaaattca 167760
cagcacacac tgcattactg attgtcactt ttttgcccag tgaacagtgg gaactattcc 167820
agcctgacag atacctcaga ggagcctatg ttacattctc taattgggga agccccggca 167880
```

-continued

```
agactcattg gaacaatatt ctctttttca atgtttaaac cgtcagtccc tccccctaac 167940
ccaccacgtt tgcatctgca tatttggaaa ggaaagtaaa cagagaaaca gcttagttca 168000
atatttaaca ctgcaaagta acacctataa tgtctgattc cgccaaaaaa aatttaaaaa 168060
aaggaaaaga aacaaggaaa caagcttctg agggatgagc tatagattat gatcaaaatt 168120
ccactctgga aaaatatttc aagaactgtt ccttccgaag ggggcttctt ttttgtcacc 168180
actttcttct actaaaggtg gaagattcat ttatttcccc aaaaatctta gtctgattaa 168240
tacaaaaaca tttttctaag ctgaaacaat aatcttaagc attttgtgta tgcttgtgtg 168300
tatgtcataa aggcatctta aaataaacta gatctggata ataattatat gtgaatattt 168360
gctcagaatt ggctttataa atgagaaatg gctttaaaaa ttggctcaca tagaataaat 168420
tttaaatttg cccactctgt tgtgtacatt cccaactgtc atgcttatat tctagataaa 168480
ctaaaacatt atgtttcttt gataagaaca gataatttta ttttatgatg cttcaagttt 168540
atcatattaa agtgttacct gtgtgaaaga gatccctaaa atccagccaa attctgccca 168600
tgctacctta ttctgcattc tgaatattca catgcatggg ttcatcataa agttagattt 168660
taaataaaca ttgaaaacag cacaaccacg atgtagctat tccataatgc ctcattctgg 168720
aaaggttgag tgtgtaccaa tcttaacgac agtgatacat aaatatatat tcaggttctg 168780
acagagctaa tggtaatctt atagtatgca taaaatataa tattatgata ttatgtcata 168840
aagtgtttat aaagtgtgac tctagattat gttcctgagt attccttgat atttatagct 168900
actttaagtg acaagtgttt tcattatttt taggttcgat ccatagtgag tgactttgct 168960
gtctttctta caattctgtg tatggtttta attgactatg ccattgggat cccatctcca 169020
aaactacaag taccaagtgt tttcaaggta cttactatct ctctccctct tcccatctct 169080
ctcggtctaa tcttcattta gatgatacct ataactctag tacttaggat tttcatgaaa 169140
atatgaagaa tttagattag aagaccagta aatgaaatgc acacagcatg gctaaaattt 169200
aggtctaata tttaaaaata taagaattac aaaatataaa taattataaa tataaaactt 169260
gcttgaaaaa aatttcctgt caattctgcc agttgaaata cctatatata acattcttaa 169320
aagataagga agcatttgaa actaagagaa aaggattatc ttggcagaat tgtacagtga 169380
ataaggcttg gaaaacagat aaaaatagat tgggaataga attctgaccg tgttactaat 169440
ggggtacagt ttgaatattc cttatccaaa gtgcttggga tcggaagtgt ttcagagttc 169500
attttttttt caaattttga aatatttgca aacacataat gagatatgtt tggggtgggg 169560
cccaagtcta aatacaaaat ttatgtttca tatatacctt atacatataa cctgaaggta 169620
attttataca ctattcttaa taatatatgt gacctatcac atgatgtgag gtgtgaattt 169680
tccgcttgtg gcatcatgtg agcgctcaaa agtttcagat tttggatcat ttcagatttc 169740
agcttttcaa attaggggca ccccttttgtt ttctctgtca aacagggctg gggacttcta 169800
tatagggctc ttgtcaggat gaaattttga gaatcatctc agacagcagc catgtttgga 169860
atccttccct gagcctctgc tgtgaccaag tatctttttt atcattttca ctcaatagcc 169920
tctgcacatc aaaaataaca gttacaatac cataatgatg tattttgttt agatgtctgt 169980
ctctgattct aaactgaaag aagcctctga tttatctttg tatctcagtt ctagcacagt 170040
ggtcaatgtg tcaatatgct atttgtaaat ttcaatacat tttccaatag taaatagtaa 170100
atattaatat cattttattt aatacaggta ttgattaata acacagattt ttcaacaagt 170160
ctgtcagagt ttaaatccca tctctaccac gtactagctt tgggatcttg ggcaagttac 170220
```

-continued tggatctctc tgtgcctcaa ttttcttatc tgtgtcatct ttagagtgtt gtgaagaaaa 170280
aaaaaatgag ttaaaatatt taaagcactt aaaatggttt taagtgattt atgagtatta 170340
ttattattta ttataggcca ctcagctcct ctgtttataa ttagggcttt cctagtagca 170400
tctgtaagac ctaatttgat caagtattca ttaatccagt tcataactat gcacattctt 170460
tactttatac agcccactag agatgatcgt ggctggtttg ttacgccttt aggtccaaac 170520
ccatggtgga cagtaatagc tgctataatt ccagctctgc tttgtactat tctaattttt 170580
atggaccaac agattacagc tgtcatcatc aacaggaaag agcataagct aaaggtatat 170640
tttaacatcc attttaatgt aaataattat gacaactgat atcaactgat gttcatttga 170700
cttctatatt ctgtattcat ttgcacagtg aaatatataa aataatgttt ttagatgtat 170760
aatttttatt gtcttacaag atacttggtc ttacaatgag atgagaattt acttatttgt 170820
agcacttggc tgagctcacg tctgagaact cacctccaag gcataaaata aaaaactgtc 170880
aaagttttaa cttttccata cttaacatat tttaatgaaa taacaatctg ttctggtgaa 170940
gtacaaccat accaacttgt cttacatctg agattcctct attcctctat ttaaccctaa 171000
atgtatctat tacattgaat tcattatcag aataaattac aacttcaact atttctcatt 171060
ttctttaatt atttttctgt ctgcctgtaa caacaaaatc cagacataaa cgtcacagtt 171120
tagaagtgac atctttgagt tttattgcag atttcactgt ctcttttata aaaagaataa 171180
ctatagatgt gtcttagtta cattctgacc ttgccatttt gcaattgtga ataatcgaaa 171240
ttgttcactg gtatgcaatt tgcctgagat atgtaatgta agcactgtca cttacttaca 171300
ggaatatgtt aaataaaatc gatgaaatca ttaaatggtt aaaaataatc tgcatcaaac 171360
cttgtaaaaa cataacatgc acaatcttgt ttttgttttg gtatcgtggg gtagttgcca 171420
gctattttca catacccttt aaactctagg agaaaaaatc attgtcagag caacagaaat 171480
catgctttat agaatttttt tataggaatg ttagaaagat gaaaaatatc tctgattaaa 171540
ctctgatgca atatattggg tcaatgcaaa agtaattgca gtttttgcca ttacttttaa 171600
taataataat tacataaatg taagaaagca cacttatttg caataaatct tatgaagaag 171660
gaattttgag tatatggtgg agagaatgtg tgtctatctt aaagcaaagg acatttttca 171720
ttctctttgt agaacgtaag ttaagaattc tcacaacttt atgtatttta ttaaatgata 171780
cattttaaaa aatcaactaa aaaacctgtt ttaggaagaa agtaagccat ataattatta 171840
tttacctttc aaaaagattt ttttagcctt tataattagg cagaaattct agtgtgttca 171900
ctgaaaaatt atcctctgta agggccatca gttaaatgga ttcaggcagc atttttttct 171960
tattgtaagt ggaatcatat taaaacaaag tgtggaagtg aaatgtgtgc tgagattgat 172020
attaccttcc tggccattct gaatctttgc cctttcaacc ttataaatca catgacactt 172080
gctcttactc cttgttcttc atgagccctt gacattcaca gcctttgtaa agctccacat 172140
tgacaaatac actaatttcc cccttcacat atactgtgga ataacaaaaa tgtagtaaag 172200
cattctttaa gtggtccttt caagtacttg catttataga attaaatgca gaactagaac 172260
tatttttgtc actgaaataa acctgaggct acattactaa atctgtttta ttgtgcaaat 172320
aaatgattat gtagtcaaaa gttgtgtatt tttgcccctt actactctgg atttagtaaa 172380
tgatacagca aatctggctt aatcataaac tctgctatat ggccacaggc agaagagtca 172440
gcctgttctt ggccactgtg aatctgaact ctccatcctc cttcttagat atgaatactt 172500
ttaaagcaaa tttcttccag tgaagatgta tttcatctac attgaacccc tattgggcct 172560
ataactcttg tctcctataa gcttctatag agtgtggtct gatgctactg gttttcccgt 172620

-continued taacaacaac aaaatcacct tctcagaatg ttatttactc agagtaacgg tttgttccat 172680
agtccttctc cccgcctgtt gcttcattga aatgtttgca aagtctcctg gctttgactt 172740
gaaccacatt ttcactaaaa gatgtgtttc ttgagtatat caccagacca caagctaacc 172800
acttgtgaaa gcattttcag cttttactaa ttttcttttc tcacttgaaa acccattttt 172860
gccttggttg gagcattccc cgaaattgtt taatgaatca tgttttgtag tttatgtatc 172920
aaacacttgg tagactccac atcatgtatc taagtctaca tacacccaag tcaactcaga 172980
attcctcatt tcattcttta tctctcccaa acatatttta gatcttttta ctttttcttc 173040
acctctattg ccagaactag tagctggttt tcttttagat gatatttctc ctgctgataa 173100
aaatgttttt attggccagg cacagtggct cacgcctgta atcccagcac tttgggaggc 173160
cgagacaggt ggatcacgag gtcaggagtt agagaccagc ctggccaaca tggtgaaacc 173220
ccatctctac taaaaacaca aagattagct gggcgtagtg gcgggcacct gtaatcccag 173280
ctactcagga ggctgaggca ggagaatcgt ctgaacctgg aaggcagagg ttgcagtgag 173340
atgagatcat gccattgcac cctggcctgg gcgacagggt gagactccgt ctcaaaaaaa 173400
aaaaatgttt ttatcatttc atgagtgtca ctatgtacac aataaagctg tgttgcactg 173460
cataggtgac ttactactcc cgaagaatgg gggagctcaa aatcagtaaa cctcgaactc 173520
attgcatcct atgatccttt ggatggctcc agagtgaaag aagaggcaaa tacaaaaatt 173580
tgagaatgtg aagtatcatg tatattatac ataaatgtac atataaatcc atactctctc 173640
tagcatttgt ttgtttgttt ctcccttaga gaagtggatt aggcataagt taactgaatc 173700
cttttgaaaa gcattaaaaa tatctacttg ggttttttaa agcacattct ctaaatgtga 173760
aaagagagat aaaatcttat aaaaaagaaa gtttctgtta agatacaact gtgggctttt 173820
ctacatgttt ctgtagacag ttcaggcttc ttttgacatc atttttaata aacagcaata 173880
caatcccgga tcacttgagt aaatgaatgc atttgcaaca ttcatttggc accatattct 173940
cttgatgatt atggcatttg atatgttctt ttttgccctc tttgtcagcc tggttcttca 174000
tgtcaatcta tagtctttta tgtggttaac ttgacagatg caggaaattg ctgccaagct 174060
ttgaaatgaa ttttttcagc agtggcatct gggtatcaga tggtcctctt ggctggcctc 174120
ttgtcttgct gcatgttggt tttagtgggg tctggtgtag catcacctgt tgctatgctc 174180
ccttttcctc ccatatgtcc atttcctgtg attcatggat gaatgtgaga ataaaagctc 174240
tagctctgtc tttatttgag aaaaaaatct acagaaatat gttagaaggt gtagagttct 174300
ctgtctgaca aagggatact tctctttggc tggcatgcct atcagctaat aattttgtta 174360
caaagtccaa gtttttaaag acattttaaa tgaaaggcaa gaaggatact ggttagttag 174420
gggaagagca agaactgctt tatttatttc ctttggttta cgttaaatca agatgctgcc 174480
attgttgtac agcataatta ggggaaatta tatttttgtt tttgttatat atttatatat 174540
tacaaaacta gctttataaa tttagaaaag aaattatttc ctctgaaaga attattttgc 174600
ctacttcctg caattcagaa tcccactgtt tacatttgta tcatattttt aaaacattca 174660
ataagagcta ttggaaatca ctatcgcgac aaagatctcc ctcatattat tgagatgtag 174720
tgaatgtgga ctctgagaaa gtccaggtgt gctaaaaagt acaagcctga ctctcaaggc 174780
cccctgtctt ctgccctcct ctgatgctca tctcacagcc accagctcct cttccatctt 174840
ttgatttctc ttagcagtac cataattttg caaaatagct ccaagggggc accattcaca 174900
ttgtactccc tcagaggcag aggcttaagt atgaggtcct tccctgttct acatccttct 174960

-continued

```
cactccagag ttgctaggac aaaacacttc tcaaactgct taagacattg tcctttaaag 175020
ggaccaaaat ctgagttcta ttctatggaa ttacatcttc caaaatgttt tgcaaaaggg 175080
ccaagggatg atattatggt cctggcaaaa ctgtttccta tgcttttttg gttatgctga 175140
caccaggcag tttctcttcc tactcttcaa ctcttactaa tcaaattctt tcttgagtta 175200
cttgcaaaga aaagtttcca gagtcatatt cattcaggaa attgagttag atattttggt 175260
aaattgtagt attgccccag taagctgaat caatgaaggg taccattgct ttggtgtcaa 175320
cataggagga acaggtcctt aggcacataa ctctcattgt ctcctcacta tcatctcttg 175380
cacttttata atttggaaag gatgagcaga aaggaaagaa agtacaactg actttaagaa 175440
ccttcttact aagaaaacaa gaaaacaaaa tcacagagaa aagactacca tgacaaatat 175500
gcaacaaata ctcagtgtgt ttcacactcc aggctataag agctctcata ctgactacaa 175560
actgcttgaa gttatataaa actacctcta aaaaagacta ttattctcct agaagaattg 175620
gtaatttctg ctcatggtca taataacaaa tttaactgct gtatttattt taaaattaca 175680
cttactaaat ttgattctga aatgtttgat gcgtatttta ttttcaaaaa agtcaatttg 175740
taacttttat tgattgctta ttgtgtgcca atgattgtgc taaaaactag aggaaatact 175800
gagaaattat ataagttatc tgatcttaag aaacatatta atagttttat taaggagcct 175860
tgaaacctaa tgagtacaaa agaaacattt attgtttaac cactagaata taatagtacc 175920
taacatttta ctgattgctt tctattcaac agatattatt ccaaatgatt tacaacatca 175980
actaatttaa ttatcacaac agcccagtga ggtgccttct actatcatca tcatcgtttt 176040
tcagataggg aaaaagaggc acaagagctt aagtgattta ttggttgagc tagcatttca 176100
ttccaggcag tctgactcca gaacttatat tcttaaccac tttattatac tgcctctcat 176160
aaagcagtca ctaaaaatta aaaataaaag gtggaacata aaataggcca tccctttggc 176220
tgcttctgag gctctacact tcgattcctg cagggtatgg agggagtgct cttccccatc 176280
tttgatttcc ctcctcagag agcaccctgt ctgcaagagg gcagttttca cacaccccat 176340
tgcacctatt tttcctcctt tacatttcct acctggtcct aggaggcact tagtttgcaa 176400
cacctggaga tcagtgacag tggagtagca taacagagga aatagaaaac aaaaaaaccgt 176460
gatttctaag gaggggctta atttgtctag tgctgaaact gaagcaaatt agaacaagat 176520
agcactatat taaggagaaa atgactatac aggggagctt aggctccatg atattatttt 176580
ttctaataga agtcacccaa tgagacaaac gagggcaatt ggaaactgag tgtttgttta 176640
agagttactc caggagatct gatatgaagg gcttgttgag tatcatcagg aagtggtttc 176700
tattcgcaat caggccaccc ttagccctgt tattgacaca gtttctttct ctctttcttt 176760
ctttttttaaa cagaaaggtt gtgggtacca tctggaccta ttaatggtgg ctgtcatgct 176820
cggtgtatgc tccatcatgg gcctgccatg gtttgtggct gccacagtcc tctccatcac 176880
tcatgtcaat agcctaaaac tggaatcaga atgctcagct ccaggagaac aacccaaatt 176940
tctcggcatt cgggagcaaa gggttactgg gcttatgatt tttattctta tgggttcatc 177000
agtctttatg accagtattc tgaaggtaac aaaatctgtc tttatgaact tgagagaaag 177060
aatacattta tcatcattta agattttcat ttgaatctga gccataaatt tgcaaatatt 177120
gtgtggcatg tgatgaaagt gatgaatttc tgaaccatgt ttatataatt cttcataacc 177180
taagggaggg aaattacgtc ctatatttta aaacccttaa atacataaaa atttagtctg 177240
gcaaagtaaa atttgatgag taaattattg taacaatttt gaatcggtga tcaagctatg 177300
ggaaaaagtc actcattgtt tctgactgac ttgtgacccg aatccattac aggcattcat 177360
```

-continued aaagattcta ttttcttgtc agtggataaa tatattagca gttaatatta cttactatta 177420
ataagagata gaggtgaagg gatgagcctg gttatagtca catacgcagt tttccatttt 177480
aagtgctctg taaaaccact gtctggacat catcattgca tatagtgatt tttttttcac 177540
acaaaacttg aaatctattt ttaagaggat taactagtaa ttattttgtc atgtaatttt 177600
gtcagatatt tccaaggtgt gtcaattgcg ctataaatta caacacattt tatttgccta 177660
taatttgaca ttttaattaa attatttaat gatttacact agtttacttg tatttgatca 177720
ttaacacaag tacctttgca agaattaatc tctgttatat aagtaattat gttatagaca 177780
taagatgatg tgaactattc caataaaaag agaaaatctg aattatccat atatttacaa 177840
atacctggta taatacagga aacacatcta aatgttagct tcatttttaa tccaccttta 177900
atccaaatat cttatctttg taaagcaaaa ttcaagttgt ctccaaagta gcataataat 177960
aatattattg ttcattatat actacatggt ttttaaaaat agattttgac ctattaaata 178020
attataacaa ccctattgtt atcatctcct tttagatatt gggaaactaa ggcacagaga 178080
gcttaagtaa cttacctaag gttacacagc taaaaatgct agagctggaa cttgaatcct 178140
tgtcttctga atctgtacta tactgtttct attcaaaaat gccttttttc cctgtttttt 178200
tctttgataa atgcaaaacc acaatctatt tgaaaatgat ttctgccttt tctccaattg 178260
ttcttttaca gtttattccc atgccagtgc tatatggagt gtttctttat atgggtgctt 178320
catctctaaa gggaattcag gtaaattact tacagtacta caggcacatc tgtgatgact 178380
gaccttaagg tctactgata agtcatgtga cagctgagaa aatgccacca cctgaggaac 178440
agcttttaga ccacaattaa atttcttcaa acttgtcaga gttacaaaag ttaaagaaga 178500
ttctctccag catctaaggt tcataatctt atggtaattt tctttatcat aagtatatta 178560
aaactgtaag aggcttagat tttacagcat ttttagaaaa atcatagtag tatatttcaa 178620
tatatatcca aatatttata atatttgaca ctttaatcat gtgtatggac atctattggt 178680
aagaatagga aaagtcttta tgcacgaaga tgttcattgt aacacatact attaaaatat 178740
tggaaacaac ccaattctct aactgcagtc aaataattag gtaacctatg gtatattcac 178800
tgaaaattga taattatagg aaccacaaaa gtaacatggc aaaaatgctt acaacataat 178860
acaaagtaag aaactattga ccataggttt ataaagctat gagtttgagc tgggttgtga 178920
aggaaggtgt agaaataaga acaatttgtt gagatagtga tatcccgggg gttttccccc 178980
ttgttttgtt tgttttactg ttatatttat aggattattt ttaaaattag actaaaataa 179040
agatataagc agtttcaagt ataaggggaa ctttatgaat tatttaagta agtattggtt 179100
aaataaatat tttaggcatg aatttggcaa cagatcagcc agatggttct ggttcaggat 179160
gtcccatgtg gtcactgtca gggtgtggac aaggtccaca gcatctgaag gtttgatagt 179220
gctggaggat ctgcttgcaa aatggctatt ccacaactgt gggcatgagg gcatcagttc 179280
ttttctacct gttggtagga tgactcagtc ttttgccaca gtggcctctc catggaatcc 179340
ttagtgtgtc ctcaaaccat ggaatgtgac tccttcagag tgagcaatat aaaagagaga 179400
gagagagata gaggagaaag gagagaagag aatgagaaag aagatgaagt gctttttgac 179460
ttagtcttca aagtcataca tggtctttcc atgttttcta tttgttagag gctatccact 179520
actaagtcca gcttgcaccc aagtgaaggg aaaagggaga ctatctcttg aagagaagag 179580
tatcaaagaa tttgtagaca cattttaaaa cctccacaag tgtattctaa atttttacag 179640
aagctgtagg caaattcttc ccacgtattt ctttgatgat actgttattg gttgaatagt 179700

-continued gagtgtttcc tgaaaattta tgtccacctg gagtctcaaa atgtgacctt acttgggaaa 179760
tagactattt gcctatgtaa ttagatatgg gtttcaagac aagataatca tnnnnnnnnn 179820
nnnnnnnnnn nnnnnnnnnn nnnnnnnnnn nnnnnnnnnn nttgagtgtg gtgtggctca 179880
tgcctgtaat cccagcactt tgggaagccg agtgggcgga tcatgaggtc aagagatcga 179940
gaacatcctg gccagcatgg tgaaacccca tctctactaa aaatataaaa attagctggg 180000
catggtggtg ggcgcctgta gtcctagcca cttgggaggc tgaggcagga gaattgcttg 180060
aacctgggag gcggaggttg cagtgagtgg aaattgcacc actgcactcc agcctgggag 180120
gcagaaagag actctgtctc aaaaaaaaaa aaaaaaaaaa aaagaagagg ggagaacaca 180180
gagagacaca ggacagggaa gaaggctata tgaagatgta ggaaggccag gcacggtcag 180240
ctcacacttc taatgccaga ccaaggcggg tggatcacct gaggtcagga gttcgagacc 180300
agcctgacca atatggcaaa atctagtctc tactaaaaat acaaaaatca gacgggtgtg 180360
gtggtgcatg cctgtaatcc cagctactca ggaggttgag atagaagaat tacttgaacc 180420
cgggaggtga agatcgcatt gagccgagat catgctactg cactccagcc tggacgacag 180480
agggatactc tgtctcaaaa aaaaagaaaa aaaaaaaagg gagaaagaga ttagagtttt 180540
gttgccataa atcaagggtg ctaggagcca cctggagctg gaaggggcaa ggaagttttc 180600
tcccctaaga ccttcaaagg gagtgtggcc ctggcaatat cttgctttag gcttctggcc 180660
tccacaagtg tggaagaata tatttctatt gatttaaacc accaagttgt ggtaatttgt 180720
taggacagtc ctagcaaact aatagatttc tacttaaatt gtcccttgaa aagtcttgtt 180780
ttataattta acattattta gcccaacact ccaatgttct tgaaaaagag actagagact 180840
tattcatcat atagtatttt gtcaactgaa aagcaaaaat aaattgcagc tttttctata 180900
acacagctag actcactgat gttcatagca tataagagaa tagttaacct gcaggacagg 180960
cagcacggga tctctgttcc tgagcaaatg actaaccagc ttctgacttt gggagaaaaa 181020
gcagaactta ggccttaaga caatactggc tgccagtctg ggggaaactt aagtatgaag 181080
tcattgcagg tcacggaaca cccaaagttg atagtatgac tgactcttca tcctgacact 181140
gggaaaaatg aactgggaga gggagatggt tgagccatgt tatatgtttt aattttactc 181200
aaattagatt taatttgctc atttaaaatt tcatgtatga aaagtgtagt ttgatagaat 181260
ttgtttagta agccattagg gaagaatatg gaagaggttt tgtttatttg tttttctttt 181320 tcccttttttt ttttttttgc ctttggcaaa agttccatga gtactaattt catctgtaag 181380
tgaaaagcat ttattattag gccccaggct cacataaata cagcagcaga gtttaagaaa 181440
caatgtaaaa tcattttgat gataggtttc aacagatttt ctcctctaat tccacatgat 181500
tttatactca tgagatttag aattgaacaa gaacgtcaag ttttggaatt atttggggtg 181560
tgaatctttt aaatgaaaat tgaagaaaac gttatcaaaa gcccatgagt taaatataat 181620
gagttttaaa gaacacaaat gaaacatcaa tctggggcac atgttgatga acagggtctc 181680
acactgagaa acagtgttcg tgaaaattta agtgagcccc aagagcaggg agctgaaatt 181740
cctatttgga attgtagcta actgggtggg gaaatgtgat attgatacta ggatataata 181800
aaaaccaaat gtaaaactca gaatacattt atcatgatga tgattattat ttaaacatat 181860
gctaaatata atcagttcca gcagcatgtt actgtcttac cctattgaag gaatctatgt 181920
tacctgcttg tttggcaata ttaagaaact tattatctgg gcttctcact gtgaaacatg 181980
gcagaaaaaa cagatcacag tgttctcatg aatgctgttt ctgcattcag atatataccc 182040
acatctatat tcattccaac acttcaggaa tccaaagtaa agcaaatgtg ccatttaaac 182100

-continued aataacaatt gaagcaccca cacactgaag tacacttatg caataacata gcttcacaaa 182160
tggagaaatg gtggctggga aaaactagtt ctatagaaaa ggaaatattc cattgtaagc 182220
cagaagattt tattttattt ctttcctatt cctacctcta ccatgcacca agtttttgtt 182280
tatttaatga cttttaagtt taaataatat ttaggaaata gaaattttaa aacttaatga 182340
catgtacatg gacagaatgg agagacatta ttcaggaatg agttcagcac ttagtagcct 182400
gcatagaatg tttcaataat atttttggaa tatataaatg aatatgaata aatgaatggt 182460
cagggaatga actaatatat gtatgattct tatttagata actgaggaaa ggaaggccat 182520
gtcatgccat aagacataga acacagaagg gaagataggt ttatgttgag tttgagattc 182580
ctattatgta tacaagcagg tcttggtaaa acagggtgtt ttgactctaa cattttgact 182640
caatggacaa ctgttccttt gcatattaat atgacacatt tgatgagaat tgcctacagt 182700
ttttaaaata agttagttaa gaaataaaat ctaatattac tttttgaaaa tgcataatgg 182760
atgttactgt agagatggca tgaaataaaa cagtgactga cagtgattga aaccattatt 182820
ttctaaataa tcgcctctag ttggaaacac tgaaaattgc aaaaattggc cgaagaacaa 182880
taaaccaaat aatctatata aaataaaact atcatgcagt atgatttgtt agtaaataaa 182940
atgtgattaa agatttaagc ttcctgtgtg catttaattt ataaaattca aaaaaagaaa 183000
aattggtttg cttgattaaa aaagccctca aagtcaaagc tgtaacataa tagtatgaag 183060
tactataaca atagtgttat gtaatactat gtactatctt tatggcaaga ttgaaacaaa 183120
taacattgat tgagatgaaa ataattttaa taaaatacaa ctgaaaatat ataaatgacg 183180
tgacagtgct gtatataaag ttaatcaaga aattaaatag agttaacaaa atttgctctg 183240
gaacatactt tattaacaaa atttatttag gttaaatttt tatggttaag atgtttgtgt 183300
ccataaagac agcatctaaa cttttgttgg ggattaaagg gacaaagtca aaacagcaga 183360
gtcaaaataa ggaggttaaa ataccgtact tagcagctgg ataagggtct agaactcagg 183420
agagagctaa ggcagagacg taggtccgtg aatcattagc aagtctgtga aagtcaaagc 183480
catgggtatg gatgaactat tccaggagaa aagaaaacag agaatgagag tccaggaatc 183540
ccaatgttga ggggcaaata aaggaagaga ttgtgttgtg acaatgaaaa agaagatggt 183600
taattatgtt ttgcttcaca gggctccact cttcaaggta gcaatattta acattggctt 183660
tctattttta aactcttcta aattgtaacc cgtctccata ttcaagaaaa tgtgggctat 183720
tgtttaactg aaattgtagt gtttcagagg gtaagcataa caatcccatt gtcttgatgc 183780
cgagatatca acttagtgtt atccaggtat gtcatttaac ccaaaattgt ggaccatatt 183840
aaacatcaac ttgtcctact tttattgttg tcttacacct aaaaacaatt tagtctgttt 183900
aatcttttag ttctttgata ggataaagct cttctggatg ccggcaaaac atcaaccaga 183960
ttttatatac ctaaggcacg taccgcttcg aaaagtgcat ctcttcacaa ttattcagat 184020
gagttgcctt ggccttttgt ggataataaa agtttcaaga gctgctattg tctttcccat 184080
gatggtatga aacttctgtc aactattttt ctctttctct gatttgctgg tctctttgga 184140
aacataaaca catgaattga aactggaaca acagagtcat tttgaacaat tattggaaaa 184200
tataagtttt ggcactgaaa gtgtgactaa gatagggttt aagaatgcct atgaatttca 184260
gtgattccta ttagttttgt ctctatcact ctgaatgttt gtggtagtct gaattaattg 184320
aagctggatg gaaaaatgca ttcttccaaa atttaacatt aaagatacta gcaaatatga 184380
aaaattagga tttttaaaat aacattgtat taaatgtttc aggcaagttt caaatacttc 184440

-continued aaaaactata gtgaatttga atgactaaat aatttcataa ttattagtat agataagaat 184500
gttctcgtgt tcatttaata tagtataaac tattaactac atgtatttaa ggaaacatag 184560
tcaaatacat tttataggtt ttttaaaata gcttatttaa tagactccca tattggttaa 184620
aatcatagtc attattgtgg tgatgtagta agaaaagaaa atgaaggaag cagaagacta 184680
gacaatgttt tatacatata tatctttaat ttttacttta atctcaggcc taatagaaat 184740
tgtttctacc aaaaaccata caggcaaatc tacacctctc attttaattt tttttccact 184800
ttaaactagt ttattattta cttcaggtgt tagccctggt atttgtaaga aagttgatgg 184860
acttgttgtt cacgaagcgg gaactcagct ggttggatga tttgatgccc gagagtaaga 184920
aaaagaaact ggaagatgct gaaaaagaag taagagcaaa atcaatgttt tataaagaaa 184980
gaaaaaagga acatagtaat atttctttgc aaaactaaat tattgttttt atctttagac 185040
agttttgtct ttagacagtg atcactaaca accacaagta gactagtttg gaagtttaat 185100
gtttaaaatc ataaagattt gaacagagag agaatgaaga tcttatagga ggaaaccaaa 185160
tcctaatgaa atatggaaat actttgtact aaaataccct ccaaattgta aggctcattt 185220
ttctgattcc tctcctatgg atggcagaaa cttgctaata cttaactatt tccaaattat 185280
gatcatgcag tgattgtttt tttgttacat atgtgagaac aaaaagaaga gacattatta 185340
ctgttggtat tttcctaggg aacagagttt taatcaaaat attctaatga ataattattt 185400
attcttgaaa taggtgaaat gtttagtagg aaaaatgttg atctgatttg ctttcaaagt 185460
gatttaagat tgagtagatg ttgcagaaac ttctggaatt tatttttaca ggctacttat 185520
ttattttatt ctattttata tggtataaca atgtattata agtttcgtgg catatttaaa 185580
gtttatatgt aagcctgagt ctattttgaa agcacttaat caacattttt ttaagtatat 185640
aaaaactaca aagagtgtaa atgagggaaa aataactagc gtaacattta gcaggatgat 185700
tgagcccata caatgtaaaa cacaacaaag ttttcacata aatagaaatg agattgaaat 185760
aaaatatttg atgagaatta tactattttt ctctataagt agtcagtaaa tgtattcaac 185820
tttctatttc ctcaaaccat agatatattt cctatttcct ttggggaatt catttgcaga 185880
tgtttcagag gtcttagtca tttaatgagg tcagatcagg ccataaatca aatgaggttt 185940
tttctttctc agaaatttat accaatatgg ttacataatg tgtaattggt aattccctta 186000
ctctacatgg tgttctatca ctaacaatgg attcccacag atagagattc atcatgatga 186060
tgtgtcttaa tcctgtaaga atgtttcaat ttttccaaat attgtagaag gcaatactta 186120
gactcatact tctagtaata ttaatgttaa cacaaaaaat gatattatac aattgttatt 186180
atttattttt ctgtttgata tatttttatt taaatattag tgcttttttta aaaaataata 186240 ctttgagtca ggcgcagtgg ctcatgcctg taatgctagc agtttgggag gctgaggcgg 186300
gcagatcacg agatcaggag ataagaccat attggctaac atggtgaaac cccgtgtcca 186360
ctaaaaatac aaaaattagc tgggcatggt ggtgcacacc tgtagtctca gctactcagg 186420
aggctgaggc aggaggatca cttgaaccgg gaggtggacg ttgcagtgag ccactgcact 186480
ccagcctggt gacagagcga gactccgtct caaaaaaaaa aaaaacaaaa aacaaaaaac 186540
tttgactagg atattttgat agtctctatt tctttttagg cctttagtaa acgtttgctt 186600
tcatcctcag atactcttca agaaaatatg gtataatttg gcacaagtta aatttaaata 186660
aaacggacac tagaacacag aaattctaaa atcttaagtt atctatattt gatgtaaata 186720
aaattattga gatcaaacac aacacccaag aaggtttaaa ttaatttaat tttgatgaaa 186780
aagctcttgg ctgtgagctt gcctttcagt ctttttgata atgtcagtac agcagaccct 186840

-continued tgaataatat agcattgtta taatgttgat gagaaaagaa aaaaaaaatt ccctggccag 186900
ggccactgtc tgtagggagt ttgcacattc tcctcatatc tgtgtgggtt ttctctggac 186960
acttcggttt cctcccacat ccccaaaatg tgcccattag gttcattggc gtgtctacat 187020
tggctcagtg tgagtgaatg tgggtgtgtg tgtgagtgtg tgctgcaagg gaatagcgtc 187080
ttggccagtc ttatttctca tcttgtaccc tgagctgcca agataggctc cagccaccct 187140
cgaccttgaa ctggaataag tgggttggaa aaggaatgaa taaatgaata caaatgactg 187200
taaaataaaa attcatcaag tatacgataa tcacacaaat gtacgacaac aatttggtat 187260
gaaaatgctc agtgaaccca gccatatttg ctattgtttt tgaactgctt ggtggtaaga 187320
tgtgctcctt acaattttca ctttgcaaac atttattcct gatttaatcc acccctacta 187380
tggcctcagt cactctctca ctcaccagaa atttggtaat tcaatatctt acttgctttt 187440
attaactttt cttacatgtt tgtatagctc acatttattt caatgtttaa tattaaaaac 187500
attttgggtc tttagttaga agtttggtga tgtttttgtg accagatatt gccataggaa 187560
tttaactctt gtttatatca attagcctat ggtaaaattg gttttattta ttcttaatgt 187620
cacagtctcc gagaacctat caataacttt atgtgagcac ttattgtact attaattata 187680
ctcaagcagt aacttacata tctaattttg ctttattttt ctgctttttt ttgttaactg 187740
tctttactgc ttctggaaaa aaaaaaaacg aacacagccc cagacatata atcatctctt 187800
tcacagtatt ctccttagat catactcata ccgtgaaaca ttcttgcctt ttagaagttc 187860
acaaaatgaa aaatgatatg taatctatta tgtaatgttt aatatttctg tgactgtgat 187920
tcaaagataa tttcagattc tccttttatt ttctgtgaaa caggagagaa caagtttaat 187980
aataattgta aatttattag aatttgccat tcccactgcc cagaaccact cacatagcta 188040
tgcatgtatg gtacttatat gtgtgtgtgc catatgccca ttttggaatt tatgaatctc 188100
atagggcaga gaacatatgt aatcagtgtc taatcttttt atattatata cccactgtac 188160
tttaatgggc atttactgtt ctctgattat gaagataaag attttaaaag taactaaata 188220
gcactaaatt tcctagaact catgctttct gaaaagatac aaaaatggat taaagatttc 188280
ctggggcaat tttactgcta aatccttcat atccaagtta gagggaaaag ccttgcagta 188340
cattaactag gcaggtttat agatccttaa aatctcagat gggttaatat gatgatactt 188400
tcatgtgatc ctcagtacat ggaaagaaac aagaaaatca ataatatagt caagaaataa 188460
tctataattg aacaataaaa tatagctctg actagtgcaa agacagctaa ttctccatcg 188520
aacaggaaag aaaataggaa gtttaaagag gttcgctttc tagcttagaa ttagtattaa 188580
aagagtatgg tcactaaaga cattaggaag atttaggaat aattatacta aaagttaaat 188640
tcctggttga tttgtttgcc cggatcttgg tattctattt tcttgaggct tacagactca 188700
gtagaaggat gtgatcttac tgtggcatct tatactaagg cccagtcttc taagagattg 188760
tgtgttaagg tggtaaacgg acaagttctc cagaaatgtt gcatttctgc aattgctcaa 188820
attaattgag taactttgat catgaactgg caagatggta aatagcagaa atgtctcagc 188880
tccctgagac ttgaatttaa agtaggctca cctcttgtcc ttttgatgat agatacaagc 188940
ttttaccttt agcctccagg gttttcctat cagtagccca tttctggtct tatggcactg 189000
agaaaacatt catttgacct taaaattcaa taatgagtta agcagaataa atagctacac 189060
aggccagtcc aaggtcgcag agcttctgtt ccaaattttc atgtacttca tgcatatgca 189120
tatgcatatg cttcagtttt tagaaagaaa ggattataat cagggtagaa atgaatattg 189180

-continued gaaccctgac attttgcaca ttgctctgtg taaagggaag actgcagaat caaattctgg 189240
atgtccaaat gtgctcagag taccaacatg ccttccttcc tacttaaata ttctctaggc 189300
cattgtacac atttgacaaa aggctactta ctgttaaagg cagaaaatcc cagcagaatg 189360
tttgctcctg ggtaggagga aaggggttta gtgttggata aatcctagaa attctactct 189420
gtggaagtga tcatgatagt gatacttctt gatttactgg ggcttcactc ttaacatata 189480
cactatagga gaaaacaaaa agagggcaaa tgggaccctg tgatcccaat gcaggatcat 189540
gaaaaaggtc aagaaaaaag caatctaaaa acaagtgcaa ctaaacaaat tacagaggac 189600
gacttactgc taagataggt cagaattggt tatggatttg ggaagcatgg ccaaattatt 189660
acannnnnnn nnnnnnnnnn nnnnnnnnnn nnnnnnnnnn nnnnnnnnnn nnnaacaaag 189720
tatgctagct atgggaagat gagggcacag tacaactccc attggaaggg cactataggt 189780
aagacataaa tttaaaaaca catcaattaa agtaatgaaa tgcattgtta tatactttaa 189840
gaatttcata ctgtgtagat cctcagagag gtttcttgaa attgtataag agtagaaaga 189900
acgaagagtt agataacatg ggtcctactg ctaagttttg ccaataatag ccgtgtgact 189960
ataatcaaat tgcattaaat gaagtgaagc aggaagctgt tgtctgaagt ttttcttgct 190020
cctgttttat aatgtgtatg aaaaatccct ttcatattct cagaaagtag caccagaaga 190080
cagatcaagg ttcctttttt gtataagtga ctagttattc actaagttga tcacaggtaa 190140
atgttttaac tctgggaatt tgccgctaaa agtggaattt ccaatgacat aatctatttc 190200
ttaagtgatt cagttgtatc agtcatttta ggatatattt atgcaattct ccaaaatttt 190260
ctaatcttct ttatgtacaa agacatagca aaagaaagca aactactgaa gttataaaga 190320
aaacatttgc aagcatttgg cccagaattc tcccctctct ctctcttctc tgtctccctc 190380
tcaatatagt ttagtttaaa cggttatctt gtacaattct aagtatcaat tagtgcccaa 190440
ttttatagtc tcaaagtctt tatgaataat ttaaggttat gccaataaaa atacagagaa 190500 tacttttttta tgagaaggga atttgtcata gtgttaaaaa ccaaaatagg agagaatttt 190560
ctagatcttt agggtctgac tctaagatta tattccctag aatttaagaa aatgtgatta 190620
cctccctctt aagaggggc acaagtataa gatgttttat cttttttttc ttttttacaa 190680
catttaaatt ttaaaatcct gttgattttt tagctgaacc agcatatttc caagtgtatt 190740
aggtagaaac ctagtcttgt gtgataccac tctcgaaagg gctgtgtggt taaataagtt 190800
tgaaaaaatg tgccaaactg cattccagtt tggagattca caatgcatat tagcaaatga 190860
aacaatctaa gtagtactgc attttaaaaa attgtatagc ttcgttcaat caagtattta 190920
aaaaaatctt ttgctcagaa gactcttcct cacataatat catgaaaaat gtctattcca 190980
catgatgctt tttttaagaa agtagtcaat ctggtgcttt gaattaccag gaaactatct 191040
ttctaggaag accaaaacag ctggagggtt tagaggaact gaagaacaca tttccagatt 191100
gggcaagaga gggagaccca aggttttgtt cctcttaaaa gttgcatttg ttcctctcct 191160
gtgacctatc accaatcagg gtcatatgaa aaggcggcat ttgaacaaag aaggggcaag 191220
gttgctccat gtgaagggac atgataagca gagggaagag caaggacaag gcccccaggc 191280
agcaccatgc ccattgtgtt ccagaacagt caggaggcta ctgaaatggg gctggaaagg 191340
agtgagcagg gatgcagtgg caggaggtga aatcagagtg aggtggggac agagccttta 191400
ggccattata aggacttggc attgactctg agtgactggg agccactgca aggtctgagc 191460
aaaggaggga agtgatctgg ttgctatgat gttaggggca agcgtttaag caatggacat 191520
gcggaaccca ttctctgtaa tttgaaatga attaagaata ccacaggcca actcagtatc 191580

-continued tattcaacta gaatatttc tttagttttt ttatttttca cagattgttt tcaataattg 191640
agagaaatat tcaatacttc ttcattttta attatcaaaa atattgtaca ataaacaaaa 191700
tggggcatac acatacaatg gaacattatc caggtttaaa aaggaggaaa ttctgacata 191760
tgctacaaca tggatgcacc ttgaggatgt tgtactaact gaaataaacc agtcacaaaa 191820
agacaaatac tgtatgattc tgcttatatg aggcacttag agaagtcaga aacctagaga 191880
cagaaagtgg aattatagtt gccagggacc gggaacaaga ggaaatggag agttgtggtt 191940
tagtgggtat ggagttccag ttttatagga taaaaagagt tctggaaatg gatggtggtg 192000
atggttgcac aacattatga atgtatttag taaccctgaa ctgtactttt aaaaatagtt 192060
aaggtagtaa attttatgtt atgtgtattt taccacaatt taaaaattgg gaaaaatatt 192120
cttcatagat atatgattgc cctatattta gtttctgtca ttgaaaaact gcagttactt 192180
atgtaatgtt tattatttca tttggggaaa ctcctgtcta gagatgatcc atctgtgatc 192240
aatatatctg atgaaatgtc aaagactgcc ttgtggagga accttctgat tactgccgat 192300
aactcaaaag ataaggagtc aagctttcct tccaaaaggt ttggatttta aaataatgag 192360
aatttatact aattccaatt gtttttgac ataaaccata agcaaaagaa taatattagt 192420
ttccatcaaa tttagatata aaatattcca gaaaattctt tccaaaagtg ggtagaaatt 192480
gtaattattt caaatgttgg tatgtttttc ataccaactg tggtatgggg aactgtgcta 192540
gaaatgagtc acaatgcatg acatttttgg acattcatct tggcctactg tttttcagta 192600
tgattttatt ttattccctc atcacccact tcccccagga cccctttaga catctggcca 192660
cattttgcac tcctttattt tcccttttt agactgatat gcactgtgtg tattttatat 192720
ttatatttta taaatatgca taaatattta tatttagtat agttctagtc ctgactccaa 192780
ccccctgaaa gtcttcccta aacttcttat cccaaaactt tcaactcctg aaagttctat 192840
ccattctttc ttctctgtgt gtaaatgtac aaacaactcc tgtagttgtg gatggtagtt 192900
ttaagtgcat gctggaggaa gagtgtgtcc ctaaatatca acagtcatca aaggatttcc 192960
aagtgaatct tctaggattt ataaataaga gttcaagtca cccagtcttc ttagatgctg 193020
atctgaagaa agaggaattc ctatgttatg ctaatatctc tttttgttag agagtgattg 193080
agggaattgg gacagtgttt actataatta taaagttcct ttattttcgt aaccttaaat 193140
taactttttc tacttaattt ttatattaca tttttgtcat aagctcccct tcctaatcac 193200
tctagaagct gattccccaa aggtaagacc ctctccctca aatctattcc ttggttgcat 193260
ttccttatgt taaatggtgt cttctagaaa cctggtcagt ctatgtcctc tgtgtgagtt 193320
ttggggaggc aaaaggcatg gagagtgttg ggctcagatc cagtagcaga ctgagtttga 193380
tgatatatct gtaacaactc agctctttaa gttagtctga aacttgaata aactttattc 193440
cttccttgat ttatacagat gcatcatgta taaatcaaca agtttcacag aactgtagtt 193500
agtaatggca tcaaatttct ggatagggaa aattaaattt gtccctttaa gaaattgaaa 193560
agcttgcctg gtgtggtgac tcatgcttgt aatcccagca ttttgggatg ccaaggtgag 193620
cggatcactt gaggtcagga gttcgagaca agcttcgtca acatggtgaa accttttctg 193680
tactaaaaat acaaaaaaat tagccaggcg tggtggcgga tgcctgtaat cccagctact 193740
tggaggatga ggcaggagga tcgctgagcc caagaggnnn nnnnnnnnnn nnnnnnnnnn 193800
nnnnnnnnnn nnnnnnnnnn nnnnnnnaaa tgcccttgag gtcaatgtgt tgagtaattt 193860
gaaacaaacc tgtaaaaaat tttcttcctg tattatatgg attcaaagtc caaacttttc 193920

-continued ctctattttt ctttggttca agcaaaagtc ttgtgacgtg atattttagc tactccttaa 193980
agtcaagtga tacttttcac cagaaaaatc tttttgtttt aaaaatatat atccagatga 194040
cttcacatag tgggttgact ctagtgaaca atataatgtg ctttaaagca ggtccaattt 194100
tcaatagact atcctttata tttagatata accacttgtt tcttattctt taaatgtact 194160
ttcactgacg tgaggttcag actattgtgg aatgaaagtt tatccagctt tccttacctt 194220
ttgatgtgat cgcatttgtg gttttccatg tgagaaacat cttttggttg gtagttaatc 194280
tcttttatcc tcattacagt agaaactctg gcagaaagtg tatgacttac agaattctaa 194340
aactactgat actaataagg ctcccaaagc cacttccttt ttgtggtatc tgttaaaggc 194400
tttaaagcat catgaccagg aactgtgaaa atttagtacg tggtagagta tccattggca 194460
aaaagagacc caaagagcag gttactaggg tctgagtcct gagctggcac ccatgcagcc 194520
tttgacaccc cccattctga gttattttcc atcctgtgct gtaatgtgtc agagaagcct 194580
agaaaccctt ttttcatgga attttgaata gaaattatat tttctcaatt atatcattca 194640
ctttttgttg tcaaaaatat tttatctcgt ttaactgaca gtagaatcta agaactaacg 194700
gcaaattctg tcttatctgg aggatgtcta attttgatcc tgatgtcata catgcatgtg 194760
acaagagcct ctgcagctta ttaaatgggc tggtgaaaat agggctcatt aacgaccaca 194820
ttgcatcaga ataggttagc aactgctacg ttttttaaac tgatgcccaa gatcagtgtg 194880
tctggaggtc cttggcaatg ttaggaaaag cagcacttag ctttgccttg gtgacagagg 194940
ctagtctctg ggactatccg ctctaccccc caacacccac ccctgcactc ccccaccacc 195000
tttttctatc ccagattctt tctttgctct gattgcctag gcttaggctc tctcatgact 195060
tcttggaaat attattcata aaaacaactt tagcctgggc gtggtggctc aggcctataa 195120
tctcagcact ttgggaggcc gaggcgagca gatcacttga gctcgggagc tcaagatcgg 195180
cctggccaac atggtgaaac cccatctcta ctaaaaatac aaaaattagt tgggtatggt 195240
aacgcacacc tgtaatccca gctactcagg aggctgaggc aggagaatcc cttcaacctg 195300
cgacgtggag gttgcagtga gccaagattg tgccactgca ctccagcctg ggcaacagag 195360
caacactctg tctcaaaaaa aacaaccact attttagtga cattaaaaag taatagtttc 195420
atagtttact tagcatcatg acagtaccag gtcacttttt gccctcttga aatattactt 195480
ccttatattt taaattttaa ctcctcaggg acagggacac tcttatctat cttgtactcc 195540
taggtcatta tggagttcct ggcatataat agatatgcaa catatgttta ttacaatgac 195600
agataacaga tgcataatac atgtttgtta caatgaaagc ttaaaattga ttggcctcca 195660
caaaagcgaa cttaacaagt aattccgaac aatggatcct agaggtcttg agctggttat 195720
aaaatttctg cttcatagtt tgctgaaatc taatctgata ccaaaactat ggttatgatg 195780
aagagggaaa aaaacccaga catttaatag gttattgttt tgtaaccaaa caaccaaagc 195840
agagtcagga ggaagcacat ctatggatca agttgatatt atgaatcttt ttatttatga 195900
cttggtgact aatagtgcca cttggcacac attcatttat caaaaggtta tggaacacct 195960
cccacgtttc aaagtattgt gcacacagta attgcacatg tgtagagacc agtatatctc 196020
tgtcctacaa tctcctacat ataggatctg ttattctatc tttcaaaaaa taagagttca 196080
ttggaattgg gaataccagc ctcagaattc tggaattctc actacaagag agcctagagg 196140
ccatctagtc caaaaccaat tttacagatg aagaaaccaa gtctcagaga gattaaataa 196200
ctagtccaag gtcatgcagc tcattctgag tttctgaaaa ctgaacctag atcttccaac 196260
accaagccca gtgctgccct ttttcattga ctttgtttgg caaaagagac tggaaggcag 196320

-continued gtagagctta aggaaaagtt aatttggaaa gcaggagagc atacacttgt catataaaag 196380
gaacttaaag tagaagaaag tgagtcatac agatagagga gttaaaaata cgagttaggg 196440
ctctcaacac atcatgtgca cactgtcatc ttttctcatg gaaggagaaa agaaaaggga 196500
ggaaagttgc tttgctctga cctgtaagta gtatgtgctg agaagtgtgg caggcacaaa 196560
cccgggcgcc atagacacgc gctcacacca gctctcagag ctggcagcgt gccacagatg 196620
gcagaagctc cggcacttct tacctgatgg tgccgggtgg tggtgacaac tgagaagggc 196680
tgtttctagc ttgaattgga ggaaaaacaa tttaaaaaac acactcttag aatgtgtcta 196740
agttattgac cacttagaaa gttgtacagg aggccccata gaaaaatgga gttttattac 196800
tttattactt ggagaagagt tataaaacca agggtgcggt ccattgtcaa gtgtttcata 196860
aatttatatt aagggccgaa gttaacagta aaaatgtatg gatacttaca gcccagggcc 196920
tcagtagctg gctatgggct gccctttgtg tcagcagtgg ggagggtcac atagaagcct 196980
cagatgagga gggttttgct gtgtgctgca agtatcaggg agaaagcatt tctgccctct 197040
ctggaacatg gtgtgaactt catccctgta atgatattgt ttgaattttc catgaaaaat 197100
tgtcagcatg agagtaagaa aagtgtacga tgggaaaata ttgaaccaaa cagacaaaaa 197160
tggtagagtc acatgaccag tttactcatt ggtaaagtta atgagagggt gagattaaac 197220
agaaattggt aaagttaatg agagggtgag attaaacaga gggtgagatt aaacttggga 197280
atgagtttgt ctgaggagtg aggtgaagca tcattcctct gatgcacagg gtaagggttt 197340
gtctgtaaag agatagcaca ggtgtctgga gagcagcgtg catggtaacc tgtcctccag 197400
gccagtggag ctgtctgtct aacctggcca aggtacagtc ttcatcaaag gtcaggatcc 197460
agtccatgca caagggagga gccatttgca gcagagccca gaaatgcctc ctgcgacatc 197520
ttgtttgtgt catttactag agttggcact gtcttaagat gggggcatgg ctgacatttt 197580
caactatcat cagtgagtca cttgcccaaa tgaggaccat ggtattaatc ttgcatgttt 197640
ttggaactgt ttaaaaaatg tctgattttt gttgtttagt gtctgttttt gaatttcccc 197700
ttctctgcag ttcttggttt ctatctcact gagtgcagag gattttaatt gttgctgtct 197760
atctgtgctt cgcagcatga gagagcaatg cctacgggct cttgtggtgc tttggggttg 197820
acgggtttta tgtctgagca agcagatgtc atagtagcca tgctggattg cagtaataaa 197880
tgtgtccttt ttttccttct gtagcattga aagccgaaaa gagaagaaag ctgactcagg 197940
gaaaggtgtt gacagggaga cttgtctatg actcgatctt caatttattt tttacatata 198000
tatgagaaga gtgtcacaat tattaataaa actgctttga tcatgtattg taaattctgt 198060
ccctcaaccc aaatccacct tcatactgta agtagtgcaa tacttgtttc atttctgtgt 198120
ttaaacttct gagcagtgag acatccctgt gagcagatac aatagccaat gcaagaatct 198180
gtgtgttcct tgctgtacgt tagacatttg taaactggat tctgattgtc agttttatga 198240
gagcaatagc ttccttaaag agataagtca tatttaccta gtttgtattt tcctacttta 198300
gtgacctgaa gatgcctgat aatttcattc agaagaattt ttgaaaggta gtcttacttc 198360
tttttagttt ttatagctta gcattagtga cttatttcaa aagacccaaa tcaaaaagtt 198420
agtttgaaag catttttttaa taattgtatt tatgcatttc cttgatttaa tatgataaat 198480
ttaatactta acaatttata tgtaactaaa acttaaagtc atttgaaaaa tatatagaaa 198540
cctatttaca acttgttaag gacaatcaga cataatgcag agttaagtag tatttgctta 198600
aaattcaagt tgtgactaat gatcaaatac taggcttgta cgaaatgctt tagaaaaact 198660

-continued

```
ttgtaacagt tttgtgggat ttttcaatat aaacctttat cagaaatata ctaagtttgt 198720
ctcccactga caacagatgt tttccaaata aacatattct atacatactt gtggaatgcc 198780
acatggtgaa tcattgtata tgaaattcca ctcctgtaca gttactctgc agctaatggt 198840
catgcactgc ttaatgctgg tcctgaatca tgttctcatg ttagaccaac agctctccaa 198900
ttgtcatttt ttttctgcag agtttttttt ttccactttt aaattaaatg catgttgtgg 198960
aaaaacagtc ttttaaaatg aaatttcaga ttccatttga gaaggttctg tagatatttc 199020
agtccatata aaataataca tctttactaa acttatataa ggggagagaa agttatgaag 199080
ttttggacat tactaaaagt acagtatttg atttcacttt caatgaatgg tgaagttaat 199140
aaaactaaat ctcataatgc tcttggttcc taagaatgag tagtaatcat caactttata 199200
atactccaat attccgtttt ataataattc agagccctgt ggcttttaca caccgttaat 199260
tatgtactct gttggaagtg cacatgaaaa gtgaagaaaa gttcctcttg tgattaaact 199320
aatgggagga aataaatcaa caaagtctcc attaagttct acattttgag accttttaaa 199380
aattcccctc acaattcttt aaggagcccc cctttttatg gaacatgagc ctaaaaatta 199440
tagaaagaag aattttaagt taataaagtt tgtatttata aatgctgaaa aaatacagaa 199500
actttctgtt ccaaatgtgt tgcctttgtg tattttataa tacagatact acattgtaaa 199560
catttccatt gttttatgat ttagccagtg attccccaaa gcagcctctt agtgttttaa 199620
tatattaata actgttttgt taaaaatgat catagtgaat ttaaatcttc acatgatcac 199680
ctatttgaat aagcaatcat atccaatgaa attctgtatt tctgagtatt tttatagtca 199740
ttttgttctt gtgtgaattt taaagctatc cctatgttaa tcctaatatt ttgaaatcat 199800
ataaaatata ataaaaatgt agtattatat atttacttct aatttcagat tcctggtcaa 199860
aattactaaa tatcttgaat gtaatttagt gccaagttta aataatgtgt aaatgtgact 199920
aggatattgt gtttttcaca attaagaaat gttatgtgga aataaatatt tatcctaact 199980
tccttgcaca ttttaaattg tgatacaaag tgtcttgtct tttttctttg ttttaattag 200040
taaatcagtg taaaacattt tgattgtttg aatataatat ttaaatttag acagccccaa 200100
agctaagaac tcttggtgat gtaaacaatt tatgagtatg tttcaagagt aaacaatttg 200160
aactttatga acagaagatt atgagaacta tataaagata tatttactca tttttccaga 200220
aatgggtgca gatgacacgg tttcttatgc taggaaaaac ctccaaggtc gttagtagta 200280
gtattcctca ttattagaac tctatttaga cttccgtttt taacttccat ggggaaagca 200340
ttgcctaaaa tttgtctcct ccctgtttct tacaaaagtc agatgggacc attattcttt 200400
ggtagccatc tggcagtgtg ttgtggagat aattgcattc agaattctat ctaacctact 200460
gcttggtatt tttctcttga ctagtgagtt tactttgtaa ttgctcctgt ttcacagcct 200520
acaatattgg aaagtttttt tcctgtataa tataatatag gaatatatat attcctatgt 200580
atgtatagga tatcctatat atcctgtata gatgaatgtc tccttggtat agtttaaacc 200640
cgagtttgaa agaaactctc cactgatgat ccaaaagcaa cttgtatttc aacatgattc 200700
ctagatcttt ttggattttt cttgactctt agaagtgtga cttacctgtt ttctatggca 200760
ctgacctacc tctgttttgg tttaacttta gcctattagc tcctgggcac ttgtctattt 200820
tactatcatt gcaagattgc tctctcattt ttccaatata ttaatatcta tctcatatat 200880
tcacacaatg aaatgaaatg agattacatc catttgaaag ttttatgaga gtcatttgga 200940
taatatgatg gttctctaaa tgtctacatc aagaggctaa ttgtagttag tccccttgaa 201000
gaggcttaat aatcaaagat tactggtaat actttatttt agagatctcc ttcgatgttc 201060
```

-continued

```
ttcatggaat gctgtggcta actgatacaa ctgtcacacc aattccgttc ctgttggtgt 201120
actgggtact atcatttctg ctggaacttt gaaaatagga ctatgatcct tgcttctaag 201180
ggcagggtgg atacatagct gtaaataatg tgatatgtgc tgagttggcc atatgagtaa 201240
agccattttt tgaatagggc agagtttgac gaaaacatta tagtagaggt agcacgtgaa 201300
ttagaatgga aatggggaag gaaatgtact ccagatgttg aaggaacccc tgcctactag 201360
gcctctggtc taatgaagta tgaccagaat gactccatct tgaagtgaag agctagaaca 201420
ctcttaaggc acctataaga ttaatgcttg tggtctgaaa atagccactt tccaagctgg 201480
ctacaaccta ttattacaga atatttatga ccatacagag catctcccac catgcctgca 201540
gaatgtccct atgtcctaag aattcagccc tccttactta gagataacgt taatgaacaa 201600
gcttaggtta aaagattaag ggtcatgtaa tatcaatgac actgaaggcc cctgccttta 201660
gtgagcacat agacacattc caagtttaat tgtagctctt tgtaactcct tataaaagta 201720
gaggcgctaa caaaggacag ggcattcctc cttttgcttt cagaggatat cccacactgt 201780
aacgaaacgg tttctgaaaa acttacttct tccactatgc tctgtggctt tccttgaatt 201840
ctctcctttg caagatccaa ggacccattt ttggggtctg gatcaggacc ccttttccag 201900
caacaccgga actacaaaga ttctcaaacc tatgtcggta ttgaaataaa gatgaaattt 201960
aaaagtaaag ctatatggca taactagagc ctggcatatt t                     202001
```

<210> SEQ ID NO 4
<211> LENGTH: 1085
<212> TYPE: PRT
<213> ORGANISM: Mus musculus

<400> SEQUENCE: 4

```
Met Pro Ala Gly Ser Asn Glu Pro Asp Gly Val Leu Ser Tyr Gln Arg
 1               5                  10                  15

Pro Asp Glu Glu Ala Val Val Asp Gln Gly Gly Thr Ser Thr Ile Leu
            20                  25                  30

Asn Ile His Tyr Glu Lys Glu Glu Leu Glu Gly His Arg Thr Leu Tyr
        35                  40                  45

Val Gly Val Arg Met Pro Leu Gly Arg Gln Ser His Arg His His Arg
    50                  55                  60

Thr His Gly Gln Lys His Arg Arg Arg Gly Gly Arg Gly Lys Gly Ala
65                  70                  75                  80

Ser Gln Gly Glu Glu Gly Leu Glu Ala Leu Ala His Asp Thr Pro Ser
                85                  90                  95

Gln Arg Val Gln Phe Ile Leu Gly Thr Glu Glu Asp Glu Glu His Val
            100                 105                 110

Pro His Glu Leu Phe Thr Glu Leu Asp Glu Ile Cys Met Lys Glu Gly
        115                 120                 125

Glu Asp Ala Glu Trp Lys Glu Thr Ala Arg Trp Leu Lys Phe Glu Glu
    130                 135                 140

Asp Val Glu Asp Gly Gly Glu Arg Trp Ser Lys Pro Tyr Val Ala Thr
145                 150                 155                 160

Leu Ser Leu His Ser Leu Phe Glu Leu Arg Ser Cys Leu Ile Asn Gly
                165                 170                 175

Ser Val Leu Leu Asp Met Arg Ala Ser Ser Ile Glu Glu Ile Ser Asp
            180                 185                 190

Leu Ile Leu Asp Gln Gln Glu Leu Leu Arg Asp Leu Ser Asp Ser Val
```

-continued

```
        195                 200                 205

Arg Val Lys Val Arg Glu Ala Leu Leu Lys Lys His His His Gln Asn
    210                 215                 220

Glu Arg Arg Arg Asn Asn Leu Ile Pro Ile Val Arg Ser Phe Ala Glu
225                 230                 235                 240

Val Gly Lys Lys Gln Ser Asp Pro His Ser Met Asp Arg Asp Gly Gln
                245                 250                 255

Thr Met Ser Pro Gln Ser Ala Thr Asn Leu Glu Val Lys Asn Gly Val
            260                 265                 270

Asn Cys Glu His Ser Pro Val Asp Leu Ser Lys Val Asp Leu His Phe
        275                 280                 285

Met Lys Lys Ile Pro Thr Gly Ala Glu Ala Ser Asn Val Leu Val Gly
    290                 295                 300

Glu Val Asp Thr Leu Asp Arg Pro Ile Val Ala Phe Val Arg Leu Ser
305                 310                 315                 320

Pro Ala Val Leu Leu Ser Gly Leu Thr Glu Val Pro Ile Pro Thr Arg
                325                 330                 335

Phe Leu Phe Ile Leu Leu Gly Pro Val Gly Lys Gly Gln Gln Tyr His
            340                 345                 350

Glu Ile Gly Arg Ser Met Ala Thr Ile Met Thr Asp Glu Ile Phe His
        355                 360                 365

Asp Val Ala Tyr Lys Ala Lys Glu Arg Asp Asp Leu Leu Ala Gly Ile
    370                 375                 380

Asp Glu Phe Leu Asp Gln Val Thr Val Leu Pro Pro Gly Glu Trp Asp
385                 390                 395                 400

Pro Ser Ile Arg Ile Glu Pro Pro Lys Asn Val Pro Ser Gln Glu Lys
                405                 410                 415

Arg Lys Met Pro Gly Val Pro Asn Gly Asn Val Cys His Ile Glu Pro
            420                 425                 430

Glu Pro His Gly Gly His Ser Gly Pro Glu Leu Glu Arg Thr Gly Arg
        435                 440                 445

Leu Phe Gly Gly Leu Val Leu Asp Val Lys Arg Lys Ala Pro Trp Tyr
    450                 455                 460

Trp Ser Asp Tyr Arg Asp Ala Leu Ser Leu Gln Cys Leu Ala Ser Phe
465                 470                 475                 480

Leu Phe Leu Tyr Cys Ala Cys Met Ser Pro Val Ile Thr Phe Gly Gly
                485                 490                 495

Leu Leu Gly Glu Ala Thr Glu Gly Arg Ile Ser Ala Ile Glu Ser Leu
            500                 505                 510

Phe Gly Ala Ser Met Thr Gly Ile Ala Tyr Ser Leu Phe Ala Gly Gln
        515                 520                 525

Pro Leu Thr Ile Leu Gly Ser Thr Gly Pro Val Leu Val Phe Glu Lys
    530                 535                 540

Ile Leu Phe Lys Phe Cys Lys Asp Tyr Ala Leu Ser Tyr Leu Ser Leu
545                 550                 555                 560

Arg Ala Leu Ile Gly Leu Trp Thr Ala Phe Leu Cys Ile Val Leu Val
                565                 570                 575

Ala Thr Asp Ala Ser Ser Leu Val Cys Tyr Ile Thr Arg Phe Thr Glu
            580                 585                 590

Glu Ala Phe Ala Ser Leu Ile Cys Ile Ile Phe Ile Tyr Glu Ala Ile
        595                 600                 605

Glu Lys Leu Ile His Leu Ala Glu Thr Tyr Pro Ile His Met His Ser
    610                 615                 620
```

-continued

```
Gln Leu Asp His Leu Ser Leu Tyr Tyr Cys Arg Cys Val Leu Pro Glu
625                 630                 635                 640

Asn Pro Asn Asn His Thr Leu Gln Tyr Trp Lys Asp His Asn Ile Leu
                645                 650                 655

Ala Ala Glu Val Asn Trp Ala Asn Leu Thr Val Ser Glu Cys Gln Glu
            660                 665                 670

Met His Gly Glu Phe Met Gly Ser Ala Cys Gly His His Gly Pro Tyr
        675                 680                 685

Thr Pro Asp Val Leu Phe Trp Ser Cys Ile Leu Phe Phe Ala Thr Phe
    690                 695                 700

Ile Val Pro Ser Thr Leu Lys Thr Phe Lys Thr Ser Arg Tyr Phe Pro
705                 710                 715                 720

Thr Arg Val Arg Ser Met Val Ser Asp Phe Ala Val Phe Leu Thr Ile
                725                 730                 735

Phe Thr Met Val Val Leu Asp Phe Leu Ile Gly Val Pro Ser Pro Lys
            740                 745                 750

Leu Gln Val Pro Asn Val Phe Lys Pro Thr Arg Asp Asp Arg Gly Trp
        755                 760                 765

Phe Ile Asn Pro Ile Gly Pro Asn Pro Trp Trp Thr Val Ile Ala Ala
    770                 775                 780

Ile Ile Pro Ala Leu Leu Cys Thr Ile Leu Ile Phe Met Asp Gln Gln
785                 790                 795                 800

Ile Thr Ala Val Ile Ile Asn Arg Lys Glu His Lys Leu Lys Lys Gly
                805                 810                 815

Cys Gly Tyr His Leu Asp Leu Leu Met Val Ala Val Met Leu Gly Val
            820                 825                 830

Cys Ser Ile Met Gly Leu Pro Trp Phe Val Ala Ala Thr Val Leu Ser
        835                 840                 845

Ile Thr His Val Asn Ser Leu Lys Leu Glu Ser Glu Cys Ser Ala Pro
    850                 855                 860

Gly Glu Gln Pro Lys Phe Leu Gly Ile Arg Glu Gln Arg Val Thr Gly
865                 870                 875                 880

Leu Met Ile Phe Val Leu Met Gly Cys Ser Val Phe Met Thr Ala Val
                885                 890                 895

Leu Lys Phe Ile Pro Met Pro Val Leu Tyr Gly Val Phe Leu Tyr Met
            900                 905                 910

Gly Val Ser Ser Leu Gln Gly Ile Gln Phe Phe Asp Arg Leu Lys Leu
        915                 920                 925

Phe Gly Met Pro Ala Lys His Gln Pro Asp Phe Ile Tyr Leu Arg His
    930                 935                 940

Val Pro Leu Arg Lys Val His Leu Phe Thr Leu Val Gln Leu Thr Cys
945                 950                 955                 960

Leu Val Leu Leu Trp Val Ile Lys Ala Ser Pro Ala Ala Ile Val Phe
                965                 970                 975

Pro Met Met Val Leu Ala Leu Val Phe Val Arg Lys Val Met Asp Leu
            980                 985                 990

Cys Phe Ser Lys Arg Glu Leu Ser Trp Leu Asp Asp Leu Met Pro Glu
        995                 1000                1005

Ser Lys Lys Lys Lys Leu Asp Asp Ala Lys Lys Lys Glu Glu Glu Glu
    1010                1015                1020

Ala Glu Lys Met Leu Asp Ile Gly Gly Asp Lys Phe Pro Leu Glu Ser
1025                1030                1035                1040
```

-continued

```
Arg Lys Leu Leu Ser Ser Pro Gly Lys Ser Ser Ser Phe Arg Cys Asp
                1045                1050                1055

Pro Ser Glu Ile Asn Ile Ser Asp Glu Met Pro Lys Thr Thr Val Trp
            1060                1065                1070

Lys Ala Leu Ser Ile Asn Ser Gly Asn Thr Lys Glu Lys
        1075                1080                1085
```